US008329742B2

(12) United States Patent  
Boivin et al.

(10) Patent No.: US 8,329,742 B2
(45) Date of Patent: Dec. 11, 2012

(54) MACROCYCLIC COMPOUNDS USEFUL AS PHARMACEUTICALS

(75) Inventors: Roch Boivin, Lawrence, MA (US); Kenichi Chiba, Tsuchiura (JP); Jesse Chow, Hooksett, NH (US); Hong Du, North Andover, MA (US); Yoshihito Eguchi, Kashiwa (JP); Masanori Fujita, Ushiku (JP); Masaki Goto, Tsuchiura (JP); Fabian Gusovsky, Andover, MA (US); Jean-Christophe Harmange, Andover, MA (US); Atsushi Inoue, Tsukuba (JP); Yimin Jiang, Londonderry, NH (US); Megumi Kawada, Ushiku (JP); Takatoshi Kawai, Tsukuba (JP); Yoshiyuki Kawakami, Tsukuba (JP); Akifumi Kimura, Tsukuba (JP); Makoto Kotake, Abiko (JP); Yoshikazu Kuboi, Tsukuba (JP); Charles-André Lemelin, North Chelmsford, MA (US); Xiang-Yi Li, Andover, MA (US); Tomohiro Matsushima, Ushiku (JP); Yoshiharu Mizui, Tsukuba (JP); Kenzo Muramoto, Tsukuba (JP); Hideki Sakurai, Tsukuba (JP); Yong-Chun Shen, Tewksbury, MA (US); Hiroshi Shirota, Belmont, MA (US); Mark Spyvee, Hampstead, NH (US); Isao Tanaka, Tsukuba (JP); John (Yuan) Wang, Andover, MA (US); Satoshi Yamamoto, Moriya (JP); Naoki Yoneda, Tsukuba (JP)

(73) Assignee: EISAI Co., Ltd., Tokyo (JP)

( * ) Notice: Subject to any disclaimer, the term of this patent is extended or adjusted under 35 U.S.C. 154(b) by 0 days.

(21) Appl. No.: 12/839,873

(22) Filed: Jul. 20, 2010

(65) Prior Publication Data

US 2011/0144101 A1      Jun. 16, 2011

Related U.S. Application Data

(62) Division of application No. 10/507,067, filed as application No. PCT/US03/07377 on Mar. 7, 2003, now Pat. No. 7,799,827.

(60) Provisional application No. 60/362,883, filed on Mar. 8, 2002, provisional application No. 60/380,711, filed on May 14, 2002.

(51) Int. Cl.
*A61K 31/355* (2006.01)
*C07D 313/00* (2006.01)
(52) U.S. Cl. ........................ 514/450; 549/355
(58) Field of Classification Search .............. 514/450; 549/355
See application file for complete search history.

(56) References Cited

U.S. PATENT DOCUMENTS

| 5,674,892 | A | 10/1997 | Giese et al. |
| 5,728,726 | A | 3/1998 | Giese et al. |
| 5,795,910 | A | 8/1998 | Giese et al. |
| 6,265,603 | B1 | 7/2001 | Lewis et al. |
| 7,799,827 | B2 | 9/2010 | Boivin et al. |
| 7,915,306 | B2 | 3/2011 | Chiba et al. |
| 2009/0082313 | A1 | 3/2009 | Agoulnik |
| 2011/0046398 | A1 | 2/2011 | Fang |
| 2011/0237805 | A1 | 9/2011 | Boivin |

FOREIGN PATENT DOCUMENTS

| EP | 0606044 A1 | 11/1993 |
| GB | 2323845 A | 10/1998 |
| JP | 6228122 | 8/1994 |
| JP | 840893 | 2/1996 |
| JP | 10508024 | 8/1998 |
| JP | 2001294527 | 10/2001 |
| JP | 2004292314 | 10/2004 |
| JP | 2004292315 | 10/2004 |
| WO | WO9613259 | 5/1996 |
| WO | WO0038674 | 7/2000 |
| WO | WO0039314 | 7/2000 |
| WO | WO0136003 A2 | 5/2001 |
| WO | WO0248135 A1 | 6/2002 |
| WO | WO0248136A1 | 6/2002 |
| WO | WO03076424 A1 | 9/2003 |

OTHER PUBLICATIONS

International Search Report for PCT/US03/07377.
Agatsuma, et al., "Revised Structure and Stereochemistry of Hypothemycin", Chem.Pharm.Bull.; 41(2):373-375 1993.
Chen, et al., "Activation of p38 MAP kinase and ERK are required for ultraviolet-B induced c-fos gene expression gene expression in human keratinocytes", Oncogene, 18: 7649-7476, 1999.
Dombrowski, et al., "Production of a Family of Kinase-inhibiting Lactones from Fungal Dermentations", J. Antibiot, 52 (12): 1077-1085, 1999.
Ellestad, et al., "New Zearalenone Related Macrolides and Isocoumarins from an Unidentified Fungus", J. Org. Chem., 43(12):2339-2343, 1978.
Li, et al. "Rays and arrays: the transcriptional program in the response of human epidermal keratinocytes to UVB illumination", The FASEB Journal, Article 10.1096/fj.01-0172fje, published online Sep. 17, 201.
Kastelic, et al., "Induction of Rapid IL=Iβ mRNA Degradaton in THP-1 Cells Mediated Through the AU-Rich Region in the 3'UTR by a Radicocol Analogue", Cytokine 8(10): 751-761, 1996.
Matsuoka, et al., "Inhibition of HgCl2-induced mitogen-activated protein kinase activation by LL-Z1640-2 in CCRF-CEM cells", Eur. J. Pharmacol., 409(2): 155-158, 2000.

(Continued)

*Primary Examiner* — Shawquia Young
(74) *Attorney, Agent, or Firm* — Lathrop & Gage LLP; Brian C. Trinque

(57) ABSTRACT

The present invention provides methods for the use of compounds having formula (I) in the treatment of various disorders including inflammatory or autoimmune disorders, and disorders involving malignancy or increased angiogenesis, wherein $R_1$-$R_{11}$, t, X, Y, Z, and n are as defined herein.

32 Claims, No Drawings

OTHER PUBLICATIONS

Rawlins, et al., "Inhibition of endotoxin-induced TNF-α production in macrophases by 5Z-7 oxozeanol and other fungal resorcylic acid lactones", Int. J. Immunopharmacol., 21(12): 799-814, 1999.

Tak, et al., "NF-κB pathway in the treatment of inflammation and cancer", J. Clin.Investigation, 107(2), 135-142, 2001.

Takehana, et al., "A radicicol-Related Macrocyclic Nonaketide Compound, Antibiotic LL-Z1640-2, Inhibits the JNK/p38 Pathways in Signal-Specific Manner", Biochem. Biophys. Res. Commun., 257(1): 19-23, 1999.

Tatsuta, et al., "The First Total Synthesis of a Macrocyclic Antiprotozoan, LL-Z16040-2", Chem. Lett., vol. 2, 172-173, 2001.

Yamamoto, et al., "Therapeutic potential of inhibition of the NF-κB Pathway in the treatment of inflammation and cancer", J. Clin. Investigation, 107(2), 135-142, 2001.

Partial file history of related U.S. Appl. No. 10/657,910 (documents dating from May 6, 2009 through Sep. 14, 2009).

Japanese Office Action for Application No. 2003-574642, dated Jul. 15, 2009.

Partial file history of U.S. Appl. No. 10/657,910 (documents dating from Dec. 1, 2003 through Jan. 7, 2009).

MACROCYCLIC COMPOUNDS USEFUL AS PHARMACEUTICALS

PRIORITY CLAIM

This Application is a divisional of U.S. application Ser. No. 10/507,067, filed Nov. 10, 2004, which is a 35 U.S.C. §371 filing of International Application Number PCT/US03/07377, filed Mar. 7, 2003, which claims priority to U.S. Provisional Patent Application Nos. 60/362,883, filed Mar. 8, 2002, and 60/380,711, filed May 14, 2002, each of which is incorporated herein by reference in its entirety. The contents of any patents, patent applications, and references cited throughout this specification are hereby incorporated by reference in their entireties.

BACKGROUND OF THE INVENTION

F152 (LL-Z1640-2) (1) is a zearalenone-like macrolide, isolated from shake flask fermentation, crude extracts of which inhibited the ciliated protozoan *Tetrahymena pyriformis* (see, McGahren et al. *J. Org. Chem.* 1978, 43, 2339). It was reported that initial biological studies using this natural product failed to yield any particularly interesting activities.

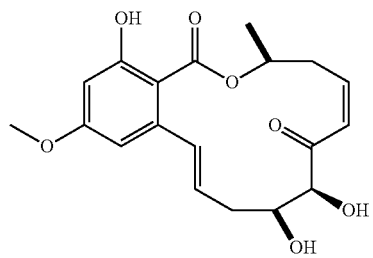

After initial isolation and reporting of this compound, several other groups explored the possibility of preparing additional derivatives and/or further exploring their biological activity. For example, scientists at Merck reported that F152 and certain isomers thereof inhibit the phosphorylating enzyme Map/Erk kinase (MEK) and thus are useful for the treatment of certain cancers and other diseases characterized by the formation of neoangiogenesis (see, GB 323 845). Other groups have also reported derivatives of F152 having activity as tyrosine kinase inhibitors, which are useful, for example, for the treatment of cancer and inflammatory disorders (see, EP 606 044; WO 00/38674; JP 8-40893; WO 96/13259; U.S. Pat. Nos. 5,728,726; 5,674,892; 5,795,910). Each of these groups, however, was only able to obtain F152 and derivatives thereof by fermentation techniques and by modifications to the natural product, respectively, and thus were limited in the number and types of derivatives that could be prepared and evaluated for biological activity. Additionally, although F152 and certain derivatives thereof have demonstrated potent in vitro activities, these compounds are biologically unstable (for example, they are susceptible to enone isomerization in mouse and human plasma), thereby limiting the development of these compounds as therapeutics for the treatment of humans or other animals.

Clearly, there remains a need to develop synthetic methodologies to access and examine the therapeutic effect of a variety of novel analogues of F152, particularly those that are inaccessible by making modifications to the natural product. It would also be of particular interest to develop novel compounds that exhibit a favorable therapeutic profile in vivo (e.g., are safe and effective, while retaining stability in biological media).

SUMMARY OF THE INVENTION

As discussed above, there remains a need for the development of novel analogues of F152 and the evaluation of their biological activity. The present invention provides novel compounds of general formula (I),

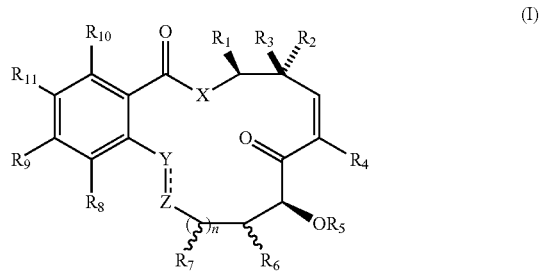

and pharmaceutical compositions thereof, as described generally and in subclasses herein, which compounds are useful as inhibitors of NF-κB activation, AP-1 activation and protein kinases (e.g., MEKK1, MEK1, VEGFr, PDGFr), exhibit antiangiogenic activity, and/or have an anti-anflammatory effect. Thus these compounds are useful, for example, for the treatment of various disorders including inflammatory or autoimmune disorders, and disorders involving malignancy or increased angiogenesis. The inventive compounds also find use in the prevention of restenosis of blood vessels subject to traumas such as angioplasty and stenting.

DESCRIPTION OF CERTAIN PREFERRED EMBODIMENTS OF THE INVENTION

In recognition of the need to access and further explore the biological activity of novel analogues of F152, and this class of macrocycles in general, the present invention provides novel macrocyclic compounds, as described in more detail herein, which demonstrate increased stability and are potent inhibitors of NF-κB activation, AP-1 activation and protein kinases (for example, MEKK, MEK1, PDGFr, VEGFr). Based on these mechanisms of action, the compounds inhibit the production of various pro-inflammatory and/or immunologic cytokines such as TNFα, IL-1, IL-6, IL-8, IL-2 etc, and also inhibit the production of various pro-inflammatory molecules under the regulation of NF-κB pathway such as prostaglandins produced from COX-2, ICAM-1 and MMP-1 and 3 etc. Also, the compounds have ability to inhibit cell proliferation under the regulation of AP-1 pathway through the inhibition of MEK1. In addition, the compounds have ability to inhibit angiogenesis mainly based on the inhibitory activities on VEGFr and PDGFr kinases. Thus, the compounds of the invention, and pharmaceutical compositions thereof, are useful as anti-inflammatory and/or immunosuppressive agents for the treatment of various inflammatory diseases, and abnormal cell proliferation or as antiangiogenesis agents for the treatment of cancer. In certain embodiments, the compounds of the present invention can be used for the treatment of diseases and disorders including, but not limited to sepsis, rheumatoid arthritis, psoriatic arthritis, osteoarthritis, inflammatory bowel disease (Crohn's disease and ulcerative colitis), multiple sclerosis, atopic dermatitis, psoriasis, asthma, osteoporosis, allergic rhinitis, ocular inflammation, hepatitis, autoimmune disorders, systemic lupus erthematosus, allograft rejection/graft versus host disease, diabetes, AIDS, solid tumor cancers, leukemia, lymphomas, non-hodgkin's B-cell lymphomas, chronical lymphocytic leukemia (CLL), multiple myeloma, eczema, urticaria, myasthenia gravis, idiopathic thrombocytopenia purpura, cardiovascular disease (e.g., myocardial infarction, atherosclerosis), hepatitis, glomerulonephropathy, productive nephritis, adenovirus, diseases/disorders of the central nervous system (e.g., stroke, Alzheimer's disease, epilepsy) and for the treatment of the symptoms of malaria, to name a few. The inventive compounds also find use in the prevention of restenosis of blood vessels subject to traumas such as angioplasty and stenting.

In addition, it has been shown that photoaging of undamaged skin due to UVB irradiation exposure is inhibited by administering an agent that inhibits one or both of the transcription factors AP-1 and NF-κB to the skin prior to such exposure (See, for example, U.S. Pat. No. 5,837,224). Therefore, the inventive compounds, and pharmaceutical compositions thereof, are useful in the treatment of photoaging-related disorders/conditions.

1) General Description of Compounds of the Invention

In certain embodiments, the compounds of the invention include compounds of the general formula (I) as further defined below:

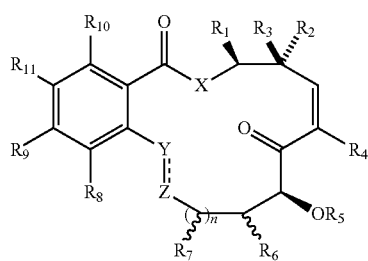

(I)

wherein $R_1$ is hydrogen, aliphatic, heteroaliphatic, alicyclic, heteroalicyclic, aryl or heteroaryl;

$R_2$ and $R_3$ are each independently hydrogen, halogen, hydroxyl, protected hydroxyl, or an aliphatic, heteroaliphatic, alicyclic, heteroalicyclic, aryl or heteroaryl moiety; or $R_1$ and $R_2$, when taken together, may form a substituted or unsubstituted, saturated or unsaturated cyclic ring of 3 to 8 carbon atoms; or $R_1$ and $R_3$, when taken together, may form a substituted or unsubstituted, saturated or unsaturated cyclic ring of 3 to 8 carbon atoms;

$R_4$ is hydrogen or halogen;

$R_5$ is hydrogen, an oxygen protecting group or a prodrug;

$R_6$ is hydrogen, hydroxyl, or protected hydroxyl;

n is 0-2;

$R_7$, for each occurrence, is independently hydrogen, hydroxyl, or protected hydroxyl;

$R_1$ is hydrogen, halogen, hydroxyl, protected hydroxyl, alkyloxy, or an aliphatic moiety optionally substituted with hydroxyl, protected hydroxyl, $SR_{12}$, or $NR_{12}R_{13}$;

$R_9$ is hydrogen, halogen, hydroxyl, protected hydroxyl, $OR_{12}$, $SR_{12}$, $NR_{12}R_{13}$, $-X_1(CH_2)_pX_2-R_{14}$, or is lower alkyl optionally substituted with hydroxyl, protected hydroxyl, halogen, amino, protected amino, or $-X_1(CH_2)_pX_2-R_{14}$;

wherein $R_{12}$ and $R_{13}$ are, independently for each occurrence, hydrogen, aliphatic, heteroaliphatic, alicyclic, heteroalicyclic, aryl or heteroaryl; or a protecting group, or $R_{12}$ and $R_{13}$, taken together may form a saturated or unsaturated cyclic ring containing 1 to 4 carbon atoms and 1 to 3 nitrogen or oxygen atoms, and each of $R_{12}$ and $R_{13}$ are optionally further substituted with one or more occurrences of hydroxyl, protected hydroxyl, alkyloxy, amino, protected amino, alkylamino, aminoalkyl, or halogen, wherein $X_1$ and $X_2$ are each independently absent, or are oxygen, NH, or —N(alkyl), or wherein $X_2$—$R_{14}$ together are $N_3$ or are a saturated or unsaturated heterocyclic moiety, p is 2-10, and $R_{14}$ is hydrogen, or an aryl, heteroaryl, alkylaryl, or alkylheteroaryl moiety, or is $-(C=O)NHR_{15}-(C=O)OR_{15}$, or $-(C=O)R_{15}$, wherein each occurrence of $R_{15}$ is independently hydrogen, aliphatic, heteroaliphatic, alicyclic, heteroalicyclic, aryl or heteroaryl; or $R_{14}$ is $-SO_2(R_{16})$, wherein $R_{16}$ is an aliphatic moiety, wherein one or more of $R_{14}$, $R_{15}$, or $R_{16}$ are optionally substituted with one or more occurrences of hydroxyl, protected hydroxyl, alkyloxy, amino, protected amino, alkylamino, aminoalkyl, or halogen; or $R_8$ and $R_9$ may, when taken together, form a saturated or unsaturated cyclic ring containing 1 to 4 carbon atoms and 1 to 3 nitrogen or oxygen atoms and is optionally substituted with hydroxyl, protected hydroxyl, alkyloxy, amino, protected amino, alkylamino, aminoalkyl, or halogen;

$R_{10}$ is hydrogen, hydroxyl, protected hydroxyl, amino, or protected amino;

$R_{11}$ is hydrogen, hydroxyl or protected hydroxyl;

X is absent or is O, NH, N-alkyl, $CH_2$ or S;

Y is $CHR_{17}$, O, C=O, $CR_{17}$ or $NR_{17}$; and Z is $CHR_{18}$, O, C=O, $CR_{18}$ or $NR_{18}$, wherein each occurrence of $R_{17}$ and $R_{18}$ is independently hydrogen or aliphatic, or $R_{17}$ and $R_{18}$ taken together is —O—, —$CH_2$— or —$NR_{19}$—, wherein $R_{19}$ is hydrogen or lower alkyl, and Y and Z may be connected by a single or double bond; and pharmaceutically acceptable derivatives thereof.

In certain embodiments of compounds described directly above and compounds as described in certain classes and subclasses herein, the following groups do not occur simultaneously as defined:

X is oxygen, $R_1$ is methyl with S-configuration, $R_2$ and $R_3$ are each hydrogen, $R_4$ is hydrogen, $R_5$ is hydrogen, lower alkyl or lower alkanoyl, $R_6$ is OR', where R' is hydrogen, lower alkyl or lower alkanoyl with S-configuration, $R_7$ is hydrogen, Y and Z together represent —$CHR_{17}$—$CHR_{18}$— or —$CR_{17}$=$CR_{18}$—, wherein $R_{17}$ and $R_{18}$ are independently hydrogen, or when Y and Z are —$CHR_{17}$—$CHR_{18}$, $R_{17}$ and $R_{18}$ taken together are —O—;

$R_8$ is hydrogen or OR', where R' is hydrogen, lower alkyl or lower alkanoyl, $R_9$ is OR', where R' is hydrogen, lower alkyl or lower alkanoyl, $R_{10}$ is OR", where R" is hydrogen, lower alkyl or lower alkanoyl; and $R^{11}$ is hydrogen.

In certain other embodiments, compounds of formula (I) are defined as follows:

$R_1$ is hydrogen, straight or branched lower alkyl, straight or branched lower heteroalkyl, or aryl, wherein the alkyl, heteroalkyl, and aryl groups may optionally be substituted with one or more occurrences of halogen, hydroxyl or protected hydroxyl;

$R_2$ and $R_3$ are each independently hydrogen, halogen, hydroxyl, protected hydroxyl, straight or branched lower alkyl, straight or branched lower heteroalkyl, or aryl, wherein the alkyl, heteroalkyl, and aryl groups may optionally be substituted with one or more occurrences of halogen, hydroxyl or protected hydroxyl; or $R_1$ and $R_2$, when taken together, may form a saturated or unsaturated cyclic ring of 3 to 8 carbon atoms, optionally substituted with one or more occurrences of halogen; or $R_1$ and $R_3$, when taken together, may form a saturated or unsaturated cyclic ring of 3 to 8 carbon atoms, optionally substituted with one or more occurrences of halogen;

$R_4$ is hydrogen or halogen;

$R_5$ is hydrogen or a protecting group;

$R_6$ is hydrogen, hydroxyl, or protected hydroxyl;

n is 0-2;

$R_7$, for each occurrence, is independently hydrogen, hydroxyl, or protected hydroxyl;

$R_8$ is hydrogen, halogen, hydroxyl, protected hydroxyl, alkyloxy, or lower alkyl optionally substituted with hydroxyl, protected hydroxyl, $SR_{12}$, or $NR_{12}R_{13}$;

$R_9$ is hydrogen, halogen, hydroxyl, protected hydroxyl, $OR_{12}$, $SR_{12}$, $NR_{12}R_{13}$, $-X_1(CH_2)_pX_2-R_{14}$, or is lower alkyl optionally substituted with hydroxyl, protected hydroxyl, halogen, amino, protected amino, or $-X_1(CH_2)_pX_2-R_{14}$;

wherein $R_{12}$ and $R_{13}$ are, independently for each occurrence, hydrogen, lower alkyl, aryl, heteroaryl, alkylaryl, or alkylheteroaryl, or a protecting group, or $R_{12}$ and $R_{13}$, taken together may form a saturated or unsaturated cyclic ring containing 1 to 4 carbon atoms and 1 to 3 nitrogen or oxygen atoms, and each of $R_{12}$ and $R_{13}$ are optionally further substituted with one or more occurrences of hydroxyl, protected hydroxyl, alkyloxy, amino, protected amino, alkylamino, aminoalkyl, or halogen, wherein $X_1$ and $X_2$ are each independently absent, or are oxygen, NH, or $-N(alkyl)$, or wherein $X_2-R_{14}$ together are $N_3$ or are a saturated or unsaturated heterocyclic moiety, p is 2-10, and $R_{14}$ is hydrogen, or an aryl, heteroaryl, alkylaryl, or alkylheteroaryl moiety, or is $-(C=O)NHR_{15}-(C=O)OR_{15}$, or $-(C=O)R_{15}$, wherein each occurrence of $R_{15}$ is independently hydrogen, alkyl, heteroalkyl, aryl, heteroaryl, alkylaryl, or alkylheteroaryl, or $R_{14}$ is $-SO_2(R_{16})$, wherein $R_{16}$ is an alkyl moiety, wherein one or more of $R_{14}$, $R_{15}$, or $R_{16}$ are optionally substituted with one or more occurrences of hydroxyl, protected hydroxyl, alkyloxy, amino, protected amino, alkylamino, aminoalkyl, or halogen; or $R_8$ and $R_9$ may, when taken together, form a saturated or unsaturated cyclic ring containing 1 to 4 carbon atoms and 1 to 3 nitrogen or oxygen atoms and is optionally substituted with hydroxyl, protected hydroxyl, alkyloxy, amino, protected amino, alkylamino, aminoalkyl, or halogen;

$R_{10}$ is hydrogen, hydroxyl, protected hydroxyl, amino, or protected amino;

$R_{11}$ is hydrogen, hydroxyl or protected hydroxyl;

X is absent or is O, NH, N-alkyl, $CH_2$ or S;

Y is $CHR_{17}$, O, $C=O$, $CR_{17}$ or $NR_{17}$; and Z is $CHR_{18}$, O, $C=O$, $CR_{18}$ or $NR_{18}$, wherein each occurrence of $R_{17}$ and $R_{18}$ is independently hydrogen or lower alkyl, or $R_{17}$ and $R_{18}$ taken together is $-O-$, $-CH_2-$ or $-NR_{19}-$, wherein $R_{19}$ is hydrogen or lower alkyl, and Y and Z may be connected by a single or double bond; and pharmaceutically acceptable derivatives thereof.

In certain other embodiments, compounds of formula (I) are defined as follows:

$R_1$ is hydrogen, straight or branched lower alkyl, straight or branched lower heteroalkyl, or aryl, wherein the alkyl, heteroalkyl, and aryl groups may optionally be substituted with one or more occurrences of halogen, hydroxyl or protected hydroxyl;

$R_2$ and $R_3$ are each independently hydrogen, halogen, hydroxyl, protected hydroxyl, straight or branched lower alkyl, straight or branched lower heteroalkyl, or aryl, wherein the alkyl, heteroalkyl, and aryl groups may optionally be substituted with one or more occurrences of halogen, hydroxyl or protected hydroxyl; or $R_1$ and $R_2$, when taken together, may form a saturated or unsaturated cyclic ring of 3 to 8 carbon atoms, optionally substituted with one or more occurrences of halogen;

$R_4$ is hydrogen or halogen;

$R_5$ is hydrogen or a protecting group;

$R_6$ is hydrogen, hydroxyl, or protected hydroxyl;

n is 0-2;

$R_7$, for each occurrence, is independently hydrogen, hydroxyl, or protected hydroxyl;

$R_8$ is hydrogen, halogen, hydroxyl, protected hydroxyl, alkyloxy, or lower alkyl optionally substituted with hydroxyl or protected hydroxyl;

$R_9$ is hydrogen, halogen, hydroxyl, protected hydroxyl, $OR_{12}$, $NR_{12}R_{13}$, $-X_1(CH_2)_pX_2-R_{14}$, or is lower alkyl optionally substituted with hydroxyl, protected hydroxyl, halogen, amino, protected amino, or $-X_1(CH_2)_pX_2-R_{14}$;

wherein $R_{12}$ and $R_{13}$ are, independently for each occurrence, hydrogen, lower alkyl, aryl, heteroaryl, alkylaryl, or alkylheteroaryl, or a protecting group, or $R_{12}$ and $R_{13}$, taken together may form a saturated or unsaturated cyclic ring containing 1 to 4 carbon atoms and 1 to 3 nitrogen or oxygen atoms, and each of $R_{12}$ and $R_{13}$ are optionally further substituted with one or more occurrences of hydroxyl, protected hydroxyl, alkyloxy, amino, protected amino, alkylamino, aminoalkyl, or halogen, wherein $X_1$ and $X_2$ are each independently absent, or are oxygen, NH, or $-N(alkyl)$, or wherein $X_2-R_{14}$ together are $N_3$ or are a saturated or unsaturated heterocyclic moiety, p is 2-10, and $R_{14}$ is hydrogen, or an aryl, heteroaryl, alkylaryl, or alkylheteroaryl moiety, or is $-(C=O)NHR_{15}-(C=O)OR_{15}$, or $-(C=O)R_{15}$, wherein each occurrence of $R_{15}$ is independently hydrogen, alkyl, heteroalkyl, aryl, heteroaryl, alkylaryl, or alkylheteroaryl, or $R_{14}$ is $-SO_2(R_{16})$, wherein $R_{16}$ is an alkyl moiety, wherein one or more of $R_{14}$, $R_{15}$, or $R_{16}$ are optionally substituted with one or more occurrences of hydroxyl, protected hydroxyl, alkyloxy, amino, protected amino, alkylamino, aminoalkyl, or halogen; or $R_8$ and $R_9$ may, when taken together, form a saturated or unsaturated cyclic ring containing 1 to 4 carbon atoms and 1 to 3 nitrogen or oxygen atoms and is optionally substituted with hydroxyl, protected hydroxyl, alkyloxy, amino, protected amino, alkylamino, aminoalkyl, or halogen;

$R_{10}$ is hydrogen, hydroxyl, protected hydroxyl, amino, or a protected amino group;

$R_{11}$ is hydrogen, hydroxyl, or protected hydroxyl;

X is absent or is O, NH, or $CH_2$;

Y is —CHR$_{17}$, O, C═O, CR$_{17}$ or NR$_{17}$, and Z is CHR$_{15}$, O, C═O, CR$_{18}$ or NR$_{18}$, wherein each occurrence of R$_{17}$ and R$_{18}$ is independently hydrogen or lower alkyl; and pharmaceutically acceptable derivatives thereof.

In certain embodiments, the present invention defines certain classes of compounds which are of special interest. For example, one class of compounds of special interest includes those compounds having the structure of formula (I) in which X is O, and n is 1 and the compound has the structure:

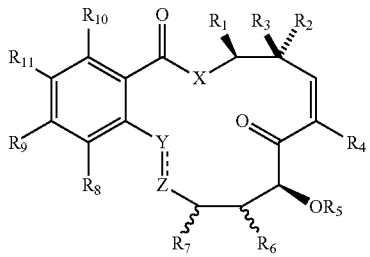

wherein R$_1$-R$_{11}$, Y and Z are as previously defined.

Another class of compounds of special interest includes compounds having the structure of formula (I) in which R$_4$ is halogen (Hal), and the compound has the structure:

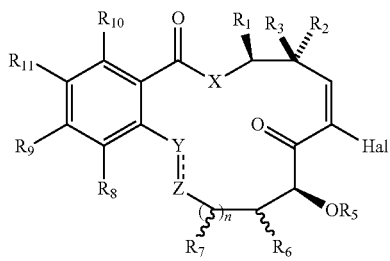

wherein R$_1$-R$_3$, R$_5$-R$_{11}$, X, Y, Z and n are as previously defined, and wherein Hal is a halogen selected from fluorine, bromine, chlorine and iodine.

Another class of compounds of special interest includes compounds having the structure of formula (I) in which Y and Z together represent —CH═CH—, and the compound has the structure:

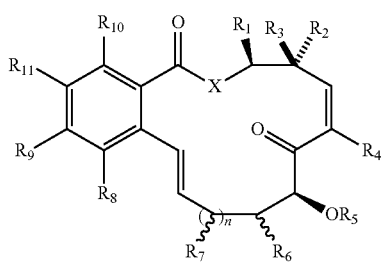

wherein R$_1$-R$_{11}$, X and n are as previously defined.

Another class of compounds of special interest includes compounds having the structure of formula (I) in which R$_1$ and R$_2$ are each methyl, and R$_3$ is hydrogen and the compound has the structure:

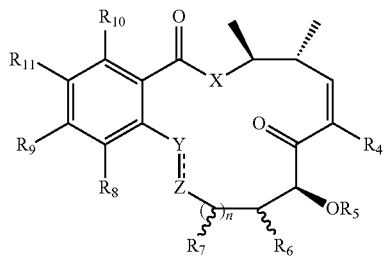

wherein R$_4$-R$_{11}$, n, X, Y and Z are as previously defined.

Another class of compounds of special interest includes compounds having the structure of formula (I) in which R$_9$ is NR$_{12}$R$_{13}$, and the compound has the structure:

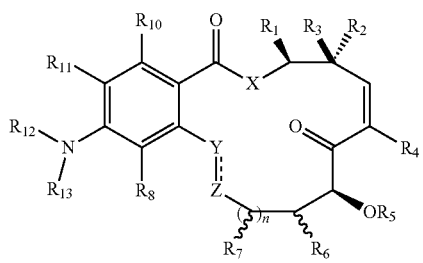

wherein R$_1$-R$_{13}$, n, X, Y and Z are as previously defined, and R$_{13}$ and R$_8$ may additionally, when taken together, form a saturated or unsaturated cyclic ring containing 1 to 4 carbon atoms and 1 to 3 nitrogen or oxygen atoms and is optionally substituted with hydroxyl, protected hydroxyl, alkyloxy, amino, protected amino, alkylamino, aminoalkyl, and halogen.

Another class of compounds of special interest includes compounds having the structure of formula (I) in which R$_9$ is OR$_{12}$, and the compound has the structure:

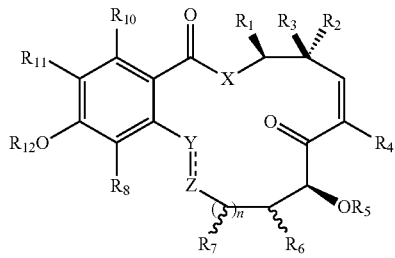

wherein R$_1$-R$_{12}$, n, X, Y and Z are as previously defined.

Another class of compounds of special interest includes compounds having the structure of formula (I) in which R$_9$ is —X$_1$(CH$_2$)$_p$X$_2$R$_{14}$, and the compound has the structure:

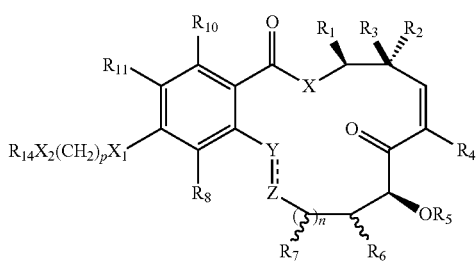

wherein $R_1$-$R_{11}$, $R_{14}$, X, Y, Z, n, $X_1$, $X_2$ and p are as defined above.

The following structures illustrate several exemplary types of compounds of these classes. Additional compounds are described in the Exemplification herein. Other compounds of the invention will be readily apparent to the reader:

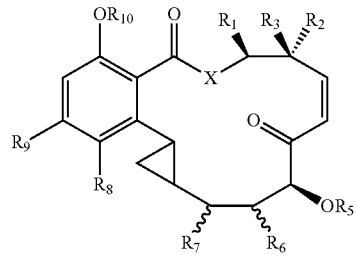

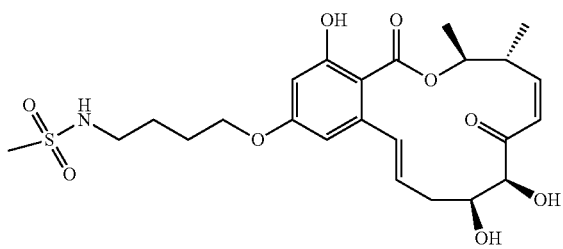

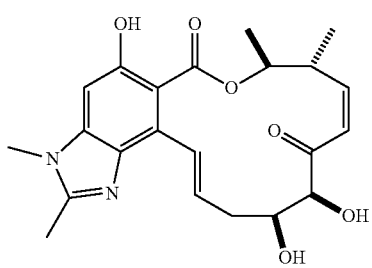

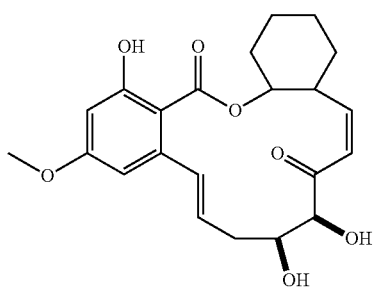

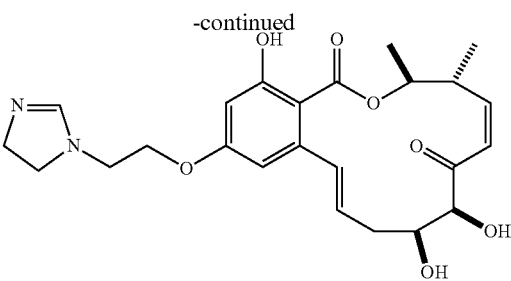

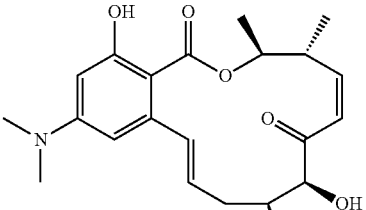

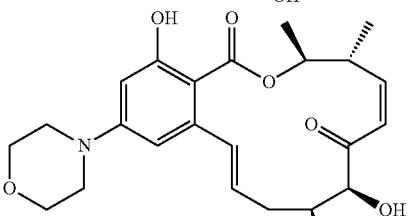

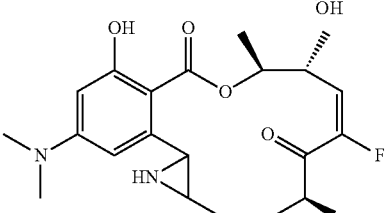

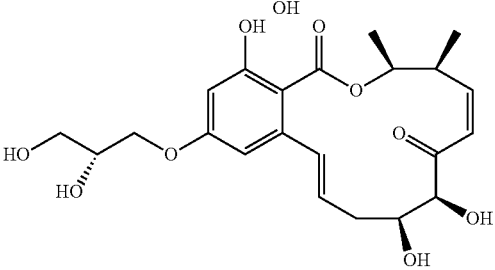

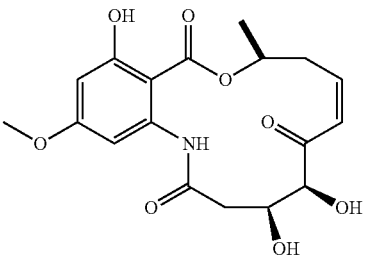

A number of important subclasses of each of the foregoing classes deserve separate mention; these subclasses include subclasses of the foregoing classes in which:
  i) $R_1$ is hydrogen, aryl or lower alkyl;
  ii) $R_1$ is hydrogen, phenyl, methyl or ethyl;
  iii) $R_1$ is methyl;
  iv) $R_2$ is hydrogen, halogen or lower alkyl;

v) $R_2$ is hydrogen, F, methyl or ethyl;
vi) $R_2$ is methyl;
vii) $R_3$ is hydrogen;
viii) $R_1$ and $R_2$ are each methyl and $R_3$ is hydrogen;
ix) $R_1$ and $R_2$, taken together, form a 5- to 6-membered cycloalkyl moiety;
x) $R_1$ and $R_3$, taken together, form a 5- to 6-membered cycloalkyl moiety;
xi) $R_4$ is a halogen selected from fluorine, chlorine, bromine, and iodine;
xii) $R_4$ is a hydrogen;
xiii) $R_4$ is fluorine;
xiv) $R_5$ is a protecting group, hydrogen or a prodrug moiety;
xv) $R_5$ is an oxygen protecting group;
xvi) $R_5$ is an oxygen protecting group selected from methyl ether, substituted methyl ether, substituted ethyl ether, substituted benzyl ether, silyl ether, ester, carbonate, cyclic acetal and ketal;
xvii) $R_6$ is hydrogen, hydroxyl or protected hydroxyl;
xviii) $R_6$ is protected hydroxyl and the protecting group is an oxygen protecting group;
xix) $R_6$ is protected hydroxyl and the protecting group is an oxygen protecting group selected from methyl ether, substituted methyl ether, substituted ethyl ether, substituted benzyl ether, silyl ether, ester, carbonate, cyclic acetal and ketal;
xx) $R_6$ is protected hydroxyl and the protecting group is a prodrug moiety;
xxi) n is 1;
xxii) $R_7$ is hydrogen;
xxiii) $R_7$ is hydroxyl;
xxiv) $R_7$ is protected hydroxyl and the protecting group is an oxygen protecting group;
xxv) $R_7$ is a protected hydroxyl and the protecting group is an oxygen protecting group selected from methyl ether, substituted methyl ether, substituted ethyl ether, substituted benzyl ether, silyl ether, ester, carbonate, cyclic acetal and ketal;
xxvi) $R_7$ is protected hydroxyl and the protecting group is a prodrug moiety;
xxvii) Y and Z together represent —CH═CH—;
xxviii) Y and Z together represent trans —CH═CH—;
xxix) Y and Z together represent —$CR_{17}$═$CR_{18}$—;
xxx) Y and Z together represent trans $CR_{17}$═$CR_{18}$—;
xxxi) Y and Z together are an epoxide;
xxxii) Y and Z together are an aziridine;
xxxiii) Y and Z together are cyclopropyl;
xxxiv) Y and Z together are —$CH_2$—$CH_2$—;
xxxv) Z is O;
xxxvi) Y is O;
xxxvii) Z is C═O and Y is $CHR_{17}$;
xxxviii) Z is $NR_{18}$ and Y is $CHR_{17}$;
xxxix) Z is $CHR_{18}$ and Y is C═O;
xl) Z is $CHR_{18}$ and Y is $NR_{17}$;
xli) X is O or NH;
xlii) $R_8$ is hydrogen;
xliii) $R_8$ is halogen, hydroxyl, protected hydroxyl, alkyloxy, or lower alkyl optionally substituted when one or more hydroxyl or protected hydroxyl groups;
xliv) $R_9$ is hydrogen;
xlv) $R_9$ is $OR_{12}$, wherein $R_{12}$ is methyl, ethyl, propyl, isopropyl, butyl, —$CH_2COOMe$, Bn, PMB (MPM), 3,4-ClBn, or $R_9$ is

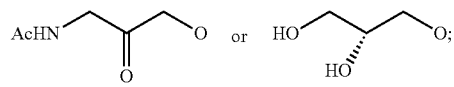

xlvi) $R_9$ is $NR_{12}R_{13}$, wherein $R_{12}$ is methyl, ethyl, propyl, isopropyl, or butyl, optionally substituted with one or more occurrences of hydroxyl or protected hydroxyl, and $R_{13}$ is hydrogen or lower alkyl, or $NR_{12}R^{13}$ together represents a 5- or 6-membered heterocyclic moiety;

xlvii) $R_9$ is $O(CH_2)_pX_2R_{14}$, wherein $X_2R_{14}$ together represent $N_3$, $NMe_2$, NHAc, $NHSO_2Me$, NHCONHMe, NHCONHPh, morpholine, imidazole, aminopyridine, or any one of:

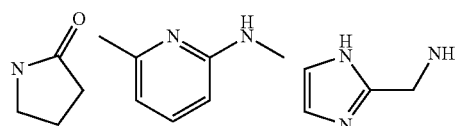

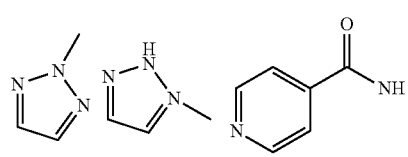

xlviii) $R_{10}$ is hydroxyl or protected hydroxyl;
xlix) $R_{10}$ is hydroxyl; and/or
l) $R_{11}$ is hydrogen.

As the reader will appreciate, compounds of particular interest include, among others, those which share the attributes of one or more of the foregoing subclasses. Some of those subclasses are illustrated by the following sorts of compounds:

I) Compounds of the Formula (and Pharmaceutically Acceptable Derivatives Thereof):

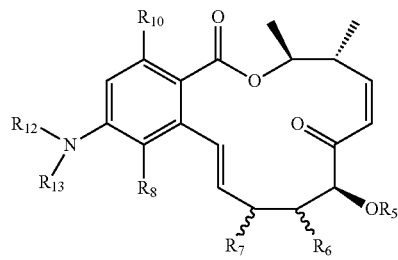

wherein $R_5$-$R_8$, $R_{10}$-$R_{13}$ are as defined above and in subclasses herein.

II) Compounds of the Formula (and Pharmaceutically Acceptable Derivatives Thereof):

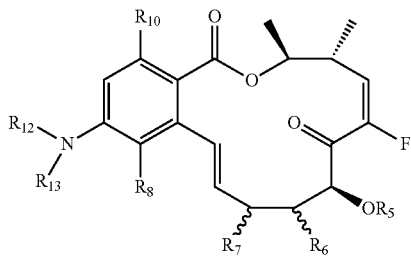

wherein $R_5$-$R_8$, $R_{10}$-$R_{13}$ are as defined above and in subclasses herein.

III) Compounds of the Formula (and Pharmaceutically Acceptable Derivatives Thereof):

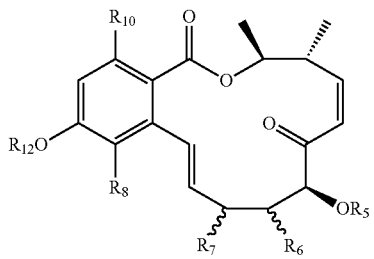

wherein $R_5$-$R_8$, $R_{10}$, and $R_{12}$ are as defined above and in subclasses herein.

IV) Compounds of the Formula (and Pharmaceutically Acceptable Derivatives Thereof):

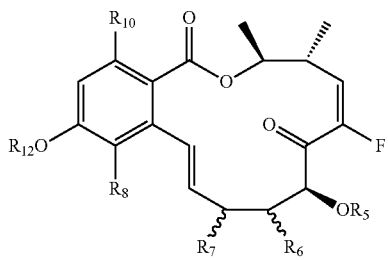

wherein $R_5$-$R_8$, $R_{10}$ and $R_{12}$ are as defined above and in subclasses herein.

V) Compounds of the Formula (and Pharmaceutically Acceptable Derivatives Thereof):

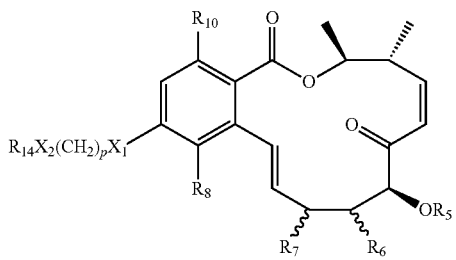

wherein $R_5$-$R_8$, $R_{10}$, $R_{14}$, $X_1$, $X_2$ and p are as defined above and in subclasses herein.

VI) Compounds of the Formula (and Pharmaceutically Acceptable Derivatives Thereof):

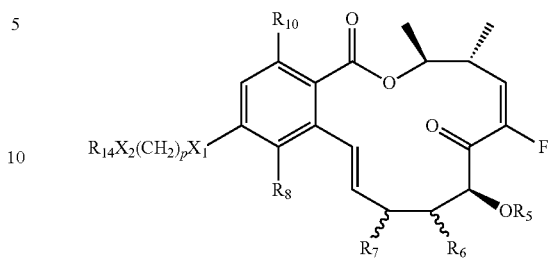

wherein $R_5$-$R_8$, $R_{10}$, $R_{14}$, $X_1$, $X_2$ and p are as defined above and in subclasses herein.

It will also be appreciated that for each of the subgroups I-VI described above, a variety of other subclasses are of special interest, including, but not limited to those classes described above 0-1) and classes, subclasses and species of compounds described above and in the examples herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Compounds and Definitions

As discussed above, this invention provides novel compounds with a range of biological properties. Compounds of this invention have biological activities relevant for the treatment of inflammatory and immune disorders, photoaging and cancer. In certain embodiments, the compounds of the invention are useful for the treatment of rheumatoid arthritis, psoriasis, Multiple sclerosis, and asthma. In certain other embodiments, the inventive compounds also find use in the prevention of restenosis of blood vessels subject to traumas such as angioplasty and stenting.

Compounds of this invention include those specifically set forth above and described herein, and are illustrated in part by the various classes, subgenera and species disclosed elsewhere herein.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of inflammatory and proliferative disorders, including, but not limited to rheumatoid arthritis, psoriasis, asthma and cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. It will also be appreciated that aryl and heteroaryl moieties, as defined herein may be attached via an aliphatic, alicyclic, heteroaliphatic, heteroalicyclic, alkyl or heteroalkyl moiety and thus also include -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, -(heteroaliphatic)heteroaryl, -(alkyl) aryl, -(heteroalkyl)aryl, -(heteroalkyl)aryl, and -(heteroalkyl) heteroaryl" are interchangeable. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR—(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroalicyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl;

alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR—(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substitutents described above and herein may be substituted or unsubstituted. Additional examples or generally applicable substituents are illustrated by the specific embodiments shown in the Examples, which are described herein.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

3) Synthetic Methodology

As described above, the present invention provides novel macrocycles having formula (I) a described above and in certain classes and subclasses herein. An overview of an exemplary synthesis of the inventive compounds is provided below, as detailed in Schemes 1-7, and in the Exemplification herein. It will be appreciated that the methods as described herein can be applied to each of the compounds as disclosed herein and equivalents thereof. Additionally, the reagents and starting materials are well known to those skilled in the art. Although the following schemes describe certain exemplary compounds, it will be appreciated that the use of alternate starting materials will yield other analogs of the invention. For example, compounds are described below where X is O; however, it will be appreciated that alternate starting materials and/or intermediates can be utilized to generate compounds where X is NH, N-alkyl, CH$_2$, etc.

In general, compounds as provided herein especially modification where Y and Z together as CH=CH or CH$_2$CH$_2$, are prepared from assembly of these three segments in two different orders depending on position of modifications on the ring, as depicted below.

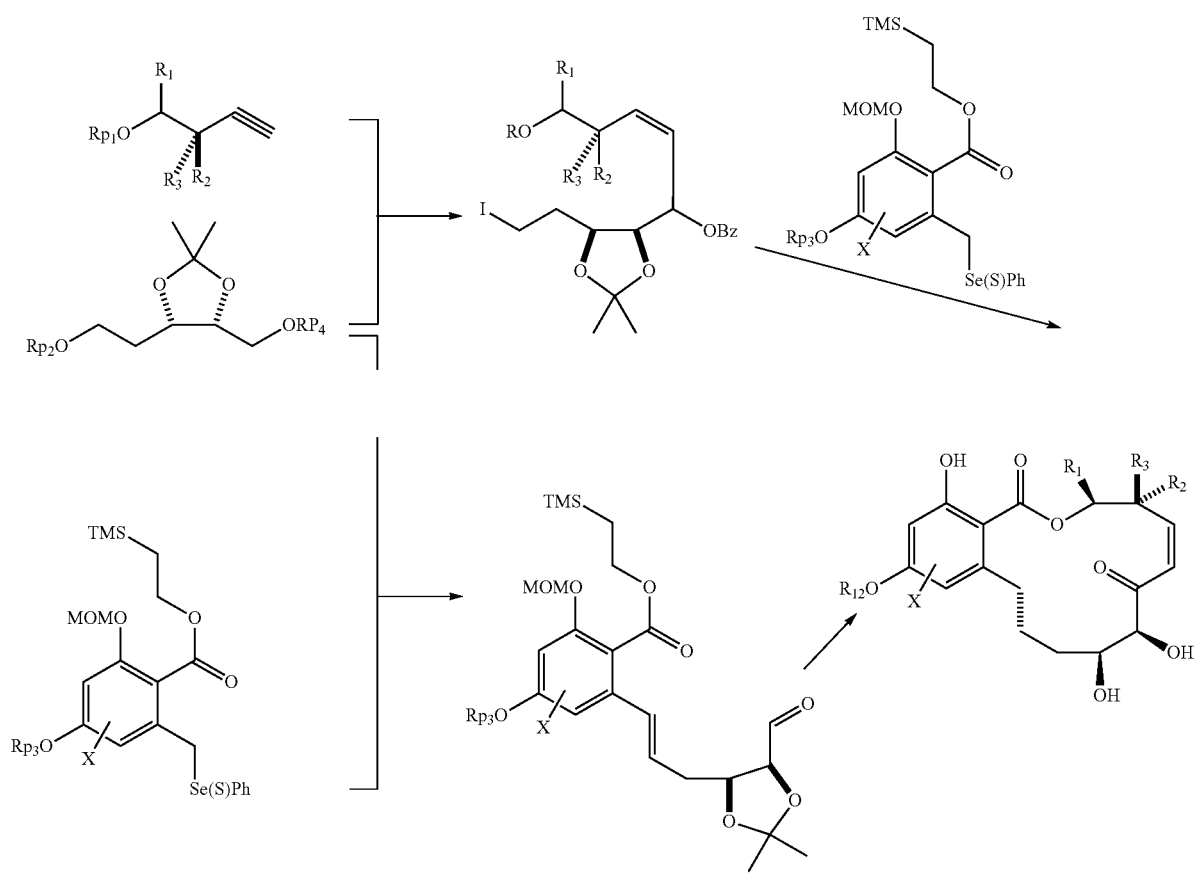

For $R_4$ modifications, a third route was use to incorporate $R_4$ as depicted below:

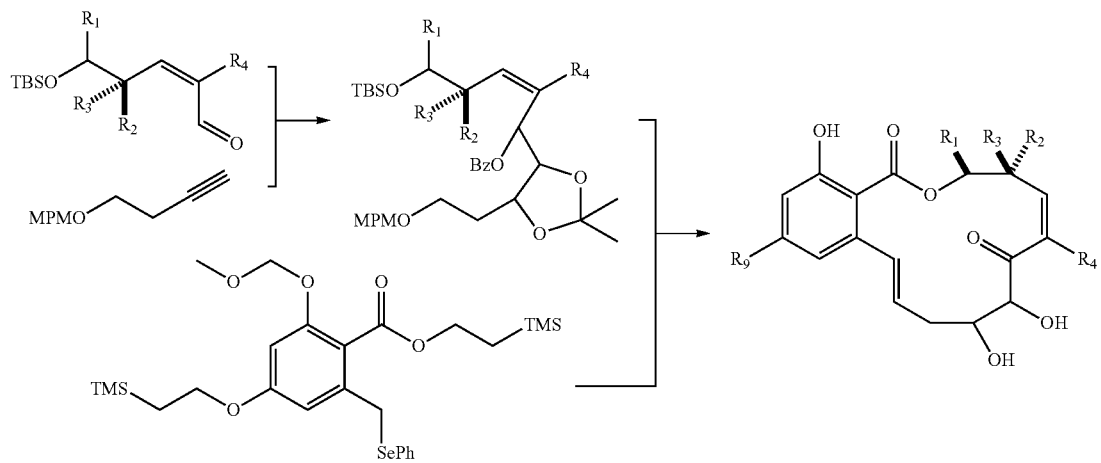

For compounds with Y and Z are heteroatom such N, O or CO, a different set of reaction condition was used to form these bonds in place of a C—C bond formation. Certain analogs were prepared using variation of these methods shown above.

For $R_9$ analogs, compounds as provided herein, are prepared from a general advance intermediate in additional to the general methods described above, as depicted below (2):

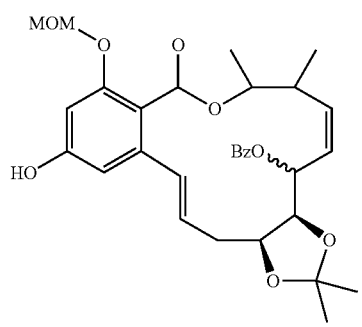
(2)

In certain embodiments, this general advance intermediate can be synthesized from two components, an aromatic component, the synthesis of which is depicted in Scheme 1 and is described in more detail in examples herein, and a protected diol component, the synthesis of which is depicted in Scheme 2 and is described in more detail in examples herein. As depicted in Scheme 3, and as described in more detail in examples herein, these two components are coupled, and subsequent reduction to generate the double bond occurs. Finally, macrocyclization is effected to generate the macrolactone intermediate.

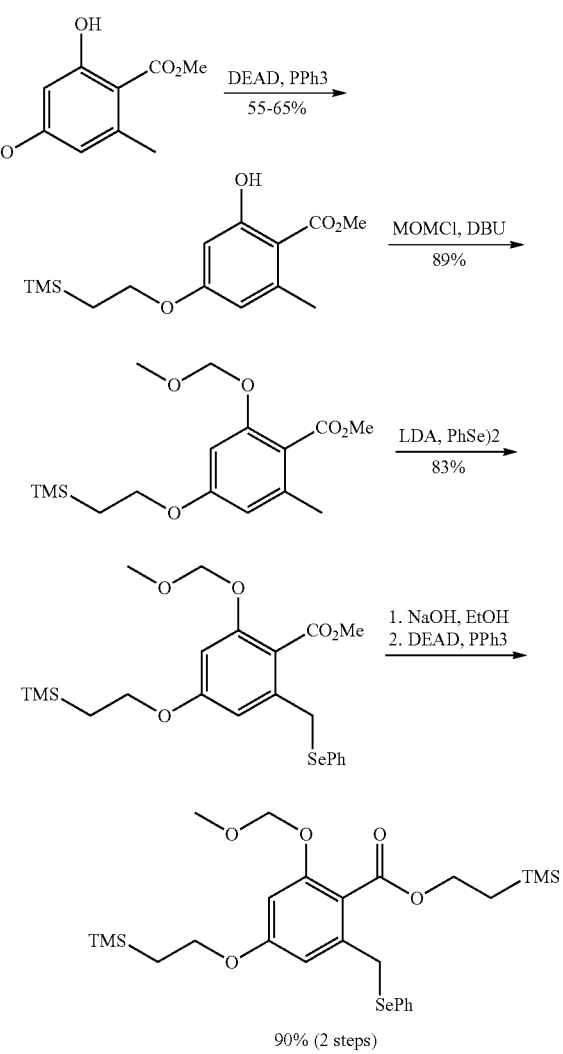

Scheme 1

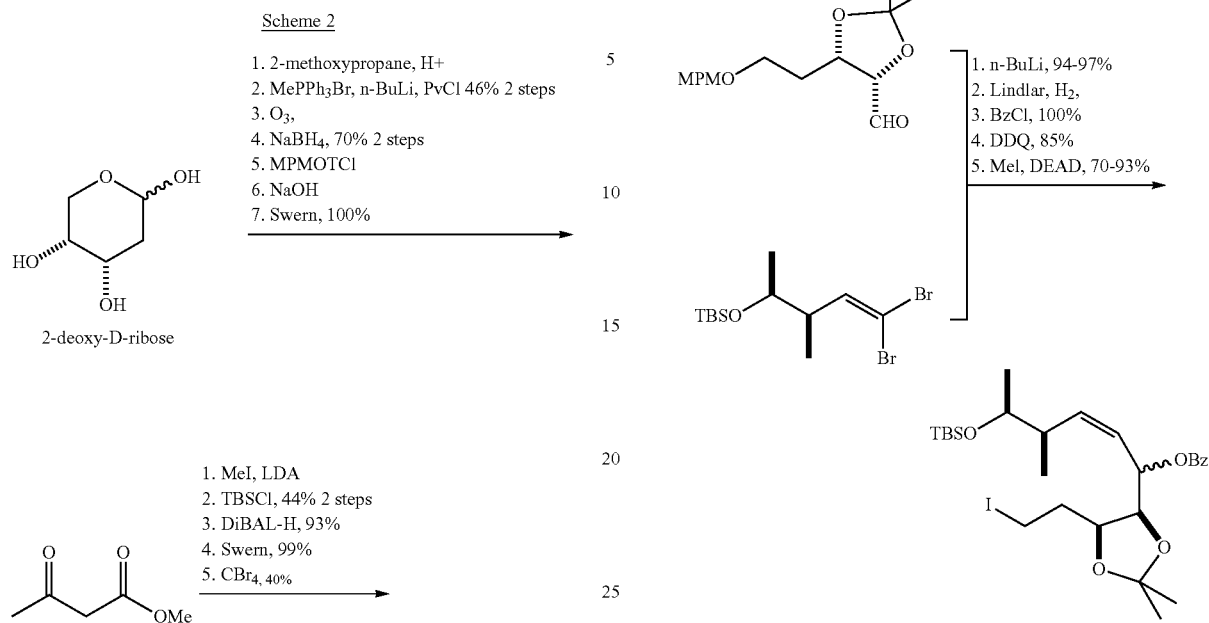

As depicted in Scheme 4, and as described in the examples herein, an alternate route to the protected diol intermediate provides facile access to compounds where $R_4$ is halogen. Coupling of this intermediate with the aromatic component described above and herein, provides additional structures where $R_4$ is halogen, or, as depicted, F.

Scheme 4

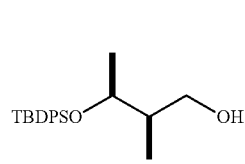
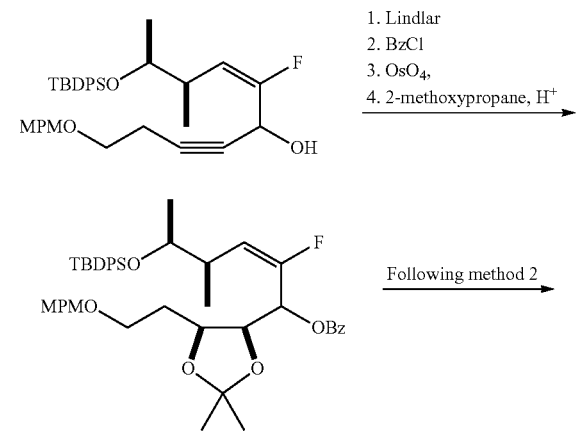
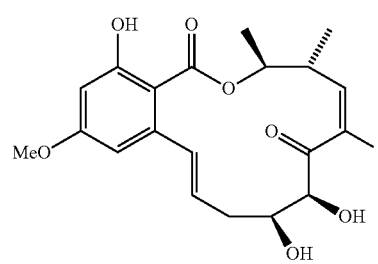

Scheme 5

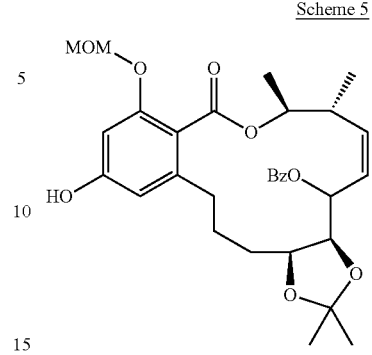
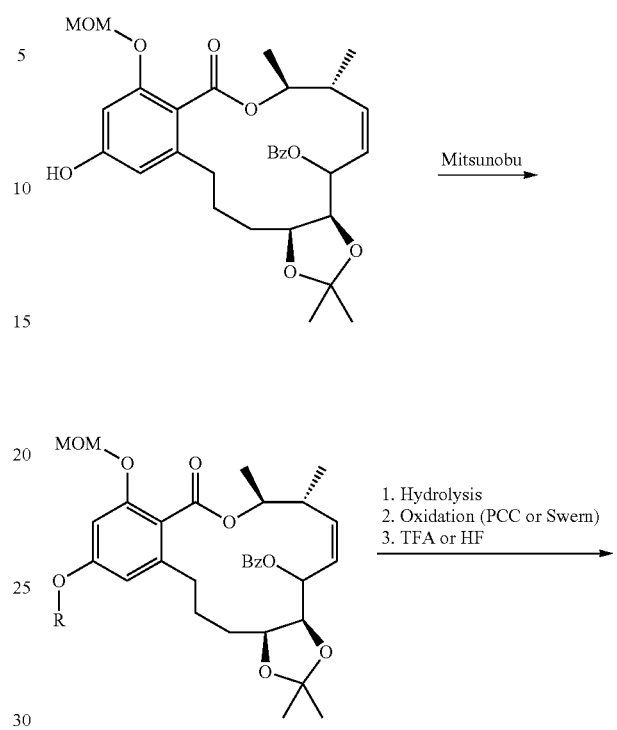
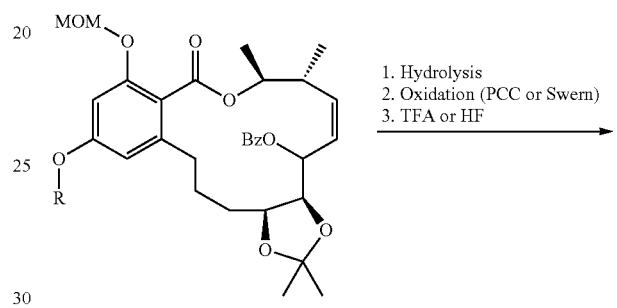

Alternatively, as depicted in Scheme 6, the hydroxyl functionality in the advance intermediate can be replaced with an amine functionality. This amine can be further substituted (e.g., with methyl groups, as depicted in Scheme 6) with a variety of functional groups as described herein, using methods available to one of ordinary skill in the art.

Scheme 6

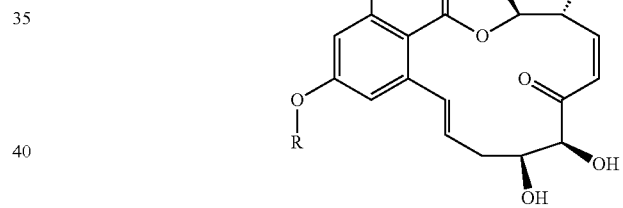
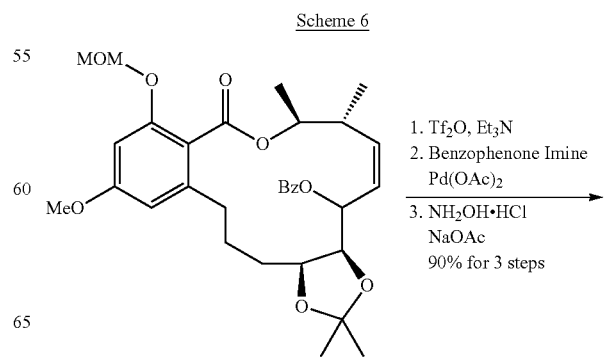

It will be appreciated that once the core intermediate structures are constructed a variety of other analogues can be generated. In but one example, C14-O analogues are provided ($R_9$ as described herein). For example, Scheme 5 depicts the synthesis of these analogues using a Mitsunobu reaction to functionalize the C14 hydroxyl moiety.

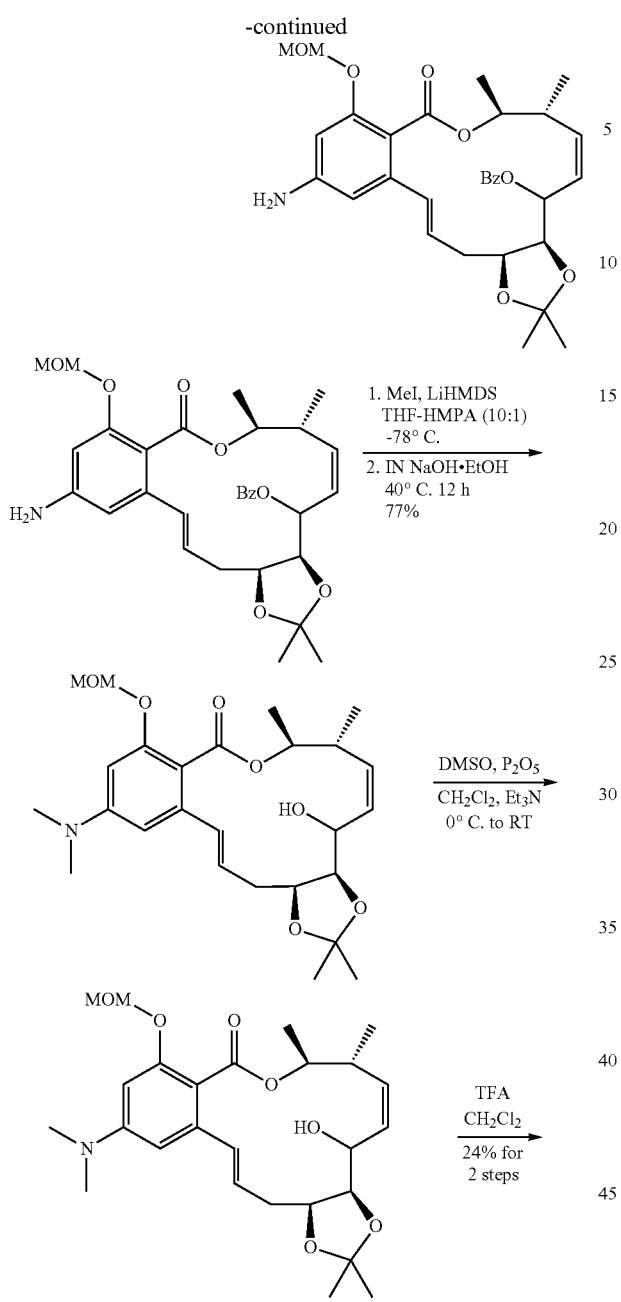

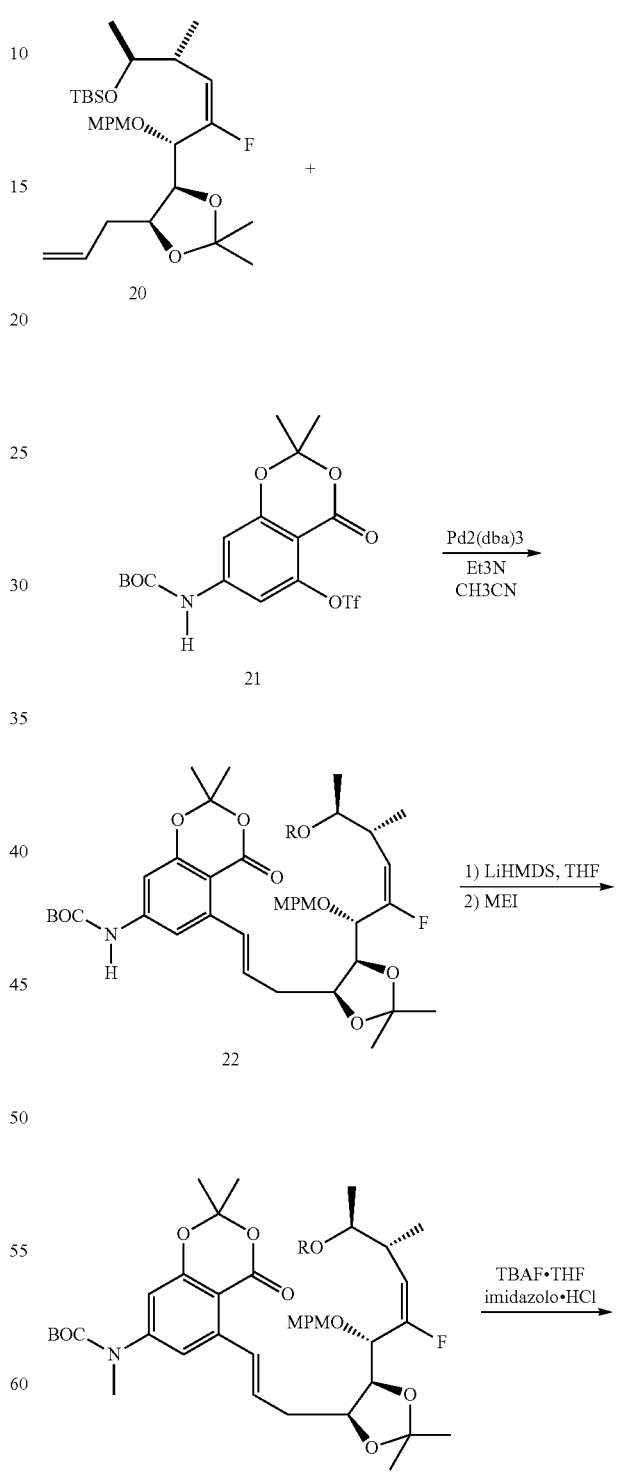

able to one of ordinary skill in the art. A synthesis of acyclic intermediate 20 is depicted in Scheme 8.

Alternatively, as depicted in Schemes 7 and 9, the amine functionality may be introduced earlier in the synthesis. This amine can be further substituted (e.g., with methyl or ethyl groups, as depicted in Schemes 7 and 9) with a variety of functional groups as described herein, using methods avail-

31
-continued
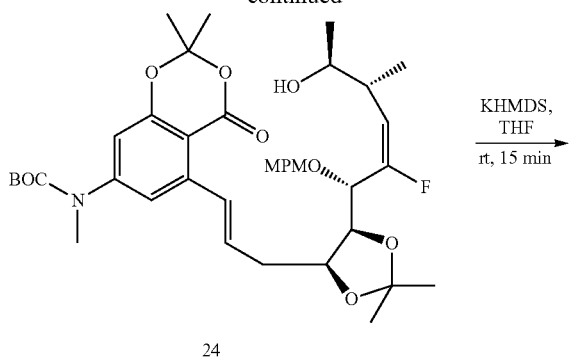
32
-continued
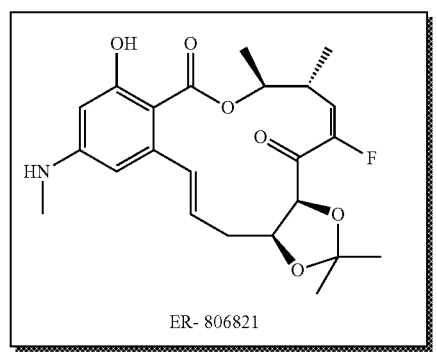
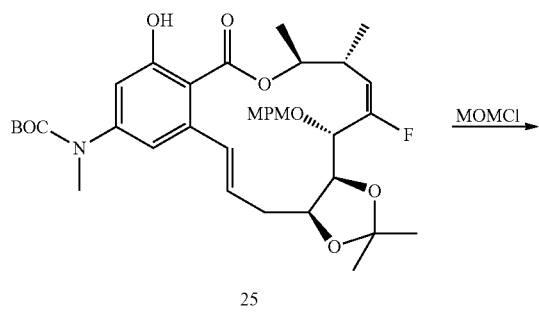
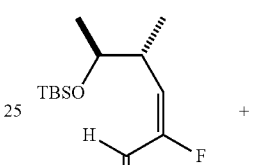
Scheme 8
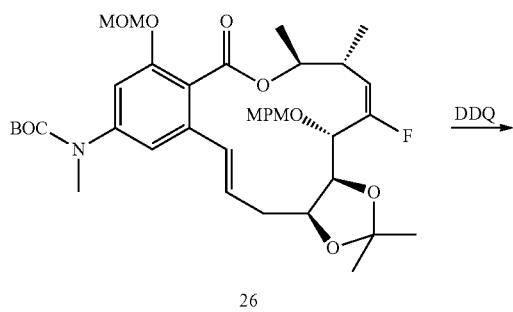
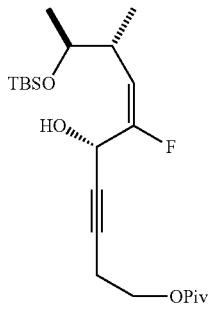
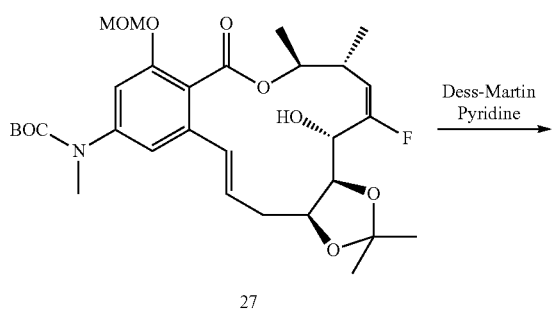
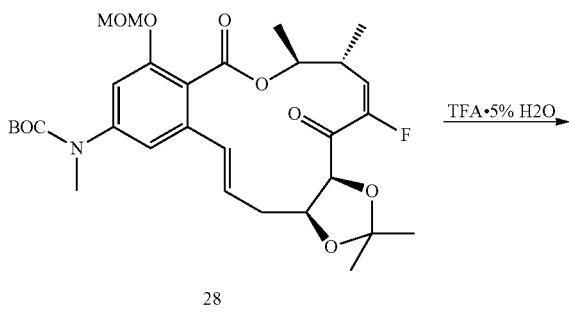
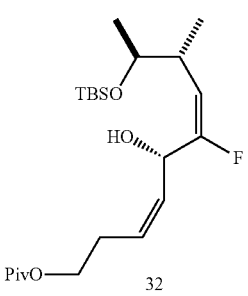

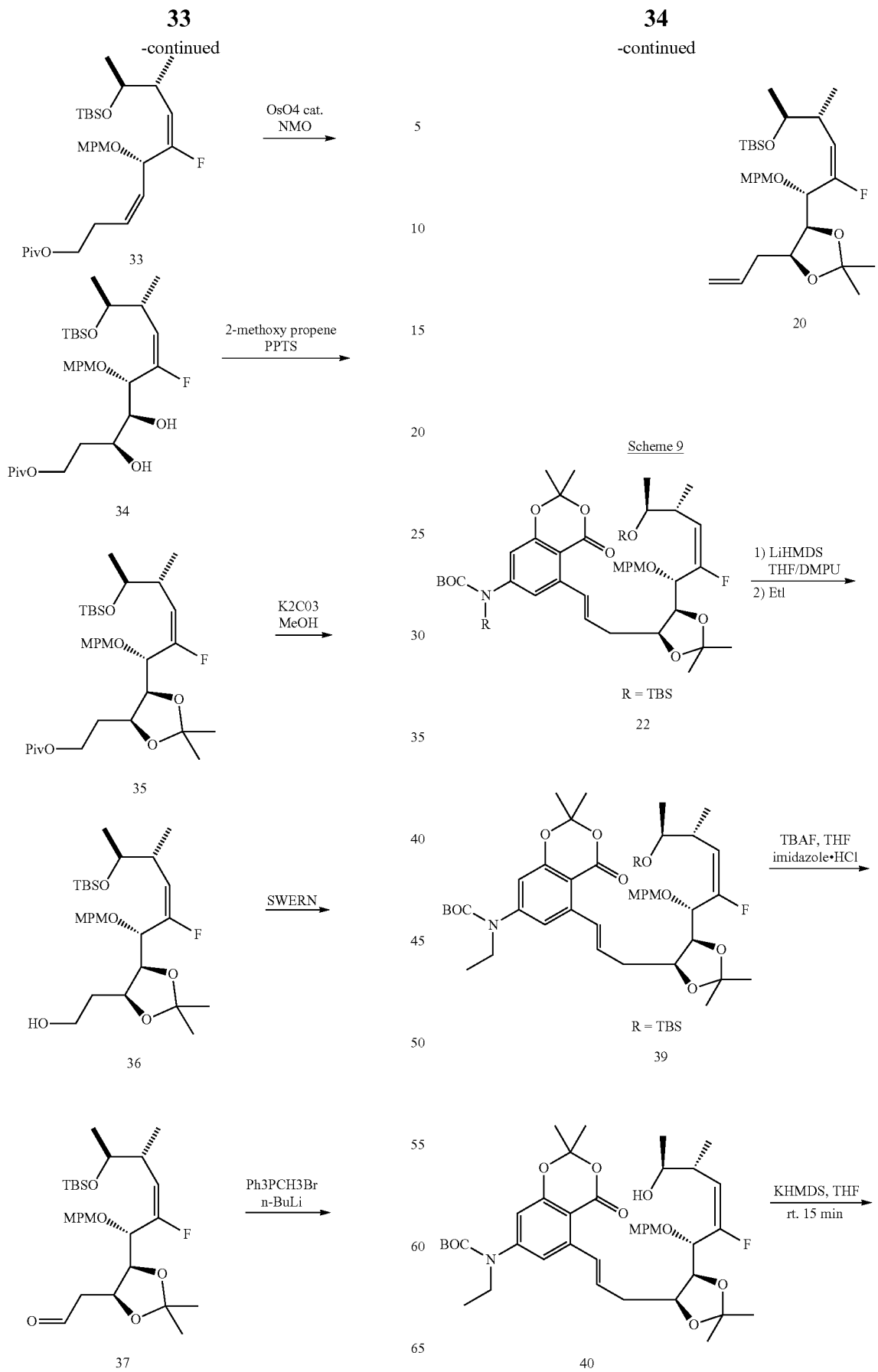

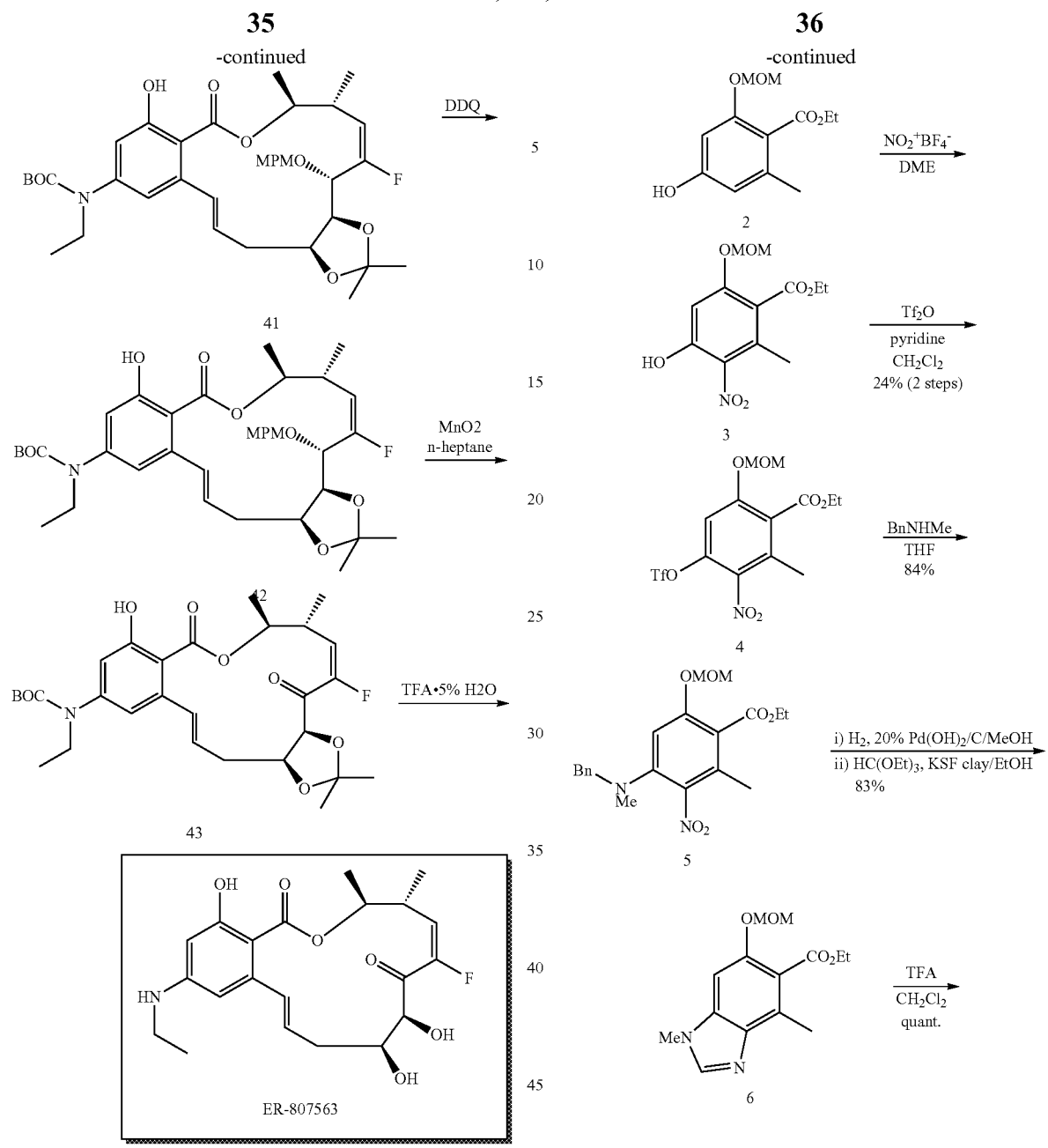
For special fused ring systems on the aromatic component, a different aromatic segment is used in the place of the phenol. While synthesis of the aromatic fragment required special synthetic techniques, the overall flow remained, as depicted below (Scheme 10)
Synthetic Route to NF-2561
Scheme 10
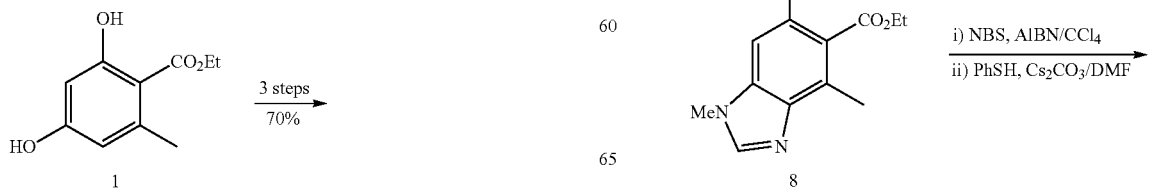

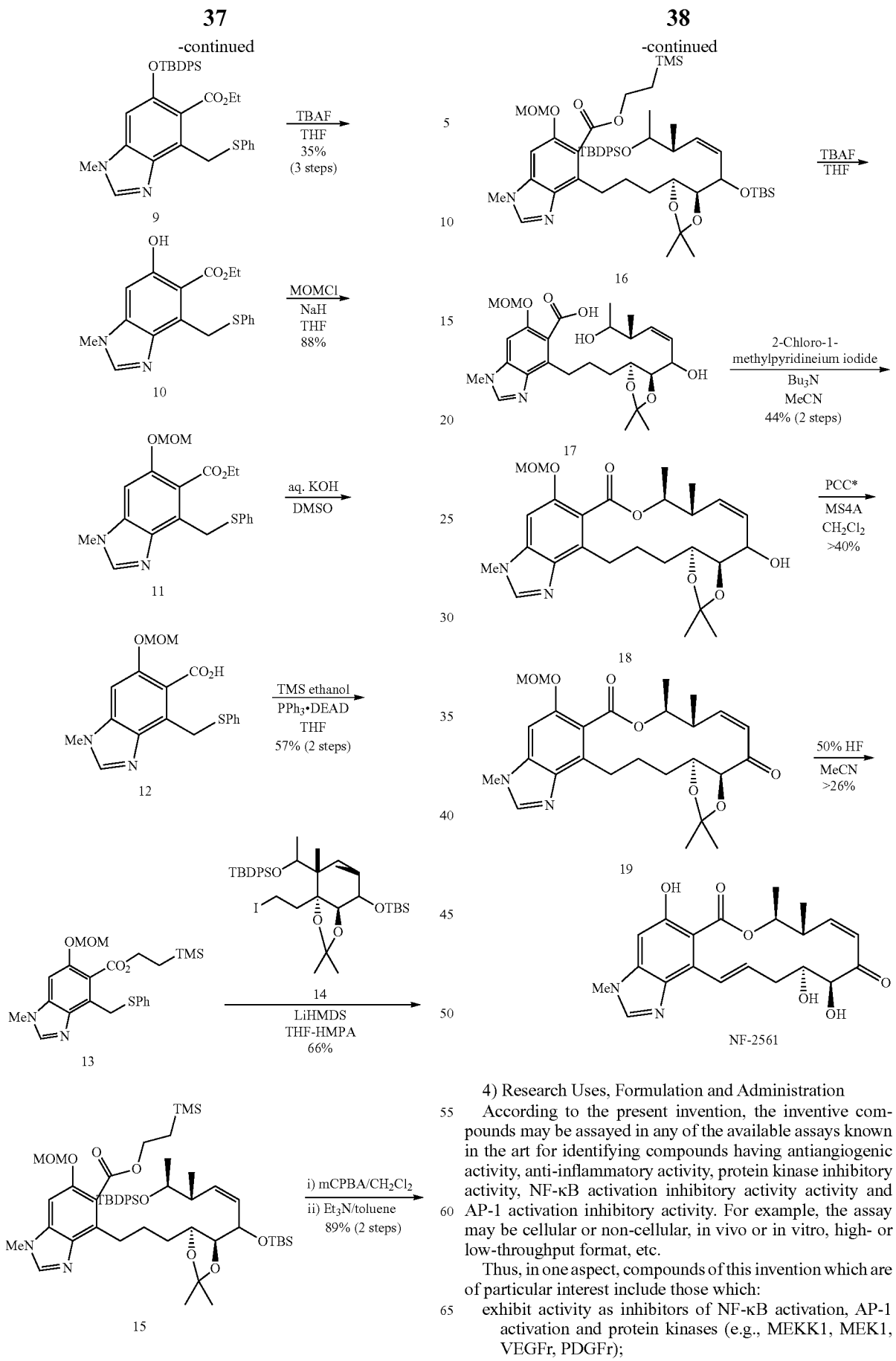

4) Research Uses, Formulation and Administration

According to the present invention, the inventive compounds may be assayed in any of the available assays known in the art for identifying compounds having antiangiogenic activity, anti-inflammatory activity, protein kinase inhibitory activity, NF-κB activation inhibitory activity activity and AP-1 activation inhibitory activity. For example, the assay may be cellular or non-cellular, in vivo or in vitro, high- or low-throughput format, etc.

Thus, in one aspect, compounds of this invention which are of particular interest include those which:

exhibit activity as inhibitors of NF-κB activation, AP-1 activation and protein kinases (e.g., MEKK1, MEK1, VEGFr, PDGFr);

exhibit an antiproliferative or an antiangiogenic effect on solid tumors;

exhibit an anti-inflammatory effect on suitable cell lines maintained in vitro, or in animal studies using a scientifically acceptable model;

are useful for the treatment of photoaging-related disorders/conditions; and/or exhibit a favorable therapeutic profile (e.g., safety, efficacy, and stability).

As discussed above, certain of the compounds as described herein exhibit activity generally as inhibitors of NF-κB activation, AP-1 activation and protein kinases. More specifically, compounds of the invention demonstrate immunosuppressive activity and thus the invention further provides a method for treating an inflammatory disorder or autoimmune disorders. Certain of the compounds as described herein also act as inhibitors of tumor growth and angiogenesis. The method involves the administration of a therapeutically effective amount of the compound or a pharmaceutically acceptable derivative thereof to a subject (including, but not limited to a human or animal) in need of it. In certain embodiments, the inventive compounds as useful for the treatment of sepsis, glomerulonephropathy, rheumatoid arthritis (including ankylosing spondylitis), psoriatic arthritis, osteoarthritis, osteoporosis, allergic rhinitis, ocular inflammation, inflammatory bowel disease (crohn's disease and ulcerative colitis), multiple sclerosis, atopic dermatitis, psoriasis, asthma, inflammatory pulmonary disease, hepatitis, autoimmune disorders, systemic lupus erthematosus, allograft rejection/graft versus host disease, diabetes, AIDS, solid tumor cancers, leukemia, lymphomas, non-hodgkin's B-cell lymphomas, chronical lymphocytic leukemia (CLL), multiple myeloma, eczema, urticaria, myasthenia gravis, idiopathic thrombocytopenia purpura, cardiovascular disease (e.g., myocardial infarction, atherosclerosis), hepatitis, glomerulonephropathy, productive nephritis, adenovirus, diseases/disorders of the central nervous system (e.g., stroke, Alzheimer's disease, epilepsy) and for the treatment of the symptoms of malaria, to name a few.

In certain other embodiments, compounds of the invention are useful for reducing photodamage, and thus, the invention further provides a method for treating photoaging-related disorders/conditions. In certain exemplary embodiments, compounds of the invention are useful for the treatment and/or prevention of skin coarseness, wrinkling, mottled pigmentation, sallowness, laxity, telangiectasia, lentigines, purpura and easy bruising, atrophy, fibrotic depigmented areas, and ultimately premalignant and malignant neoplasms. In certain other exemplary embodiments, compounds of the invention are useful for the treatment and/or prevention of wrinkles and/or skin cancer.

Pharmaceutical Compositions

As discussed above this invention provides novel compounds that have biological properties useful for the treatment of inflammatory and autoimmune disorders, photoaging and cancer. The inventive compounds also find use in the prevention of restenosis of blood vessels subject to traumas such as angioplasty and stenting. Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an immunomodulatory agent (e.g., an agent for the treatment of, rheumatoid arthritis, psoriasis, multiple sclerosis, or asthma) or antiangiogenesis agent or anticancer agent approved for the treatment of cancer, as discussed in more detail herein, or it may be any one of a number of agents undergoing approval in the Food and Drug Administration that ultimately obtain approval for the treatment of an immune disorder or cancer. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses and Formulations of Compounds of the Invention

As described in more detail herein, in general, the present invention provides compounds useful for the treatment of inflammatory or immune disorders and the treatment of cancer, particularly solid tumors. Without wishing to be bound by any particular theory, more generally, the compounds of the invention have been shown to inhibit NF-κB activity and the identification of NF-κB as a key player in the pathogenesis of inflammation suggest that NF-κB targeted therapeutics may be effective in inflammatory and immune disorders (see, generally, NF-κB in Defense and Disease, *J. Clin. Investig.* 2001, 107, 7). Furthermore, certain compounds of the invention have also been shown to inhibit receptor tyrosine kinase activity such as VEGFr and PDGFr in vitro, as described in more detail herein, and are useful for the treatment of cancer, including solid tumors (see, Angiogenesis: Potentials for Pharmacologic Intervention in the Treatment of Cancer, Cardiovascular Diseases, and Chronic Inflammation, *Pharmacological Reviews,* 2000, 52, 237).

As detailed in the exemplification herein, in assays to determine the ability of compounds to inhibit NF-κB, certain inventive compounds exhibited $IC_{50}$ values less than 10 μM. In certain other embodiments, inventive compounds exhibit $IC_{50}$ values less than 7.5 μM. In certain embodiments, inventive compounds exhibit $IC_{50}$ values less than 5 μM. In certain other embodiments, inventive compounds exhibit $IC_{50}$ values less than 2.5 μM. In certain embodiments, inventive compounds exhibit $IC_{50}$ values less than 1 μM. In certain embodiments, inventive compounds exhibit $IC_{50}$ values less than 0.75 μM. In certain embodiments, inventive compounds exhibit $IC_{50}$ values less than 0.5 μM. In certain embodiments, inventive compounds exhibit $IC_{50}$ values less than 0.25 μM. In certain embodiments, inventive compounds exhibit $IC_{50}$ values less than 0.1 μM. In certain other embodiments, inventive compounds exhibit $IC_{50}$ values less than 750 nM. In certain other embodiments, inventive compounds exhibit $IC_{50}$ values less than 500 nM. In certain other embodiments, inventive compounds exhibit $IC_{50}$ values less than 250 nM. In certain other embodiments, inventive compounds exhibit $IC_{50}$ values less than 100 nM. In other embodiments, exemplary compounds exhibited $IC_{50}$ values less than 75 nM. In other embodiments, exemplary compounds exhibited $IC_{50}$ values less than 50 nM.

In still other embodiments, certain compounds were tested for their ability to inhibit the growth of tumor cell lines in vitro. Certain of these compounds exhibited $IC_{50}$ values less than 10 μM. In certain other embodiments, inventive compounds exhibit $IC_{50}$ values less than 7.5 μM. In certain embodiments, inventive compounds exhibit $IC_{50}$ values less than 5 μM. In certain other embodiments, inventive compounds exhibit $IC_{50}$ values less than 2.5 μM. In certain embodiments, inventive compounds exhibit $IC_{50}$ values less than 1 μM. In certain embodiments, inventive compounds exhibit $IC_{50}$ values less than 0.75 μM. In certain embodiments, inventive compounds exhibit $IC_{50}$ values less than 0.5 μM. In certain embodiments, inventive compounds exhibit $IC_{50}$ values less than 0.25 μM. In certain embodiments, inventive compounds exhibit $IC_{50}$ values less than 0.1 μM. In certain other embodiments, inventive compounds exhibit $IC_{50}$ values less than 750 nM. In certain other embodiments, inventive compounds exhibit $IC_{50}$ values less than 500 nM. In certain other embodiments, inventive compounds exhibit $IC_{50}$ values less than 250 nM. In certain other embodiments, inventive compounds exhibit $IC_{50}$ values less than 100 nM. In other embodiments, exemplary compounds exhibited $IC_{50}$ values less than 75 nM. In other embodiments, exemplary compounds exhibited $IC_{50}$ values less than 50 nM.

As discussed above, compounds of the invention exhibit immunomodulatory activity and exhibit activity for the inhibition of angiogenesis through inhibition of receptor tyrosine kinases. As such, the inventive compounds as useful for the treatment of a variety of disorders, including, but not limited to, sepsis, glomerulonephropathy, rheumatoid arthritis (including ankylosing spondylitis), psoriatic arthritis, osteoarthritis, osteoporosis, allergic rhinitis, ocular inflammation, inflammatory bowel disease, atopic dermatitis, psoriasis, asthma, Crohn's disease, ulcerative colitis, inflammatory pulmonary disease, hepatitis, autoimmune disorders, diabetes, AIDS, solid tumor cancers, Leukemia, lymphomas, non-hodgkin's B-cell lymphomas, chronical lymphocytic leukemia (CLL), multiple myeloma, systemic lupus erythematosus, allograft rejection/graft versus host disease, eczema, uticaria, myasthenia gravis, idiopathic thrombocytopenia purpura, cardiovascular disease (e.g., myocardial infarction, atherosclerosis), hepatitis, productive nephritis, adenovirus, diseases/disorders of the central nervous system (stroke, Alzheimer's disease, epilepsy) and for the treatment of the symptoms of malaria, to name a few. In certain embodiments, compounds of the invention are particularly useful for the treatment of rheumatoid arthritis, psoriasis, multiple sclerosis, asthma and cancer.

Rheumatoid Arthritis is a chronic syndrome characterized by nonspecific, usually symmetric inflammation of the peripheral joints, potentially resulting in progressive destruction of articular and periarticular structures, with or without generalized manifestations (See, generally, The Merck Manual, 1999, Seventeenth Ed. Merck & Co., the entire contents of which are hereby incorporated by reference). Studies in the past established that presence of inflammatory cells and pro-inflammatory cytokines, such as TNFα, IL-1β are abundant in the diseased synovium. Increased macrophage-derived lining cells are prominent along with some lymphocytes and vascular changes in early disease. Although there is not a cure, reduction of circulatory pro-inflammatory cytokines (e.g. TNFα, IL-1β) through intervention of biological agents, such as Enbrel, Remicade or Anakinra demonstrated efficacy in reduction of symptoms and retarding the disease progression in clinical trials. Thus developing of an agent such as described in this patent in modulation of pro-inflammatory cytokines through NF-κB inhibition could bring great benefit to RA patients.

Psoriasis is a disorder for which there is no curative therapy, although in most cases acute attacks can be controlled. Psoriasis is a chronic, recurrent disease characterized by dry, well-circumscribed, silvery, scaling papules and plaques of various sizes, and has traditionally been attributed to increased epidermal cell proliferation and concomitant dermal inflammation. The response of psoriasis to the immunosuppressive drug cyclosporine suggests that the primary pathogenic factor may be immunologic. Proliferation of epidermal cells has been also linked to AP-1 activation via stimulation from injury, radiation or stress to the skin (see, P. Angel et al., "Function and regulation of AP-1 subunits in skin physiology and pathology", *Oncogene*, 2001, 20:2413-2423; and A. Grandjean-Laquerriere et al., "Relative contribution of NF-kB and AP-1 in the modulation by Curcumin and pyrrolidine dithiocarbamate of the UVB-induced cytokine expression by keratinocytes", *Cytokine*, 2002, 18(3): 168-177, each of which is hereby incorporated by reference in its entirety). Currently available treatment regimens for psoriasis include the use of lubricants, keratolytics, topical cortisosteroids, sunlight, topical vitamin D derivatives, anthralin, and systemic antimetabolites (e.g., methotrexate), immunosuppressive drugs (e.g., cyclosporine, tacrolimus, mycophenolate, and mofetil). However, immunosuppressive drugs are not yet approved for the treatment of psoriasis and other drugs, including corticosteriods, have severe side effects, including exacerbations or pustular lesions (See, generally, The Merck Manual, 1999, Seventeenth Ed. Merck & Co., the entire contents of which are hereby incorporated by reference). This invention is certainly applicable to this disease as well as a host of other related diseases, such as, psoriatic arthritis, ankylosing spondylitis, just to name a few.

Asthma is also believed to involve immunologic abnormalities and increased inflammatory responses. Similarly to psoriasis, there is no curative therapy. Thus the development of novel therapies such as this, preferably safe and curative, is desirable. This is also applied to related immunologic disorders such as, graft rejection, SLE etc.

Angiogenesis, or the formation of new blood vessels out of pre-existing capillaries, is a sequence of events that is fundamental to many physiologic and pathologic processes such as cancer, ischemic diseases, and chronical inflammation. With the identification of several proangiogenic molecules such as vascular endothelial cell growth factor (VEGF), the fibroblast growth factors (FGFs) (see, Angiogenesis: Potentials for Pharmacologic Intervention in the Treatment of Cancer, Cardiovascular Diseases, and chronic Inflammation, *Pharmacological Reviews*, 2000, 52, 253). Thus, inhibition of receptor tyrosine kinase (such as VEGFr) activity has been subjects of various ongoing clinical trails. Certain compounds in this invention showed potent VEGFr inhibition. Thus, such application is expected.

As discussed above, the inventive compounds also find use in the prevention of restenosis of blood vessels subject to traumas such as angioplasty and stenting. For example, it is contemplated that the compounds of the invention will be useful as a coating for implanted medical devices, such as tubings, shunts, catheters, artificial implants, pins, electrical implants such as pacemakers, and especially for arterial or venous stents, including balloon-expandable stents. In certain embodiments inventive compounds may be bound to an implantable medical device, or alternatively, may be passively adsorbed to the surface of the implantable device. In certain other embodiments, the inventive compounds may be formulated to be contained within, or, adapted to release by a surgical or medical device or implant, such as, for example, stents, sutures, indwelling catheters, prosthesis, and the like.

In certain exemplary embodiments, the inventive compounds may be used as coating for stents. A stent is typically an open tubular structure that has a pattern (or patterns) of apertures extending from the outer surface of the stent to the lumen. It is commonplace to make stents of biocompatible metallic materials, with the patterns cut on the surface with a laser machine. The stent can be electro-polished to minimize surface irregularities since these irregularities can trigger an adverse biological response. However, stents may still stimulate foreign body reactions that result in thrombosis or restenosis. To avoid these complications, a variety of stent coatings and compositions have been proposed in the prior art literature both to reduce the incidence of these complications or other complications and restore tissue function by itself or by delivering therapeutic compound to the lumen. For example, drugs having antiproliferative and anti-inflammatory activities have been evaluated as stent coatings, and have shown promise in preventing retenosis (See, for example, Presbitero P. et al., "Drug eluting stents do they make the difference?", *Minerva Cardioangiol*, 2002, 50(5):431-442; Ruygrok P. N. et al., "Rapamycin in cardiovascular medicine", *Intern. Med. J.*, 2003, 33(3):103-109; and Marx S. O. et al., "Bench to bedside: the development of rapamycin and its application to stent restenosis", *Circulation,* 2001, 104(8): 852-855, each of these references is incorporated herein by reference in its entirety). Accordingly, without wishing to be bound to any particular theory, Applicant proposes that inventive compounds having anti-inflammatory and/or antiproliferative effects can be used as stent coatings and/or in stent drug delivery devices, inter alia for the prevention of restenosis or reduction of restenosis rate. A variety of compositions and methods related to stent coating and/or local stent drug delivery for preventing restenosis are known in the art (see, for example, U.S. Pat. Nos. 6,517,889; 6,273,913; 6,258,121; 6,251,136; 6,248,127; 6,231,600; 6,203,551; 6,153,252; 6,071,305; 5,891,507; 5,837,313 and published U.S. patent application No.: US2001/0027340, each of which is incorporated herein by reference in its entirety). For example, stents may be coated with polymer-drug conjugates by dipping the stent in polymer-drug solution or spraying the stent with such a solution. In certain embodiment, suitable materials for the implantable device include biocompatible and nontoxic materials, and may be chosen from the metals such as nickel-titanium alloys, steel, or biocompatible polymers, hydrogels, polyurethanes, polyethylenes, ethylenevinyl acetate copolymers, etc. In certain embodiments, the inventive compound, is coated onto a stent for insertion into an artery or vein following balloon angioplasty.

The invention may be described therefore, in certain broad aspects as a method of inhibiting arterial restenosis or arterial occlusion following vascular trauma comprising administering to a subject in need thereof, a composition comprising an inventive compound conjugated to a suitable polymer or polymeric material. In the practice of the method, the subject may be a coronary bypass, vascular surgery, organ transplant or coronary or any other arterial angioplasty patient, for example, and the composition may be administered directly, intravenously, or even coated on a stent to be implanted at the sight of vascular trauma.

In another aspect, the invention encompasses implants and surgical or medical devices, including stents and grafts, coated with or otherwise constructed to contain and/or release any of the inventive compounds disclosed herein. In certain embodiments, the compounds have anti-inflammatory and/or antiproliferative activities. In certain other embodiments, the compounds inhibit smooth muscle cell proliferation. Representative examples of the inventive implants and surgical or medical devices include cardiovascular devices (e.g., implantable venous catheters, venous ports, tunneled venous catheters, chronic infusion lines or ports, including hepatic artery infusion catheters, pacemaker wires, implantable defibrillators); neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g., chronic indwelling catheters, feeding tubes, portosystemic shunts, shunts for ascites, peritoneal implants for drug delivery, peritoneal dialysis catheters, implantable meshes for hernias, suspensions or solid implants to prevent surgical adhesions, including meshes); genitourinary devices (e.g., uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vasovasostomy); phthalmologic implants (e.g., multino implants and other implants for neovascular glaucoma, drug eluting contact lenses for pterygiums, splints for failed dacrocystalrhinostomy, drug eluting contact lenses for corneal neovascularity, implants for diabetic retinopathy, drug eluting contact lenses for high risk corneal transplants); otolaryngology devices (e.g., ossicular implants, Eustachian tube splints or stents for glue ear or chronic otitis as an alternative to transtempanic drains); plastic surgery implants (e.g., prevention of fibrous contracture in response to gel- or saline-containing breast implants in the subpectoral or subglandular approaches or post-mastectomy, or chin implants), and orthopedic implants (e.g., cemented orthopedic prostheses).

Implants and other surgical or medical devices may be coated with (or otherwise adapted to release) compositions of the present invention in a variety of manners, including for example: (a) by directly affixing to the implant or device an inventive compound or composition (e.g., by either spraying the implant or device with a polymer/drug film, or by dipping the implant or device into a polymer/drug solution, or by other covalent or noncovalent means); (b) by coating the implant or device with a substance such as a hydrogel which will in turn absorb the inventive compound or composition; (c) by interweaving inventive compound- or composition-coated thread (or the polymer itself formed into a thread) into the implant or device; (d) by inserting the implant or device into a sleeve or mesh which is comprised of or coated with an inventive compound or composition; (e) constructing the implant or device itself with an inventive compound or composition; or (f) by otherwise adapting the implant or device to release the inventive compound. In certain embodiments, the composition should firmly adhere to the implant or device during storage and at the time of insertion. The inventive compound or composition should also preferably not degrade during storage, prior to insertion, or when warmed to body temperature after insertion inside the body (if this is required). In addition, it should preferably coat the implant or device smoothly and evenly, with a uniform distribution of inventive compound, while not changing the stent contour. Within preferred embodiments of the invention, the inventive implant or device should provide a uniform, predictable, prolonged release of the inventive compound or composition into the tissue surrounding the implant or device once it has been deployed. For vascular stents, in addition to the above properties, the composition should not render the stent thrombogenic (causing blood clots to form), or cause significant turbulence in blood flow (more than the stent itself would be expected to cause if it was uncoated).

In the case of stents, a wide variety of stents may be developed to contain and/or release the inventive compounds or compositions provided herein, including esophageal stents, gastrointestinal stents, vascular stents, biliary stents, colonic stents, pancreatic stents, ureteric and urethral stents, lacrimal stents, Eustachian tube stents, fallopian tube stents and tracheal/bronchial stents (See, for example, U.S. Pat. No. 6,515,016, the entire contents of which are incorporated herein by reference). Stents may be readily obtained from commercial sources, or constructed in accordance with well-known techniques. Representative examples of stents include those described in U.S. Pat. No. 4,768,523, entitled "Hydrogel Adhesive"; U.S. Pat. No. 4,776,337, entitled "Expandable Intraluminal Graft, and Method and Apparatus for Implanting and Expandable Intraluminal Graft"; U.S. Pat. No. 5,041,126 entitled "Endovascular Stent and Delivery System"; U.S. Pat. No. 5,052,998 entitled "Indwelling Stent and Method of Use"; U.S. Pat. No. 5,064,435 entitled "Self-Expanding Prosthesis Having Stable Axial Length"; U.S. Pat. No. 5,089,606, entitled "Water-insoluble Polysaccharide Hydrogel Foam for Medical Applications"; U.S. Pat. No. 5,147,370, entitled "Nitinol Stent for Hollow Body Conduits"; U.S. Pat. No.

5,176,626, entitled "Indwelling Stent"; U.S. Pat. No. 5,213,580, entitled "Biodegradable Polymeric Endoluminal Sealing Process"; and U.S. Pat. No. 5,328,471, entitled "Method and Apparatus for Treatment of Focal Disease in Hollow Tubular Organs and Other Tissue Lumens."

As discussed above, the stent coated with (or otherwise adapted to release) compositions of the present invention may be used to eliminate a vascular obstruction and prevent restenosis or reduce the rate of restenosis. Within other aspects of the present invention, stents coated with (or otherwise adapted to release) compositions of the present invention are provided for expanding the lumen of a body passageway. Specifically, a stent having a generally tubular structure, and a surface coated with (or otherwise adapted to release) an inventive compound or composition may be inserted into the passageway, such that the passageway is expanded. In certain embodiments, the stent coated with (or otherwise adapted to release) compositions of the present invention may be used to eliminate a biliary, gastrointestinal, esophageal, tracheal/bronchial, urethral or vascular obstruction.

In another aspect of the invention, methods for the treatment of immune disorders and cancer are provided comprising administering a therapeutically effective amount of a compound of formula (I), as described herein, to a subject in need thereof. In certain embodiments, the inventive compounds are useful for the treatment of rheumatoid arthritis, psoriasis, multiple sclerosis, asthma and cancer. It will be appreciated that the compounds and compositions, according to the method of the present invention, may be administered using any amount and any route of administration effective for the treatment of inflammatory disorders, including but not limited to rheumatoid arthritis, psoriasis, multiple sclerosis, asthma and cancer. Thus, the expression "effective amount" as used herein, refers to a sufficient amount of agent to inhibit the growth of tumor cells, or refers to a sufficient amount to reduce the effects of rheumatoid arthritis, psoriasis, asthma and cancer, (or any inflammatory response or disorder). The exact amount required will vary from subject to subject, depending on the species, age, and general condition of the subject, the severity of the diseases, the particular anticancer agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

In certain other embodiments, methods are provided for using the inventive implants and other surgical or medical devices coated with (or otherwise adapted to release) compounds and compositions of the present invention. In certain embodiments, methods are provided for preventing restenosis, comprising inserting a stent into an obstructed blood vessel, the stent having a generally tubular structure, the surface of the structure being coated with (or otherwise adapted to release) an inventive compound or composition, such that the obstruction is eliminated and the inventive compound or composition is delivered in amounts effective to prevent restenosis. In other embodiments, methods are provided for preventing restenosis, comprising inserting a stent into an obstructed blood vessel, the stent having a generally tubular structure, the surface of the structure being coated with (or otherwise adapted to release) an inventive compound or composition, such that the obstruction is eliminated and the inventive compound or composition is delivered in amounts effective to inhibit smooth muscle cell proliferation.

Within other aspects of the present invention, methods are provided for expanding the lumen of a body passageway, comprising inserting a stent into the passageway, the stent having a generally tubular structure, the surface of the structure being coated with (or otherwise adapted to release) an inventive compound or composition, such that the passageway is expanded. In certain embodiments, the lumen of a body passageway is expanded in order to eliminate a biliary, gastrointestinal, esophageal, tracheal/bronchial, urethral and/or vascular obstruction.

In certain embodiments, methods are provided for eliminating biliary obstructions, comprising inserting a biliary stent into a biliary passageway, the stent having a generally tubular structure, the surface of the structure being coated with (or otherwise adapted to release) an inventive compound or composition, such that the biliary obstruction is eliminated. Briefly, tumor overgrowth of the common bile duct results in progressive cholestatic jaundice which is incompatible with life. Generally, the biliary system which drains bile from the liver into the duodenum is most often obstructed by (1) a tumor composed of bile duct cells (cholangiocarcinoma), (2) a tumor which invades the bile duct (e.g., pancreatic carcinoma), or (3) a tumor which exerts extrinsic pressure and compresses the bile duct (e.g., enlarged lymph nodes). Both primary biliary tumors, as well as other tumors which cause compression of the biliary tree may be treated utilizing stents Implants and other surgical or medical devices may be coated with (or otherwise adapted to release) compositions of the present invention. One example of primary biliary tumors are adenocarcinomas (which are also called Klatskin tumors when found at the bifurcation of the common hepatic duct). These tumors are also referred to as biliary carcinomas, choledocholangiocarcinomas, or adenocarcinomas of the biliary system. Benign tumors which affect the bile duct (e.g., adenoma of the biliary system), and, in rare cases, squamous cell carcinomas of the bile duct and adenocarcinomas of the gallbladder, may also cause compression of the biliary tree and therefore, result in biliary obstruction. Compression of the biliary tree is most commonly due to tumors of the liver and pancreas which compress and therefore obstruct the ducts. Most of the tumors from the pancreas arise from cells of the pancreatic ducts. This is a highly fatal form of cancer (5% of all cancer deaths; 26,000 new cases per year in the U.S.) with an average of 6 months survival and a 1 year survival rate of only 10%. When these tumors are located in the head of the pancreas they frequently cause biliary obstruction, and this detracts significantly from the quality of life of the patient. While all types of pancreatic tumors are generally referred to as "carcinoma of the pancreas" there are histologic subtypes including: adenocarcinoma, adenosquamous carcinoma, cystadenocarcinoma, and acinar cell carcinoma.

Hepatic tumors, as discussed above, may also cause compression of the biliary tree, and therefore cause obstruction of the biliary ducts.

In certain embodiments, a biliary stent is first inserted into a biliary passageway in one of several ways: from the top end by inserting a needle through the abdominal wall and through the liver (a percutaneous transhepatic cholangiogram or "PTC"); from the bottom end by cannulating the bile duct through an endoscope inserted through the mouth, stomach, and duodenum (an endoscopic retrograde cholangiogram or "ERCP"); or by direct incision during a surgical procedure. In certain embodiments, a preinsertion examination, PTC, ERCP, or direct visualization at the time of surgery is performed to determine the appropriate position for stent insertion. A guidewire is then advanced through the lesion, and over this a delivery catheter is passed to allow the stent to be inserted in its collapsed form. If the diagnostic exam was a PTC, the guidewire and delivery catheter is inserted via the abdominal wall, while if the original exam was an ERCP the stent may be placed via the mouth. The stent is then positioned under radiologic, endoscopic, or direct visual control taking particular care to place it precisely across the narrowing in the bile duct. The delivery catheter is then removed leaving the stent standing as a scaffolding which holds the bile duct open. A further cholangiogram may be performed to document that the stent is appropriately positioned.

In certain embodiments, methods are provided for eliminating esophageal obstructions, comprising inserting an esophageal stent into an esophagus, the stent having a generally tubular structure, the surface of the structure being coated with (or otherwise adapted to release) an inventive compound or composition, such that the esophageal obstruction is eliminated. Briefly, the esophagus is the hollow tube which transports food and liquids from the mouth to the stomach. Cancer of the esophagus or invasion by cancer arising in adjacent organs (e.g., cancer of the stomach or lung) results in the inability to swallow food or saliva. In certain embodiments, a preinsertion examination, usually a barium swallow or endoscopy is performed in order to determine the appropriate position for stent insertion. A catheter or endoscope may then be positioned through the mouth, and a guidewire is advanced through the blockage. A stent delivery catheter is passed over the guidewire under radiologic or endoscopic control, and a stent is placed precisely across the narrowing in the esophagus. A post-insertion examination, usually a barium swallow x-ray, may be utilized to confirm appropriate positioning.

In certain embodiments, methods are provided for eliminating colonic obstructions, comprising inserting a colonic stent into a colon, the stent having a generally tubular structure, the surface of the structure being coated with (or otherwise adapted to release) an inventive compound or composition, such that the colonic obstruction is eliminated. Briefly, the colon is the hollow tube which transports digested food and waste materials from the small intestines to the anus. Cancer of the rectum and/or colon or invasion by cancer arising in adjacent organs (e.g., cancer of the uterus, ovary, bladder) results in the inability to eliminate feces from the bowel. In certain embodiments, a preinsertion examination, usually a barium enema or colonoscopy is performed in order to determine the appropriate position for stent insertion. A catheter or endoscope may then be positioned through the anus, and a guidewire is advanced through the blockage. A stent delivery catheter is passed over the guidewire under radiologic or endoscopic control, and a stent is placed precisely across the narrowing in the colon or rectum. A post-insertion examination, usually a barium enema x-ray, may be utilized to confirm appropriate positioning.

In certain embodiments, methods are provided for eliminating tracheal/bronchial obstructions, comprising inserting a tracheal/bronchial stent into a trachea or bronchi, the stent having a generally tubular structure, the surface of the structure being coated with (or otherwise adapted to release) an inventive compound or composition, such that the tracheal/bronchial obstruction is eliminated. Briefly, the trachea and bronchi are tubes which carry air from the mouth and nose to the lungs. Blockage of the trachea by cancer, invasion by cancer arising in adjacent organs (e.g., cancer of the lung), or collapse of the trachea or bronchi due to chondromalacia (weakening of the cartilage rings) results in inability to breathe. In certain embodiments, preinsertion examination, usually an endoscopy, is performed in order to determine the appropriate position for stent insertion. A catheter or endoscope is then positioned through the mouth, and a guidewire advanced through the blockage. A delivery catheter is then passed over the guidewire in order to allow a collapsed stent to be inserted. The stent is placed under radiologic or endoscopic control in order to place it precisely across the narrowing. The delivery catheter may then be removed leaving the stent standing as a scaffold on its own. A post-insertion examination, usually a bronchoscopy may be utilized to confirm appropriate positioning.

In certain embodiments, methods are provided for eliminating urethral obstructions, comprising inserting a urethral stent into a urethra, the stent having a generally tubular structure, the surface of the structure being coated with (or otherwise adapted to release) an inventive compound or composition, such that the urethral obstruction is eliminated. Briefly, the urethra is the tube which drains the bladder through the penis. Extrinsic narrowing of the urethra as it passes through the prostate, due to hypertrophy of the prostate, occurs in virtually every man over the age of 60 and causes progressive difficulty with urination. In certain embodiments, a preinsertion examination, usually an endoscopy or urethrogram is first performed in order to determine the appropriate position for stent insertion, which is above the external urinary sphincter at the lower end, and close to flush with the bladder neck at the upper end. An endoscope or catheter is then positioned through the penile opening and a guidewire advanced into the bladder. A delivery catheter is then passed over the guidewire in order to allow stent insertion. The delivery catheter is then removed, and the stent expanded into place. A post-insertion examination, usually endoscopy or retrograde urethrogram, may be utilized to confirm appropriate position.

In certain embodiments, methods are provided for eliminating vascular obstructions, comprising inserting a vascular stent into a blood vessel, the stent having a generally tubular structure, the surface of the structure being coated with (or otherwise adapted to release) an inventive compound or composition, such that the vascular obstruction is eliminated. Briefly, stents may be placed in a wide array of blood vessels, both arteries and veins, to prevent recurrent stenosis at the site of failed angioplasties, to treat narrowings that would likely fail if treated with angioplasty, and to treat post-surgical narrowings (e.g., dialysis graft stenosis). Suitable sites include, but are not limited to, the iliac, renal, and coronary arteries, the superior vena cava, and in dialysis grafts. In certain embodiments, angiography is first performed in order to localize the site for placement of the stent. This is typically accomplished by injecting radiopaque contrast through a catheter inserted into an artery or vein as an x-ray is taken. A catheter may then be inserted either percutaneously or by surgery into the femoral artery, brachial artery, femoral vein, or brachial vein, and advanced into the appropriate blood vessel by steering it through the vascular system under fluoroscopic guidance. A stent may then be positioned across the vascular stenosis. A post-insertion angiogram may also be utilized in order to confirm appropriate positioning.

In certain other embodiments, compounds of the invention are useful for reducing photodamage, and thus, the invention further provides a method for treating photoaging-related disorders/conditions. Photoaging is a term used to describe the changes in appearance and function of skin as a result of repeated exposure to sunlight. The ultraviolet (UV) component of sunlight, particularly middle UV (called UVB, 290-320 nm wavelength) is the principal causative agent of photoaging. The extent of UVB exposure required to cause photoaging is not currently known. Repeated exposure to UVB at levels that cause erythema and tanning are, however, commonly associated with photoaging. Clinically, photoaging is characterized by coarseness, wrinkling, mottled pigmentation, sallowness, laxity, telangiectasia, lentigines, purpura and easy bruising, atrophy, fibrotic depigmented areas, and ultimately premalignant and malignant neoplasms. Photoaging commonly occurs in skin that is habitually exposed to sunlight such as the face, ears, bald areas of the scalp, neck, and hands.

Procedures for preventing photoaging of unaged skin and treating already photoaged skin are available. Sunscreens are commonly used to prevent photoaging of skin areas that are habitually exposed to sunlight. Sunscreens are topical preparations that absorb, reflect or scatter UV. Some are based on opaque particulate materials such as zinc oxide, titanium oxide, clays and ferric chloride. Because such preparations are visible and occlusive many people consider these opaque formulations cosmetically unacceptable. Other sunscreens contain chemicals such a p-aminobenzoic acid (PABA), oxybenzone, dioxybenzone, ethylhexyl-methoxy cinnamide and butylmethoxydibenzoylmethane that are nonopaque and colorless because they do not absorb light of visible wavelengths. While these nonopaque sunscreens may be more acceptable cosmetically they are still relatively short-lived and susceptible to being removed by washing or perspiration. Additionally all sunscreens reduce vitamin D production.

It is known that transcription factors AP-1 and NF-κB are activated in mammalian cells exposed to UV light. It has also been shown that inhibition of MAP kinase/ERK kinase 1 (MEK-1) significantly inhibited UVB induced ERK activation (See, Chen et al., "Activation of p38 MAP kinase and ERK are required for ultraviolet-B induced c-fos gene expression in human keratinocytes", *Oncogene*, 18:7469-7476, 1999; the entire contents of which are incorporated herein by reference). Accordingly, without wishing to be bound to any particular theory, Applicant proposes that the compounds of the invention may find use in the treatment of skin damages caused by UVB exposure. For additional references on MAP kinases and photoaging, see Li et al., "Rays and arrays: the transcriptional program in the response of human epidermal keratotinocutes to UVB illumination", The FASEB Journal express article 10.1096/fj.01-01172fje, published online Sep. 17, 2001; U.S. Pat. No. 5,837,224 and U.S. Patent Application No.: 20020106339, each of which is hereby incorporated by reference in its entirety.

Thus the invention provides compositions for preventing or treating UVB-induced photodamage comprising an inventive compound; and a pharmaceutically acceptable carrier. In certain embodiments, the inventive compound is present in an amount effective to inhibit Map/Erk kinase. In certain other embodiments, the inventive compositions further comprise a cosmetic ingredient. In certain exemplary embodiments, the cosmetic ingredient is a fragrance. In certain other exemplary embodiments, the cosmetic ingredient is a sunscreen. In certain embodiments, the inventive compositions exist as pharmaceutically acceptable topical formulations.

The present invention additionally encompasses methods of providing protection against long-term UVB induced photodamage to a subject, said method comprising: administering to the subject in need thereof a composition comprising an inventive compound; and a pharmaceutically acceptable carrier or diluent. In certain embodiments, the composition is administered topically. The present invention additionally encompasses methods of providing protection against long-term UVB induced photodamage to a subject, said method comprising: providing the subject with a composition comprising an inventive compound; and providing the subject with instructions for using said composition to prevent photodamage. In certain embodiments, the composition is formulated so that it may be administered topically. In certain embodiments, the inventive compound is present in an amount effective to inhibit Map/Erk kinase. In certain embodiments, the instructions comprise directions to apply the composition to the skin prior to sun exposure. In certain exemplary embodiments, the composition further comprises a cosmetic ingredient. In certain exemplary embodiments, the cosmetic ingredient is a fragrance. In certain other exemplary embodiments, the cosmetic ingredient is a sunscreen. In certain embodiment, a method is provided for treating and/or preventing skin coarseness, wrinkling, mottled pigmentation, sallowness, laxity, telangiectasia, lentigines, purpura and easy bruising, atrophy, fibrotic depigmented areas, and ultimately premalignant and malignant neoplasms. In certain exemplary embodiments, the present invention provides a method for treating and/or preventing wrinkles and/or skin cancer.

In certain embodiments, the present invention provides kits for preventing long-term UVB induced photodamage in a subject, said kit comprising: a composition comprising an inventive compound; and instructions for using the composition to prevent photodamage. In certain embodiments, the composition is formulated for topical administration. In certain embodiments, the inventive compound is present in an amount effective to inhibit Map/Erk kinase. In certain embodiments, the instructions comprise directions to apply the composition to the skin prior to sun exposure. In certain exemplary embodiments, the composition further comprises a cosmetic ingredient. In certain exemplary embodiments, the cosmetic ingredient is a fragrance. In certain other exemplary embodiments, the cosmetic ingredient is a sunscreen.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, creams or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions, which can be used, include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

In certain embodiments, after application of the topical formulation to the epidermis, the area may be covered with a dressing. The term "dressing", as used herein, means a covering designed to protect a topically applied drug formulation. "Dressing" includes coverings such as a bandage, which may be porous or non-porous and various inert coverings, e.g., a plastic film wrap or other non-absorbent film. The term "dressing" also encompasses non-woven or woven coverings, particularly elastomeric coverings, which allow for heat and vapor transport. These dressings allow for cooling of the treated area, which provides for greater comfort.

In certain exemplary embodiments, pharmaceutically acceptable topical formulations of the invention are contained in a patch that is applied adjacent to the area of skin to be treated. As used herein a "patch" comprises at least a topical formulation and a covering layer, such that, the patch can be placed over the area of skin to be treated. Preferably, but not necessarily, the patch is designed to maximize drug delivery through the stratum corneum and into the epidermis or dermis, reduce lag time, promote uniform absorption, and/or reduce mechanical rub-off. In certain embodiments, when the intended use comprises the treatment of a skin condition (e.g., psoriasis), the patch is designed to minimize absorption into the circulatory system. Preferably, the patch components resemble the viscoelastic properties of the skin and conform to the skin during movement to prevent undue shear and delamination. Advantages of a patch comprising the topical formulation of the invention over conventional methods of administration include (i) that the dose is controlled by the patch's surface area, (ii) constant rate of administration, (iii) longer duration of action (the ability of to adhere to the skin for 1, 3, 7 days or longer), (iv) improved patient compliance, (v) non-invasive dosing, and (vi) reversible action (i.e., the patch can simply be removed).

In certain embodiments, a patch suitable for use with the invention contains at least: (1) a backing layer and (2) a carrier formulated with a compound of the invention. Examples of patch systems suitable for practicing the invention include, but are not limited to, matrix-type patches; reservoir-type patches; multi-laminate drug-in-adhesive-type patches; and monolithic drug-in-adhesive type-patch. See, for example Ghosh, T. K.; Pfister, W. R.; Yum, S. I. Transdermal and Topical Drug Delivery Systems, Interpharm Press, Inc. p. 249-297, which is incorporated herein by reference in its entirety. These patches are well known in the art and generally available commercially.

The matrix patch comprises matrix containing an inventive compound, an adhesive backing film overlay, and preferably, but not necessarily, a release liner. In some cases, it may be necessary to include a impermeable layer to minimize drug migration into the backing film (e.g., U.S. Pat. No. 4,336,243, incorporated herein by reference). In certain embodiments, the matrix containing the inventive compound is held against the skin by the adhesive overlay. Examples of suitable matrix materials include but are not limited to lipophilic polymers, such as polyvinyl chloride, polydimethylsiloxane, and hydrophilic polymers like polyvinylpyrrolidone, polyvinyl alcohol, hydrogels based on gelatin, or polyvinylpyrrolidone/polyethylene oxide mixtures. Suitable release liners include but are not limited to occlusive, opaque, or clear polyester films with a thin coating of pressure sensitive release liner (e.g., siliconefluorsilicone, and perfluorcarbon based polymers.

The reservoir type patch design is characterized by a backing film coated with an adhesive, and a reservoir compartment comprising a drug formulation preferably, in the form of a solution or suspension, that is separated from the skin by a semipermeable membrane (e.g., U.S. Pat. No. 4,615,699, incorporated herein by reference). The adhesive coated backing layer extends around the reservoir's boundaries to provide a concentric seal with the skin and hold the reservoir adjacent to the skin.

The monolithic drug-in-adhesive patch design is characterized by the inclusion of the drug formulation in the skin contacting adhesive layer, a backing film and preferably, a release liner. The adhesive functions both to release the compound and adhere the compound matrix to the skin. The drug-in-adhesive system does not require an adhesive overlay and thus the patch size is minimized. Also, drug-in-adhesive type patches are thin and comfortable (e.g., U.S. Pat. No. 4,751,087, incorporated herein by reference).

The multi-laminate drug-in-adhesive patch design further incorporates an additional semi-permeable membrane between two distinct drug-in-adhesive layers or multiple drug-in-adhesive layers under a single backing film (Peterson, T. A. and Dreyer, S. J. Proceed. Intern. Symp. Control. Rel. Bioact. Mater. 21: 477-478, incorporated herein by reference).

Semi permeable membranes, useful with the reservoir or multi-laminate patch, include thin non-porous ethylene vinyl acetate films or thin macroporous films of polyethylene employed in microlaminate solid state reservoir patches.

Adhesives for use with the drug-in-adhesive type patches are well known in the art and a practitioner skilled in the relevant art would know how to select an adhesive suitable for the intended use. Examples of adhesives include, but are not limited to, polyisobutylenes, silicones, and acrylics. Preferably, adhesives can function under a wide range of conditions, such as, high and low humidity, bathing, sweating etc. Preferably the adhesive is a composition based on natural or synthetic rubber; a polyacrylate such as, polybutylacrylate, polymethylacrylate, poly-2-ethylhexyl acrylate; polyvinylacetate; polydimethylsiloxane; pressure sensitive acrylic adhesives, for example Durotak.RTM. adhesives (e.g., Durotak.RTM. 2052, National Starch and Chemicals) or hydrogels (e.g., high molecular weight polyvinylpyrrolidone and oligomeric polyethylene oxide). The adhesive may contain a thickener, such as a silica thickener (e.g., Aerosil, Degussa, Ridgefield Park, N.J.) or a crosslinker such as, aluminumacetylacetonate.

Backing films may be occlusive or permeable and may be derived from synthetic polymers like polyolefin oils polyester, polyethylene, polyvinylidine chloride, and polyurethane or from natural materials like cotton, wool, etc. Occlusive backing films, such as synthetic polyesters, result in hydration of the outer layers of the stratum corneum while non-occlusive backings allow the area to breath (i.e., promote water vapor transmission from the skin surface).

Selection of the appropriate dosage for the application site is an important consideration. The rate of compound intradermal administration from the topical formulation or patch is a function of skin permeability, and skin permeability has been shown to vary between anatomical sites depending on the thickness of the stratum corneum. For example, the permeability, in general, increases in order from planter foot arch, lateral ankle, palm, ventral forearm, dorsal forearm, back, chest, thigh, abdomen, scalp, axilla, forehead, and scrotum (Wester, R. C. and Maibach, H. I. (1989) Regional variation in Percutaneous Absorption: In Percutaneous Absorption, Mechanism, Methodology, Drug Delivery, $2^{nd}$ ed., Eds. R. L. Bronaugh and H. I. Maibach, Marcel Dekker, Inc., New York, pp. 111-119 (incorporated herein by reference)). Typically, the dosages and dosing frequency will be determined by a trained medical professional.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent, anticancer agent or agent useful for the treatment of psoriasis), or they may achieve different effects (e.g., control of any adverse effects).

For example, other therapies or anticancer agents that may be used in combination with the inventive compounds of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (CM) website (www.nci.nih.gov) and the Food and Drug Administration (FDA) website for a list of the FDA approved oncology drugs (www.fda.gov/cder/cancer/druglistframe—See Appendix A).

In certain embodiments, the pharmaceutical compositions of the present invention further comprise one or more additional therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

In certain embodiments, compounds of the invention are useful for the treatment of psoriasis and pharmaceutical compositions containing them may be administered in combination with any of the antipsoriatic therapies or therapeutic agents known in the art. For example, therapies or antipsoriatic agents that may be used in combination with the inventive compounds of the present invention include Ultraviolet light treatment (e.g., sunlight), lubricants, keratolytics, emollients (e.g., Aqueous Cream, E45, and Emulsifying ointment), ammoniated mercury, topical vitamin D analogs (e.g., Calcipotriol (Dovonex), Tacalcitol (Curatoderm)), dithranol (e.g., Dithrocream and Miconal), tar (e.g., Alphosyl, anthralin), topical steroids (e.g., corticosteroids, halobetasol), topical retinoids (e.g., zorac, Tazarotene), systemic antimetabolites (e.g., oral methotrexate), immunosuppressive drugs (e.g., oral cyclosporine, tacrolimus, mycophenolate, and mofetil) and oral retinoids (e.g., acitretin).

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a a well-established literature of macrolide chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/ or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

Certain exemplary compounds of the invention are listed below and are referred to by compound number as indicated.

B2193
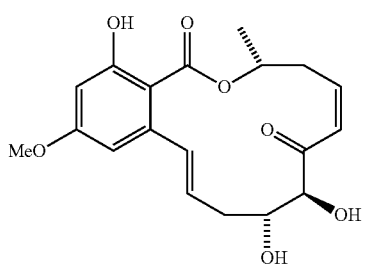
Racemic
B2194
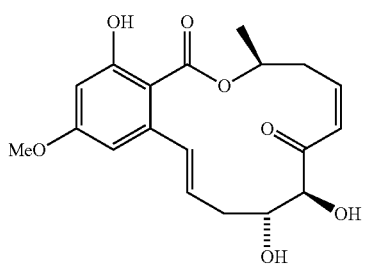
Racemic
B2215
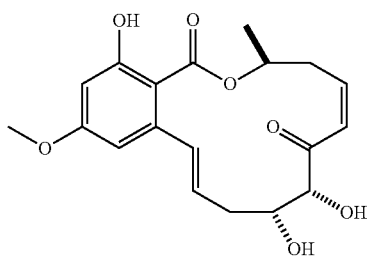
B2292
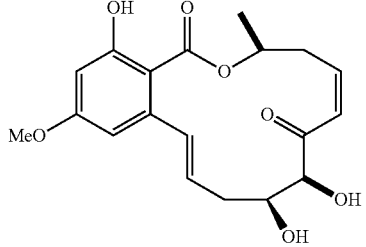
B2293
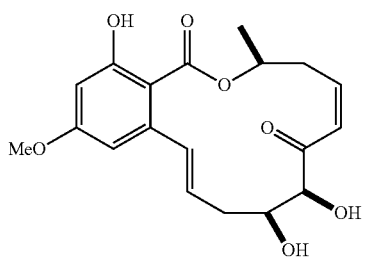
B2297
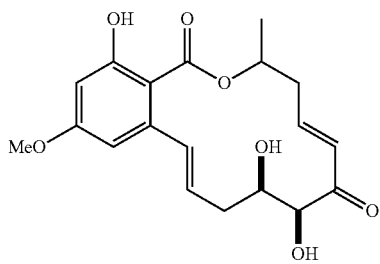
B2329
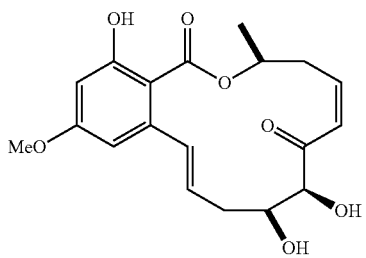
B2331
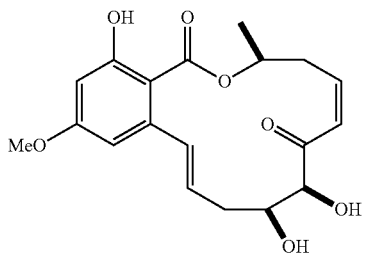
B2337
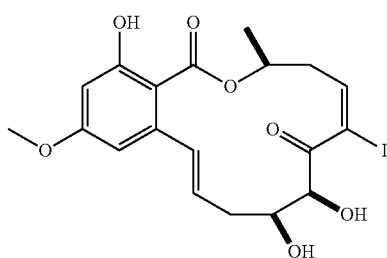
B2338
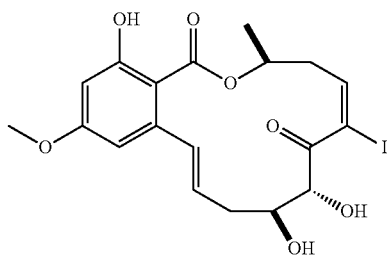
B2356
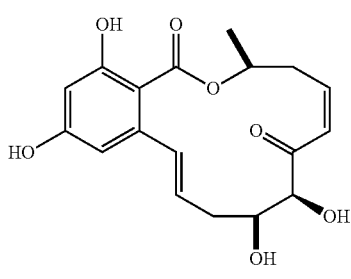
B2357
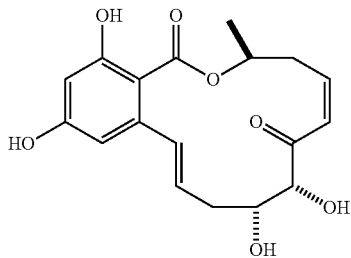

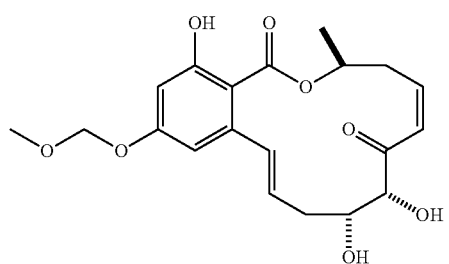
B2358
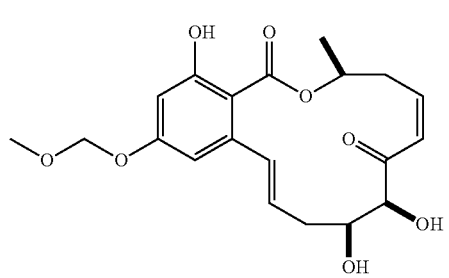
B2359
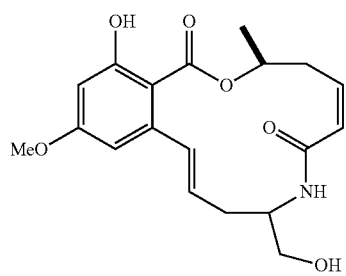
B2366&B2365
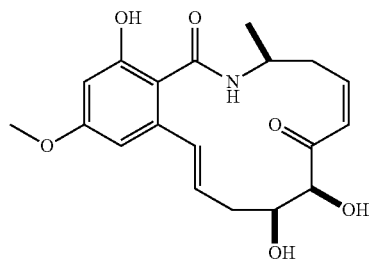
B2395
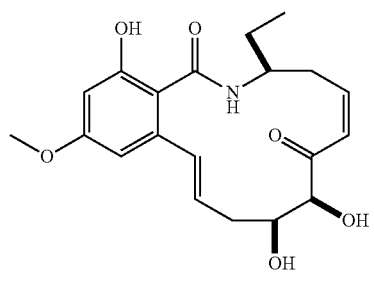
B2396
racemic
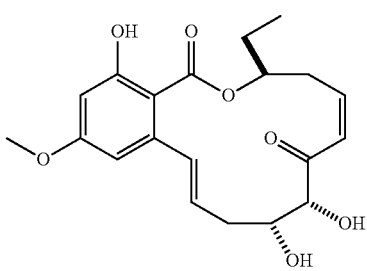
B2397
Racemic
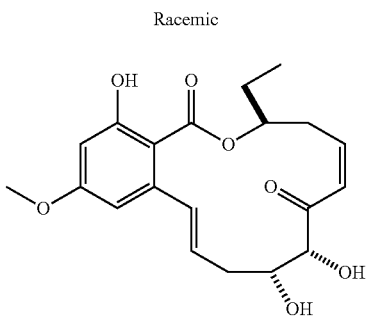
B2500
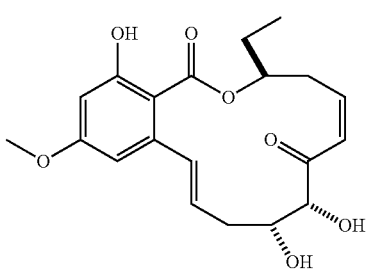
B2501
single enantimer
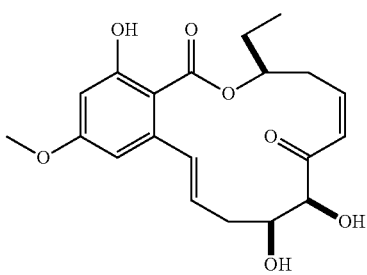
B2522
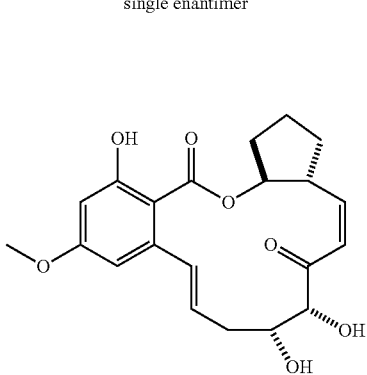
B2526
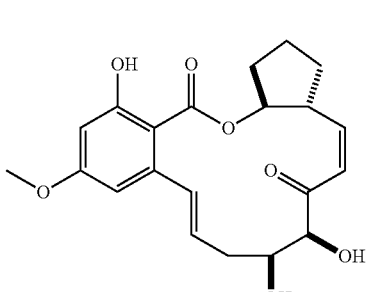

B2538
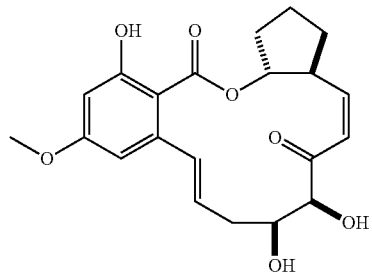
B2543
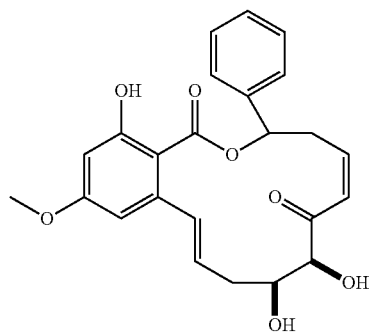
racemic diasteriomer 1
B2544
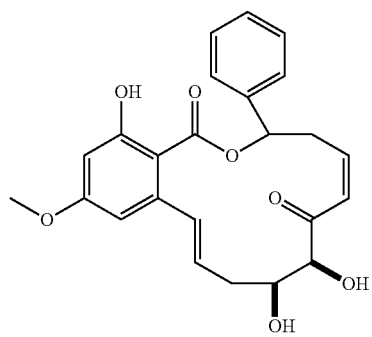
racemic diasteriomer 2
B2545
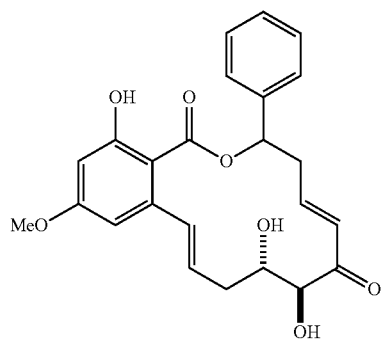
Racemic isomer 1
ER803026
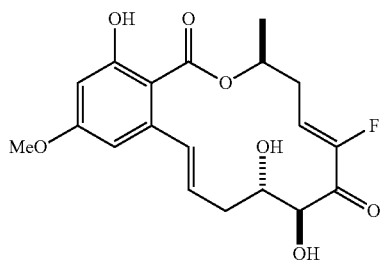
ER803029
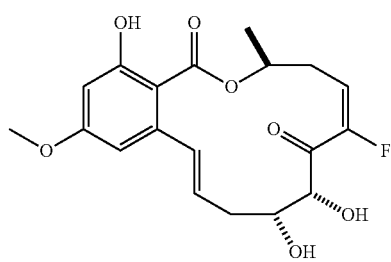
ER803030
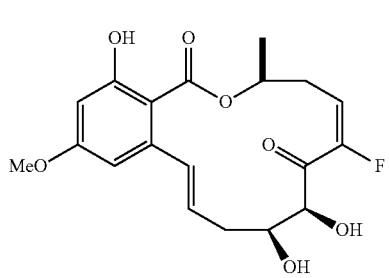
ER803064
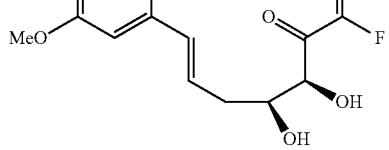
ER803591
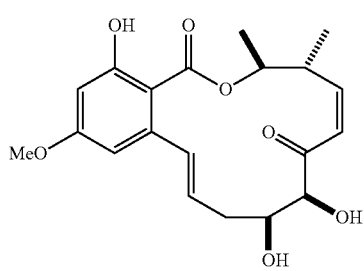
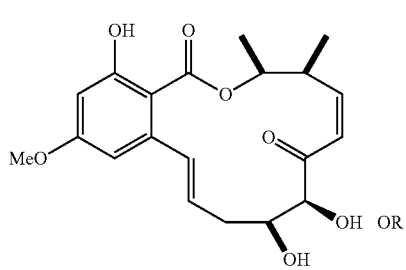
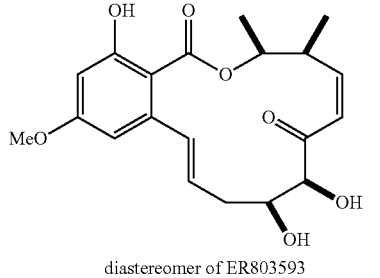
diastereomer of ER803593

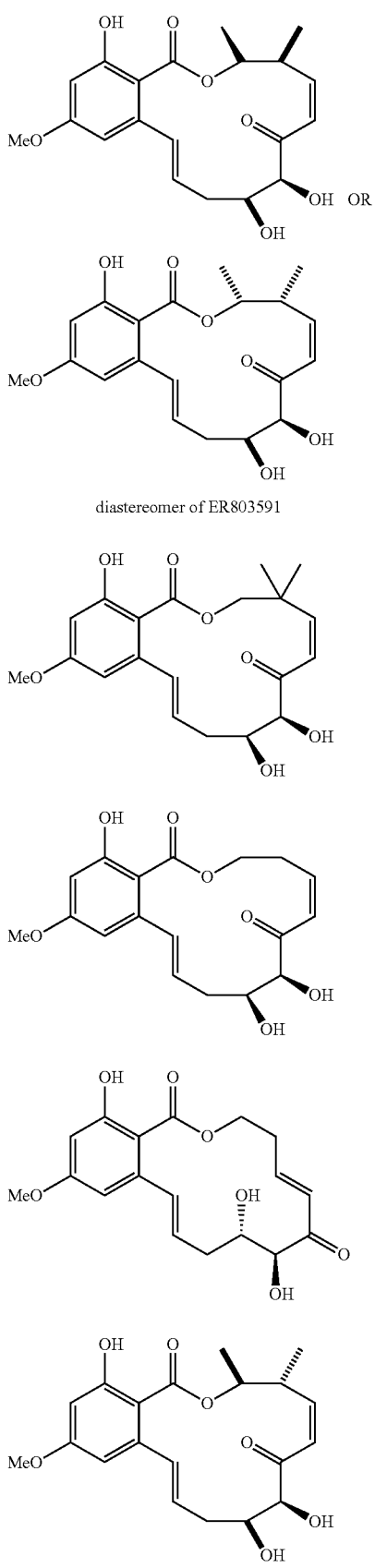
ER803593
diastereomer of ER803591
ER803604
ER803734
ER803758
ER803829
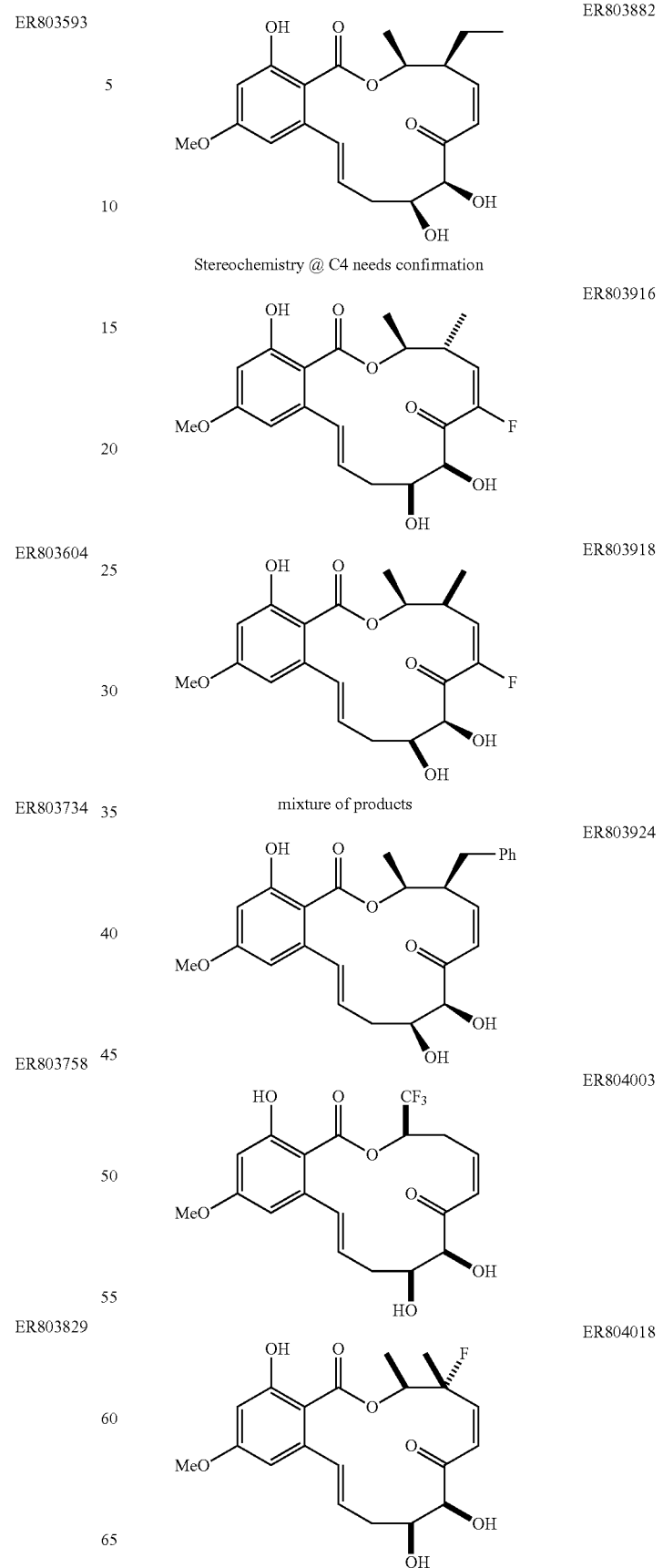
ER803882
Stereochemistry @ C4 needs confirmation
ER803916
ER803918
mixture of products
ER803924
ER804003
ER804018

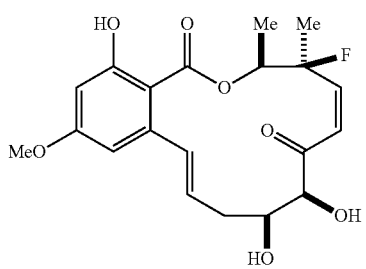
ER804019
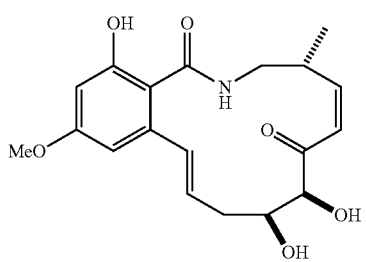
ER804022
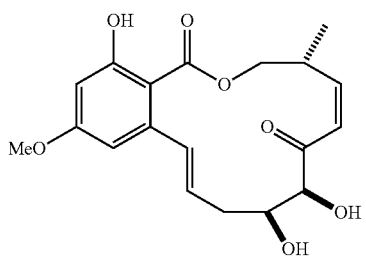
ER804035
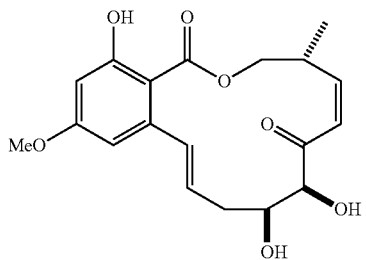
ER804060
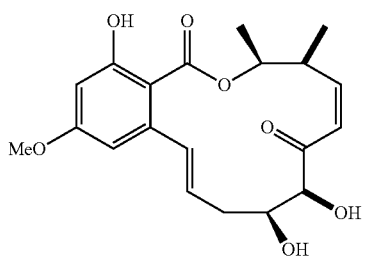
ER804103
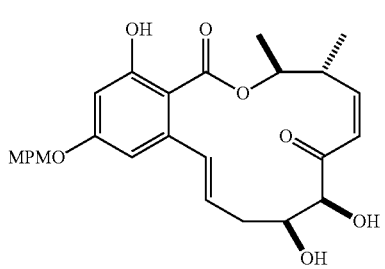
ER804104
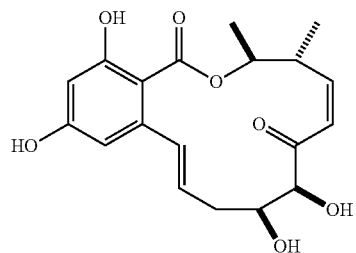
ER804131
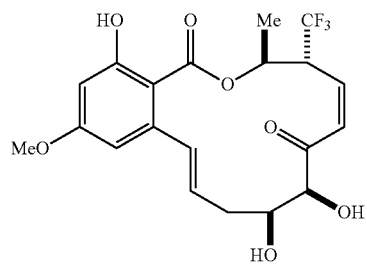
ER804142
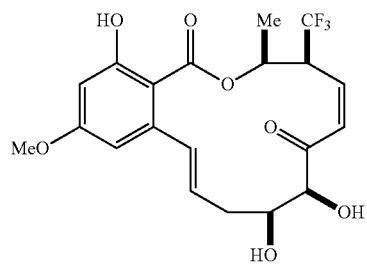
ER804143
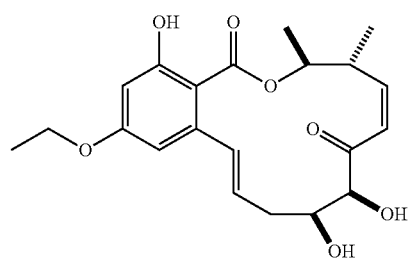
ER804168
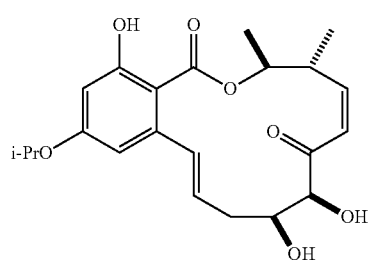
ER804189
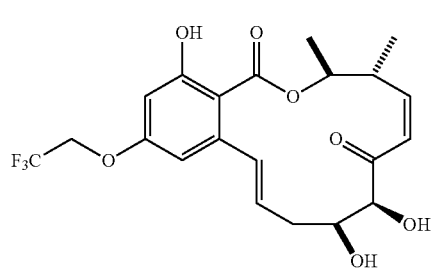
ER804387

ER804401
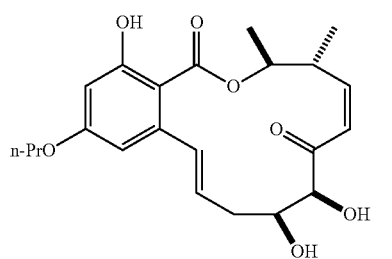
ER804428
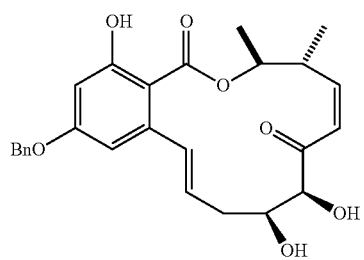
ER804446
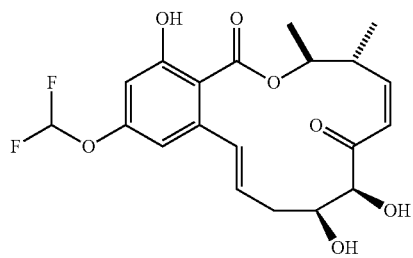
ER804504
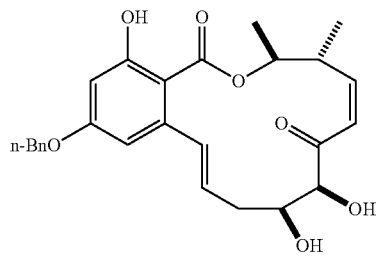
ER804505
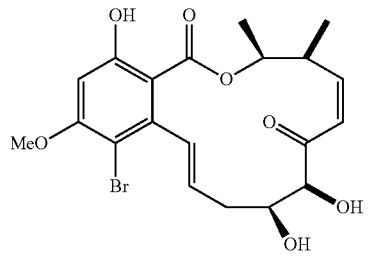
ER804555
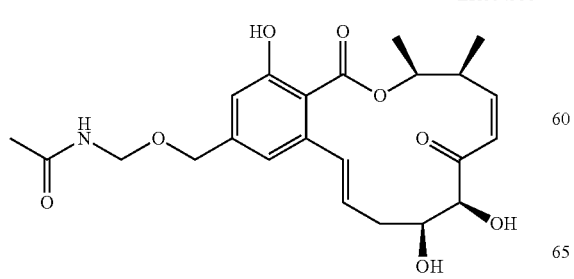
ER804556
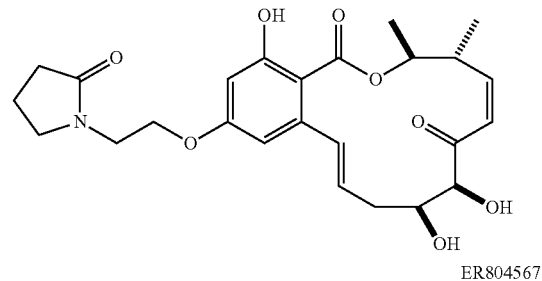
ER804567
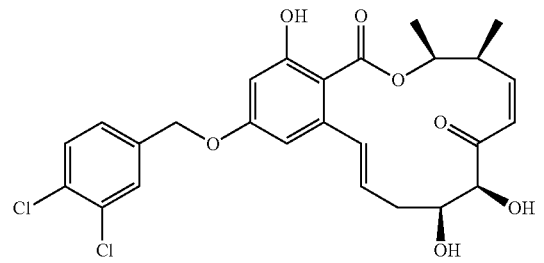
ER804584
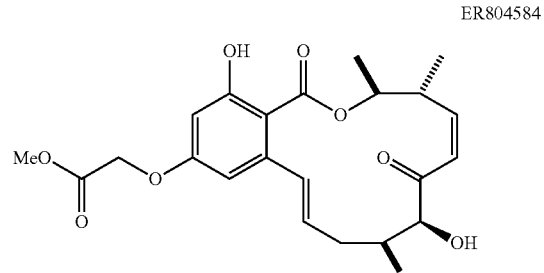
ER804595
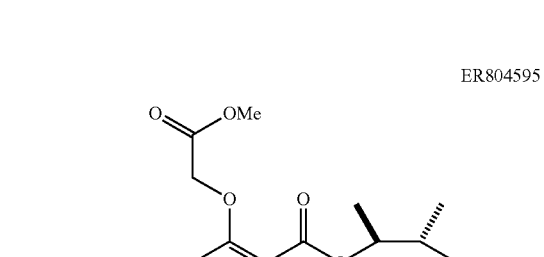
ER804606
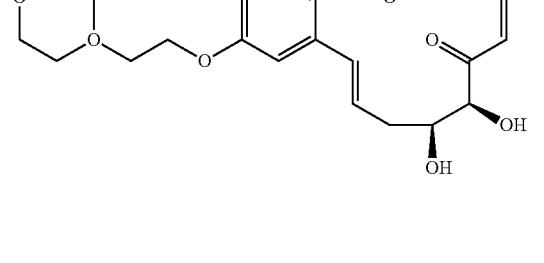

ER804622
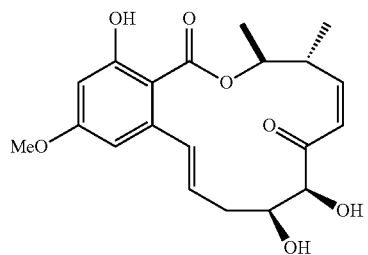
ER804630
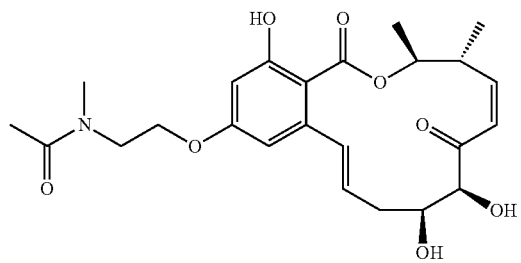
ER804710
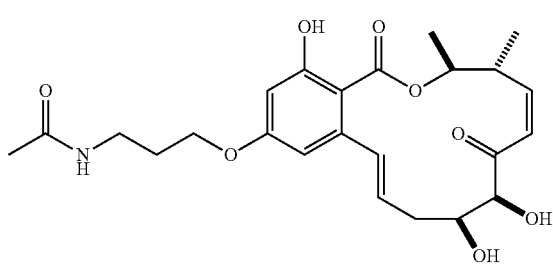
ER804730
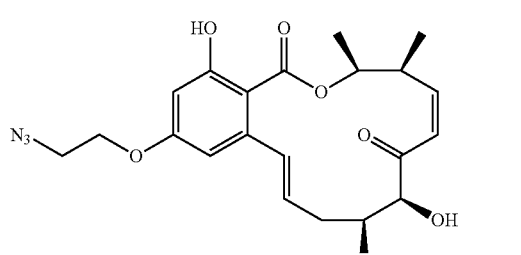
ER804731
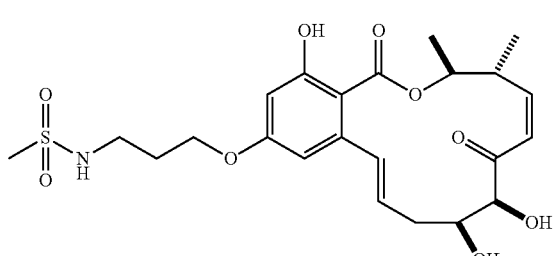
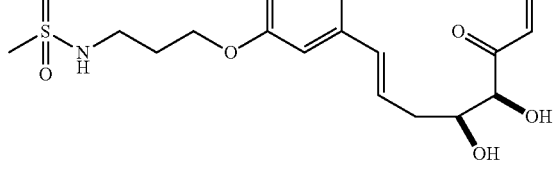
ER804734
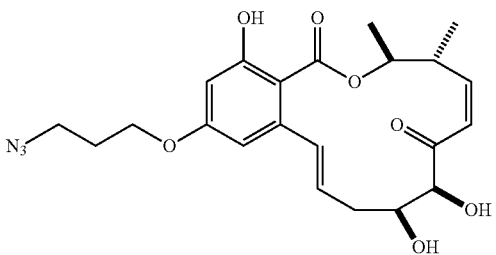
ER804744
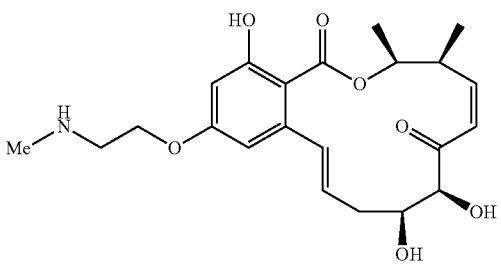
ER804745
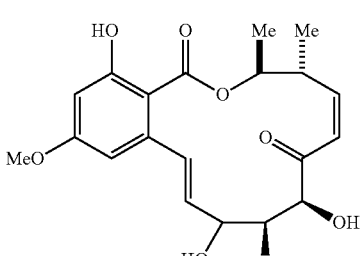
ER804746
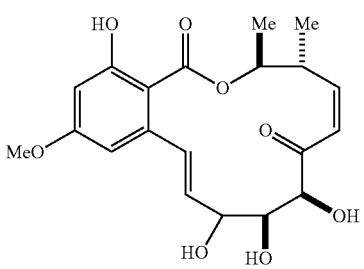
ER804747
ER804755 & ER804756
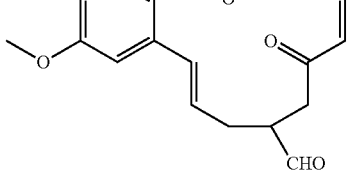

75
-continued
ER804758
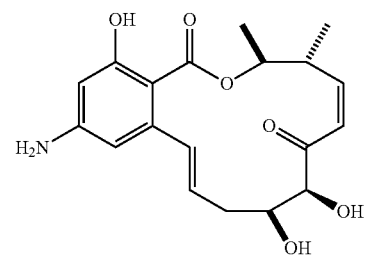
ER804759
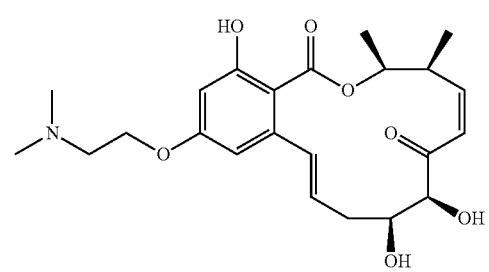
ER804778
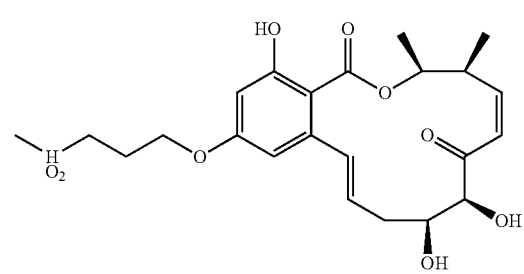
ER804779
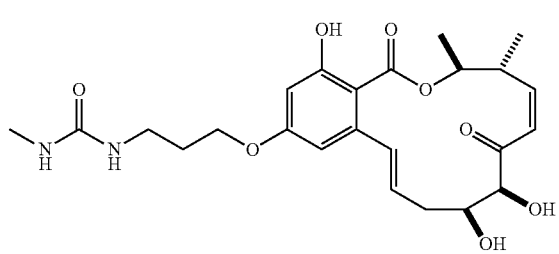
ER804784
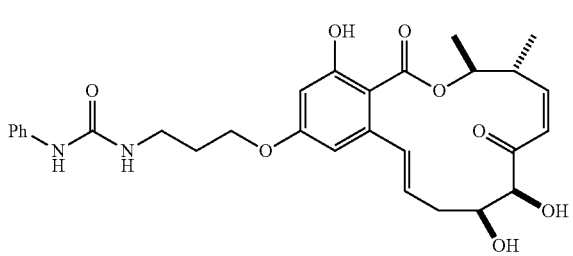
ER804793
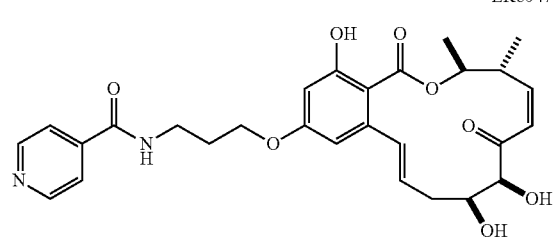
76
-continued
ER804863
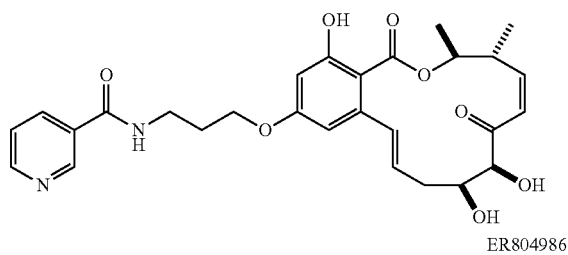
ER804986
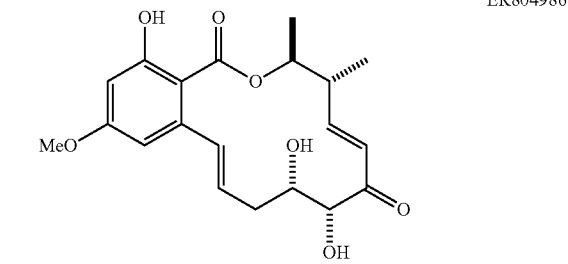
ER805023
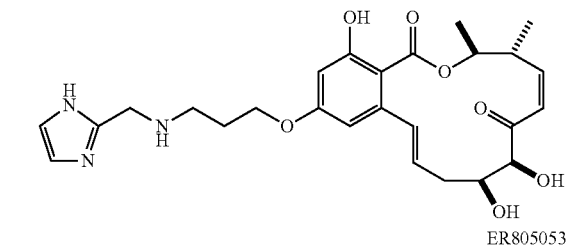
ER805053
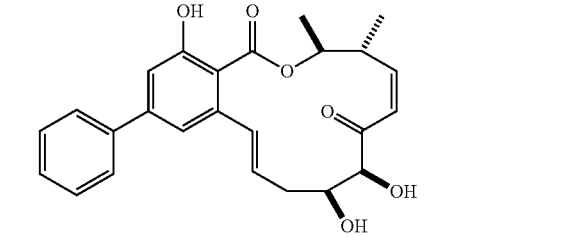
ER805125
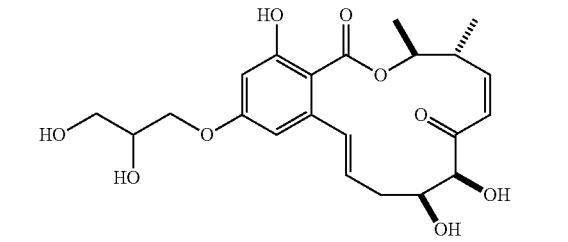
ER805135
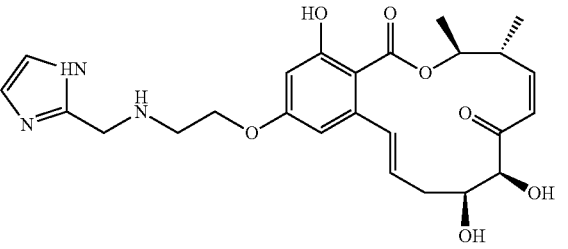

77
-continued
ER805146
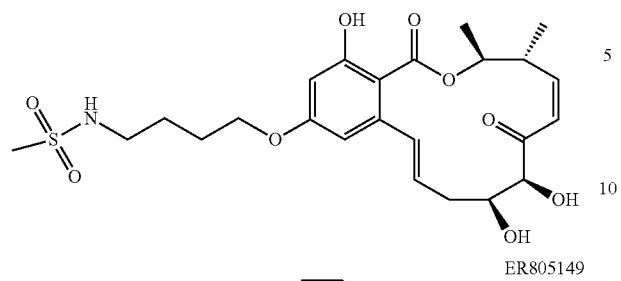
ER805149
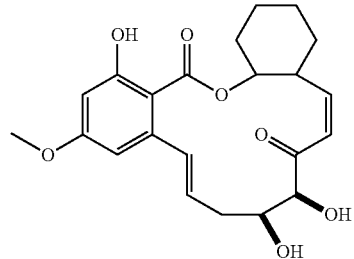
ER805189
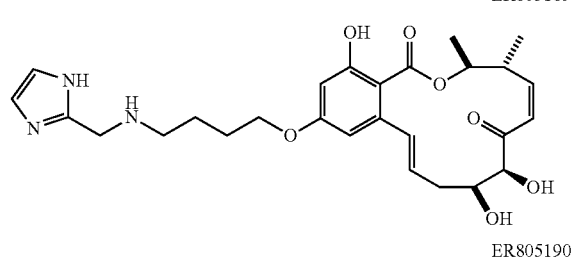
ER805190
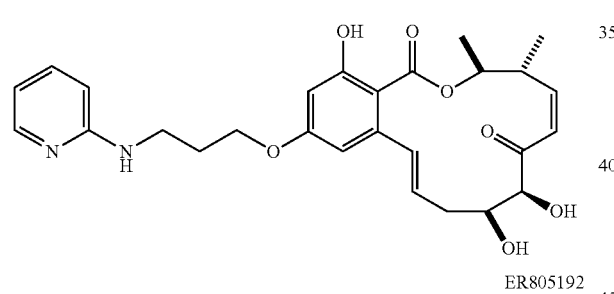
ER805192
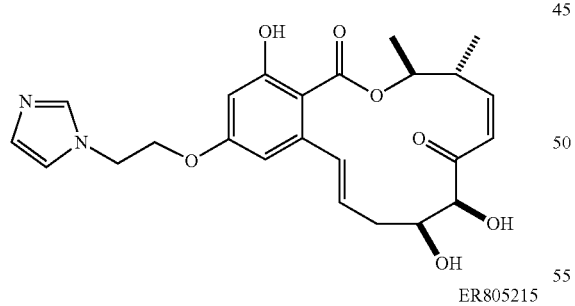
ER805215
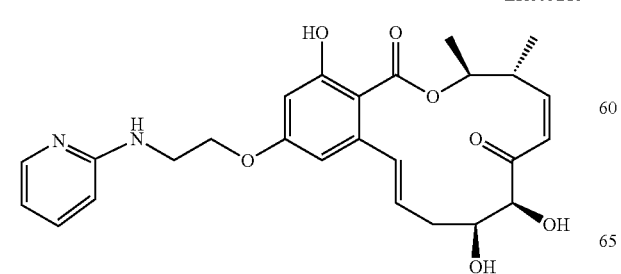
78
-continued
ER805216
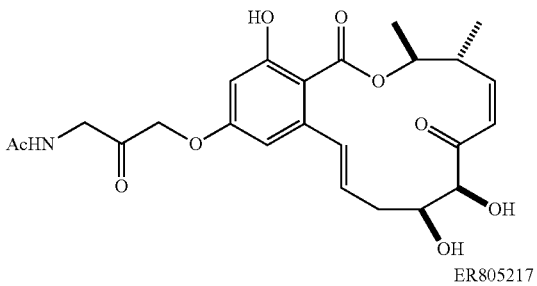
ER805217
ER805218
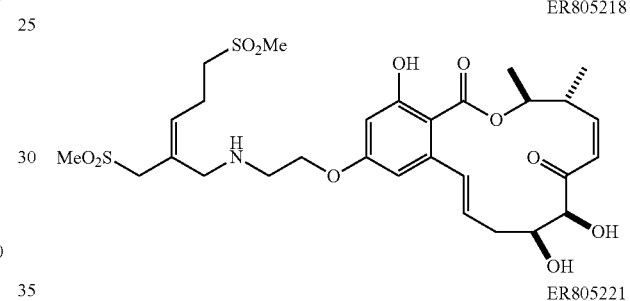
ER805221
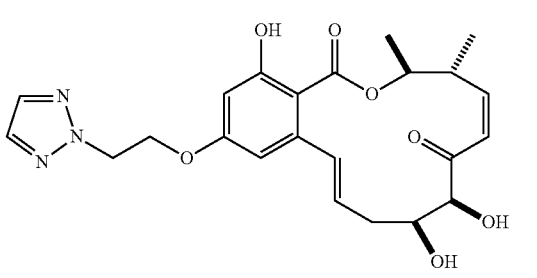
ER805223
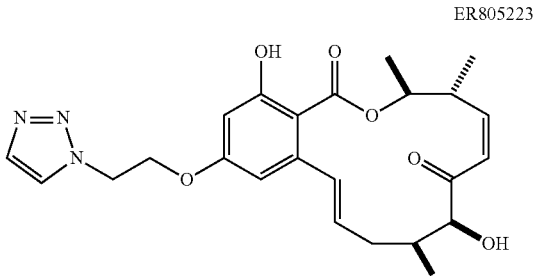
ER805227
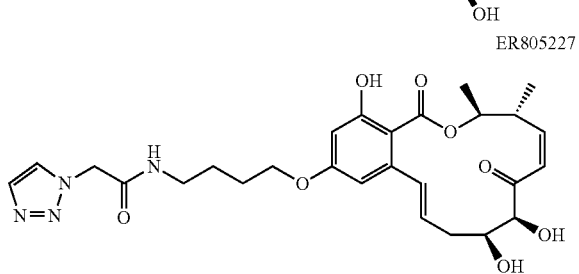

79
-continued
ER805228
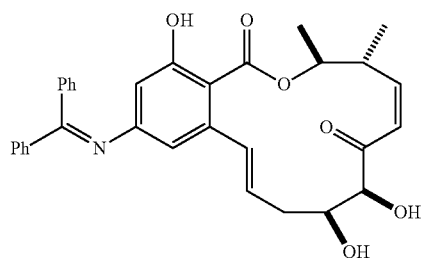
ER805229
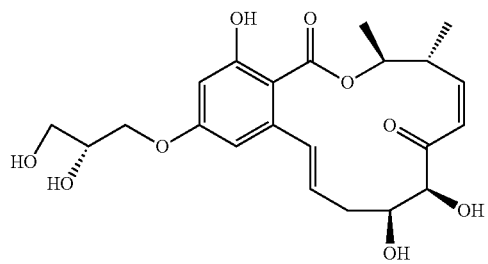
ER805232
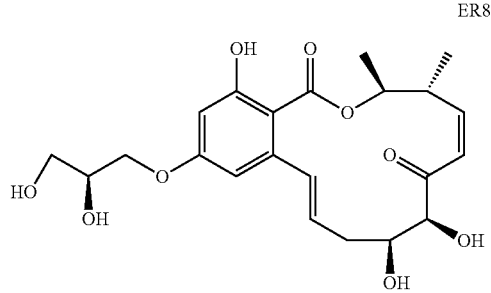
ER805233
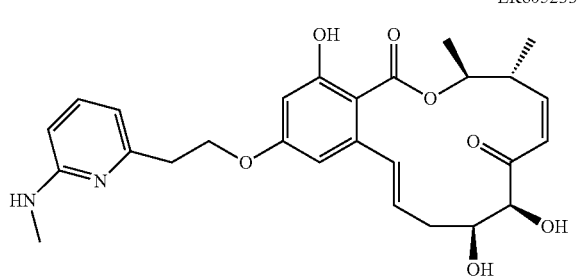
ER805709
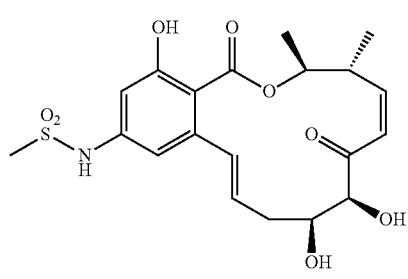
ER805855
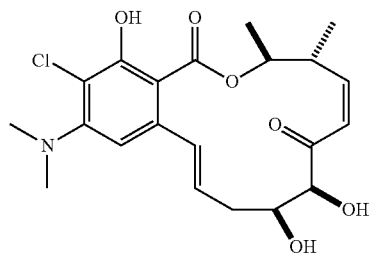
80
-continued
ER805882
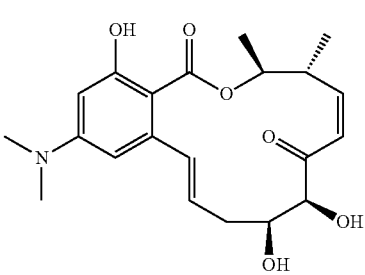
ER805911
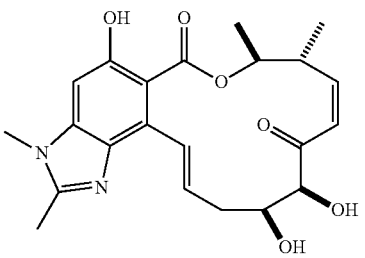
ER805940
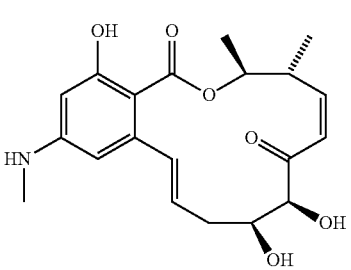
ER805977
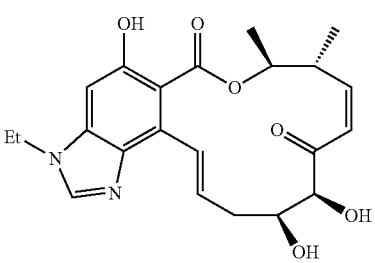
ER805998
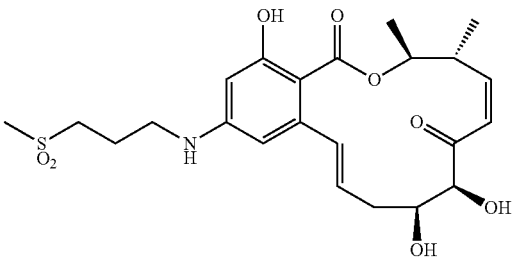
ER806201
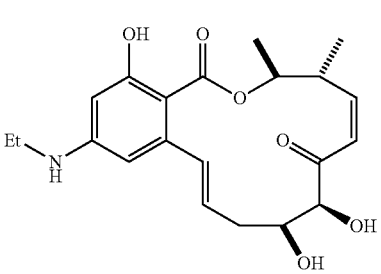

ER806203
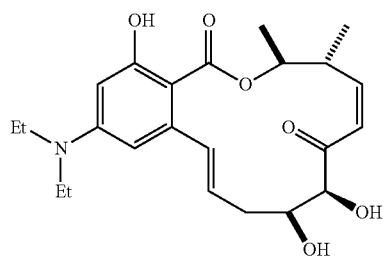
ER806204
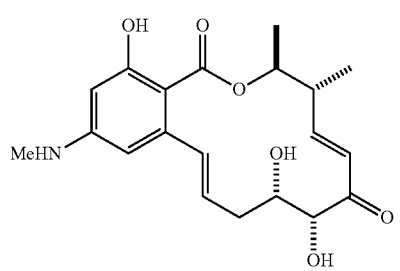
ER806328
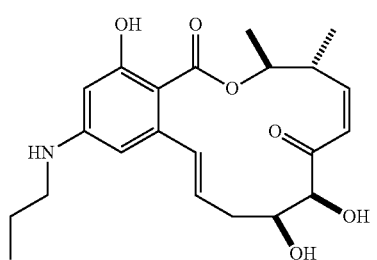
ER8066563
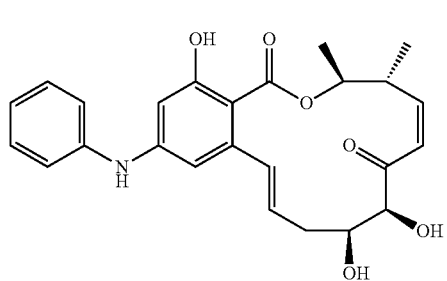
ER806621
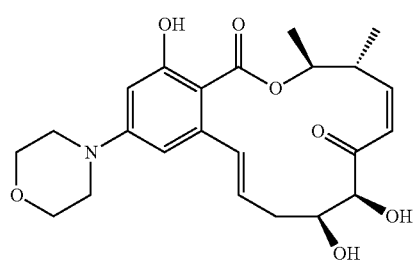
ER806624
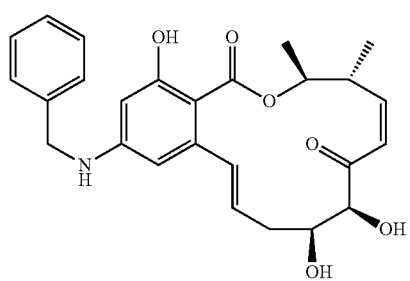
ER806752
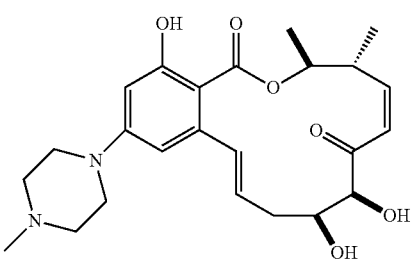
ER806776
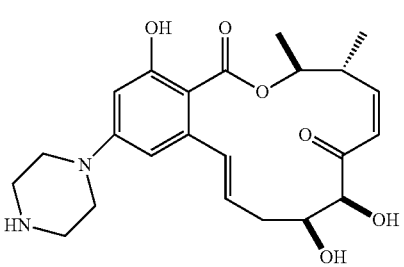
ER806795
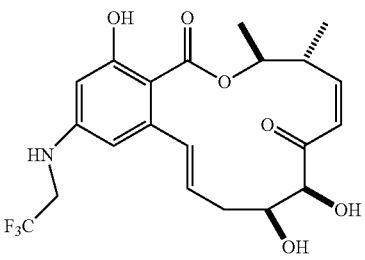
ER806821
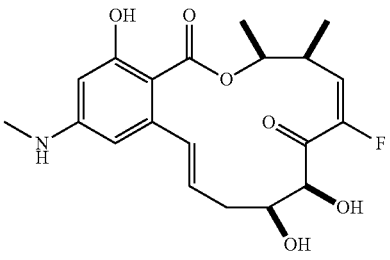
ER806907
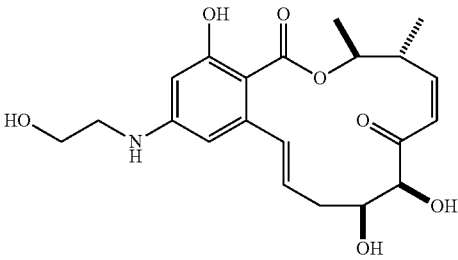
ER807209
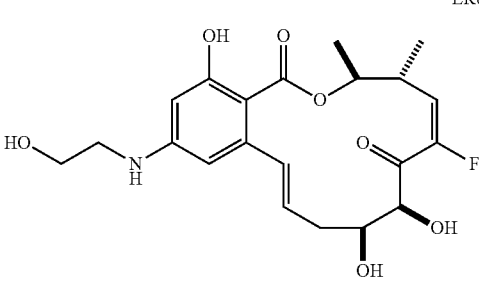

-continued
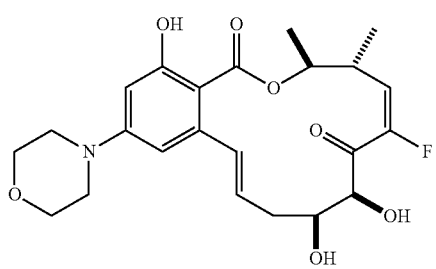
ER807551
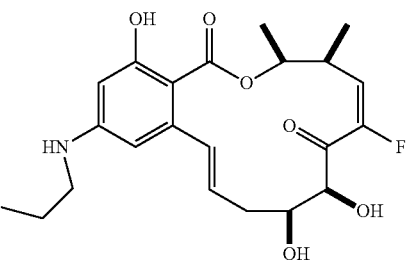
ER890005
ER807563
ER890006
ER808064
ER890007
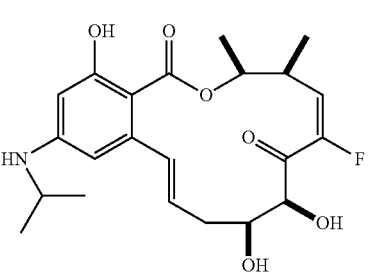
ER808129
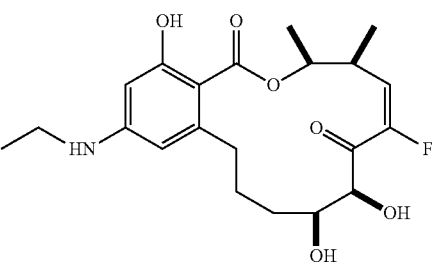
ER890003
ER890008
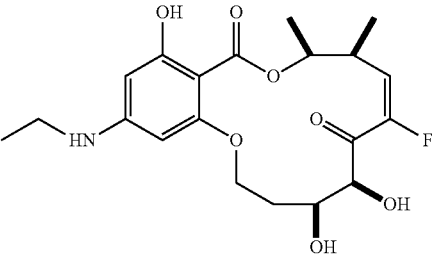
ER890004
ER890009
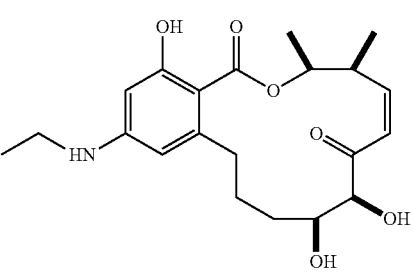

85
-continued
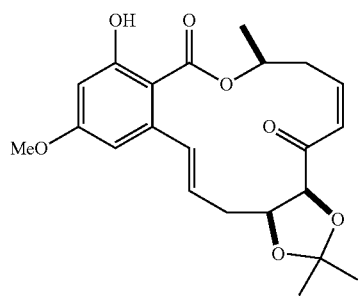
F152acetonite
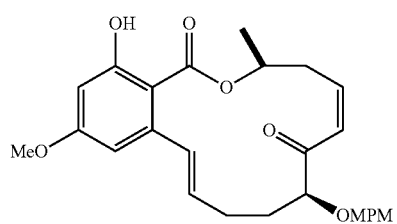
NF0530
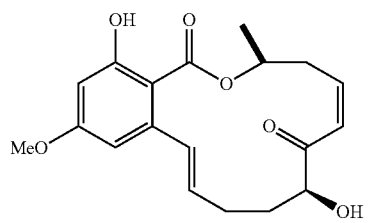
NF0531
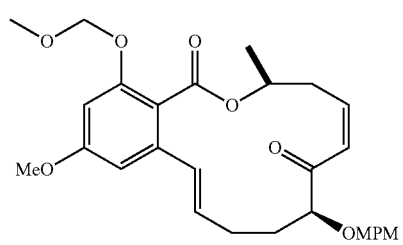
NF0552
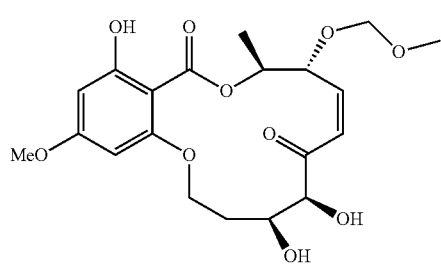
NF0675
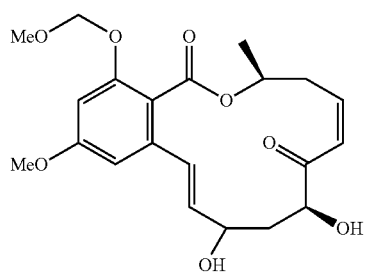
NF0761
86
-continued
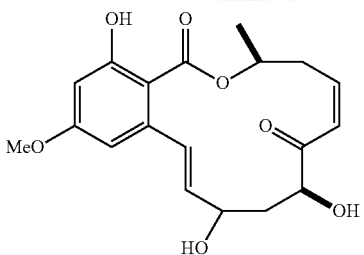
C10 stereochemistry undefined
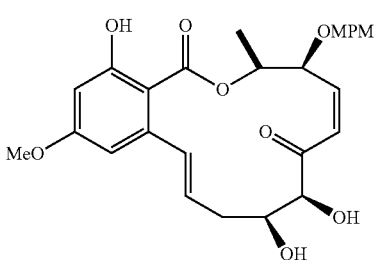
NF0879
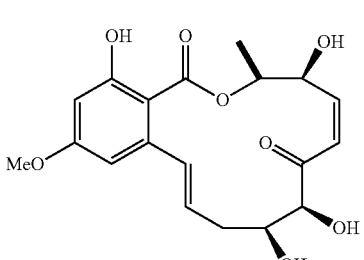
NF0880
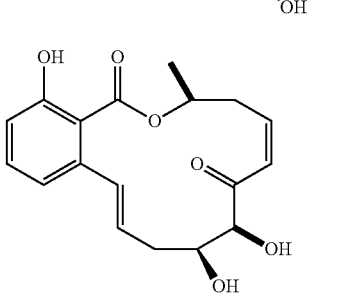
NF0887
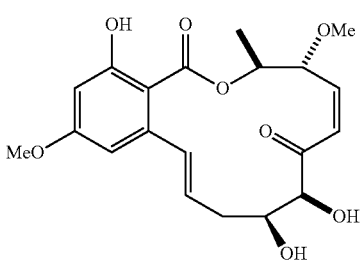
NF0905
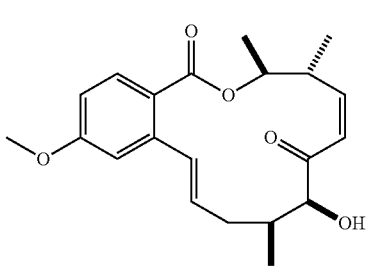
NF0934

-continued
NF1226 and NF1227
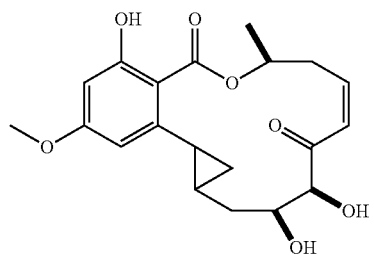
NF1418
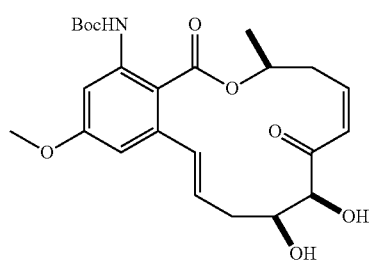
NF1419
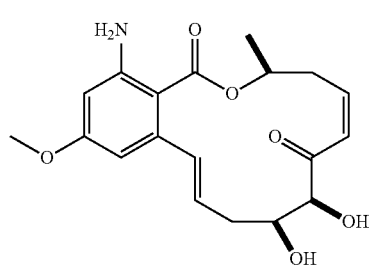
NF1535
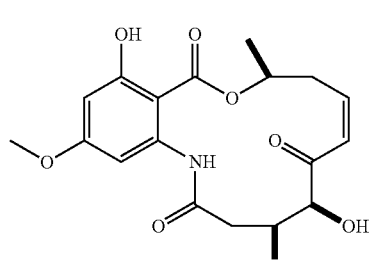
NF1537
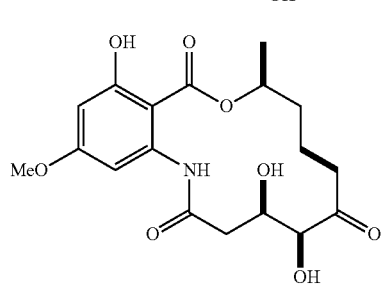
cis/trans, 1:10
NF1774
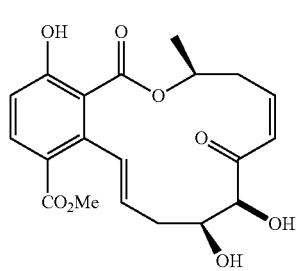
-continued
NF1872
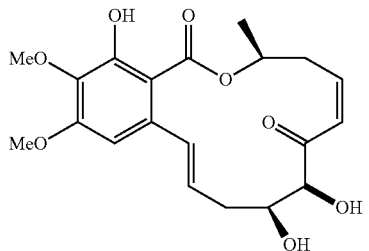
NF2306
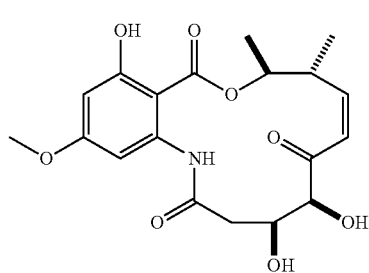
NF2432
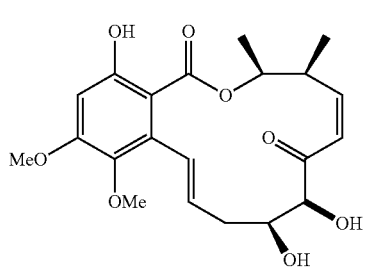
NF2433
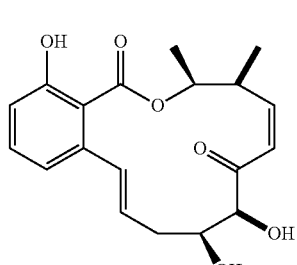
NF2435
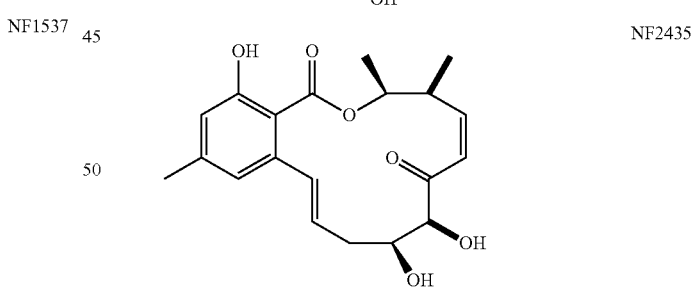
NF2436
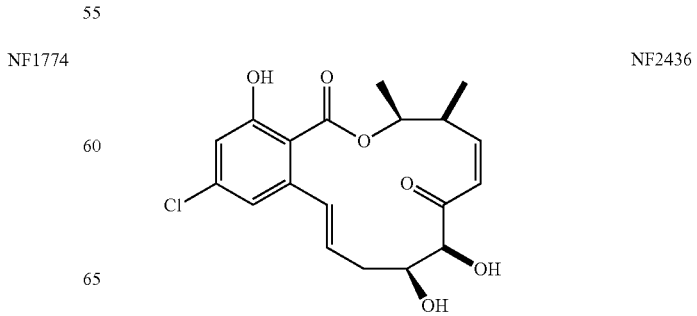

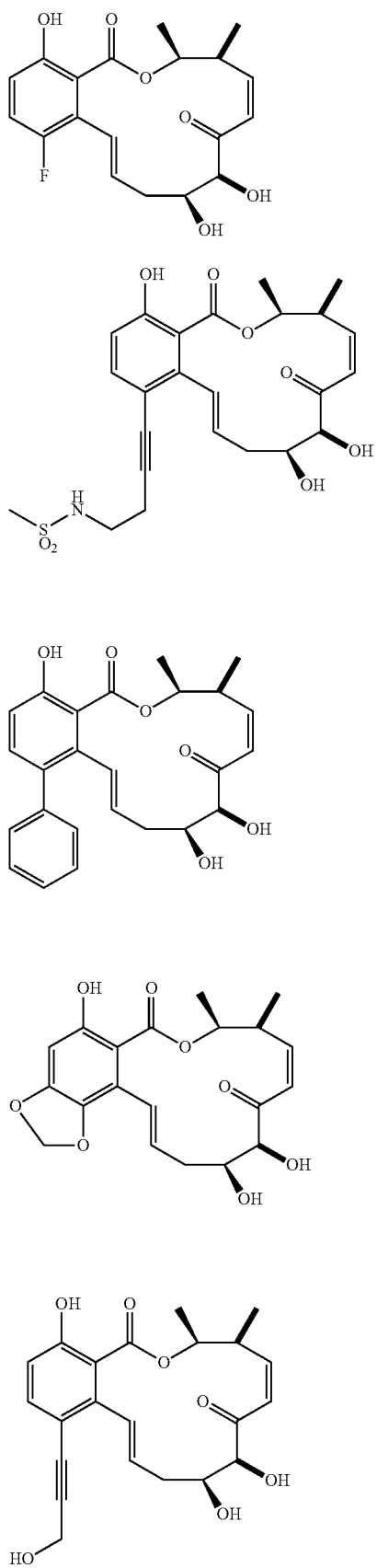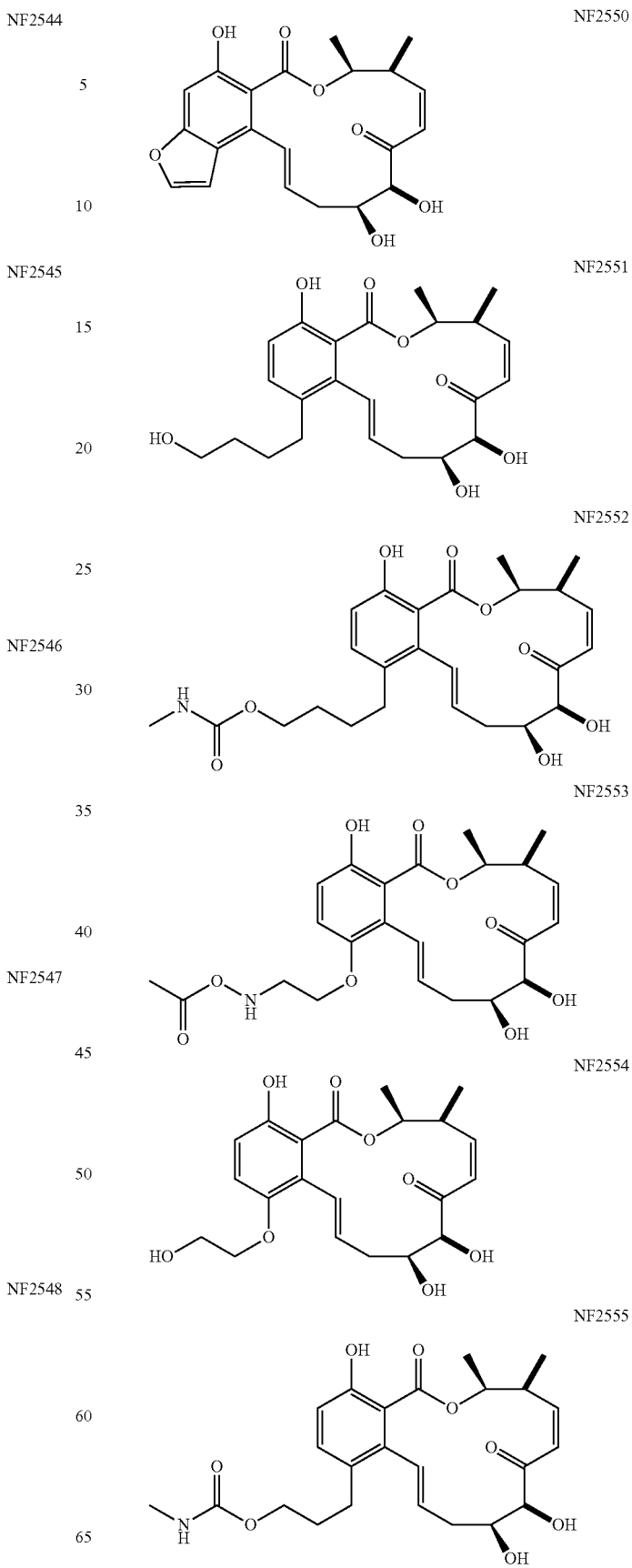

NF2556
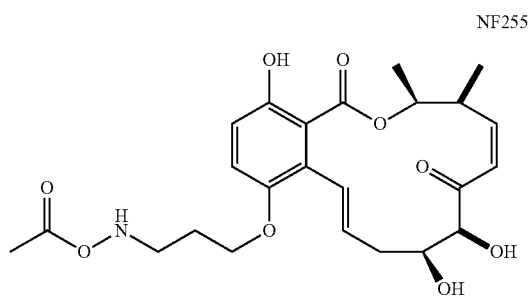

NF2557
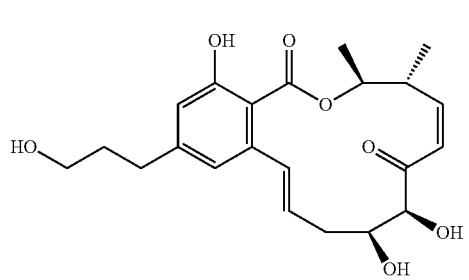

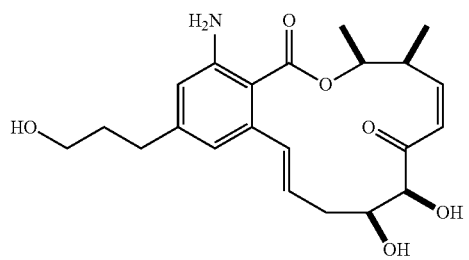

NF2558
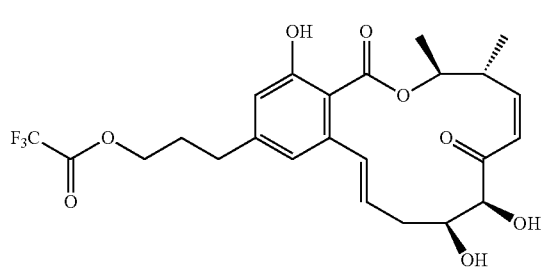

NF2559
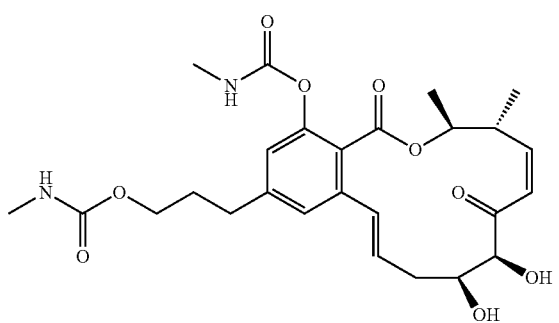

NF2560
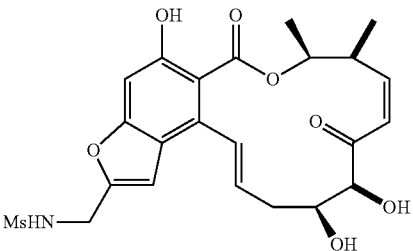

NF2561
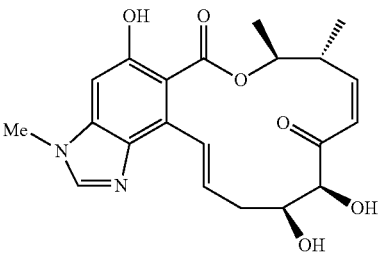

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

Listed below are abbreviations used for some common organic reagents referred to herein:

m-CPBA: meta-chloroperbenzoic acid
DDQ: 2,3-Dichloro-5,6-dicyano-1,4-benzoquinone
DEAD Diethyl azodicarboxylate
DIBAL-H: Diisobutyl aluminum hydride
DMAP: N,N-Dimethylaminopyridine
DMF: N,N-Dimethylformamide
HMPA: Hexamethylphosphoramide
LDA: Lithium diisopropyl amide
LiHMDS: Lithium bis(trimethylsilyl)amide
PCC: Pyridinium chlorochromate
TBAF: Tetrabutylammonium fluoride
THF: Tetrahydrofuran General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

On occasions where triphenylphosphine oxide was a major byproduct of the reaction, the reaction mixture was added directly to a large volume of well-stirred hexane. The resultant precipitate of triphenylphosphine oxide was removed by filtration and the filtrate processed in the usual manner.

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

Synthesis for Commonly Used Intermediates:

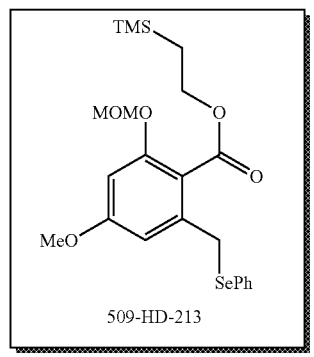

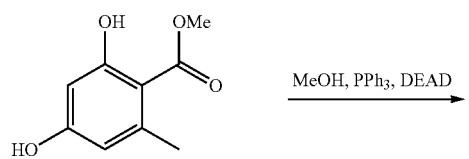

Starting material (50.0 g, 0.27 mol) was dissolved in 650 mL of THF at 0° C. Triphenylphosphine (93.6 g, 0.35 mol) was added, followed by methanol (12.2 mL, 0.30 mol) and diethyl azodicarboxylate (56.2 ml, 0.35 mol). After stirring at 0° C. for 1.5 h, the reaction mixture was concentrated, redissolved in diethyl ether, washed with 1N sodium hydroxide solution. The aqueous layer was acidified with concentrated hydrochloric acid and extracted with diethyl ether. After purification on silica gel column, 42.0 g of 509-HD-207 was obtained as a pale yellow solid in 78% yield.

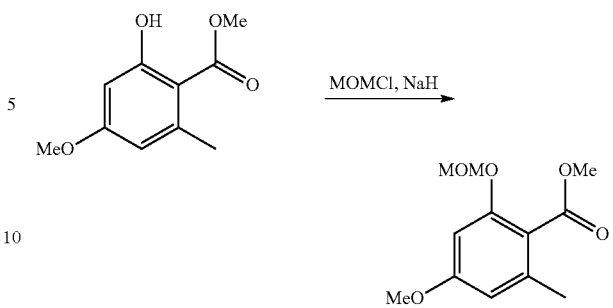

To the reaction flask containing NaH (95%, 14.5 g, 0.57 mol) in 1 L of THF at 0° C. was added 509-HD-207 (75.0 g, 0.38 mol) in 0.5 L of THF. After stirred for 0.5 h, chloromethyl methyl ether (43.6 mL, 0.57 mol) was added. After stirred at 0° C. for 1 h, it was warmed up to room temperature. The reaction was quenched with water and extracted with pentane. After purification on silica gel column, 83 g of 509-HD-209 was obtained as colorless oil in 92% yield.

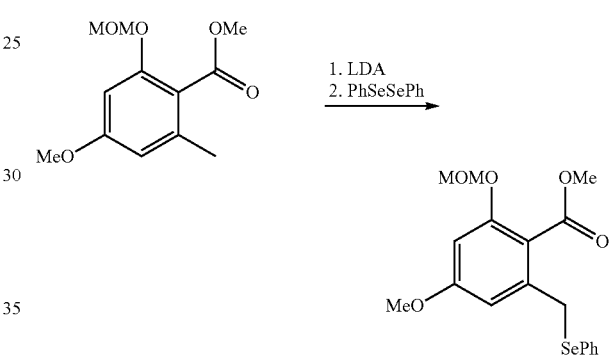

Diisopropyl amine (68.1 mL, 486 mol) was dissolved in 1 L of THF at 0° C. n-BuLi (2.5 M, 207 mL) was added. The solution was stirred for 20 min, and then cooled down to −78° C. The solution of 509-HD-209 (77.8 g, 324 mol) in 250 mL of THF was added slowly. 1 h later the solution of diphenyl diselenide (85.9 g, 275 mol) in 250 ml of THF was added. After stirring at −78° C. for 1 h, the reaction was quenched with saturated ammonium chloride solution, and extracted with diethyl ether. After purification on silica gel column, 90.2 g of 509-HD-211 was obtained as pale yellow oil in 68% yield.

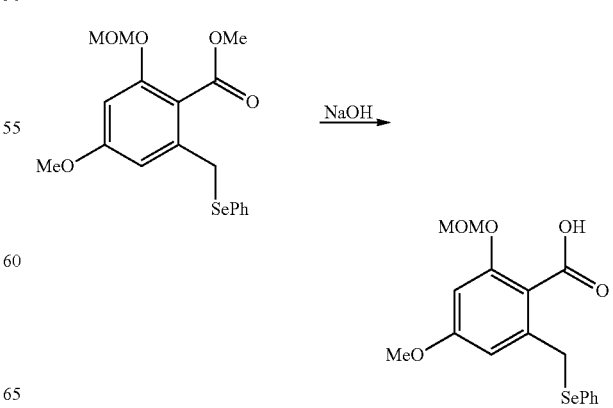

509-HD-211 (90.2 g, 228 mmol) was dissolved in 500 mL of ethanol. Sodium hydroxide solution (1N, 456 mL) was added. The resulting solution was heated under reflux for 12 h. The reaction mixture was acidified with 1N hydrochloric acid, extracted with diethyl ether and concentrated, giving 84.6 g of 509-HD-212 as a pale yellow solid in 97% yield.

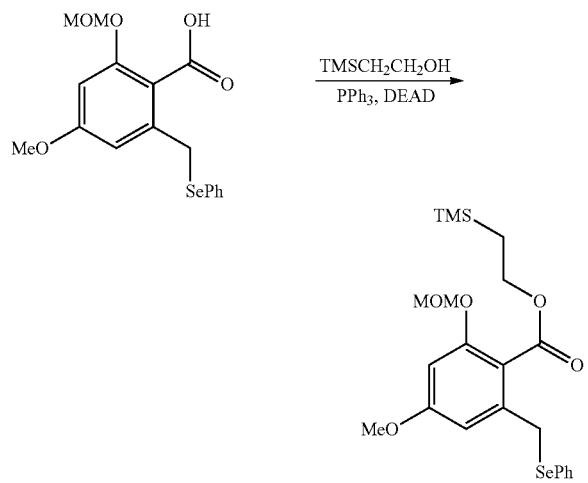

509-HD-212 (84.6 g, 222 mmol) and triphenylphosphine (75.7 g, 289 mmol) was dissolved in a mixture of 500 mL of diethyl ether and 125 mL of toluene at 0° C. 2-(trimethylsilyl) ethanol (38.2 mL, 266 mmol) and diethyl azodicarboxylate (45.4 mL, 289 mmol) were added respectively. After stirred for 10 min, it was warmed up to room temperature. Large amount of pentane was added to precipitate the solid. After filtration, the crude product was purified on silica gel column and 80.0 g of 509-HD-213 was obtained as pale yellow oil in 75% yield.

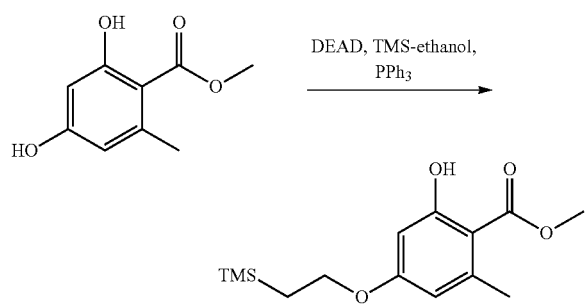

To a solution of starting material (157 g, 0.86 mol) in 1.6 L of toluene (slightly cloudy), TMS-ethanol (150 g, 1.27 mol, 1.48 eq.), and PPh$_3$ (440 g, 1.68 mol, 1.95 eq.) were added. After cooled to 0° C., DEAD (725 mL of 40% solution, 1.29 mol, 1.5 eq.) was slowly added by dropping funnel while maintaining internal temp below 10° C. in three hours. After stirred at rt for 48 h, it was poured into a rapid stirred solution of hexanes (12 L). The solid was filtered through a celite pad and the pad was washed with 1 L of hexanes. The filtrates were combined and concentrated to give the crude product as brown oil. The oil was purified on silica gel with hexanes/EtOAc (15:1, 10:1, 6:1) to give 140 g of product as an off white solid.

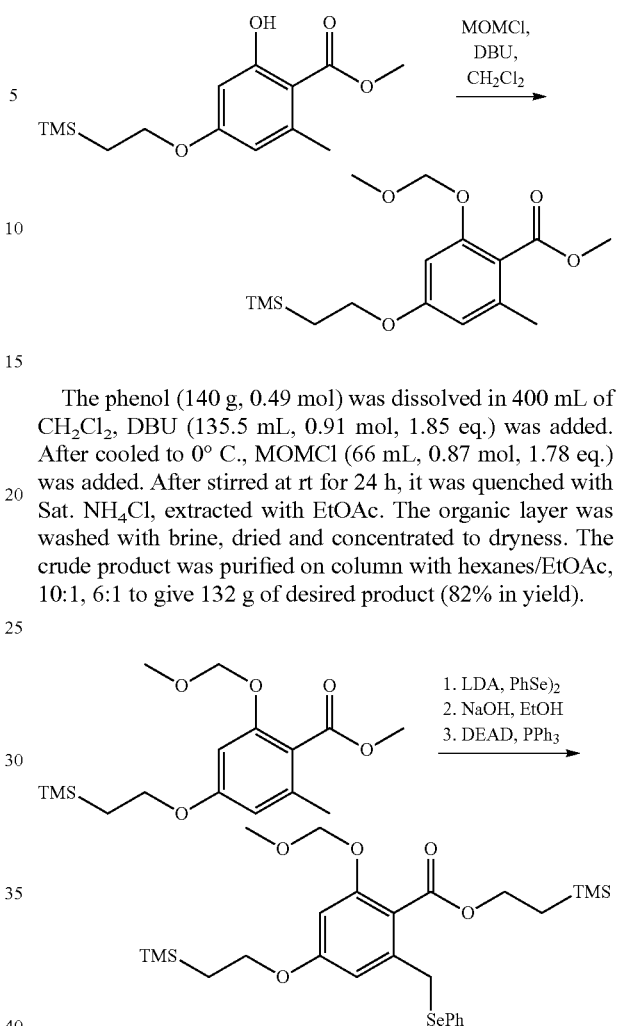

The phenol (140 g, 0.49 mol) was dissolved in 400 mL of CH$_2$Cl$_2$, DBU (135.5 mL, 0.91 mol, 1.85 eq.) was added. After cooled to 0° C., MOMCl (66 mL, 0.87 mol, 1.78 eq.) was added. After stirred at rt for 24 h, it was quenched with Sat. NH$_4$Cl, extracted with EtOAc. The organic layer was washed with brine, dried and concentrated to dryness. The crude product was purified on column with hexanes/EtOAc, 10:1, 6:1 to give 132 g of desired product (82% in yield).

To a solution of diisopropylamine (143.6 mL, 1.02 mol, 2.3 eq.) in 320 mL of THF, n-BuLi (422.6 mL, 2.5 M) was added at 0° C. by addition funnel, while controlling the internal temperature around 5° C. After 5 min at that temperature, the reaction was cooled to −78° C. A solution of starting material (145 g, 0.44 mol) in 475 mL of THF was added by addition funnel while internal temperature controlled at or below −70° C. After addition, it was stirred at −70° C. for 30 min. Then at that temperature, a solution of PhSe$_2$ (140 g, 0.45 mol, 1 eq.) in 400 mL of THF was added by addition funnel. After addition, it was stirred at −78° C. for 45 min. The reaction was quenched with sat. NH$_4$Cl, diluted with EtOAc. It was warmed to rt. The organic layer was washed with brine, dried and concentrated to dryness. The crude product was used without purification for next step.

The crude product from last step was dissolved in 300 mL of EtOH. Then 300 mL of 1N NaOH was added. The reaction was heated at 80° C. overnight. After cooled, it was transferred to a separatory funnel and washed with hexanes. The aq. Layer was acidified at 0° C. with 1N HCl to pH=3. Then it was extracted with EtOAc (3x). The combined organic layers were washed with brine, dried and concentrated to dryness. The crude acid was used for next step without purification.

The esterification was run according to the first step using DEAD (200 g), PPh$_3$ (330 g) and TMS-ethanol (150 g) in 1.4 L of toluene to give 145 g of product after column chromatography.

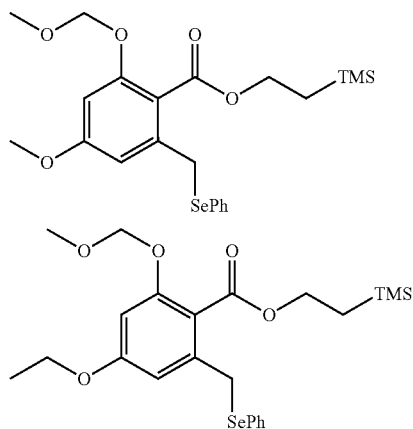

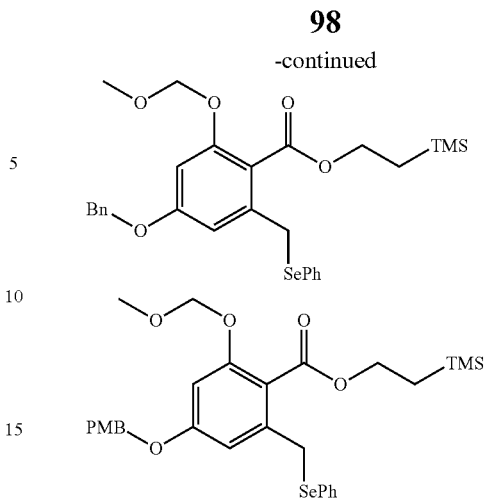

Other C14-substitutions aromatic pieces such as methyl, ethyl, Benzyl, PMB (MPM) etc. were made in analogues manner by substituting the first step with corresponding alcohols such as methanol, ethanol, benzyl alcohol, or PMB alcohol etc.

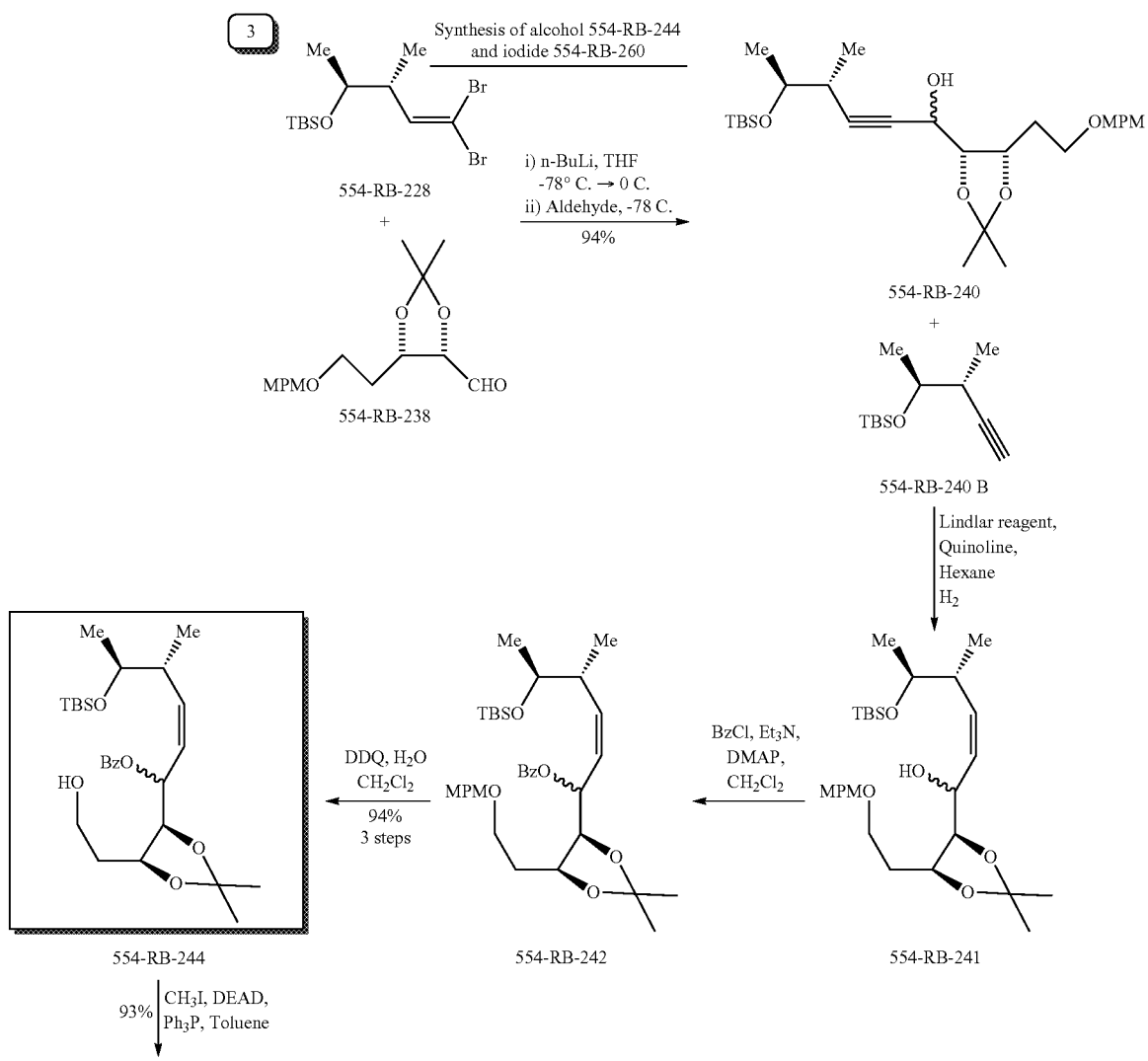

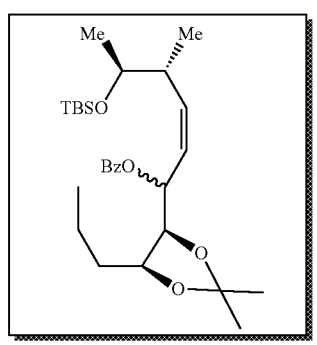

554-RB-260

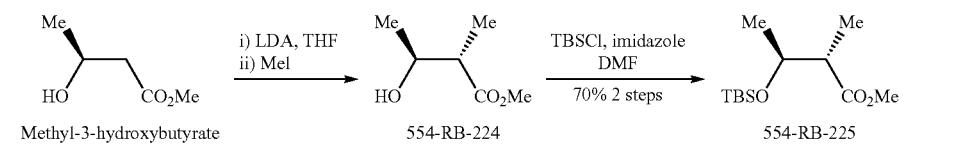

To a stirring solution of diisopropylamine (2 eq., 366 mmol, 51.3 mL) in dry THF (200 mL) at −78° C. was added slowly a 1.6 M solution of n-BuLi (2 eq., 366 mmol, 230 mL) over a period of 20 min. The reaction mixture was warmed to 0° C. and allowed to stir for 45 min after which the solution was cooled back to −78° C. Then, a solution of methyl-3-hydroxybutyrate (21.6 g, 183 mmol) in thy THF (100 mL) was added slowly over a period of 20 min after which neat MeI (5 eq, 915 mmol, 57 mL) was added over a period of 5 min. The reaction mixture was allowed to stir for 10 min at −78° C. then warmed to rt, and stirred for 2 h. The reaction was quenched with a saturated solution of $NH_4Cl$ (350 mL), extracted with $Et_2O$ (3×400 mL), the combined organic extracts were washed with a saturated solution of $NH_4Cl$ (350 mL), water (2×450 mL), brine (450 mL), dried with $K_2CO_3$, filtered and concentrated. The crude alcohol 555-RB-224 was dissolved in dry DMF (100 mL), imidazole (2.5 eq, 363 mmol, 24.7 g) was added and the mixture was cooled to 0° C. in ice/water bath. Then TBSCl (1.2 eq, 33.0 mmol, 5 g) was added, the mixture was allowed to warm slowly to rt and stirred for 16 h after which a saturated solution of $NaHCO_3$ (250 mL) was added. The mixture was extracted with $Et_2O$ (3×250 mL) and the combined organic extracts were washed with a saturated solution of $NaHCO_3$ (350 mL), water (3×350 mL), brine (350 mL), dried with $Na_2SO_4$, filtered and concentrated. The crude product was purified by chromatography on silica gel using 5% EtOAc/hexane to give 31.7 g (129 mmol, 70% 2 steps) of the protected compound 554-RB-225.

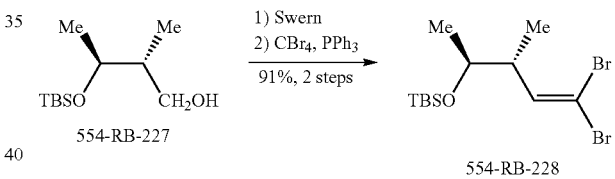

In a 5 L three neck flask equipped with mechanical stirring was placed 554-RB-225 (221 mmol, 54.5 g) dissolved in toluene (750 mL). The mixture was cooled to −78° C. and DIBAL-H (1M in toluene, 2.5 eq., 553 mmol, 553 mL) was added slowly. The mixture was allowed to stir at −78° C. for 15 min after which it was warmed to 0° C. and stirred for 2 h. Reaction was quenched with MeOH (10 eq., 2.2 mol, 89 mL) at −78° C. and allowed to warm to rt, $Et_2O$ (2.5 L) and a saturated solution of $Na_2SO_4$ (1 L) were added and the solution was stirred overnight. Mixture was filtered through celite and the solid was washed with $Et_2O$ (2×1 L). The filtrate was concentrated under reduced pressure and the resulting residue was purified by chromatography on silica gel using 10-15% EtOAc/hexane to give 40.6 g (186 mmol, 76%) of alcohol 554-RB-227.

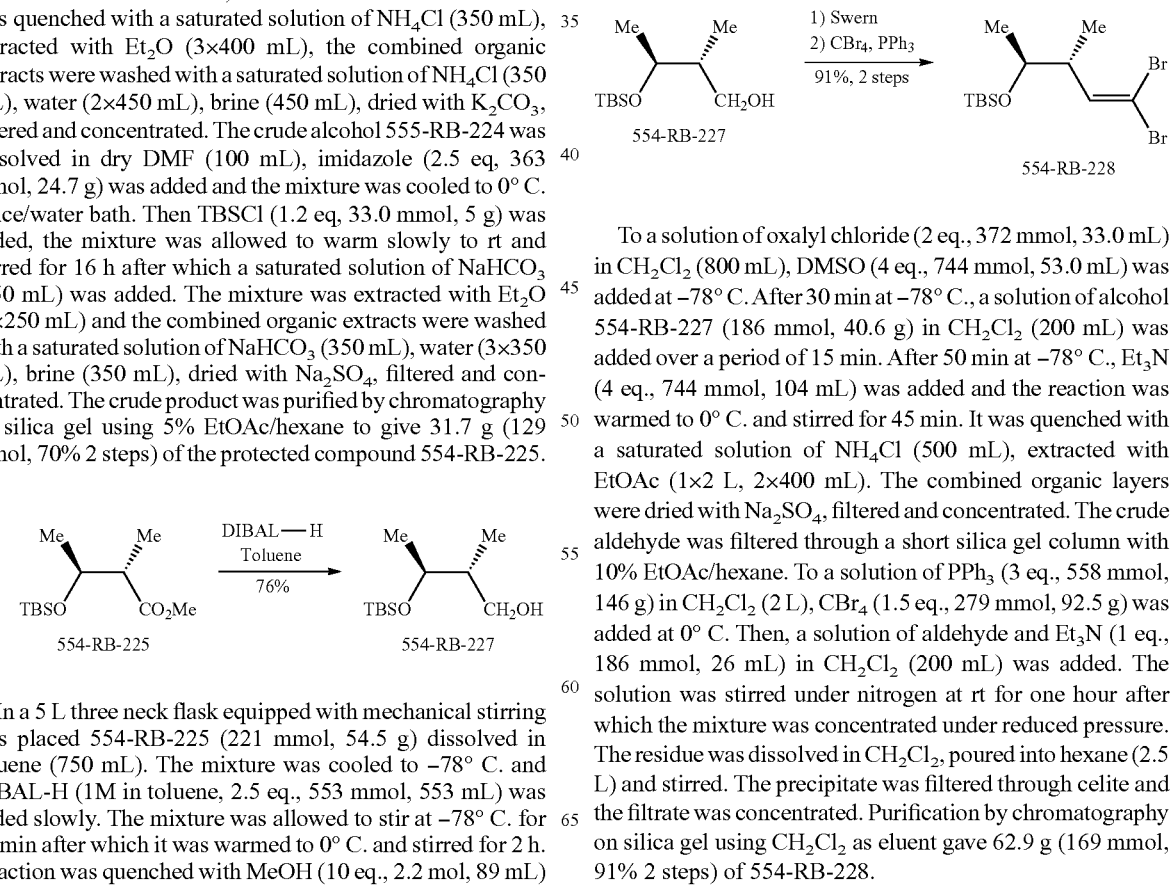

To a solution of oxalyl chloride (2 eq., 372 mmol, 33.0 mL) in $CH_2Cl_2$ (800 mL), DMSO (4 eq., 744 mmol, 53.0 mL) was added at −78° C. After 30 min at −78° C., a solution of alcohol 554-RB-227 (186 mmol, 40.6 g) in $CH_2Cl_2$ (200 mL) was added over a period of 15 min. After 50 min at −78° C., $Et_3N$ (4 eq., 744 mmol, 104 mL) was added and the reaction was warmed to 0° C. and stirred for 45 min. It was quenched with a saturated solution of $NH_4Cl$ (500 mL), extracted with EtOAc (1×2 L, 2×400 mL). The combined organic layers were dried with $Na_2SO_4$, filtered and concentrated. The crude aldehyde was filtered through a short silica gel column with 10% EtOAc/hexane. To a solution of $PPh_3$ (3 eq., 558 mmol, 146 g) in $CH_2Cl_2$ (2 L), $CBr_4$ (1.5 eq., 279 mmol, 92.5 g) was added at 0° C. Then, a solution of aldehyde and $Et_3N$ (1 eq., 186 mmol, 26 mL) in $CH_2Cl_2$ (200 mL) was added. The solution was stirred under nitrogen at rt for one hour after which the mixture was concentrated under reduced pressure. The residue was dissolved in $CH_2Cl_2$, poured into hexane (2.5 L) and stirred. The precipitate was filtered through celite and the filtrate was concentrated. Purification by chromatography on silica gel using $CH_2Cl_2$ as eluent gave 62.9 g (169 mmol, 91% 2 steps) of 554-RB-228.

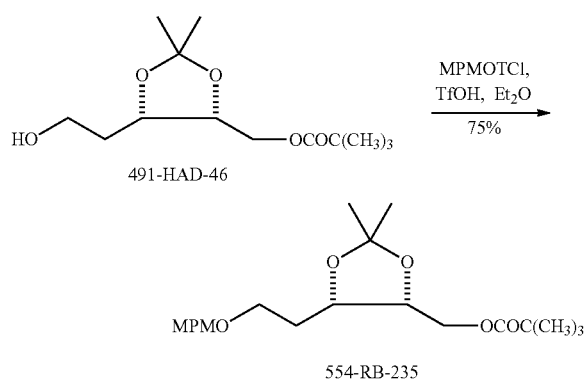

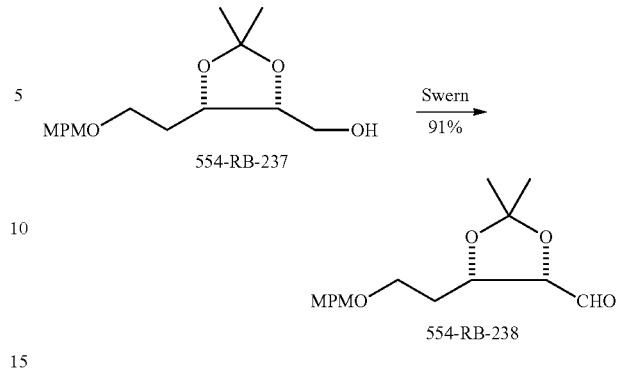

A 5 L, 3-neck flask was equipped with mechanical stirring, cooling bath and flushed with nitrogen. Then, a solution of alcohol 491-HAD-46 (202 mmol, 52.5 g) and MPMOTCl (2 eq., 404 mmol, 115.5 g) in $Et_2O$ (1 L) was added to the flask and cooled to 0° C. A solution of TfOH (1.5 mL) in $Et_2O$ (120 mL) was added slowly with a syringe pump over a period of 50 min. Then, a saturated solution of $NaHCO_3$ (500 mL) was added, the mixture was extracted with $Et_2O$ (2×700 mL); the combined organic extracts were washed with brine (2×1 L), dried over $Na_2SO_4$ and concentrated. The residue was dissolved in $CH_2Cl_2$, poured in hexane (2.5 L), the precipitated was filtered through celite and the filtrate was concentrated under reduced pressure. The crude material was purified by chromatography on silica gel using 5-10% EtOAc/hexane as eluent to give 57.3 g (151 mmol, 75%) of the protected alcohol 554-RB-235.

To a solution of oxalyl chloride (2 eq., 202 mmol, 18 mL) in $CH_2Cl_2$ (650 mL), DMSO (4 eq., 404 mmol, 29 mL) was added at −78° C. After 30 min at −78° C., a solution of alcohol 554-RB-237 (101 mmol, 30 g) in $CH_2Cl_2$ (100 mL) was added over a period of 30 min. After 45 min at −78° C., $Et_3N$ (4 eq., 404 mmol, 56 mL) was added and the reaction was warmed to 0° C. and stirred for 45 min. It was quenched with a saturated solution of $NH_4Cl$ (250 mL), extracted with EtOAc (1×2 L, 2×250 mL). The combined organic layers were dried with $Na_2SO_4$, filtered and concentrated. The crude aldehyde was purified by chromatography on silica gel with 10% EtOAc/hexane to give 27 g (91.7 mmol, 91%) of aldehyde 554-RB-238.

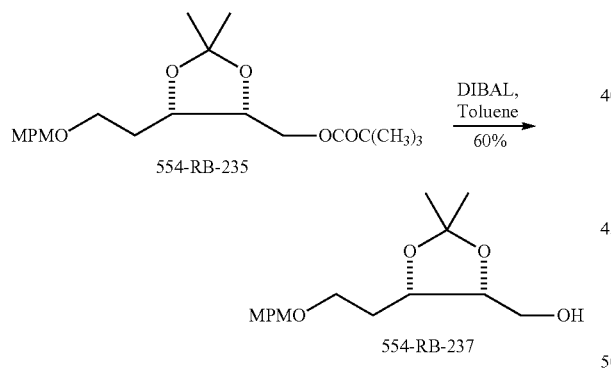

In a 3 L, three neck flask equipped with mechanical stirring was placed 554-RB-235 (151 mmol, 57.3 g) dissolved in toluene (750 mL). The mixture was cooled to −78° C. and DIBAL-H (1M in toluene, 2.65 eq., 400 mmol, 400 mL) was added slowly. The mixture was allowed to stir at −78° C. for 10 min after which it was warmed to 0° C. and stirred for 20 min. Reaction was quenched with MeOH (10 eq., 1.5 mol, 61 mL) at −78° C. and allowed to warm to rt. $Et_2O$ (2.5 L) and a saturated solution of $Na_2SO_4$ (1 L) were added and the solution was stirred overnight. Mixture was filtered through celite and the solid was washed with $Et_2O$ (2×1 L). The filtrate was concentrated under reduced pressure and the resulting residue was purified by chromatography on silica gel using 20-40% EtOAc/hexane to give 27 g (91 mmol, 60%) of alcohol 554-RB-237.

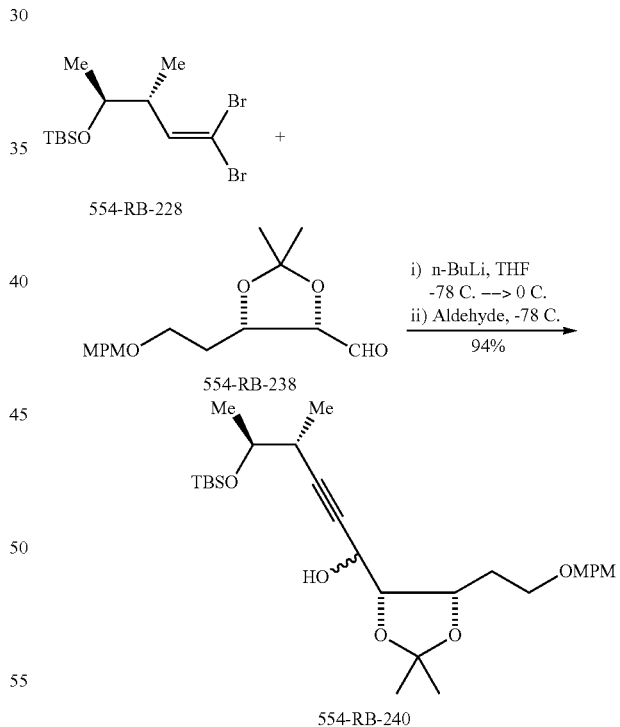

Dibromoolefin 554-RB-228 (1.5 eq., 138 mmol, 51.2 g) was dissolved in THF (1 L) and cooled to −78° C., under nitrogen. Then, n-BuLi (1.6M/hexane, 3.3 eq., 302 mmol, 189 mL) was added and the reaction was stirred at −78° C. for 40 min, at 0° C. for 30 min, then cooled back to −78° C. Aldehyde 554-RB-238 (91.7 mmol, 27.0 g) dissolved in THF (200 mL) was added to the solution and stirred for 30 min at −78° C. The solution was allowed to warm to rt and was stirred for 1.5 hrs. The mixture was quenched with water (700 mL), extracted with EtOAc (3×750 mL) and the combined organic extracts were washed with brine (1 L), dried with Na₂SO₄, filtered and concentrated. The residue was purified by chromatography on silica gel using 10-30% EtOAc/hexane to give 43.7 g (86 mmol, 94%) of 554-RB-240.

with a 0.2N solution of NaOH (5×500 mL), brine, dried with Na₂SO₄, filtered and concentrated. The crude compound was filtered through a silica gel column with 5% EtOAc/hexane to give a quantitative yield of protected compound 554-RB-242.

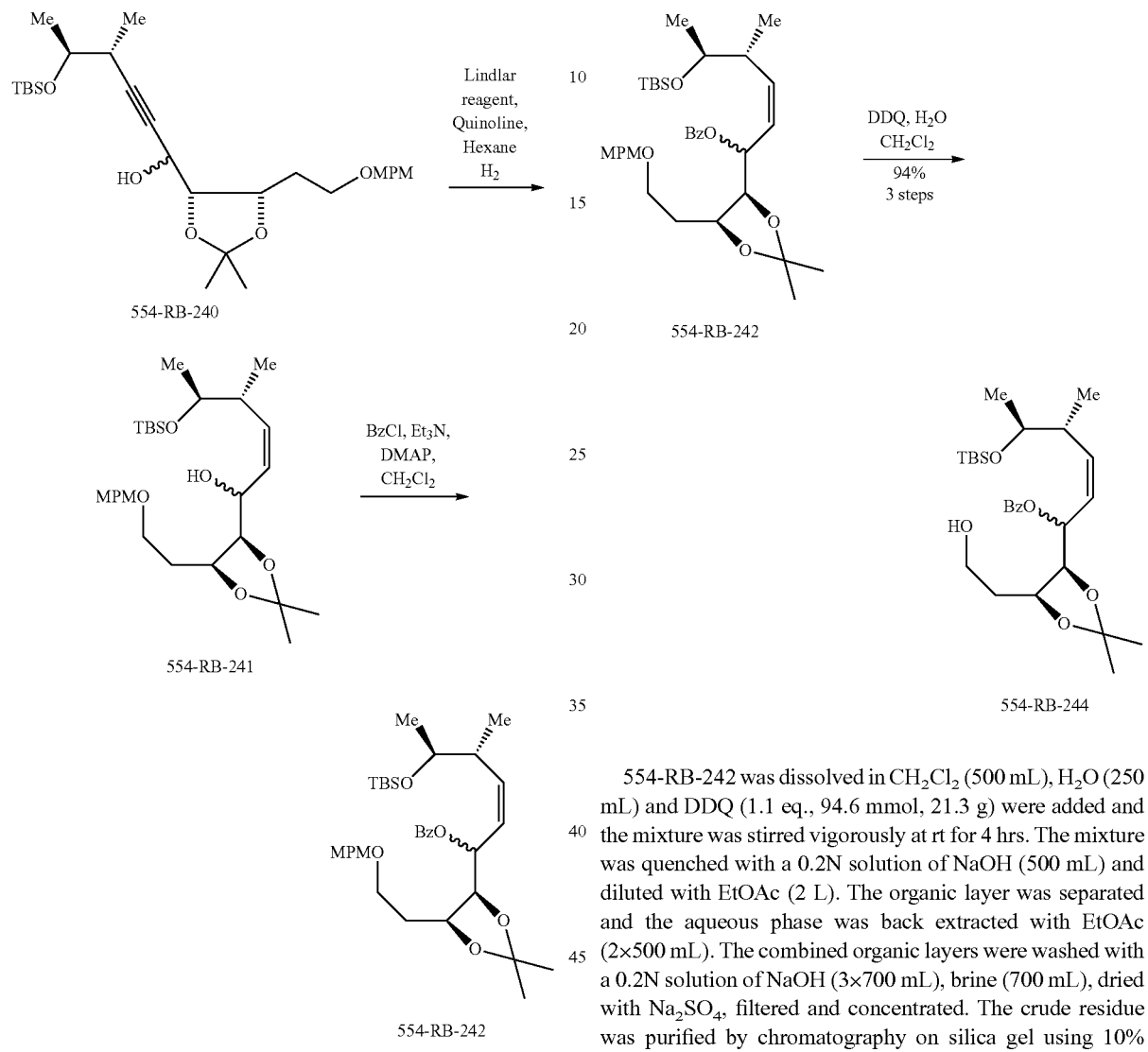

554-RB-240 (86 mmol, 43.7 g) was dissolved in hexane (1 L). Then, quinoline (1 mL) and Lindlar catalyst (10 g) were added. H₂ balloon was mounted and the mixture was purged 5× with H₂. Reaction was stirred under hydrogen. After 13 hrs, 17 hrs, 22 hrs, and 38 hrs, catalyst was filtered and new catalyst (10 g) and quinoline (1 mL) were added each time. After 42 hrs, reaction was stopped, catalyst was filtered through celite and mixture was concentrated under reduced pressure. Then, crude 554-RB-241 was dissolved in CH₂Cl₂ (700 mL), Et₃N (3.75 eq., 323 mmol, 45 mL), BzCl (3 eq., 258 mmol, 30 mL) and DMAP (0.075 eq., 6.45 mmol, 788 mg) were added and the mixture was stirred for 96 hrs at rt under nitrogen. The mixture was diluted with EtOAc (2 L) and a 0.1N solution of NaOH (800 mL). Organic layer was separated and the aqueous phase was extracted with EtOAc (2×500 mL). The organic combined extracts were washed 554-RB-242 was dissolved in CH₂Cl₂ (500 mL), H₂O (250 mL) and DDQ (1.1 eq., 94.6 mmol, 21.3 g) were added and the mixture was stirred vigorously at rt for 4 hrs. The mixture was quenched with a 0.2N solution of NaOH (500 mL) and diluted with EtOAc (2 L). The organic layer was separated and the aqueous phase was back extracted with EtOAc (2×500 mL). The combined organic layers were washed with a 0.2N solution of NaOH (3×700 mL), brine (700 mL), dried with Na₂SO₄, filtered and concentrated. The crude residue was purified by chromatography on silica gel using 10% EtOAc/hexane to give 39.9 g (81 mmol, 94% 3 steps from acetylene) of free alcohol 554-RB-244.

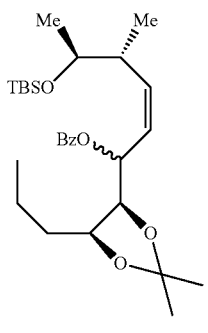

554-RB-260

To a solution of 554-RB-244 (6.09 mmol, 3.0 g) in toluene (100 mL), Ph₃P (1.7 eq., 10.4 mmol, 2.71 g) was added at rt. Then, CH₃I (1.3 eq., 7.92 mmol, 0.49 mL) and DEAD (1.1 eq., 6.70 mmol, 1.45 mL) were added at the same time. The mixture was stirred for 1.5 hrs at rt after which it was poured in hexane and stirred for 10 min. The precipitate was filtered and the filtrate was concentrated. The residue was purified by chromatography on silica gel using 5% EtOAc/hexane to give 3.40 g (5.64 mmol, 93%) of iodide 554-RB-260.

Preparation of C4-H Series Acyclic Segment:

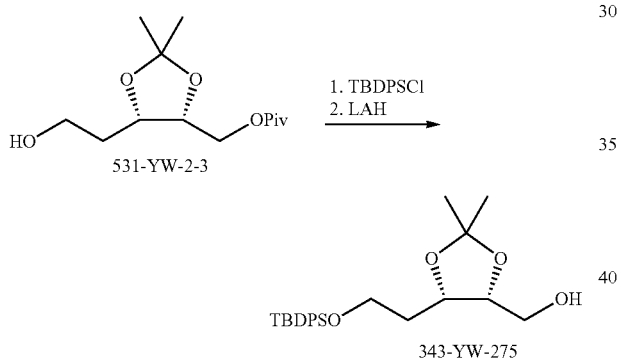

531-YW-2-3

343-YW-275

To a solution of 531-YW-2-3 (7.5 g) in 20 mL of DMF, imidazole (5 g) and TBDPSCl (8.4 g) were added. During the addition exotherm was observed. After 3 h, it was diluted with EtOAc, washed with aq. Sat. NH₄Cl and brine. After drying and filtration, it was concentrated. The crude product was purified on silica gel with Hexanes/EtOAc, 20:1, and 10:1 to give 11.0 g of desired product.

The product was dissolved in 200 mL of THF. LAH (1.4 g) was added at 0° C. After 10 min at 0° C., it was quenched with water, 1N NaOH. The mixture was stirred at rt for 1 h. Then it was filtered. The combined filtrates were concentrated to dryness. The crude product was purified on silica gel with Hexanes/EtOAc, 10:1, 4:1, and 2:1 to give 9.0 g of desired product with satisfactory 111 NMR spectra, 343-YW-275.

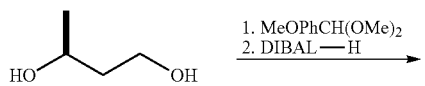

MPMO⟶OH

343-YW-203

To a solution of commercial available (s)-3-hydroxy butanol (10 g, Aldrich) in 50 mL of DMF, TsOH (20 mg, catalytic) and MeOPhCH(OMe)₂ (24 g) were added. After 3 h at 35° C. on a rotovap with slight vacuum, it was cooled and quenched with aq. Sat. NaHCO₃. The mixture was extracted with EtOAc (3×). The organic layers were washed with brine (2×), dried and concentrated. The crude product was evaporated with toluene (3×).

The crude product was dissolved in 700 mL of CH₂Cl₂. At 0° C., DIBAL-H solution (200 mL, 1.0 M, excess) was added. The reaction was warmed to room temperature overnight. Then it was quenched with methanol (50 mL), sat. Na₂SO₄ at 0° C. The mixture was diluted with Et₂O (1.5 L). After stirred for 5 h, it was filtered through a pad of celite. The filtrate was concentrated to give an oil. The oil was purified on silica gel with Hexanes/EtOAc, 10:1, 6:1, 3:1, and 1:1 to give 24 g of desired product, 343-YW-203.

MPMO⟶OH  →  1, Oxidation; 2. CBr₄, PPh₃

343-YW-203

MPMO⟶=CBr₂

343-YW-276

To a solution of DMSO (3.7 mL) in 150 mL of CH₂Cl₂, a solution of 343-W-203 (3.6 g) in 50 mL of CH₂Cl₂ was added. At 0° C., solid P₂O₅ (6.06 g) was added. The reaction was warmed to room temperature. After stirred at room temperature for 1 h, the reaction turned light pink and was cooled to 0° C. Et₃N (12 mL) was added. After 15 min at 0° C., it was warmed to room temperature. After 10 min, it was quenched with sat. NH₄Cl, and extracted with CH₂Cl₂ (2×). The organic layers were dried and concentrated. The crude product was suspended in Et₂O and filtered. The filtrates were concentrated to dryness.

To a solution of PPh₃ (11.6 g) in 30 mL of CH₂Cl₂, CBr₄ (7.4 g) was added at 0° C. The internal temperature was controlled below 10° C. After 10 min, a solution of aldehyde in 20 mL of CH₂Cl₂ was added. The internal temperature went up to 20° C. It was warmed to room temperature and stirred for 1 h. Then it was poured into a rapid stirring pentane solution. The precipitation was filtered. The filtrates were concentrated. The crude product was purified on silica gel column with hexanes/EtOAc, 20:1, 15:1, 10:1 to give 4.4 g of the desired product, 343-W-276.

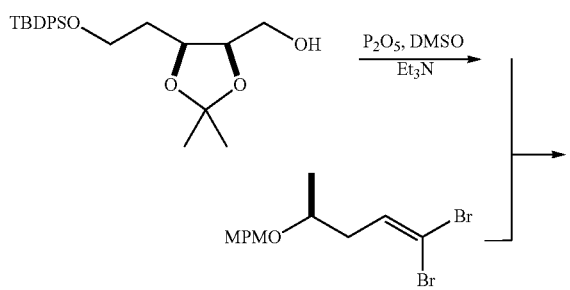
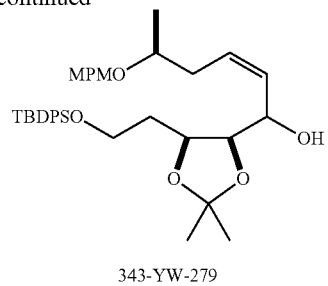

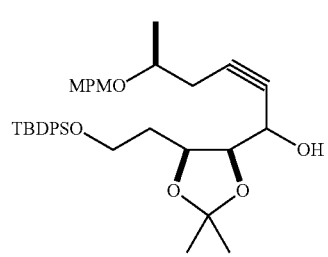

Oxidation of Alcohol:

To a solution of 343-YW-275 (3.6 g) in 25 mL of CH$_2$Cl$_2$, DMSO (1.84 mL) was added followed by P$_2$O$_5$ (3.65 g) solid at 0° C. Then it was warmed to room temperature for 1 h. After cooled to 0° C., Et$_3$N (5.94 mL) was added. After stirred at 0° C. for 30 min, it was warmed to room temperature. After stirred at room temperature for 3 h, it was quenched with sat. NH$_4$Cl, and extracted with CH$_2$Cl$_2$ (2×). The organic layers were washed with brine, dried and concentrated. The crude product was purified on silica gel with Hexanes/EtOAc, 10:1, 6:1, and 4:1 to give 2.5 g of aldehyde, 343-YW-277.

Coupling:

To a solution of 343-YW-276 (4.5 g, 12.36 mmol, 2 eq.) in 35 mL of THF, n-BuLi (5.4 mL, 2.5M, 2.2 eq.) was added at −78° C. After 10 min at −78° C., it was warmed to room temperature for 30 min. After cooled back to −78° C., a solution of 343-YW-277 (2.5 g, 6.06 mmol, 1 eq.) in 10 mL of THF was added. It was then warmed to 0° C., after 30 min. After 4 h at 0° C., it was quenched with aq. Sat. NH$_4$Cl, extracted with EtOAc (2×). The organic layers were washed with brine, dried and concentrated. The crude product was purified on silica gel with Hexanes/EtOAc, 20:1, 15:1, 10:1, 6:1 to give 2.5 g of desired product, 343-YW-278 along with recovered 343-YW-276.

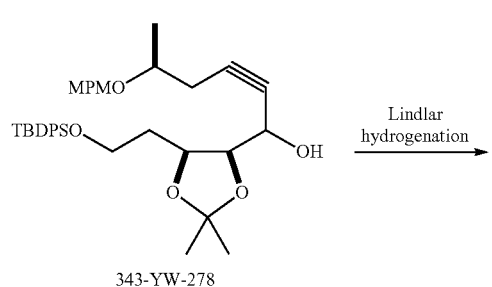

To a solution of 343-YW-278 (2.50 g) in 100 mL of hexanes, Lindlar catalyst (330 mg, catalytic) and quinoline (50 μL, catalytic) were added. After degassed under vacuum and refilled with H$_2$ for several times, it was stirred under hydrogen balloon for 3 h. Then the catalyst was filtered and fresh catalyst was added. After degassing, it was stirred under hydrogen overnight. The reaction was filtered through celite. The filtrates were combined and concentrated to dryness to give 2.4 g of desired product, 343-YW-279.

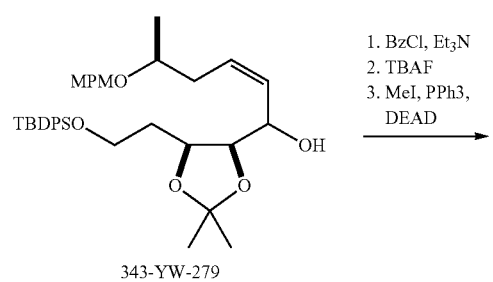

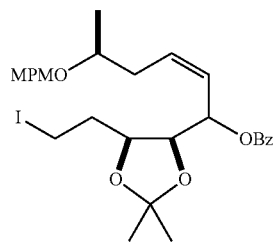

To a solution of 343-YW-279 (2.4 g) in 15 mL of CH$_2$Cl$_2$, BzCl (0.9 mL), Et$_3$N (2 mL) and DMAP (50 mg) were added. After 18 h, another 200 uL of BzCl was added. After total 24 h, it was quenched with aq. Sat. NH$_4$Cl and extracted with EtOAc (2×). The organic layers were washed with brine, dried and concentrated. The crude product was purified on silica gel with Hexanes/EtOAc, 20:1, 10:1, and 6:1 to give 2.2 g of desired ester.

To a solution of the ester from last step in 10 mL of THF, solid TBAF was added. After 18 h, it was quenched with sat. NH$_4$Cl and extracted with EtOAc. The organic layer was washed with brine, dried and concentrated. The crude product was purified on silica gel with Hexanes/EtOAc, 10:1, 6:1, 4:1, and 2:1 to give 1.45 g of alcohol.

To a solution of the alcohol from last step and PPh$_3$ (1.3 g) in 20 mL of toluene, DEAD (750 μL) and MeI (250 μL) were added simultaneously at room temperature. After 30 min, it was diluted with CH$_2$Cl$_2$ to a clear solution. Then it was poured into pentanes with rapid stirring. The precipitation was filtered through a celite pad. The filtrate was concentrated. The crude product was purified on silica gel with Hexanes/EtOAc, 20:1, 10:1, 8:1 to give 1.5 g of desired product, 343-YW-281. A satisfactory ¹H NMR was obtained.
Preparation of Advance Phenol Intermediate for C14-Analog Synthesis:

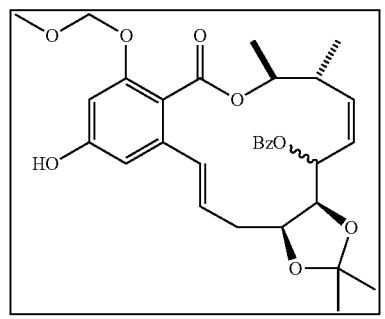

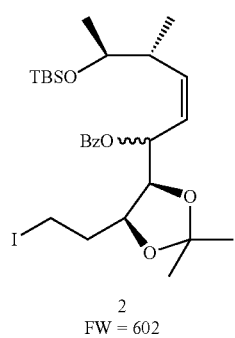

2
FW = 602

+

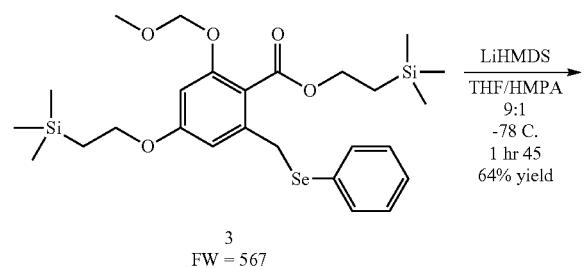

3
FW = 567

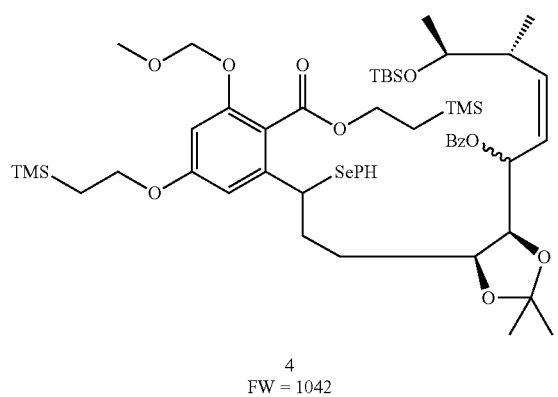

4
FW = 1042

Iodide 2 (4.94 g, 8.2 mmol, 1.0 eq.) and selenide 3 (7.00 g, 12.3 mmol, 1.5 eq.) were dissolved in HMPA (10.0 mL) and THF (90 mL). The resulting mixture was magnetically stirred at −78'C and slowly added over 50 min LiHMDS (18.0 mL, 9.0 mmol, 1.1 eq., LiHMDS 0.5M in THF, addition rate of 0.32 mL/min). The reaction mixture was stirred 1 h and 45 min at −78° C., quenched with NH$_4$Cl sat. (200 mL), diluted with H$_2$O, added ethyl acetate (500 mL). The layers were separated and the aqueous one was extracted with ethyl acetate (2×500 mL). The combined organic layers were washed with H$_2$O (2×300 mL), dried with Na$_2$SO$_4$, filtered, and concentrated under reduced pressure. The crude oil was purified on a SiO$_2$ column (230-400 Mesh silica). The products were dissolved in hexane prior to be loaded on the column. Elution: 3%, then 5% ethyl acetate/hexane. The desired product 4 (5.43 g, 64% yield) was isolated as viscous brownish oil.

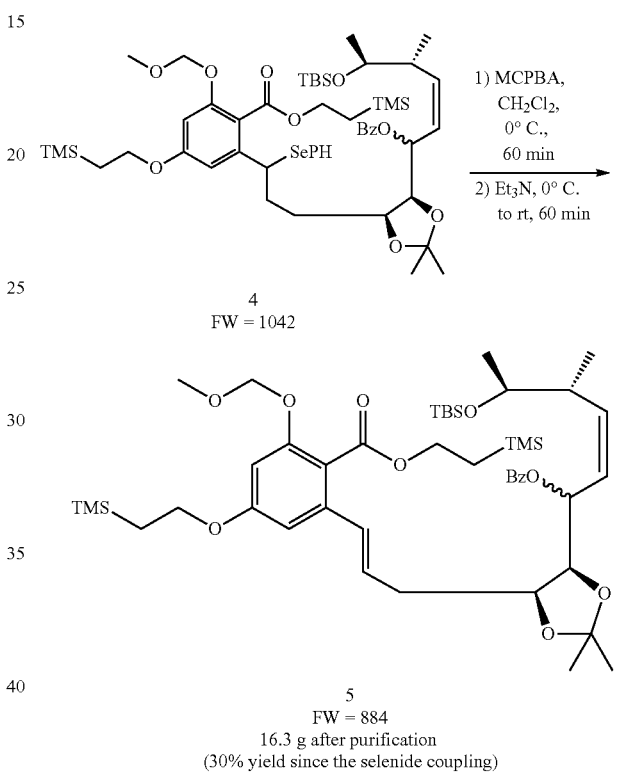

4
FW = 1042

5
FW = 884
16.3 g after purification
(30% yield since the selenide coupling)

The crude substrate 4 (mixture of selenide 3 and coupled material 4, <58.9 mmol) was dissolved in CH$_2$Cl$_2$ (750 mL), cooled down to 0° C. and added in small portions MCPBA (Aldrich 57-86%, 43.5 g, >144 mmol, 2.4 eq.).

The first portions are exothermic and towards the end of the addition, no exotherm was noticed, Tmax was 4° C. Stirred for 45 min at 0° C., triethylamine (50 mL, 357 mmol, 6 eq.) was added SLOWLY! EXOTHERMIC! Tmax=10° C. Once the exotherm had ceased, the reaction mixture was warmed up to it. Stirred for 60 min at that temperature, a solution of NaS$_2$O$_3$ (51.5 g) was prepared using NaHCO$_3$ saturated and distilled water. Layers were separated; the aqueous one was extracted twice with CH$_2$Cl$_2$. The combined organic layers were dried with Na$_2$SO$_4$, filtered, concentrated down, added crude material from a previous small-scale run, purified on a SiO$_2$ column (1.25 kg of 230-400 Mesh silica from Silicycle). The crude material was loaded on the column as a slurry prepared with 3% ethyl acetate/hexane and 230-400 Mesh silica. Elution: 3% (8 L), 7.5% (8 L) and 10% (6 L) ethyl acetate/hexane. The desired material 5 (16.3 g, 30% combined yield since the selenide coupling) is viscous oil.

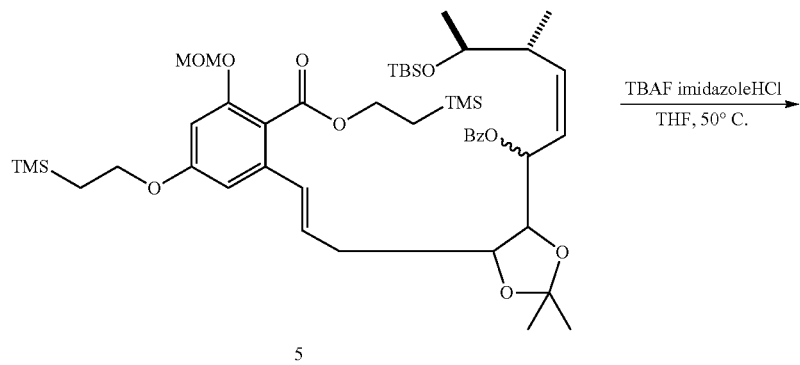

5

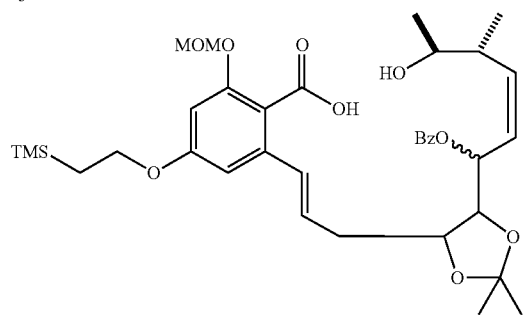

6

Substrate 5 was dissolved in THF (43 mL), added an imidazole.HCl buffered TBAF solution (60.5 mL, 60.5 mmol of TBAF, 3.4 eq. of TBAF 1 M in THF and 45 mmol of imidazole.HCl, 2.5 eq. of imidazole.HCl). That buffered solution was prepared as follows: imidazole.HCl was dissolved in a commercial 1 M TBAF/THF solution to give a resulting imidazole.HCl molarity of 0.75 M. The resulting reaction mixture was stirred 2 min at rt then it was added drop-wisely a regular TBAF solution (76 mL, 76 mmol, TBAF 1.0 M in THF). The reaction mixture was stirred in an oil bath at 50° C. during a total of 88 h, cooled down to rt, added NH$_4$Cl sat. (300 mL) and Et$_2$O (300 mL). The layers were separated and the aqueous was extracted with Et$_2$O (3×150 mL). The organic layers were combined, washed with brine (3×100 mL), dried with Na$_2$SO$_4$, filtered, concentrated to dryness, azeotroped twice with Et$_2$O (2×100 mL) giving desired 6 that was used crude for the next step.

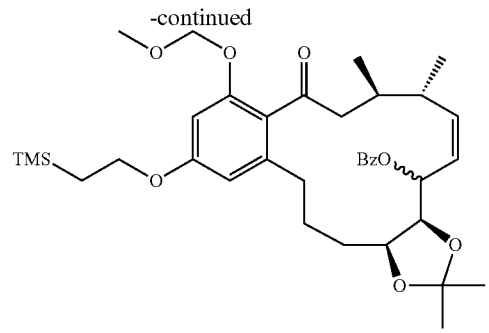

7
FW = 652
product partially purified: 7 g.

In a three neck 5 L flask equipped with a condenser and an addition funnel, was added CH$_2$Cl$_2$ (2 L) followed by triethylamine (7.6 mL, 54.0 mmol, 3.0 eq.) and 2-chloro-1-methylpyridinium iodide (14.2 g, 54.0 mmol, 3.0 eq.). The resulting mixture was warmed up to reflux and added drop-wisely a CH$_2$Cl$_2$ solution of hydroxy-acid 6 (14.4 g of crude material in 230 mL of CH$_2$Cl$_2$). The addition took 3 h and the resulting reaction mixture was stirred at reflux for 12 h, then cooled down to it, salts were filtered and CH$_2$Cl$_2$ was removed under reduced pressure. The residue was dissolved in Et$_2$O, washed with a 1:1 mixture of saturated brine and saturated NaHCO$_3$. The aqueous layer was extracted twice with Et$_2$O. The combined organic layers were washed with brine, dried with Na$_2$SO$_4$ and concentrated under reduced pressure, purified on a SiO$_2$ column (250 g of 230-400 Mesh silica from Silicycle). The crude material was dissolved in CH$_2$Cl$_2$ prior to be loaded on the column. Elution: 15%, 25%, 35% ethyl acetate/hexane. The desired macrocycle 7 (7 g) was still slightly contaminated was used directly for the next step.

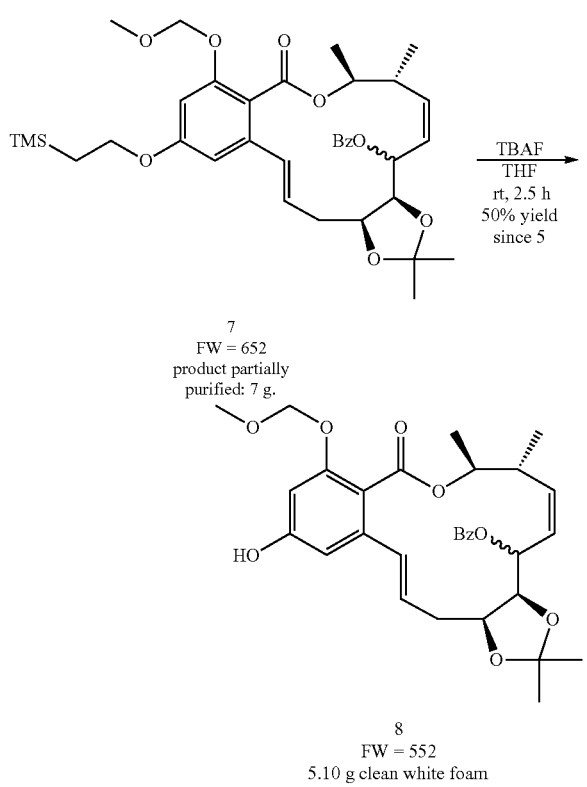

7
FW = 652
product partially
purified: 7 g.

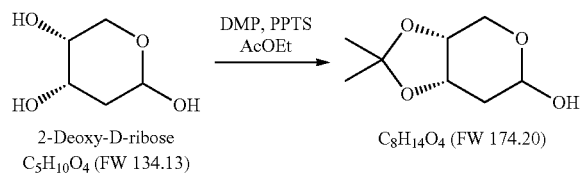

8
FW = 552
5.10 g clean white foam

To a solution of 7 (7 g, <18 mmol, 1.0 eq.) in THF (40 mL) at rt, was added drop-wisely TBAF (85 mL, 85 mmol, 4.7 eq., TBAF 1 M in THF). The reaction mixture was stirred at rt for 3 h, and then quenched with NH$_4$Cl sat. (250 mL) and Et$_2$O (250 mL). The layers were separated and the aqueous was extracted with Et$_2$O (2×150 mL). The combined organic layers were washed with brine (2×100 mL), dried with Na$_2$SO$_4$ and concentrated under reduced pressure, purified on a SiO$_2$ column (75 g of 230-400 Mesh silica from Silicycle). The crude material was dissolved in CH$_2$Cl$_2$ (15-20 mL) prior to be loaded on the column. The column was prepared using 25% ethyl acetate/hexane. Elution: 25%, 35%, 50% ethyl acetate/hexane. The desired material 8 (5.10 g, 50% combined yield from 5) is a white foam.

Preparation of Intermediate for C3-C4 Modification Series:

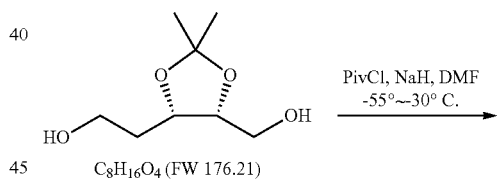

2-Deoxy-D-ribose
C$_5$H$_{10}$O$_4$ (FW 134.13)

C$_8$H$_{14}$O$_4$ (FW 174.20)

To the stirred suspension of 2-deoxy-D-ribose (100.8 g, 0.75 mol, commercially available from TCI) in EtOAc (800 ml), were added 2-methoxypropene (94 ml, 0.98 mol, 1.3 eq., Aldrich) and PPTS (4.16 g, 17 mmol, 2 mol %, Aldrich) at room temperature under N$_2$.

The mixture was stirred vigorously for 3 hr.

Then the insoluble residue (remained SM) was filtrated out and TEA (4.6 ml, 2 eq. to PPTS) was added to the filtrate. The resultant filtrate was concentrated under reduced pressure and the residue was purified by silica gel flash column chromatography (silica gel 4 kg, hexane-EtOAc 9:1 to 1:1 as eluent) to give 68 g of desired compound as colorless oil (52%).

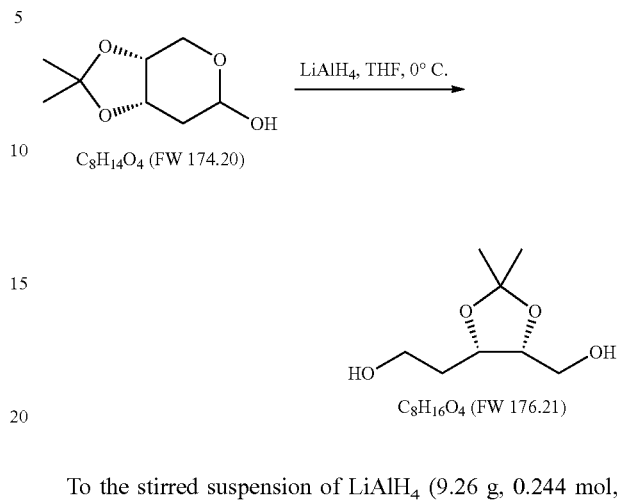

C$_8$H$_{14}$O$_4$ (FW 174.20)

C$_8$H$_{16}$O$_4$ (FW 176.21)

To the stirred suspension of LiAlH$_4$ (9.26 g, 0.244 mol, 1.25 eq., Wako) in THF (200 mL) cooled in ice/brine bath, was added drop wise SM (68 g, 0.39 mol) in THF (600 mL+100 mL rinse) under N$_2$ (in ca. 1.5 hr). Then the mixture was stirred for additional 15 min. After quenching by careful addition of MeOH, 9.26 ml of water, 9.26 ml of 10% NaOH aq., 27.78 mL of water were added successively and the mixture was stirred vigorously for 1 hr. Then, the insoluble material was filtered out using Celite and washed with EtOAc (500 mL×4), and the resultant filtrate was concentrated under reduced pressure, dried in vacuo to give 62.23 g of the crude product as light yellow oil (90.5%).

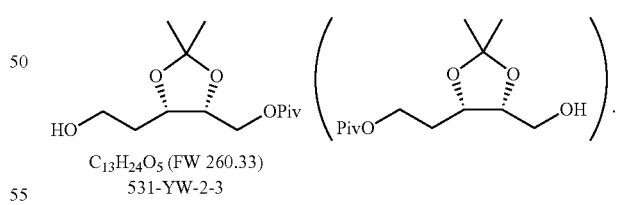

C$_8$H$_{16}$O$_4$ (FW 176.21)

C$_{13}$H$_{24}$O$_5$ (FW 260.33)
531-YW-2-3

To the stirred suspension of NaH (8.09 g, 60% oil dispersion, 202 mmol, 2.2 eq., Wako) in DMF (200 mL) cooled in ice/brine bath, was added drop wise (16.2 g, 91.9 mmol) in DMF (500 mL+100 mL rinse) under N$_2$. The resultant mixture was stirred for 75 min. at room temperature. Then the mixture was cooled to −55° C. (inner temp.)**, PivCl (12.5 mL, 102 mmol, 1.1 eq., TCI) was added drop wise (in ca 10 min). After addition, the mixture was allowed to warm to −30° C.

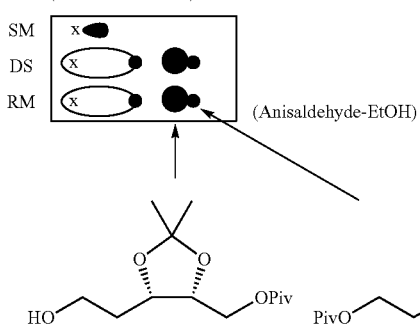

Quenching was performed by careful addition of sat. NH₄Cl aq., then the mixture was extracted with EtOAc (1 L). After re-extraction of the aqueous layer with EtOAc (500 mL), the combined organic phase was washed with water (0.6 L×3), brine (0.3 L) and dried over anhydrous Na₂SO₄. After filtration of drying agent, the filtrate was concentrated and the residual brown oil (25.43 g) was purified by silica gel flash column chromatography (silica gel 2.8 kg, hexane-EtOAc 2:1 to 1:1 as eluent) to give 3.73 g of less polar undesired protected mono-ol, 531-YW-2-2 (16%) and 13.14 g of polar desired product, 531-YW-2-3 (55%), respectively as colorless oil.

Iodide Formation:

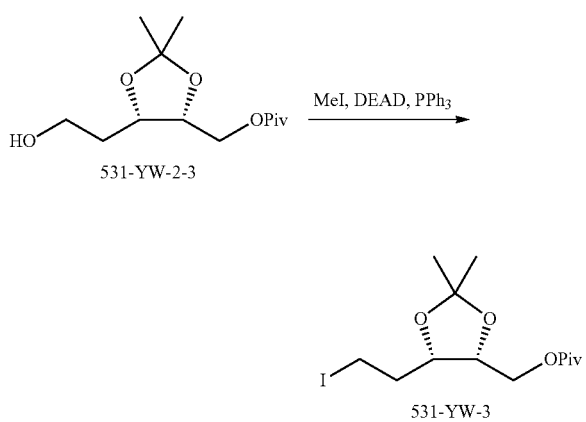

To a solution of 531-YW-2-3 (9.5 g, 36.5 mmol) in 400 mL of toluene, PPh₃ (18.3 g, 62.1 mmol, 1.9 eq.) was added. Then MeI (2.94 mL, 47 mmol, 1.3 eq.) and DEAD (6.29 mL) were added simultaneously by two syringe-pumps in 20 min. After stirred at room temp for 20 min, it was poured into a rapid stirred pentane solution. The solid was dissolved by small amount of CH₂Cl₂ and added into the pentane. The precipitation was filtered through celite, the pad was washed with pentane. The combined filtrates were concentrated. The crude oil was purified quickly on a short silica gel column with 20:1, 10:1, 6:1 Hex/EtOAc. It gave 11.6 g of the iodide 531-YW-3.

Coupling:

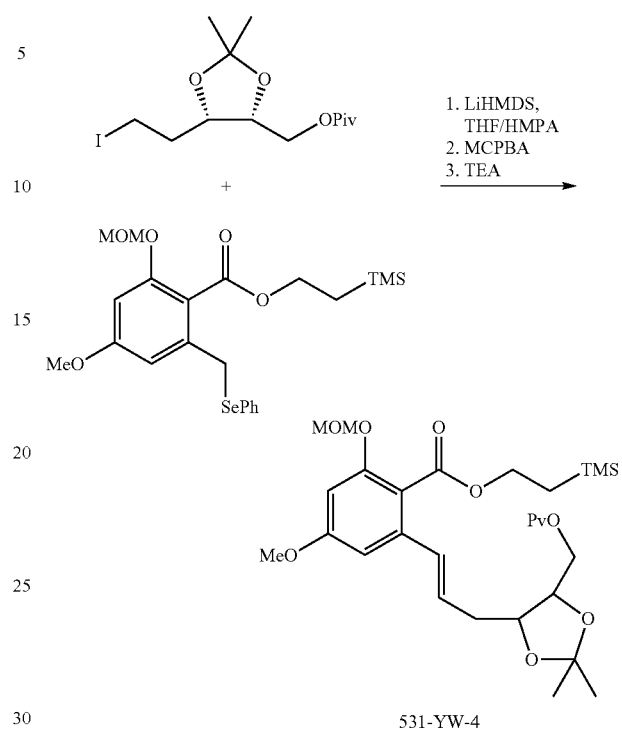

To a solution of iodide (531-YW-3, 11.6 g, 31.3 mmol) and selenide (509-HD-213, 24.5 g, 50.9 mmol, 1.6 eq.) in a mixed solvent of THF and HMPA (130 mL, 10:1 ratio), a solution of LiHMDS (94 mL, 0.5 M) was added by a syringe pump in one and half hour at −78° C. After 20 min at −78° C., it was warmed to 0° C. After cooled back to −10° C., it was quenched with aq. sat. NH₄Cl and extracted with EtOAc (2×). The organic layers were washed with brine, dried and concentrated. The crude product was purified on silica gel with Hexanes/EtOAc, 20:1, 10:1, 6:1, 4:1, and 2:1 to give 16.0 g.

The product from the above (16 g) was dissolved in CH₂Cl₂ (200 mL), MCPBA (16 g, 50.9 mmol, 1.6 eq., 55%) was added at 0° C. After 15 min at 0° C., Triethylamine (20 mL, excess) was added. After 30 min, it was quenched with aq. Sat. Na₂S₂O₃. After stirred for 20 min, it was extracted with EtOAc (2×). The organic layers were washed with sat. Na₂S₂O₃, sat. NaHCO₃, brine, dried and concentrated. The crude product was purified on silica gel with Hexanes/EtOAc, 20:1, 10:1, 3:1, gave 12.5 g of the desired product, 531-YW-4 (83% in three steps).

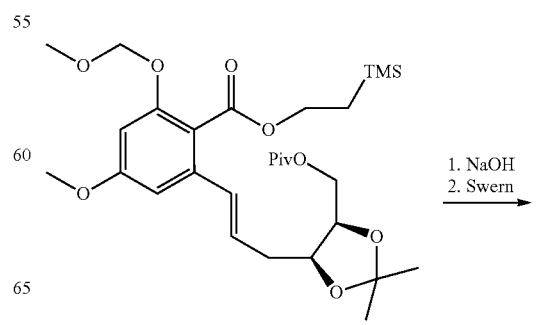

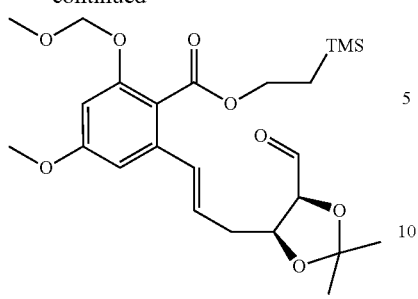

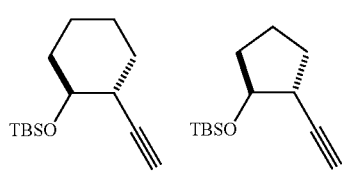

Preparation of ER803064:

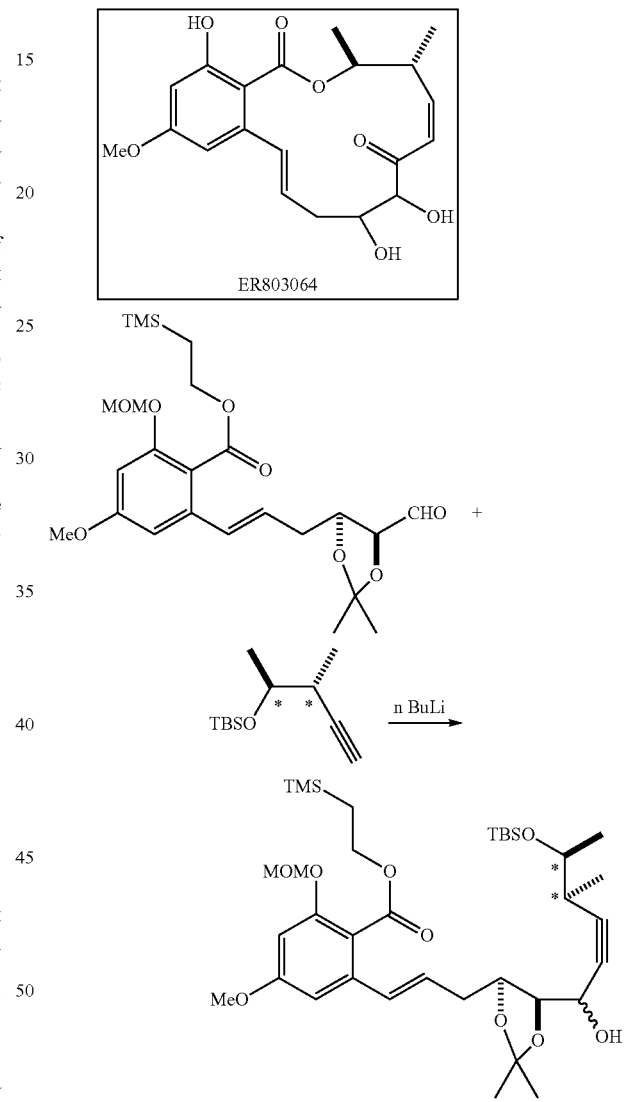

To a solution of ester (5.66 g, 10 mmol) In EtOH (100 mL), 50 mL of 1N NaOH was added. The reaction was stirred at rt overnight. The reaction was then diluted with water, extracted with EtOAc (3×). The combined organic layers were washed with brine, dried and concentrated. It was purified on silica gel column to give 4.42 g of desired product as an oil (92%).

To a solution of $(COCl)_2$ (2.2 mL, 3 eq.) in 50 mL of $CH_2Cl_2$, DMSO was added slowly at −78° C. After 15 min at −78° C., a solution of alcohol (4.1 g, 3.5 mmol) was added into the reaction at −78° C. After 30 min at that temperature, TEA (10.7 mL, 9 eq.) was added. The reaction was warmed to rt. It was quenched with Sat. $NH_4Cl$, extracted with EtOAc (2×). The combined organic layers were washed with brine, dried and concentrated to dryness. It was used in next reaction without purification.

The aldehyde was used as a general intermediate for the synthesis of C3-C4 modification by coupling with appropriate acetylene or equivalent.

Preparation of Acetylenes for C3-C4 Modifications:

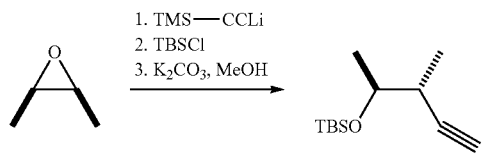

To a solution of TMS-acetylene (38.8 mL) In 1 L of THF at −60° C., n-BuLi (110 mL, 2.5 M) was added. The reaction was warmed to 0° C. briefly, then cooled back down to −60° C. $BF_3.Et_2O$ (33.8 mL) was then slowly added, followed by the epoxide (15 mL) via syringe pump. After stirred at −60° C. for 1.5 h, it was warmed to rt, quenched by Sat. $NH_4Cl$, extracted with EtOAc (2×). The organic layers were dried and concentrated. The crude product was purified by silica gel column with 4:1 Hexanes/EtOAc to give 13.9 g of desired product as an oil.

The alcohol was silylated under standard condition with TBSCl and Imidazole in methylene chloride.

A mixture of TBS protected TMS-acetylene (8.7 g) and $K_2CO_3$ (8 g) in methanol (120 mL) were stirred for 5 h at rt. It was extracted with EtOAc (2×). The organic layers were dried and concentrated. The crude product was purified on silica gel with hexanes to give 6.17 g of colorless oil (95%)

The following acetylenes were prepared analogous to the preparation described:

Acetylene (2.65 g, 12.5 mmol) was dissolved in 30 mL of THF and cooled down to −78° C. n-BuLi (2.5 N, 6.24 mL) in Hexane was added. The reaction mixture was stirred at −78° C. for 10 min, and then a solution of aldehyde (3.0 g, 6.24 mmol) in 30 mL of THF was added via cannula. The reaction mixture was stirred at −78° C. for 30 min and warmed up gradually to room temperature. It was quenched with water and extracted with EtOAc. After purification on silica gel column, 3.7 g of 509-HD-108 was obtained as a pale yellow oil in 78% yield.

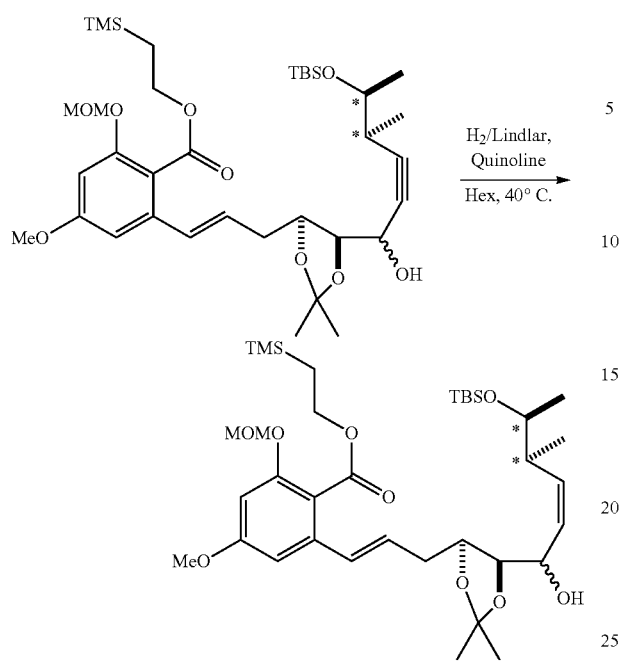

509-HD-108 (3.4 g, 4.91 mmol) was dissolved in 200 mL hexane. Quinoline (200 µL) and Lindlar catalyst (500 mg) were added. The reaction mixture was stirred at 40° C. under H$_2$ balloon atmosphere for a total of 18 h. Then the catalyst was filtered away. Quantitative amount of 509-HD-112 was obtained as a pale yellow oil.

509-HD-112 (3.4 g, 4.9 mmol) was dissolved in 60 mL of dichloromethane at room temperature. Triethylamine (1.71 mL, 9.8 mmol), benzoyl chloride (1.14 mL, 12.2 mmol) and catalytic amount of DAMP were added, respectively. After stirring for 12 h, 0.1N sodium hydroxide solution was added and the reaction mixture was extracted with EtOAc. The crude product was purified on silica gel column, giving 509-HD-115 as a colorless oil in 94% yield.

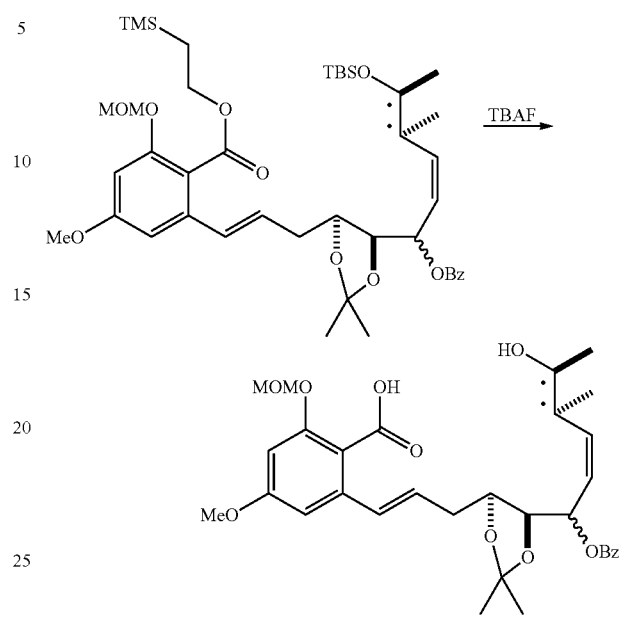

509-HD-115 (3.7 g, 4.64 mmol) was dissolved in 50 mL of THF. The THF solution of TBAF (1N, 25 mL) was added. The reaction mixture was heated at 50° C. for 24 h. It was diluted with Et$_2$O and washed with H$_2$O. After purification on silica gel column, 509-HD-116 was obtained as a pale yellow foam in 68% yield.

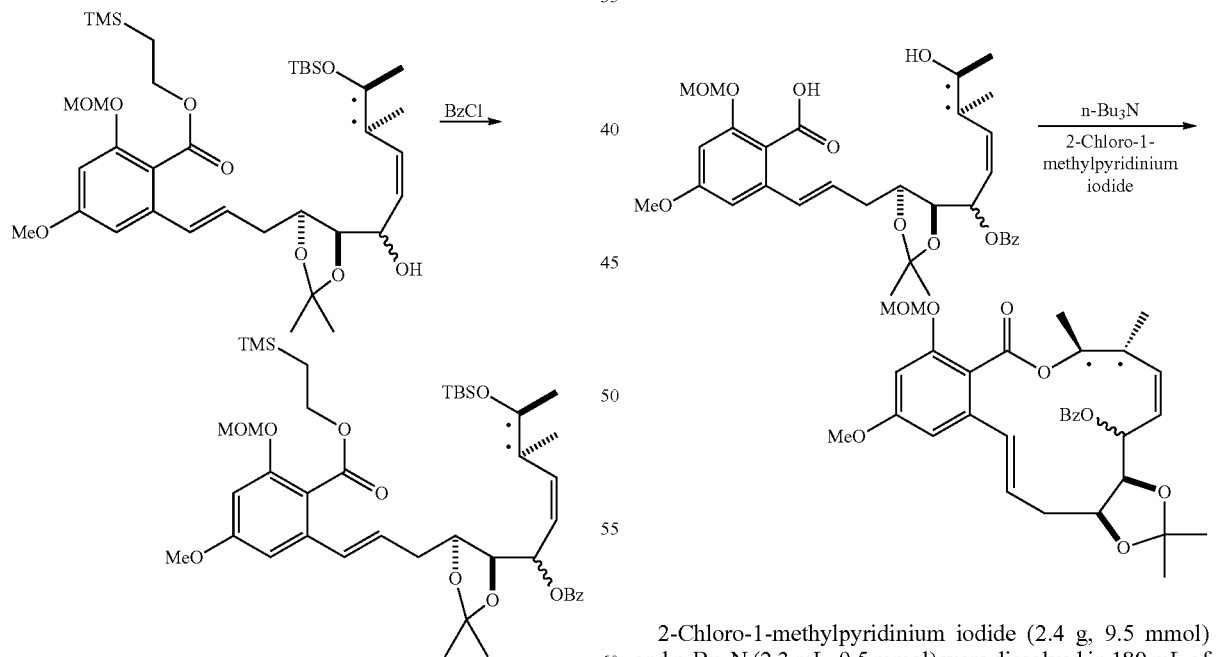

2-Chloro-1-methylpyridinium iodide (2.4 g, 9.5 mmol) and n-Bu$_3$N (2.3 mL, 9.5 mmol) were dissolved in 180 mL of dichloromethane and heated to reflux. The solution of 509-HD-116 (1.85 g, 3.2 mmol) in 50 mL of THF was added slowly. The reaction mixture was heated for 30 min. It was washed with 0.02 N hydrochloric acid, sat. sodium bicarbonate solution and brine, respectively. After purification on silica gel column, 509-HD-118 was obtained as a pale yellow foam in 62% yield.

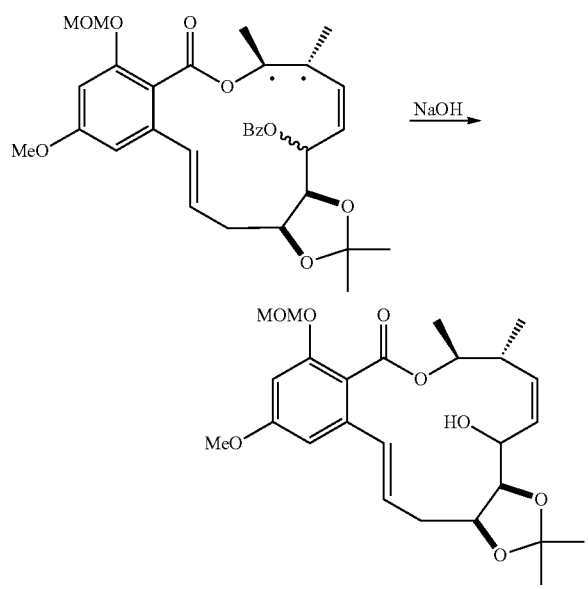

509-HD-118 (1.22 g, 2.2 mol) was dissolved in 30 mL of ethanol. Sodium hydroxide (1N, 21.5 mL) solution was added. The reaction mixture was stirred for 48 h at room temperature. It was diluted with H₂O, extracted with EtOAc. After purification on silica gel column, 346 mg of the major desired single isomer 509-HD-119B was obtained as a colorless oil.

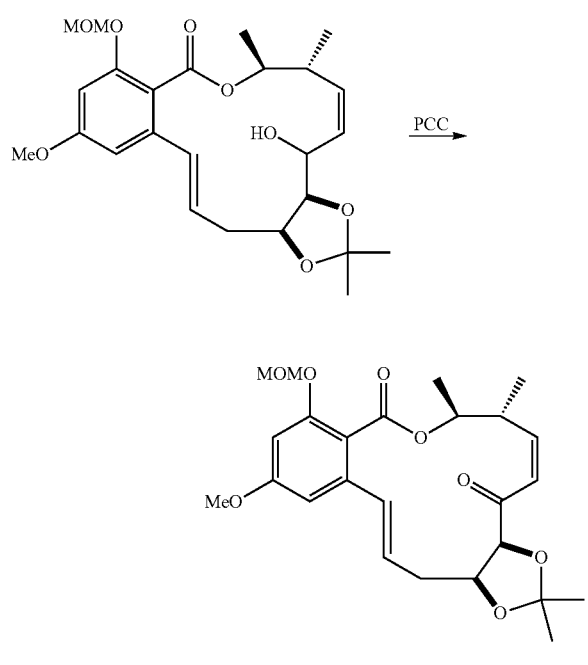

509-HD-119B (155 mg, 0.34 mmol) was dissolved in 9 mL of dichloromethane. Molecular sieve (4 A, 360 mg) and PCC (360 mg, 1.7 mmol) were added. The reaction mixture was stirred for 1 h at room temperature. After passing through celite, 509-HD-125 was obtained as colorless oil in quantitative yield.

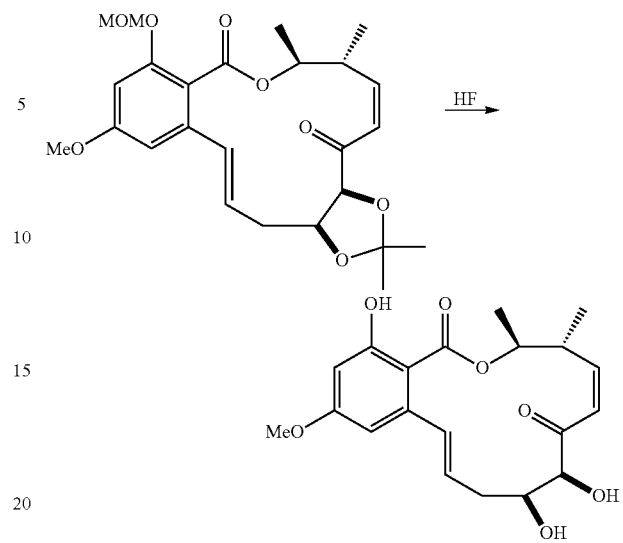

509-HD-125 was dissolved in 2.5 mL of dichloromethane. Then hydrofluoric acid (6 N, 10 mL) was added. The reaction mixture was stirred at room temperature for 30 min. It was diluted with more dichloromethane, washed with water and sat. sodium bicarbonate solution. After purification on a plug of silica gel, ER803064 was obtained as a white solid in 86% yield.

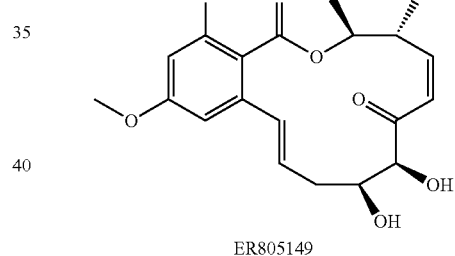

ER805149

ER805149 were synthesized in similar manner starting from the corresponding acetylene.

Preparation of B2526 (Trans Cyclopentane with Desired Diol Configuration)

Step 1

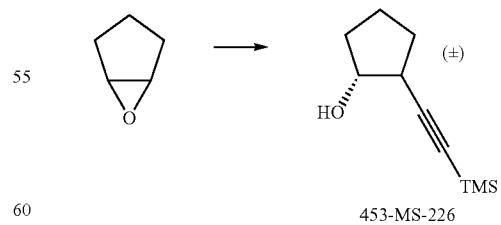

453-MS-226

To a solution of (trimethylsilyl)acetylene (8.8 mL, 62 mmol) in dry THF (100 mL), at −78° C. under an inert atmosphere, were added a 2.5M solution of n-butyllithium (24.9 mL, 62 mmol) and boron trifluoride diethyl etherate (7.66 mL, 62 mmol). The reaction mixture was then treated drop wise with a solution of cyclopentene oxide (2.71 mL, 31 mmol). The reaction mixture was stirred at −78° C. for 1 hour then warmed to room temperature. The usual work up gave compound 453-MS-226 (3.92 g; 69%).

Step 2

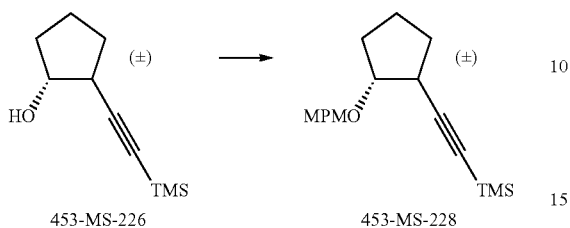

To a mixed solution of 453-MS-226 (3.77 g, 20.67 mmol) and 4-methoxybenzyl 2,2,2-trichloroacetimidate (7 g, 24.8 mmol) in diethyl ether (80 mL), at room temperature under an inert atmosphere, was added a 1M solution of trifluoromethane sulphonic acid in diethyl ether (0.62 mL) drop wise over approximately 15 minutes. Two extra aliquots (1 mL each) of the 1M trifluoromethane sulphonic acid solution were added at 10 minutes and at 60 minutes. The usual work up, with subsequent partial purification by chromatography, gave impure compound 453-MS-228 (3.37 g, approximately 54%), which was used in the next step without further purification.

Step 3

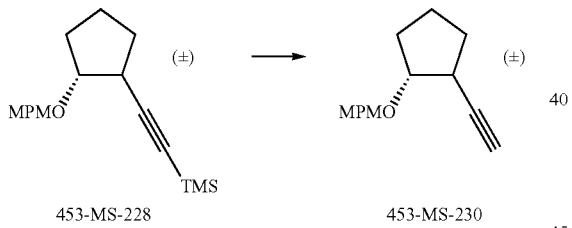

A solution of impure 435-MS-228 (3.37 g, approximately 0.011 mol) in methanol (33 mL) was treated with potassium carbonate (3.075 g, 0.022 mol) and stirred for 3.5 hours. The usual work up, followed by chromatographic purification, gave compound 453-MS-230 (2.22 g, approximately 88%).

Step 4

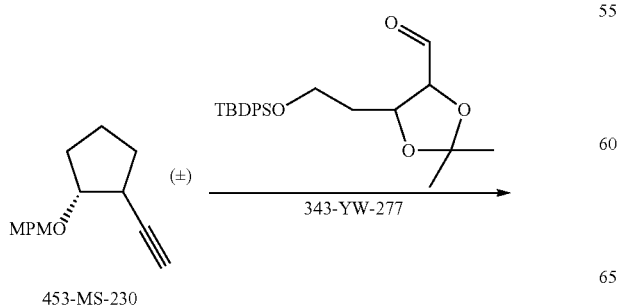

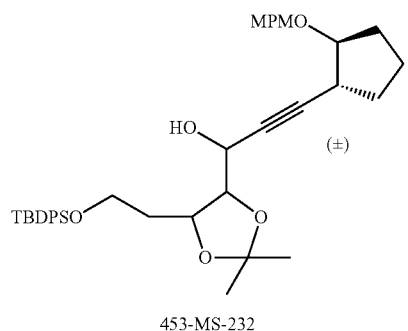

To a solution of 453-MS-230 (1 g, 4.37 mmol) in dry THF (10 mL), at −78° C. under an inert atmosphere, was added drop wise a 1.6M solution of n-butyllithium (2.73 mL, 4.37 mmol). The reaction mixture was stirred at −78° C. for 10 minutes, then warmed momentarily to 0° C., and cooled to −78° C. A solution of the 343-YW-277 (1.5 g, 3.63 mmol) in dry THF (15 mL) was added drop wise. The reaction mixture was stirred at −78° C. for 30 minutes then warmed to room temperature. The usual work up, followed by chromatographic purification, gave compound 453-MS-232 (1.90 g, 82%).

Step 5

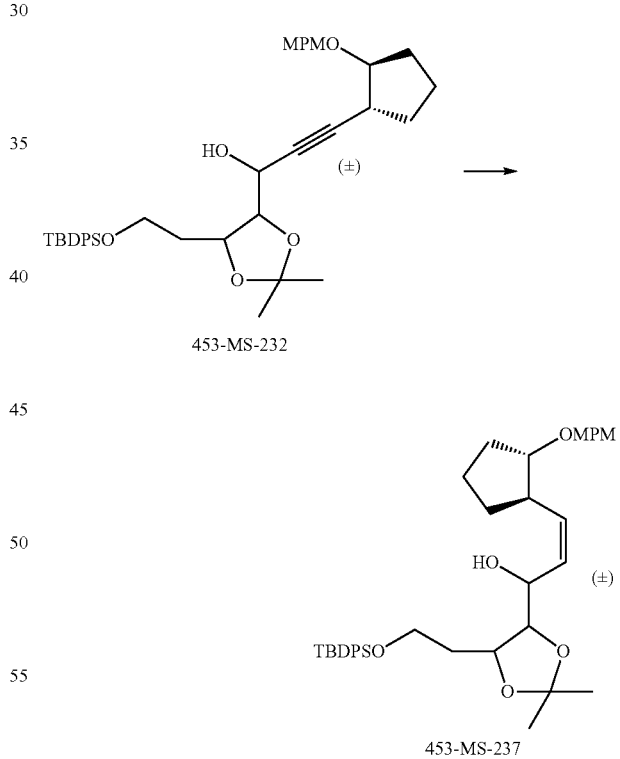

A solution of compound 453-MS-232 (1.68 g, 2.61 mmol) in hexane (30 mL) was hydrogenated, at room temperature and pressure, in the presence of Lindlar's catalyst (168 mg) and quinoline (30 μL) for 20 hours. Filtration and concentration in vacuo gave compound 453-MS-237 (1.68 g, assumed quantitative) which was used in the next stage without purification.

Step 6

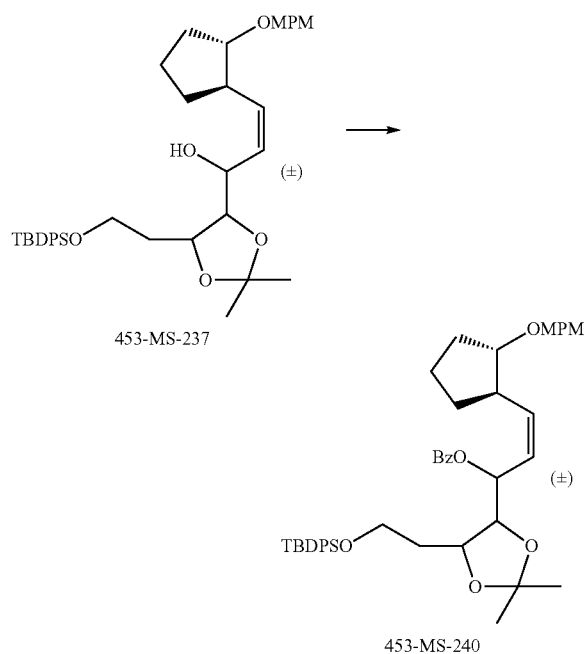

To a solution of compound 453-MS-237 (1.61 g, 2.5 mmol) in dry dichloromethane (20 mL) were added triethylamine (2.09 mL, 15 mmol), DMAP (30 mg, 0.25 mmol), and benzoyl chloride (0.58 mL, 5 mmol). The reaction mixture was stirred at room temperature for 3 days then worked up in the usual manner. Chromatographic purification gave compound 453-MS-240 (1.29 g, 69%).

Step 7

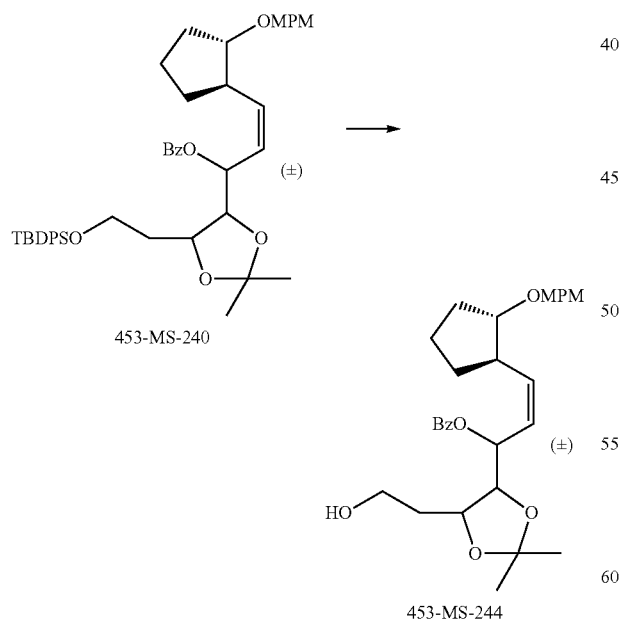

To a solution of compound 453-MS-240 (300 mg, 0.4 mmol) in THF (6 mL) was added TBAF (210 mg, 0.8 mmol). The reaction mixture was stirred at room temperature for 2.5 hours then worked up in the usual manner to give compound 453-MS-244 (145 mg, 71%) (m/z: 533.2516 measured [M+23], 533.2510 calculated).

Step 8

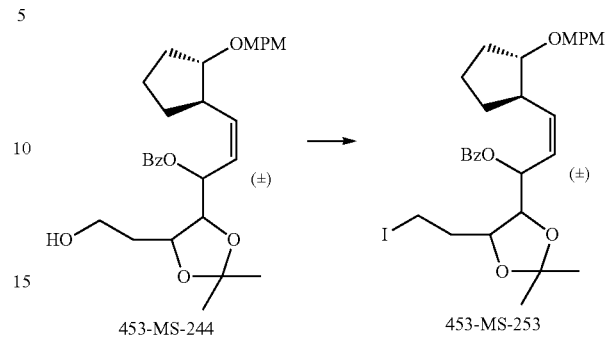

A mixed solution of compound 453-MS-244 (737 mg, 1.44 mmol) and triphenylphosphine (682 mg, 2.6 mmol) in dry toluene (10 mL) was cooled to 0° C. under an inert atmosphere. A solution of dibenzyl azidodicarboxylate (1.033 g, 3.46 mmol) in toluene (5 mL), and methyl iodide (117 µl; 1.88 mmol) were added, separately and simultaneously, to the reaction mixture over approximately 15 seconds. The reaction mixture was stirred at 0° C. for 15 minutes then allowed to warm to room temperature. After 30 minutes at room temperature the reaction mixture was worked up in the usual manner. Chromatographic purification gave compound 453-MS-253 (550 mg, 61%).

Step 9

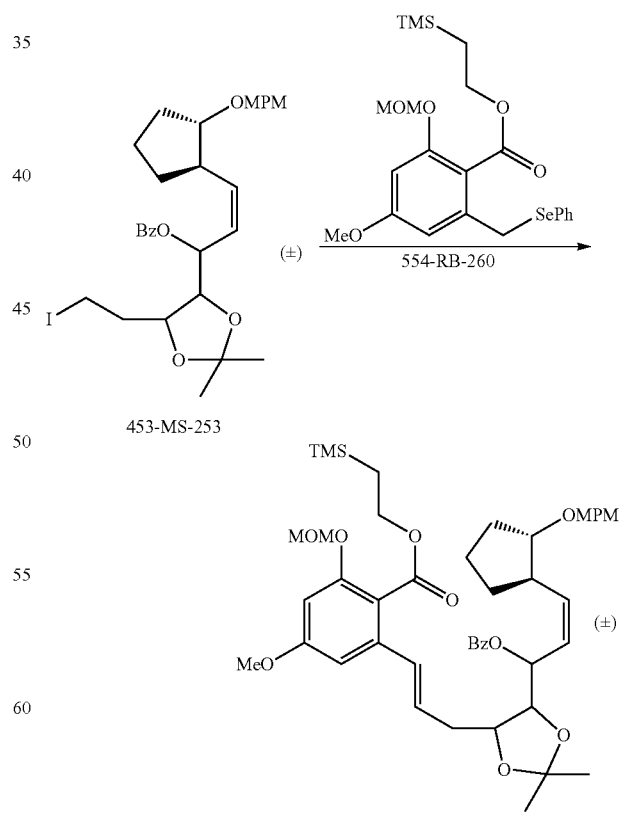

A mixture of compound 453-MS-253 (475 mg, 0.765 mmol) and compound 554-RB-260 (519 mg, 0.86 mmol) was dissolved in a solution of 10% HMPA in THF (6 mL) and cooled to −78° C. under an inert atmosphere. A 0.5 M solution of LiHMDS in THF (1.83 mL, 0.916 mmol) was then added drop wise over approximately 30 minutes. The reaction mixture was stirred at −78° C. for 1 hour then treated with a 1M solution of LiHMDS in THF (0.916 mL; 0.916 mmol). After 20 minutes the reaction mixture was warmed to 0° C. The intermediate crude product was worked up in the usual manner and purified partially by chromatography. The intermediate was dissolved in dichloromethane (8 mL) and cooled to 0° C. A solution of approximately 65% meta-chloroperbenzoic acid (249 mg) in dichloromethane (2 mL) was added portion wise. After 30 minutes triethylamine (0.65 mL) was added and the usual work up, followed by chromatographic purification, gave compound 453-MS-262 (348 mg, 47%).

Step 10

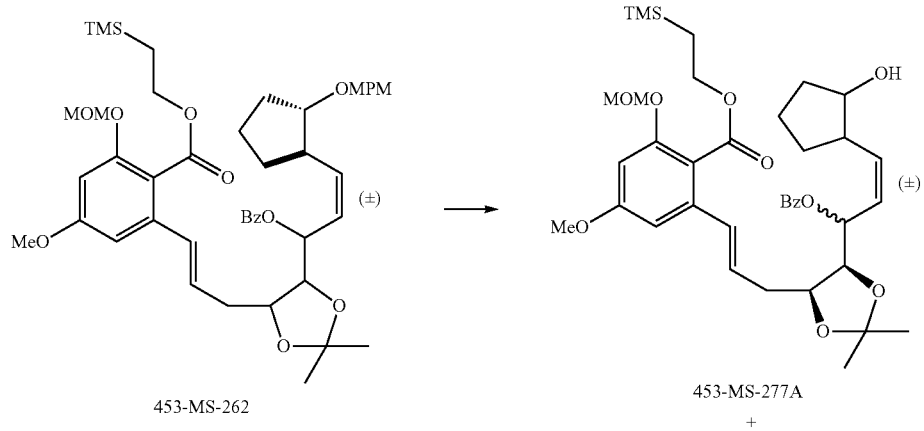

453-MS-262

453-MS-277A

+

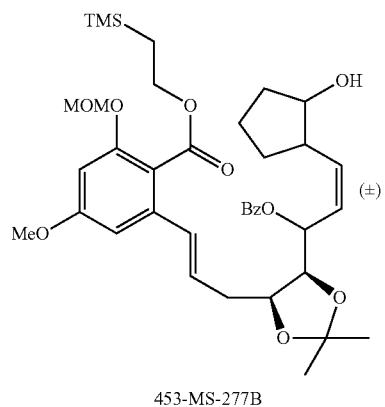

453-MS-277B

To a vigorously stirred biphasic mixture of compound 453-MS-262 (440 mg, 0.538 mmol), dichloromethane (20 mL) and water (10 mL), was added drop wise a solution of DDQ (147 mg, 0.646 mmol) in dichloromethane (15 mL). After 1 hour at room temperature the reaction mixture was worked up in the usual manner. Chromatographic purification gave two fractions of partially resolved diastereoisomers: Fraction A (less polar): a mixture of 3 co-eluted diastereoisomers—compound 453-MS-277A (190 mg); Fraction B (more polar): a single diastereoisomer—compound 453-MS-277B (122 mg); (total yield: 312 mg, 83%)

Step 11

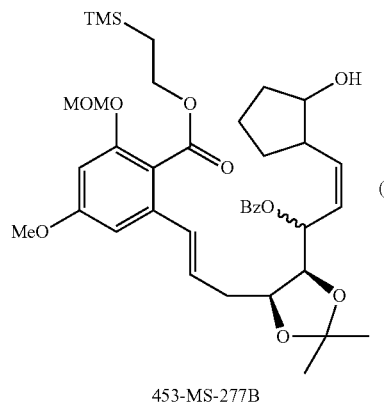

453-MS-277B

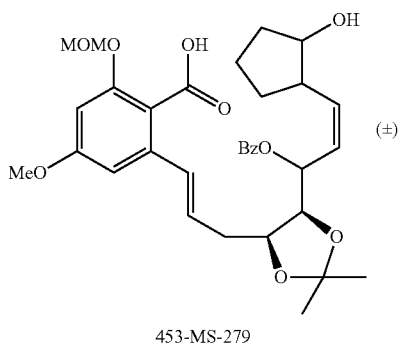

453-MS-279

A solution of compound 453-MS-277B (122 mg, 0.175 mmol) in tetrahydrofuran (5 mL) was treated with a solution of TBAF (92 mg, 0.35 mmol) in THF (1 mL). The reaction mixture was stirred at room temperature for 6 hours then worked up in the usual manner to give impure compound 453-MS-279 (104 mg), which was used in the next stage without purification.

Step 12

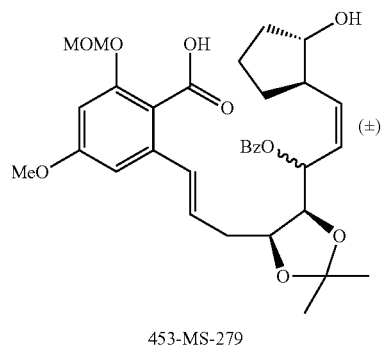

453-MS-279

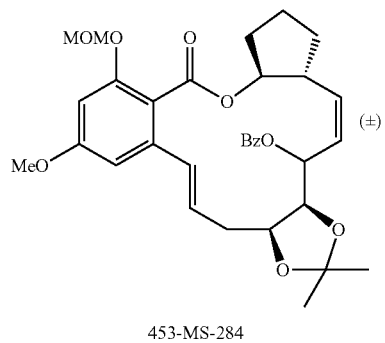

453-MS-284

A solution of crude compound 453-MS-279 (80 mg, assumed to contain 0.134 mmol) in dichloromethane (30 mL) was treated with 2-chloro-1-methylpyridinium iodide (45 mg, 0.174 mmol) and tri-n-butylamine (42 µL, 0.174 mmol). The reaction mixture was heated under reflux for 25 minutes then cooled to room temperature. The usual work up and chromatographic purification gave compound 453-MS-284 (30 mg, 39% from compound 453-MS-277B).

Step 13

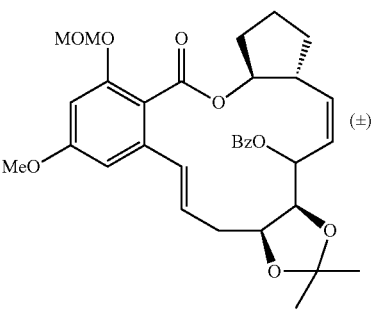

453-MS-284

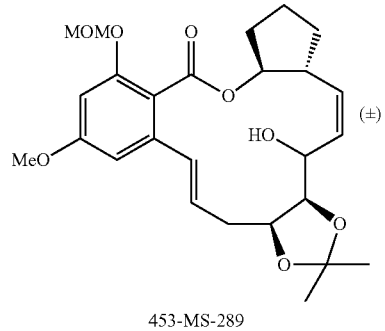

453-MS-289

A solution of compound 453-MS-284 (30 mg, 51 µmol) in a mixture of ethanol (1 mL) and tetrahydrofuran (0.5 mL) was treated with 1M aqueous sodium hydroxide (518 µL) and stirred for approximately 3 days at room temperature. The usual work up, followed by chromatographic purification, gave compound 453-MS-289 (16 mg, 65%).

Step 14

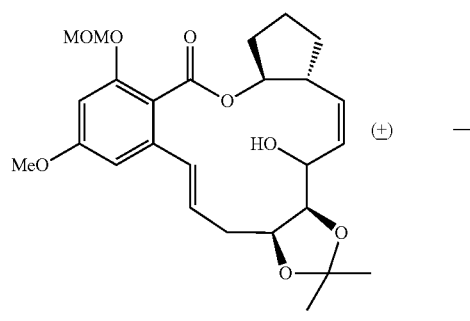

453-MS-289

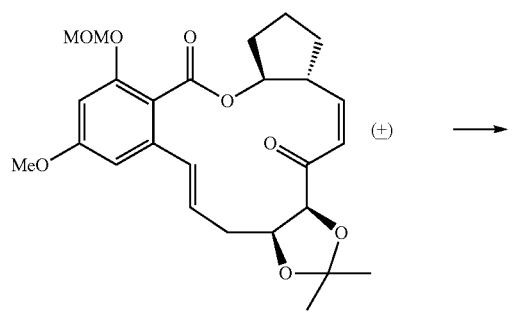

453-MS-296

A solution of compound 453-MS-289 (15 mg, 31.6 μmol) in dichloromethane (1.5 mL) was treated with PCC (81 mg, 0.375 mmol) in the presence of powdered 4 Å molecular sieves (81 mg). The reaction mixture was stirred vigorously for 70 minutes at room temperature. Basification with excess triethylamine, followed by partial chromatographic purification gave impure compound 453-MS-296 (approximately 7 mg), which was used in the next stage without further purification.

Step 15

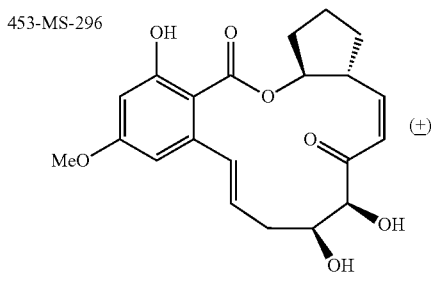

453-MS-296

B2526

A solution of impure compound 453-MS-296 (approximately 7 mg) in a mixture of acetonitrile (1600 μL) and dichloromethane (400 μL) was treated with 48% aqueous hydrofluoric acid (400 μL). After 25 minutes the usual work up followed by chromatographic purification gave compound B2526 (1.1 mg, approximately 6% from compound 453-MS-289).

Preparation of B2538 (Cis Cyclopentane with Desired Diol Configuration)

Step 1

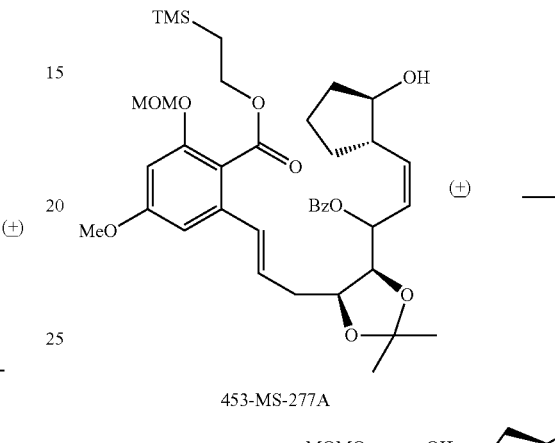

453-MS-277A

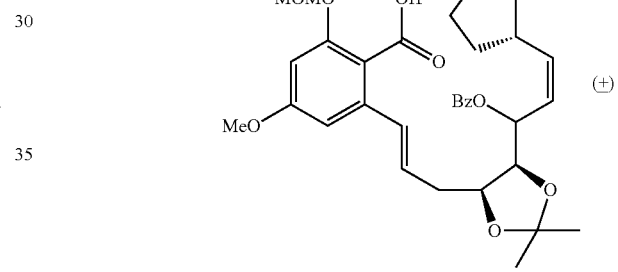

453-MS-281

To a solution of compound 453-MS-277A (190 mg, 0.273 mmol) in tetrahydrofuran (7 mL) was added a solution of TBAF (143 mg, 0.545 mmol) in THF (2 mL). After 1 hour at room temperature the reaction mixture was treated with additional TBAF (20 mg, 0.076 mmol). After a further 3 hours the reaction mixture was worked up in the usual manner to give impure compound 453-MS-281 (186 mg), which was used in the next stage without purification.

Step 2

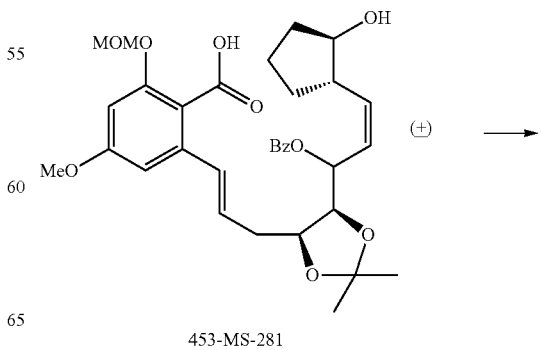

453-MS-281

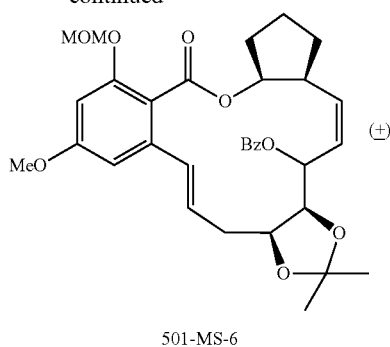

501-MS-6

To a solution of triphenylphosphine (31.5 mg, 0.12 mmol) in dry tetrahydrofuran (2.5 mL) was added diethyl azidodicarboxylate (19 mL; 0.12 μmol), at room temperature under an inert atmosphere. A solution of impure compound 453-MS-281 (36 mg, 0.06 mmol) in dry tetrahydrofuran (2.5 mL) was added. After 90 minutes additional triphenylphosphine (31.5 mg, 0.12 mmol) and diethyl azidodicarboxylate (19 ml, 0.12 mmol) were added. After a further 30 minutes the reaction mixture was worked up in the usual manner. Chromatographic purification gave compound 501-MS-6 (19 mg, 54% from compound 453-MS-277A).

Step 3

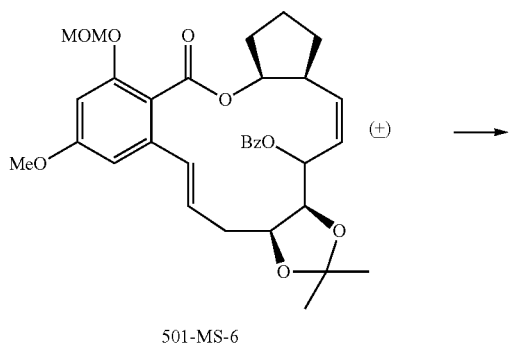

501-MS-6

501-MS-8

A solution of compound 501-MS-6 (19 mg, 32.8 μmol) in a mixture of ethanol (1 mL) and THF (0.5 mL) was treated with 1M aqueous NaOH (380 μL) and stirred for approximately 17 hours at room temperature. The reaction mixture was then heated to 100° C. for approximately 30 minutes. The usual work up gave compound 501-MS-8 (15.5 mg, quantitative).

Step 4

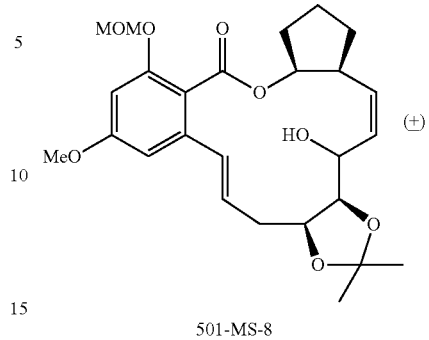

501-MS-8

501-MS-11

A solution of compound 501-MS-8 (15.5 mg, 32 μmol) in dichloromethane (3.2 mL) was treated with PCC (85 mg, 0.39 mmol) in the presence of powdered 4 Å molecular sieves (85 mg). The reaction mixture was stirred vigorously for 2 hours at room temperature. Basification with excess triethylamine, followed by chromatographic purification gave compound 501-MS-11 (12.5 mg, 83%).

Step 5

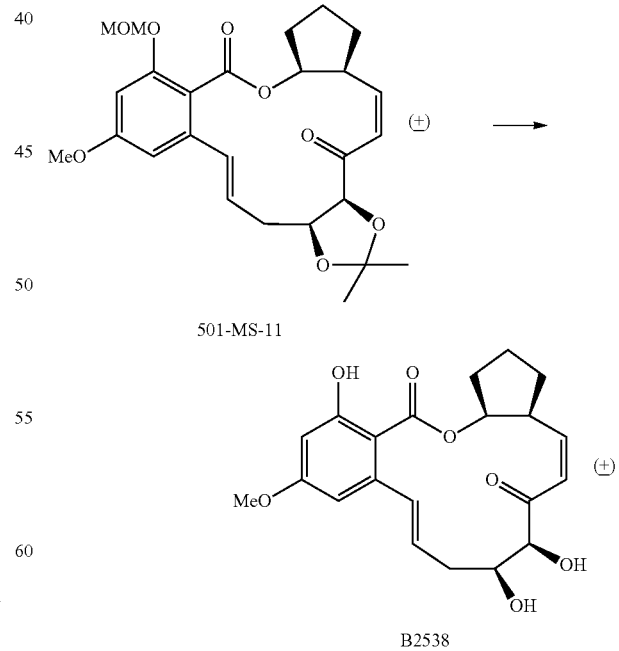

501-MS-11

B2538

A solution of compound 501-MS-11 (12 mg, 25 mmol) in a mixture of acetonitrile (2400 μL) and dichloromethane (600

μL) was treated with 48% aqueous hydrofluoric acid (600 μL). After 1 hour the usual work up followed by chromatographic purification gave compound B2538 (4 mg, 41%) (m/z: 411.1 [M+23, 100%], 412.1 [35%]).

Preparation of B2522 (Trans Cyclopentane with Undesired Diol Configuration)

Step 1

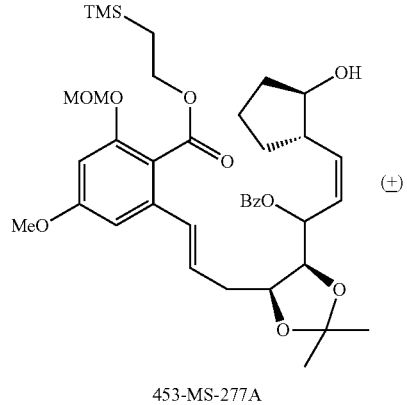

453-MS-277A

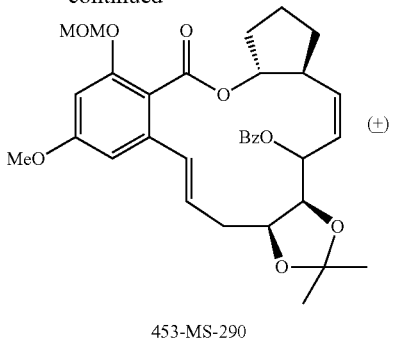

453-MS-290

A solution of crude compound 453-MS-281 (150 mg, assumed to contain 0.251 mmol) in dichloromethane (15 mL) was treated with 2-chloro-1-methylpyridinium iodide (84 mg, 0.327 mmol) and tri-n-butylamine (78 μL, 0.327 mmol). The reaction mixture was heated under reflux for 40 minutes then treated with additional 2-chloro-1-methylpyridinium iodide (84 mg, 0.327 mmol) and tri-n-butylamine (78 μL, 0.327 mmol). The reaction mixture was heated under reflux for a further 1 hour then cooled to room temperature. The usual work up and chromatographic purification gave compound 453-MS-290 (72 mg, 50% from compound 453-MS-277A).

Step 3

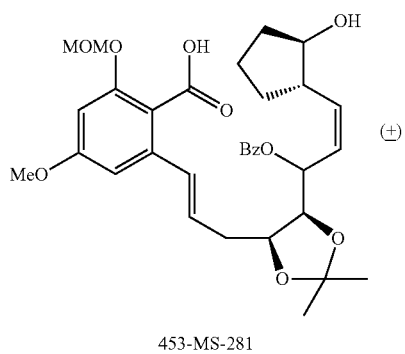

453-MS-281

A solution of compound 453-MS-277A (190 mg, 0.273 mmol) in THF (7 mL) was treated with a solution of TBAF (143 mg, 0.545 mmol) in THF (2 mL). The reaction mixture was stirred at room temperature for 6 hours then worked up in the usual manner to give impure compound 453-MS-281 (186 mg), which was used in the next stage without purification.

Step 2

453-MS-281

453-MS-290

453-MS-292B

A solution of compound 453-MS-290 (72 mg, 0.124 mol) in a mixture of ethanol (2.4 mL) and THF (1.2 mL) was treated with 1M aqueous NaOH (1.24 mL, 1.24 mmol) and stirred for approximately 4 days at room temperature. The usual work up, followed by chromatographic purification, gave three fractions of partially resolved compounds:

Fraction A (less polar): an unascertained mixture of diastereoisomers (10 mg);

Fraction B (more polar): a mixture of 2 diastereoisomers—compound 453-MS-292B (46 mg);

Fraction C (most polar): single diastereoisomer of starting material 453-MS-290 (2 mg);
(total yield: 56 mg; 95%)

Step 4

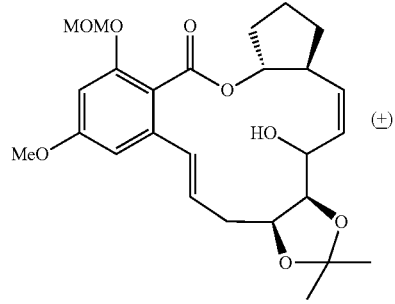

453-MS-292B

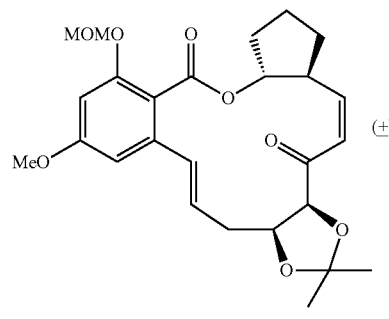

453-MS-299

A solution of compound 453-MS-292B (20 mg, 42 μmol) in dichloromethane (2 mL) was treated with PCC (109 mg, 0.505 mmol) in the presence of powdered 4 Å molecular sieves (109 mg). The reaction mixture was stirred vigorously for 55 minutes at room temperature. Basification with excess triethylamine, followed by chromatographic purification, gave compound 453-MS-299 (17 mg, 86%).

Step 5

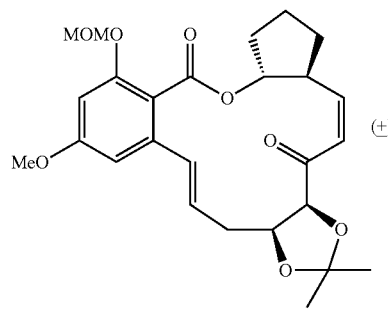

453-MS-299

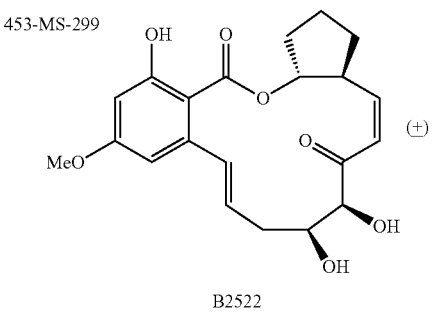

B2522

A solution of compound 453-MS-299 (19 mg, 0.04 mmol) in a mixture of acetonitrile (4 mL) and dichloromethane (1 mL) was treated with 48% aqueous hydrofluoric acid (1 mL). After 35 minutes the usual work up followed by chromatographic purification gave compound B2522 (9 mg, 58%) (m/z: 411.1443 measured [M+23], 411.1420 calculated).

ER804018 and ER804019 (C4-F):

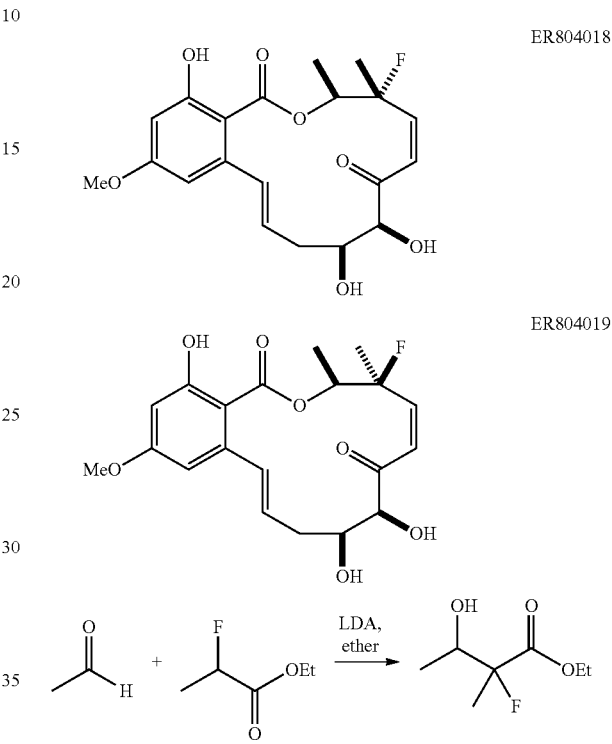

LDA (2.0 M, 36 mL) was added to the solution of ethyl 2-fluoropropanate (7.23 g) and acetaldehyde (13.5 mL) in ether (100 mL) at −78° C. After the addition finished the reaction flask was kept in ice bath and gradually warm to room temperature. The reaction was quenched with aqueous ammonium chloride after overnight stirring. The aqueous phase was extracted with ether and the combined organic phase was dried over sodium sulfate. The solvent was stripped off and the residue was distilled in vacuo to give 541-YJ-97 (4.22 g).

Chloro-t-butyldiphenylsilane was added to the mixture of 541-YJ-97 (4.22 g) and imidazole (3.5 g) in methylene chloride (50 mL) and stirred overnight. Aqueous sodium bicarbonate was added to the reaction mixture. The aqueous phase was extracted with ether and the combined organic phase was dried over sodium sulfate. The solvent was stripped off and the residue was purified with flush chromatograph (hexane/acetate 50/1) to give 541-YJ-99 (7.55 g).

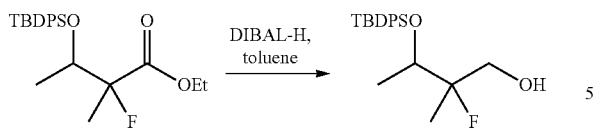

DIBAL-H in toluene (1.0 M, 25 ml) was added to 541-YJ-99 in toluene (85 mL) at 0° C. The reaction was quenched in one hour with methanol/water and filtrated through Celite. The residue was purified by flash chromatograph to yield 541-YJ-101 (536 mg).

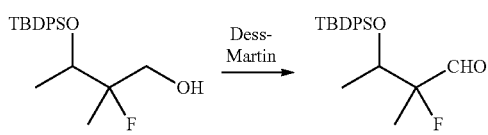

Dess-Martin periodinane was added to 541-YJ-101 (511 mg) in methylene chloride (15 ml) at room temperature. The mixture was diluted with ether in 40 minutes and filtrated through Celite. The filtrate was concentrated, and the residue was purified by prepTLC (hex/acetate 7/1) to give 541-Yj-105 (355 mg, 70%).

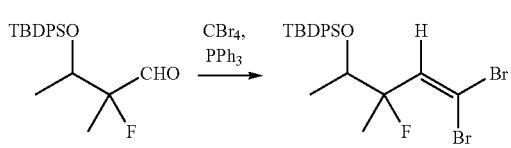

Triphenylphosphine (2.08 g) was added to carbon tetrabromide (1.31 g) in methylene chloride at room temperature. After stirring for 40 minutes 541-YJ-105 was added and stirred for 2 hours. The mixture was concentrated and filtrated through silica gel (hexane/acetate 7/1) to produce 541-YJ-106 (452 mg, 89%).

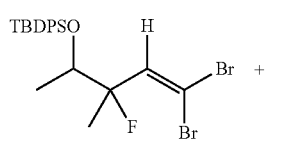

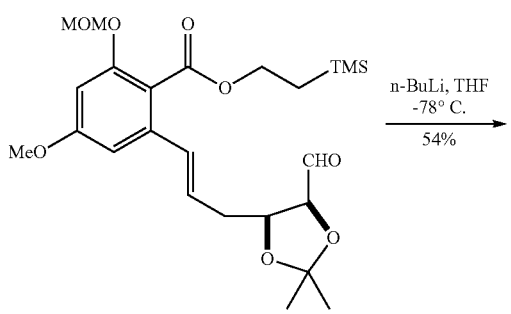

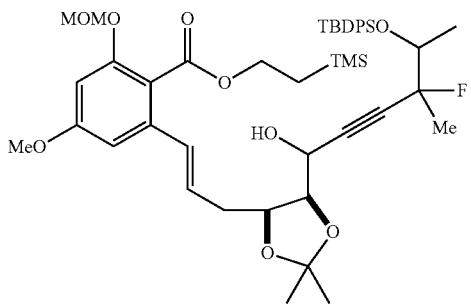

n-Butyllithium (2.5 M, 0.74 mL) was added to 541-YJ-106 (450 mg) in THF (10 mL) at −78° C. After one hour 541-YJ-108 was added. The reaction was kept at 0° C. for one hour and warmed to room temperature before it was quenched with aqueous ammonium chloride. The aqueous phase was extracted with ether and the combined organic phase was dried over sodium sulfate. The solvent was stripped off and the residue was purified with TLC (hexane/acetate 4/1) to 541-YJ-109 (394 mg, 54%).

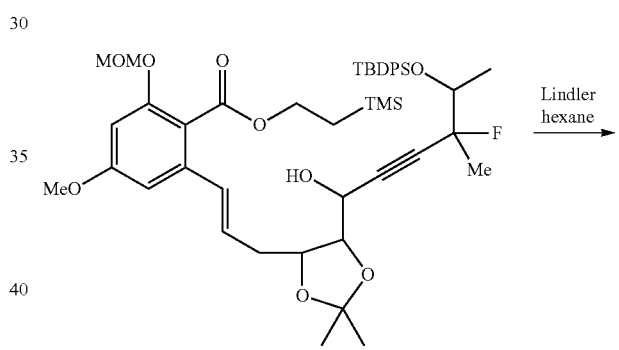

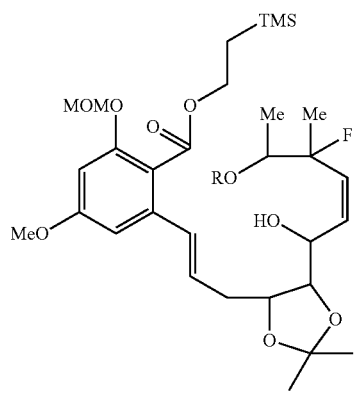

The suspension of Lindlar catalyst (420 mg) and 541-YJ-109 (390 mg) in hexane (8 mL) was charged with hydrogen and stirred overnight. The suspension was filtrated through Celite and rinsed with acetate. The filtrate was concentrated to give 541-YJ-111 (378 mg).

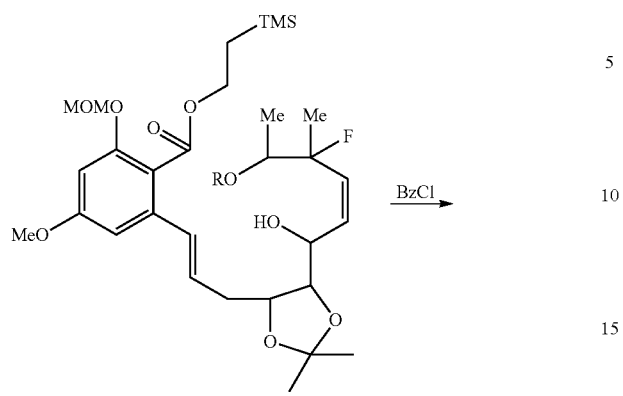

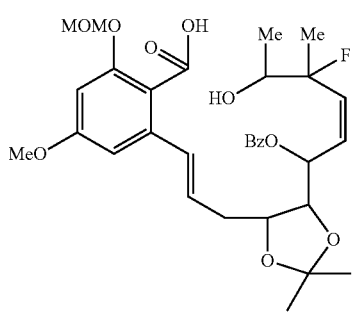

The solution of 541-YJ-115 (419 mg) and TBAF (1.0 M, 2.2 mL) in THF (8 mL) was kept stirring overnight, and then diluted with water. The aqueous phase was extracted with ether and concentrated. The residue was purified with TLC (methylene chloride/methanol 10/1) to give 541-YJ-116 (194 mg).

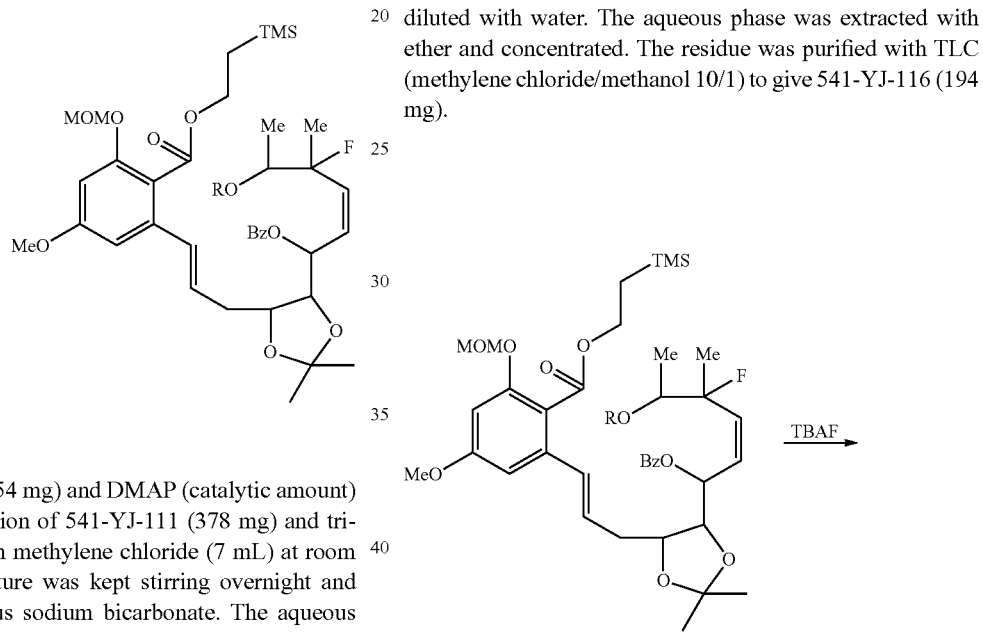

Benzoyl chloride (254 mg) and DMAP (catalytic amount) was added to the solution of 541-YJ-111 (378 mg) and triethylamine (0.5 mL) in methylene chloride (7 mL) at room temperature. The mixture was kept stirring overnight and quenched with aqueous sodium bicarbonate. The aqueous phase was extracted with ether and the combined organic phase was dried over sodium sulfate. The solvent was stripped off and the residue was purified with TLC (hexane/acetate 7/1) to 541-YJ-115 (419 mg).

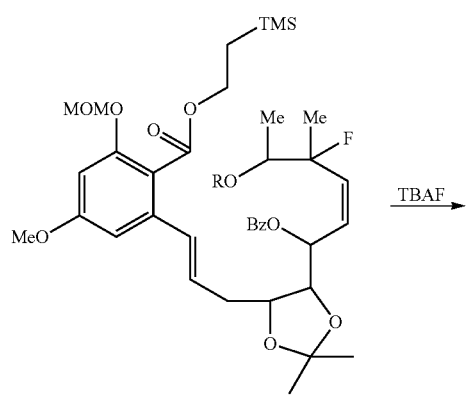

The solution of 541-YJ-115 (419 mg) and TBAF (1.0 M, 2.2 mL) in THF (8 mL) was kept stirring overnight, and then diluted with water. The aqueous phase was extracted with ether and concentrated. The residue was purified with TLC (methylene chloride/methanol 10/1) to give 541-YJ-116' (21 mg).

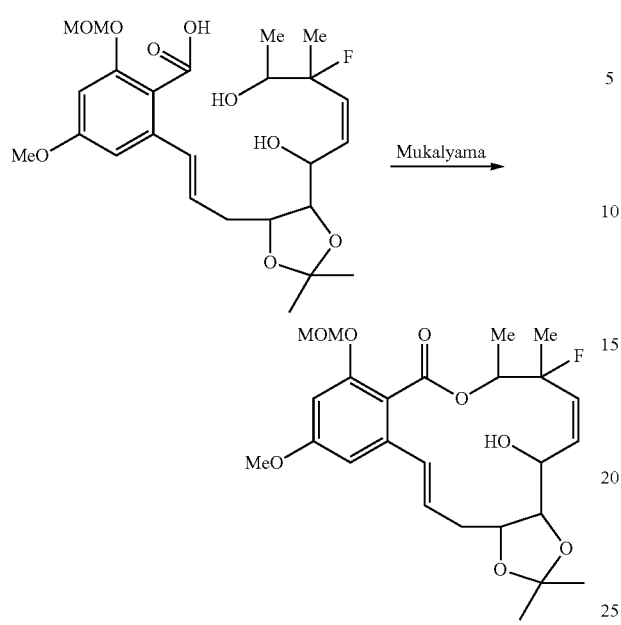

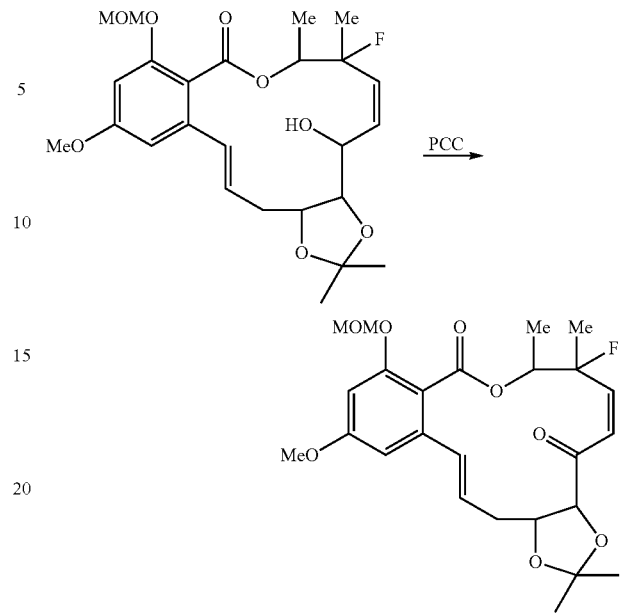

541-YJ-116 (21 mg) was added to the reflux of 2-chloro-1-methylpyridium iodide (32 mg) and tributylamine (23 mg) in methylene chloride (4 mL). After 2 hours reflux the mixture was stirred overnight. The mixture was diluted with ether and washed with HCl (1.0 N) and water. The residue was purified with TLC (hexane/acetate 1/1) to give 541-YJ-118-1 (7.7 mg) and 541-YJ-118-2 (8.4 mg).

PCC was added to 541-YJ-118-2 (8.4 mg) and MS 4 A suspension in methylene chloride (2 mL) at room temperature. The mixture was stirred for 3 hours and filtrated through silica gel. The silica gel was eluted with acetate and concentrated to give 541-YJ-120 (3.0 mg).

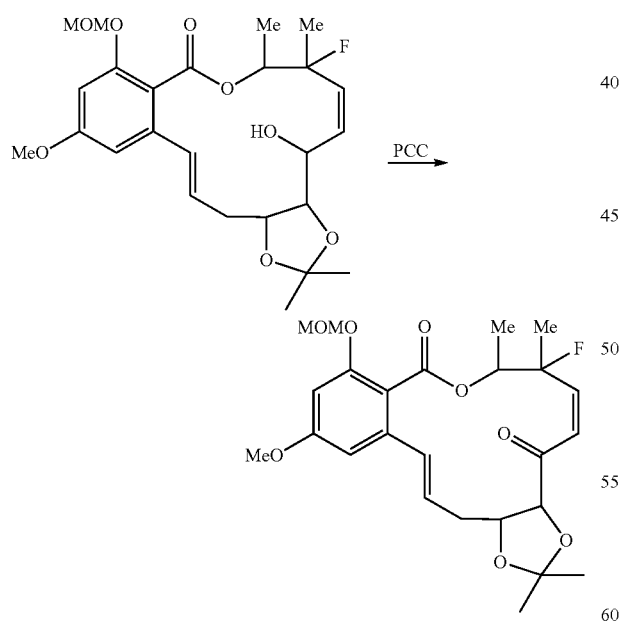

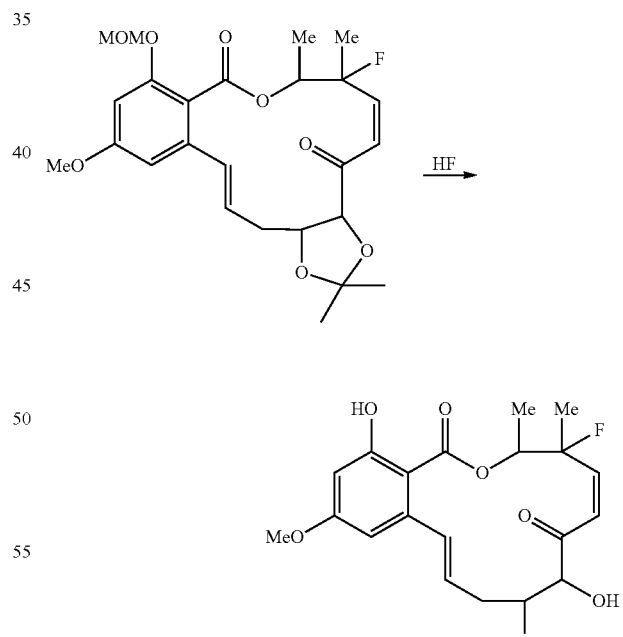

PCC was added to 541-YJ-118-1 (7.7 mg) and MS 4 A suspension in methylene chloride (2 mL) at room temperature. The mixture was stirred for 3 hours and filtrated through silica gel. The silica gel was eluted with acetate and concentrated to give 541-YJ-119 (3.3 mg).

Hydrofluoric acid (49%, 1 mL) was added to 541-YJ-119 (8.0 mg) in acetonitrile (3 mL) and stirred for 15 minutes. The mixture was diluted with water and extracted with methylene chloride. The organic phase was concentrated and purified with a short silica gel pad to produce 541-YJ-126 (5.1 mg, ER-804018).

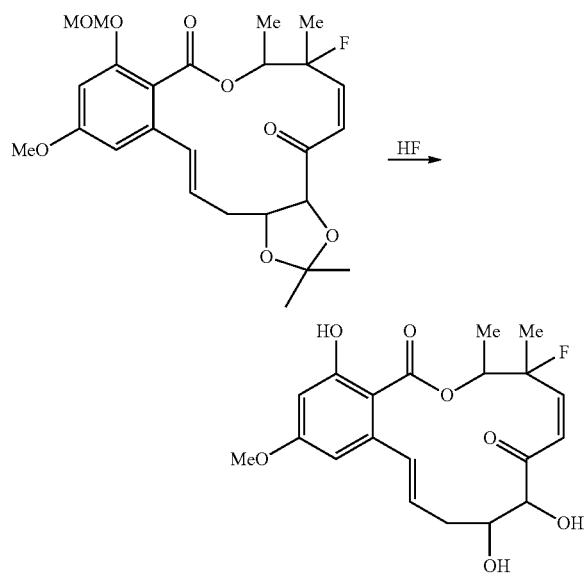

Hydrofluoric acid (49%, 1 mL) was added to 541-YJ-120 (6.0 mg) in acetonitrile (3 mL) and stirred for 15 minutes. The mixture was diluted with water and extracted with methylene chloride. The organic phase was concentrated and purified with a short silica gel pad to produce 541-YJ-126 (3.1 mg, ER-804019).

Preparation of ER804142 and ER804143, C4-CF3 Analog:

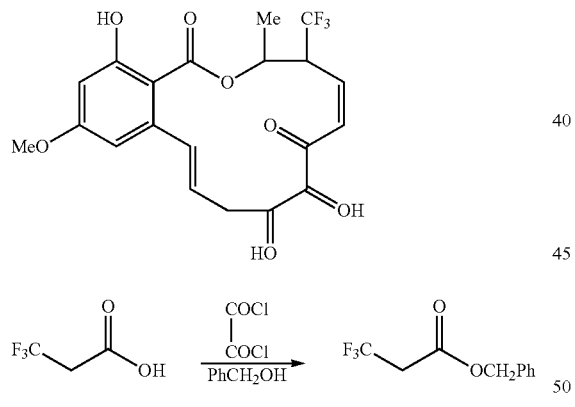

To neat trifluoropropanic acid (10.0 g) was added oxalyl chloride (7.5 mL) at room temperature and kept the mixture at 50° C. overnight. Then benzyl alcohol was added and kept stirring for 10 hours. The reaction was quenched with aqueous sodium bicarbonate and extracted with chloroform. The solvent was stripped off and the residual was purified with flush chromatograph (hexane/acetate 20/1) to afford 541-YJ-139 (16.05 g, 94%).

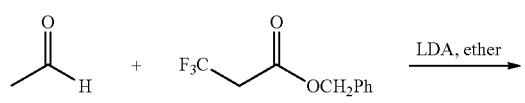

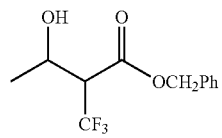

LDA (1.5 M, 53.9 ml) was added to the solution of 541-YJ-139 (7.23 g) and acetaldehyde (20.6 ml) in THF (180 mL) at −78° C. After the addition finished the reaction flask was kept in ice bath and gradually warm to room temperature. The reaction was quenched with aqueous ammonium chloride after overnight stirring. The aqueous phase was extracted with ether and the combined organic phase was dried over sodium sulfate. The solvent was stripped off and the residue was purified with flush chromatograph (hexane/acetate 20/1 to 10/1) to afford 541-YJ-141 (10.26 g, 53%).

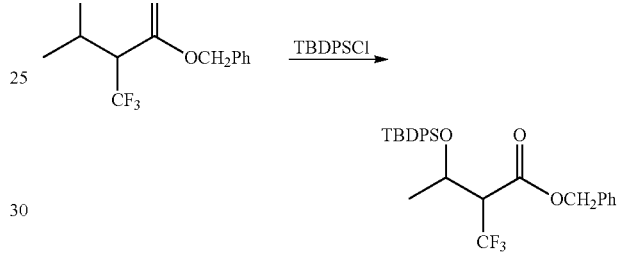

Chloro-t-butyldiphenylsilane (12.2 ml) was added to the mixture of 541-YJ-141 (10.26 g) and imidazole (10.7 g) in methylene chloride (200 ml) and stirred overnight. Aqueous sodium bicarbonate was added to the reaction mixture. The aqueous phase was extracted with chloroform and the combined organic phase was dried over sodium sulfate. The solvent was stripped off and the residue was purified with flush chromatograph (hexane/acetate 40/1) to give 541-YJ-143 (14.94 g, 76%).

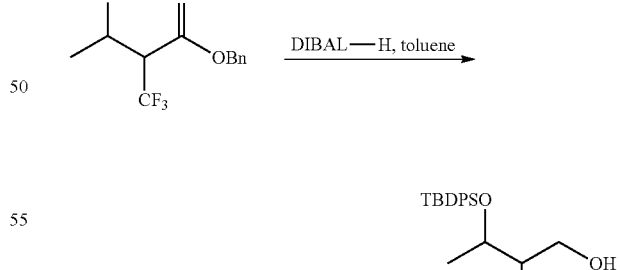

DIBAL-H in toluene (1.0 M, 89.4 mL) was added to 541-YJ-143 in toluene (300 mL) at 0° C. The reaction was quenched in one and half hour with methanol/water (70 mL/45 mL) and filtrated through Celite. The residue was purified by flash chromatograph (hexane/acetate 10/1) to yield 541-YJ-144 (7.38 g, 62%).

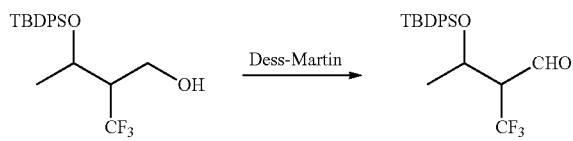

Dess-Martin periodinane (9.47 g) was added to 541-YJ-144 (7.38 g) in methylene chloride (150 mL) at room temperature. The mixture was diluted with ether in one hour and filtrated through Celite. The filtrate was concentrated and the residue was purified by flash chromatograph (hexane/acetate 10/1) to yield 541-YJ-145 (7.37 g).

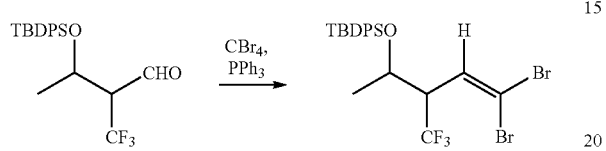

Triphenylphosphine (39.2 g) was added to carbon tetrabromide (24.74 g) in methylene chloride at room temperature. After stirring for 45 minutes 541-YJ-145 (7.37 g) was added and stirred for 3 hours. The mixture was concentrated and purified by flash chromatograph (methylene chloride) to yield 541-YJ-146 (8.74 g, 85%).

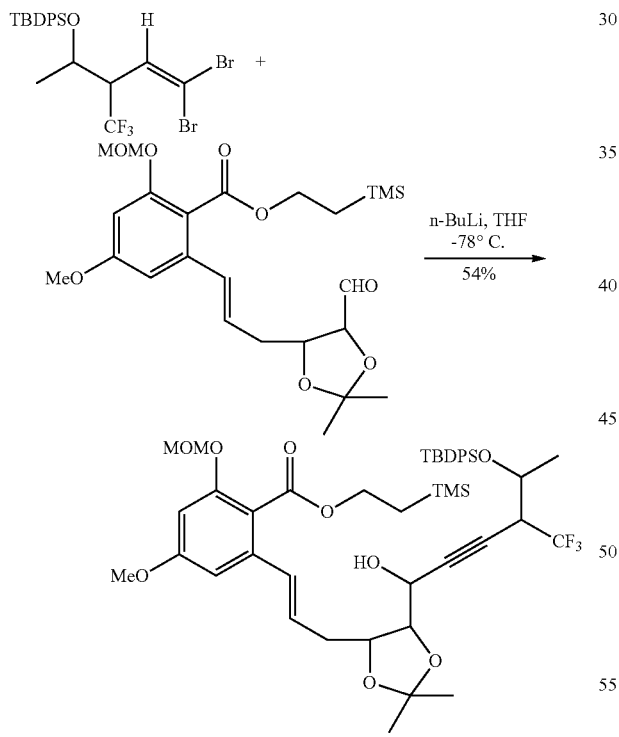

n-Butyllithium (2.5 M, 3.47 mL) was added to 541-YJ-106 (2.39 g) in THF (20 mL) at −78° C. After one hour 343-YW-277 (0.98 g) was added at −78° C. The reaction was kept at 0° C. for one hour and then warmed to room temperature before it was quenched with aqueous ammonium chloride. The aqueous phase was extracted with ether and the combined organic phase was dried over sodium sulfate. The solvent was stripped off and the residue was purified with flash chromatograph (hexane/acetate, 3/1) to 541-YJ-148 (1.40 g, 65%).

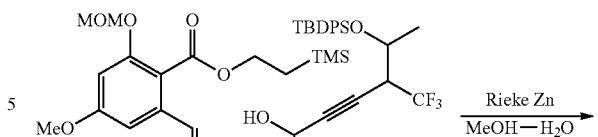

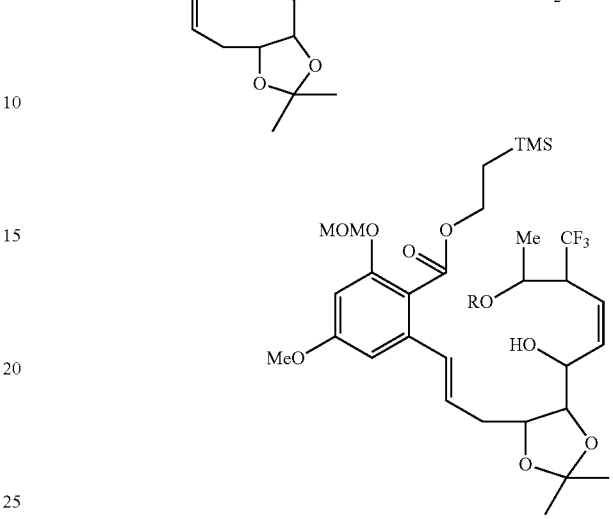

The suspension of Rieke zinc (9.0 mL) was carefully added to 541-YJ-148 (390 mg) in methanol-water (20 mL/2 mL) at room temperature. The suspension was heated at 70° C. for one and half hour. The mixture was filtrated through Celite and rinsed with acetate. The filtrate was concentrated to give 541-YJ-151 (1.09 g) without purification.

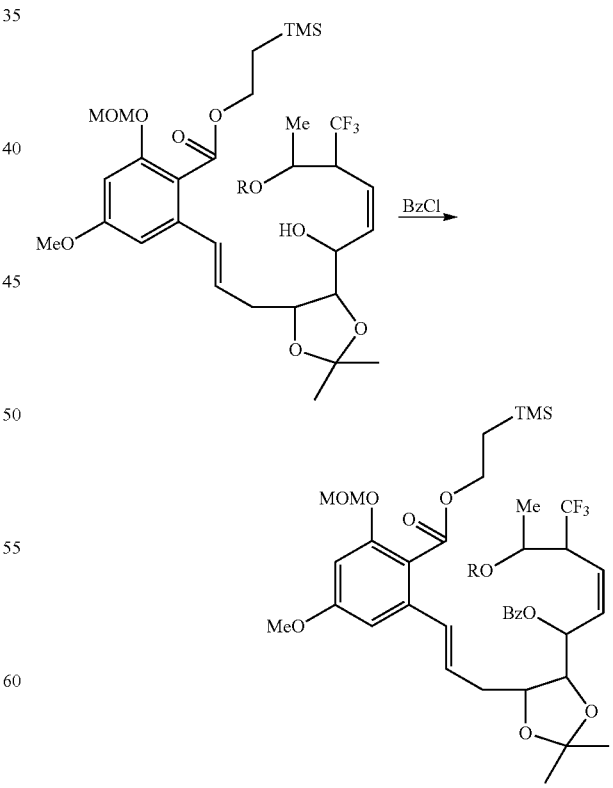

Benzoyl chloride (0.52 ml) and DMAP (catalytic amount) was added to the solution of 541-YJ-151 (0.97 g) and triethylamine (1.24 mL) in methylene chloride (15 mL) at room temperature. The mixture was kept stirring overnight and quenched with aqueous sodium bicarbonate. The aqueous phase was extracted with chloroform and the combined organic phase was dried over sodium sulfate. The solvent was stripped off and the residue was purified with flash chromatograph (hexane/acetate 5/1) to 541-YJ-158 (0.96 g, 88%).

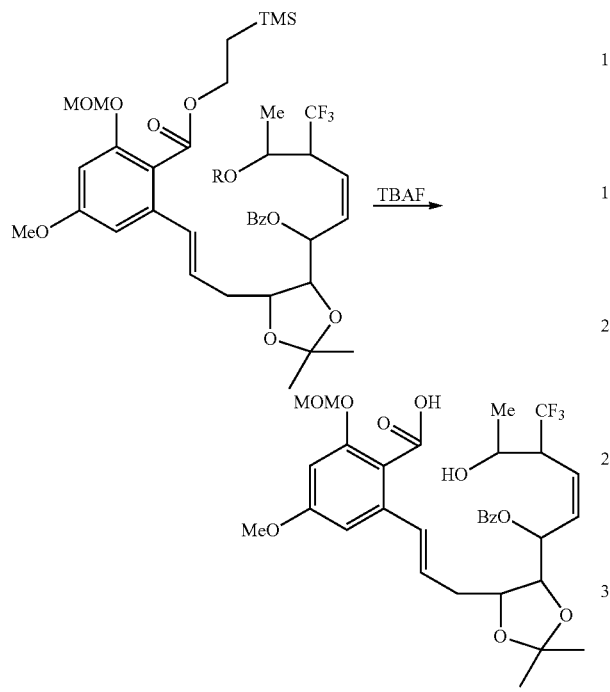

The solution of 541-YJ-158 (0.96 g) and TBAF (1.0 M, 4.9 mL) in THF (20 mL) was kept at 50° C. overnight and then diluted with water. The aqueous phase was extracted with ether and concentrated. The residue was purified with flash chromatograph (acetate) to give 541-YJ-159 (186 mg, 30%).

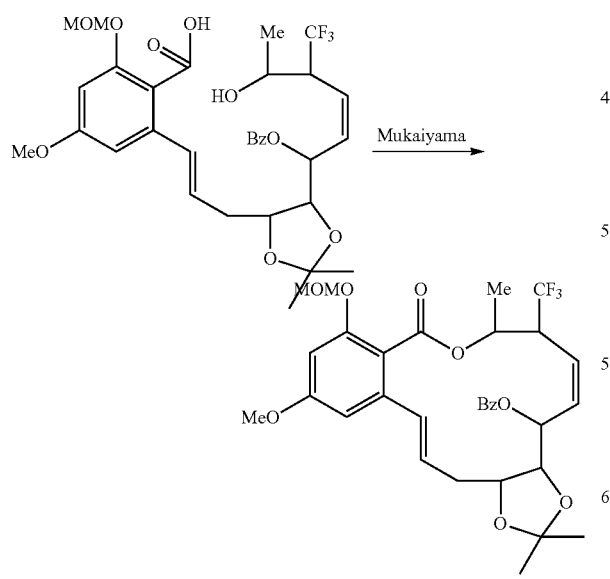

541-YJ-159 (186 mg) was added to the reflux of 2-chloro-1-methylpyridium iodide (223 mg) and tributylamine (162 mg) in methylene chloride (25 mL). After 2 hours reflux the mixture was cooled down. The mixture was diluted with ether and washed with HCl (1.0 N) and water. The residue was purified with TLC (hexane/acetate 1/1) to give 541-YJ-160 (169 mg).

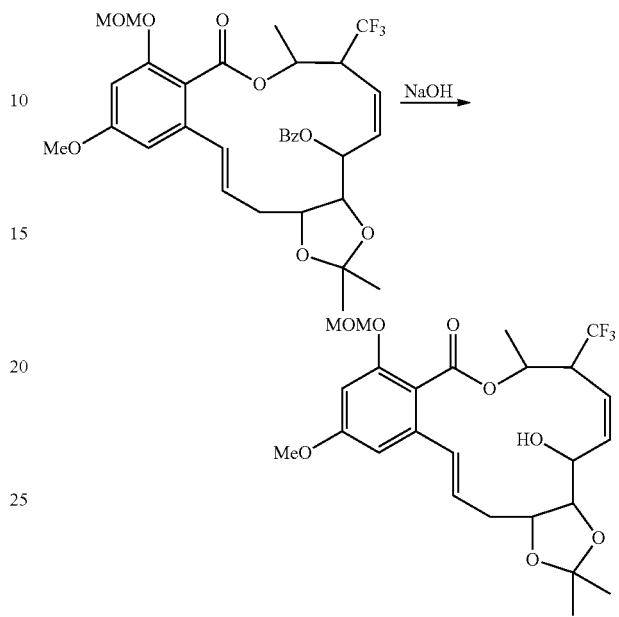

The solution of 593-YJ-160 (169 mg) and sodium hydroxide (1.0 N, 0.5 mL) in ethanol (5 mL) was kept at 75° C. overnight. The mixture was concentrated and diluted with aqueous ammonium chloride. The aqueous phase was extracted with ether and the combined organic phase was concentrated. The residue was purified by TLC (hexane/acetate, 1/1) to yield 593-YJ-161 (39 mg, 28%).

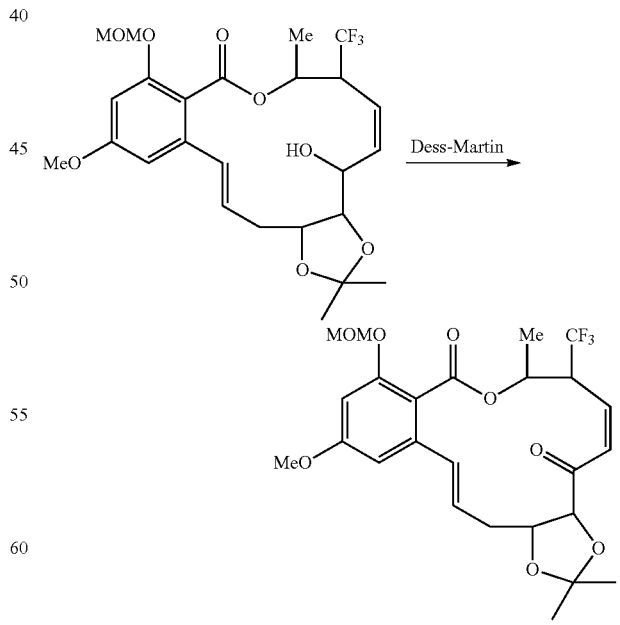

Dess-Martin periodinane (50 mg) was added to 541-YJ-161 (39 mg) in methylene chloride (2 mL) at room temperature. The mixture was stirred for 3 hours and diluted with ether. The mixture was filtrated through Celite and purified with TLC (hexane/acetate, 2/1) to give 541-YJ-168-1 (6.7 mg) and 541-YJ-168-2 (5.3 mg).

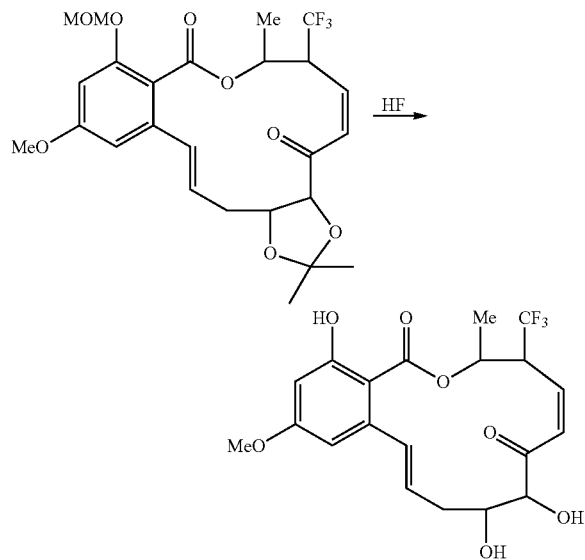

Hydrofluoric acid (49%, 1 mL) was added to 541-YJ-168-1 (6.7 mg) or 541-YJ-168-2 (5.3 mg) in acetonitrile (3 mL) and stirred for 15 minutes. The mixture was diluted with water and extracted with chloroform. The organic phase was concentrated and purified with TLC (hexane/acetate 1/4) to produce 541-YJ-174 (1.5 mg, ER-804142) or 541-YJ-175 (0.5 mg, ER-804143).

Preparation of C4-Oxo Analogs, NF0675, NF0879, NF0880, and NF0905

Synthetic Procedure for NF0675

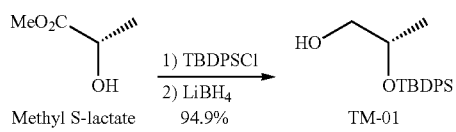

Methyl S-lactate (20.8 g, 0.2 mol) was dissolved in dry THF (500 mL), imidazole (17.7 g, 0.26 mol) was added and the mixture was cooled to 0° C. in ice/water bath. Then TBDPSCl (60.5 g, 0.22 mol) was added, the mixture was allowed to warm slowly to rt and stirred overnight after which a saturated solution of NaHCO$_3$ was added. The mixture was extracted with EtOAc and the organic extract was washed with a saturated solution of NaHCO$_3$, water, brine, dried with anhydrous Na$_2$SO$_4$, filtered and concentrated.

The crude product (74.59 g) was dissolved in dry Et$_2$O (300 mL) and the solution was cooled to 0° C. in ice/water bath. Then LiBH$_4$ (4.36 g, 0.2 mol) was added portionwise, the mixture was allowed to warm slowly to rt and stirred for 2 days after which a saturated solution of NH$_4$Cl was added slowly. The mixture was extracted with EtOAc and the organic extract was washed with a saturated solution of NH$_4$Cl, water, brine, dried with anhydrous Na$_2$SO$_4$, filtered and concentrated. The crude product was purified by chromatography on silica gel using 20% EtOAc/hexane to give 59.67 g (0.19 mol, 95% 2 steps) of the protected compound TM-01.

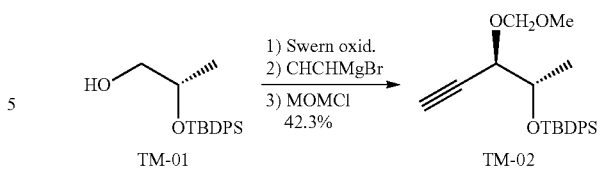

To a solution of oxalyl chloride (2.5 eq., 75 mmol, 6.54 mL) in CH$_2$Cl$_2$ (60 mL), DMSO (5 eq., 150 mmol, 10.6 mL) was added at −78° C. After 15 min at −78° C., a solution of alcohol TM-01 (30 mmol, 9.44 g) in CH$_2$Cl$_2$ (100 mL) was added over a period of 40 min. After 30 min at −78° C., Et$_3$N (6.5 eq., 195 mmol, 27.2 mL) was added and the reaction was warmed to −50° C. and stirred for 30 min. It was quenched with a saturated solution of NH$_4$Cl (100 mL), extracted with EtOAc. The organic layer was dried with Na$_2$SO$_4$, filtered and concentrated. The crude aldehyde (9.55 g) was dissolved in dry THF (100 mL) and cooled to −78° C. Then 0.5M solution of propargyl magnesium bromide in dry THF (1.7 eq., 50 mmol, 100 mL) was added dropwise over a period of 30 min and the reaction was warmed to −10° C. It was quenched with a saturated solution of NH$_4$Cl, extracted with EtOAc. The organic layer was dried with Na$_2$SO$_4$, filtered and concentrated. The crude alcohol was purified by chromatography on silica gel using 5% EtOAc/hexane to give 5.125 g (15.1 mmol, 50% 2 steps) of the desired alcohol.

The alcohol (5.124 g, 15.1 mmol) was dissolved in CH$_2$Cl$_2$ (55 mL), diisopropylethylamine (15.84 mL, 90.8 mmol) was added and the mixture was cooled to 0° C. in ice/water bath. Then chloromethyl methyl ether (3.45 mL, 45.4 mmol) was added and the mixture was allowed to warm to rt. After 2 days, it was quenched with a saturated solution of NH$_4$Cl, extracted with EtOAc. The organic layer was dried with Na$_2$SO$_4$, filtered and concentrated. The crude product was purified by chromatography on silica gel using 5% EtOAc/hexane to give 4.866 g (12.7 mmol, 84%) of TM-02.

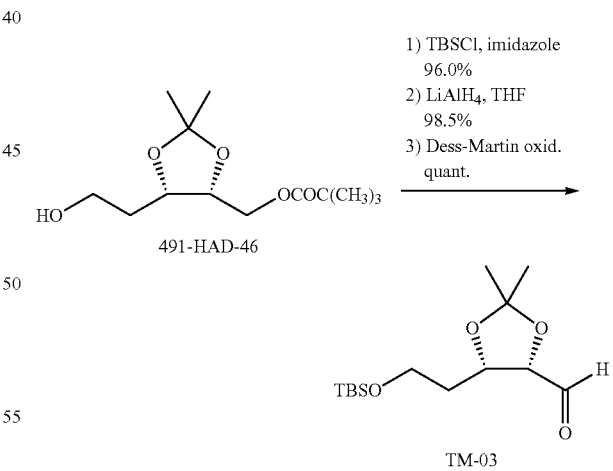

491-HAD-46 (620 mg, 2.4 mmol) was dissolved in dry DMF (10 mL), imidazole (243 mg, 3.6 mmol) was added and the mixture was cooled to 0° C. in ice/water bath. Then TBSCl (430 mg, 2.9 mmol) was added, the mixture was allowed to warm slowly to rt and stirred for 30 min after which a saturated solution of NaHCO$_3$ was added. The mixture was extracted with EtOAc and the organic extract was washed with a saturated solution of NaHCO$_3$, water, brine, dried with anhydrous Na$_2$SO$_4$, filtered and concentrated. The crude product was purified by chromatography on silica gel using 5% EtOAc/hexane to give 856 mg (2.3 mmol, 96%) of the silyl ether.

To a suspension of LiAlH₄ (65 mg, 1.7 mmol) in dry THF (7 mL) was added a solution of the silyl ether (856 mg, 2.3 mmol) in dry THF (13.5 mL) at 0° C. The mixture was allowed to warm slowly to rt and stirred for 50 min after which EtOAc and 1N HCl were added. The mixture was extracted with EtOAc and the organic extract was washed with water, a saturated solution of NH₄Cl, water, brine, dried with anhydrous Na₂SO₄, filtered and concentrated. The crude product was purified by chromatography on silica gel using 25% EtOAc/hexane to give 654 mg (2.3 mmol, 99%) of the alcohol.

The alcohol (654 mg, 2.3 mmol) was dissolved in dry CH₂Cl₂ (25 mL). Then Dess-Martin periodinane (1.67 g, 3.94 mmol) was added and stirred for 4 hr after which a saturated solution of Na₂S₂O₃ and a saturated solution of NaHCO₃ were added. The mixture was extracted with EtOAc and the organic extract was washed with a saturated solution of NaHCO₃, water, brine, dried with anhydrous Na₂SO₄, filtered and concentrated to give 648 mg (2.3 mmol, quant.) of TM-03.

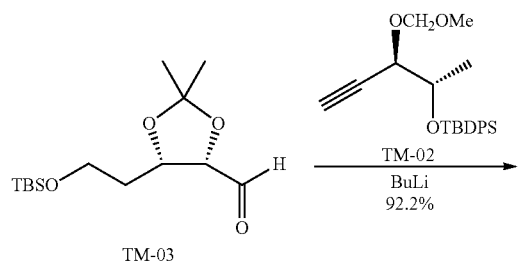

TM-03

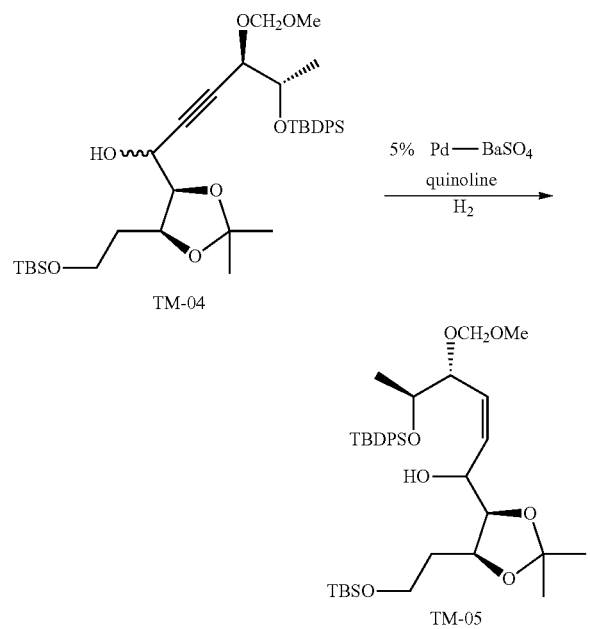

TM-04

TM-04 (2.1 mmol, 1.39 g) was dissolved in hexane (40 mL). Then, quinoline (27 mg) and 5% Pd—BaSO₄ on carbon (88 mg) were added. H₂ balloon was mounted and the mixture was purged 5× with H₂. Reaction was stirred under hydrogen. After 27 hrs, reaction was stopped, catalyst was filtered through celite and mixture was concentrated under reduced pressure. The crude product was purified by chromatography on silica gel using 15% EtOAc/hexane to give 957 mg (1.4 mmol, 69%) of TM-05 as major isomer and 267 mg (0.4 mmol, 19%) of the diastereomer of allylic hydroxy position.

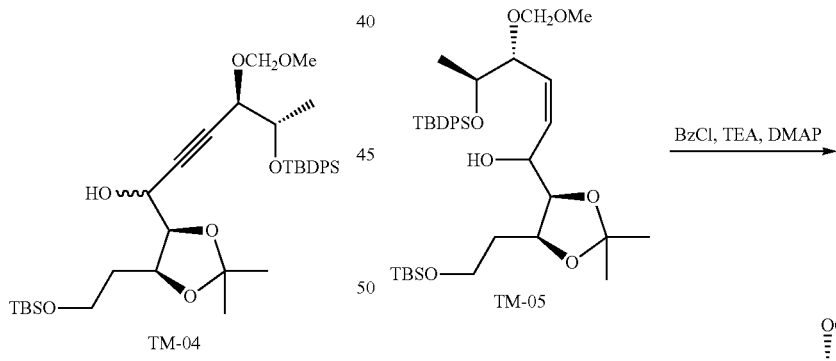

TM-02 (2.2 eq., 5.0 mmol, 1.89 g) was dissolved in THF (20 mL) and cooled to −78° C., under nitrogen. Then, n-BuLi (1.6M/hexane, 2.0 eq., 4.5 mmol, 2.8 mL) was added and the reaction was stirred at −78° C. for 60 min. Aldehyde TM-03 (2.3 mmol, 648 mg) dissolved in THF (8 mL) was added to the solution and stirred for 60 min at −78° C. The solution was allowed to warm to rt and stirred for 1.5 hrs. The mixture was quenched with water, extracted with EtOAc and the organic extract was washed with brine, dried with Na₂SO₄, filtered and concentrated. The residue was purified by chromatography on silica gel using 15% EtOAc/hexane to give 1.393 g (2.1 mmol, 92%) of TM-04.

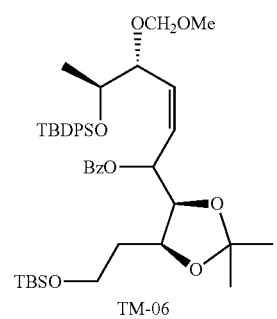

TM-06

Using same procedure for 554-RB-242, TM-05 (954 mg, 1.4 mmol) was converted to TM-06 (913 mg, 1.2 mmol, 83%).

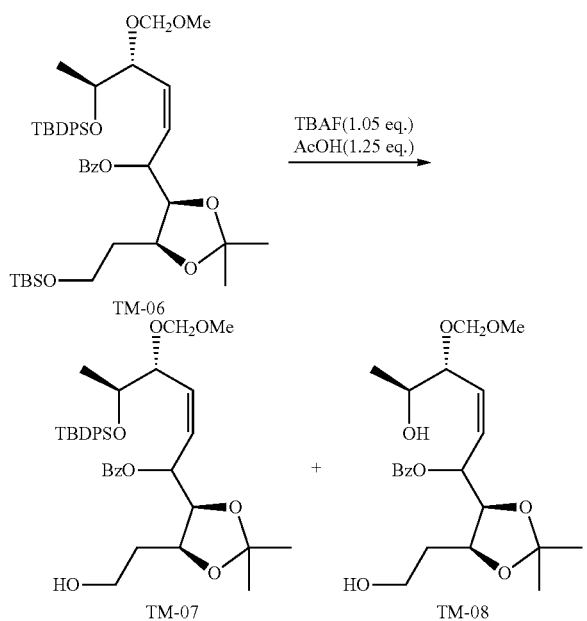

TM-06 (912 mg, 1.2 mmol) was dissolved in THF (23 mL). Then, acetic acid (0.084 mL, 1.5 mmol) and 1.0M solution of tetrabutylammonium fluoride in THF (1.23 mL, 1.23 mmol) were added at rt. The mixture was stirred overnight after which a saturated solution of $NH_4Cl$ was added. The mixture was extracted with EtOAc and the organic extract was washed with a saturated solution of $NaHCO_3$, water, brine, dried with anhydrous $Na_2SO_4$, filtered and concentrated. The crude product was purified by chromatography on silica gel using 30% EtOAc/hexane to EtOAc as eluents to give 362 mg (0.55 mmol, 47%) of TM-07 and 212 mg (0.50 mmol, 43%) of TM-08.

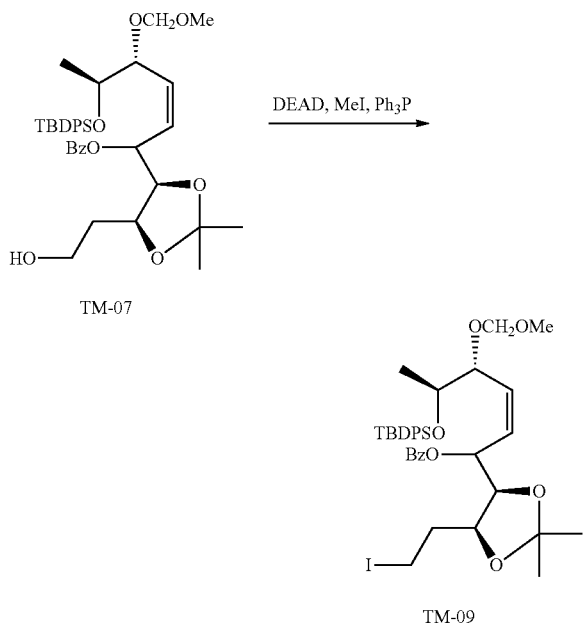

Using same procedure for 554-RB-260, TM-07 (359 mg, 0.54 mmol) was converted to TM-09 (374 mg, 0.48 mmol, 89%).

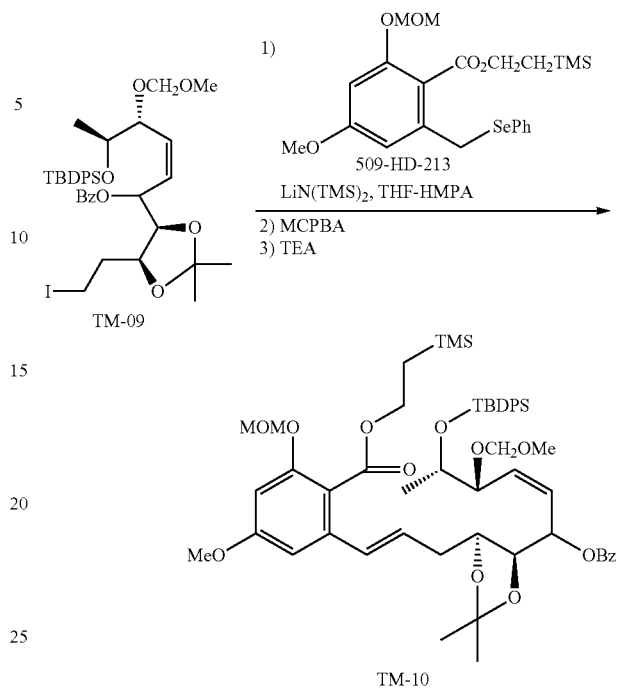

Using same procedure for 5, TM-09 (372 mg, 0.48 mmol) was converted to TM-10 (339 mg, 0.35 mmol, 72%).

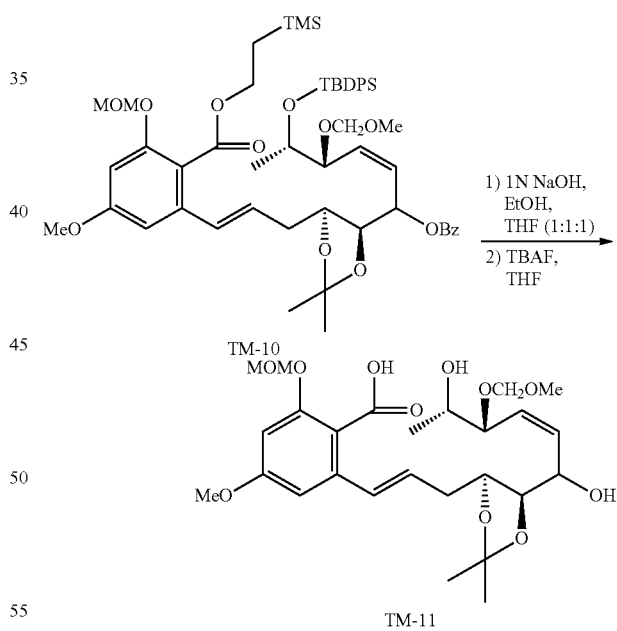

To a stirred solution of TM-10 (172 mg, 0.18 mmol) in THF (2 mL) and EtOH (2 mL) was added 1N NaOH aq. (2 mL) at rt. After 2.5 hrs, it was quenched by 1N HCl and extracted with EtOAc. The organic extract was washed with water, brine, dried with anhydrous $Na_2SO_4$, filtered and concentrated. The crude product was purified by chromatography on silica gel using 30% EtOAc/hexane to give 143 mg (0.16 mmol, 93%) of the allyl alcohol.

The allyl alcohol (143 mg, 0.16 mmol) was dissolved in THF (3 mL). Then, 1.0M solution of tetrabutylammonium fluoride in THF (0.49 mL, 0.49 mmol) was added at rt. The mixture was stirred for 3 hrs after which 1N HCl was added. The mixture was extracted with EtOAc and the organic extract was washed with water, brine, dried with anhydrous Na$_2$SO$_4$, filtered and concentrated. The crude product was purified by chromatography on silica gel using 10% MeOH/ EtOAc to give 87 mg (0.16 mmol, quant.) of TM-11.

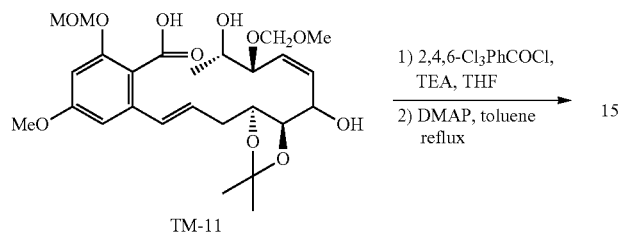

TM-11

To a stirred solution of TM-11 (87 mg, 0.16 mmol) in THF (3 mL) were added triethylamine (0.029 mL, 0.2 mmol) and 2,4,6-trichlorobenzoyl chloride (0.032 mL, 0.2 mmol) at rt. After 16 hrs, the reaction mixture was diluted with toluene (80 mL) and added dropwise to a solution of N,N-dimethylaminopyridine (498 mg, 4.1 mmol) in toluene (80 mL) over a period of 8 hrs under reflux. The resultant mixture was stirred for 15 hrs under reflux. After concentration under reduced pressure, the residue was dissolved in EtOAc and washed with 5% citric acid aq., water, brine and dried over anhydrous Na$_2$SO$_4$, filtered and concentrated. The crude product was purified by chromatography on silica gel using 30% EtOAc/hexane to give 53 mg (0.10 mmol, 64%) of TM-12.

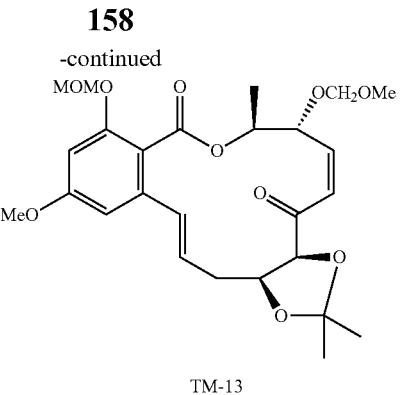

TM-13

Using similar procedure for 509-HD-125, TM-12 (39.4 mg, 0.078 mmol) was converted to TM-13 (36.8 mg, 0.073 mmol, 94%).

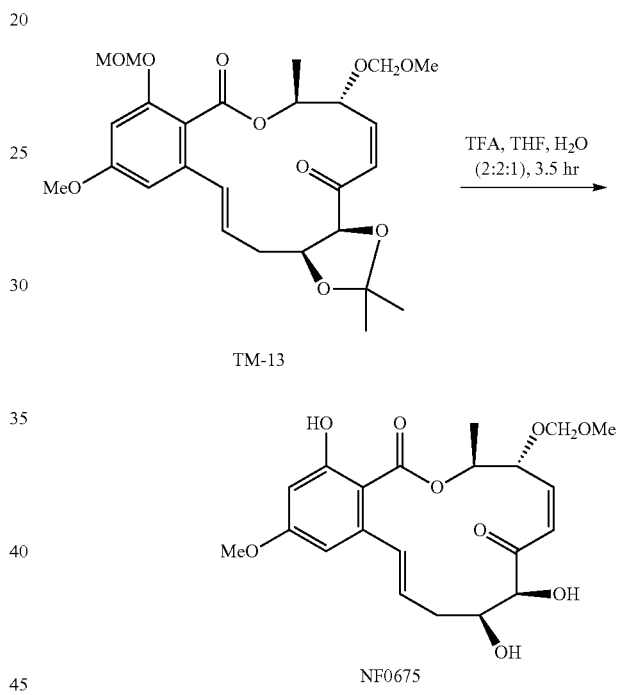

NF0675

To a stirred solution of TM-13 (12 mg, 0.024 mmol) in THF (1 mL)-H$_2$O (0.5 mL) was added trifluoroacetic acid (1 mL) at 0° C. The mixture was then allowed to warm to rt. After 3.5 hrs, the mixture was poured into a saturated solution of NaHCO$_3$ and extracted with EtOAc. The organic extract was washed with water, brine and dried over anhydrous Na$_2$SO$_4$, filtered and concentrated. The crude product was purified by chromatography on silica gel using 30% EtOAc/hexane to give 1.2 mg (0.0028 mmol, 12%) of NF0675.

Synthetic Procedure for NF0879 and NF0880

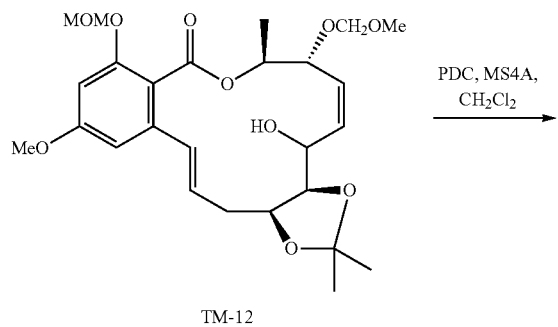

TM-12

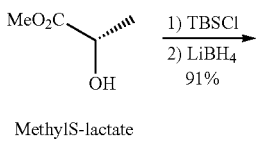

MethylS-lactate

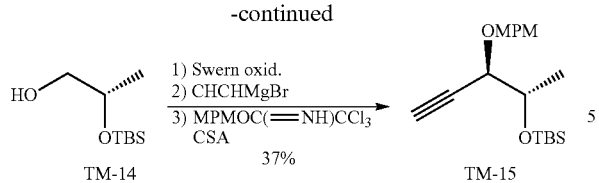
Using modified procedure for TM-02, TM-15 (10.56 g, 31.6 mmol) was obtained from 10.4 g (0.1 mol) of methyl S-lactate.
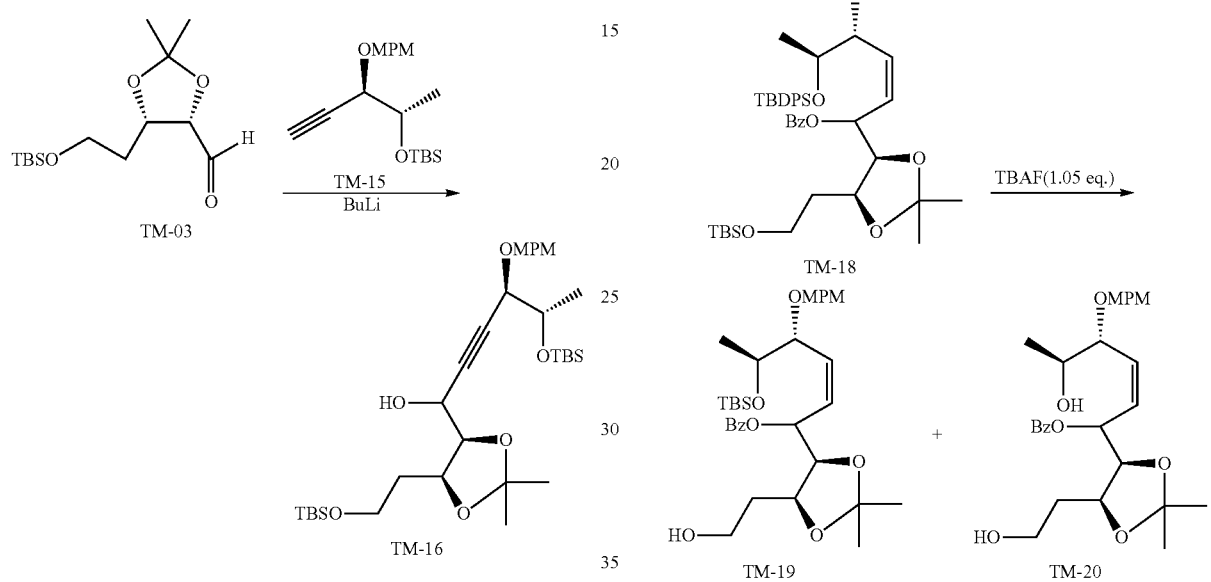
Using same procedure for TM-04, TM-03 (3.64 g, 12 mmol) was converted to TM-16 (5.29 g, 8.5 mmol, 69%).
From 4.904 g (7.8 mmol) of TM-17, TM-19 (1.120 g, 1.8 mmol, 23% 2 steps) and TM-20 (2.218 g, 4.4 mmol, 57% 2 steps) were obtained by similar procedure for TM-07.
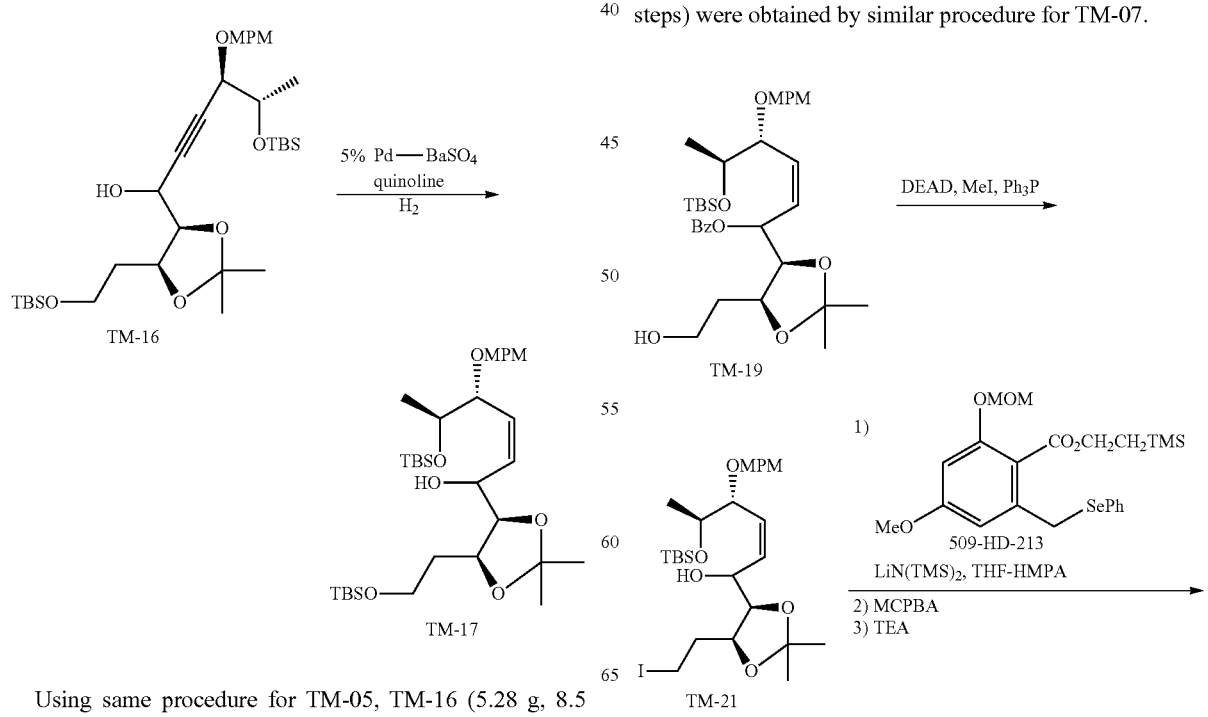
Using same procedure for TM-05, TM-16 (5.28 g, 8.5 mmol) was converted to TM-17 (4.91 g, 7.9 mmol, 93%).

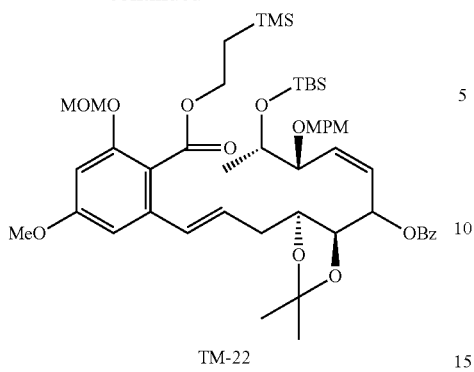

TM-22

Using similar procedure for TM-10, 1.104 g (1.8 mmol) of TM-19 was converted to TM-22 (955 mg, 1.03 mmol, 58% 4 steps).

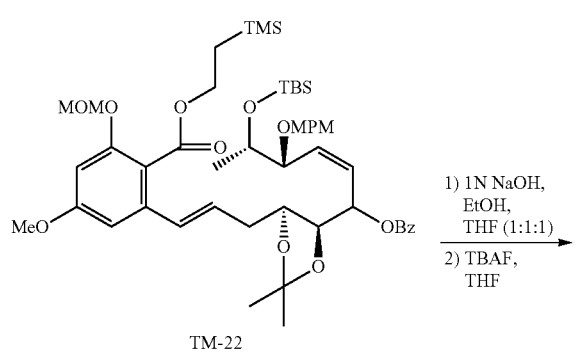

TM-22

1) 1N NaOH, EtOH, THF (1:1:1)
2) TBAF, THF

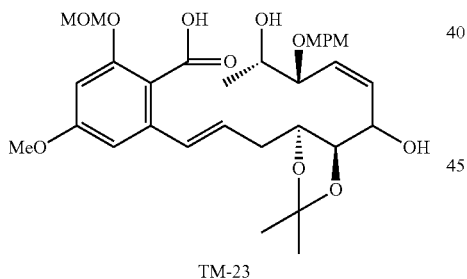

TM-23

Using similar procedure for TM-11, 955 mg (1.03 mmol) of TM-22 was converted to TM-23 (593 mg, 0.98 mmol, 95% 2 steps).

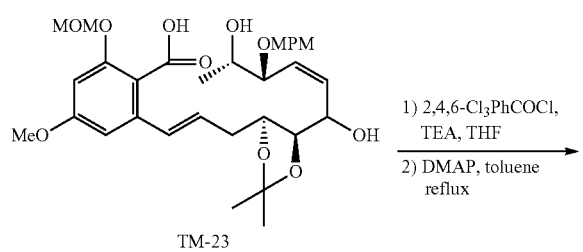

TM-23

1) 2,4,6-Cl₃PhCOCl, TEA, THF
2) DMAP, toluene reflux

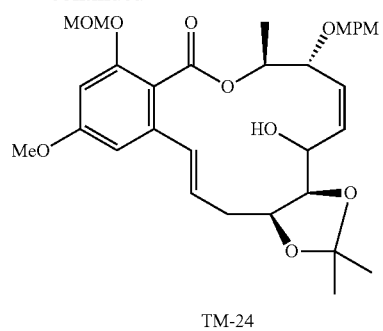

TM-24

Using similar procedure for TM-12, 590 mg (0.98 mmol) of TM-23 was converted to TM-24 (438 mg, 0.75 mmol, 77%).

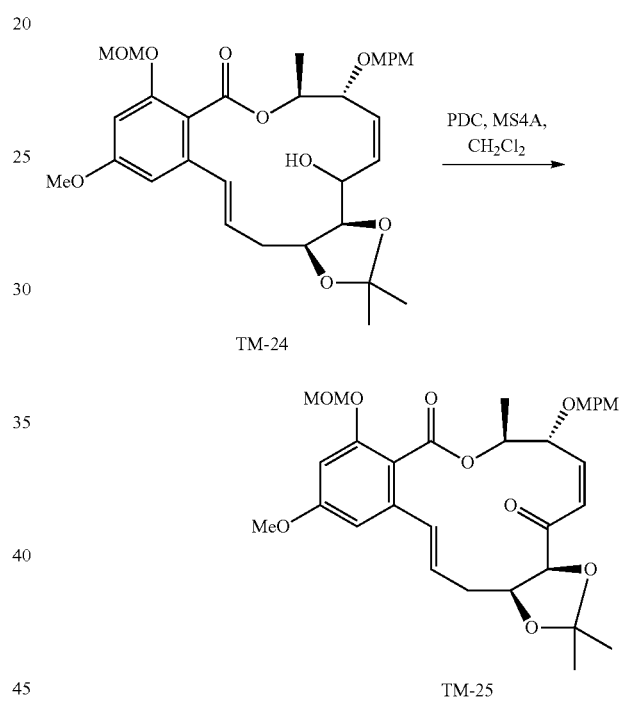

TM-24

PDC, MS4A, CH₂Cl₂

TM-25

Using similar procedure for TM-13, 209 mg (0.36 mmol) of TM-24 was converted to TM-25 (186 mg, 0.32 mmol, 89%).

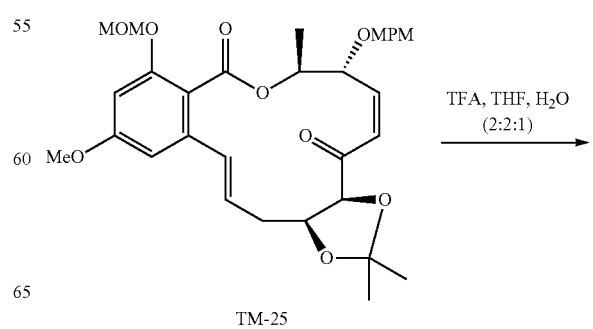

TM-25

TFA, THF, H₂O (2:2:1)

Synthetic Procedure for NF0905

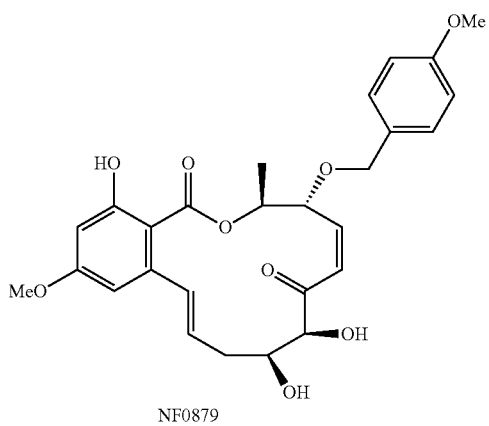

NF0879

Using similar procedure for NF0675, 186 mg (0.32 mmol) of TM-25 was converted to NF0879 (72 mg, 0.14 mmol, 45%).

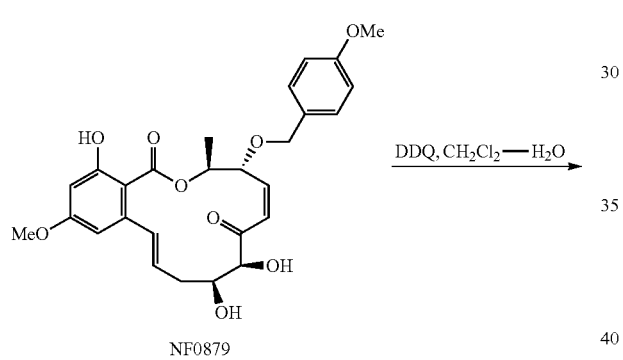

NF0879 (16 mg, 0.032 mmol) was dissolved in CH$_2$Cl$_2$ (3 mL), H$_2$O (0.3 mL) and DDQ (2 eq., 0.064 mmol, 14.9 mg) were added and the mixture was stirred vigorously at rt for 3 hrs. The mixture was quenched with a saturated solution of NaHCO$_3$ and diluted with EtOAc. The organic layer was separated and washed with a saturated solution of NaHCO$_3$, brine, dried with Na$_2$SO$_4$, filtered and concentrated. The crude residue was purified by chromatography on silica gel using 5% MeOH/CHCl$_3$ to give 5 mg (0.013 mmol, 41%) of NF0880.

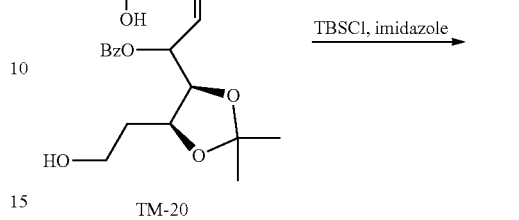

TM-20

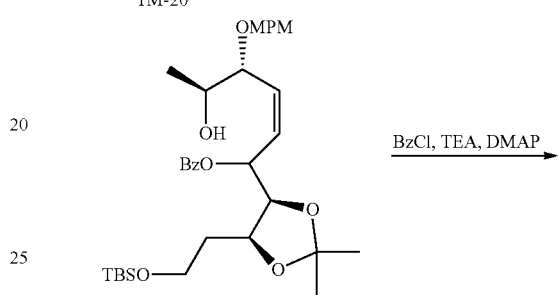

TM-26

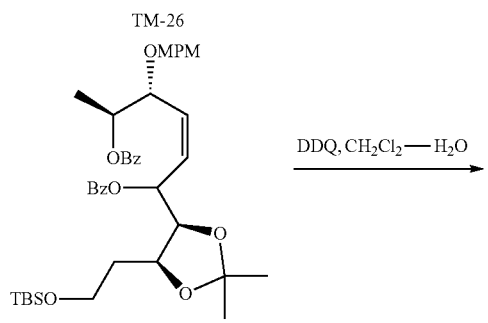

TM-27

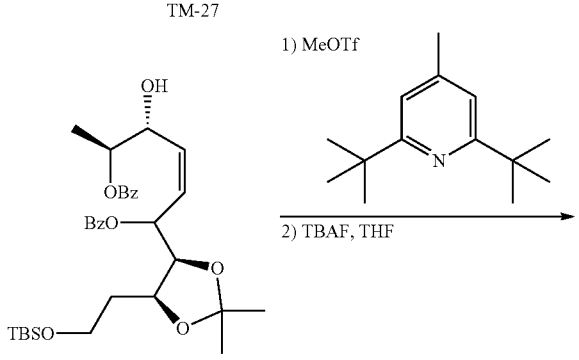

TM-28

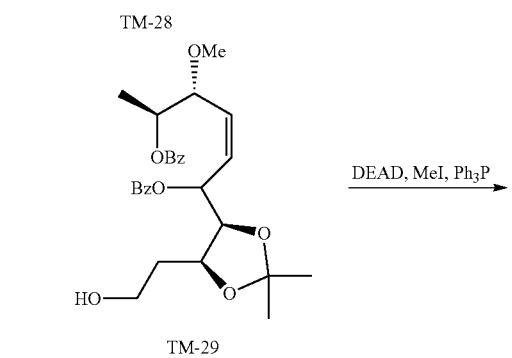

TM-29

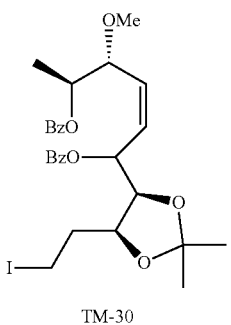

TM-20 (2.218 g, 4.4 mmol) was dissolved in CH$_2$Cl$_2$ (45 mL), imidazole (520 mg, 7.6 mmol) was added and the mixture was cooled to 0° C. in ice/water bath. Then TBSCl (768 mg, 5.1 mmol) was added, the mixture was allowed to warm slowly to rt and stirred for 1.5 hrs after which a saturated solution of NaHCO$_3$ was added. The mixture was extracted with EtOAc and the organic extract was washed with a saturated solution of NaHCO$_3$, water, brine, dried with anhydrous Na$_2$SO$_4$, filtered and concentrated to give 2.79 g of TM-26 as crude product.

TM-26 (2.79 g) was dissolved in CH$_2$Cl$_2$ (45 mL), triethylamine (1.85 mL, 13.3 mmol) and N,N-dimethylaminopyridine (54 mg, 0.44 mmol) were added and the mixture was cooled to 0° C. in ice/water bath. Then benzoyl chloride (1.03 mL, 8.9 mmol) was added, the mixture was allowed to warm slowly to rt and stirred overnight after which a saturated solution of NaHCO$_3$ was added. The mixture was extracted with EtOAc and the organic extract was washed with a saturated solution of NH$_4$Cl, 5% citric acid aq., water, and brine, dried with anhydrous Na$_2$SO$_4$, filtered and concentrated to give 4.33 g of TM-27 as crude product.

TM-27 (4.33 g) was dissolved in CH$_2$Cl$_2$ (50 mL), H$_2$O (5 mL) and DDQ (1.28 g, 5.5 mmol) were added and the mixture was stirred vigorously at rt for 2 hrs. The mixture was quenched with a saturated solution of NaHCO$_3$ and diluted with EtOAc. The organic layer was separated and washed with a saturated solution of NaHCO$_3$, brine, dried with Na$_2$SO$_4$, filtered and concentrated. The crude residue was purified by chromatography on silica gel using 20% EtOAc/hexane to give 2.99 g of TM-28 with slightly amount of impurities.

TM-28 (2.99 g) was dissolved in CH$_2$Cl$_2$ (60 mL), 2,6-di-tert-butyl-4-methyl-pyridine (3.34 g, 16 mmol) and methyl triflate (1.5 mL, 13 mmol) were added and the mixture was stirred under reflux overnight. The mixture was quenched with a saturated solution of NaHCO$_3$ and diluted with EtOAc. The organic layer was separated and washed with a saturated solution of NaHCO$_3$, brine, dried with Na$_2$SO$_4$, filtered and concentrated.

The crude residue (6.25 g) was dissolved in THF (60 mL). Then, 1.0M solution of tetrabutylammonium fluoride in THF (5.5 mL, 5.5 mmol) was added at rt. The mixture was stirred for 1.5 hrs after which a saturated solution of NH$_4$Cl was added. The mixture was extracted with EtOAc and the organic extract was washed with water, brine, dried with anhydrous Na$_2$SO$_4$, filtered and concentrated. The crude product was purified by chromatography on silica gel using 30% EtOAc/hexane to give 362 mg (0.73 mmol, 16% 5 steps) of TM-29.

Using similar procedure for TM-09, 359 mg (0.72 mmol) of TM-29 was converted to TM-30 (376 mg, 0.62 mmol, 86%).

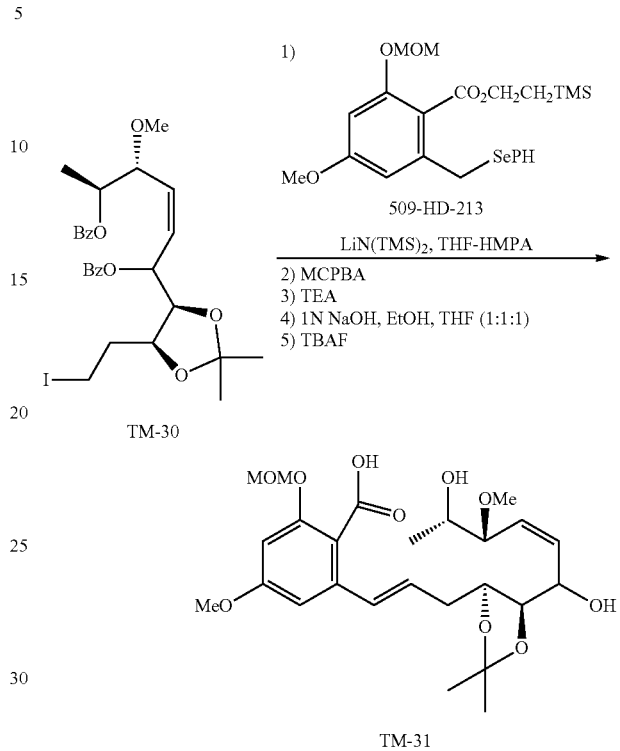

Using similar procedure for TM-23, 371 mg (0.61 mmol) of TM-30 was converted to TM-31 (207 mg, 0.42 mmol, 69% 5 steps).

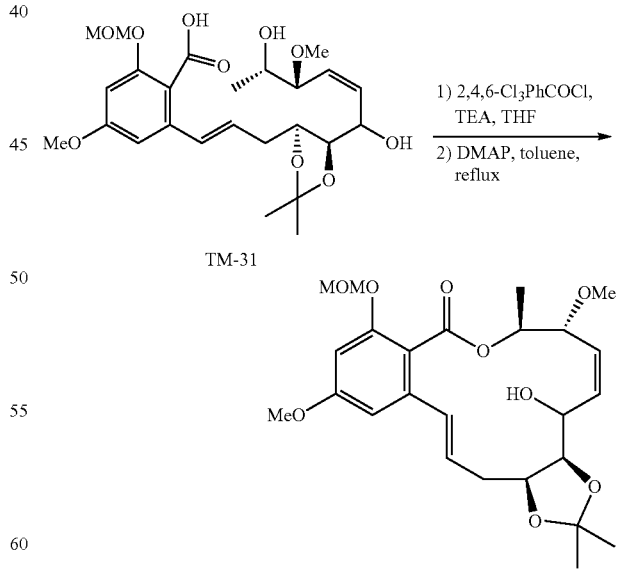

Using similar procedure for TM-12, 207 mg (0.42 mmol) of TM-31 was converted to TM-32 (206 mg, 0.42 mmol, quant.).

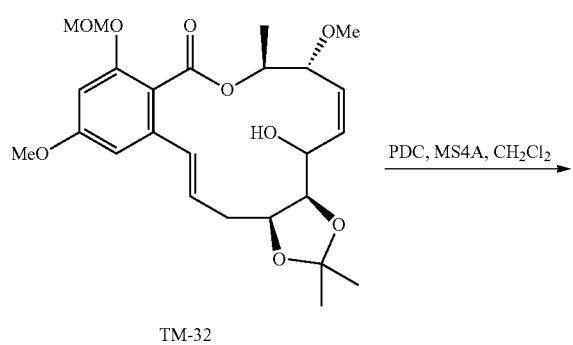

TM-32

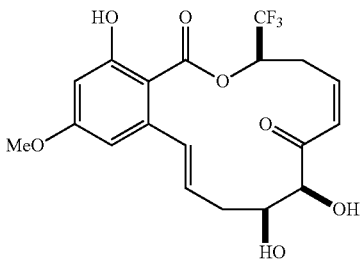

Preparation of Compound ER-804003 (C3 Trifluoromethyl)

Step 1

Using similar procedure for TM-13, 206 mg (0.42 mmol) of TM-32 was converted to TM-33 (170 mg, 0.36 mmol, 83%).

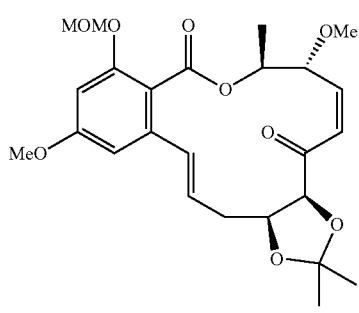

TM-33

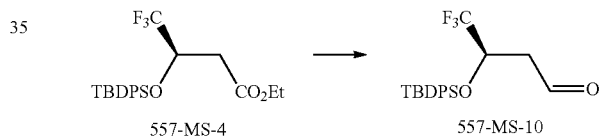

557-MS-4

A solution of ethyl (R)-3-hydroxy-4,4,4-trifluorobutanoate (2 g, 10.7 mmol) in DMF (20 mL) was treated with tert-butyldiphenylsilyl chloride (8.34 mL, 32.1 mmol) and imidazole (3.28 g, 35.3 mmol). The reaction mixture was heated at 70° C. under an inert atmosphere for 16 hours. The usual work up followed by partial purification by chromatography gave impure compound 557-MS-4 (1 g, approximately 22%).

Step 2

557-MS-4 → 557-MS-10

A solution of impure compound 557-MS-4 (380 mg, assumed to contain 0.89 mmol) in dichloromethane (5 mL) was cooled to −78° C. and treated with a 1M solution of diisobutylaluminum hydride in dichloromethane (1.79 mL, 1.79 mmol). The reaction mixture was allowed to warm to room temperature and worked up in the usual manner. Partial purification by chromatography gave impure compound 557-MS-10 (which was used in the next stage without further purification).

Step 3

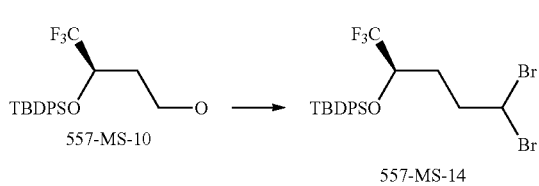

557-MS-10 → 557-MS-14

Using similar procedure for NF0675, 170 mg (0.36 mmol) of TM-33 was converted to NF0905 (50 mg, 0.13 mmol, 35%).

To a solution of triphenylphosphine (910 mg, 3.47 mmol) in dry dichloromethane (6 mL), at 0° C. under an inert atmosphere, was added drop wise a solution of carbon tetrabromide (575 mg, 1.73 mmol) in dry dichloromethane (3 mL). After 10 minutes a mixed solution of impure compound 557-MS-10 (assumed to contain 0.86 mmol) plus triethylamine (0.181 mL, 1.3 mmol) in dry dichloromethane (3 ml) was added drop wise. The reaction mixture was worked up in the usual manner to give compound 557-MS-14 (331 mg, 72% from 557-MS-4).

Step 4

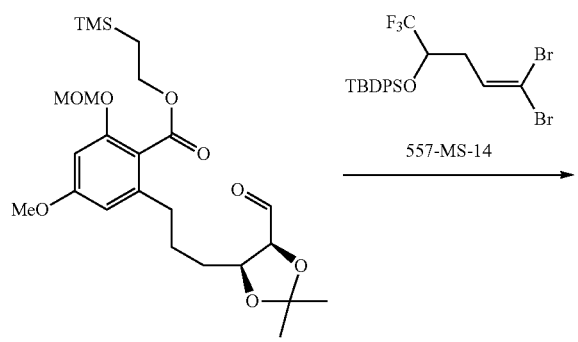

480-XYL-075

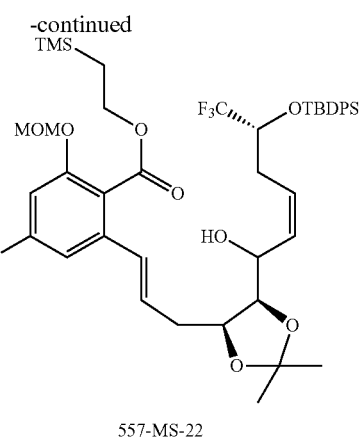

557-MS-22

A solution of compound 557-MS-19 (300 mg, 0.35 mmol) in hexane (10 mL) was hydrogenated, at room temperature and 1 atmosphere pressure, in the presence of Lindlar's catalyst (60 mg) and quinoline (4 µL) for 40 hours (fresh Lindlar catalyst (120 mg) added after 2 hours). Filtration and concentration in vacuo gave compound 557-MS-22 (302 mg) which was used in the next stage without purification.

Step 6

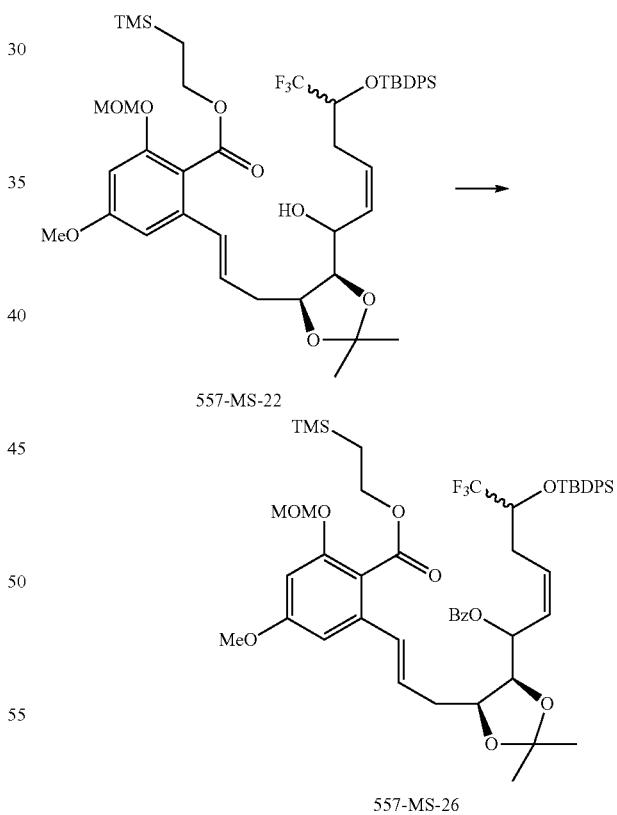

557-MS-19

To a solution of compound 557-MS-14 (331 mg, 0.61 mmol) in dry THF (2.5 mL), at −78° C. under an inert atmosphere, was added drop wise a 1.6M solution of n-butyl-lithium in hexanes (0.771 mL, 1.23 mmol). The reaction mixture was warmed momentarily to 0° C. then re-cooled to −78° C. A solution of compound 480-XYL-075 (247 mg, 0.51 mmol) in dry tetrahydrofuran (2.5 mL) was added drop wise. Warming to 0° C. followed by the usual work up and chromatographic purification gave compound 557-MS-19 (300 mg, 57%).

Step 5

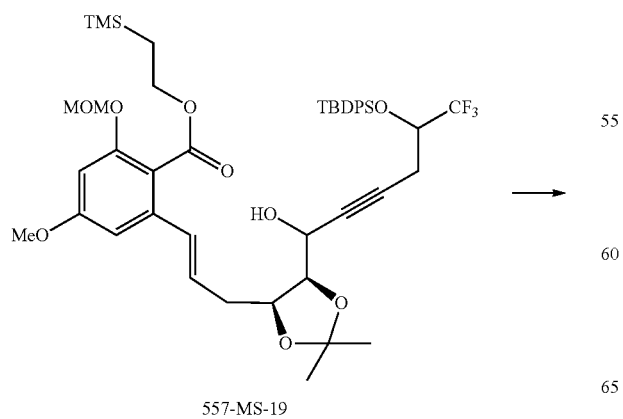

557-MS-19

A solution of crude compound 557-MS-22 (assumed to contain 0.35 mmol) in 1,2-dichloroethane (10 mL) was treated with benzoyl chloride (0.122 mL, 1.05 mmol), triethylamine (0.293 mL, 2.1 mmol) and N,N-4-dimethylaminopyridine (21 mg, 0.175 mmol). The usual work up followed by chromatographic purification gave compound 557-MS-26 (177 mg, 53% from compound 557-MS-19).

Step 7

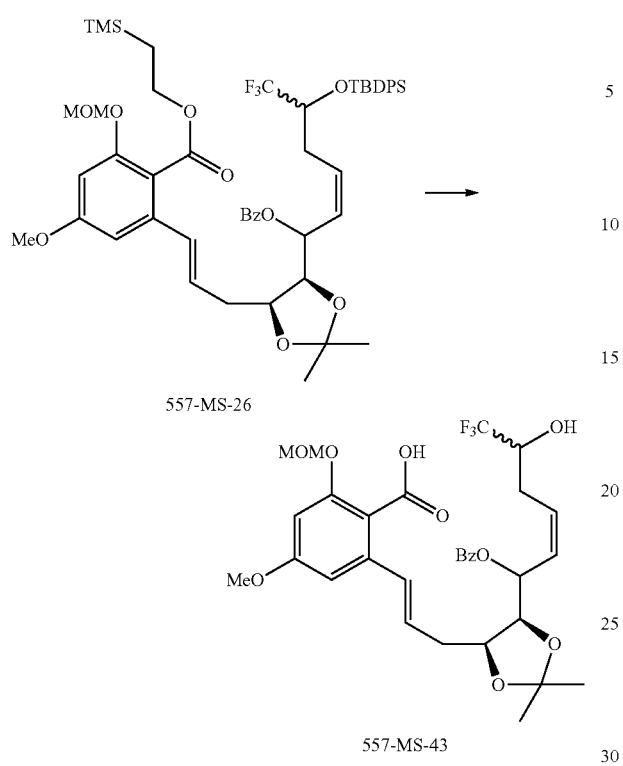

A solution of compound 557-MS-26 (177 mg, 0.183 mmol) in THF (3 mL) was treated with a 1M solution TBAF in THF (1.83 mL). The usual work up gave crude compound 557-MS-43, which was used in the next stage without further purification (m/z: 623.3 [M−1, 24%], 249.1 [100%]).

Step 8

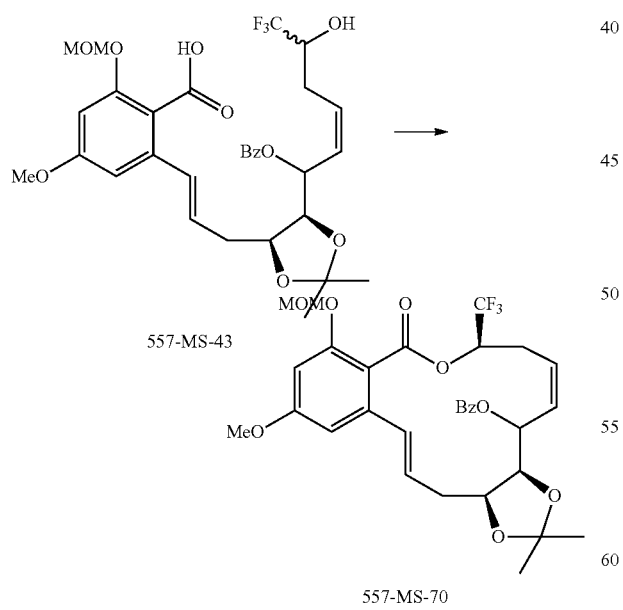

A solution of crude compound 557-MS-43 (84 mg, 0.13 mmol) in 1,2-dichloroethane (90 mL) was added slowly to a heated solution (80° C.) of 2-chloro-1-methylpyridinium iodide (210 mg, 0.81 mmol) and tri-n-butylamine (0.192 ml, 0.81 mmol) in dichloromethane (90 mL). The usual work up and chromatographic purification gave compound 557-MS-70 (15.7 mg, 20% from compound 557-MS-26).

Step 9

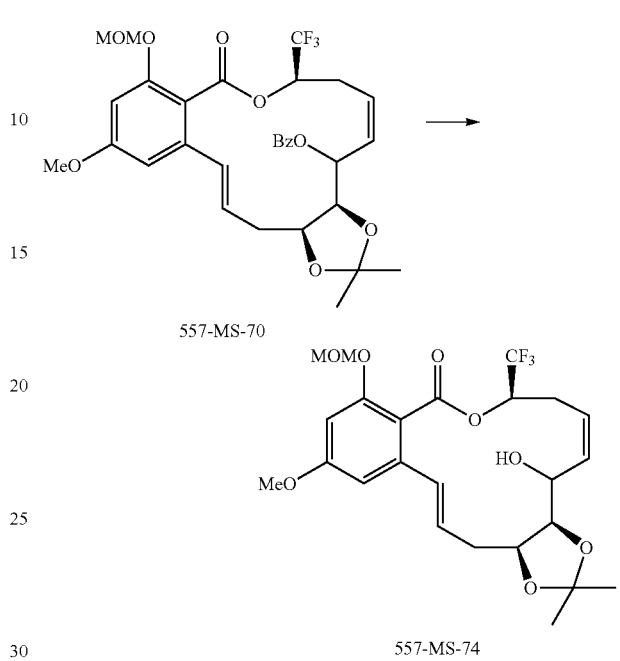

A solution of compound 557-MS-70 (15.7 mg, 25 μmol) in a mixture of ethanol (1.8 mL) and THF (0.9 mL) was treated with 1M aqueous NaOH (0.3 mL) and stirred for approximately 16 hours at room temperature. The usual work up gave compound 557-MS-74 (6 mg, 46%).

Step 10

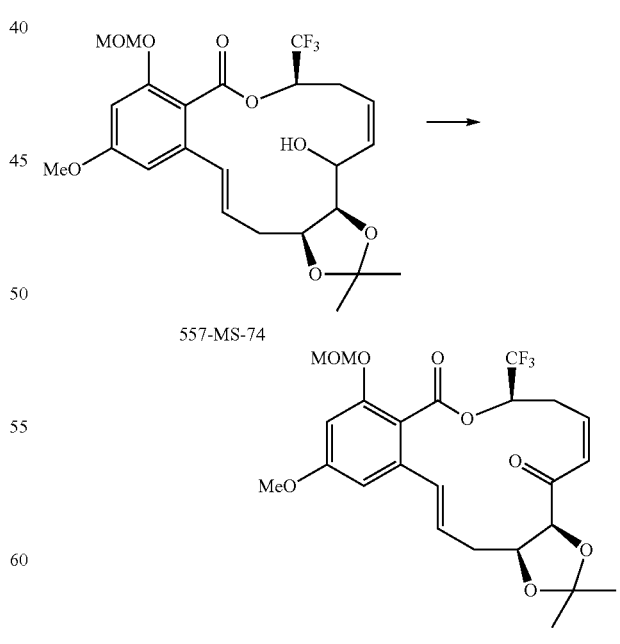

A solution of compound 557-MS-74 (9 mg, 18 μmol) in dichloromethane (3 mL) was treated with PCC (58 mg, 0.269 mmol) in the presence of powdered 4 Å molecular sieves (58 mg). The reaction mixture was stirred vigorously for 90 minutes at mom temperature. Basification with excess triethylamine, followed by partial chromatographic purification gave impure compound 557-MS-77, which was used in the next stage without further purification (m/z: 523.1 [M+23, 100%], 365.1 [22%]).

Step 11

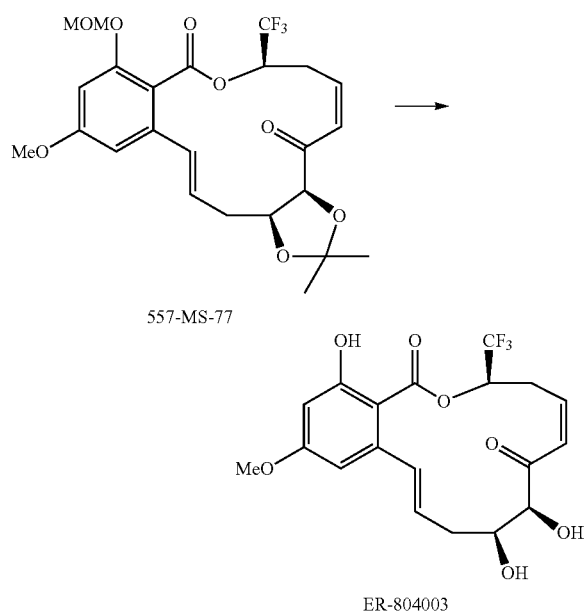

557-MS-77

ER-804003

A solution of impure compound 557-MS-77 (1 mg, assumed to contain 2 µmol) in a mixture of acetonitrile (200 µl) and dichloromethane (50 µl) was treated with 48% aqueous hydrofluoric acid (50 µl). After 25 minutes the usual work up followed by chromatographic purification gave compound ER-804003 (0.3 mg, approximately 4% from compound 557-MS-74).

Preparation of Compound ER-803924 (C4 Benzyl)

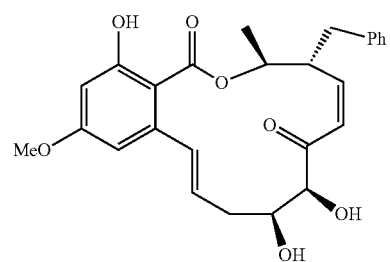

Step 1

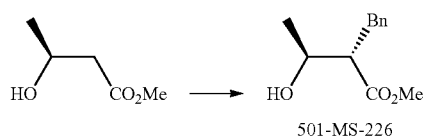

501-MS-226

To a solution of freshly prepared LDA (0.053 mmol) in dry THF (30 mL), at −78° C. under an inert atmosphere, was added drop wise a solution of methyl (S)-3-hydroxybutanoate (3 g, 0.025 mol) in dry THF (30 mL). After 2 hours at −78° C. the reaction mixture was treated drop wise with benzyl bromide (9.06 mL, 0.076 mol), then warmed to room temperature. The usual work up followed by chromatographic purification gave compound 501-MS-226 (1.28 g, 24%).

Step 2

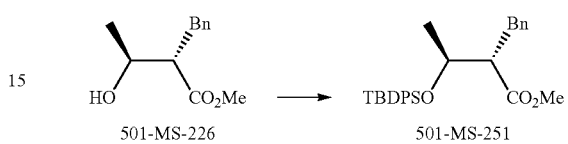

501-MS-226   501-MS-251

A solution of compound 501-MS-226 (1.28 g, 6.14 mmol) in DMF (10 mL) was treated with tert-butyldiphenylsilyl chloride (1.76 mL. 6.75 mmol) and imidazole (461 mg, 6.75 mmol) then heated at 50° C. for 4 hours. The usual work up followed by chromatographic purification gave compound 501-MS-251 (1.87 g, 68%).

Step 3

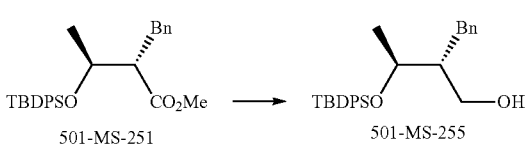

501-MS-251   501-MS-255

To a solution of compound 501-MS-251 (1.37 g, 3.06 mmol) in dry dichloromethane (50 mL), at −78° C. under an inert atmosphere, was added a 1.5M solution of DIBAL-H in toluene (5.11 mL, 7.66 mmol). The reaction mixture was then warmed to 0° C. and stirred at 0° C. for 2 hours. The usual work up followed by chromatographic purification gave compound 501-MS-255 (1.06 g, 83%).

Step 4

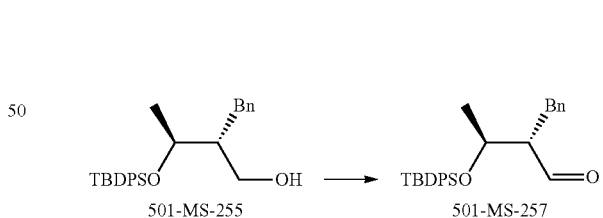

501-MS-255   501-MS-257

To a solution of oxalyl chloride (0.314 mL, 3.6 mmol) in dry dichloromethane (8 mL), at −78° C. under an inert atmosphere, was added drop wise a solution of dimethylsulfoxide (0.51 mL, 7.2 mmol) in dry dichloromethane (4 mL). After 30 minutes a solution of compound 501-MS-255 (1.369 g, 3.27 mmol) in dry dichloromethane (8 mL) was added drop wise. The reaction mixture was stirred at −78° C. for 1 hour then treated with triethylamine (2.28 mL, 16.35 mmol) then warmed slowly to room temperature. The usual work up gave compound 501-MS-257 (1.24 g, 91%).

Step 5

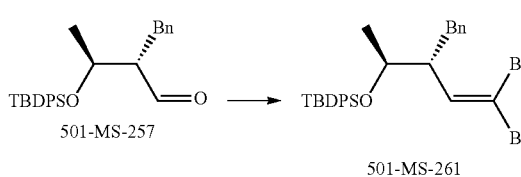

To a solution of triphenylphosphine (2.57 g, 9.81 mmol) in dry dichloromethane (16 mL), at 0° C. under an inert atmosphere, was added drop wise a solution of carbon tetrabromide (1.63 g, 4.91 mmol) in dry dichloromethane (8 mL). A mixed solution of compound 501-MS-257 (1.24 g, 2.97 mmol) and triethylamine (0.501 ml, 3.6 mmol) was added drop wise and the reaction mixture warmed to room temperature. The usual work up followed by chromatographic purification gave compound 501-MS-261 (1.47 g, 79% from 501-MS-255).

Step 6

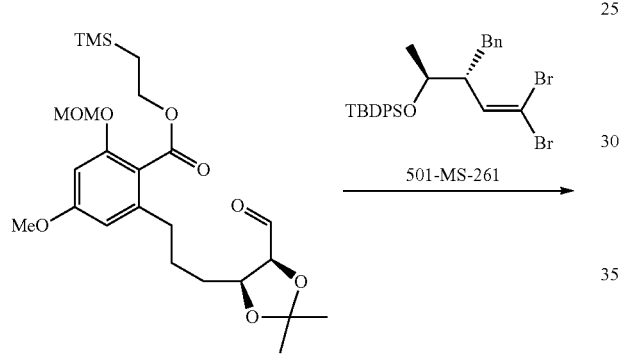

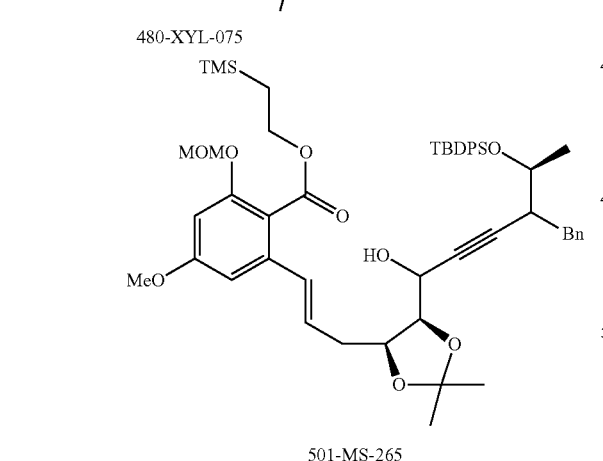

To a solution of compound 501-MS-261 (1.47 g, 2.57 mmol) in dry THF (10 mL), at −78° C. under an inert atmosphere, was added drop wise a 1.6M solution of n-butyllithium in hexanes (3.21 mL, 5.14 mmol). The reaction mixture was warmed momentarily to 15° C. then re-cooled to −78° C. A solution of compound 480-XYL-075 (950 mg, 1.976 mmol) in dry THF (10 mL) was added drop wise. Warming to 0° C. followed by the usual work up and chromatographic purification gave compound 501-MS-265 (1.11 g, 63%).

Step 7

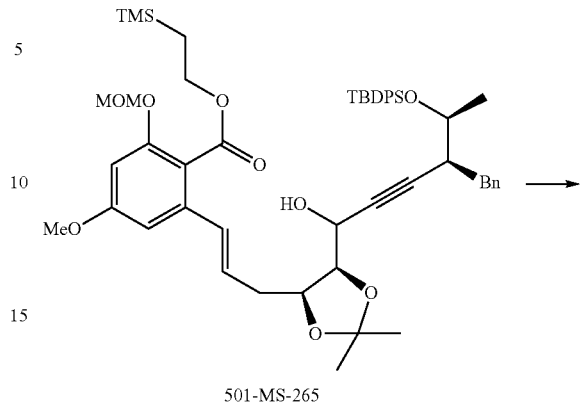

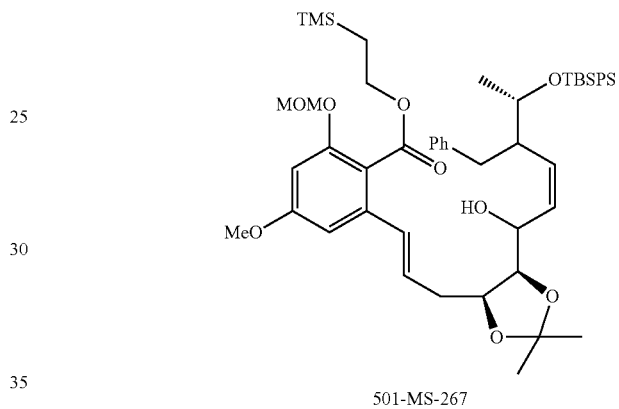

A solution of compound 501-MS-265 (1.11 g, 1.24 mmol) in hexane (70 mL) was hydrogenated, at room temperature and 1 atmosphere pressure, in the presence of Lindlar's catalyst (350 mg) and quinoline (70 µL), for 5 hours. Filtration and concentration in vacuo gave compound 501-MS-267 (1.13 g, assumed quantitative), which was used in the next stage without purification.

Step 8

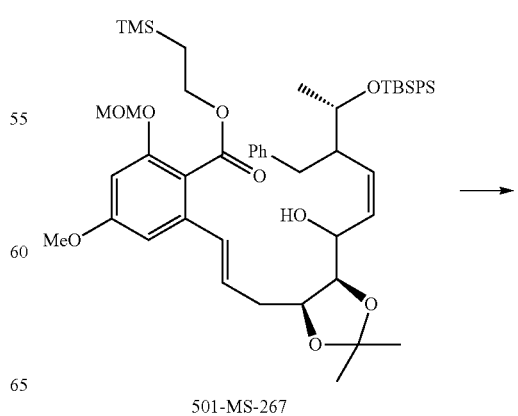

-continued

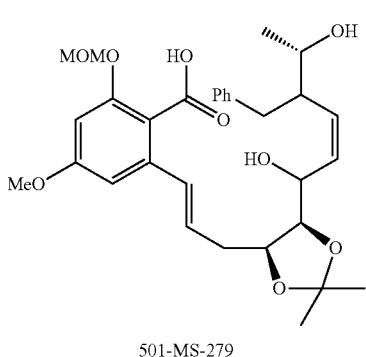
501-MS-279

A solution of compound 501-MS-267 (160 mg, 0.178 mmol) in THF (1 mL) was treated with a 1M solution of TBAF in THF (0.89 mL). After approximately 15 hours the usual work up gave crude compound 501-MS-279 (81 mg, approximately 82%).

Step 9

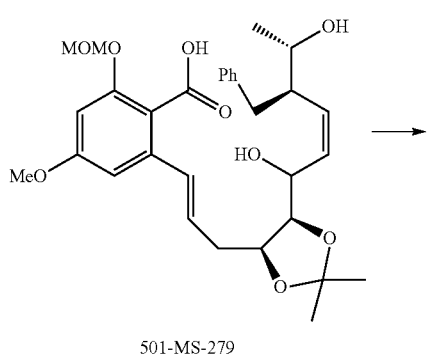
501-MS-279

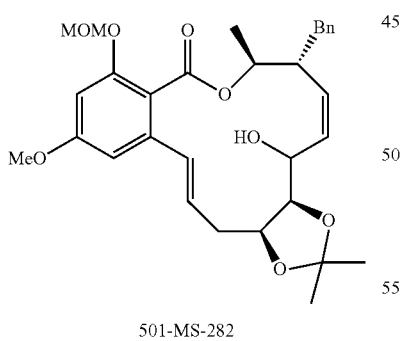
501-MS-282

A solution of compound 501-MS-279 (81 mg, 0.146 mmol) in 1,2-dichloroethane (100 mL) was added slowly to a heated solution (85° C.) of 2-chloro-1-methylpyridinium iodide (223 mg, 0.87 mmol) and tri-n-butylamine (0.207 ml, 0.87 mmol) in dichloromethane (100 mL). The usual work up and chromatographic purification gave compound 501-MS-282 (15 mg, 19%) (m/z: 555.4 [M−1; 100%], 511.4 [28%]).

Step 10

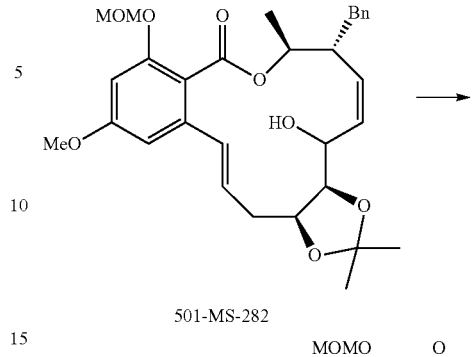
501-MS-282

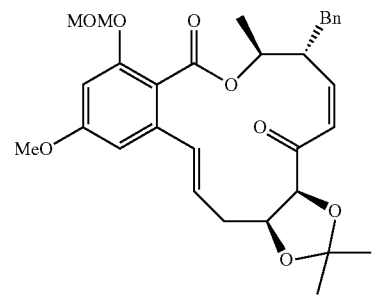
501-MS-284

A solution of compound 501-MS-282 (15 mg, 0.027 mmol) in dichloromethane (3 mL) was treated with PCC (72 mg, 0.334 mmol) in the presence of powdered 4 Å molecular sieves (72 mg). The reaction mixture was stirred vigorously for 90 minutes at room temperature. Basification with excess triethylamine, followed by chromatographic purification gave compound 501-MS-284 (12 mg, 80%).

Step 11

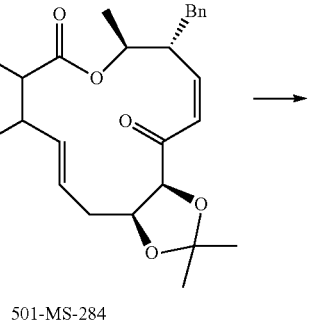
501-MS-284

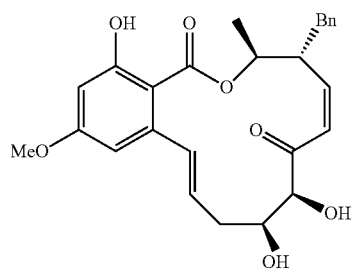
ER-803924

A solution of compound 501-MS-284 (9 mg, approximately 0.016 mmol) in a mixture of acetonitrile (1.2 mL) and dichloromethane (300 µl) was treated with 48% aqueous hydrofluoric acid (300 µL). After 20 minutes the usual work up followed by chromatographic purification gave compound ER-803924 (7.5 mg, quantitative).

Preparation of C3-hydrogen with C4-Methyl Analogs:
Synthesis of ER-804035:

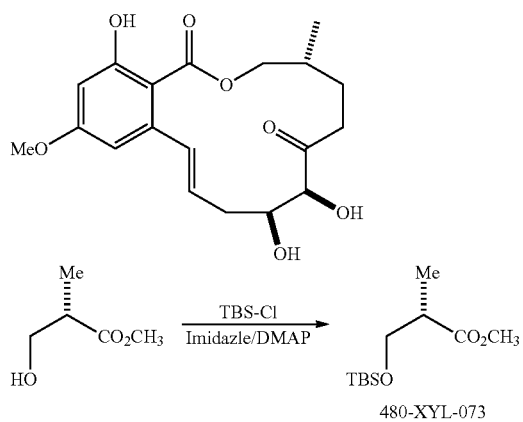

480-XYL-073

To the methyl (S)-(+)-3-hydroxy-2-methylpropionate (14.4 g, 0.121 mol) in DMF (26 mL) at 0° C. were added 4-dimethylaminopyridine (0.79 g, 0.006 mol), imidazole (14.3 g, 0.210 mol) and t-butyldimethylchlorosilane (23.8 g, 0.158 mol). The mixture was stirred at 0° C. for 10 min then at room temperature overnight. The mixture was partitioned between ether and saturated sodium bicarbonate solution. The two layers were separated and the aqueous layer was extracted with ether three times. The ether extracts were combined, dried with sodium sulfate and concentrated. The crude sample was chromatographed on a silica gel column eluting with 5% ethyl acetate in hexanes to get 29.6 g (98%) of product, 480-XYL-073 with satisfactory $^1$H-NMR data.

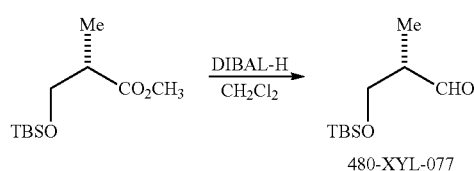

480-XYL-077

The compound 480-XYL-073 (5.04 g, 21.7 mmol) was dissolved in methylene chloride (216 mL) and cooled to −78° C. To this was added diisobutylaluminium hydride solution in methylene chloride (1.0M, 22 mL) at a rate of 13.3 mL per hour via syringe pump down the inner side of flask wall. After completion of addition, the mixture was stirred additional 30 min. The reaction was quenched slowly with methanol down the wall and added some saturated aqueous solution of potassium sodium tartrate. The mixture was warmed up to it, added additional potassium sodium tartrate solution and stirred vigorously for 1 h. The layers were separated and aqueous layer was extracted two times with methylene chloride. The combined organic layers were dried with sodium sulfate, filtered and concentrated to get 4.36 g of crude material, 480-XYL-077. The $^1$H-NMR data analysis showed the desired product aldehyde: starting material:over-rudeced alcohol ratio was 3:1.33:1. This mixture was directly used for the synthesis of 480-XYL-079.

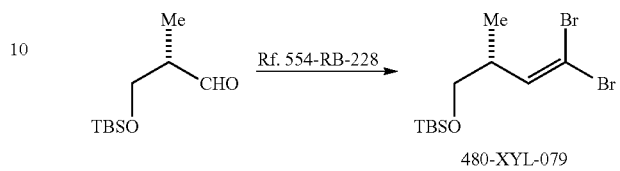

480-XYL-079

The compound 480-XYL-079 was synthesized following the same procedure as the synthesis of 554-RB-228.

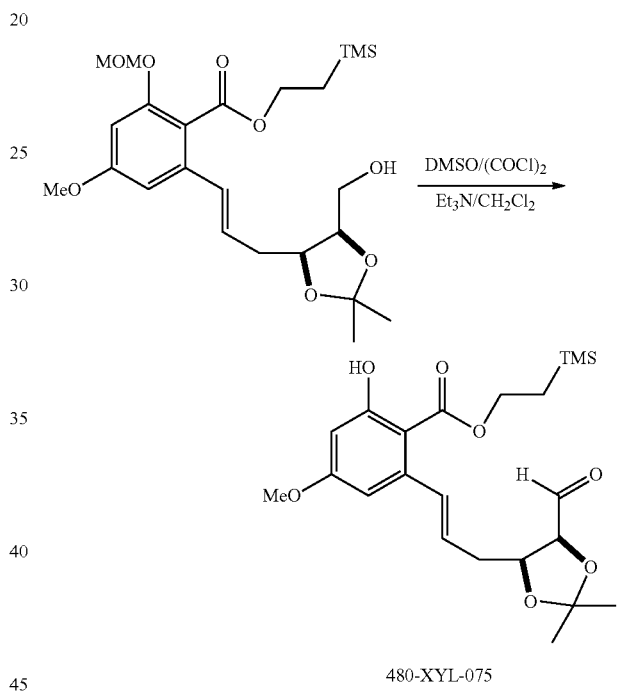

480-XYL-075

DMSO (0.5 mL) in methylene chloride (24 mL) was cooled to −78° C. To this, was added oxalyl chloride solution in methylene chloride (2.0M, 1.7 mL) and the mixture was stirred for 10 min at −78° C. The compound 531-YW-005 (1.4 g, 2.9 mmol) in a solution of methylene chloride (3 mL and rinsed, 2×2 mL) was added via a cannula, and the mixture was stirred for 10 min at −78° C. To this, was added triethylamine (2.5 mL) drop wise and the mixture was stirred for 1 hour at −78° C., was warmed to 0° C. The reaction was diluted with large amount of ether and washed once with saturated ammonium chloride solution and water (1:1), and with water (3×). The ether layer was concentrated in vacuo and re-dissolved in large amount of ether. This was washed two times with water and once with brine. The ether layer was concentrated, azeotroped with ethyl acetate and toluene and dried under high vacuum to get 1.36 g (98%), 480-XYL-075 which showed good purity by $^1$H-NMR spectrum. This material was immediately used for the synthesis of 480-XYL-081.

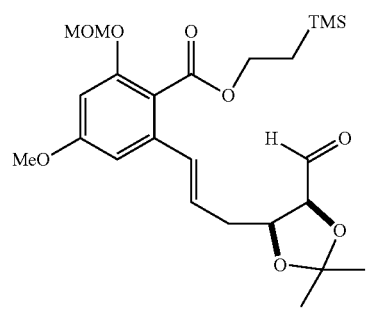

480-XYL-075

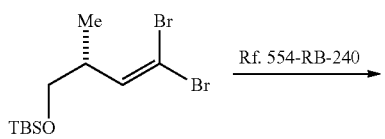

480-XYL-079

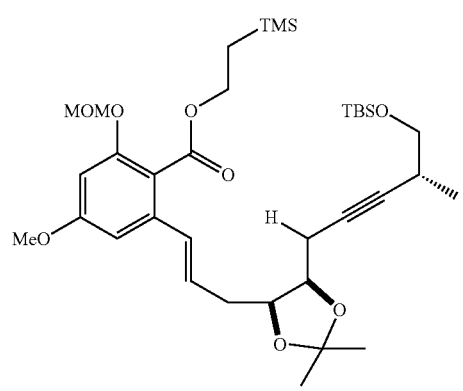

480-XYL-084

The synthesis of 480-XYL-084 followed the same procedure as the synthesis of 554-RB-240.

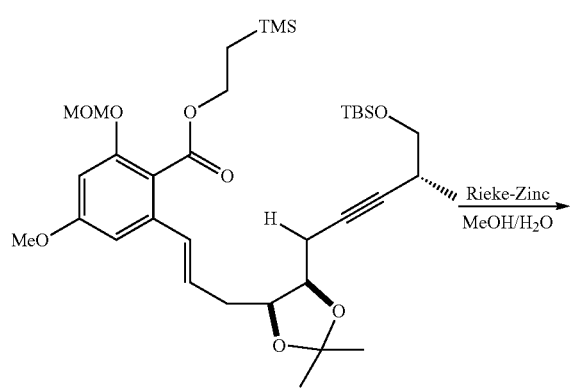

480-XYL-084

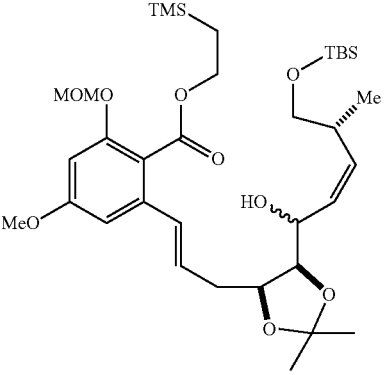

480-XYL-090

The compound 480-XYL-084 (855 mg, 1.21 mmol) was dissolved in a mixture of methanol and water (5:1, 60 mL). A slurry solution of Rieke-zinc in THF (8 mL) was added and the mixture was heated to reflux with stirring for three hours. The mixture was filtered through a plug of celite and silica gel, rising with ethyl acetate. The filtrate was concentrated, re-dissolved in methylene chloride and washed with saturated ammonium chloride solution and then with saturated sodium bicarbonate solution. The aqueous phase was back extracted two times with methylene chloride and once with ethyl acetate. The combined organic layers were dried with sodium sulfate and concentrated to get 944 mg of crude material, 480-XYL-075, which showed satisfactory purity by ¹H-NMR spectrum and directly used for the synthesis of 480-XYL-092.

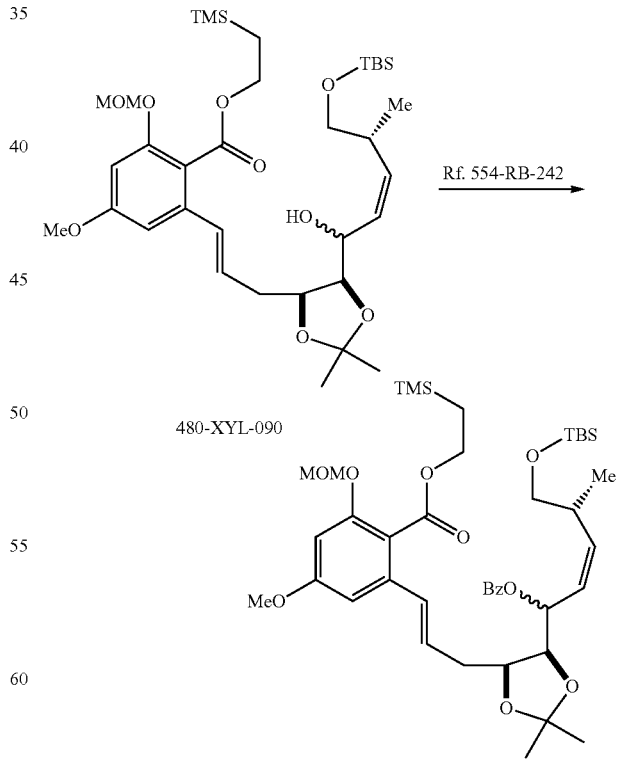

480-XYL-090

480-XYL-092

The synthesis of 480-XYL-092 was the same as the procedure of the synthesis of 554-RB-242.

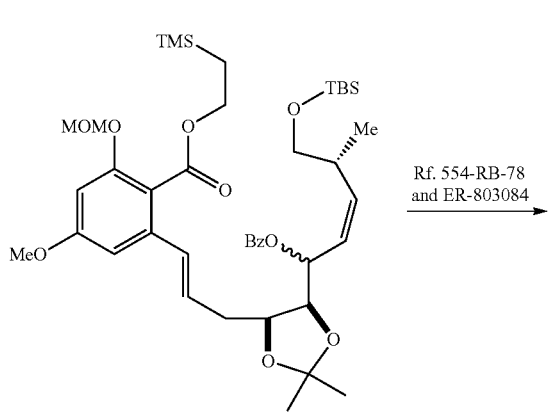

480-XYL-092

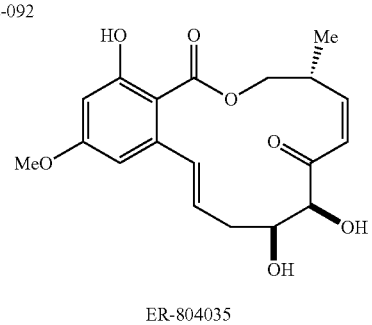

ER-804035

ER-804035
The synthesis of ER-804035 from 480-XYL-092 was followed the same procedure as for the synthesis of ER-803064.
Preparation of ER804022:

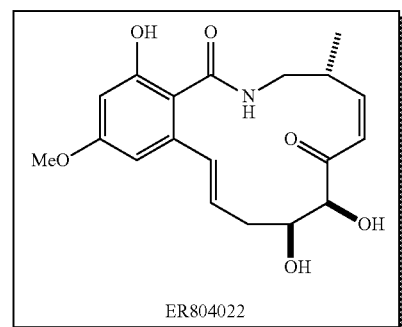

ER804022

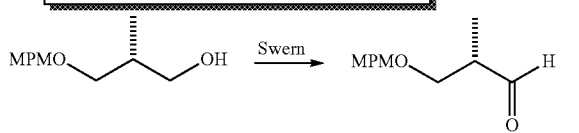

Oxalyl chloride (6.5 mL, 74.1 mmol) was dissolved in 150 ml dichloromethane at −78° C. Methyl sulfoxide (10.5 mL, 148.2 mmol) was added. After 20 min, the solution of starting material (5.2 g, 24.7 mmol) in 50 mL of dichloromethane was added at −78° C. After stirring for 1 h at −78° C., triethylamine (31.0 mL, 222 mmol) was added and the reaction mixture was warmed up to room temperature. It was quenched with sat. ammonium chloride and extracted with ethyl acetate. After purification on silica gel column, 509-HD-183 was obtained in 79% yield.

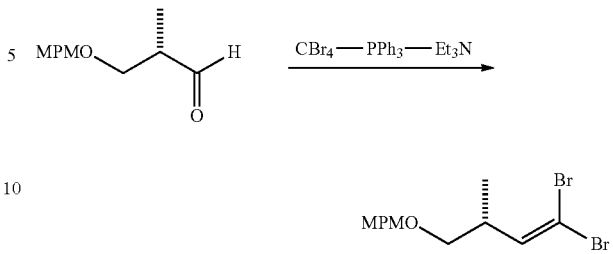

Triphenylphosphine (13.4 g, 51.2 mmol) was dissolved in 100 mL dichloromethane at 0° C. Carbon tetrabromide (8.5 g, 25.6 mmol) was added. After 15 min, the solution of 509-HD-183 (4.1 g, 19.7 mmol) and triethylamine (2.8 mL, 19.7 mmol) in 50 ml of dichloromethane was added. After stirring for 30 min, the reaction mixture was triturated with pentane. After purification on silica gel column, 509-HD-184 was obtained in 88% yield.

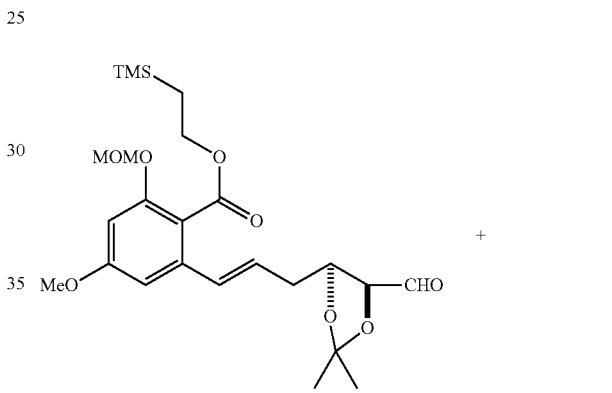

509-HD-184 (553 mg, 1.52 mmol) was dissolved in 10 mL of THF at −78° C. The solution of n-butyl lithium (2.5M, 1.33 mL) in hexane was added. After 15 min at −78° C., the solution of 531-HYW-5 in 5 ml of THF was added. After stirring for 30 min at −78° C., the reaction mixture was warmed up to room temperature. It was quenched with water and extracted with ethyl acetate. After purification on silica gel column, 509-HD-185 was obtained in 95% yield.

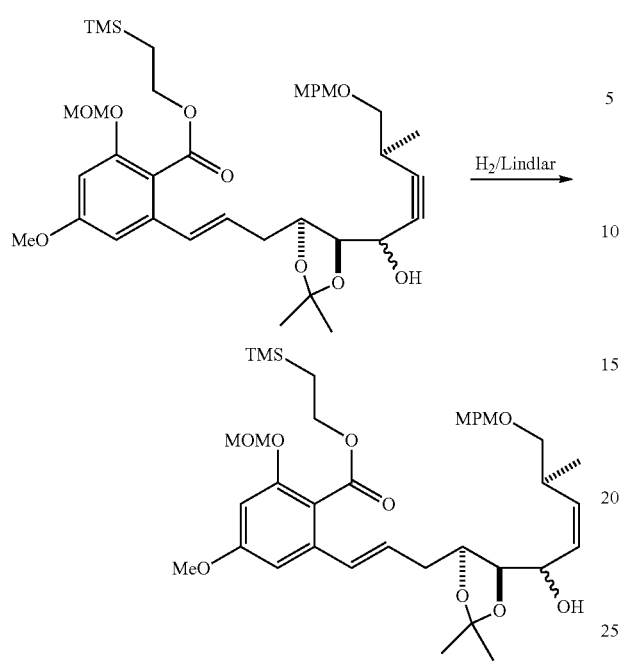

509-HD-185 (750 mg, 1.09 mmol) was dissolved in 40 mL of hexane. Quinoline (50 µL) and Lindlar catalyst (120 mg) were added. The reaction mixture was stirred at mom temperature under $H_2$ balloon atmosphere for 5 h. Then the catalyst was filtered away. Quantitative amount of 509-HD-186 was obtained.

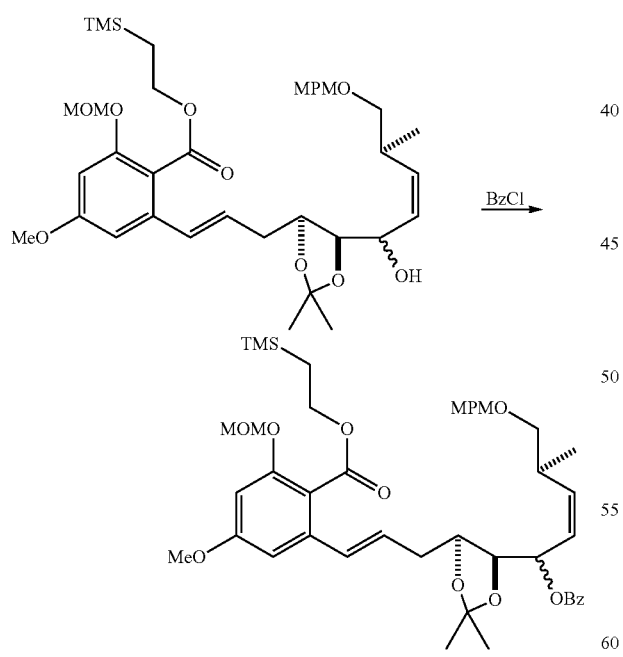

509-HD-186 (861 mg, 1.09 mmol) was dissolved in 15 mL of dichloromethane at room temperature. Triethylamine (380 µL, 2.73 mmol), benzoyl chloride (253 µL, 2.18 mmol) and catalytic amount of DAMP were added, respectively. After stirring for 20 h, 0.1N sodium hydroxide solution was added and the reaction mixture was extracted with ethyl acetate. The crude product was purified on silica gel column, giving 509-HD-187 in 95% yield.

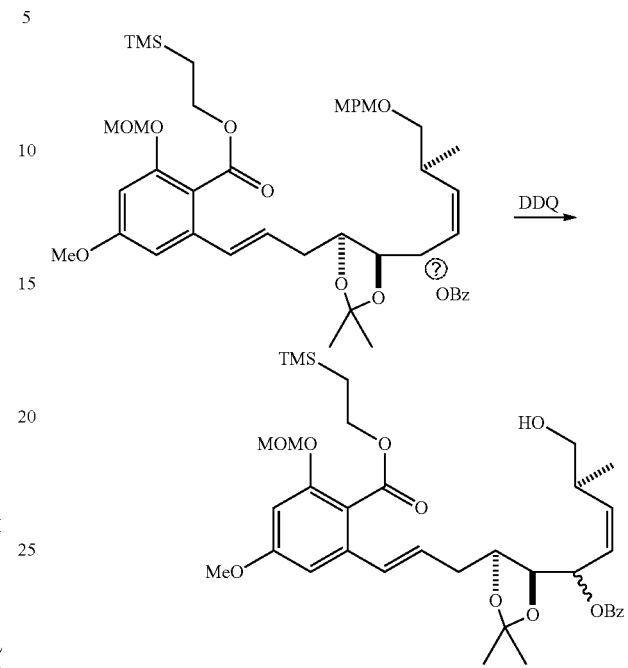

509-HD-187 (813 mg, 1.03 mmol) was dissolved in a mixture of 10 mL of dichloromethane and 5 mL of water. DDQ (234 mg, 1.03 mmol) was added. After stirring at room temperature for 1 h, the reaction mixture was quenched with sat. sodium bicarbonate solution and extracted with ethyl acetate. After purification on silica gel column, 509-HD-188 was obtained in 48% yield.

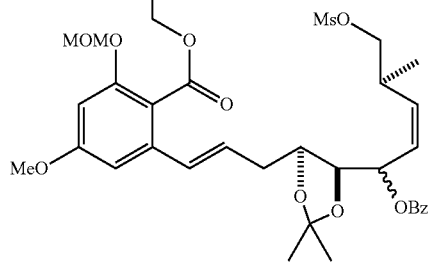

509-HD-188 (313 mg, 0.47 mmol) was dissolved in 15 mL of dichloromethane at 0° C. Triethylamine (130 µL, 0.94 mmol) and methanesulfonyl chloride (54 µL, 0.71 mmol) were added. After stirring for 20 min, the reaction mixture was quenched with sat. sodium bicarbonate and extracted with dichloromethane. After purification on silica gel column, 509-HD-189 was obtained in 93% yield.

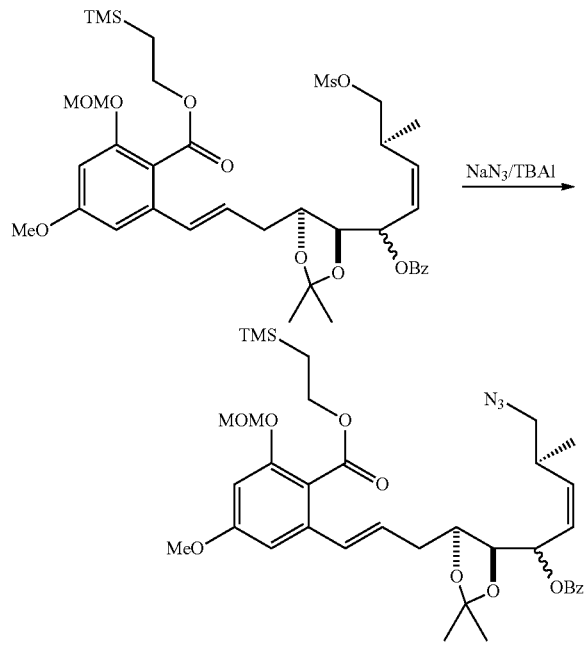

509-HD-189 (327 mg, 0.44 mmol) was dissolved in 10 mL of DMF. Sodium azide (85 mg, 1.32 mmol) and catalytic amount of tetrabutylammonium iodide were added. After stirring at 85° C. for 2 h, the reaction mixture was diluted with ethyl acetate and washed with water. After purification on silica gel column, 509-HD-190 was obtained in 93% yield.

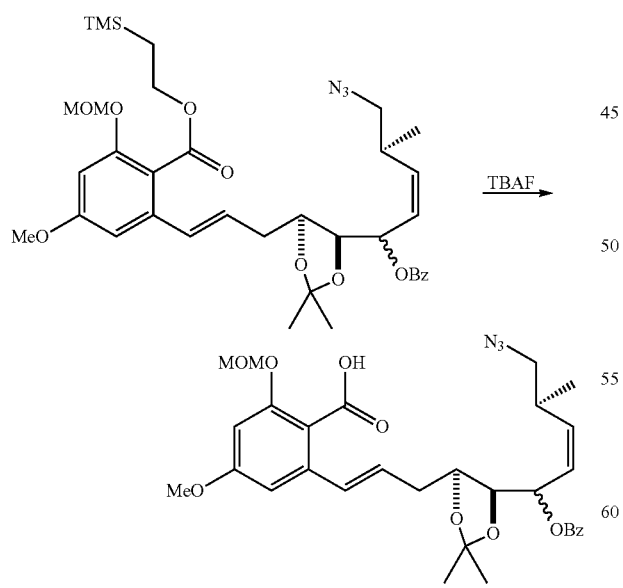

509-HD-190 (297 mg, 0.43 mmol) was dissolved in 10 mL of THF. The solution of TBAF (1N, 1.3 mL) was added. The reaction mixture was stirred at room temperature for 1 h. It was diluted with Et$_2$O and washed with H$_2$O. After purification on silica gel column, 509-HD-191 (215 mg) was obtained in quantitative yield.

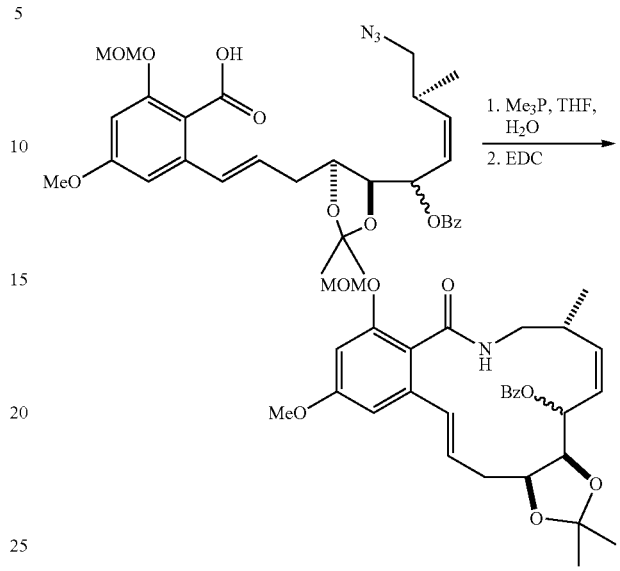

Trimethylphosphine (1N, 1.5 mL) was dissolved in a mixture of 15 mL of THF and 5 mL of water at room temperature. 509-HD-191 (215 mg, 0.31 mmol) was added. After stirring for 12 h, it was concentrated and azeotroped with toluene. The residue was re-dissolved in 50 ml dichloromethane. EDC (593 mg, 3.1 mmol) was added. After stirring for 2 h, it was diluted with water and extracted with dichloromethane. After purification on HPTLC, 509-HD-197 was obtained in 30% yield.

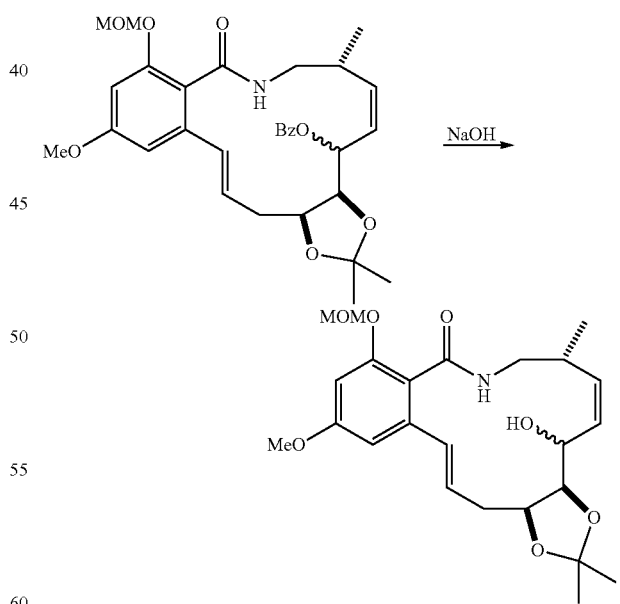

509-HD-197 (51 mg, 0.092 mmol) was dissolved in 5 mL of ethanol. Sodium hydroxide (1N, 0.92 mL) solution was added. The reaction mixture was stirred for 48 h at room temperature. It was diluted with H$_2$O, extracted with EtOAc. After purification on HPTLC, 11.5 mg of the major desired single isomer 509-HD-198 was obtained as colorless oil.

Preparation of ER-803027-00-01

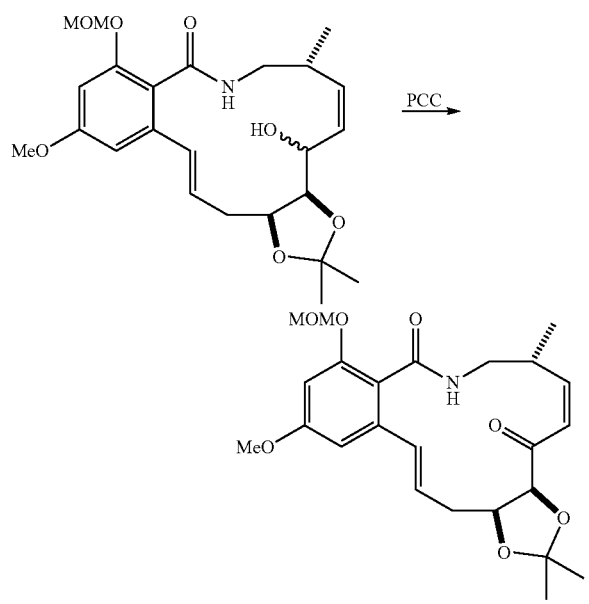

509-HD-198 (10.0 mg, 0.022 mmol) was dissolved in 3 mL of dichloromethane. Molecular sieve (4 A, 48 mg) and PCC (48 mg, 0.22 mmol) were added. The reaction mixture was stirred for 48 h at room temperature. After purification on prep TLC, 509-HD-200 was obtained in 35% yield.

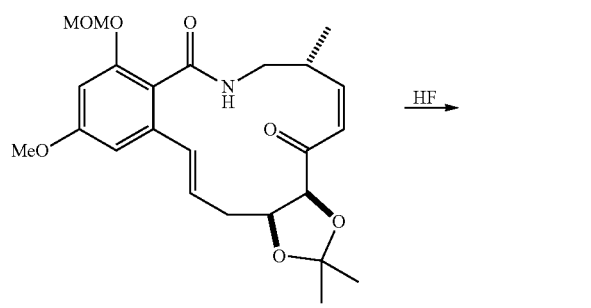

509-HD-200 (13 mg, 0.0079 mmol) was dissolved in 0.25 mL of dichloromethane. Then hydrofluoric acid (6N, 1 mL) was added. The reaction mixture was stirred at room temperature for 1 h. It was diluted with more dichloromethane, washed with water and sat. sodium bicarbonate solution. After purification on a plug of silica gel, ER804022 was obtained as a white solid in quantitative yield.

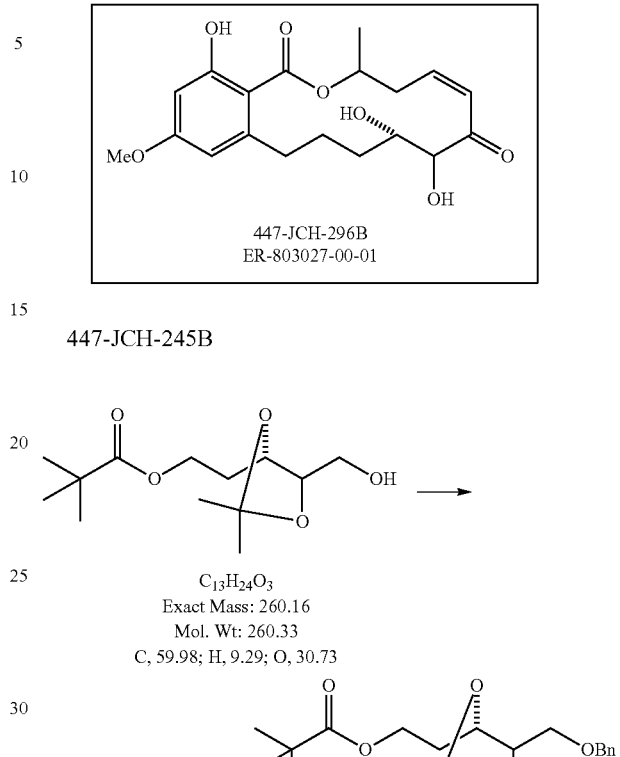

447-JCH-245B $C_{13}H_{24}O_3$
Exact Mass: 260.16
Mol. Wt: 260.33
C, 59.98; H, 9.29; O, 30.73

447-JCH-245B $C_{20}H_{30}O_5$
Exact Mass: 350.21
Mol. Wt.: 350.45
C, 68.54; H, 8.63; O, 22.83

To a magnetically stirred solution of 531-YW-2-2 (3.5 g, 13.4 mmol) in 15 mL of dry DMF cooled to −0° C. (ice/water; external thermometer) was introduced NaH (0.39 g, 16 mmol) followed by benzyl bromide (0.34 g, 20 mmol). After 18 hours of stirring at room temperature the reaction mixture was cooled down at 0° C. and water was added. The reaction mixture was diluted with water and extracted with Ethyl ether. The crude was purified on silica gel (Hexane/EtOAc: 90/10) to afford 447-JCH-245B (0.93 g, 20% yield).

447-JCH-268B

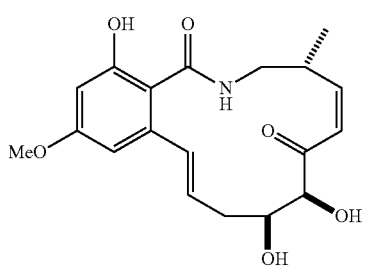

447-JCH-245B $C_{20}H_{30}O_5$
Exact Mass: 350.21
Mol. Wt: 350.45
C, 68.54; H, 8.63; O, 22.83

-continued

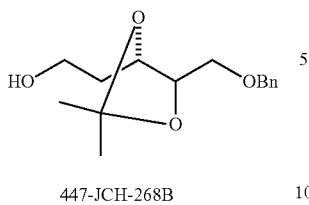

447-JCH-268B

C₁₅H₂₂O₄
Exact Mass: 266.15
Mol. Wt.: 266.33
C, 67.64; H, 8.33; O, 24.03

To a magnetically stirred solution of 447-JCH-245B (0.93 g, 2.7 mmol) in 8 mL of ethanol 1 M NaOH aqueous solution (4 mL) was added. After 18 hours of stirring at room temperature the reaction mixture was diluted with water and extracted with ethyl ether. The crude was purified on silica gel (Hexane/EtOAc: 60/40) to afford 447-JCH-268B (0.47 g, 67% yield).

447-JCH-271B

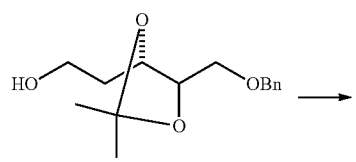

447-JCH-268B

C₁₅H₂₂O₄
Exact Mass: 266.15
Mol. Wt: 266.33
C, 67.64; H, 8.33; O, 24.03

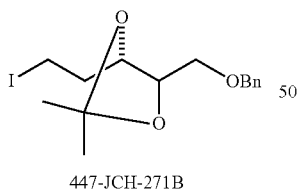

447-JCH-271B

C₁₅H₂₁IO₃
Exact Mass: 376.05
Mol. Wt.: 376.23
C, 47.89; H, 5.63; I, 33.73; O, 12.76

Using a procedure analogous to that described for the synthesis of intermediate 531-YW-3, 447-JCH-268B (0.450 g, 1.69 mmol) was reacted with triphenylphosphine (0.887 g, 3.38 mmol), DEAD (0.32 mL, 2 mmol) and methyl iodide (0.158 mL, 2.54 mmol) in toluene (16.9 mL) to afford 447-JCH-271B (0.553 g, 86% yield).

447-JCH-273B

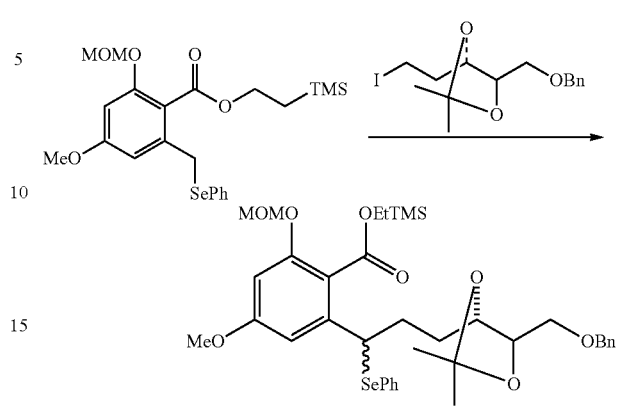

To a magnetically stirred solution of 509-HD-213 (0.553 g, 1.47 mmol) and 447-JCH-271B (1.06 g, 2.2 mmol) in 6 ml of a 10:1 ratio of HMPA/THF mixture at −78° C. (dry ice/acetone; internal thermometer) was slowly (syringe pump) introduced a 1 M solution of LiHMDS in THF (2.2 mL, 2.2 mmol) diluted with 2.2 mL of the same mixture. After 30 min. at −78° C., the reaction mixture was warmed-up to 0° C. The reaction was then quenched by addition of a saturated aqueous solution of ammonium Chloride. The reaction mixture was diluted with water and extracted with Ethyl ether. The crude was purified on silica gel (Hexane/EtOAc: 90/10 to afford 447-JCH-273B (0.910 g, 84% yield).

447-JCH-275B

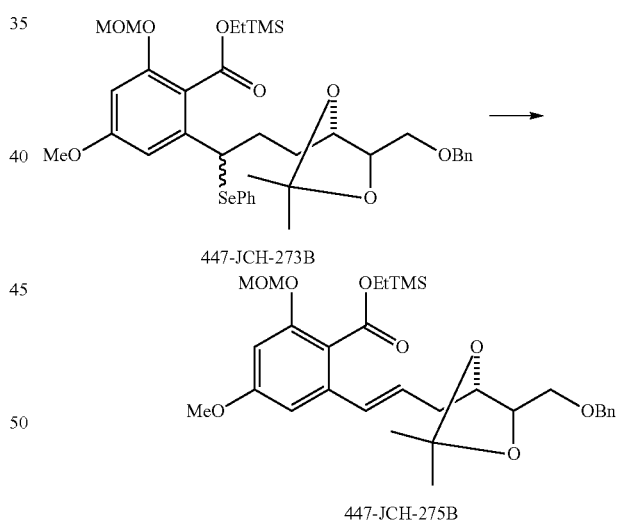

To a magnetically stirred solution of 447-JCH-273B (0.910 g, 1.25 mmol) in 24 mL of dichloromethane at 0° C. (ice/water; external thermometer), MCPBA (0.66 g, 3.8 mmol) was added. After 15 min. of stirring at 0° C., triethylamine was added (1.5 mL) and the reaction mixture was warmed-up to room temperature. After 45 min of stirring at room temperature a 10% solution of sodium thiosulfate in a saturated aqueous solution of sodium bicarbonate was added and the mixture was stirred for 30 minutes. The reaction mixture was diluted with water and extracted with Ethyl ether. The crude was purified on silica gel (Hexane/EtOAc: 80/20 to afford 447-JCH-275B (0.70 g, 98% yield).

447-JCH-277B

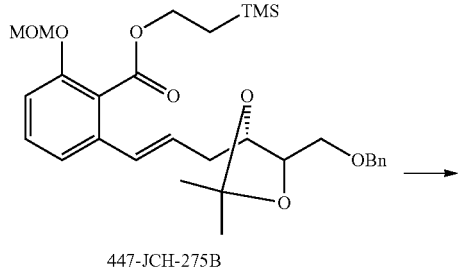

447-JCH-275B

C₃₁H₄₄O₈Si
Exact Mass: 572.28
Mol. Wt: 572.76
C, 65.01; H, 7.74; O, 22.35; Si, 4.90

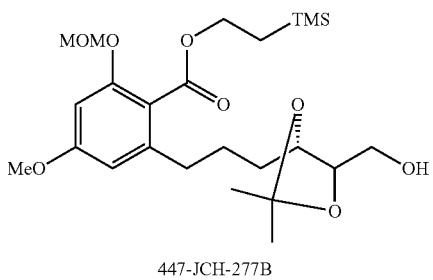

447-JCH-277B

C₂₄H₄₀O₈Si
Exact Mass: 484.25
Mol. Wt: 484.66
C, 59.48; H, 8.32; O, 26.41; Si, 5.79

To a magnetically stirred solution of 447-JCH-275B (0.71 g, 1.2 mmol) in 15 mL of methanol at room temperature was introduced a catalytic amount of Pd 10% on carbon. The reaction mixture was stirred 18 hours at room temperature and then filtered through a pad of celite. The crude was purified on silica gel (Hexane/EtOAc: 70/30) to afford 447-JCH-277B (0.58 g, 99% yield).

447-JCH-280A

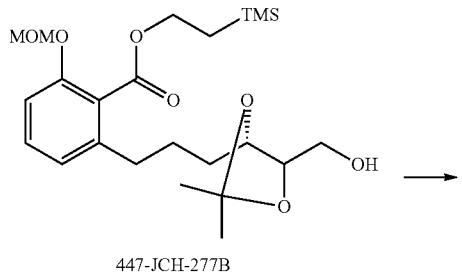

447-JCH-277B

C₂₄H₄₀O₈Si
Exact Mass: 484.25
Mol. Wt: 484.66
C, 59.48; H, 8.32; O, 26.41; Si, 5.79

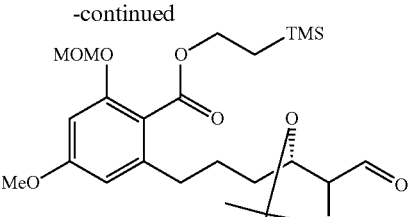

447-JCH-280A

C₂₆H₃₈O₈Si
Exact Mass: 482.23
Mol. Wt: 482.64
C, 59.73; H, 7.94; O, 26.52; Si, 5.82

Using a procedure analogous to that described for the synthesis of intermediate 480-XYL-075, 447-JCH-277B (0.6 g, 1.2 mmol) was reacted with Dess-Martin reagent (0.763 g, 1.8 mmol), and sodium bicarbonate (0.38 g) in dichloromethane (48 ml) to afford 447-JCH-280A (0.602 g).

447-JCH-282B

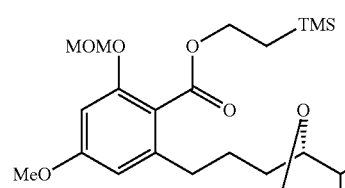

447-JCH-280A

C₂₄H₃₈O₈Si
Exact Mass: 482.23
Mol. Wt: 482.64
C, 59.73; H, 7.94; O, 26.52; Si, 5.82

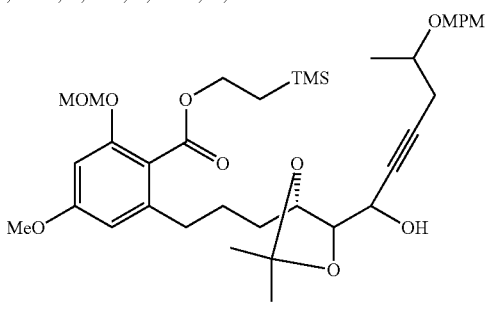

447-JCH-282B

C₃₇H₅₄O₁₀Si
Exact Mass: 686.35
Mol. Wt: 686.90
C, 64.70; H, 7.92; O, 23.29; Si, 4.09

Ⓐ indicates text missing or illegible when filed

Using a procedure analogous to that described for the synthesis of ER-803064 (stage 509-HD-108), 447-JCH-280A (0.6 g) was reacted with intermediate 343-YW-276 (0.32 g, 1.56 mmol) in THF (18 mL) to afford 447-JCH-282B (0.6 g, 70% yield from 447-JCH-277B).

447-JCH-283B

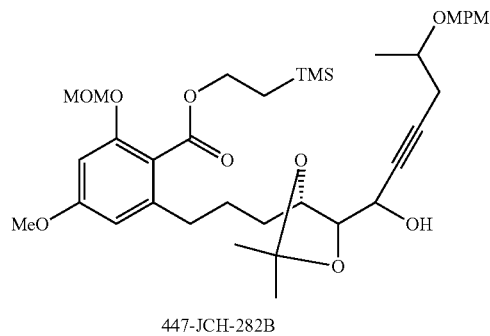

447-JCH-282B $C_{37}H_{54}O_{10}Si$
Exact Mass: 686.35
Mol. Wt: 686.90
C, 64.70; H, 7.92; O, 23.29; Si, 4.09

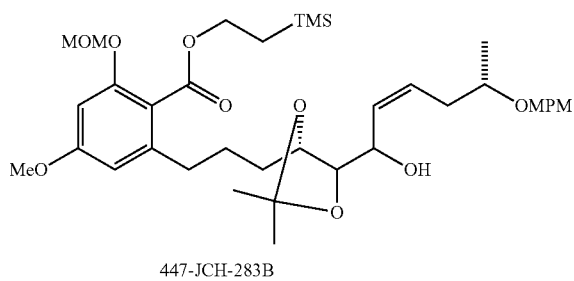

447-JCH-283B $C_{37}H_{56}O_{10}Si$
Exact Mass: 688.36
Mol. Wt: 688.92
C, 64.51; H, 8.19; O, 23.22; Si, 4.08

(?) indicates text missing or illegible when filed

Using a procedure analogous to that described for the synthesis of ER-803064 (stage 509-HD-112), 447-JCH-282B (0.6 g) hydrogenated using Lindlar catalyst to afford 447-JCH-283B (0.61 g).

447-JCH-285B

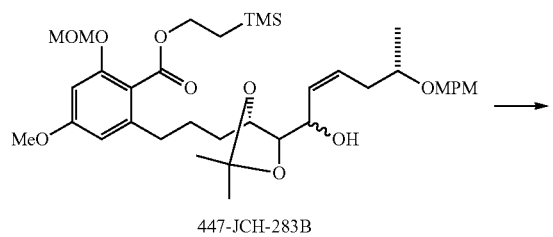

447-JCH-283B $C_{37}H_{56}O_{10}Si$
Exact Mass: 688.36
Mol. Wt: 688.92
C, 64.51; H, 8.19; O, 23.22; Si, 4.08

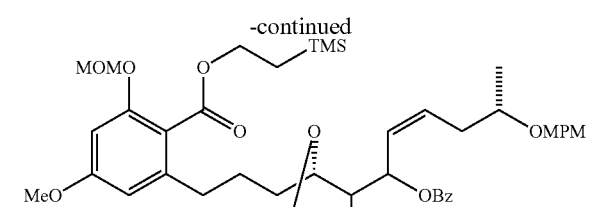

447-JCH-285B $C_{44}H_{60}O_{11}Si$
Exact Mass: 792.39
Mol. Wt: 793.03
C, 66.64; H, 7.63; O, 22.19; Si, 3.54

(?) indicates text missing or illegible when filed

Using a procedure analogous to that described for the synthesis of ER-803064 (stage 509-HD-115), 447-JCH-283A (0.72 g) was reacted with benzoyl chloride (0.37 mL, 2.63 mmol) to afford 447-JCH-285B (0.78 g, 93%).

447-JCH-287B

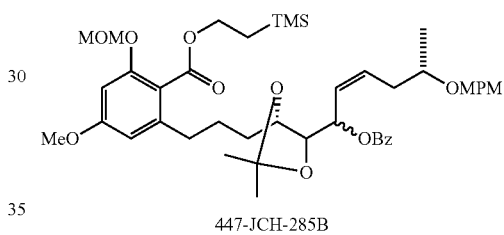

447-JCH-285B $C_{44}H_{60}O_{11}Si$
Exact Mass: 792.39
Mol. Wt: 793.03
C, 66.64; H, 7.63; O, 22.19; Si, 3.54

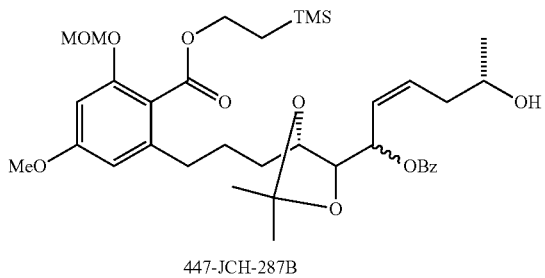

447-JCH-287B $C_{39}H_{52}O_{10}Si$
Exact Mass: 672.33
Mol. Wt: 672.88
C, 64.26; H, 7.79; O, 23.78; Si, 4.17

To a magnetically stirred solution of 447-JCH-285B (0.68 g, 0.86 mmol) in a 2/1 dichloromethane/water mixture (26 mL) at room temperature, DDQ (0.17 g) was added. After 40 minutes of stirring at room temperature, the reaction mixture was diluted with ethyl acetate washed once with an aqueous solution of sodium hydroxide (0.1 N) and twice with water. The crude product was purified by flash chromatography eluting with hexane/ethyl acetate: (60/40) to afford 447-JCH-287B (0.52 g, 88%).

447-JCH-288A

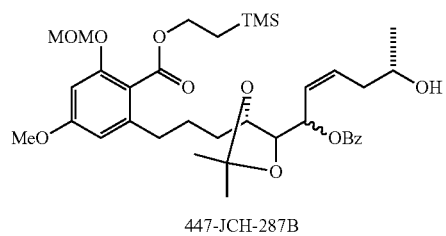

447-JCH-287B

C$_{30}$H$_{52}$O$_{10}$Si
Exact Mass: 672.33
Mol. Wt: 672.88
C, 64.26; H, 7.79; O, 23.78; Si, 4.17

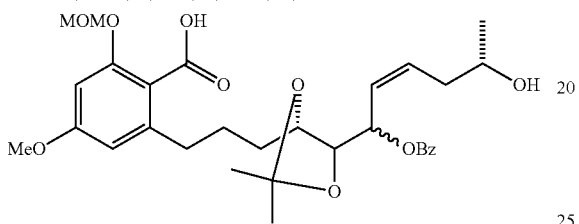

447-JCH-288A

C$_{31}$H$_{40}$O$_{10}$
Exact Mass: 572.26
Mol. Wt: 572.64
C, 65.02; H, 7.04; O, 27.94

Using a procedure analogous to that described for the synthesis of ER-803064 (stage 509-HD-116), 447-JCH-287B (0.58 g, 0.86 mmol) was reacted with TBAF (0.68 g, 2.6 mmol) in THF (2.6 mL) to afford 447-JCH-288A (0.47 g).

447-JCH-290B

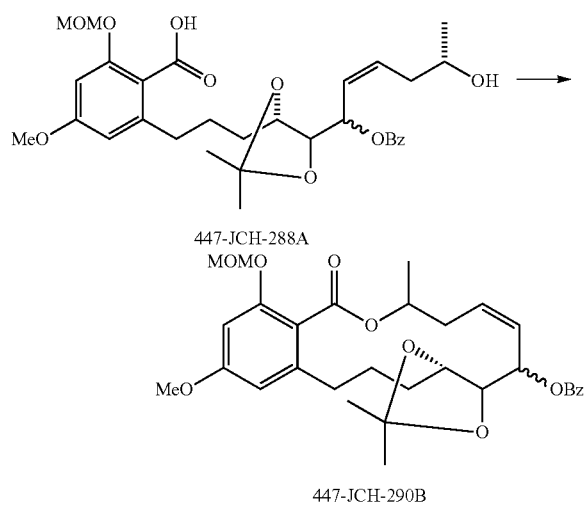

To a magnetically stirred solution of 447-JCH-288A (0.31 g, 0.54 mmol) and triphenylphosphine (0.34 g, 2.17 mmol) in THF (43 mL) at room temperature, DEAD (0.57 g, 2.17 mmol) was added. After 1 hour of stirring at room temperature, the reaction mixture was concentrated under vacuum. The crude product was purified by flash chromatography eluting with hexane/ethyl acetate: (70/30) to afford 447-JCH-290B (0.21 g, 70%).

447-JCH-294B

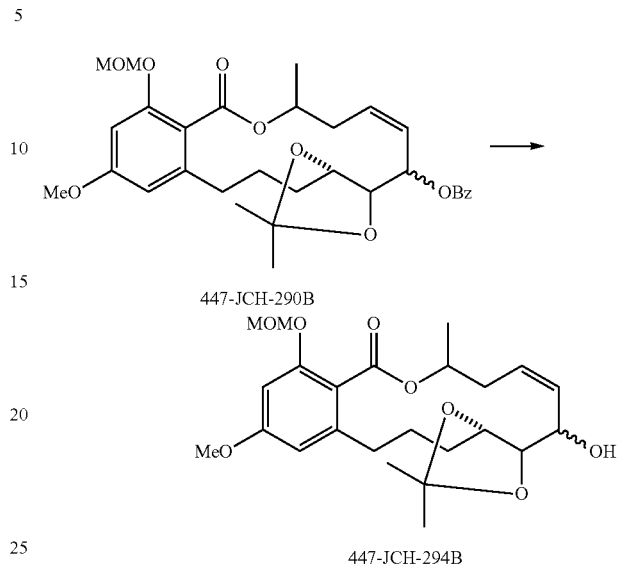

Using a procedure analogous to that described for the synthesis of ER-803064 (stage 509-HD-119), 447-JCH-290B (0.21 g, 0.38 mmol) was reacted with sodium hydroxide (1M solution, 1.9 mL, 1.9 mmol) in ethanol (5.7 mL) to afford 447-JCH-294B (0.128 g, 73%).

447-JCH-295B

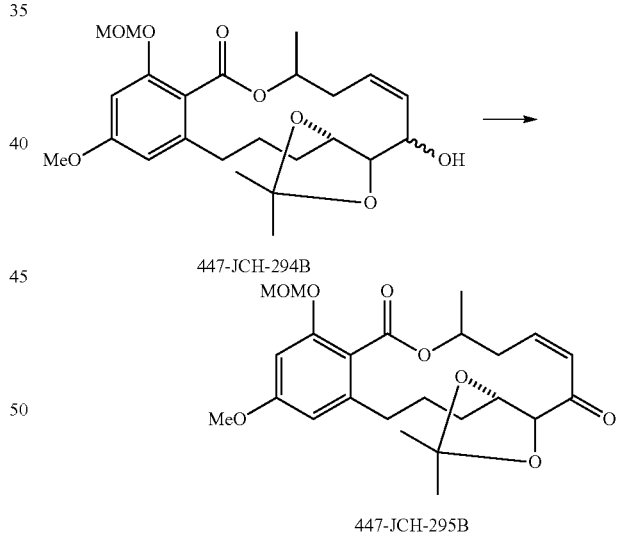

To a magnetically stirred solution of 447-JCH-294B (0.07 g, 0.155 mmol) in dichloromethane (15 mL) at room temperature sodium bicarbonate (0.08 g) and Dess-Martin reagent (165 mg, 0.388 mmol) were added. After 45 minutes of stirring at room temperature, a 10% (w/w) thiosulfate solution in saturated aqueous solution of sodium bicarbonate was added. The reaction mixture was diluted with water and extracted with ethyl ether. The crude product was purified by flash chromatography eluting with n-hexane/ethyl acetate: (60/40) 447-JCH-295B (0.06 g, 88%).

447-JCH-296B/ER-803027

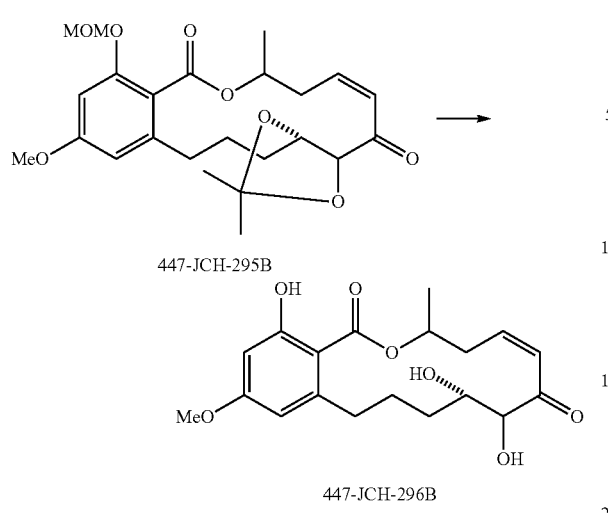

447-JCH-295B

447-JCH-296B

Using a procedure analogous to that described for the synthesis of ER-803064 (stage 509-HD-125), 447-JCH-295B (0.017 g, 0.038 mmol) was reacted with HF (48%) (0.85 ml) in acetonitrile (3.4 mL) to afford 447-JCH-296B/ER-803027 (0.006 g, 97%).

Preparation of B2329:

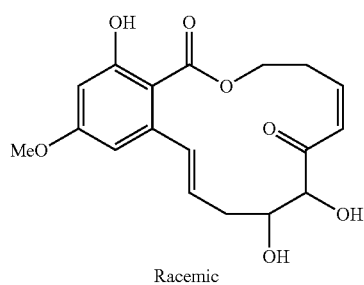

Racemic

447-SG-089A

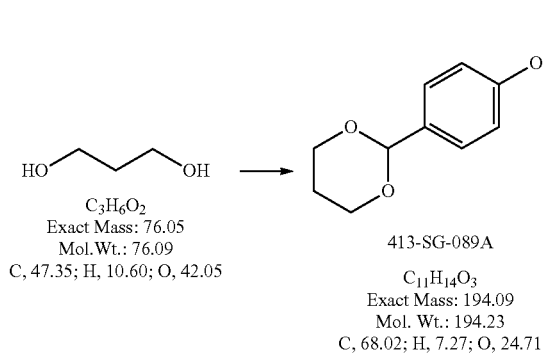

$C_3H_6O_2$
Exact Mass: 76.05
Mol.Wt.: 76.09
C, 47.35; H, 10.60; O, 42.05

413-SG-089A
$C_{11}H_{14}O_3$
Exact Mass: 194.09
Mol. Wt.: 194.23
C, 68.02; H, 7.27; O, 24.71

A mixture of 1,3-propanediol (15 g, 197 mmol), p-anisaldehyde dimethylacetal (37 mL, 217 mmol) and p-toluene sulfonic acid (35 mg) was stirred under slight vacuum for 6 hours at 35° C. in DMF (35.5 mL). The reaction mixture was cooled to room temperature, and then a saturated aqueous solution of sodium bicarbonate was added. The reaction mixture was diluted with water and extracted with ethyl acetate to afford 447-SG-089A (35.8 g). The crude was used directly into the next step without purification.

447-SG-89B

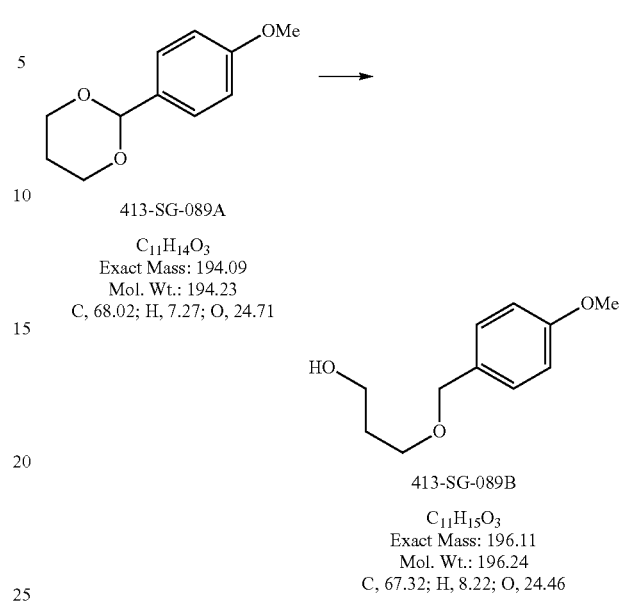

413-SG-089A
$C_{11}H_{14}O_3$
Exact Mass: 194.09
Mol. Wt.: 194.23
C, 68.02; H, 7.27; O, 24.71

413-SG-089B
$C_{11}H_{15}O_3$
Exact Mass: 196.11
Mol. Wt.: 196.24
C, 67.32; H, 8.22; O, 24.46

To a magnetically stirred solution of 413-SG-89A (12.95 g, 66.67 mmol) in dichloromethane (225 mL) cooled to −5° C. (Ice/salt, internal thermometer), 1 M solution of DIBAL-H in toluene (100 mL, 100 mmol) was added. After 2 hours of stirring at room temperature, the reaction was quenched by addition of methanol (100 mL). After 2 hours of vigorous stirring, 100 ml of a saturated aqueous solution of sodium sulfate was added. After 1 hour of stirring, the reaction mixture was diluted with 100 mL of ethyl ether and stirred at room temperature for half an hour. The reaction mixture was filtered through a plug of celite and the solvent was removed by evaporation. The crude product was purified by flash chromatography eluting with hexane/ethyl acetate (2:1 then 1/1) to afford 447-SG-89B (11.45 88% yield).

413-SG-106A

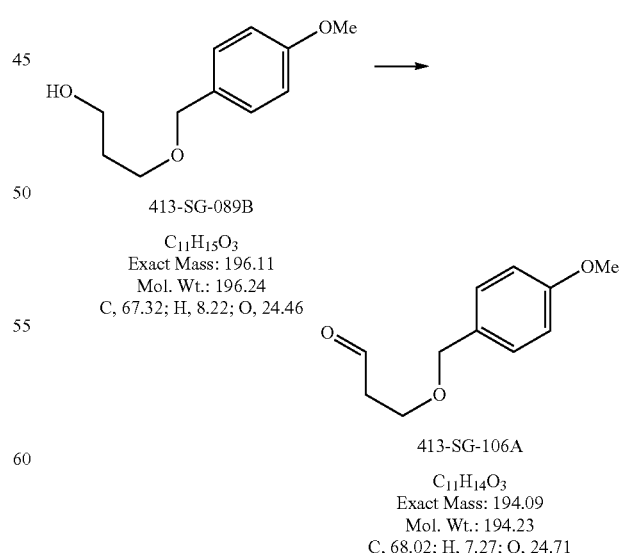

413-SG-089B
$C_{11}H_{15}O_3$
Exact Mass: 196.11
Mol. Wt.: 196.24
C, 67.32; H, 8.22; O, 24.46

413-SG-106A
$C_{11}H_{14}O_3$
Exact Mass: 194.09
Mol. Wt.: 194.23
C, 68.02; H, 7.27; O, 24.71

To a magnetically stirred solution of 413-SG-89B (2 g, 10.9 mmol) in dichloromethane (225 mL) cooled to 0° C.

(Ice/water, external thermometer) DMSO (2.5 mL, 35.67 mmol) was added, followed by P$_2$O$_5$ (5.06 g, 35.67 mmol). After one hours of stirring at room temperature the reaction was cooled down to 0° C. and triethylamine (7.1 mL, 50.95 ml) was added. After 45 minutes of stirring at room temperature. The reaction mixture was diluted with water and extracted with dichloromethane. The solvent was removed by evaporation. The residue was triturated with ether and the solid was filtered-off and wash with ether. The solvent was removed by evaporation to afford 413-SG-106A (2.1 g), the crude was used directly into the next step without purification.

413-SG-106B

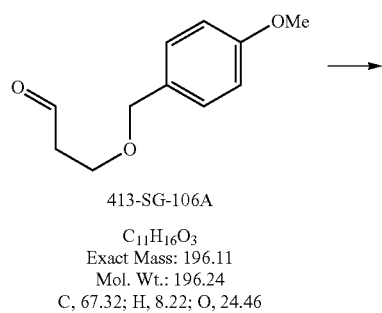

413-SG-106A

C$_{11}$H$_{16}$O$_3$
Exact Mass: 196.11
Mol. Wt.: 196.24
C, 67.32; H, 8.22; O, 24.46

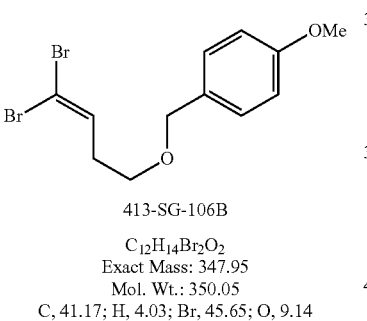

413-SG-106B

C$_{12}$H$_{14}$Br$_2$O$_2$
Exact Mass: 347.95
Mol. Wt.: 350.05
C, 41.17; H, 4.03; Br, 45.65; O, 9.14

Using a procedure analogous to that described for the synthesis of intermediate 343-YW-276, 413-SG-106A (10.9 mmol) was reacted with triphenylphosphine (7 g, 26.49 mmol), carbon tetrabromide (4.39 g, 13.25 mmol) and triethylamine (1.4 mL, 10.9 mmol) in dichloromethane (12.6 mL). The crude product was purified by flash chromatography eluting with pentane/dichloromethane (1/1) to afford 413-SG-106B (3.04 g, 85% yield).

413-SG-110B

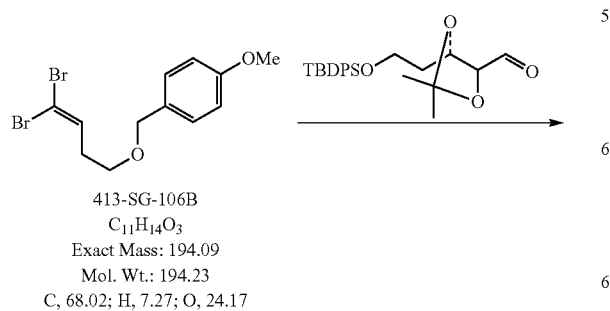

413-SG-106B
C$_{11}$H$_{14}$O$_3$
Exact Mass: 194.09
Mol. Wt.: 194.23
C, 68.02; H, 7.27; O, 24.17

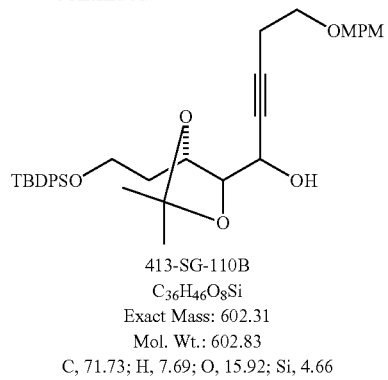

413-SG-110B
C$_{36}$H$_{46}$O$_8$Si
Exact Mass: 602.31
Mol. Wt.: 602.83
C, 71.73; H, 7.69; O, 15.92; Si, 4.66

Using a procedure analogous to that described for the synthesis of intermediate 554-RB-240B, 413-SG-106B (1.66 g, 4.73 mmol) was reacted with n-BuLi (2.5M in toluene, 4.2 mL, 10.41 mmol) in THF (32.5 mL) at −78° C. The resulting alkynyl lithium was then reacted with intermediate 343-YW-277 (1.64 g, 3.97 mmol) in THF (12 mL) at −78° C. The crude product was purified by flash chromatography eluting with hexane/ethyl acetate (3/1) to afford 413-SG-110B (2.01 g, 86% yield).

413-SG-167A

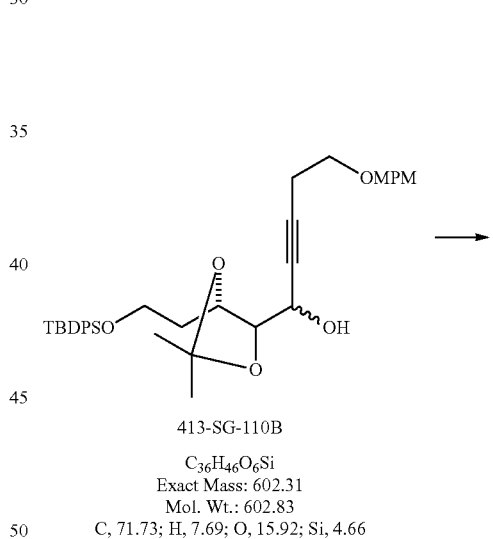

413-SG-110B
C$_{36}$H$_{46}$O$_6$Si
Exact Mass: 602.31
Mol. Wt.: 602.83
C, 71.73; H, 7.69; O, 15.92; Si, 4.66

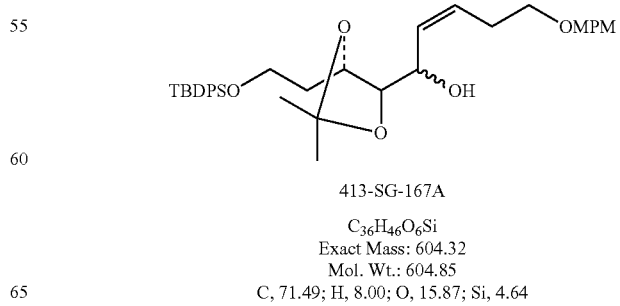

413-SG-167A
C$_{36}$H$_{46}$O$_6$Si
Exact Mass: 604.32
Mol. Wt.: 604.85
C, 71.49; H, 8.00; O, 15.87; Si, 4.64

Using a procedure analogous to that described for the synthesis of intermediate 554-RB-241, 413-SG-110B (1.4 g, 2.27 mmol) was dissolved in hexane (32 mL) and hydrogenated using Lindlar catalyst to afford 413-SG-167A (1.4 g). 413-SG-169B

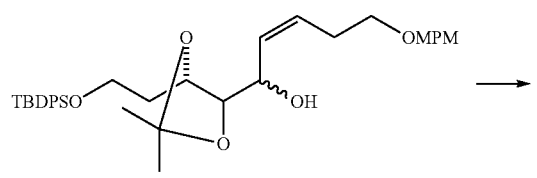

413-SG-167A $C_{36}H_{48}O_8Si$
Exact Mass: 604.32
Mol. Wt.: 604.85
C, 71.49; H, 8.00; O, 15.87; Si, 4.64

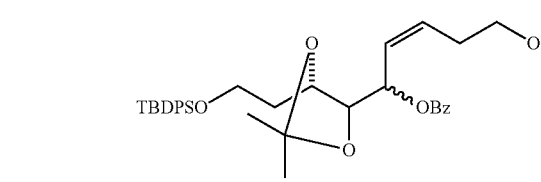

413-SG-169B $C_{43}H_{52}O_7Si$
Exact Mass: 708.35
Mol. Wt.: 708.95
C, 72.85; H, 7.39; O, 15.80; Si, 3.96

(?) indicates text missing or illegible when filed

Using a procedure analogous to that described for the synthesis of 554-RB-242, 413-SG-167A (1.37 g, 2.27 mmol) was reacted with benzoyl chloride (0.53 mL, 4.54 mmol), triethylamine (0.79 mL, 5.68 ml) and a catalytic amount of DMAP in dichloromethane (12 mL). The crude product was purified by flash chromatography eluting with hexane/ethyl acetate (3/1) to afford 413-SG-169B (1.58 g, 99% yield).
413-SG-169B

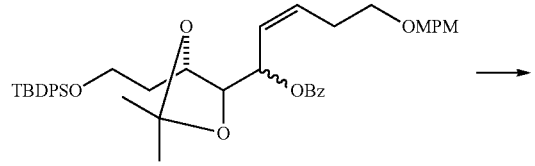

413-SG-169B $C_{43}H_{52}O_7Si$
Exact Mass: 708.35
Mol. Wt.: 708.95
C, 72.85; H, 7.39; O, 15.80; Si, 3.96

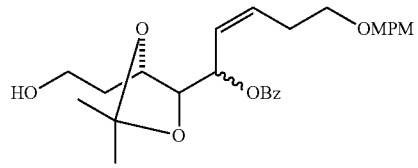

413-SG-170B $C_{27}H_{34}O_7$
Exact Mass: 470.23
Mol. Wt.: 470.55
C, 68.92; H, 7.28; O, 23.80

413-SG-169B (1.58 g, 2.22 mmol) was reacted with TBAF (0.88 g, 3.34 mmol) in THF (6 mL) at room temperature. The reaction mixture was diluted with water and extracted with ethyl ether. The crude product was purified by flash chromatography eluting with hexane/ethyl acetate (5/1 and then 1/1) to afford 413-SG-169B (1.02 g, 98% yield).

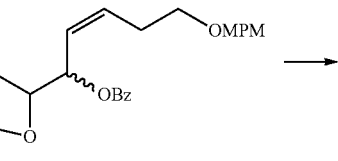

413-SG-170B $C_{27}H_{34}O_7$
Exact Mass: 470.23
Mol. Wt.: 470.55
C, 68.92; H, 7.28; O, 23.80

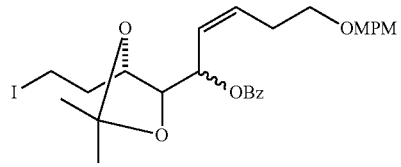

413-SG-173B $C_{27}H_{33}IO_6$
Exact Mass: 580.13
Mol. Wt.: 580.45
C, 55.87; H, 5.73; I, 21.86; O, 16.54

Using a procedure analogous to that described for the synthesis of 554-RB-260, 413-SG-170B (1.02 g, 2.17 mmol) was reacted with triphenylphosphine (0.97 g, 3.69 mmol), DEAD (0.36 mL, 2.28 mmol) and methyl iodide (0.175 mL, 2.82 mmol) in toluene (19 mL). The crude product was purified by flash chromatography eluting with hexane/ethyl acetate (9/1 and then 5/1) to afford 413-SG-163B (1.12 g, 98% yield).

413-SG-174B

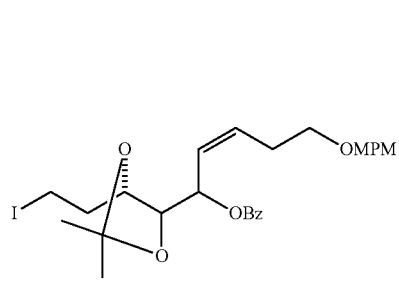

413-SG-173B
C$_{27}$H$_{33}$IO$_6$
Exact Mass: 580.13
Mol. Wt.: 580.45
C, 55.87; H, 5.73; I, 21.66; O, 16.54

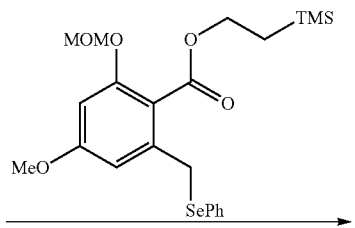

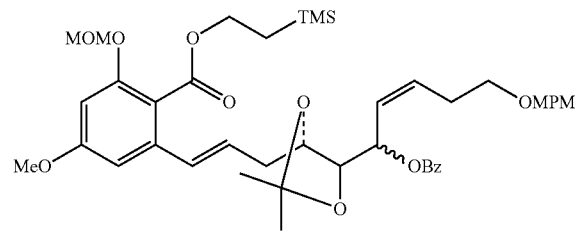

412-SG-174B
C$_{43}$H$_{56}$O$_{11}$Si
Exact Mass: 776.36
Mol. Wt.: 776.58
C, 66.47; H, 7.26; O, 22.65; Si, 3.61

Using a procedure analogous to that described for the synthesis of 531-YW-4, 413-SG-173B (1.12 g, 1.93 mmol) was reacted with intermediate 509-HD-213 (1.2 g, 2.51 mmol) and LiHMDS (1M solution in THF, 2.3 mL, 2.3 mmol) in a 10 to 1 THF/HMPA mixture (17.3 mL) to afford 413-SG-174A. 413-SG-174A (crude) was reacted with MCPBA (0.61 g, 1.93 mmol) and triethylamine (1.6 mL, 11.6 mmol). The crude product was purified by flash chromatography eluting with hexane/ethyl acetate (5/1 and then 3/1) to afford 413-SG-174B (0.895 g, 45% yield).

413-SG-177B

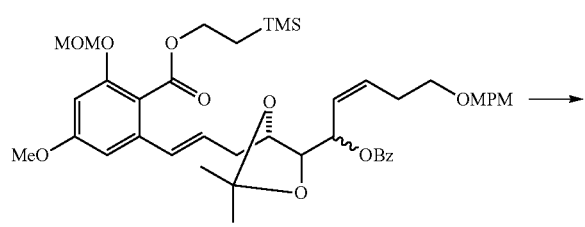

412-SG-174B
C$_{43}$H$_{50}$O$_{11}$Si
Exact Mass: 776.38
Mol. Wt.: 776.95
C, 68.47; H, 7.26; O, 22.65; Si, 3.61

-continued

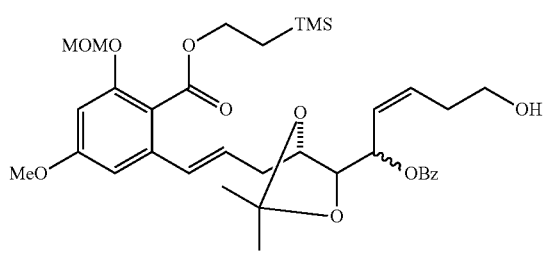

412-SG-177B
C$_{43}$H$_{56}$O$_{11}$Si
Exact Mass: 656.30
Mol. Wt.: 656.84
C, 64.00; H, 7.37; O, 24.38; Si, 4.28

Using a procedure analogous to that described for the synthesis of 453-MS-262, 413-SG-174B (0.89 g, 1.14 mmol) was reacted with DDQ (0.31 g, 1.37 mmol) in a 2/1-dichloromethane/water mixture (48 mL). The crude product was purified by flash chromatography eluting with hexane/ethyl acetate (5/1 and then 3/1) to afford 413-SG-177B (0.454 g, 61% yield).

413-SG-179B

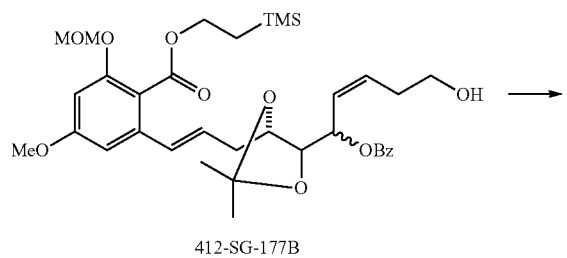

412-SG-177B
C$_{35}$H$_{48}$O$_{10}$Si
Exact Mass: 656.30
Mol. Wt.: 656.84
C, 64.00; H, 7.37; O, 24.38; Si, 4.28

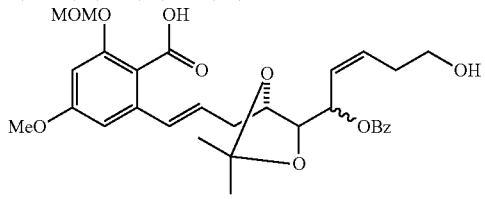

412-SG-179B
C$_{30}$H$_{34}$O$_{9}$
Exact Mass: 556.23
Mol. Wt.: 556.60
C, 64.74; H, 6.52; O, 28.74

Using a procedure analogous to that described for the synthesis of ER-803064 (stage 509-HD-116), 413-SG-177B (0.45 g, 0.691 mmol) was reacted with TBAF (0.542 g, 2.07 mmol) in THF (2.2 ml). The crude product was purified by flash chromatography with dichloromethane/methanol: (95/5) to afford 413-SG-179B (0.31 g, 79% yield).

413-SG-180B

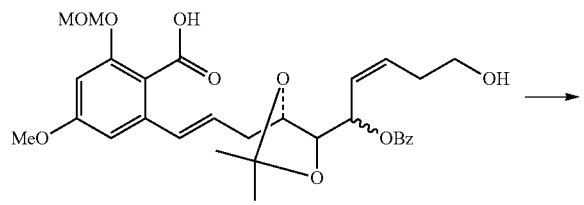

412-SG-179B
C$_{30}$H$_{36}$O$_{10}$
Exact Mass: 556.23
Mol. Wt.: 556.60
C, 64.74; H, 8.52; O, 28.74

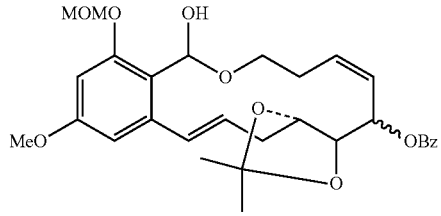

413-SG-180B
C$_{30}$H$_{34}$O$_{9}$
Exact Mass: 538.22
Mol. Wt.: 538.59
C, 66.90; H, 6.36; O, 28.74

413-SG-179B (0.31 g, 0.54 mmol) was reacted with triphenylphosphine (0.175 g, 0.658 mmol) and DEAD (0.105 ml, 0.658 mmol) in THF (43 ml). The crude product was purified by flash chromatography with hexane/ethyl acetate: (3/1) to afford 413-SG-180B (0.2 g, 69% yield).

413-SG-182A

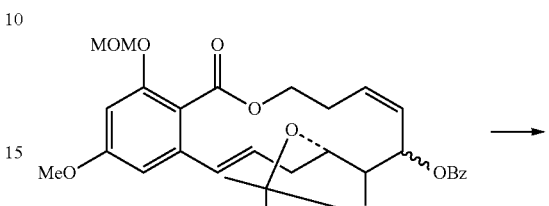

413-SG-180B
C$_{30}$H$_{36}$O$_{9}$
Exact Mass: 540.24
Mol. Wt.: 540.60
C, 66.65; H, 6.71; O, 26.64

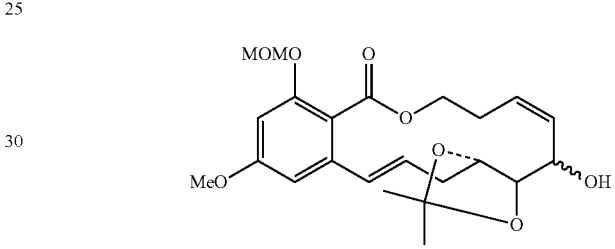

413-SG-182A
C$_{23}$H$_{30}$O$_{6}$
Exact Mass: 434.19
Mol. Wt.: 434.48
C, 63.58; H, 6.96; O, 29.46

Using a procedure analogous to that described for the synthesis of ER-803064 (stage 509-HD-119), 413-SG-180B (0.18 g, 0.334 mmol) was reacted with sodium hydroxide (1M solution, 1.7 mL, 1.7 mmol) in a 2/1 mixture ethanol/THF (10 mL) to afford 413-SG-182A (0.16 g). The crude product was used for the next step without further purification.

413-SG-188B

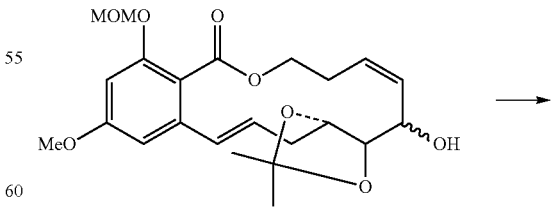

413-SG-182A
C$_{23}$H$_{30}$O$_{8}$
Exact Mass: 434.19
Mol. Wt.: 434.48
C, 63.58; H, 6.96; O, 29.46

-continued

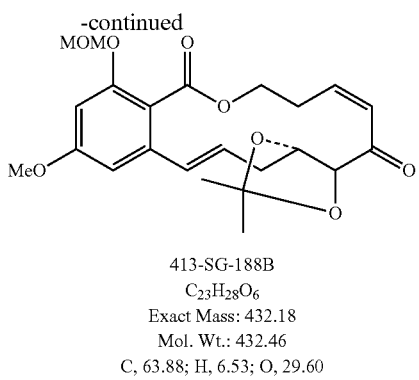

413-SG-188B
C₂₃H₂₈O₆
Exact Mass: 432.18
Mol. Wt.: 432.46
C, 63.88; H, 6.53; O, 29.60

Using a procedure analogous to that described for the synthesis of ER-803064 (stage 509-HD-125), 413-SG-182A (0.14 g, 0.32 mmol) was reacted with PCC (0.84 g, 3.87 mmol) in dichloromethane (34 mL) with molecular sieves 4 Å (800 mg). The crude product was purified by flash chromatography with hexane/ethyl acetate: (70/30) to afford 413-SG-188B (0.07 g, 52% yield).

413-SG-93B

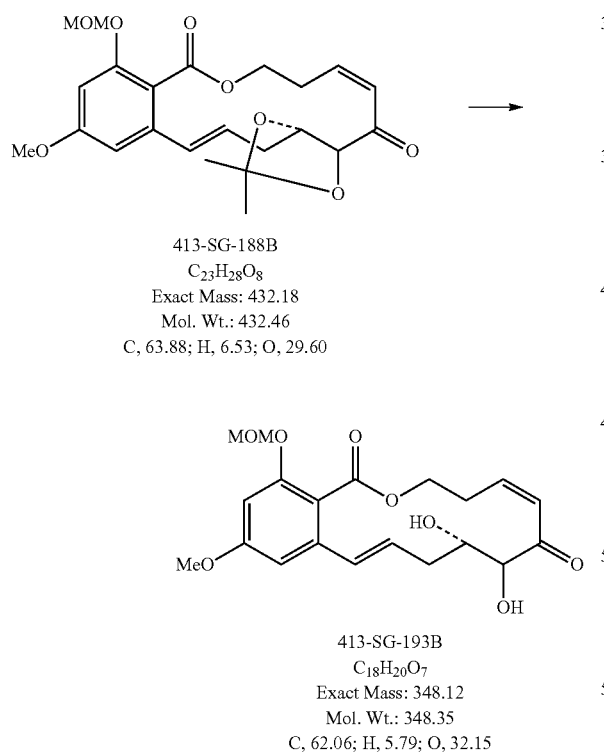

413-SG-188B
C₂₃H₂₈O₈
Exact Mass: 432.18
Mol. Wt.: 432.46
C, 63.88; H, 6.53; O, 29.60

413-SG-193B
C₁₈H₂₀O₇
Exact Mass: 348.12
Mol. Wt.: 348.35
C, 62.06; H, 5.79; O, 32.15

Using a procedure analogous to that described for the synthesis of ER-803064 (final step), 413-SG-188B (0.067 g, 0.157 mmol) was reacted with HF (6 M solution in acetonitrile, 17.7 ml) in dichloromethane (3.1 ml). The crude product was purified by flash chromatography with hexane/ethyl acetate: (60/40) to afford 413-SG-193B/B-2329 (0.05 g, 91% yield).

Preparation of B2395:

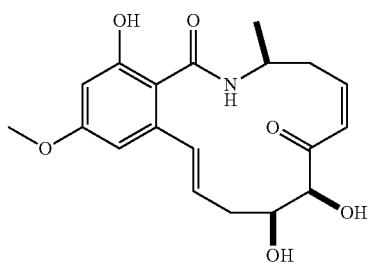

413-SG-184B

412-SG-178A
C₃₆H₅₀O₁₀Si
Exact Mass: 670.32
Mol. Wt.: 670.86
C, 64.45; H, 7.51; O, 23.85; Si, 4.19

412-SG-184B
C₃₇H₅₂O₁₂SSi
Exact Mass: 748.29
Mol. Wt.: 748.95
C, 59.34; H, 7.00; O, 25.83; S, 4.28; Si, 3.75

To a magnetically stirred solution of 413-SG-178B (0.194 g, 0.289 mmol) and triethylamine (0.08 mL, 0.578 mmol) in dry dichloromethane cooled to 0° C. (ice/water; external thermometer) was introduced methanesulfonyl chloride (0.034 ml, 0.434 mmol). After 1 hour of stirring at 0° C. a saturated aqueous solution of sodium bicarbonate was added. The reaction mixture was diluted with water and extracted with dichloromethane. The crude was purified on silica gel (Hexane/EtOAc: 1/1) to afford 413-SG-184B (0.215 g, 99% yield).

413-SG-185B

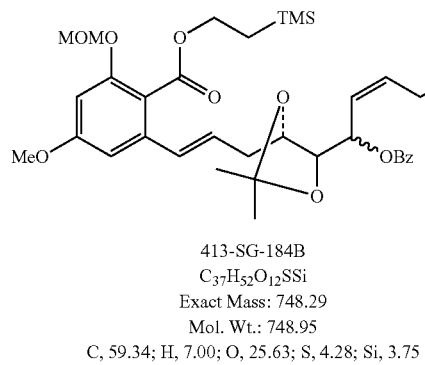

413-SG-184B
C₃₇H₅₂O₁₂SSi
Exact Mass: 748.29
Mol. Wt.: 748.95
C, 59.34; H, 7.00; O, 25.63; S, 4.28; Si, 3.75

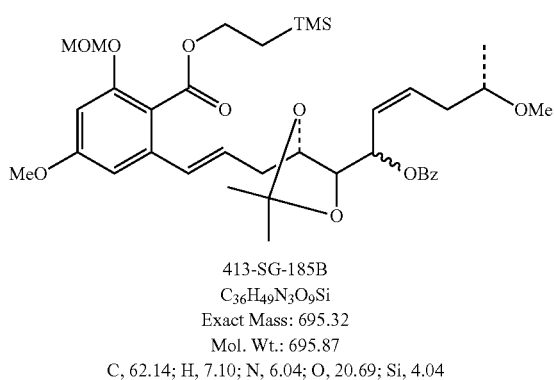

413-SG-185B
C₃₆H₄₉N₃O₉Si
Exact Mass: 695.32
Mol. Wt.: 695.87
C, 62.14; H, 7.10; N, 6.04; O, 20.69; Si, 4.04

A solution of 413-SG-184B (0.216 g, 0.288 mmol), sodium azide (0.028 g, 0.432 mmol) and catalytic amount of tetra-butyl ammonium iodide in DMF was magnetically stirred at 85° C. After 90 minutes the reaction mixture was concentrated under vacuum. The crude was purified on silica gel (Hexane/EtOAc: 5/1) to afford 413-SG-185B (0.086 g, 93% yield)

413-SG-186A

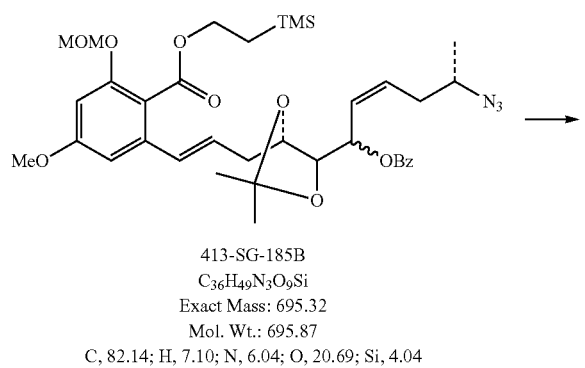

413-SG-185B
C₃₆H₄₉N₃O₉Si
Exact Mass: 695.32
Mol. Wt.: 695.87
C, 82.14; H, 7.10; N, 6.04; O, 20.69; Si, 4.04

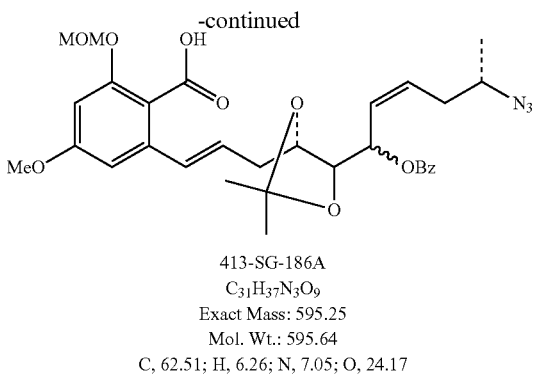

413-SG-186A
C₃₁H₃₇N₃O₉
Exact Mass: 595.25
Mol. Wt.: 595.64
C, 62.51; H, 6.26; N, 7.05; O, 24.17

Using a procedure analogous to that described for the synthesis of ER-803064 (stage 509-HD-116), 413-SG-185B (0.19 g, 0.27 mmol) was reacted with TBAF (0.21 g, 0.8 mmol) in THF (1 ml) to afford 413-SG-186A (0.14 g). The crude product was used in the next step without purification.

413-SG-217A

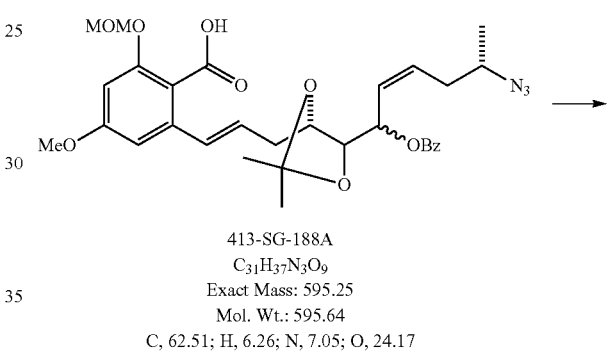

413-SG-188A
C₃₁H₃₇N₃O₉
Exact Mass: 595.25
Mol. Wt.: 595.64
C, 62.51; H, 6.26; N, 7.05; O, 24.17

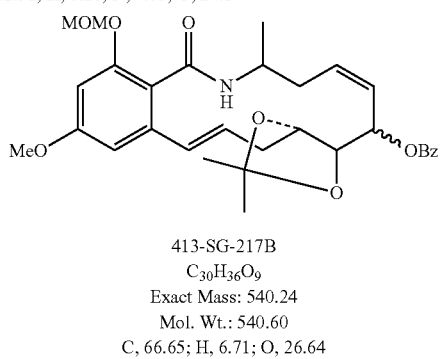

413-SG-217B
C₃₀H₃₆O₉
Exact Mass: 540.24
Mol. Wt.: 540.60
C, 66.65; H, 6.71; O, 26.64

To a magnetically stirred solution of 413-SG-186A (0.092 g, 0.156 mmol) in THF/water 4/1 (1.5 mL) at room temperature was introduced trimethylphosphine (0.78 mL, 0.778 mmol). After 18 hours of stirring at room temperature the reaction mixture was concentrated under vacuum. The residue was diluted with water and extracted with dichloromethane to afford 413-SG-217A. The crude was dried and used in the next step without purification.

To a magnetically stirred solution of 413-SG-217A (0.156 mmol) in dichloromethane (0.2 mL) at room temperature was introduced EDC (0.10 mg, 0.504 mmol). After 4 hours of stirring at room temperature the reaction mixture was Concentrated under vacuum. The crude was purified on silica gel (Hexane/EtOAc: 1/1) to afford 413-SG-217B (0.036 g, 42% yield).

413-SG-221A

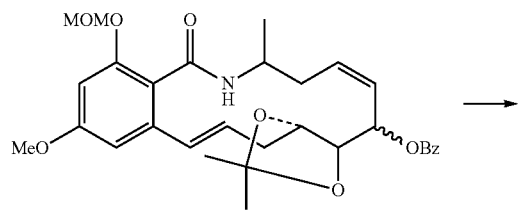

413-SG-217B
C30H36O9
Exact Mass: 540.24
Mol. Wt.: 540.60
C, 66.65; H, 6.71; O, 26.64

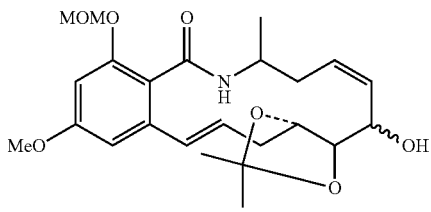

413-SG-221A
C24H33NO7
Exact Mass: 447.23
Mol. Wt.: 447.52
C, 64.41; H, 7.43; N, 3.13; O, 25.03

Using a procedure analogous to that described for the synthesis of ER-803064 (stage 509-HD-119), 413-SG-217B (0.036 g, 0.065 mmol) was reacted with sodium hydroxide (1M solution, 0.3 mL, 0.3 mmol) in a 2/1 mixture of ethanol/THF (2 mL) to afford 413-SG-221A (0.031 g). The crude product was used for the next step without further purification.

413-SG-226A

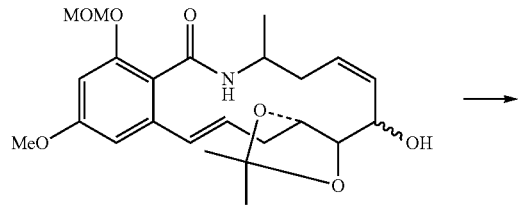

413-SG-221A
C24H33NO7
Exact Mass: 447.23
Mol. Wt.: 447.52
C, 64.41; H, 7.43; N, 3.13; O, 25.03

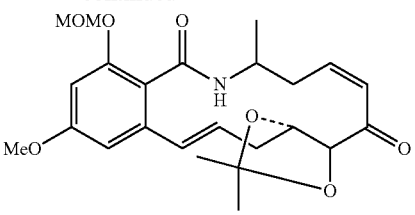

413-SG-226A
C24H31NO7
Exact Mass: 445.21
Mol. Wt.: 445.51
C, 64.70; H, 7.01; N, 3.14; O, 25.14

Using a procedure analogous to that described for the synthesis of ER-803027 (stage 447-JCH-295), 413-SG-221A (0.014 g, 0.031 mmol) was reacted with Dess-Martin reagent (80 mg, 0.188 mmol) and 2,6-lutidine (0.036 mL, 0.313 mmol) in dichloromethane (2.1 mL). The crude was purified on silica gel (dichloromethane/methanol: 98/2) to afford 413-SG-226A (0.005 g, 36% yield).

413-SG-235B

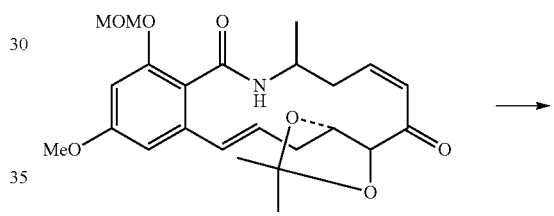

413-SG-226A
C24H31NO7
Exact Mass: 445.21
Mol. Wt.: 445.51
C, 64.70; H, 7.01; N, 3.14; O, 25.14

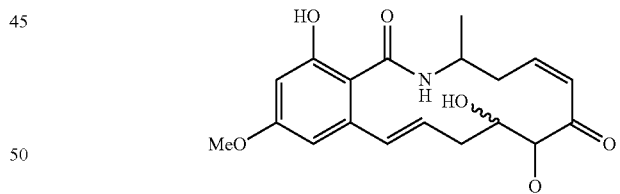

413-SG-235B
C19H23NO6
Exact Mass: 361.15
Mol. Wt.: 361.39
C, 63.15; H, 6.41; N, 3.88; O, 26.56

Using a procedure analogous to that described for the synthesis of ER-803064 (final step), 413-SG-226AB (0.01 g, 0.022 mmol) was reacted with HF (1.5 M solution in acetonitrile, 5 mL) in dichloromethane (2 mL). The crude product was purified by flash chromatography eluting with n-hexane/ethyl acetate: (3/1) to afford 413-SG-235B (0.004 g, 50% yield).

Preparation of C8-Deoxy Analogs, NF0530, NF0531, NF0552 and NF0761

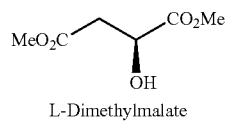

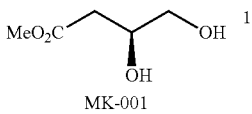

L-Dimethylmalate (50 g, 308.4 mmol) was dissolved in dry THF (308 mL) and cooled to 0° C. Then BH$_3$-Me$_2$S complex (10M, 1.1 eq., 34 mL, 0.34 mol) was added dropwise and then the mixture was allowed to warm to rt. After stirred for 90 min then re-cooled to 0° C., NaBH$_4$ (0.05 eq., 15.4 mmol, 583 mg) was added and stirred for additional 60 min. The reaction was quenched with MeOH, and concentrated under reduced pressure. The crude residue was purified by chromatography on silica gel (AcOEt/MeOH) to afford MK-001 (26 g, 63%).

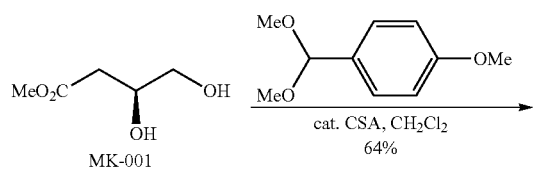

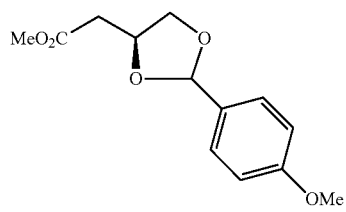

To a solution of MK-001 (10.0 g, 74.6 mmol) and p-anisaldehyde dimethyl acetal (16.5 mL, 96.9 mmol) in 150 mL of dry CH$_2$Cl$_2$ was added DL-10-CSA (35 mg, 0.15 mmol) at 0° C., then the reaction mixture was allowed to warm to rt gradually. After 1 day 0.042 mL of Et$_3$N was added then evaporated. The crude product was purified by chromatography on silica gel (Hexane/AcOEt: 5/1 to 3/1) to afford MK-002 (12.1 g, 64%).

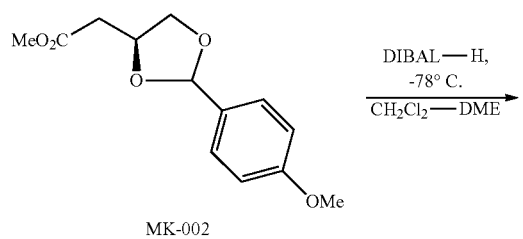

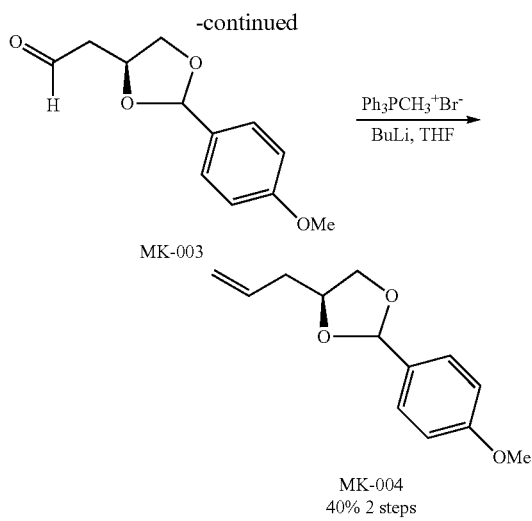

MK-002 (12.1 g, 48.0 mmol) was dissolved in dry CH$_2$Cl$_2$-DME (240 mL-240 mL) and cooled to −78° C. Then DIBAL-H in hexane (1.0 M, 50.4 mL, 50.4 mmol) was added dropwise over 30 min and the mixture was stirred for additional 100 min at −78° C. The reaction was quenched with MeOH (6 mL) then poured into a stirred solution of AcOEt and aqueous saturated Na/K tartrate. The organic extract was washed with brine, dried over Na$_2$SO$_4$, filtered and concentrated to afford crude oil of MK-003 (11.84 g), which was used for next step without purification.

Ph$_3$PCH$_3$$^+$Br$^-$ (34.3 g, 96.0 mmol) was dissolved in dry THF (320 mL). The mixture was cooled to 0° C., and n$^-$BuLi in hexane (1.6 M, 51.0 mL, 81.6 mmol) was added slowly. After stirring for 120 min, a solution of the crude MK-003 (11.84 g) in 50 mL of dry THF was added slowly. The reaction was stirred for 30 min at 0° C. and followed by overnight at rt, then quenched with saturated aqueous solution of NH$_4$Cl. The mixture was extracted with AcOEt, washed with brine, dried over MgSO$_4$, filtered and concentrated to give crude oil. The crude oil was diluted with Et$_2$O-hexane, the generated precipitate was filtered off, then the filtrate was evaporated. The residual oil was purified by chromatography on silica gel (Hexane/AcOEt: 20/1 to 8/1) to afford oil of MK-004 (4.25 g, 40% 2 steps).

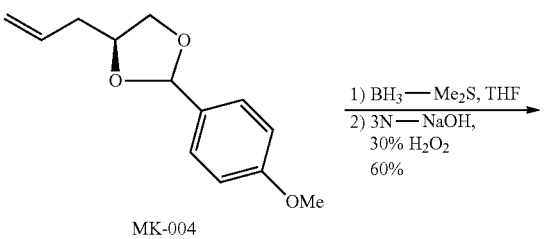

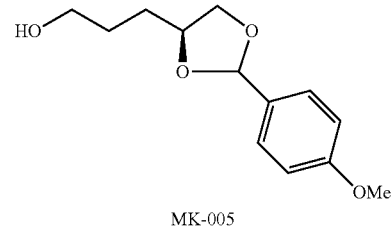

To a solution of MK-004 (4.05 g, 18.4 mmol) in 92 mL of dry THF was slowly added BH$_3$-Me$_2$S (2.0 M in THF, 4.60 mL, 9.2 mmol) at 0° C., then the reaction mixture was stirred at 0° C. for 90 min after which it was allowed to warm to it and stirred for 120 min. The solution was re-cooled to 0° C., then treated with aqueous 3N—NaOH (28 mL) and aqueous 30%-H$_2$O$_2$ (28 mL) with vigorous stirring. The mixture was extracted with Et$_2$O, washed with saturated aqueous solution of Na$_2$SO$_3$, dried over MgSO$_4$, filtered and concentrated to gave crude oil. The crude oil was purified by chromatography on silica gel (Hexane/AcOEt: 1/1 to 2/3) to afford oil of MK-005 (2.64 g, 60%).

Using similar procedure for the synthesis of the TBS-ether, intermediate of TM-03, from 491-HAD-46, MK-005 (2.64 g, 11.1 mmol) was converted to crude MK-006 (3.91 g). It was used for next step without purification.

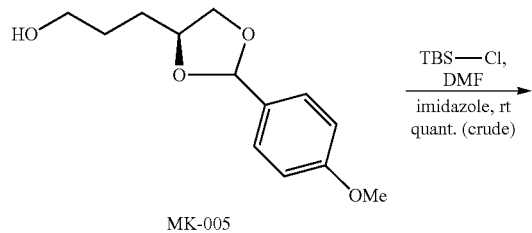

MK-005

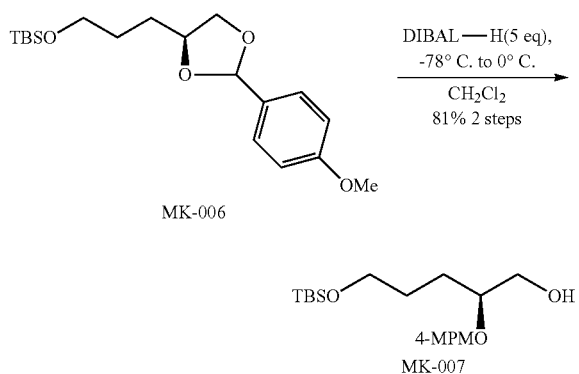

MK-006

MK-007

MK-006 (3.91 g) was dissolved in 74 mL of dry CH$_2$Cl$_2$ and cooled to −78° C. DIBAL-H in hexane (1.0 M, 5 eq., 55.3 mL, 55.3 mmol) was added dropwise over 30 min, and the solution was stirred at −78° C. for additional 60 min after which it was allowed to warm to 0° C. over 50 min. The reaction was quenched with MeOH (7 mL) then poured into a stirred solution of AcOEt and saturated aqueous Na/K tartrate. The organic extract was washed with brine, dried over Na$_2$SO$_4$, filtered and concentrated to give a crude oil. The crude oil was purified by chromatography on silica gel (Hexane/AcOEt: 3/1) to afford an oil, MK-007 (3.19 g, 81% 2 steps).

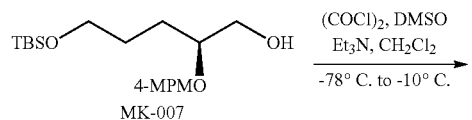

MK-007

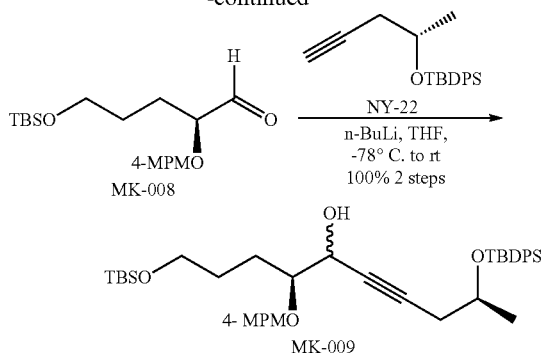

To a solution of (COCl)$_2$ (3 eq., 2.24 mL, 25.6 mmol) in 84 mL of dry CH$_2$Cl$_2$, DMSO (6 eq., 3.64 mL, 51.3 mmol) was added slowly at −78° C. After 15 min at −78° C., a solution of MK-007 (3.03 g, 8.55 mmol) was added dropwise into the reaction at −78° C. After 30 min at that temperature, Et$_3$N (9 eq., 10.7 mL, 76.9 mmol) was added slowly. The reaction mixture was allowed to warm to −10° C. gradually. It was quenched with saturated aqueous solution of NH$_4$Cl, extracted with AcOEt-hexane, washed with aqueous solution of KHSO$_4$ then brine, dried over Na$_2$SO$_4$, filtered and concentrated to gave crude oil of MK-008 (3.52 g). It was used for next step without purification.

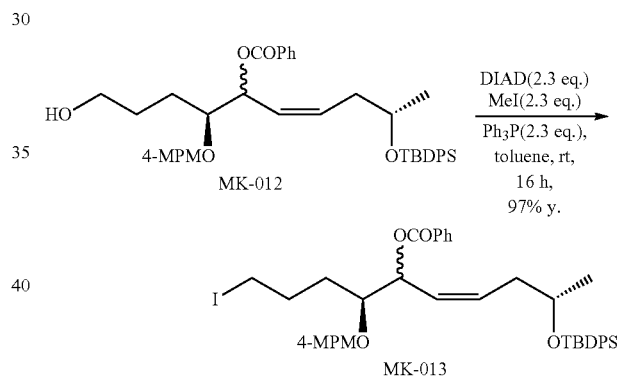

Using similar procedure for the synthesis of TM-04 from TM-03 and TM-02, MK-008 (3.52 g) was coupled with NY-22 (6.06 g) and then converted to pure MK-009 (5.76 g, 100% 2 steps) as mixture of diastereomers on propargylic position.

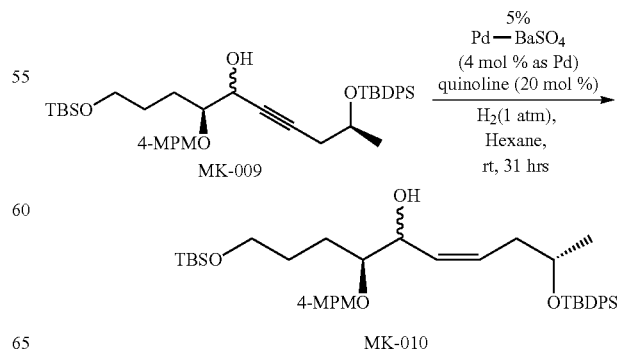

Using similar procedure for the synthesis of TM-05 from TM-04, MK-009 (5.75 g) was converted to crude MK-010 (6.11 g) as mixture of diastereomers on allylic position.

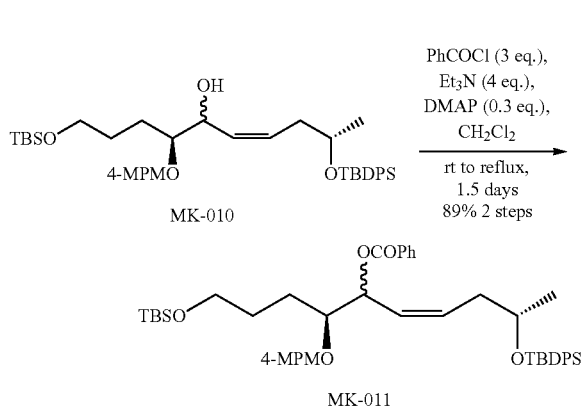

Using similar procedure for the synthesis of 554-RB-242 from 554-RB-241, crude MK-010 (6.11 g) was converted to pure MK-011 (5.93 g, 89% 2 steps) as mixture of diastereomers on allylic position.

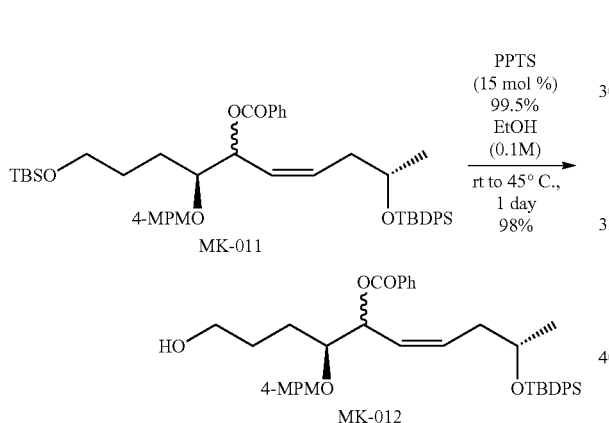

To a stirred solution of MK-011 (5.93, 7.59 mmol) in 76 mL of 99.5% EtOH, PPTS (0.15 eq., 286 mg, 1.14 mmol) was added at rt, then the mixture was warmed to 45° C. After 1 day it was diluted with AcOEt, then washed with saturated aqueous solution of NaHCO$_3$ and brine, dried over MgSO$_4$, filtered and concentrated to give crude oil. The crude oil was purified by chromatography on silica gel (Hexane/AcOEt: 2/1) to afford oil of MK-012 (4.94 g, 98%).

Using similar procedure for the synthesis of 554-RB-260 from 554-RB-244, MK-012 (4.20 g, 6.30 mmol) reacted with DIAD and methyl iodide in the presence of Ph$_3$P to give pure MK-013 (4.74 g, 97%) as mixture of diastereomers on allylic position.

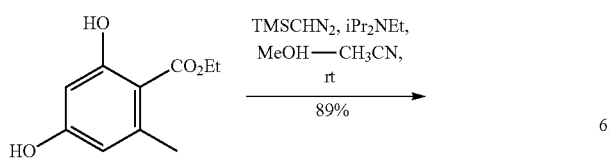

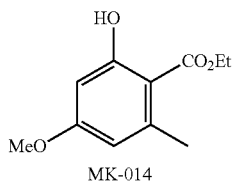

To a stirred mixture of diphenol (13.0 g, 66.3 mmol), MeOH (6.2 mL, 152 mmol), and iPr$_2$EtN (13.9 mL, 79.5 mmol) in 110 mL of CH$_3$CN, TMSCHN$_2$ in hexane (2M, 38.1 mL, 76.2 mmol) was added dropwise over 80 min at rt, then stirred overnight. The reaction was quenched with 5% citric acid aqueous solution and extracted with AcOEt. The organic extract was washed with saturated aqueous solution of NaHCO$_3$ and brine, dried over MgSO$_4$, filtered and concentrated. The crude product was purified by chromatography on silica gel (Hexane/AcOEt: 9/1) to afford crystals of MK-014 (12.4 g, 89%).

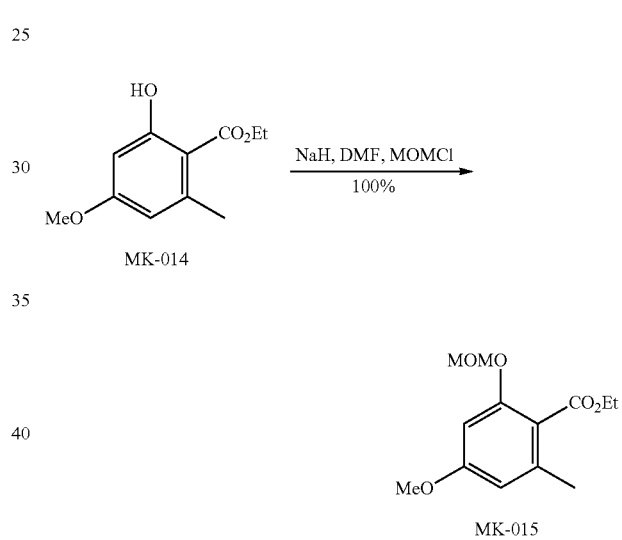

Using similar procedure for the synthesis of 509-HD-209 from 509-HD-207, MK-014 (5.2 g, 25 mmol) was converted to pure MK-015 (6.3 g, 100%).

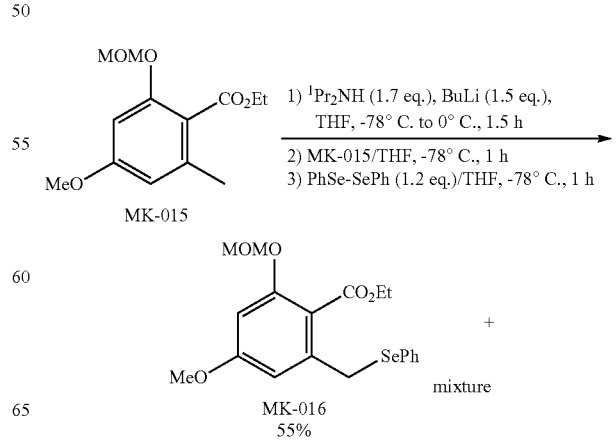

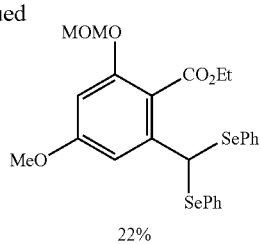

22%

Using similar procedure for the synthesis of 509-HD-211 from 509-HD-209, MK-015 (6.0 g, 23.5 mmol) was converted to a mixture of MK-016 (5.3 g, 55%) and inseparable diselenide (2.9 g, 22%)

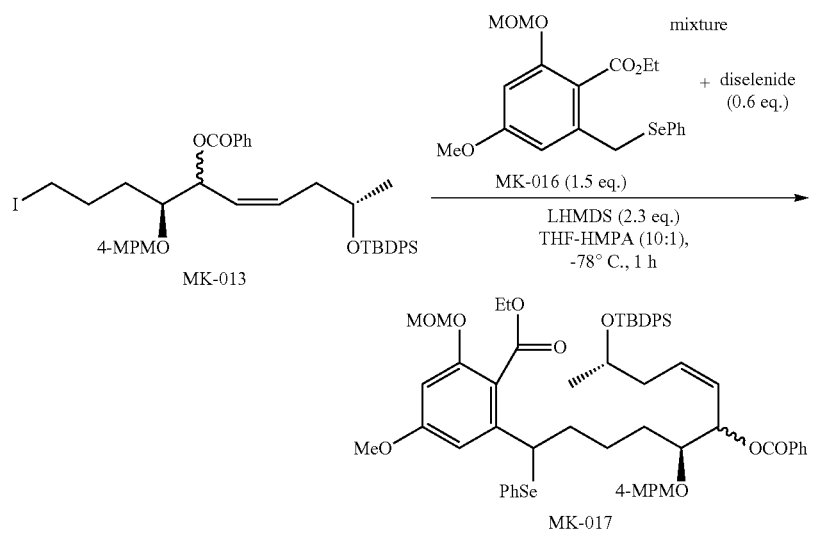

Using similar procedure for the synthesis of compound 4 from compound 2 and compound 3, MK-013 (1.5 g, 1.93 mmol) was coupled with mixture of MK-016 and diselenide (including 2.90 mmol of MK-016) to afford crude oil of MK-017 (4.3 g). It was used for next step without purification.

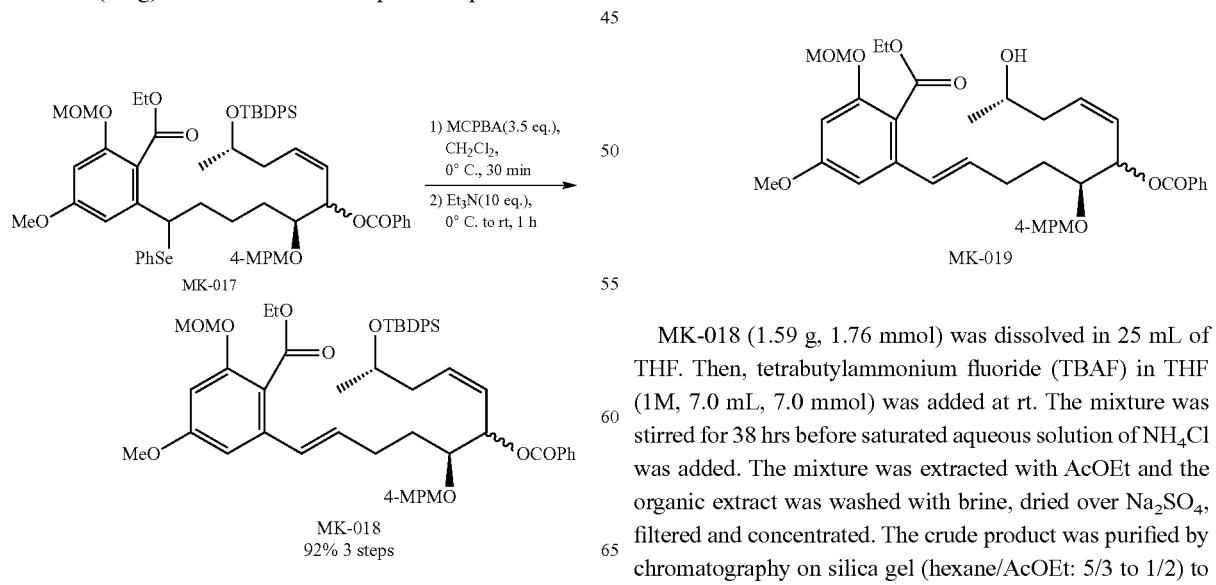

Using similar procedure for the synthesis of compound 5 from compound 4, crude MK-017 (4.3 g) was converted to MK-018 (1.60 g, 92% 3 steps) as compound purified.

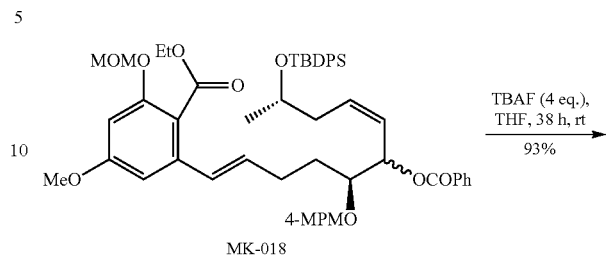

-continued

MK-018 (1.59 g, 1.76 mmol) was dissolved in 25 mL of THF. Then, tetrabutylammonium fluoride (TBAF) in THF (1M, 7.0 mL, 7.0 mmol) was added at rt. The mixture was stirred for 38 hrs before saturated aqueous solution of $NH_4Cl$ was added. The mixture was extracted with AcOEt and the organic extract was washed with brine, dried over $Na_2SO_4$, filtered and concentrated. The crude product was purified by chromatography on silica gel (hexane/AcOEt: 5/3 to 1/2) to afford oil of MK-019 (1.10 g, 93%).

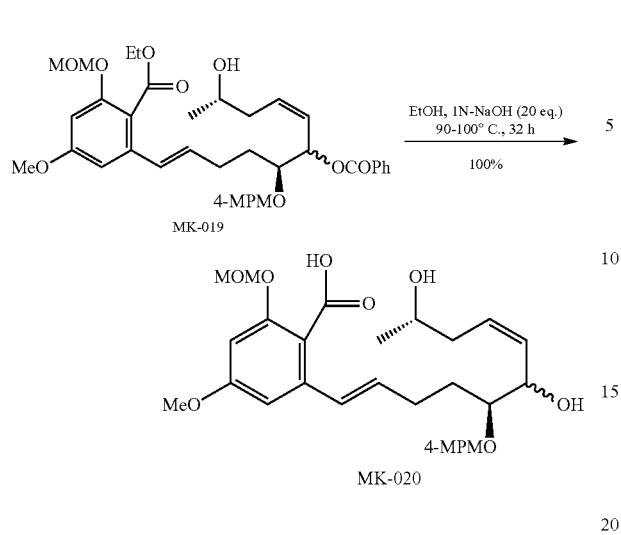

To a stirred solution of MK-019 (1.07 g, 1.61 mmol) in 20 mL of EtOH was added 32 mL of aqueous 1N—NaOH, then the mixture was warmed to 100° C. After 32 hrs, it was quenched with 32 mL of aqueous 1N—HCl and extracted with AcOEt. The organic extract was washed with brine, dried over $Na_2SO_4$, filtered and concentrated. The crude product was purified by chromatography on silica gel (AcOEt/MeOH: 9/1) to afford oil of MK-020 (860 mg, 100%).

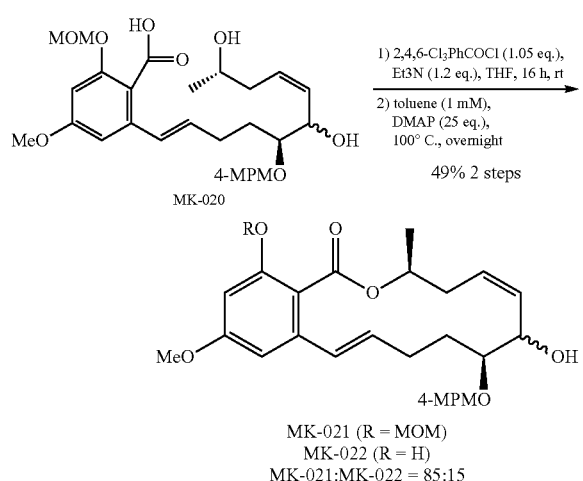

Using similar procedure for the synthesis of TM-12 from TM-11, MK-020 (860 mg, 1.61 mmol) was converted to mixture of MK-021 and MK-022 (402 mg, 49% 2 steps; MK-021: MK-022=85:15).

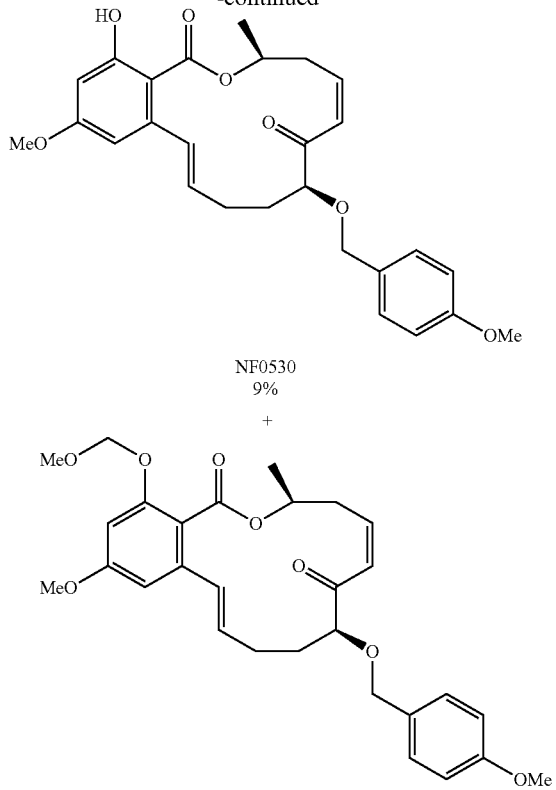

To a stirred suspension of Dess-Martin periodinane (1.01 g, 2.38 mmol) in 40 mL of dry $CH_2Cl_2$, a solution of MK-021 and MK-022 (402 mg, 0.794 mmol) in 40 mL of dry $CH_2Cl_2$ was added at 0° C., then the mixture was warmed to rt. After 14 hrs it was re-cooled to 0° C., diluted with AcOEt, washed with saturated aqueous solution of $Na_2SO_3$, $NaHCO_3$ and brine, dried over $Na_2SO_4$, filtered and concentrated to give crude oil. The crude oil was purified by chromatography on silica gel (Hexane/AcOEt: 3/1) to afford colorless crystals of NF0552 (301 mg, 74%) and colorless oil of NF0530 (35 mg, 9%).

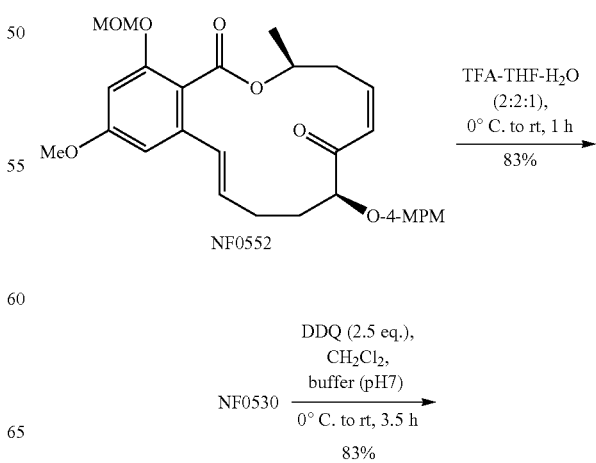

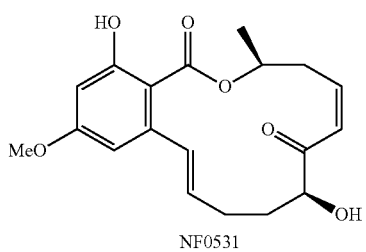

Using similar procedure for the synthesis of NF0675 from TM-13, NF0552 (263 mg, 0.515 mmol) was converted to NF0530 (199 mg, 83%) as compound purified.

To a stirred mixture of NF0530 (233 mg, 0.499 mmol) in 17 mL of $CH_2Cl_2$ and 1.7 mL of aqueous phosphate buffer (pH 6.86) was portionwise added DDQ (283 mg, 1.25 mmol) at 0° C., then the mixture was allowed to warm to rt slowly. After 3.5 hrs it was quenched with aqueous solution of $NaHCO_3$ and diluted with AcOEt. The organic extract was washed with aqueous solution of $NaHCO_3$ and brine, dried over $Na_2SO_4$, filtered and concentrated. The crude product was purified by chromatography on silica gel (hexane/AcOEt: 5/2) to afford colorless crystals of NF0531 (143 mg, 83%).

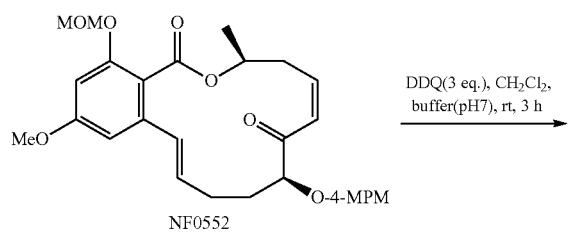

NF0552 (30 mg, 0.059 mmol) was treated with DDQ (3 eq.) at rt using similar procedure for the synthesis of NF0531 from NF0530. The messy reaction was worked up in the usual manner. Purification by chromatography on silica gel (Hexane/AcOEt: 1/3) gave colorless oil of NF0761 (1.7 mg, 7%). NF0761 was analyzed by HRMS; FAB+ m/z 407 (MH+), Anal. Calcd for C21H26O8: MH+, 407.1706. Found 407.1711 (MH+).

Preparation of C11-C12, cyclopropyl analogs, NF1226 and NF1227

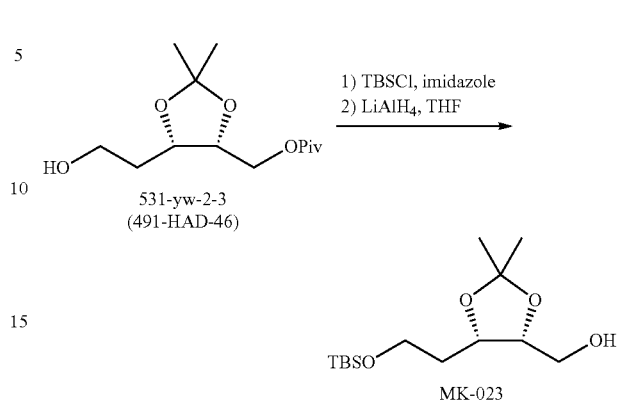

Using the same procedure for the synthesis of TM-03 from 531-yw-2-3 (491-HAD-46), MK-023 was obtained.

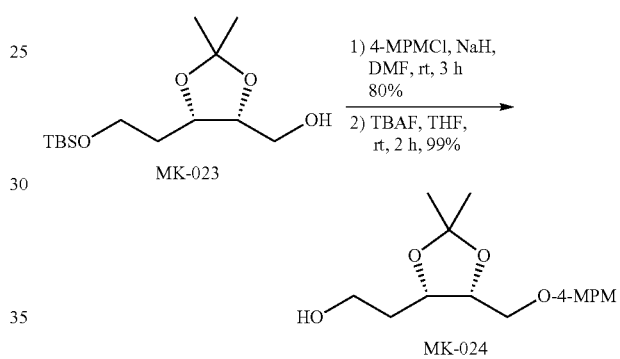

To a stirred mixture of MK-023 (2.5 g, 8.61 mmol) and 4-MPMCl (1.63 mL, 12.0 mmol) in 40 mL of DMF, NaH (66%, 344 mg, 9.47 mmol) was added portionwise at 0° C. and the mixture was warmed to rt. After stirred for 3 hrs, the reaction was quenched with saturated aqueous solution of $NH_4Cl$ and extracted with AcOEt. The organic extract was washed with saturated aqueous solution of $NaHCO_3$ and brine, dried over $Na_2SO_4$, filtered and concentrated. The crude product was purified by chromatography on silica gel (Hexane/AcOEt: 15/1) to afford colorless oil of the fully protected tetraol (2.83 g, 80%).

The fully protected tetraol (3.11 g, 7.58 mmol) was dissolved in 38 mL of THF. Then, tetrabutylammonium fluoride (TBAF) in THF (1M, 9.9 mL, 9.9 mmol) was added at rt. The mixture was stirred for 2 hrs before saturated aqueous solution of $NH_4Cl$ was added. The mixture was extracted with AcOEt and the organic extract was washed with brine, dried over $Na_2SO_4$, filtered and concentrated. The crude product was purified by chromatography on silica gel (Hexane/AcOEt: 1/1) to afford oil of MK-024 (2.22 g, 99%).

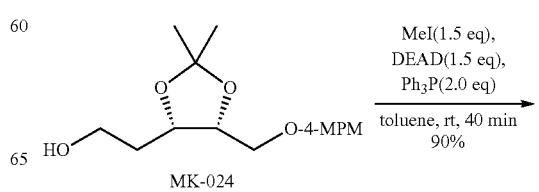

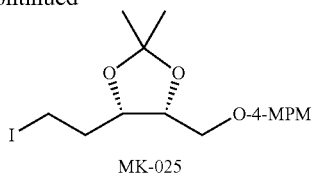

Using similar procedure for the synthesis of 531-YW-3 from 531-YW-2-3, MK-024 (1.90 g, 6.41 mmol) was converted to MK-025 (2.36 g, 90%) as compound purified.

To a stirred solution of MK-026 (2.0 g, 3.32 mmol) in 130 mL of toluene were added Et$_2$Zn in hexane (1M, 16.6 mL, 16.6 mmol) and CH$_2$I$_2$ (1.34 mL, 16.6 mmol) at −30° C. After stirred for 30 min at −30° C., it was warmed to it gradually over 2 hrs and then quenched with saturated aqueous solution of NH$_4$Cl. (Note: To avoid decomposition of target product, short reaction time, 1-2 hrs, was required regardless of conversion rate.). The mixture was extracted with AcOEt and the organic extract was washed with brine, dried over Na$_2$SO$_4$, filtered and concentrated. The crude product was purified by chromatography on silica gel (Hexane/AcOEt: 6/1 to 5/1) to afford oil of MK-027 (369 mg, <19%) including small

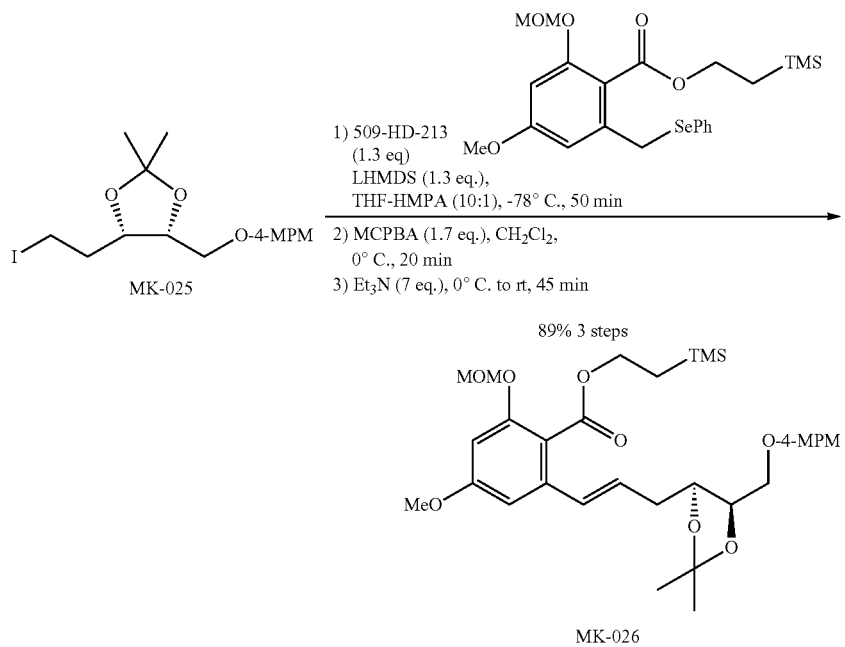

Using similar procedure for the synthesis of 531-YW-4, MK-025 (2.36 g, 5.80 mmol) coupled with 509-HD-213 (3.63 g, 7.54 mmol) was converted to MK-026 (3.10 g, 89% 3 steps) as compound purified.

amount of MK-026, and MK-026 (519 mg, <26%) including small amount of MK-027 was recovered. The recovered MK-026 was treated again in the same manner to give MK-027 (367 mg, <29%) including small amount of MK-026. Trans cyclopropane MK-027 was obtained as mixture of inseparable stereoisomers (1:1).

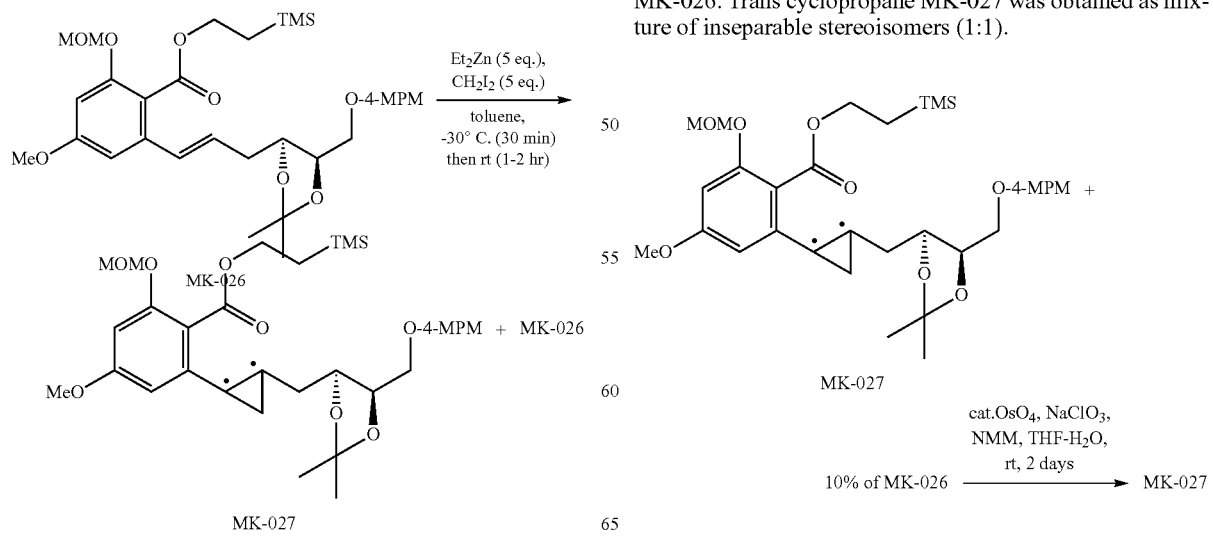

MK-027 (736 mg, ca 1.19 mmol) including 10% of MK-026 was dissolved in 24 mL of THF and 4 mL of water.

OsO₄ in ᵗBuOH (3 w/v %, 0.05 eq., 0.51 mL, 0.06 mmol), N-methylmorpholine (0.2 eq., 0.026 mL, 0.24 mmol) and NaClO₃ (0.4 eq., 51 mg, 0.48 mmol) were added into the stirred solution at rt. After 2 days, to the mixture were added Celite, AcOEt, and aqueous solution of Na₂SO₃. The suspension was filtered, and the filtrate was washed with brine, dried over Na₂SO₄, filtered and concentrated to give crude oil of MK-027 (768 mg) which included no MK-026. It was used for next step without purification.

Using similar procedure for the synthesis of NF0531 from NF0530, the crude oil of MK-027 (768 mg) was converted to MK-028 (523 mg, 88% 2 steps) as compound purified.

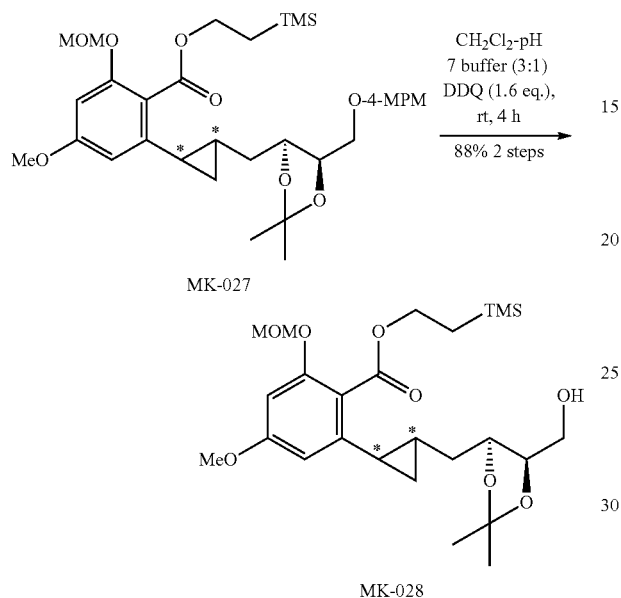

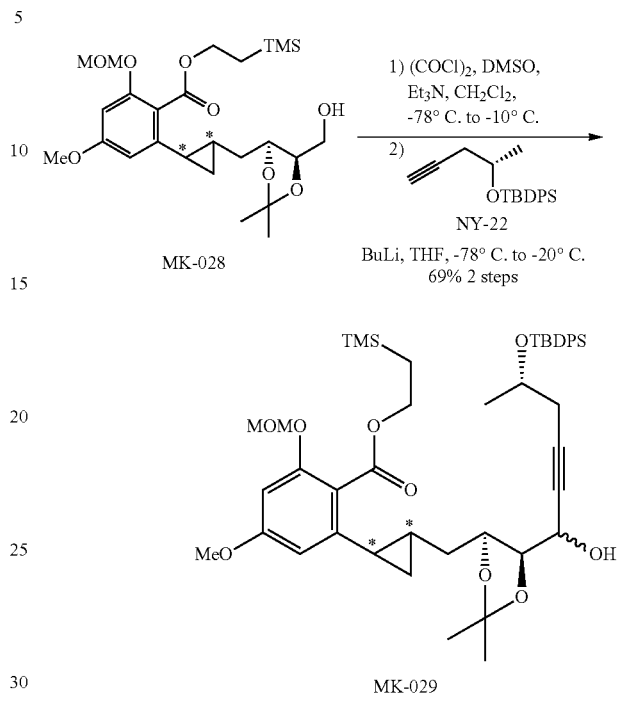

Using similar procedure for the synthesis of MK-009 from MK-007, MK-028 (204 mg, 0.411 mmol) was converted to MK-029 (231 mg, 69% 2 steps) as compound purified.

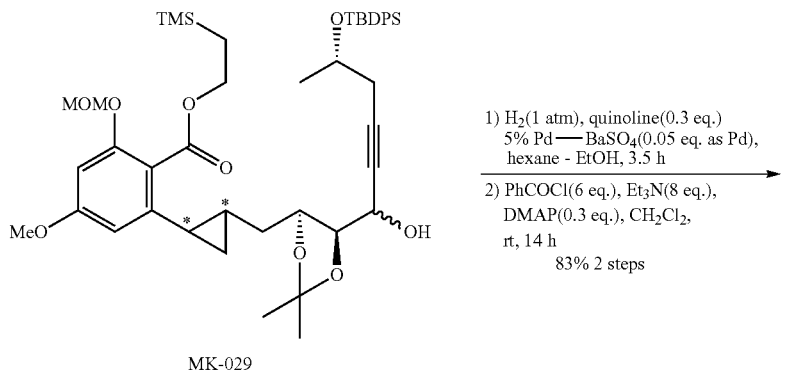

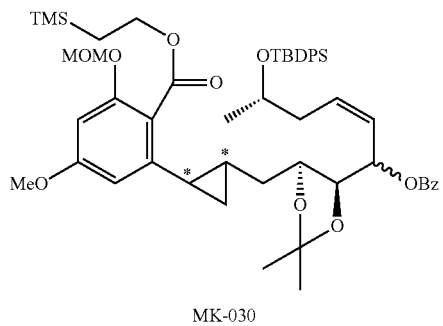

MK-029 (231 mg, 0.283 mmol) was dissolved in 7 mL of 99.5% EtOH and 7 mL of hexane (note: no reaction in hexane). Then, quinoline (0.3 eq., 0.01 mL, 0.085 mmol) and 5% Pd—BaSO$_4$ on carbon (0.05 eq., 30 mg, 0.014 mmol) were added. H$_2$ balloon was mounted and the mixture was purged with H$_2$. After stirred for 3.5 hrs under H$_2$ (1 atm) at rt, the reaction mixture was filtered through Celite and the filtrate was evaporated to give a crude oil of cis-olefin (240 mg).

Using similar procedure for the synthesis of 554-RB-242 from 554-RB-241, the crude cis-olefin (240 mg) was converted to MK-030 (216 mg, 83% 2 steps) as compound purified.

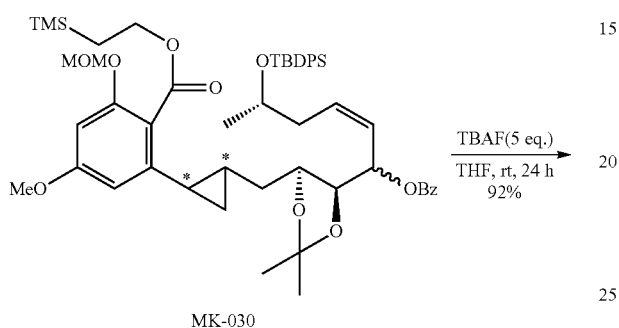

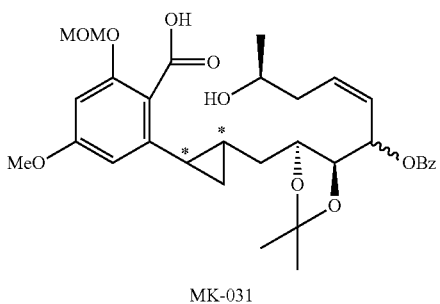

Using similar procedure for the synthesis of MK-019 from MK-018, MK-030 (215 mg, 0.233 mmol) was directly converted to a carboxylic acid MK-031 (125 mg, 92%) as compound purified.

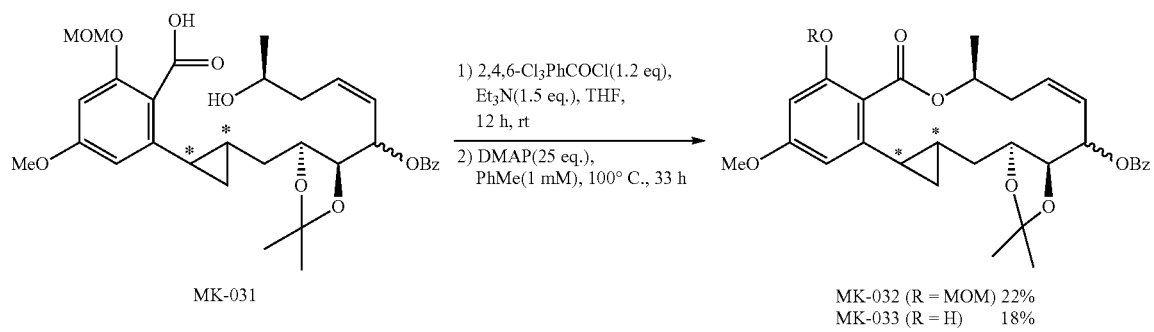

Using similar procedure for the synthesis of TM-12 from TM-11, MK-031 (123 mg, 0.210 mmol) was converted to crude lactonized product. It was purified by chromatography on silica gel (Hexane/AcOEt: 4/1, 3/1, to 1/1) to afford oil of MK-032 (27 mg, 22%) and oil of des-MOM form MK-033 (20 mg, 18%).

-continued

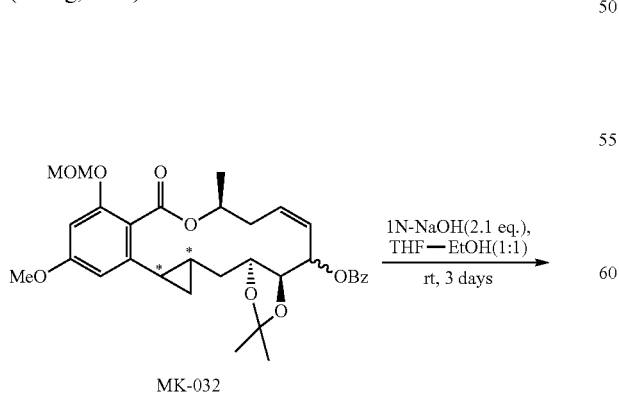

To a stirred solution of MK-032 (24 mg, 0.0424 mmol) in 0.85 mL of EtOH and 0.85 mL of THF was added aqueous 1N NaOH (2.1 eq., 0.089 mL, 0.0889 mmol). After stirred for 3 days at rt, the mixture was diluted with AcOEt and washed with brine, dried over Na$_2$SO$_4$, filtered and concentrated to give crude product of MK-034 (24 mg). It was used for next step without purification.

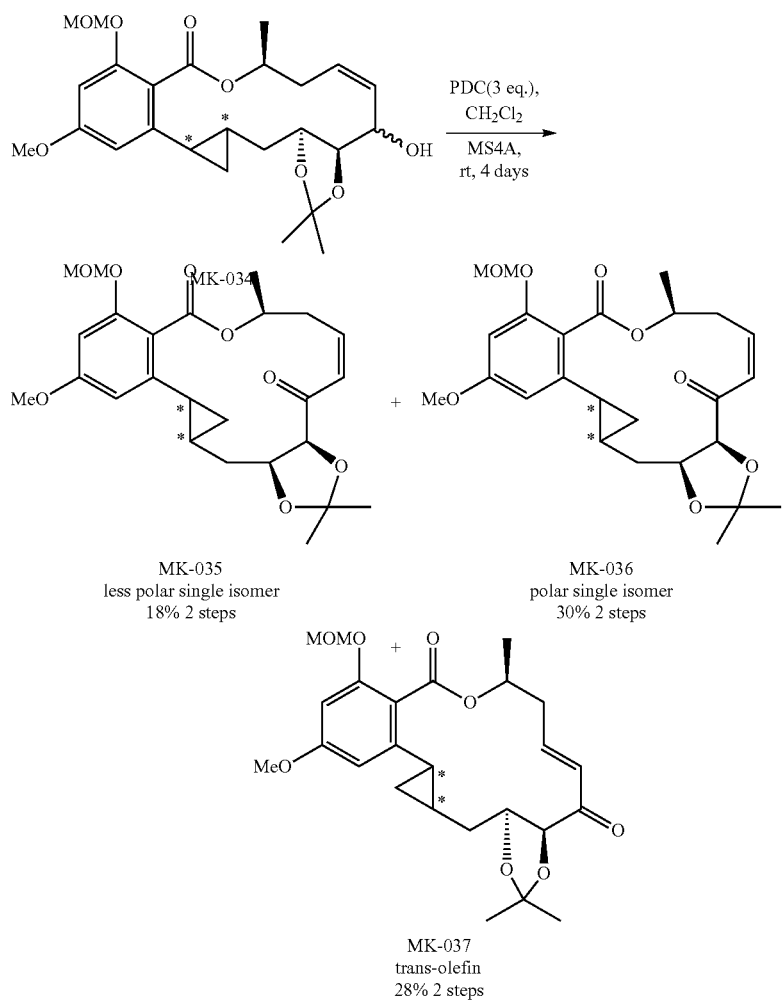

The crude MK-034 (24 mg, assumed to contain 0.0424 mmol) was dissolved in 9 mL of CH$_2$Cl$_2$. To the solution were added Molecular sieve 4A (45 mg) and PDC (3 eq., 48 mg, 0.127 mmol) at rt. The reaction mixture was stirred for 4 days at rt, then diluted with Et$_2$O and passed through a pad of Celite. The filtrate was evaporated to give crude product. It was purified by chromatography on silica gel (Hexane/AcOEt: 3/1 to 2/1) to afford colorless oil of MK-035 (less polar single isomer on trans cyclopropane, 3.6 mg, 18% 2 steps), colorless oil of MK-036 (polar single isomer on trans cyclopropane, 5.8 mg, 30% 2 steps) and pale yellow oil of MK-037 (isomerized trans olefin, 5.4 mg, 28% 2 steps).

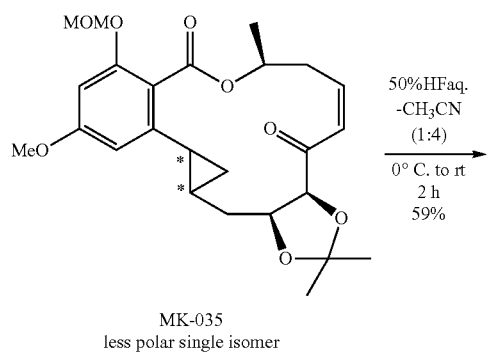

-continued

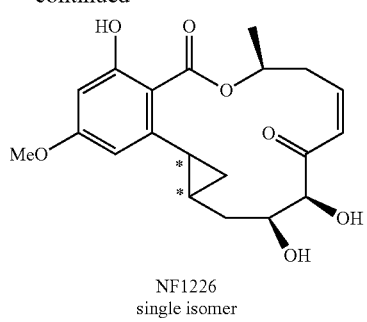

50% Hydrofluoric acid (24N, 0.2 mL) was added to less polar isomer MK-035 (3.6 mg, 0.00782 mmol) in 0.8 mL of CH$_3$CN and stirred for 1 hr at 0° C. After stirred at rt for additional 1 hr, the reaction mixture was quenched with saturated aqueous solution of NaHCO$_3$ and extracted with AcOEt. The organic extract was washed with brine, dried over MgSO$_4$, filtered and concentrated to crude product. It was purified by chromatography on silica gel (hexane/AcOEt: 1/2) to afford colorless crystals of NF1226 (2.3 mg, 59%) as single isomer.

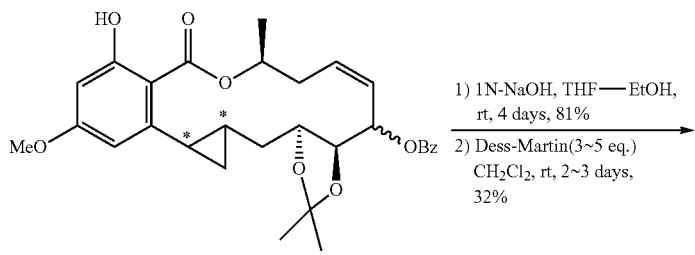

MK-033

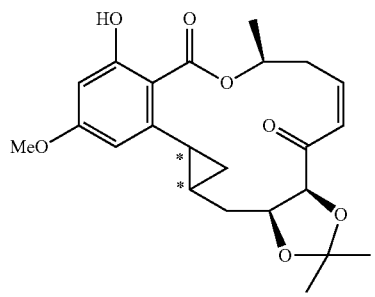

MK-038

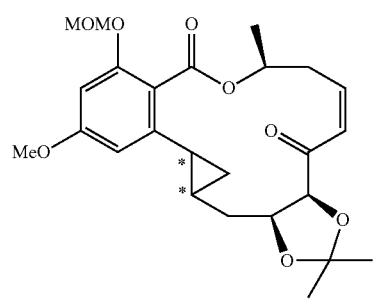

MK-036
polar single isomer

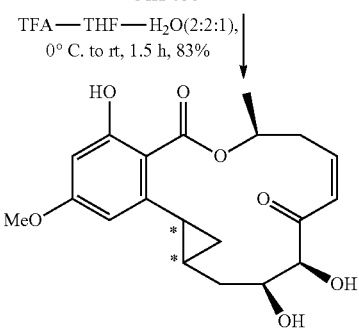

NF1227
single isomer

Using similar procedure for the synthesis of MK-034 from MK-032, MK-033 (20 mg, 0.0383 mmol) was converted to diol intermediate (13 mg, 81%).

Using similar procedure for the synthesis of NF530 from MK-022, the diol intermediate (15 mg, 0.0358 mmol) was converted to MK-038 (4.7 mg, 32%).

Using similar procedure for the synthesis of NF0675 from TM-13, MK-038 (4.8 mg, 0.0115 mmol) was converted to colorless crystals of NF1227 (3.6 mg, 83%, single isomer).

Using similar procedure for the synthesis of NF1226 from MK-035, polar isomer MK-036 (5.8 mg, 0.0126 mmol) was converted to colorless crystals of NF1227 (2.6 mg, 55%, single isomer).

NF1227 differs from NF1226 as to stereochemistry on trans cyclopropane.

Preparation of C11-C12 Amide Analogs, NF1535, NF1537, and NF2306

Exemplary Synthetic Procedure for NF1535 and NF1537

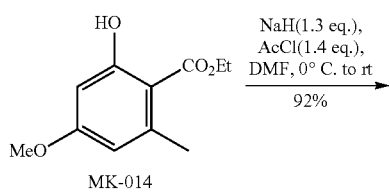

MK-014

-continued

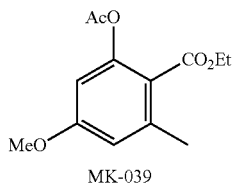

MK-039

Using similar procedure for the synthesis of NY-07 from NY-06, MK-014 (12.40 g, 59.0 mmol) was converted to MK-039 (13.68 g, 92%) and purified.

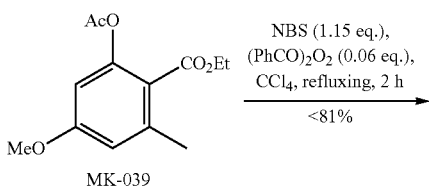

MK-039

MK-040

MK-039 (13.68 g, 54.2 mmol) was dissolved in 360 mL of $CCl_4$ and the solution was heated up to reflux. To the stirred solution was portionwise (over 1.5 hrs) added a mixture of NBS (11.1 g, 62.4 mmol, 1.15 eq.) and $(PhCO)_2O_2$ (722 mg, 2.98 mmol, 0.055 eq.) and stirred for additional 30 min at reflux. The reaction mixture was cooled to rt and insoluble material was filtered off, then the filtrate was concentrated to give crude product. The crude product was purified by chromatography on silica gel (hexane/AcOEt: 4/1 to 3/1) to afford colorless oil of MK-040 (14.51 g, <81%) including small amount of starting material and dibromide. It was used for next step without further purification.

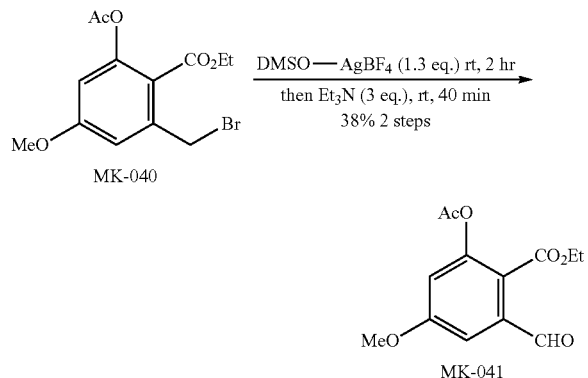

To a solution of MK-040 (14.51 g, assumed to contain 43.82 mmol) in 220 mL of DMSO was added a solution of AgBF$_4$ (11.09 g, 57.0 mmol) in 55 mL of DMSO at rt. After 2 hrs, Et$_3$N (18.3 mL, 131.4 mmol) was added and stirred for 40 min at rt. The reaction mixture was diluted with AcOEt, then washed with saturated aqueous solution of NaHCO$_3$ and brine, dried over Na$_2$SO$_4$, filtered and concentrated to give a crude oil. The crude product was purified by chromatography on silica gel (hexane/AcOEt: 3/1 to 1/1) to afford colorless oil of MK-041 (5.49 g, 38% 2 steps).

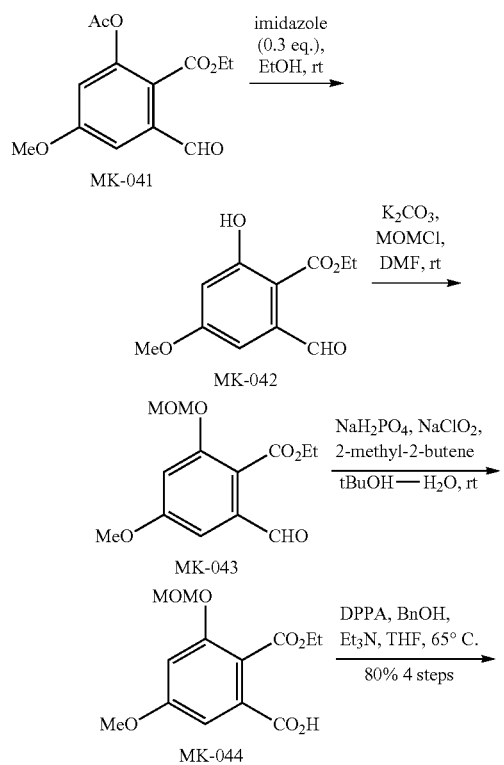

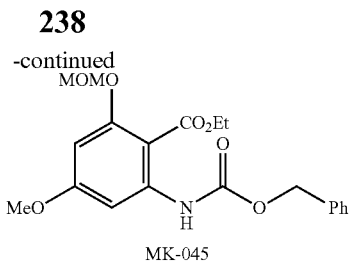

To a stirred mixture of MK-041 (5.49 g, 20.63 mmol) in 140 mL of 99.5% EtOH was added imidazole (421 mg, 6.19 mmol) at rt. After stirred for 6 days, the mixture was evaporated, diluted with AcOEt, washed with water then brine, dried over Na$_2$SO$_4$, filtered and concentrated to give crude colorless crystals of MK-042 (4.42 g, <96%). It was used for next step without purification.

To a stirred suspension of crude MK-042 (2.41 g, assumed to contain 10.75 mmol) and K$_2$CO$_3$ (3.94 g, 28.5 mmol) in 70 mL of DMF was added MOMCl (1.77 mL, 23.3 mmol) at 0° C., then the mixture was allowed to warm to rt. After 14 hrs, the reaction mixture was quenched with saturated aqueous solution of NaHCO$_3$ and extracted with AcOEt. The organic extract was washed with brine, dried over Na$_2$SO$_4$, filtered and concentrated to give crude oil of MK-043 (2.93 g, quant.). It was used for next step without purification.

Crude MK-043 (2.93 g, assumed to contain 10.75 mmol) was dissolved in 80 mL of t-BuOH and 20 mL of water. Then 2-methyl-2-butene (5.69 mL, 53.7 mmol, 5 eq.) and NaH$_2$PO$_4$·2H$_2$O (1.68 g, 10.75 mmol) were added. To the stirred suspension was portionwise added NaClO$_2$ (1.94 g, 21.5 mmol, 2 eq.) at rt. After 1 hr at rt, the mixture was diluted with AcOEt and water, then acidified with aqueous KHSO$_4$ solution to approximately pH 4. The organic extract was washed with brine, dried over Na$_2$SO$_4$, filtered and concentrated to give crude oil of MK-044 (3.20 g, quant.). It was used for next step without purification.

Crude MK-044 (3.20 g, assumed to contain 10.75 mmol) was dissolved in 72 mL of dry THF and 4.45 mL of BnOH (43.00 mmol, 4 eq.). Then Et$_3$N (1.80 mL, 12.90 mmol, 1.2 eq.) and DPPA (2.54 mL, 11.82 mmol, 1.1 eq.) were added. The mixture was heated to 65° C. and stirred for 15 hrs, then cooled to rt. The mixture was diluted with AcOEt and saturated aqueous solution of NH$_4$Cl. The organic extract was washed with saturated aqueous solution of NaHCO$_3$ then brine, dried over Na$_2$SO$_4$, filtered and concentrated to give a crude oil. The crude product was purified by chromatography on silica gel (hexane/AcOEt: 5/1) to afford colorless crystals of MK-045 (3.50 g, 80% 4 steps).

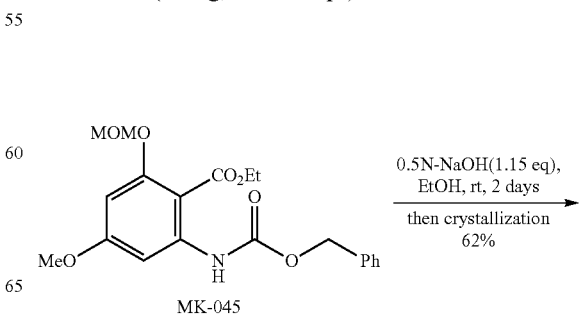

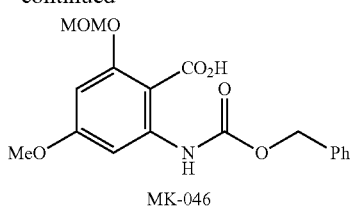

MK-046

To a stirred solution of MK-045 (2.73 g, 7.02 mmol) in 80 mL of EtOH was added aqueous 0.5N—NaOH (1.15 eq., 16.2 mL, 8.07 mmol). After stirred for 2 days at rt the reaction mixture was cooled to 0° C., quenched with aqueous 0.2N HCl (1.15 eq., 40.3 mL, 8.07 mmol) and diluted with water (40 mL) to produce a precipitation. The precipitation was filtered, washed with hexane-AcOEt (15 mL-2 mL) and dried under reduced pressure to afford pure colorless crystals of MK-046 (1.58 g, 62%).

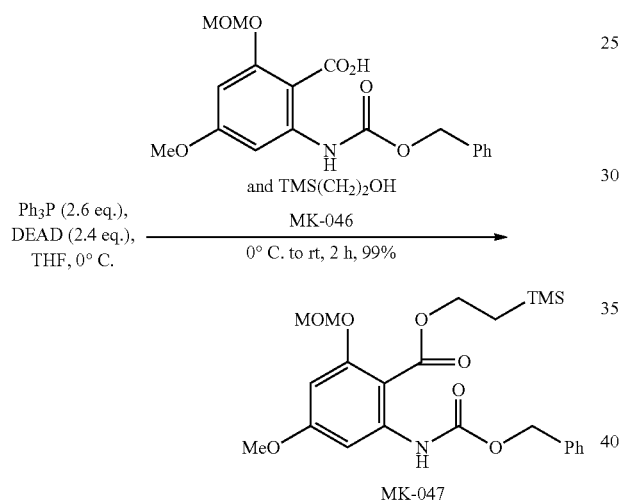

Ph$_3$P (2.98 g, 11.37 mmol, 2.6 eq.) was dissolved in 30 mL of dry THF and cooled to 0° C. 40% DEAD in toluene (4.76 mL, 10.49 mmol, 2.4 eq.) was added and stirred for 30 min at 0° C. To the stirred solution was dropwise added a mixture of MK-046 (1.58 g, 4.37 mmol) and 2-(trimethylsilyl)ethanol (0.94 mL, 6.56 mL, 1.5 eq.) in 25 mL of THF at 0° C. After 30 min, the reaction mixture was warmed up to it gradually over 1 hr. The resulting mixture was evaporated and purified by chromatography on silica gel (hexane/AcOEt: 6/1 to 5/1) to afford oil of MK-047 (2.01 g, 99%).

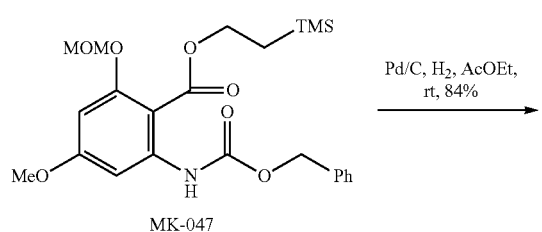

MK-047

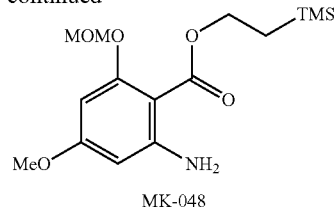

MK-048

MK-047 (2.01 g, 4.35 mmol) was dissolved in 60 mL of AcOEt. Then 10% Pd/C (50% wet, 200 mg) was added. H$_2$ balloon was mounted and the mixture was purged with H$_2$ (1 atm). After stirred overnight at rt it was worked up in usual manner and purified by chromatography on silica gel (hexane/AcOEt: 6/1 to 5/1) to afford colorless crystals of MK-048 (1.20 g, 84%).

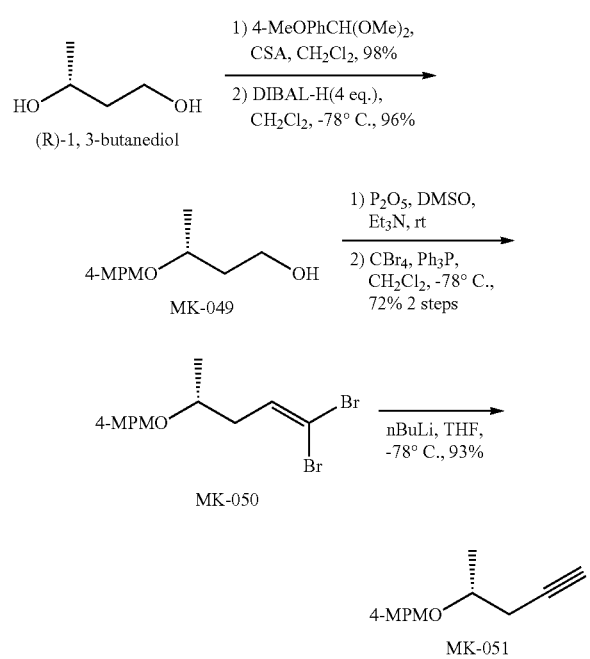

Using similar procedure for the synthesis of 343-YW-203 from (S)-1,3-butanediol, (R)-1,3-butanediol (9.80 g, 108.7 mmol) was converted to MK-049 (21.54 g, 94% 2 steps) as compound purified.

Using similar procedure for the synthesis of 343-YW-276 from 343-YW-203, MK-049 (15.57 g, 74.05 mmol) was converted to MK-050 (19.51 g, 72% 2 steps) as compound purified.

To a stirred solution of MK-050 (5.15 g, 14.16 mmol) in 35 mL of dry THF was added n-BuLi in hexane (1.6M, 19.5 mL, 31.14 mmol) at −78° C. After 1 hr the reaction mixture was quenched with saturated aqueous solution of NH$_4$Cl and diluted with AcOEt. The organic extract was washed with brine, dried over MgSO$_4$, filtered and concentrated to give crude product. It was purified by chromatography on silica gel (hexane/AcOEt: 6/1 to 5/1) to afford oil of MK-051 (2.69 g, 93%).

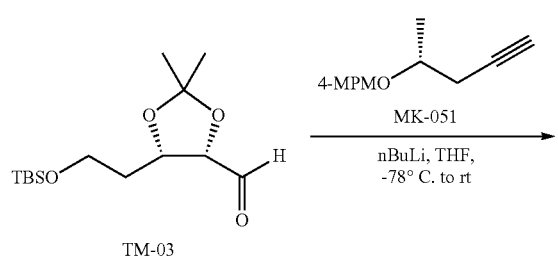

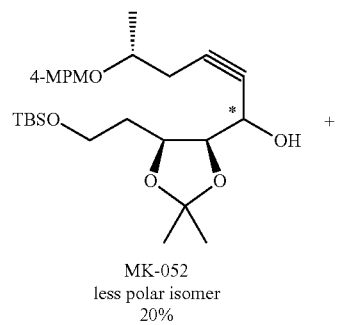

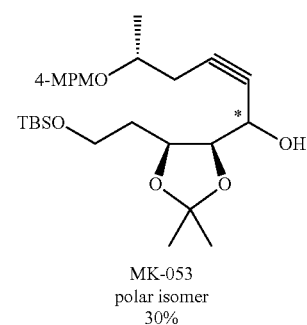

Using similar procedure for the synthesis of NY-01 from TM-03, TM-03 (2.79 g, assumed to contain 10.0 mmol) coupled with MK-051 (2.68 g, 13.1 mmol) was converted to crude alcohol. The crude product was purified by chromatography on silica gel (hexane/AcOEt: 5/1 to 3/1) to afford oil of MK-052 (less polar single isomer, 986 mg, 20%) and oil of MK-053 (polar single isomer, 1.48 g, 30%).

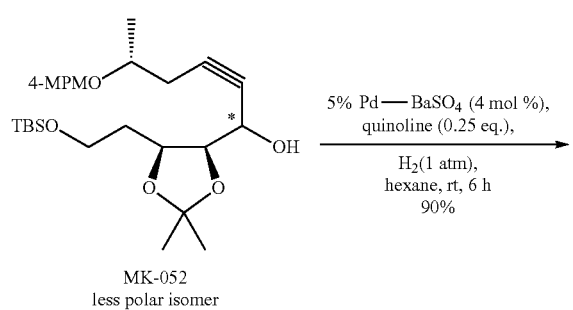

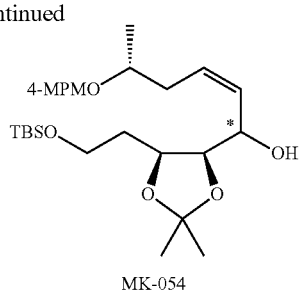

Using similar procedure for the synthesis of TM-05 from TM-04, MK-052 (less polar single isomer, 968 mg, 1.96 mmol) was converted to colorless oil of MK-054 and purified (single isomer, 870 mg, 90%).

Using similar procedure for the synthesis of MK-024 from MK-023, MK-054 (834 mg, 1.69 mmol) treated with 3-MP-MCl (0.61 mL, 4.21 mmol) was converted to colorless oil of MK-055 and purified (984 mg, 95%).

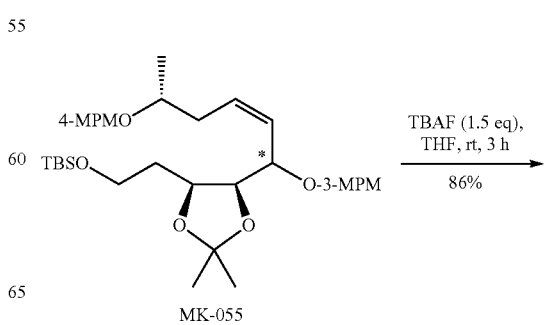

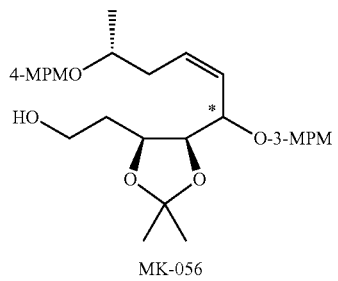

MK-056

To a stirred solution of MK-055 (998 mg, 1.62 mmol) in 16 mL of THF was added TBAF in THF (1M, 2.43 mL, 2.43 mmol) at rt. After 3 hrs the mixture was worked up in usual manner and purified by chromatography on silica gel (hexane/AcOEt: 3/1) to afford colorless oil of MK-056 (696 mg, 86%).

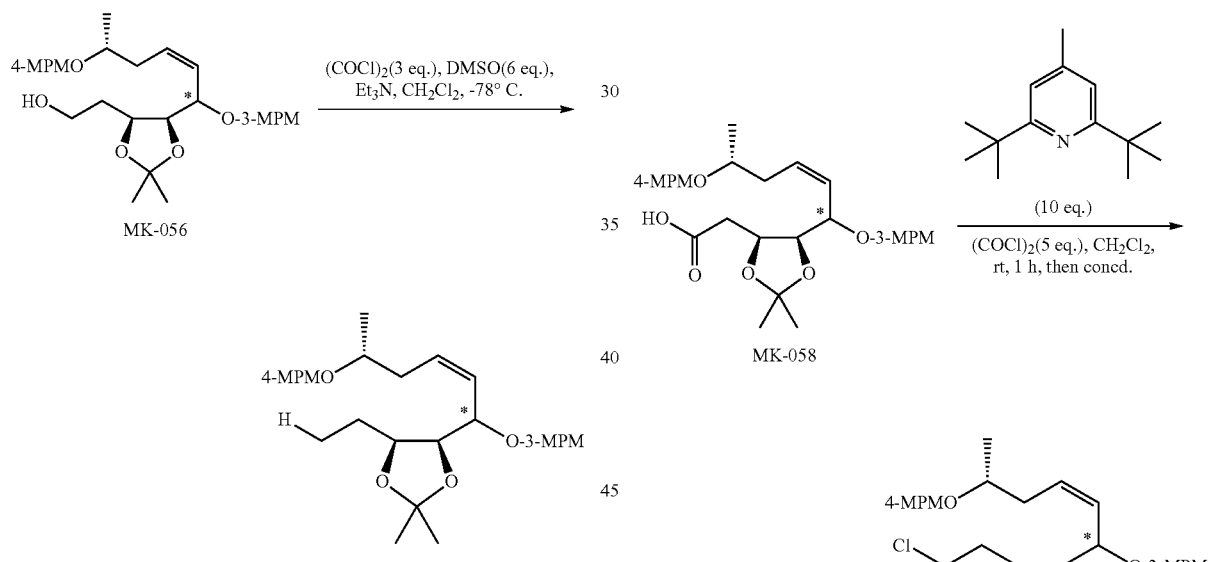

Using similar procedure for the synthesis of MK-008 from MK-007, MK-056 (695 mg, 1.39 mmol) was converted to crude aldehyde of MK-057 (728 mg). The crude aldehyde was used for next step without purification.

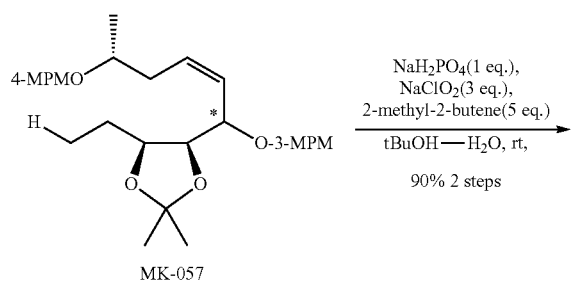

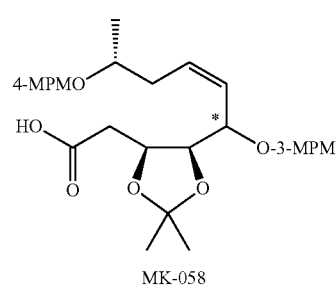

MK-058

Using similar procedure for the synthesis of MK-044 from MK-043, MK-057 (728 mg, assumed to contain 1.39 mmol) was converted to colorless oil of MK-058 and purified (643 mg, 90% 2 steps).

To a solution of MK-058 (200 mg, 0.389 mmol) and 2,6-($^t$Bu)$_2$-4-Me-pyridine (798 mg, 10 eq., 3.89 mmol) in 5 mL of dry CH$_2$Cl$_2$ was added (COCl)$_2$ in CH$_2$Cl$_2$ (2M, 0.97 ml, 5 eq., 1.94 mmol) at 0° C. and the solution was allowed to warm to rt. After stirred for 45 min the reaction mixture was concentrated in vacuo under nitrogen atmosphere to give crude product including acid chloride MK-059. The crude product was used for next step without purification.

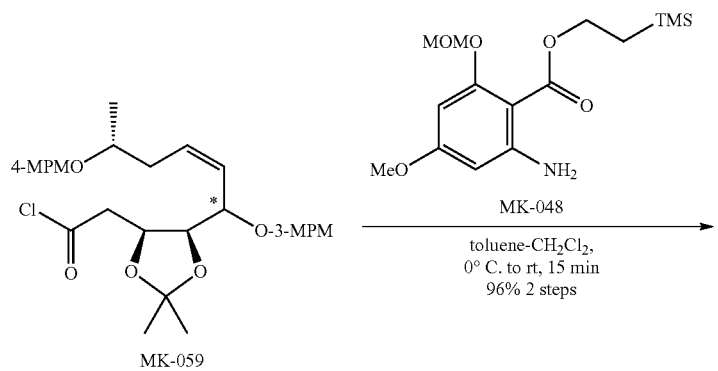

The crude product including MK-059 (assumed to contain 0.389 mmol derived from 0.389 mmol of MK-058, 1.03 eq.) was dissolved in 4 mL of dry $CH_2Cl_2$ at 0° C. A solution of MK-048 (124 mg, 0.377 mmol) in 4 mL of toluene was added and the mixture was allowed to warm to it. After stirred for 15 min the reaction mixture was quenched with saturated aqueous solution of $NaHCO_3$ and extracted with AcOEt. The organic extract was washed with brine, dried over $Na_2SO_4$, filtered and concentrated to give crude product. It was purified by chromatography on silica gel (hexane/AcOEt: 3/1) to afford pale brown oil of MK-060 (297 mg, 96%).

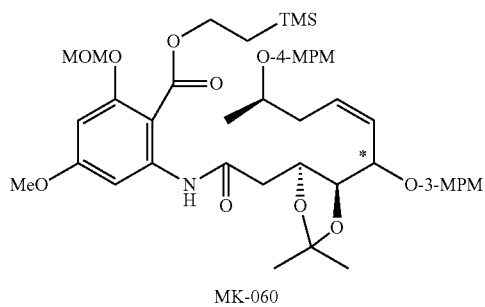

To a stirred mixture of MK-060 (194 mg, 0.235 mmol) in 4 mL of $CH_2Cl_2$ and 0.2 mL of aqueous phosphate buffer (pH 6.86) was added DDQ (59 mg, 1.1 eq., 0.259 mmol) at 0° C. After stirred for 1.5 hrs at 0° C. the reaction mixture was quenched with aqueous solution of $NaHCO_3$ and extracted with AcOEt. The organic extract was washed with saturated aqueous solution of $NaHCO_3$ and brine, dried over $Na_2SO_4$, filtered and concentrated to give crude oil. The crude product was purified by chromatography on silica gel (hexane/AcOEt: 5/2) to afford colorless oil of MK-061 (138 mg, 83%).

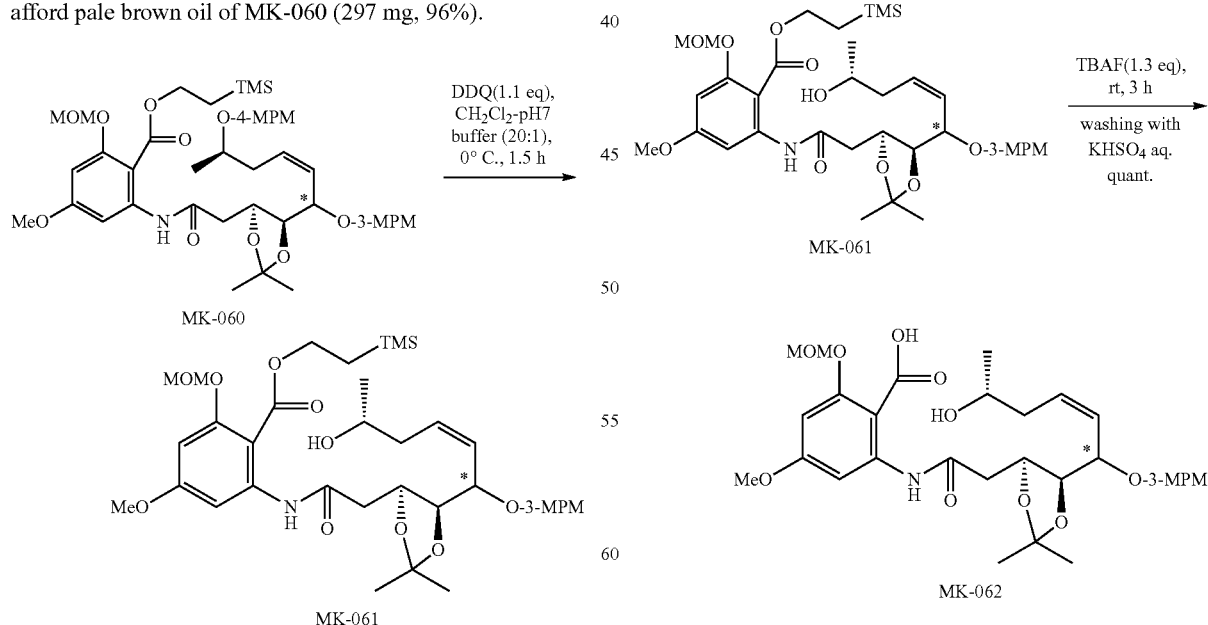

Using similar procedure for the synthesis of MK-031 from MK-030, MK-061 (165 mg, 0.234 mmol) was converted to crude MK-062 (159 mg, >100%). The crude MK-062 was used for next step without purification.

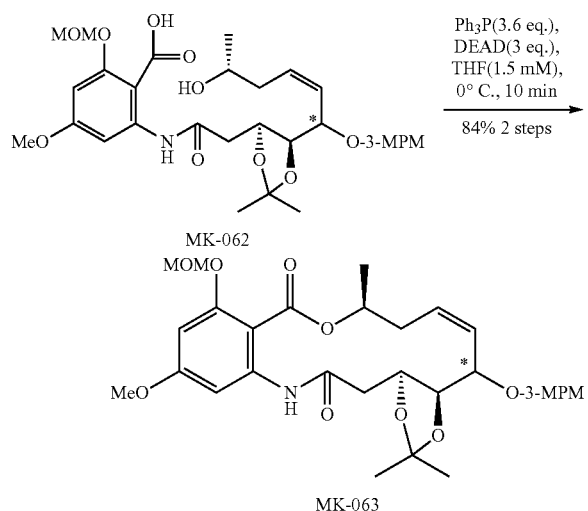

MK-062

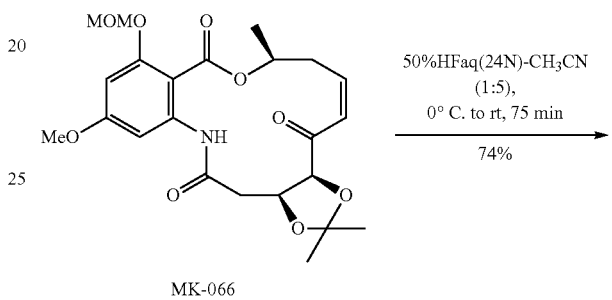

MK-063

Ph₃P (221 mg, 0.844 mmol, 3.6 eq.) was dissolved in 39 mL of dry THF and cooled to 0° C. 40% DEAD in toluene (0.32 mL, 0.703 mmol, 3.0 eq.) was added and stirred for 20 min at 0° C. To the stirred solution was added dropwise over 15 min a solution of crude MK-062 (159 mg, assumed to contain 0.234 mmol) in 39 mL of THF at 0° C. After 10 min at 0° C. the reaction mixture was evaporated and purified by chromatography on silica gel (hexane/AcOEt: 2/1 to 3/2) to afford oil of MK-063 (115 mg, 84% 2 steps).

To a stirred mixture of MK-063 (115 mg, 0.196 mmol) in 5 mL of CH₂Cl₂ and 0.5 mL of aqueous phosphate buffer (pH 6.86) was added DDQ (103 mg, 2.3 eq., 0.452 mmol) at 0° C. and the mixture was allowed to warm to rt. After stirred for 24 hrs at rt the reaction mixture was worked up in the usual manner to give a crude oil. The crude product was purified by chromatography on silica gel (hexane/AcOEt: 2/1 to 1/3) to afford colorless oil of MK-064 ($2^{nd}$ elution, 14 mg, 15%), colorless oil of MK-065 ($3^{rd}$ elution, 21 mg, 23%), and colorless oil of MK-066 ($1^{st}$ elution, 14 mg, 15%).

Using similar procedure for the synthesis of NF0552 from MK-021, MK-065 (21 mg, 0.0451 mmol) treated at low temperature was converted to colorless oil of MK-066 (15 mg, 72%) as compound purified.

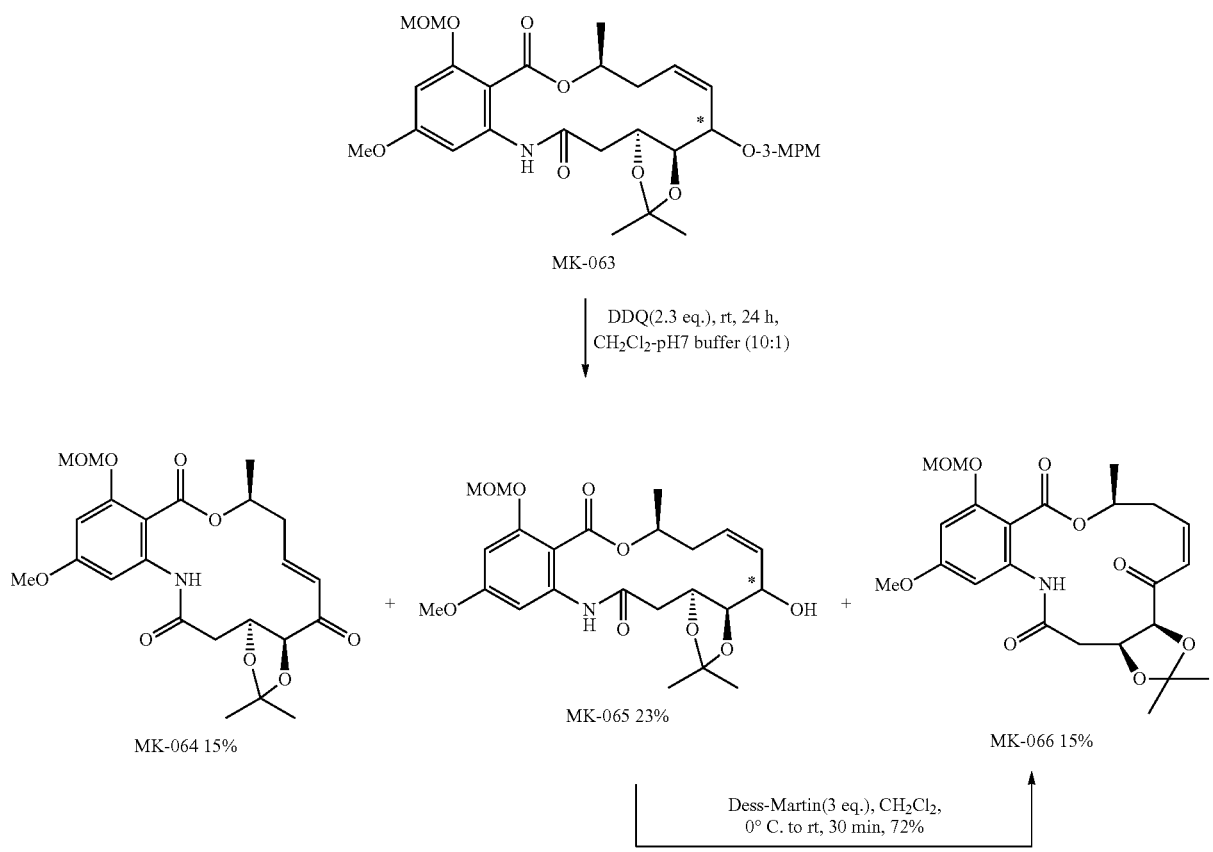

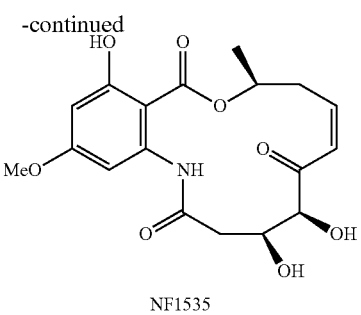

NF1535

Using similar procedure for the synthesis of NF1226 from MK-035, MK-066 (29 mg, 0.0626 mmol) was converted to crude pale yellow crystals. The crude product was purified by chromatography on silica gel (hexane/AcOEt=1/3 to AcOEt alone) to afford colorless crystals of NF1535 (17.6 mg, 74%).

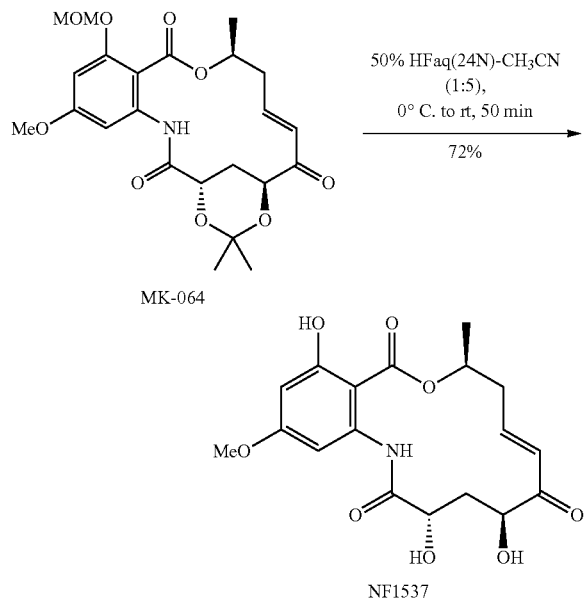

Using similar procedure for the synthesis of NF1226 from MK-035, MK-064 (14 mg, 0.0302 mmol) was converted to crude pale yellow crystals. The crude product was purified by chromatography on silica gel (CH$_2$Cl$_2$/AcOEt=4/1, 2/1, to 1/1) to afford colorless crystals of NF1537 (8.2 mg, 72%).

Synthetic Procedure for NF2306

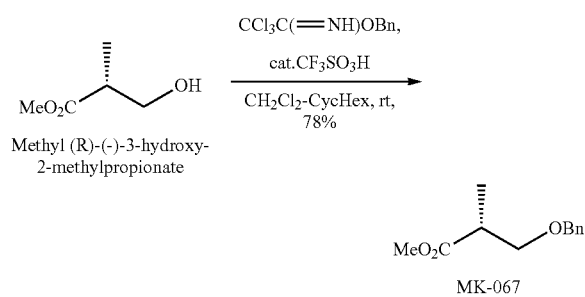

To a stirred solution of methyl (R)-(-)-3-hydroxy-2-methylpropionate (7.00 g, 59.26 mmol) in 66 mL of CH$_2$Cl$_2$ and 132 mL of cyclohexane were added CCl$_3$C(=NH)OBn (13.2 mL, 71.1 mmol) and CF$_3$SO$_3$H (cat. 0.2 mL) at rt. After 3 hrs the reaction mixture was diluted with hexane to form precipitation. After filtering precipitation off, filtrates was washed with saturated aqueous NaHCO$_3$ and brine, dried over Na$_2$SO$_4$, filtered, and concentrated to give a crude oil. The crude product was purified by chromatography on silica gel (hexane/AcOEt=20/1) to afford colorless oil of MK-067 (9.60 g, 78%).

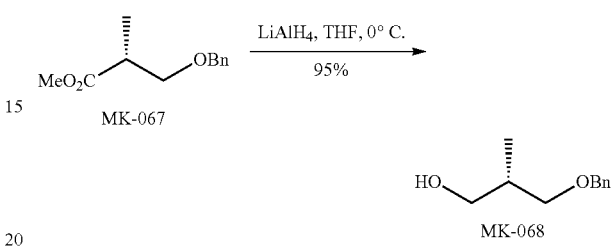

LiAlH$_4$ (2.62 g, 69.1 mmol) was suspended in 250 mL of dry THF. To the suspension was dropwise added a solution of MK-067 (9.59 g, 46.0 mmol) in 57 mL of dry THF at 0° C. After stirred for 1 hr at 0° C. the reaction mixture was quenched with MeOH (13 mL), water (2.5 mL), 10% NaOH (2.5 mL), then water (7.5 mL). The mixture was dried over MgSO$_4$, filtered and evaporated to a crude product. The crude product was purified by chromatography on silica gel (hexane/AcOEt=2/1) to afford colorless oil of MK-068 (7.89 g, 95%).

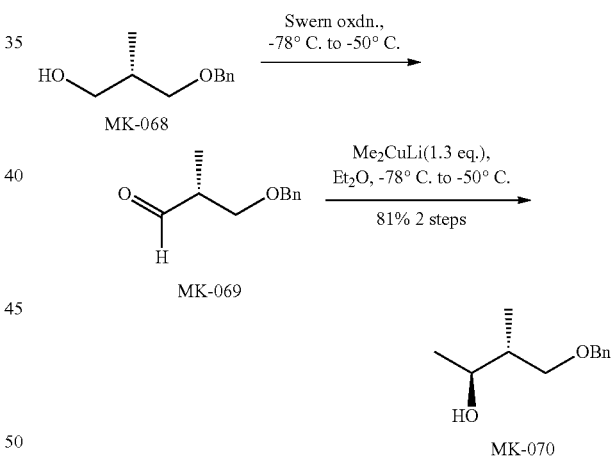

Using similar procedure for the synthesis of MK-008 from MK-007, MK-068 (7.89 g, 43.76 mmol) was converted to crude MK-069 (8.66 g, >100%). The crude MK-069 was used for next step without purification.

To a stirred suspension of CuI (10.83 g, 56.9 mmol, 1.3 eq.) in 100 mL of dry Et$_2$O was added over 15 min MeLi in Et$_2$O (1.14 M, 98.6 mL, 112.5 mmol, 2.57 eq.) at 0° C. After stirred for 30 min at 0° C., the mixture was cooled to −78° C. Crude MK-069 (8.66 g, assumed to contain 43.76 mmol) in 75 mL of dry Et$_2$O was added over 40 min at −78° C. then the mixture was stirred at −78° C. for additional 1 hr. The reaction mixture was allowed to warm to −20° C. over 1.5 hr, then quenched with 28% aqueous NH$_3$ solution and extracted with AcOEt. The organic extract was washed with brine, dried over MgSO$_4$, filtered and concentrated to give a crude oil. The crude product was purified by chromatography on silica gel (hexane/AcOEt: 5/1) to afford pale yellow oil of MK-070 (6.89 g, 81% 2 steps).

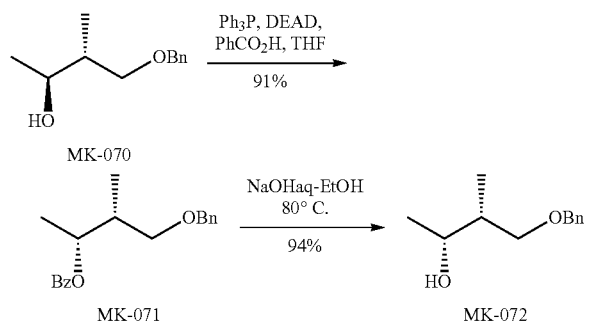

$Ph_3P$ (9.24 g, 35.24 mmol, 1.4 eq.) was dissolved in 70 mL of dry THF and cooled to 0° C. 40% DEAD in toluene (14.84 mL, 32.72 mmol, 1.3 eq.) was added and stirred for 20 min at 0° C. To the stirred solution was dropwise added a solution of MK-070 (4.89 g, 25.17 mmol) and $PhCO_2H$ (4.00 g, 32.7 mmol, 1.3 eq.) in 30 mL of dry THF at 0° C. After 30 min at 0° C. the mixture was allowed to warm to it overnight. The resulting reaction mixture was evaporated and diluted with hexane-AcOEt. After filtration of generated precipitate, the filtrate was concentrated to yield crude oil. The crude product was purified by chromatography on silica gel (hexane/AcOEt: 15/1) to afford pale yellow oil of MK-071 (6.84 g, 91%).

To a stirred solution of MK-071 (6.84 g, 22.91 mmol) in 38 mL of EtOH was added aqueous 3N—NaOH (15.3 mL, 45.81 mmol) then the mixture was stirred at 80° C. for 1 hr. The resulting mixture was evaporated, extracted with $Et_2O$, washed with brine, dried over $MgSO_4$, filtered and concentrated to yield a crude oil. The crude product was purified by chromatography on silica gel (hexane/AcOEt: 5/1 to 5/3) to afford colorless oil of MK-072 (4.17 g, 94%).

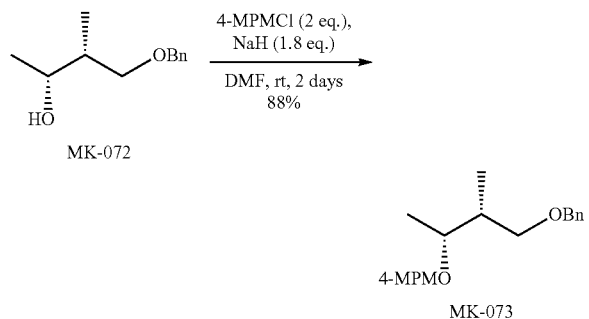

To a suspension of 66% NaH (916 mg, 25.20 mmol) in 30 mL of DMF was added a solution of MK-072 (2.72 g, 14.00 mmol) in 10 mL of DMF at 0° C. After stirring at 0° C. for 30 min 4-MPMCl (3.80 mL, 28.00 mmol) was added, then the mixture was allowed to warm to rt. After 2 days the reaction was quenched with saturated aqueous solution of $NH_4Cl$ and extracted with AcOEt. The organic extract was washed with saturated aqueous solution of $NaHCO_3$ and brine, dried over $Na_2SO_4$, filtered and concentrated. The crude product was purified by chromatography on silica gel (Hexane/AcOEt: 12/1) to afford colorless oil of MK-073 (3.88 g, 88%).

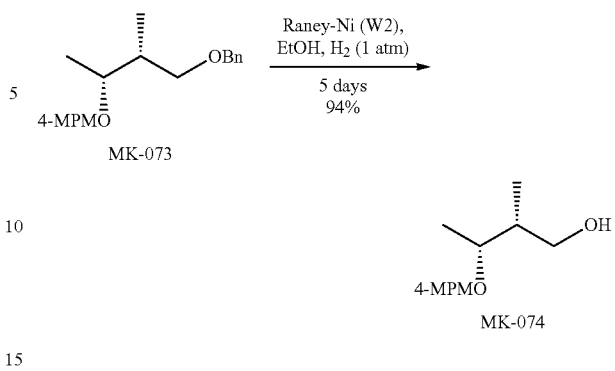

50 wt % suspension of Raney-Ni (W2) in basic water (9.5 g) was added into a flask, then the suspension was washed with water and EtOH. To this suspension was added a solution of MK-073 (3.88 g, 12.34 mmol) in 150 mL of EtOH. $H_2$ ballon was mounted and the mixture was purged with $H_2$. After stirred for 5 days under $H_2$ (1 atm) at rt, the reaction mixture was filtered through Celite and the filtrate was evaporated to give a crude oil. The crude product was purified by chromatography on silica gel (Hexane/AcOEt: 3/1) to afford colorless oil of MK-074 (2.61 g, 94%).

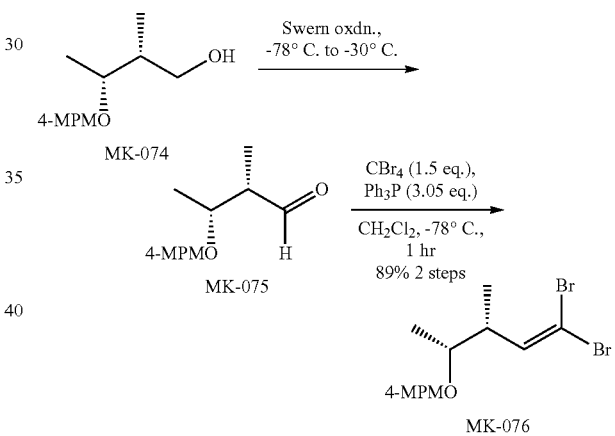

Using similar procedure for the synthesis of MK-008 from MK-007, MK-074 (2.61 g, 11.63 mmol) was converted to crude oil of MK-075 (2.70 g, quant.). The crude MK-075 was used for next step without purification.

Using similar procedure for the synthesis of 343-YW-276 from 343-YW-203, crude MK-075 (2.70 g, assumed to contain 11.63 mmol) was converted to MK-076 (3.92 g, 89% 2 steps).

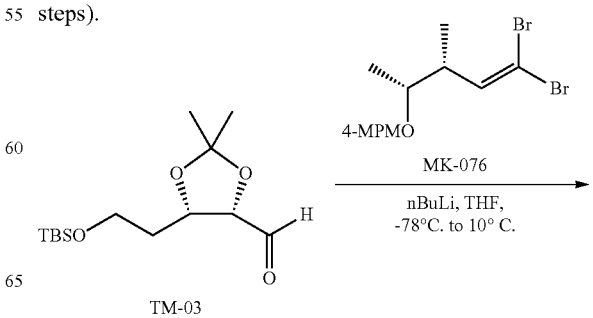

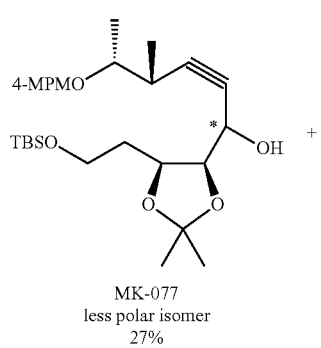

MK-077
less polar isomer
27%

+

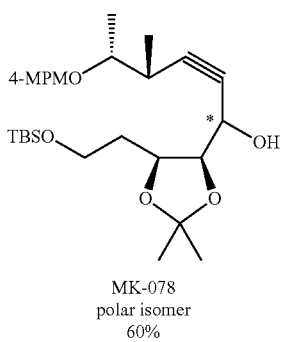

MK-078
polar isomer
60%

MK-076 (2.03 g, 5.37 mmol, 1.36 eq.) was dissolved in 27 mL of dry THF and cooled to −78° C. under nitrogen. n-BuLi in hexane (1.6M, 6.71 mL, 10.73 mmol, 2.71 eq.) was added and stirred at −78° C. for 1 hr. A solution of crude TM-03 (1.11 g, assumed to contain 3.96 mmol) in 7 mL of dry THF was dropwise added to the mixture and stirred for 30 min at −78° C. The reaction mixture was allowed to warm to 10° C. slowly over 2.5 hrs. The mixture was quenched with saturated aqueous solution of NH$_4$Cl and extracted with AcOEt. The organic extract was washed with saturated aqueous solution of NaHCO$_3$ and brine, dried over Na$_2$SO$_4$, filtered and concentrated. The crude product was purified by chromatography on silica gel (hexane/AcOEt: 7/1 to 4/1) to afford oil of MK-077 (less polar single isomer, 541 mg, 27%) and oil of MK-078 (polar single isomer, 1.21 g, 60%).

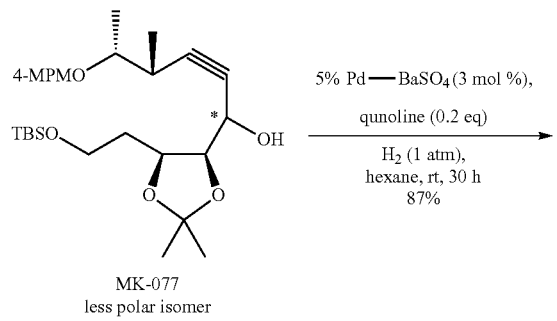

MK-077
less polar isomer

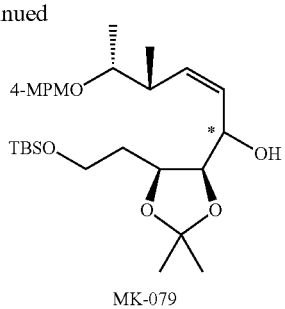

MK-079

Using similar procedure for the synthesis of TM-05 from TM-04, MK-077 (less polar single isomer, 3.85 g, 7.61 mmol) was converted to colorless oil of MK-079 (single isomer, 3.38 g, 87%).

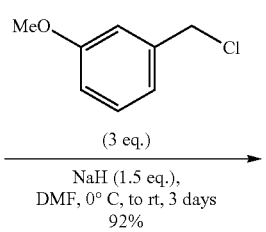

MK-079

5% Pd—BaSO$_4$ (3 mol %),
qunoline (0.2 eq)
───────────────→
H$_2$ (1 atm),
hexane, rt, 30 h
87%

(3 eq.)
───────────────→
NaH (1.5 eq.),
DMF, 0° C, to rt, 3 days
92%

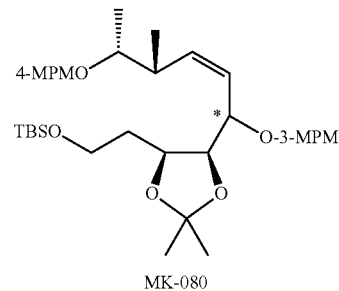

MK-080

Using similar procedure for the synthesis of MK-024 from MK-023, MK-079 (3.38 g, 6.63 mmol) treated with 3-MP-MCl (2.89 mL, 19.9 mmol) was converted to colorless oil of MK-080 (3.86 g, 92%).

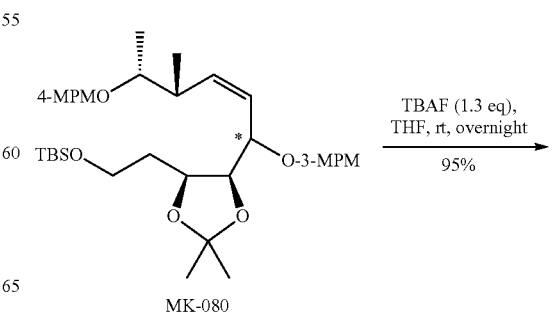

MK-080

TBAF (1.3 eq),
THF, rt, overnight
───────────────→
95%

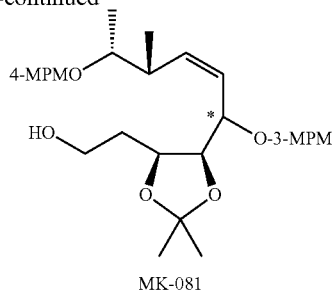
MK-081
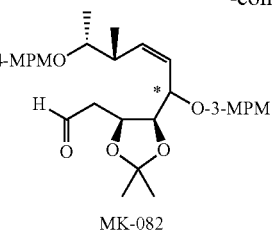
MK-082
Using similar procedure for the synthesis of MK-056 from MK-055, MK-080 (3.85 g, 6.12 mmol) was converted to colorless oil of MK-081 (3.00 g, 95%).
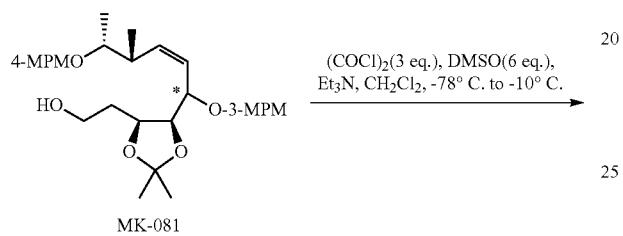
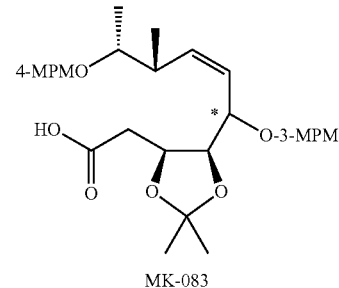
MK-083
Using similar procedure for the synthesis of MK-058 from MK-056, MK-081 (1.82 g, 3.54 mmol) was converted to colorless oil of MK-083 (1.80 g, 96% 2 steps).
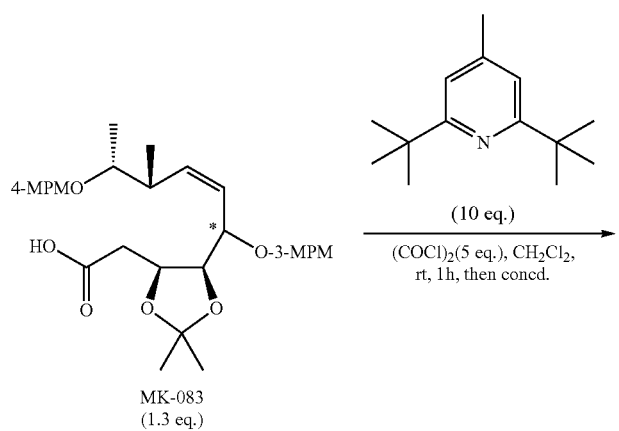
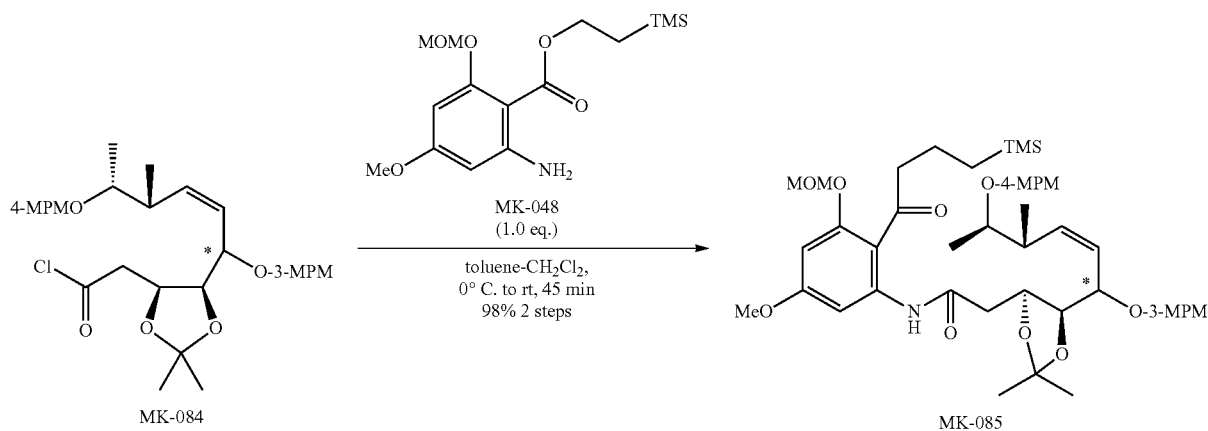

Using similar procedure for the synthesis of MK-059 from MK-058, MK-083 (1.80 g, 3.40 mmol) was converted to crude oil of MK-084. The crude MK-084 was used for next step without purification.

Using similar procedure for the synthesis of MK-060 from MK-059, crude MK-084 coupled with MK-048 (853 mg, 2.60 mmol) was converted to pale brown oil of MK-085 (2.14 g, 98% 2 steps).

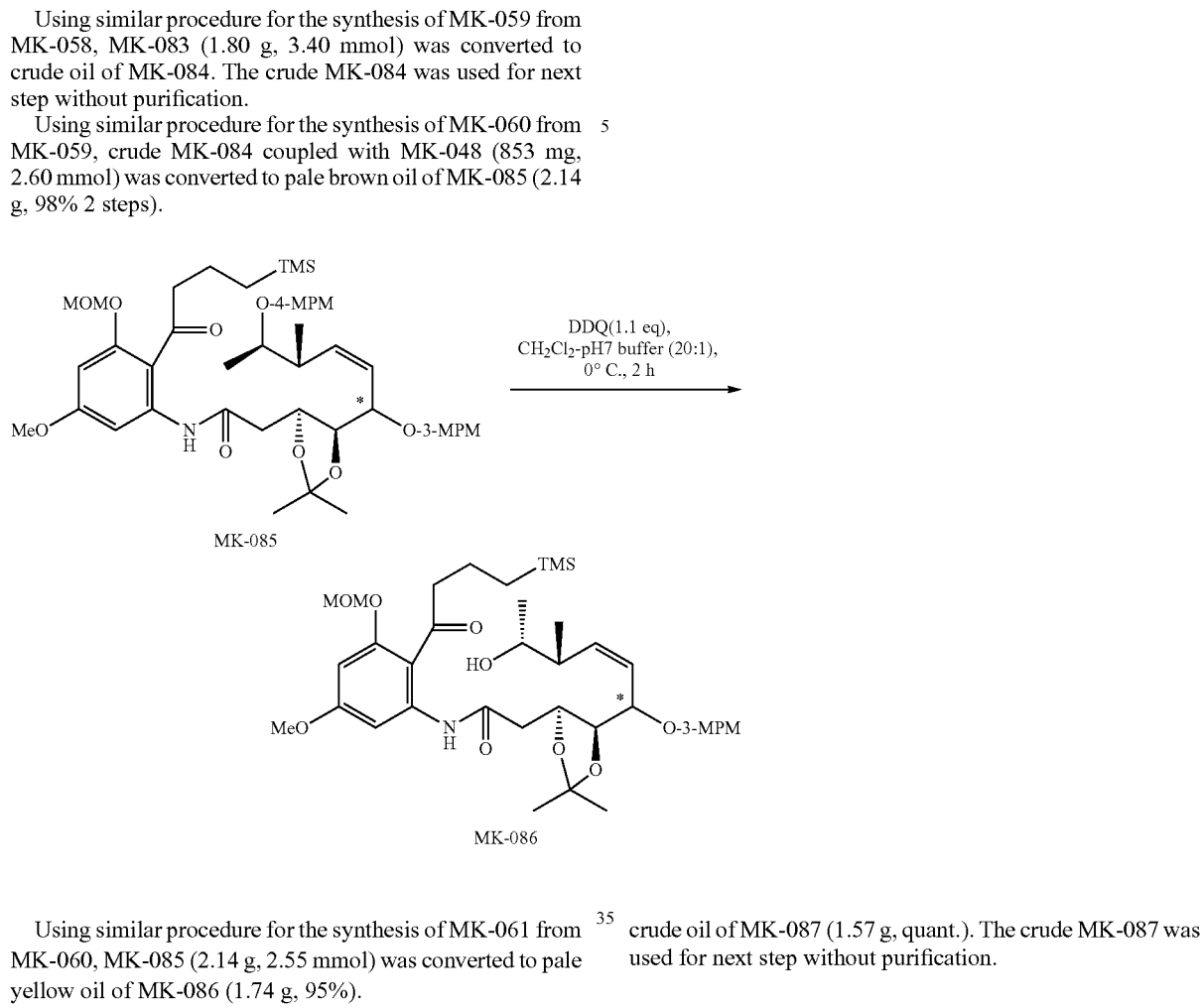

Using similar procedure for the synthesis of MK-061 from MK-060, MK-085 (2.14 g, 2.55 mmol) was converted to pale yellow oil of MK-086 (1.74 g, 95%).

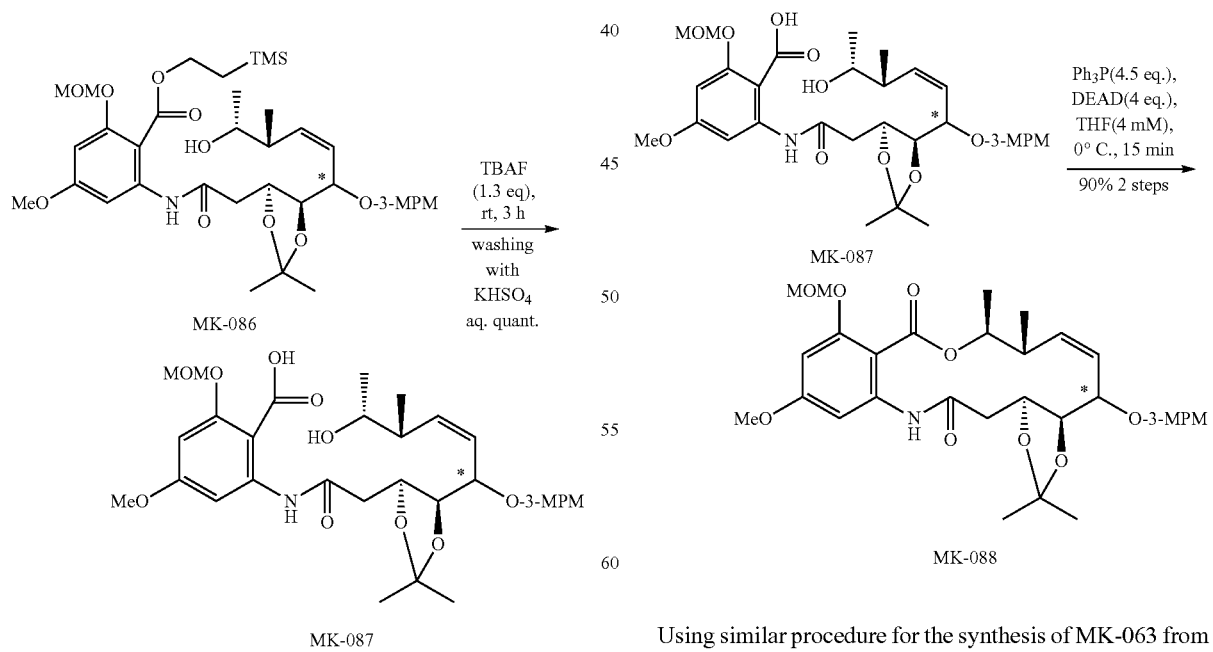

Using similar procedure for the synthesis of MK-031 from MK-030, MK-086 (1.74 g, 2.42 mmol) was converted to crude oil of MK-087 (1.57 g, quant.). The crude MK-087 was used for next step without purification.

Using similar procedure for the synthesis of MK-063 from MK-062, crude MK-087 (1.57 g, assumed to contain 2.42 mmol) was converted to pale yellow oil of MK-088 (1.68 g, including ca 0.38 g of inseparable impurity derived from DEAD, ca 90% 2 steps).

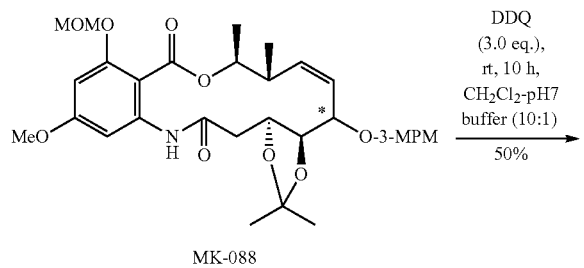

MK-088

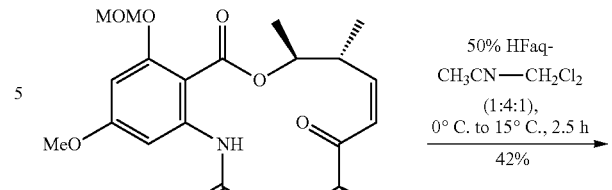

MK-090

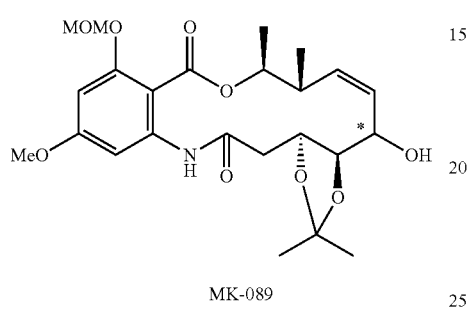

MK-089

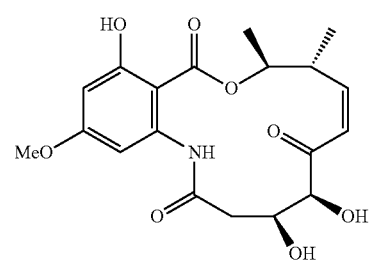

NF2306

Using similar procedure for the synthesis of MK-065 from MK-063, MK-088 (1.68 g, including ca 0.38 g of inseparable impurity derived from DEAD, assumed to contain 2.17 mmol) was converted to colorless solid of MK-089 (525 mg, 50%).

MK-090 (250 mg, 0.524 mmol) was dissolved in 3.5 mL of $CH_2Cl_2$ and cooled to 0° C. A mixture of 50% Hydrofluoric acid (24N, 3.5 mL) and 14 mL of $CH_3CN$ was added to the solution and stirred for 1 hr at 0° C. before the mixture was allowed to warm to 15° C. slowly over 1.5 hrs. Then, the reaction mixture was poured into a stirred biphasic solution of saturated aqueous solution of $NaHCO_3$ and AcOEt. The organic extract was washed with brine, dried over $Na_2SO_4$, filtered and concentrated to crude product. The crude product was purified by chromatography on silica gel ($CH_2C_2$/MeOH: 13/1) to afford colorless crystals of NF2306 (174 mg, 42%).

Preparation of C13-Oxygen and Fluoro Analog, NF2432, NF2544, NF2547, NF2553 and NF2556

Synthetic Procedure for NF2432

1) Preparation of the Macrocyclic Part

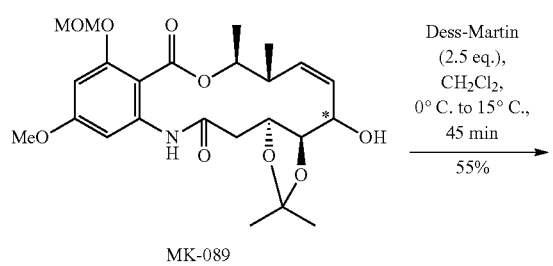

MK-089

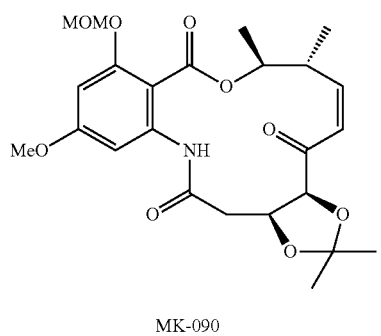

MK-090

Using similar procedure for the synthesis of NF0552 from MK-021, MK-089 (458 mg, 0.955 mmol) was treated with Dess-Martin reagent at low temperature to give a pale yellow solid of MK-090 (250 mg, 55%).

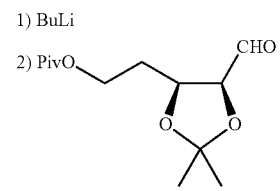

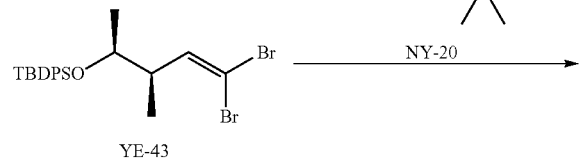

YE-43

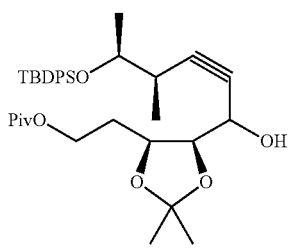

YE-01 less polar isomer of allylic alcohol
YE-02 more polar isomer of allylic alcohol To a stirred THF solution of dibromide YE-43 (18.6 g, 37 mmol), which was prepared using similar procedure for the intermediate 554-RB-228 from methyl (S)-3-hydroxybutyrate (47%, 5 steps), was added n-butyllithium (1.6M in hexane solution, 47 ml, 75 mmol) at −78° C. The mixture was allowed to warm to 0° C. for 30 min and then stirred at −78° C. for additional 30 min. A THF solution of aldehyde NY-20 (6.17 g, 24 mmol) was added, the mixture was allowed to warm to 0° C. and stirred at 0° C. for 30 min, after which a saturated solution of NH$_4$Cl was added. The mixture was extracted with EtOAc and the organic extract was washed with a saturated solution of NaHCO$_3$, brine, dried over anhydrous Na$_2$SO$_4$, filtered and concentrated. The crude product was purified by chromatography on silica gel using 12% EtOAc/hexane to give 3.55 g (5.9 mmol, 25%) of the less polar isomer YE-01 and 5.5 g (0.093 mol, 39%) of the more polar isomer YE-02.

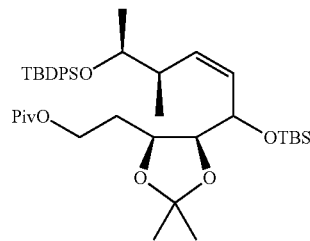

YE-04

To a solution of YE-02 (10.1 g, 17.0 mmol) in n-hexane (170 mL), quinoline (0.25 eq., 4.25 mmol, 0.50 mL) and 5 wt. % Pd on BaSO$_4$ (0.05 eq., 0.85 mmol, 1.81 g) was added at rt. And the reaction mixture was purged with H$_2$ and stirred under H$_2$ atmosphere for 11 hrs. The catalyst was filtered off and the filtrate was concentrated. The crude product (11.5 g) was purified by chromatography on silica gel using 16% EtOAc/hexane to give 8.19 g (13.7 mmol, 81% 2 steps) of the desired allylic alcohol YE-03.

The alcohol YE-03 (8.04 g, 13.5 mmol) was dissolved in CH$_2$Cl$_2$ (200 mL), 2,6-lutidine (7.8 mL, 67.0 mmol) was added and the mixture was cooled to 0° C. in ice/water bath. Then TBSOTf (7.7 mL, 33.5 mmol) was added and the mixture was allowed to warm to rt. After 2 hrs, it was cooled to 0° C. and was quenched with MeOH and a saturated solution of NaHCO$_3$. The mixture was extracted with EtOAc, the organic layer was washed with a saturated solution of NaHCO$_3$, 5% citric acid aq., a saturated solution of NaHCO$_3$, and brine. The organic layer was dried over Na$_2$SO$_4$, filtered and concentrated. The crude product was purified by chromatography on silica gel using 2-4% EtOAc/hexane to give 9.60 g (13.5 mmol, quant.) of YE-04.

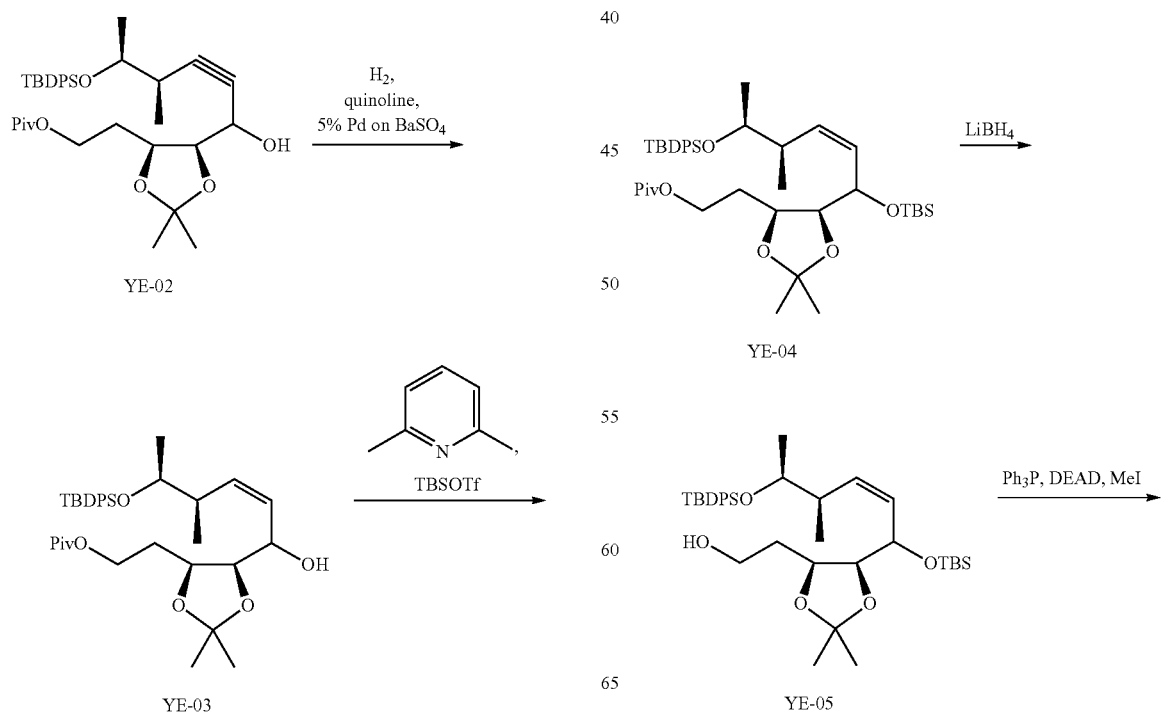

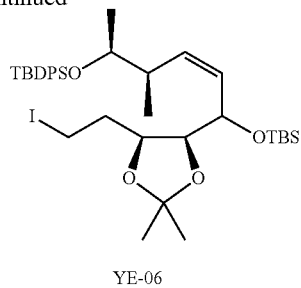

YE-06

To a stirred ether solution (200 ml) of YE-04 (9.60 g, 13.5 mmol) at 0° C. was added lithium tetrahydroborate (0.60 g, 27.5 mmol). The mixture was allowed to warm to rt and stirred for 2 days. Then the mixture was cooled to 0° C. and lithium tetrahydroborate (0.30 g, 13.8 mmol) was added again. The mixture was allowed to warm to rt and stirred overnight. The mixture was cooled to 0° C., then a saturated solution of $NH_4Cl$ (2 ml) was added slowly. After the stirring for 20 min, a saturated solution of $NH_4Cl$ (100 ml) was added. The mixture was extracted with EtOAc and the organic extract was washed with a saturated solution of $NH_4Cl$, brine, dried over anhydrous $Na_2SO_4$, filtered and concentrated. The crude product was purified by chromatography on silica gel using 12-15% EtOAc/hexane to give 8.51 g (13.5 mmol, quant.) of the alcohol YE-05.

To a stirred solution of YE-05 (1.90 g, 3.03 mmol) in toluene (45 ml) was added triphenylphosphine (1.6 g, 6.1 mmol), a mixture of diethyl azodicarboxylate (40% in toluene, 2.1 ml, 4.6 mmol) and iodomethane (0.29 ml, 4.7 mmol). The mixture was stirred for 40 min after which a mixture of diethyl azodicarboxylate (in toluene, 0.5 ml, 1.1 mmol) and iodomethane (0.06 ml, 1.2 mmol) was added. The mixture was stirred for 20 min and the solvent was evaporated in vacuo. The concentrate was purified by chromatography on silica gel using 1-1.5% EtOAc/hexane to give 2.05 g (2.78 mmol, 92%) of the iodide YE-06.

2) Preparation of the Aromatic Part

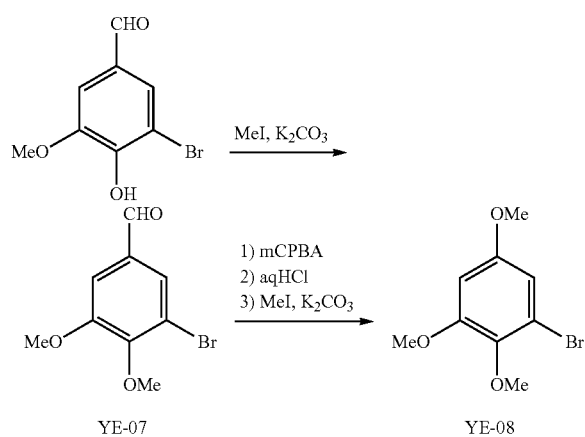

3-Bromo-4-hydroxy-5-methoxybenzaldehyde (24.8 g, 0.107 mol) was dissolved in DMF (400 ml). $K_2CO_3$ (20 g, 0.14 mol) and iodomethane (8.8 ml, 0.14 mol) was added. The mixture was stirred for 4 hrs and was then cooled to 0° C. in ice/water bath and diluted with ether (300 ml). Then ice-water (600 ml) was added slowly. The mixture was extracted with ether and the organic extract was washed with water, brine, dried over anhydrous $Na_2SO_4$, filtered and concentrated to give 22.1 g (90 mmol, 84%.) of YE-07.

YE-07 (13.3 g, 54.2 mmol) was dissolved in chloroform (350 mL) under nitrogen. m-CPBA (>70%, 31 g, 126 mmol) was added and the solution was gently refluxed for 1 hr. The reaction mixture was cooled to 0° C. and was poured into saturated stirred solution of $NaHCO_3$. After stirring for 15 min, the organic layer was separated, washed with saturated $Na_2SO_3$, saturated $NaHCO_3$, dried over $Na_2SO_4$, filtered and concentrated The concentrate was dissolved in MeOH (150 ml) and 6N HCl (150 ml) was added. The mixture was stirred for 15 min. and partially concentrated. The mixture was extracted with EtOAc and the organic extract was washed with water, dried over $Na_2SO_4$, filtered and concentrated. to give 10.8 g of crude phenol.

The crude phenol was methylated using the same procedure as the preparation of YE-07 to give 9.8 g (39.7 mmol, 73%) of YE-08.

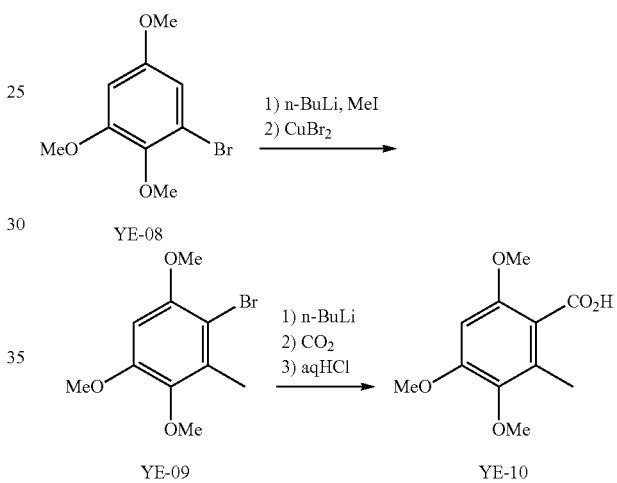

To a stirred ether solution of bromobenzene YE-08 (14.6 g, 59.1 mmol) at −78° C. was added n-butyllithium (1.6M in hexane solution, 50 ml, 1.3 eq., 80 mmol), and the mixture was stirred at −78° C. for 1.5 hrs. A solution of iodomethane (10 ml, 161 mmol) in ether (20 ml) was added, and the mixture was allowed to warm to rt and stirred for 1.5 hrs, after which a saturated solution of $NH_4Cl$ was added. The mixture was extracted with ether and the organic extract was washed with brine, dried over anhydrous $Na_2SO_4$, filtered and concentrated. The concentrate was purified by chromatography on silica gel using 6-9% EtOAc/hexane to give 9.6 g (52.6 mmol, 89%) of 2,3,5-trimethoxytoluene.

The toluene 9.6 g (52.6 mmol, 89%) was dissolved in DME (130 mL) and copper (II) bromide (25 g, 112 mmol) was added portionwise over 6 hrs. After stirring another 1 hr, the reaction mixture was filtrated and the filtrate was concentrated. The concentrate was purified by chromatography on silica gel using 5-12% EtOAc/hexane to give 12.7 g (48.6 mmol, 92%) of YE-09.

To a stirred ether solution of YE-09 (45.6 mmol, 11.9 g) at −78° C. was added n-butyllithium (1.6M in hexane solution, 37 ml, 59 mmol) and the mixture was stirred at −78° C. for 1 hr. A finely crushed dry-ice was added slowly and the mixture was allowed to warm to −10° C. After 2 hrs, the reaction was quenched with water (200 ml). The mixture was washed with ether then acidified with 1N HCl. The mixture was extracted with EtOAc and the organic extract was washed with water, brine, dried over anhydrous Na$_2$SO$_4$, filtered and concentrated to give 9.7 g (42.8 mmol, 94%) of YE-10.

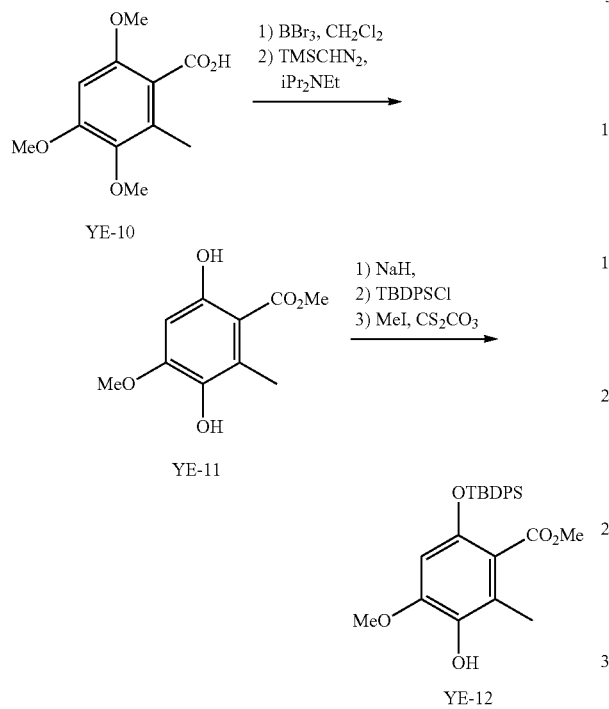

To a stirred solution of YE-10 (1.4 g, 6.3 mmol) in dry CH$_2$Cl$_2$ (40 mL) was added BBr$_3$ (1M solution, 28 mL, 28 mmol) at −78° C. under nitrogen atmosphere and the mixture was allowed to warm to rt. After 8 hrs, the mixture was cooled to 0° C. and poured into water. The organic layer was separated and washed with a solution of 5% glycerol, brine, dried over anhydrous Na$_2$SO$_4$, filtered and concentrated to give 0.9 g of the crude product.

To a stirred solution of the crude product (0.9 g, 4.8 mmol) in dry acetonitrile (20 mL) were added MeOH (0.78 ml) followed by N,N-diisopropylethylamine (1.7 ml, 9.7 mmol). To the mixture was added TMSCHN$_2$ (2.0M in hexane, 4.8 mL, 9.6 mmol) and the mixture was stirred at 30° C. After 1 hr., the mixture was cooled to 0° C., poured into water and extracted with EtOAc. The organic extract was washed with a saturated solution of NH$_4$Cl, water, brine, dried with anhydrous Na$_2$SO$_4$, filtered and concentrated. The crude product was purified by chromatography on silica gel using 6% EtOAc/hexane to give 0.37 g (1.74 mmol, 28% 2 steps) of YE-11.

To a stirred suspension of NaH (0.16 g, 4.4 mmol) in dry THF (10 mL) was added YE-11 (0.37 g, 1.7 mmol) in dry THF (8 mL) at 0° C. After stirring for 30 min at 0° C., TBDPSCl (0.5 ml, 1.9 mmol) was added. The mixture was allowed to warm to rt and stirred for 15 min. The mixture was cooled to 0° C., poured into water and extracted with EtOAc. The organic extract was washed with water, brine, dried with anhydrous Na$_2$SO$_4$, filtered and concentrated. The concentrate was purified by chromatography on silica gel using 6% EtOAc/hexane to give 0.63 g (1.39 mmol, 80%) of silyl ether.

To a stirred solution of the silyl ether (3.7 g, 8.3 mmol) in DMF (50 mL) was added Cs$_2$CO$_3$ (3.0 g, 9.2 mmol) and iodomethane (1.3 mL, 20.8 mmol). The mixture was stirred overnight and was cooled to 0° C. in ice/water bath. Then the mixture was poured into ice-cold, saturated solution of NH$_4$Cl (100 mL) and extracted with EtOAc. The organic extract was washed with water, brine, dried over anhydrous Na$_2$SO$_4$, filtered and concentrated. The concentrate was purified by chromatography on silica gel using 5% EtOAc/hexane to give 2.83 g (6.09 mmol, 73%) of YE-12.

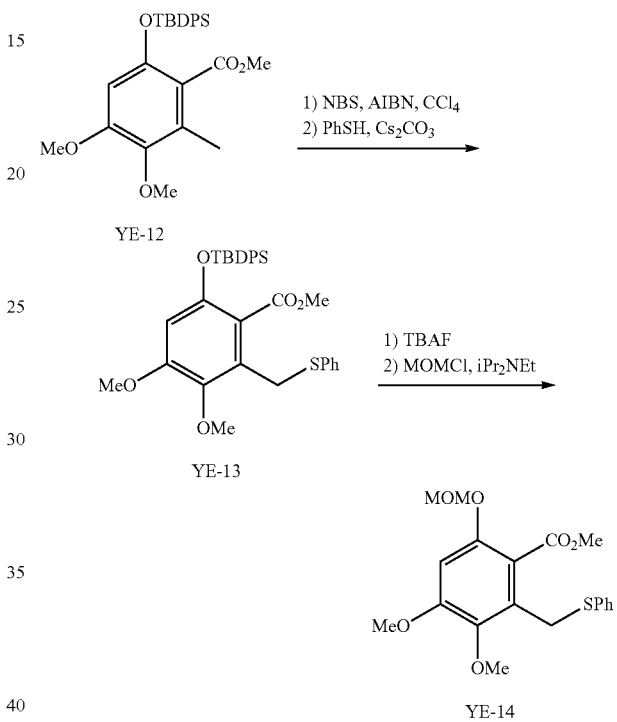

Using similar procedure for the intermediate 10 of NF2561, YE-12 (0.30 g, 0.64 mmol) was converted to YE-13 (0.29 g, 0.51 mmol, 80% 2 steps).

YE-13 (0.29 g, 0.51 mmol) was dissolved in THF (10 mL). Then 1.0M solution of TBAF in THF (1.5 mL, 1.5 mmol) were added at rt. The mixture was stirred overnight after which a saturated solution of NH$_4$Cl was added. The mixture was extracted with EtOAc and the organic extract was washed with a saturated solution of NaHCO$_3$, water, brine, dried with anhydrous Na$_2$SO$_4$, filtered and concentrated. The crude product was purified by chromatography on silica gel using 10% EtOAc/hexane to EtOAc as eluents to give 0.17 g (0.51 mmol, quant.) of phenol.

To a stirred suspension of sodium hydride (0.28 g, 7.7 mmol) in dry THF (10 mL) was added the phenol (2.0 g, 5.9 mmol) in dry THF (20 mL) at 0° C. After stirring for 15 min, chloromethyl methyl ether (0.57 mL, 7.5 mmol) at 0° C. After 3 hr, the mixture was poured into a saturated solution of NH$_4$Cl and extracted with EtOAc. The organic extract was washed with a saturated solution of NaHCO$_3$, brine, dried over anhydrous Na$_2$SO$_4$, filtered and concentrated. The crude product was purified by chromatography on silica gel using 15% EtOAc/hexane to give 1.4 g (3.7 mmol, 62%) of YE-14.

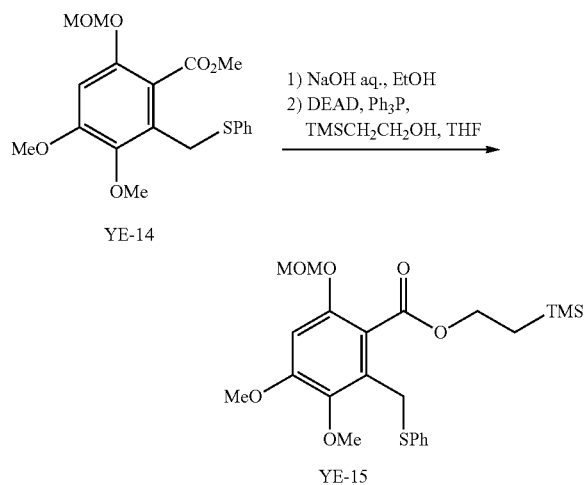

Using similar procedure for the intermediate 14 of NF2561, YE-14 (1.4 g, 3.7 mmol) was converted to YE-15 (1.6 g, 3.4 mmol, 93% 2 steps).

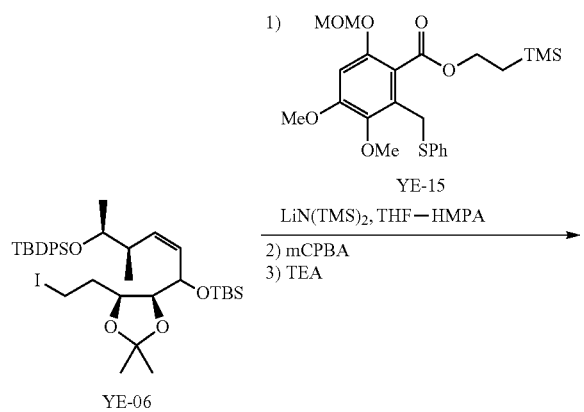

Using similar procedure for the intermediate 18 of NF2561, the iodide (502 mg, 0.68 mmol) was converted to YE-16 (315 mg, 0.33 mmol, 48% 3 steps).

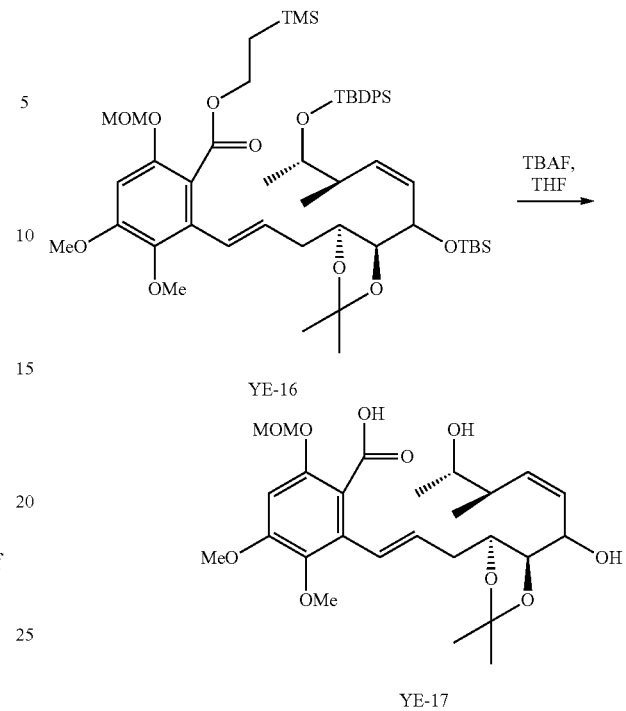

YE-16 (310 mg, 0.32 mmol) was dissolved in THF (12 mL). Then, 1.0M solution of tetrabutylammonium fluoride in THF (1.6 mL, 1.6 mmol) was added at 0° C. The mixture was stirred at rt for 2 days after which 10% KHSO$_4$ solution was added. The mixture was extracted with EtOAc and the organic extract was washed with water, brine, dried with anhydrous Na$_2$SO$_4$, filtered and concentrated. The crude product was dried by azeotropic distillation with toluene to give 270 mg of YE-17 with silyl impurity.

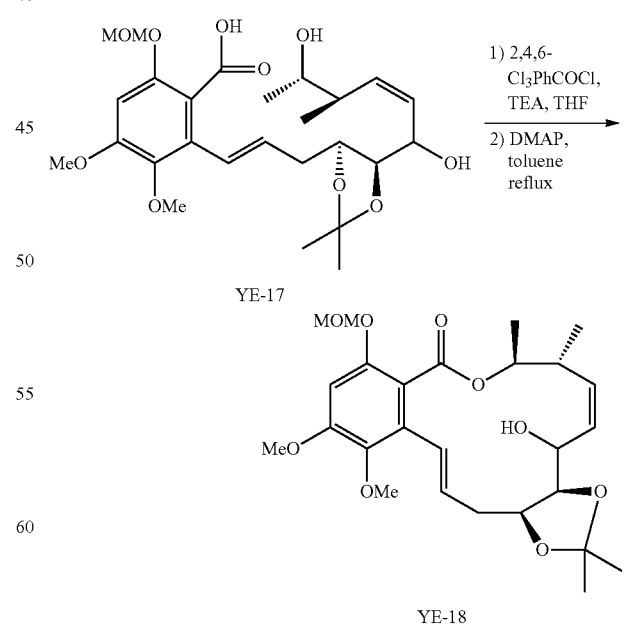

To a stirred solution of crude YE-17 (270 mg) in THF (20 mL) were added triethylamine (0.090 mL, 0.64 mmol) and 2,4,6-trichlorobenzoyl chloride (0.085 mL, 0.54 mmol) at rt. After 16 hrs, the reaction mixture was diluted with toluene (300 mL) and added dropwise to a solution of 4-(dimethylamino)pyridine (980 mg, 8.0 mmol) in toluene (320 mL) over a period of 6 hrs under reflux. The resultant mixture was stirred for 0.5 hr under reflux. After concentration under reduced pressure, the residue was dissolved in EtOAc and washed with 10% KHSO$_4$ aq sol., water, brine and dried over anhydrous Na$_2$SO$_4$, filtered and concentrated. The crude product was purified by chromatography on silica gel using 6-30% EtOAc/hexane to give 114 mg (0.23 mmol, 72% 3 steps) of YE-18.

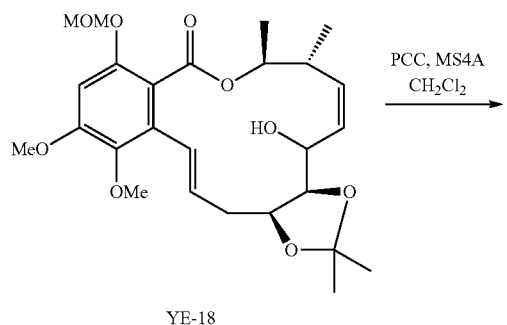

YE-18

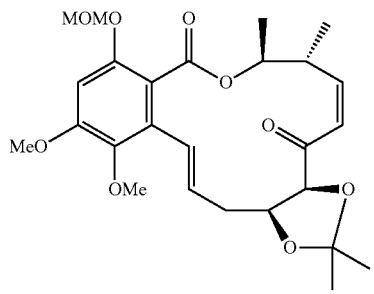

YE-19

Using similar procedure for 509-HD-125, YE-18 (20 mg, 0.041 mmol) was converted to YE-19 (22 mg, quant.).

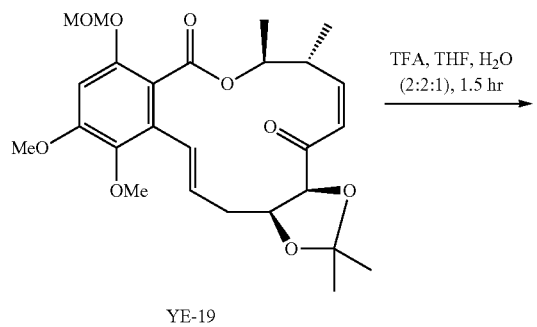

YE-19

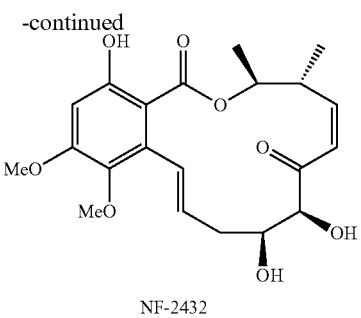

NF-2432

To a stirred solution of YE-19 (22 mg, 0.041 mmol) in THF (1.4 mL)-H$_2$O (0.7 mL) was added trifluoroacetic acid (1.4 mL) at 0° C. The mixture was then allowed to warm to rt. After 1.5 hrs, the mixture was poured into a saturated solution of NaHCO$_3$ and extracted with EtOAc. The organic extract was washed with water, brine and dried over anhydrous Na$_2$SO$_4$, filtered and concentrated. The crude product was purified by chromatography on silica gel using 30% EtOAc/hexane to give 13.3 mg (0.033 mmol, 81%) of NF2432.

Synthetic Procedure for NF2544

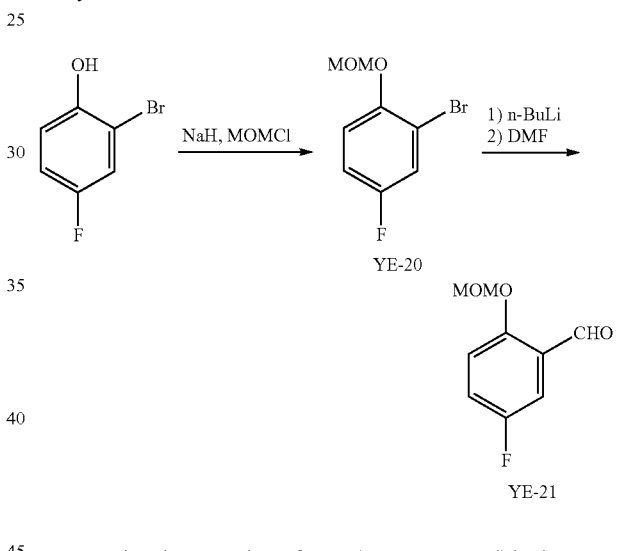

To a stirred suspension of NaH (2.3 g, 63 mmol) in dry THF (100 mL) were added 2-bromo-4-fluorophenol (10 g, 52 mmol) in thy THF (20 mL) at 0° C. After stirring for 30 min at 0° C., chloromethyl methyl ether (4.8 mL, 63 mmol) was added. The mixture was allowed to warm to rt and stirred for 1.5 hrs. The mixture was cooled to 0° C., poured into water and extracted with EtOAc. The organic extract was washed with water, brine, dried with anhydrous Na$_2$SO$_4$, filtered and concentrated. The concentrate was purified by chromatography on silica gel using 10% EtOAc/hexane to give 10.7 g (45.5 mmol, 87%) of YE-20.

To a stirred suspension of YE-20 (10.7 g, 46 mmol) in dry ether (150 mL) was added 1.6M n-BuLi in hexane (34 mL, 54.4 mmol) at −78° C. under nitrogen atmosphere. After 1 hr, dry DMF (15 mL) was added and the mixture was allowed to warm to it. It was quenched with a saturated solution of NH$_4$Cl and extracted with EtOAc. The organic extract was washed with a saturated solution of NH$_4$Cl, water, brine, dried over anhydrous Na$_2$SO$_4$, filtered and concentrated. The crude product was purified by chromatography on silica gel using 10% EtOAc/hexane to give 7.8 g (42 mmol, 93%) of YE-21.

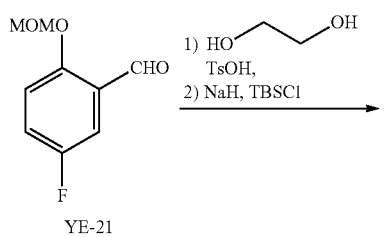

YE-21

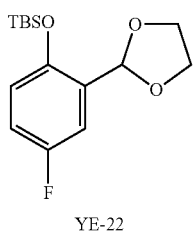

YE-22

To a stirred solution of YE-21 (6.8 g, 37 mmol) in toluene (200 mL) was added ethylene glycol (12 g, 193 mmol) and p-toluenesulfonic acid monohydrate (0.3 g) at rt. and refluxed using Dean-Stark apparatus. After 4 hr, the mixture was cooled to 0° C. in ice/water bath. Then TEA (15 ml, 0.10 mol) was added, the mixture was stirred for 10 min, then poured into a saturated solution of NaHCO$_3$. The mixture was extracted with EtOAc and the organic extract was washed with a saturated solution of NaHCO$_3$, brine, dried over anhydrous Na$_2$SO$_4$, filtered and concentrated to give 6.7 g of phenol as crude product.

To a stirred suspension of NaH (1.5 g, 41 mmol) in dry THF (120 mL) were added the phenol (6.7 g, 36 mmol) in dry THF (20 mL) at 0° C. After stirring for 10 mm at 0° C., TBSCl (6.3 g, 42 mmol) was added. The mixture was allowed to warm to rt and stirred overnight. The mixture was cooled to 0° C., poured into water and extracted with EtOAc. The organic extract was washed with water, brine, dried over anhydrous Na$_2$SO$_4$, filtered and concentrated. The concentrate was purified by chromatography on silica gel using 2% EtOAc/hexane (containing 0.2% of triethylamine) to give 8.75 g (29.3 mmol, 79% 2 steps) of YE-22.

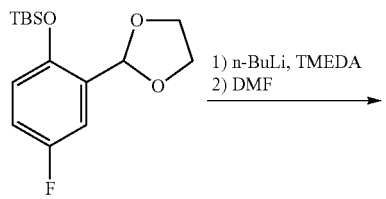

YE-22

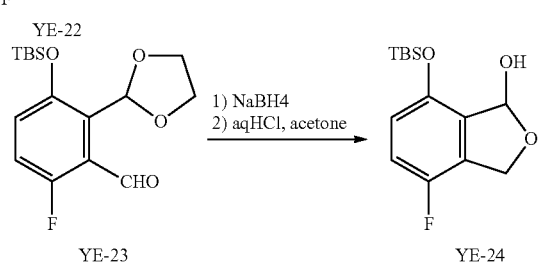

YE-23 YE-24

To a stirred suspension of YE-22 (20 g, 67 mmol) in THF (350 mL) was added 1.6M n-BuLi in hexane (50 mL, 80 mmol) at −78° C. under nitrogen atmosphere. After 1 hr TMEDA (15 mL, 99 mmol) was added and stirred at −78° C. for another 10 min. To the mixture was added dry DMF (5.0 mL, 65 mmol) and the mixture was allowed to warm to −20° C. and stirred for 40 min. It was quenched with AcOH (14 mL), and poured into water. The mixture was extracted with EtOAc and the organic extract was washed with a saturated solution of NaHCO$_3$, brine, dried over anhydrous Na$_2$SO$_4$, filtered and concentrated. The crude product was purified by chromatography on silica gel using 2-5% EtOAc/hexane to give 15.8 g (48.4 mmol, 72%) of YE-23.

To a stirred MeOH solution (350 mL) of YE-23 (15.8 g, 48.4 mmol) at 0° C. was added NaBH$_4$ (2.0 g, 53 mmol). The mixture was stirred at 0° C. for 30 min. Then the mixture was quenched with AcOH (10 mL), and poured into a saturated solution of NaHCO$_3$. The mixture was extracted with ether and the organic extract was washed with a saturated solution of NaHCO$_3$, brine, dried over anhydrous Na$_2$SO$_4$, filtered and concentrated to give 16.4 g (48.4 mmol, quant.) of alcohol.

To a stirred acetone solution (300 mL) of the alcohol (16.4 g, 48.4 mmol) at 0° C. was added 1N HCl (8 mL, 8 mmol). The mixture was stirred at 0° C. for 70 min, then was poured into a saturated solution of NaHCO$_3$. The mixture was partially concentrated to remove acetone and the concentrate was extracted with ether. The organic extract was washed with brine, dried over anhydrous Na$_2$SO$_4$, filtered and concentrated to give 13.6 g (47.8 mmol) of YE-24.

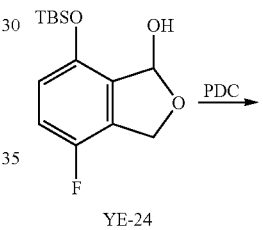

YE-24

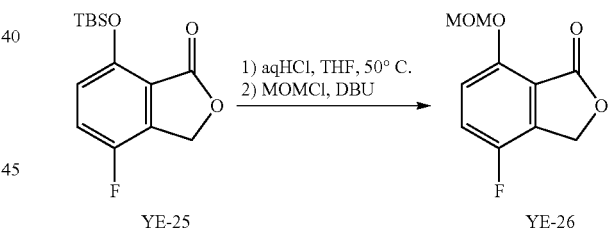

YE-25 YE-26

YE-24 (13.6 g, 47.8 mmol) was dissolved in 900 mL of dichloromethane and PDC (53.7 g, 143 mmol) were added to the solution. The reaction mixture was stirred for 7 d at rt and the mixture was diluted with ether (300 mL). After passing through Florisil column, YE-25 was obtained as colorless oil (11.7 g, 86%, 3 steps).

YE-25 (11.7 g, 41.4 mmol) was dissolved in THF (120 mL), 1.7N hydrochloric acid (60 mL, 100 mmol) were added and the mixture was stirred at 50° C. for 1 hrs, then refluxed for 3 hrs. The mixture was cooled to rt and filtrated. To the filtrated was added 5N NaOH (18 mL) and the organic layer was separated. The aqueous layer was saturated with NaCl and was extracted with EtOAc. The combined organic extract was concentrated and the concentrate was triturated with ether to give phenol (4.9 g, 32.2 mmol).

Using similar procedure for TM-37, the phenol (4.2 g, 27.6 mmol) was converted to YE-26 (4.2 g, 21.2 mmol, 77%).

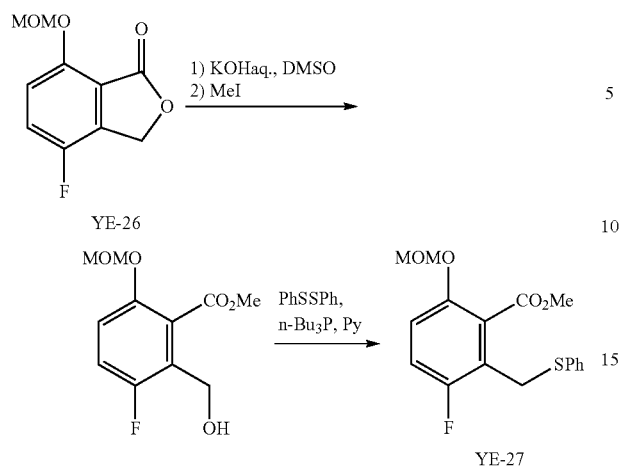
Using similar procedure for TM-50, YE-26 (4.1 g, 20.9 mmol) was converted to YE-27 (4.9 g, 14.6 mmol, 70% 3 steps).
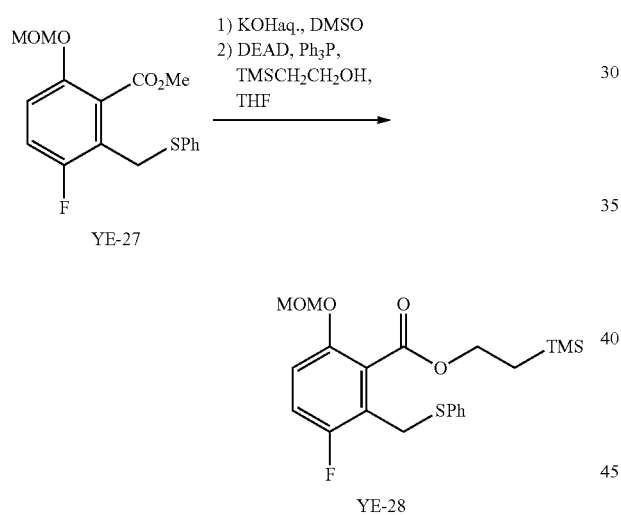
Using similar procedure for TM-39, YE-27 (1.5 g, 4.5 mmol) was converted to YE-28 (1.60 g, 3.8 mmol, 85% 2 steps).
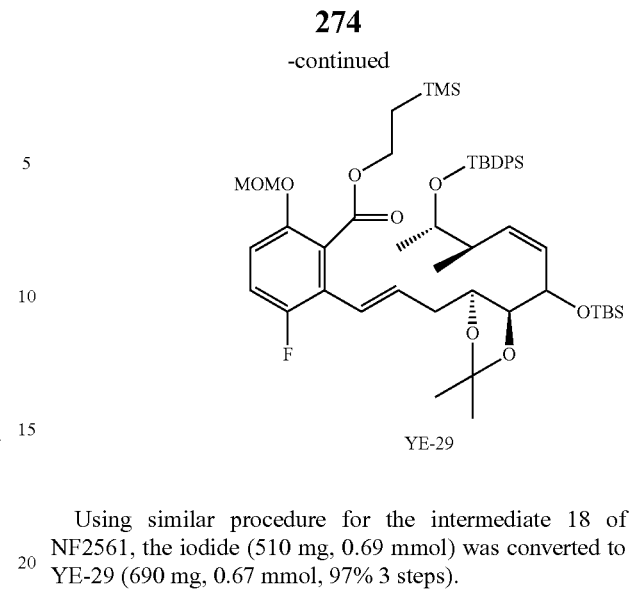
Using similar procedure for the intermediate 18 of NF2561, the iodide (510 mg, 0.69 mmol) was converted to YE-29 (690 mg, 0.67 mmol, 97% 3 steps).
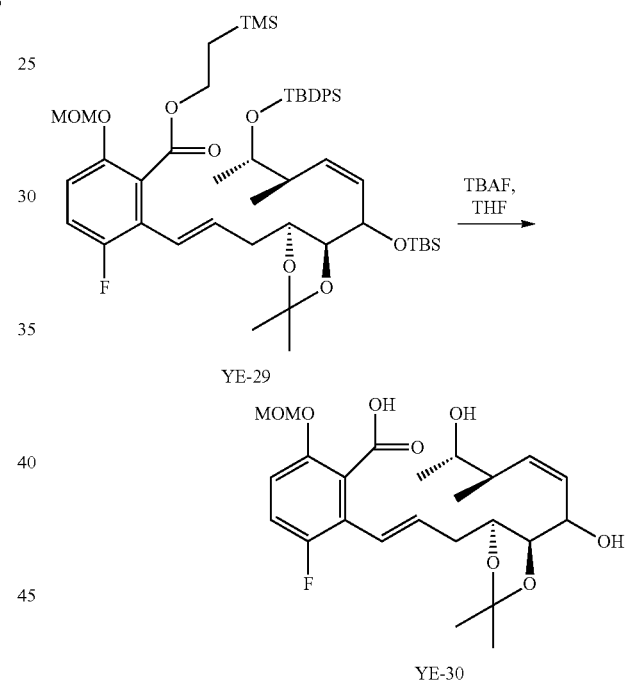
Using similar procedure for the intermediate YE-17, YE-29 (520 mg, 0.57 mmol) was converted to YE-30 (430 mg) with silyl impurity.
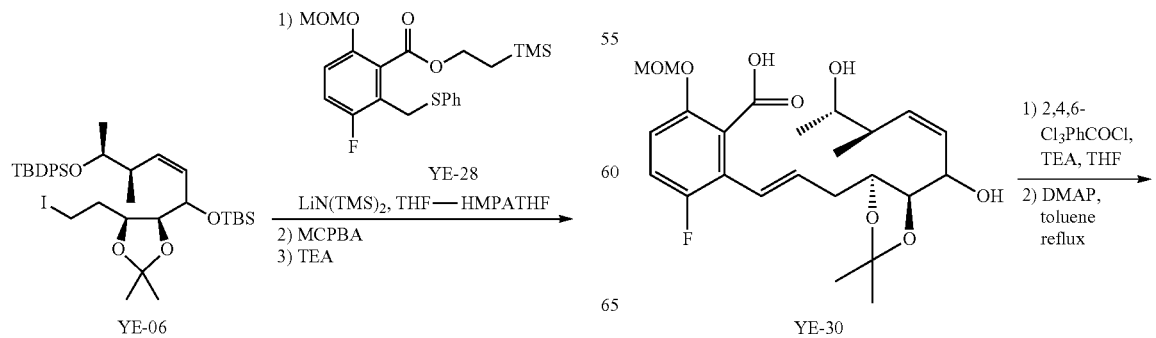

-continued

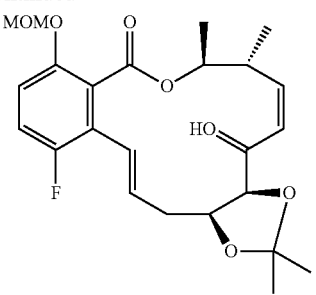

YE-31

Using similar procedure for YE-18, YE-30 (430 mg) was converted to YE-31 (94 mg, 0.21 mmol, 36.5% 3 steps).

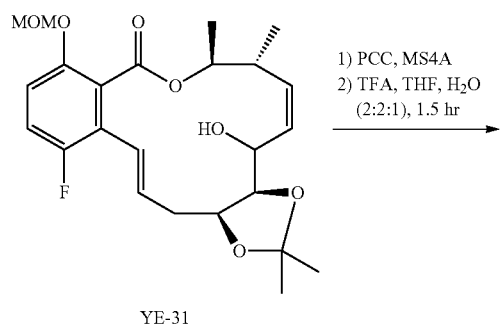

Using similar procedure for ER803064, YE-31 (45 mg, 0.099 mmol) was converted to NF-2544 (13 mg, 0.036 mmol, 36% 2 steps).

Synthetic Procedure for NF2547

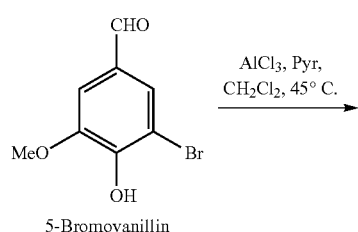

-continued

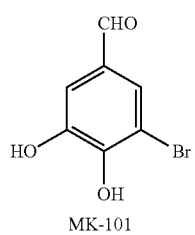 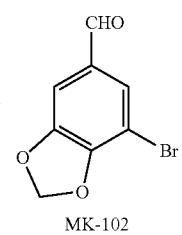

5-Bromovanillin (20.0 g, 86.56 mmol) and AlCl$_3$ (12.70 g, 95.22 mmol) were dissolved in 145 mL of dry CH$_2$Cl$_2$. To the stirred solution was dropwise added pyridine (30.80 mL, 380.9 mmol) over 10 min at rt (exothermic reaction). Then the mixture was warmed to 45° C. and stirred for 20 hrs after which it was cooled to rt. The resulting mixture was acidified with 3N HCl aq and extracted with AcOEt. The organic extract was washed with brine, dried over Na$_2$SO$_4$, filtered and concentrated to give crude colorless crystals of MK-101 (18.4 g, <98%). The crude MK-101 was used for next step without purification.

Crude MK-101 (13.15 g, assumed to contain 60.59 mmol), Br—CH$_2$—Cl (6.50 mL, 96.9 mmol), and Cs$_2$CO$_3$ (31.59 g, 96.9 mmol) were suspended in 200 mL of DMF and the mixture was stirred at 110° C. for 20 hrs. The resulting mixture was diluted with water and extracted with AcOEt. The organic extract was washed with brine, dried over Na$_2$SO$_4$, filtered and concentrated to give crude brown solid of MK-102. The crude product was purified by chromatography on silica gel (hexane/AcOEt: 6/1 to 5/1) to afford colorless crystals of MK-102 (11.1 g, 77% 2 steps).

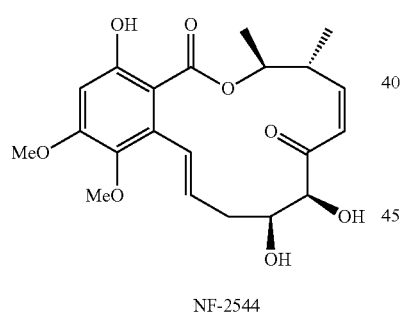 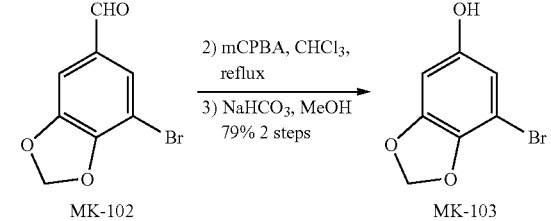

70% mCPBA (13.1 g, 53.1 mmol) was added to a stirred solution of MK-102 (5.07 g, 22.12 mmol) in 110 mL of CHCl$_3$ and the mixture was heated up to reflux. After 3 hrs at reflux the mixture was cooled to 0° C., quenched with aqueous solution of Na$_2$SO$_3$, and extracted with CH$_2$Cl$_2$. The organic extract was washed with saturated aqueous solution of NaHCO$_3$ and brine, then evaporated to give crude pale brown solid of intermediate formate.

The crude formate was dissolved in 100 mL of MeOH. NaHCO$_3$ (3.7 g, 44 mmol) was added and the suspension was stirred at rt for 30 min. Water and AcOEt were added to the mixture and organic extract was washed with brine, dried over Na$_2$SO$_4$, filtered and concentrated to give a crude oily solid of MK-103. The crude product was purified by chromatography on silica gel (hexane/AcOEt: 4/1) to afford colorless crystals of MK-103 (3.78 g, 79% 2 steps).

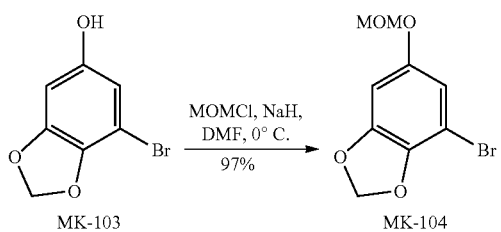

Using similar procedure for the synthesis of 509-HD-209 from 509-HD-207, MK-103 (3.78 g, 17.40 mmol) was converted to colorless oil of MK-104 (4.42 g, 97%).

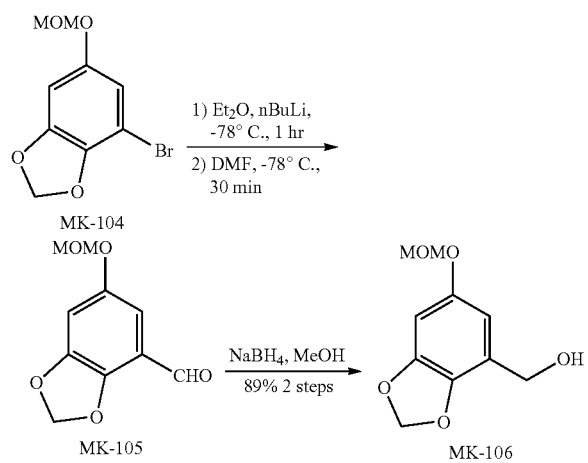

To a stirred solution of MK-104 (2.00 g, 7.66 mmol) in 26 mL of dry Et$_2$O was dropwise added n-BuLi in hexane (1.6M, 5.74 mL, 9.19 mmol, 1.2 eq.) at −78° C. After 1 hr dry DMF (1.20 mL, 15.3 mmol, 2.0 eq.) was added in one portion to the mixture and stirred at −78° C. for 30 min after which saturated aqueous solution of NH$_4$Cl was added. The resulting mixture was extracted with AcOEt and the organic extract was washed with brine, dried over Na$_2$SO$_4$, filtered, and concentrated to give crude yellow oil of MK-105 (1.60 g). The crude product was used for next step without purification.

The crude MK-105 (1.60 g, assumed to contain 7.66 mmol) was dissolved in 26 mL of MeOH and the stirred solution was cooled to 0° C. NaBH$_4$ (290 mg, 7.66 mmol) was added in some portions. After 20 min at 0° C. the reaction mixture was quenched with aqueous solution of NH$_4$Cl and extracted with AcOEt. The organic extract was washed with brine, dried over Na$_2$SO$_4$, filtered and concentrated to give crude oil. The crude product was purified by chromatography on silica gel (hexane/AcOEt: 3/1 to 2/1) to afford colorless crystals of MK-106 (1.44 g, 89% 2 steps).

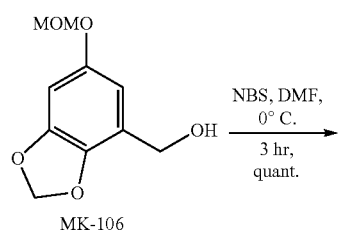

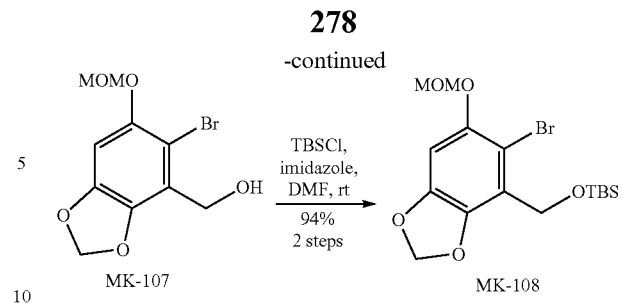

To a stirred solution of MK-106 (1.26 g, 5.92 mmol) in 30 mL of DMF was added NBS (1.16 g, 6.51 mmol, 1.1 eq.) at 0° C. The mixture was stirred at 0° C. for 3 hrs before aqueous solution of Na$_2$SO$_3$ and AcOEt were added. The organic extract was washed with brine, dried over Na$_2$SO$_4$, filtered, and concentrated to give crude colorless crystals of MK-107 (1.73 g, quant.). The crude product was used for next step without purification.

Crude MK-107 (1.73 g, assumed to contain 6.51 mmol) and imidazole (1.01 g, 14.80 mmol) were dissolved in 39 mL of DMF. TBS-Cl (1.78 g, 11.84 mmol) was added to the solution and the mixture was stirred at rt overnight after which AcOEt was added. The resulting mixture was washed with aqueous solution of NaHCO$_3$ and brine, dried over Na$_2$SO$_4$, filtered and concentrated to give crude crystals. The crude product was purified by chromatography on silica gel (hexane/AcOEt: 9/1) to afford colorless crystals of MK-108 (2.25 g, 94% 2 steps).

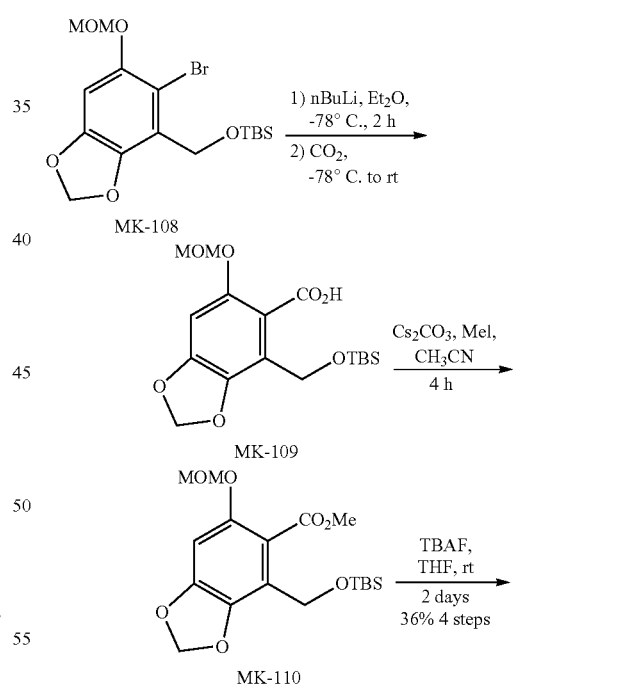

MK-108 (2.25 g, 5.56 mmol) was suspended in 90 mL of dry Et$_2$O. To the stirred suspension was added n-BuLi in hexane (1.6M, 4.52 mL, 7.23 mmol, 1.3 eq.) and the mixture was stirred at −78° C. After 1.5 hr the suspension turned homogeneous. The mixture was stirred for additional 30 min at −78° C. Then, excessive dry CO$_2$ gas (ca 30 eq.) was added by bubbling through an inlet over 15 min. The resulting mixture was stirred at −78° C. for 40 min after which it was allowed to warm to rt. After 1 hr the reaction mixture was quenched with saturated aqueous solution of Na$_2$CO$_3$ and washed with Et$_2$O. The basic aqueous layer was acidified with KHSO$_4$ and extracted with AcOEt. The organic extract was washed with brine, dried over Na$_2$SO$_4$, filtered, and concentrated to yield crude pale yellow crystals of MK-109 (1.93 g). The crude product was used for next step without purification.

Using similar procedure for the synthesis of MK-093 from MK-092, crude MK-109 (1.93 g) was converted to a crude brown oil of MK-110 (1.73 g). The crude product was used for next step without purification.

Crude MK-110 (1.73 g) was dissolved in 75 mL of THF. Then, TBAF in THF (1M, 9.0 mL, 9.0 mmol, 2 eq.) was added at rt. The mixture was stirred for 2 days before AcOEt and aqueous solution of KHSO$_4$C were added. The organic extract was washed with brine, dried over Na$_2$SO$_4$, filtered and concentrated. The crude product was purified by chromatography on silica gel (hexane/AcOEt: 2/1) to afford colorless crystals of MK-111 (476 mg, 36% 4 steps).

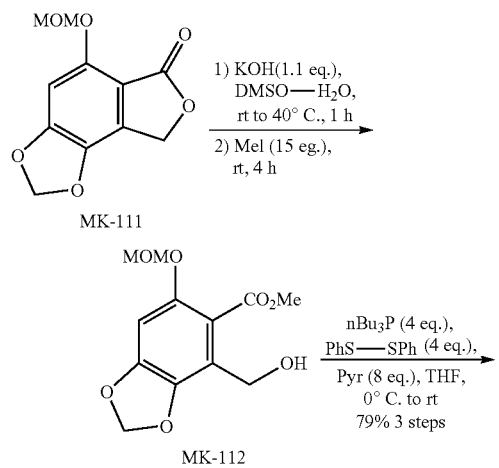

Using similar procedure for the synthesis of NY-90 from NY-89, MK-111 (412 mg, 1.73 mmol) was converted to crude pale yellow oil of MK-112 (435 mg). The crude product was used for next step without purification.

Using similar procedure for the synthesis of NY-91 from NY-90, crude MK-112 (435 mg) was converted to colorless oil of MK-113 (494 mg, 79% 3 steps).

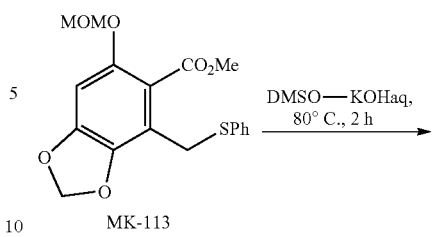

MK-113

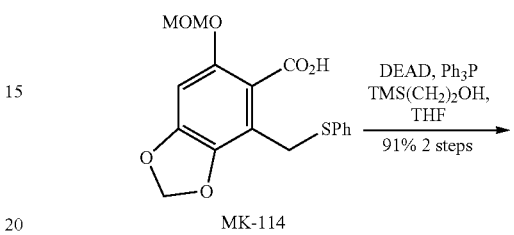

MK-114

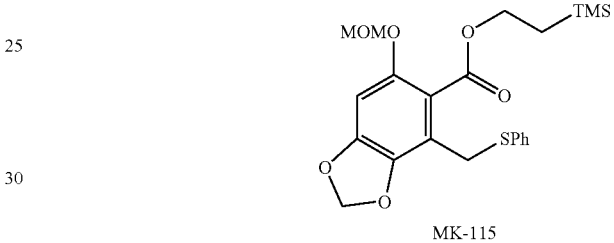

MK-115

To a stirred solution of MK-113 (423 mg, 1.17 mmol) in 9 mL of DMSO was added a solution of KOH (196 mg, 3.50 mmol) in 4.5 mL of water and the mixture was heated to 80° C. After stirred for 2 hrs, the mixture was cooled to rt and diluted with Et$_2$O. The mixture was acidified with aqueous solution of KHSO$_4$ and extracted with AcOEt. The organic extract was washed with brine, dried over Na$_2$SO$_4$, filtered, and concentrated to give crude pale yellow crystals of MK-114 (428 mg). It was used for next step without purification.

Using similar procedure for the synthesis of MK-047 from MK-046, crude MK-114 (428 mg) was converted to pale pink oil of MK-115 (476 mg, 91% 2 steps) as compound purified.

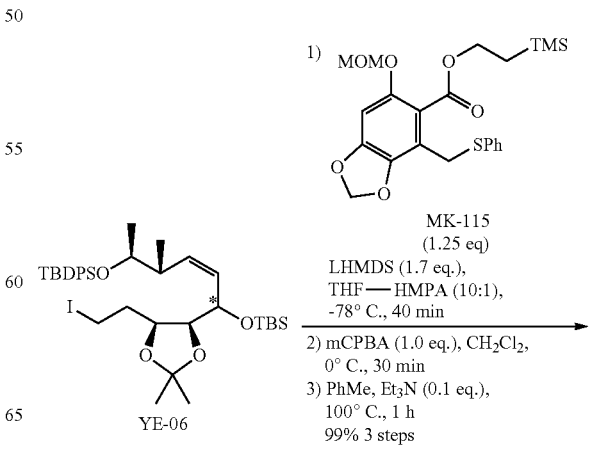

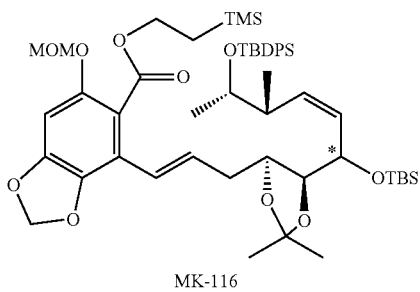

MK-116

Using similar procedure for the synthesis of compound 18, the intermediate of NF2561, from compound 16, YE-06 (627 mg, 0.851 mmol) coupled with MK-115 (474 mg, 1.06 mmol) was converted to pale yellow oil of MK-116 (804 mg, 99% 3 steps).

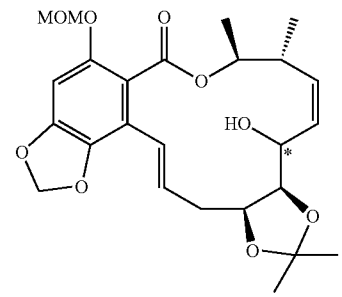

MK-118

Using similar procedure for the synthesis of YE-18 from YE-17, the crude MK-117 (735 mg, assumed to contain 0.844 mmol) was converted to a colorless solid of MK-118 (192 mg, 48% 3 steps).

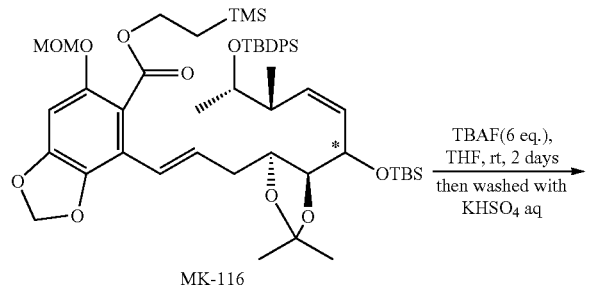

MK-116 → [TBAF (6 eq.), THF, rt, 2 days then washed with KHSO₄ aq]

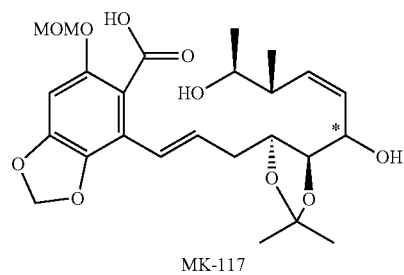

MK-117

Using similar procedure for the synthesis of YE-17 from YE-16, MK-116 (800 mg, 0.844 mmol) was converted to crude oil of MK-117 (735 mg, including silyl impurity). The crude product was used for next step without purification.

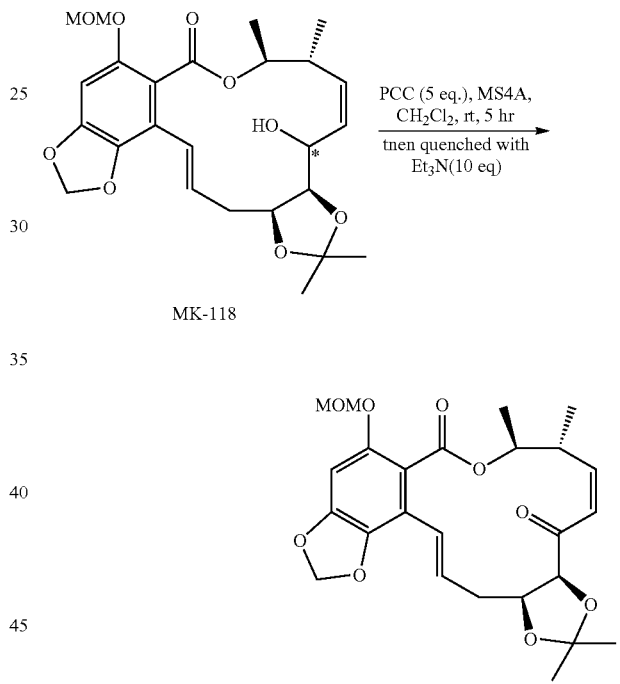

MK-118 → [PCC (5 eq.), MS4A, CH₂Cl₂, rt, 5 hr then quenched with Et₃N (10 eq)] → MK-119

Using similar procedure for the synthesis of 509-HD-125 from 509-HD-119B, MK-118 (141 mg, 0.296 mmol) was converted to crude pale yellow solid of MK-119 (104 mg, <74%). The crude MK-119 was used for next step without purification.

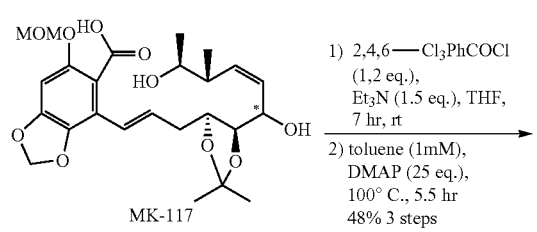

MK-117 → 1) 2,4,6—Cl₃PhCOCl (1,2 eq.), Et₃N (1.5 eq.), THF, 7 hr, rt  2) toluene (1mM), DMAP (25 eq.), 100° C., 5.5 hr  48% 3 steps

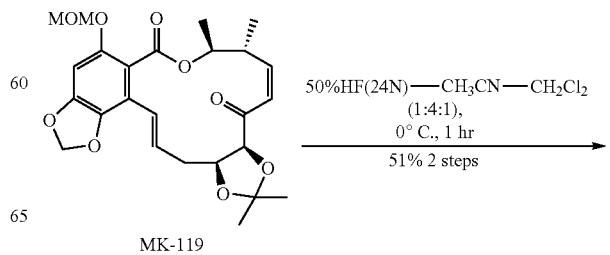

MK-119 → [50% HF (24N)—CH₃CN—CH₂Cl₂ (1:4:1), 0° C., 1 hr, 51% 2 steps]

-continued

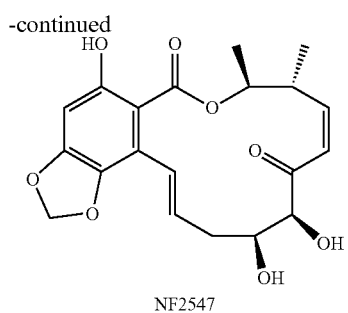

NF2547

Using similar procedure for the synthesis of NF2306 from MK-090, crude MK-119 (104 mg) was converted to crude pale yellow oil. The crude product was purified by chromatography on silica gel (hexane/AcOEt: 1/2) to afford pale yellow crystals of NF2547 (59 mg, 51% 2 steps).

Synthetic Procedure for NF-2553

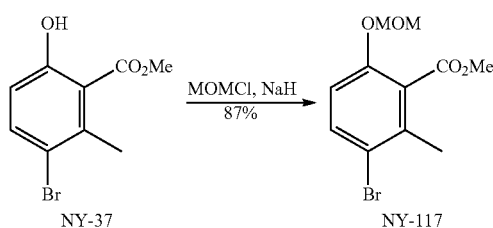

Using same procedure for 509-HD-209, NY-37 (4.8 g, 19.59 mmol) was converted to NY-117 (4.93 g).

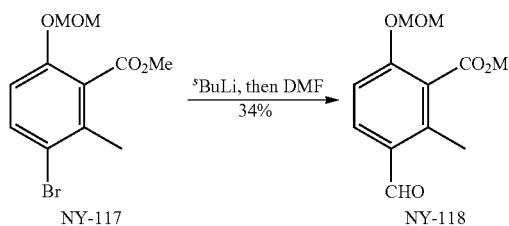

NY-117 (2.89 g, 10 mmol) was dissolved in Et$_2$O (40 mL) and cooled to −78° C., under nitrogen. Then, sec-BuLi (1.3M/cyclohexane, 9.3 mL, 12.09 mmol) was slowly added and the reaction was stirred at −78° C. for 30 min. DMF (1.55 mL, 20 mmol) was added to the solution, then the solution was stirred at −78° C. for 10 min. The mixture was quenched with sat. NH$_4$Cl and extracted with EtOAc. The organic layer was washed with water, brine and dried over Na$_2$SO$_4$, filtered and concentrated. The crude product was purified on silica gel column with hexane/EtOAc, 15:1, 10:1, 8:1, 6:1, 5:1, 4:1 to give 811 mg of NY-118.

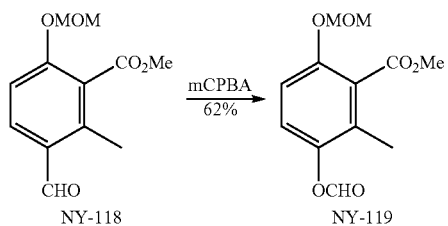

A mixture of NY-118 (4.09 g, 17.17 mmol), mCPBA (10 g, 40.56 mmol) and CHCl$_3$ (15 mL) was refluxed for 2.5 hrs. The reaction mixture was quenched with sat. Na$_2$S$_2$O$_3$ and extracted with EtOAc. The organic layer was washed with sat. Na$_2$S$_2$O$_3$, sat. NaHCO$_3$ (×2), brine, dried over Na$_2$SO$_4$, filtered and concentrated. The crude product was purified on silica gel column with hexane/EtOAc, 10:1, 8:1 to give 2.58 g of NY-119.

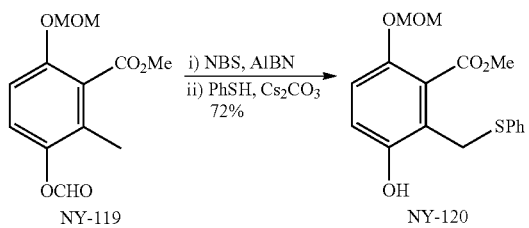

Using same procedure for 10, NY-119 (2.58 g, 10.15 mmol) was converted to NY-120 (2.45 g).

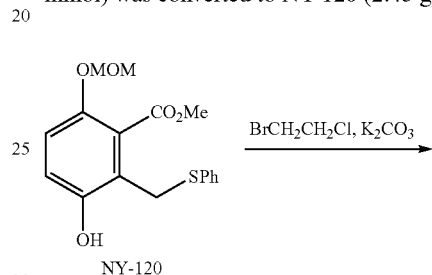

A mixture of NY-120 (470 mg, 1.41 mmol), 2-bromo-1-chloroethane (0.35 ml, 4.22 mmol), K$_2$CO$_3$ (292 mg, 2.11 mmol) was refluxed for 6 hrs. Then, additional 2-bromo-1-chloroethane (0.35 ml, 4.22 mmol) was added and the mixture was refluxed for 15 hrs. K$_2$CO$_3$ (450 mg, 3.26 mmol) and 2-bromo-1-chloroethane (1.05 ml, 12.67 mmol) were added and the mixture was refluxed for 4 hrs. The insoluble material was filtered and the filtrate was concentrated. The residue was diluted with EtOAc and washed with water, brine, dried over Na$_2$SO$_4$, filtered and concentrated to give 519 mg of NY-121.

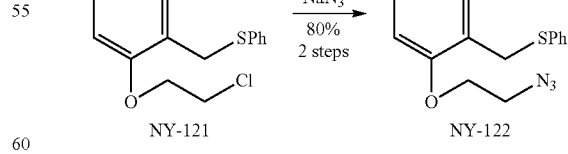

A mixture of NY-121 (519 mg, 1.31 mmol), NaN$_3$ (212 mg, 3.26 mmol) and DMF (10 mL) was stirred at 80° C. for 3 hrs. The mixture was diluted with EtOAc and washed with water (×3), brine, dried over Na$_2$SO$_4$, filtered and concentrated. The crude product was purified on silica gel column with hexane/EtOAc, 8:1 to give additional 452 mg of NY-122.

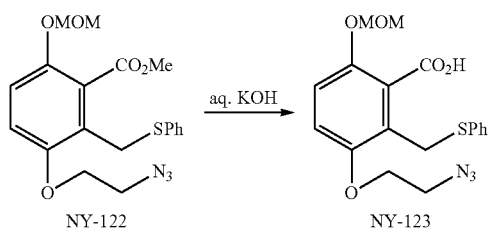
Using same procedure for NY-110, NY-122 (450 mg, 1.12 mmol) was converted to NY-123 (442 mg).
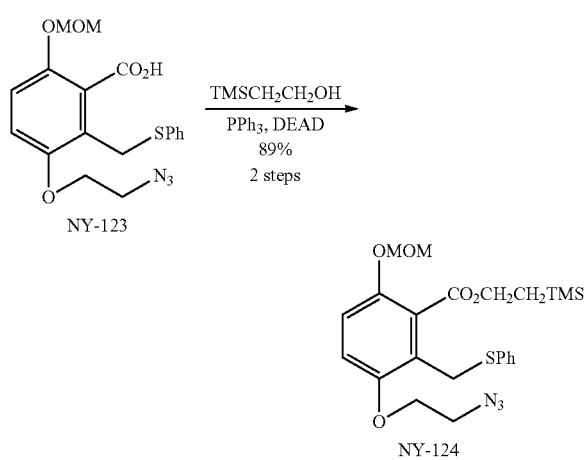
Using same procedure for 509-HD-213, NY-123 (322 mg, 0.827 mmol) was converted to NY-124 (365 mg).
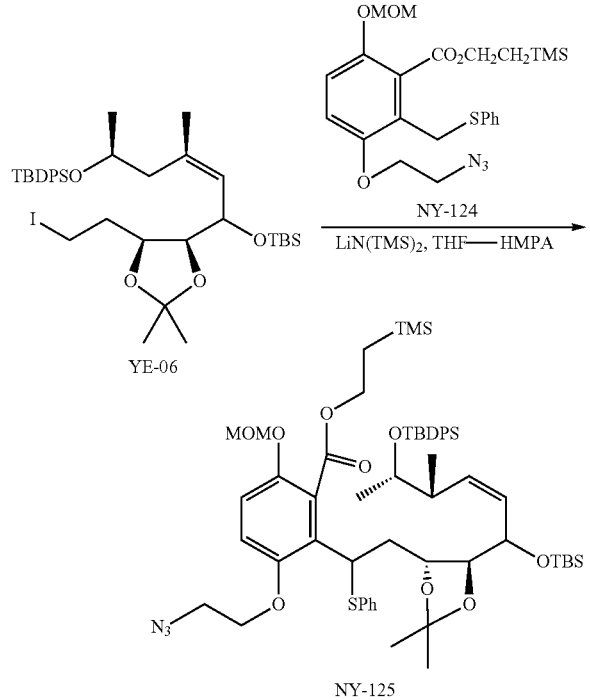
Using same procedure for 16, YE-06 (441 mg, 0.598 mmol) was converted to crude product of NY-125 (857 mg).
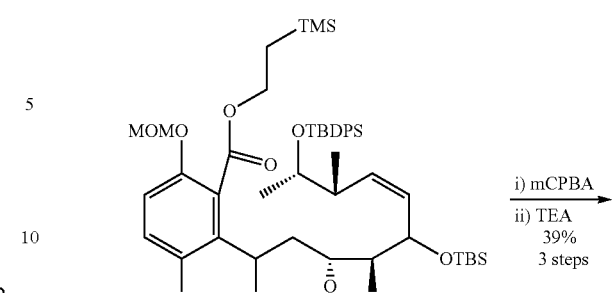
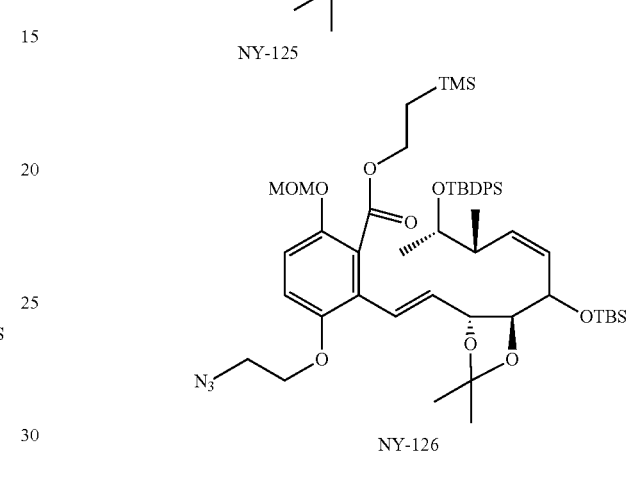
Using same procedure for 18, NY-125 (857 mg) was converted to NY-126 (231 mg).
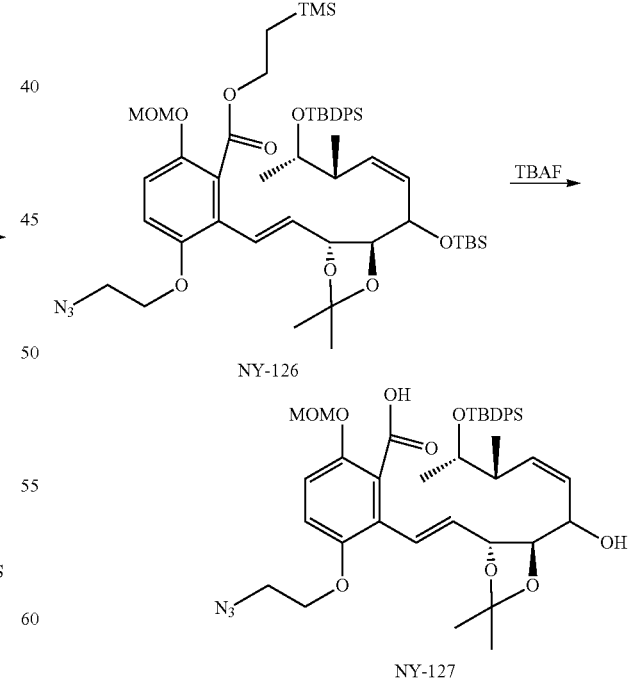
Using same procedure for 509-HD-116, NY-126 (230 mg, 0.233 mmol) was converted to NY-127 (197 mg). NY-127 was used without purification for the next step.

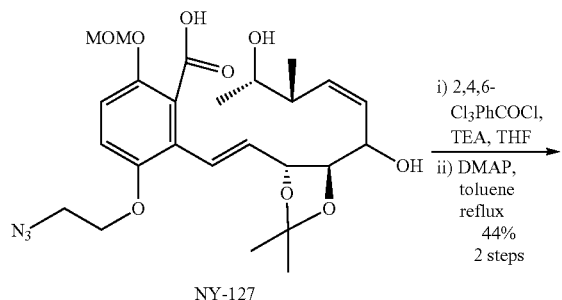

NY-127

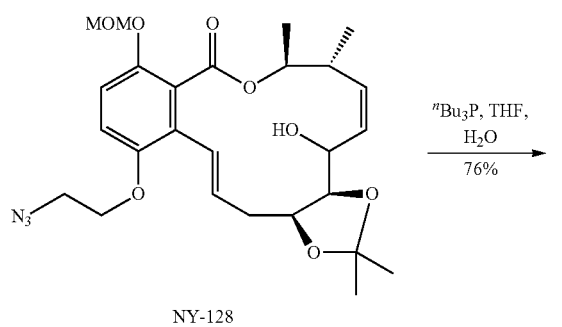

NY-128

Using same procedure for TM-12, NY-127 (197 mg, 0.233 mmol) was converted to NY-128 (53 mg).

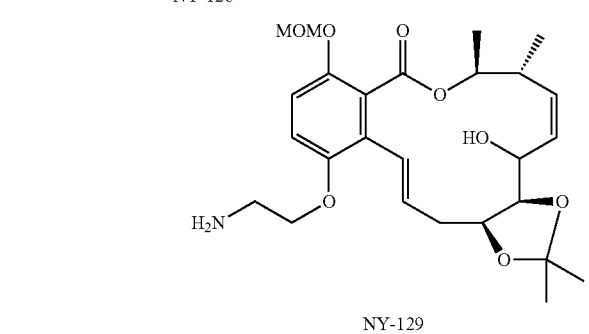

NY-128

To a solution of NY-128 (7.2 mg, 0.0139 mmol) in THF (1 mL), n-Bu$_3$P (3.5 µL) was added and stirred at room temperature for 80 min. Additional n-Bu$_3$P (3.5 µL) was added and the mixture was stirred for 80 min. Then, water (50 µL) was added to the reaction mixture, and the mixture was stirred at room temperature for 3 hrs. The reaction mixture was dried over Na$_2$SO$_4$, filtered and concentrated. The crude product was purified on silica gel column with CH$_2$Cl$_2$/MeOH, 98:2, 95:5, 9:1 to give 5.2 mg of NY-129.

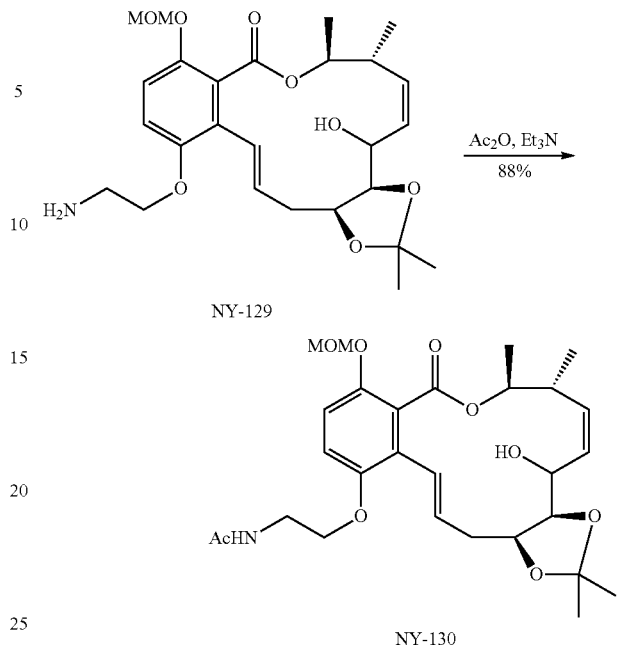

NY-129

NY-130

To a solution of NY-129 (5.2 mg, 0.0106 mmol), Et$_3$N (5 µL, 0.0359 mmol), Ac2O (1.5 µL, 0.0159 mmol) was added at 0° C. and stirred for 40 min. The reaction mixture was quenched with sat. NH$_4$Cl and extracted with EtOAc. The organic layer was washed with water, sat. NaHCO$_3$, brine, dried over Na$_2$SO$_4$ filtered and concentrated to give 5 mg of NY-130.

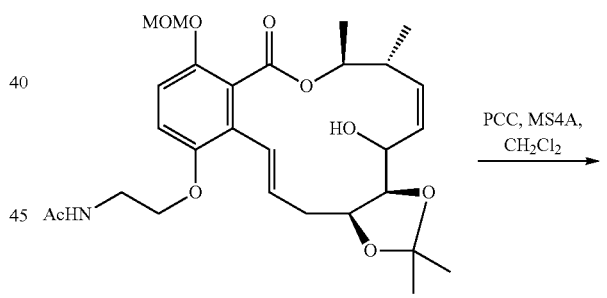

NY-130

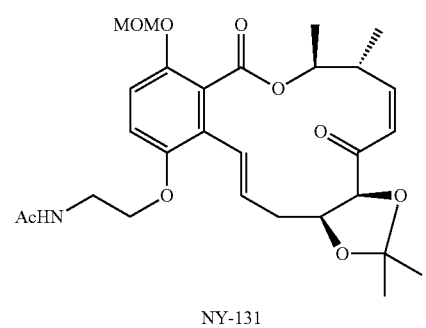

NY-131

Using same procedure for 509-HD-125, NY-130 (5 mg, 0.00937 mmol) was converted to NY-131 (6.5 mg). NY-131 was used without purification for the next step.

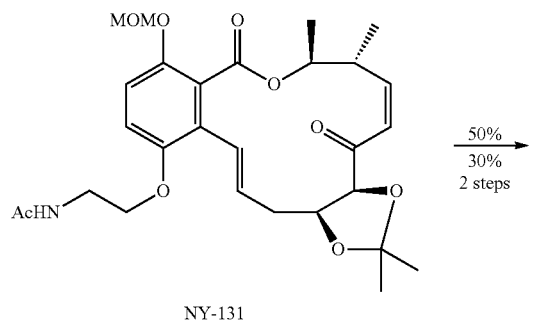
NY-131
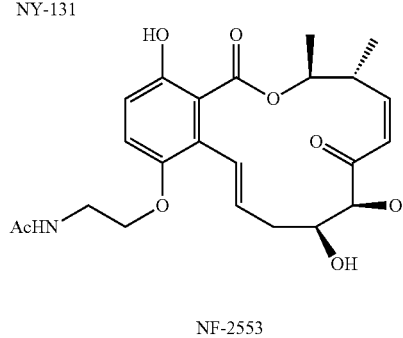
NF-2553
Using same procedure for B2538, NY-131 (6.4 mg, 0.00937 mmol) was converted to NF-2553 (1.3 mg).
Synthetic Procedure for NF-2556
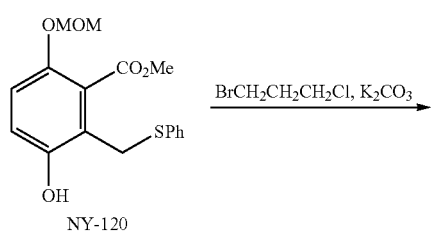
NY-120
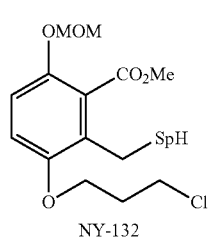
NY-132
Using same procedure for NY-121, NY-120 (670 mg, 2 mmol) was converted to NY-132 (875 mg).
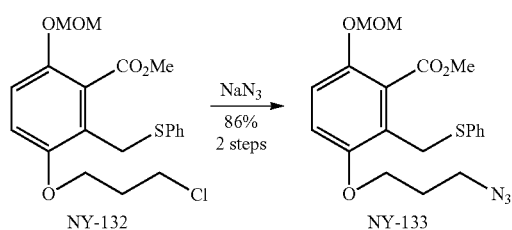
Using same procedure for NY-122, NY-132 (873 mg, 2 mmol) was converted to NY-133 (716 mg).
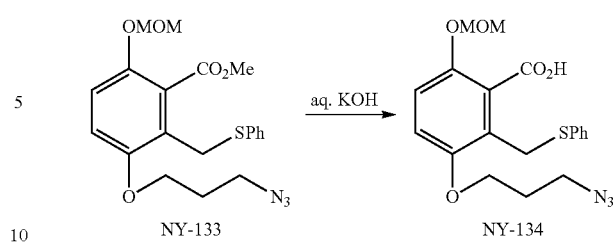
Using same procedure for NY-123, NY-133 (708 mg, 1.7 mmol) was converted to NY-134 (694 mg).
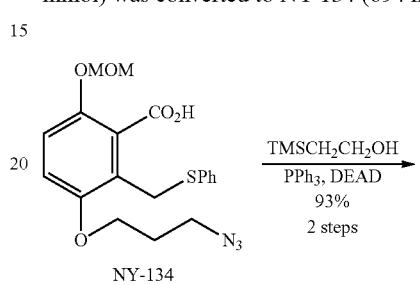
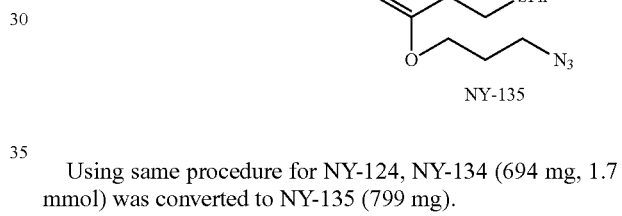
Using same procedure for NY-124, NY-134 (694 mg, 1.7 mmol) was converted to NY-135 (799 mg).
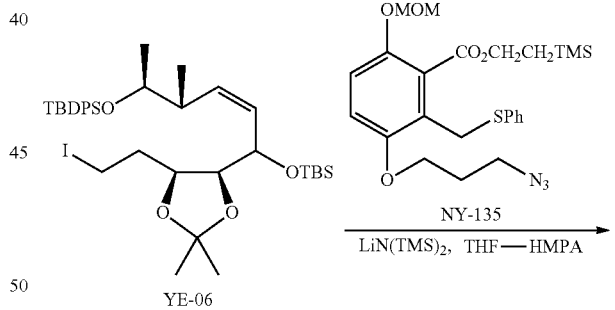
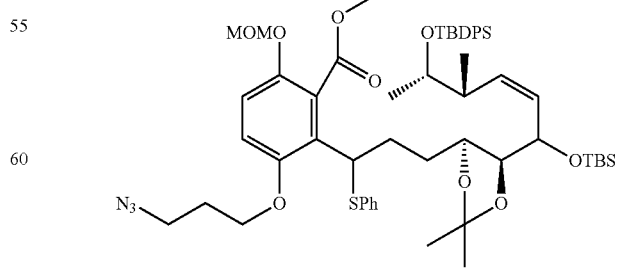
NY-136

Using same procedure for 16, YE-06 (318 mg, 0.432 mmol) was converted to crude product of NY-136 (683 mg).

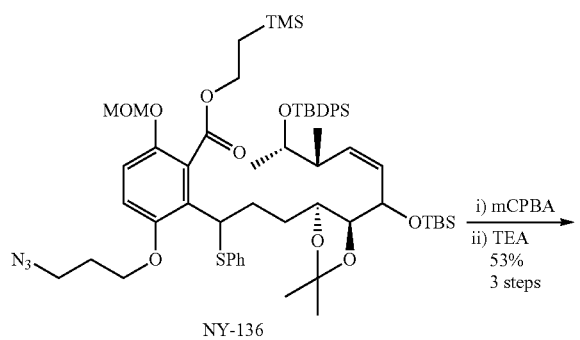

NY-136

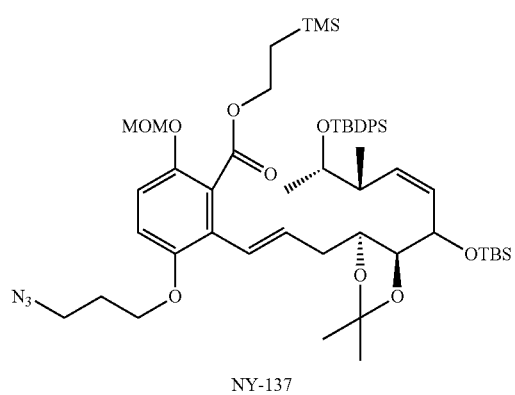

NY-137

Using same procedure for 18, NY-136 (682 mg) was converted to NY-126 (229 mg).

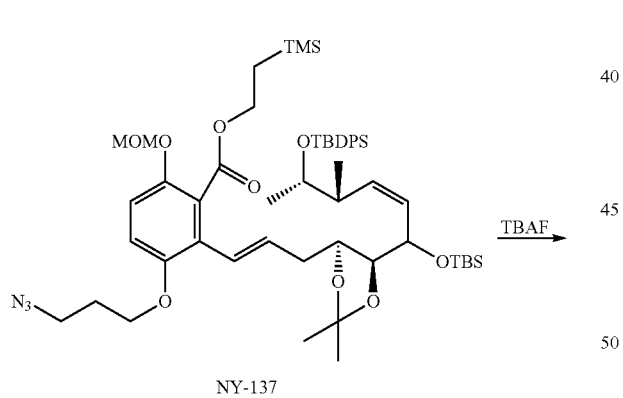

NY-137

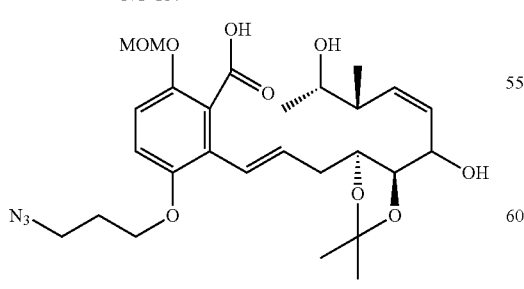

NY-138

Using same procedure for 509-HD-116, NY-137 (225 mg, 0.224 mmol) was converted to NY-138 (207 mg). NY-138 was used without purification for the next step.

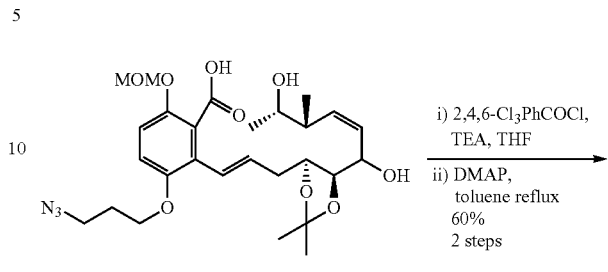

NY-138

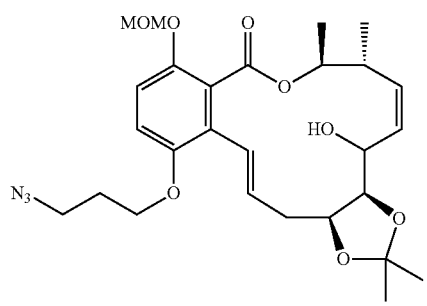

NY-139

Using same procedure for TM-12, NY-138 (207 mg, 0.224 mmol) was converted to NY-139 (72 mg).

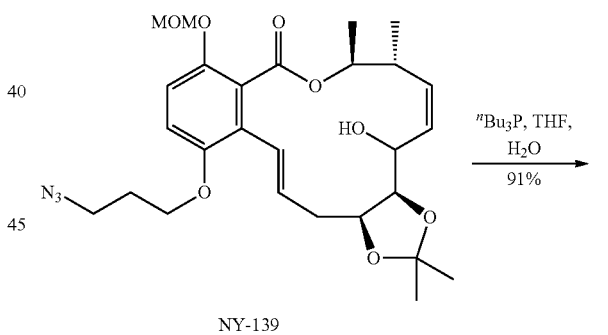

NY-139

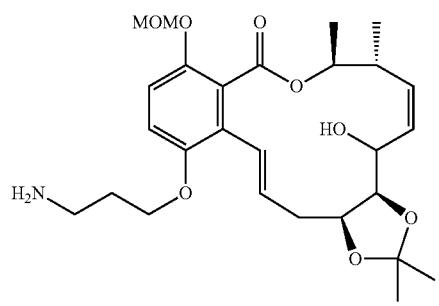

NY-140

Using same procedure for NY-129, NY-139 (33 mg, 0.0621 mmol) was converted to NY-140 (28.5 mg).

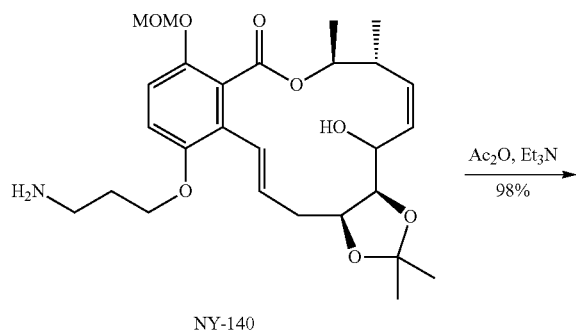

NY-140

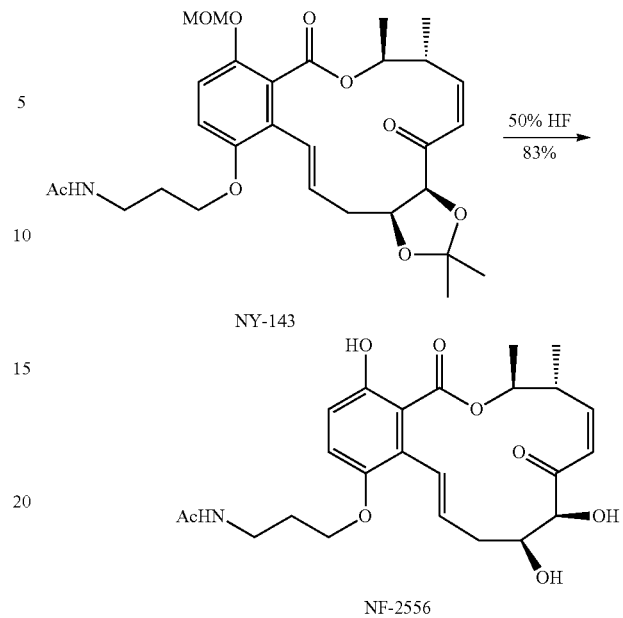

NY-143

Using same procedure for B2538, NY-143 (18 mg, 0.033 mmol) was converted to NF-2556 (12.6 mg).

Preparation of C13-C analogs, NF1774, NF2546, NF2550, NF2551, NF2552, NF2554, NF2555, and NF2560

Synthetic Procedure for NF-1774

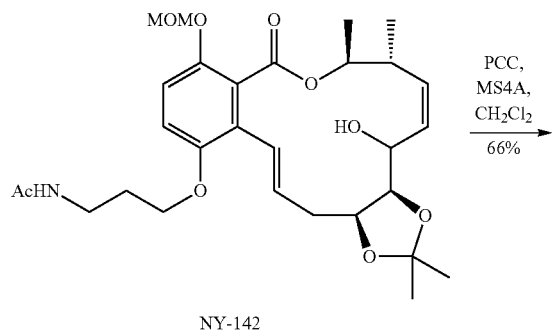

NY-141

Using same procedure for NY-130, NY-140 (28 mg, 0.0554 mmol) was converted to NY-141 (29.8 mg).

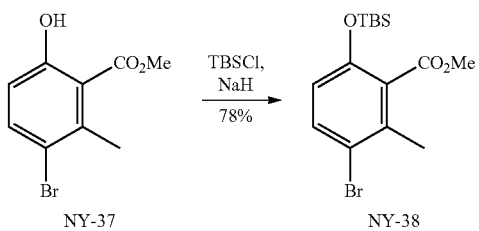

Using same procedure for 9, NY-37 (8.1 g, 33.05 mmol) was converted to NY-38 (9.28 g).

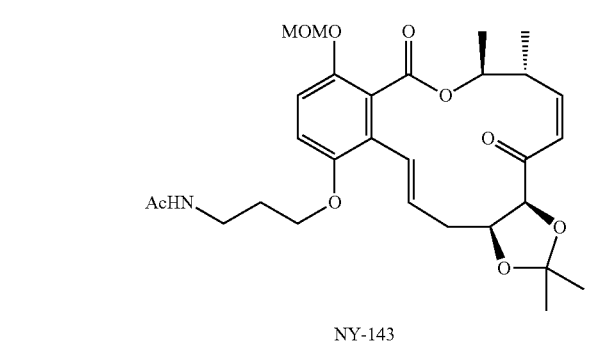

NY-142

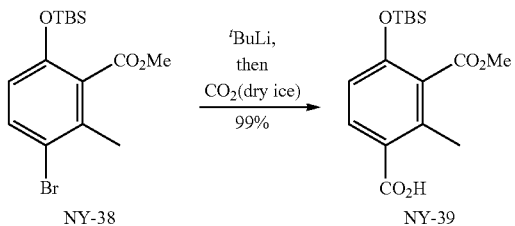

NY-38 (31.76 g, 88.39 mmol) was dissolved in Et$_2$O (300 mL) and cooled to −78° C., under nitrogen. Then, t-BuLi (1.7M/pentane, 100 mL, 170 mmol) was slowly added and the reaction was stirred at −78° C. for 20 min. Dry ice was added to the solution, then the solution was allowed to warm to rt and was stirred for 1.5 hrs. The mixture was quenched with sat. NH$_4$Cl, acidified with 10% citric acid, extracted with EtOAc (×2). The organic layers were washed with water, brine and dried over Na$_2$SO$_4$, filtered and concentrated to give 28.39 g of NY-39.

NY-143

Using same procedure for 509-HD-125, NY-130 (5 mg, 0.00937 mmol) was converted to NY-131 (18 mg).

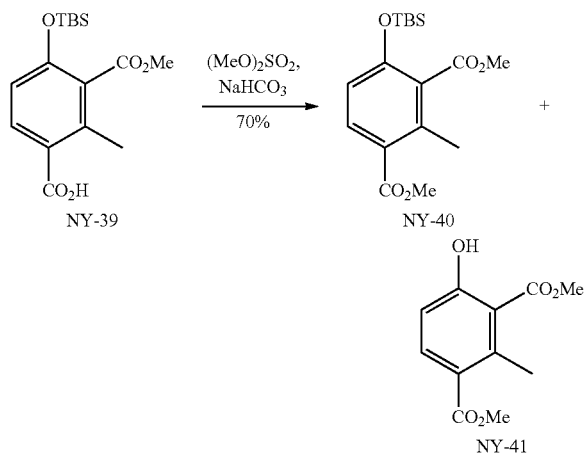

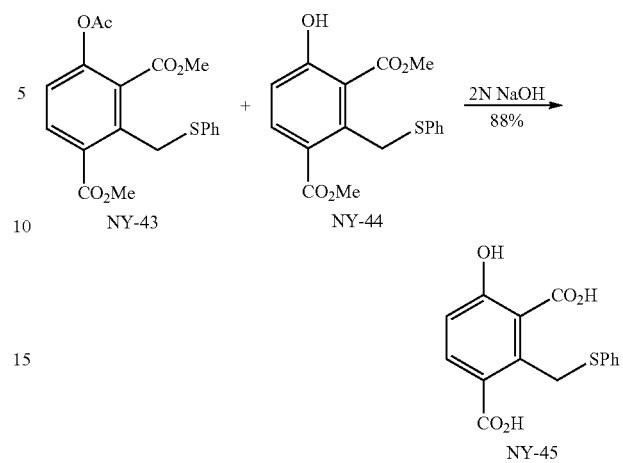

A mixture of NY-39 (25.48 g, 78.54 mmol), dimethyl sulfate (7.8 mL, 82.43 mmol), NaHCO$_3$ (9.9 g, 117.8 mmol) and acetone (200 mL) was refluxed for 14 hrs. The insoluble material was filtered and the filtrate was concentrated. The residue was diluted with EtOAc and washed with sat. NH$_4$Cl, water, brine, dried over Na$_2$SO$_4$, filtered and concentrated. The crude product was purified on silica gel column with hexane/EtOAc, 50:1, 40:1, 30:1, 15:1 to give 7.95 g of NY-40 and 6.97 g of the desilylated product NY-41.

A mixture of NY-43 (8.74 g, 23.34 mmol), NY-44 (7.86 g, 23.65 mmol), 2N NaOH (230 mL) and MeOH (300 mL) was refluxed for 24 hrs. The mixture was concentrated and the residue was acidified with 2N HCl, extracted with EtOAc. The organic layer was washed with water, brine, dried over Na$_2$SO$_4$, filtered and concentrated to give 12.62 g of NY-45.

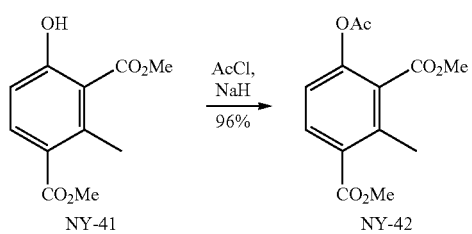

Using same procedure for NY-07, NY-41 (11.75 g, 52.41 mmol) was converted to NY-42 (13.43 g).

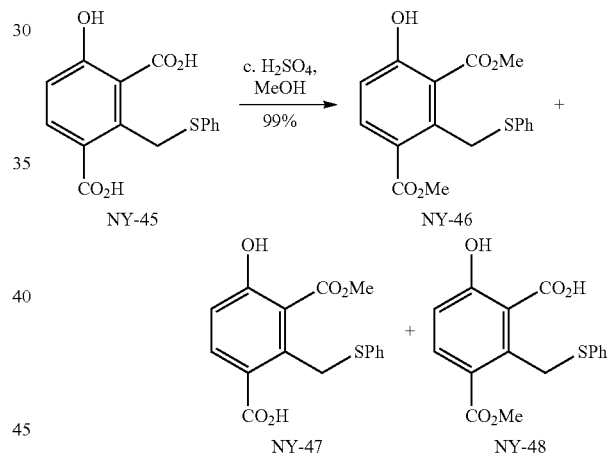

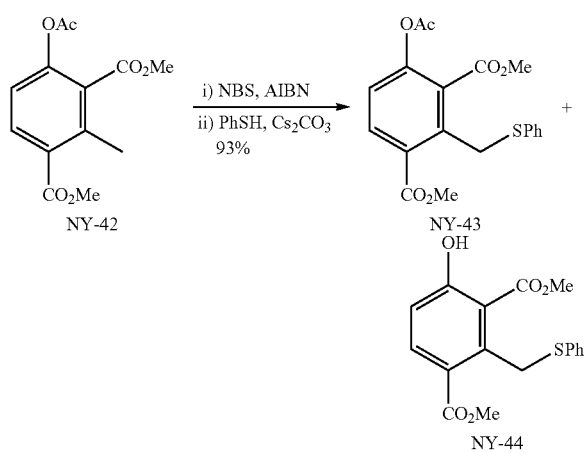

A mixture of NY-45 (12.62 g, 41.47 mmol), conc. sulfuric acid (0.8 mL) and MeOH (200 mL) was refluxed for 15 hrs. The mixture was concentrated and the residue was diluted with EtOAc and washed with water, brine, dried over MgSO$_4$, filtered and concentrated. The crude product was purified on silica gel column with hexane/EtOAc, 6:1, 5:1, 4:1, 1:1 to give 2 g of NY-46 and 11.1 g of mixture of NY-47 (small amount) and NY-48.

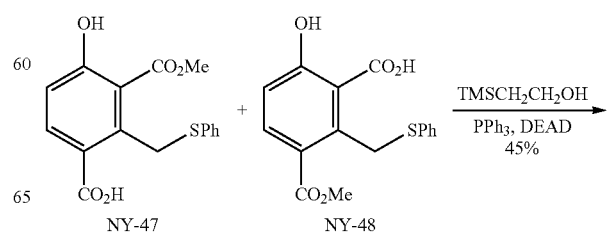

Using same procedure for 10, NY-42 (13.43 g, 50.44 mmol) was converted to NY-43 (8.74 g) and the deacetylated product NY-44 (7.86 g).

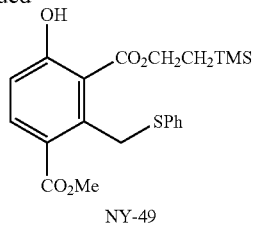

Using same procedure for 509-HD-213, a mixture of NY-47 and NY-48 (500 mg, 1.57 mmol) was converted to NY-49 (297 mg).

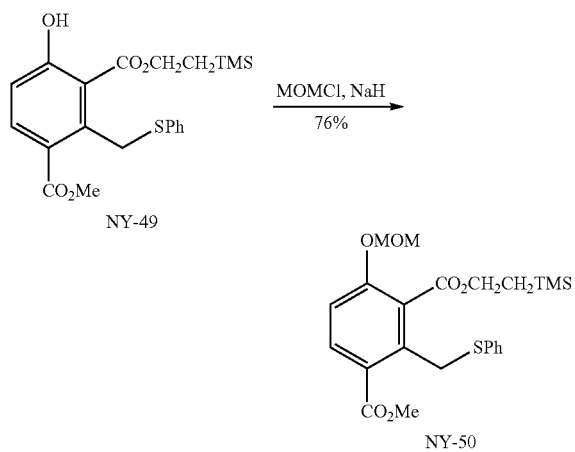

Using same procedure for 509-HD-209, NY-49 (297 mg, 0.71 mmol) was converted to NY-50 (250 mg).

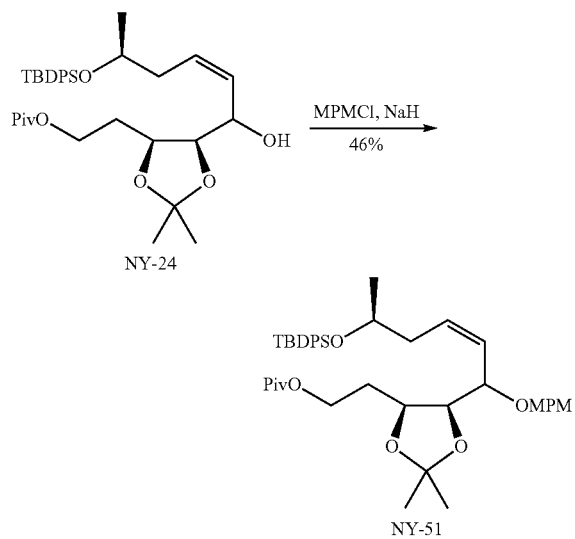

To a mixture of 60% NaH in mineral oil (330 mg, 8.25 mmol) and DMF (20 mL), a solution of NY-24 (3.46 g, 5.94 mmol) in DMF (20 mL) was gradually added at 0° C. and stirred for 30 min. Then, MPMCl (1.2 ml, 8.85 mmol) was added and the reaction mixture was allowed to warm to room temperature and stirred for 12 hrs. The reaction mixture was poured into ice-cooled sat. NH₄Cl and extracted with EtOAc. The organic layer was washed with water (×2), brine, dried over Na₂SO₄, filtered and concentrated. The crude product was purified on silica gel column with hexane/EtOAc, 18:1, 15:1 to give 1.9 g of NY-51.

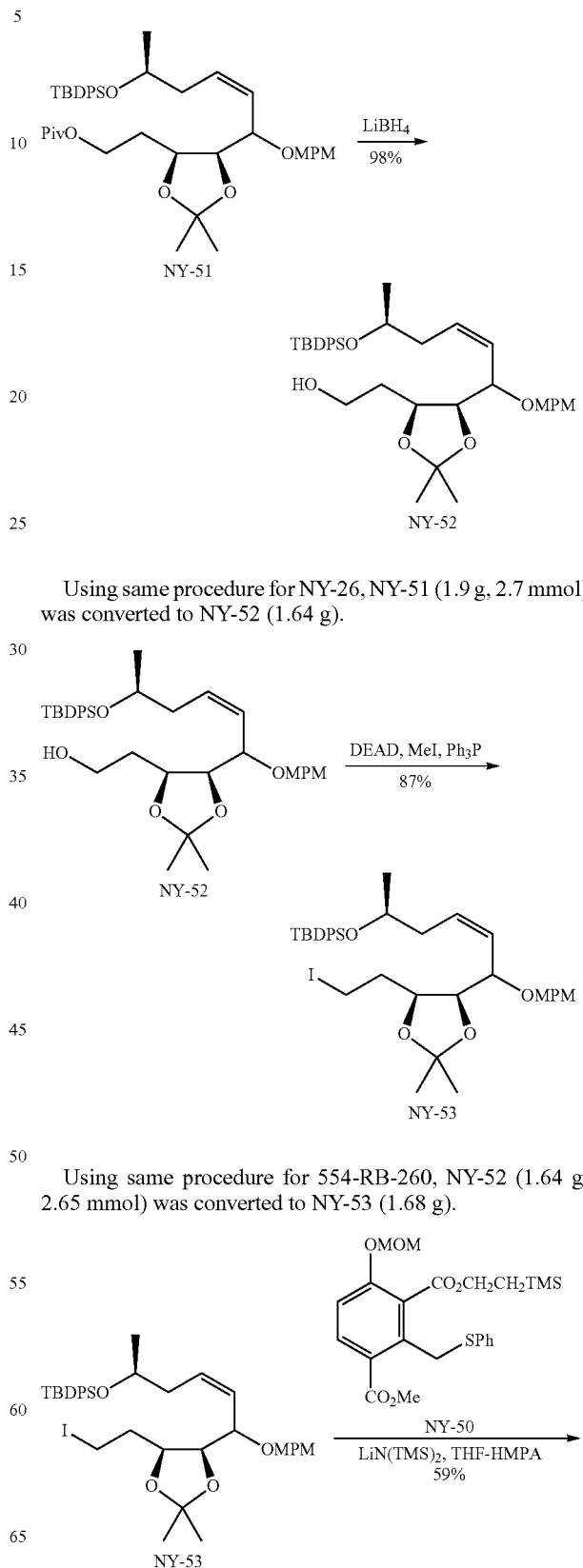

Using same procedure for NY-26, NY-51 (1.9 g, 2.7 mmol) was converted to NY-52 (1.64 g).

Using same procedure for 554-RB-260, NY-52 (1.64 g, 2.65 mmol) was converted to NY-53 (1.68 g).

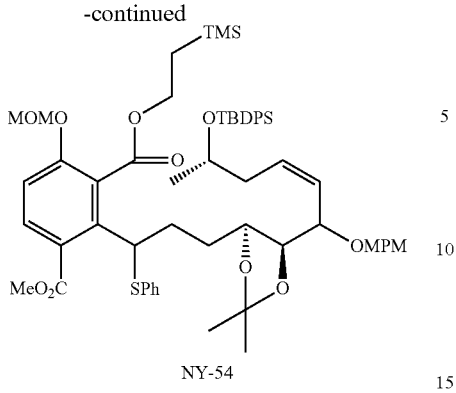
NY-54
Using same procedure for 16, NY-53 (540 mg, 0.741 mmol) was converted to NY-54 (465 mg).
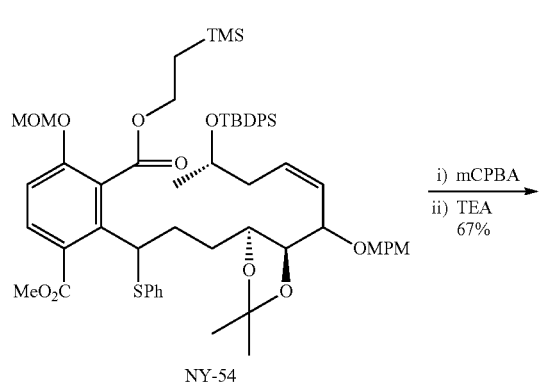
NY-54
i) mCPBA
ii) TEA
67%
NY-55
Using same procedure for 18, NY-54 (458 mg, 0.431 mmol) was converted to NY-55 (274 mg).
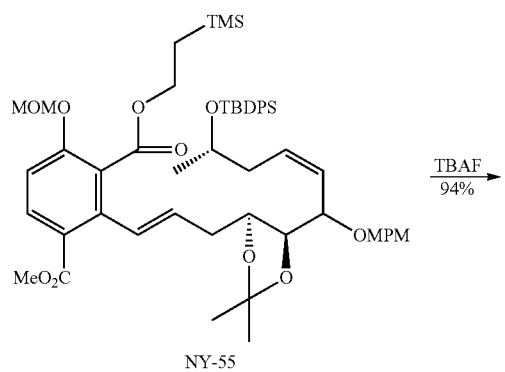
NY-55
TBAF
94%
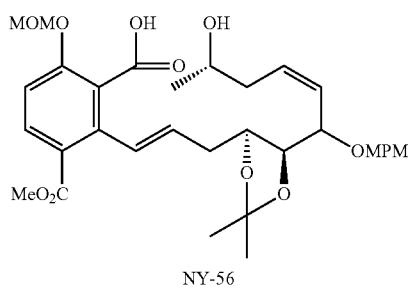
NY-56
Using same procedure for 509-HD-116, NY-55 (273 mg, 0.286 mmol) was converted to NY-56 (166 mg).
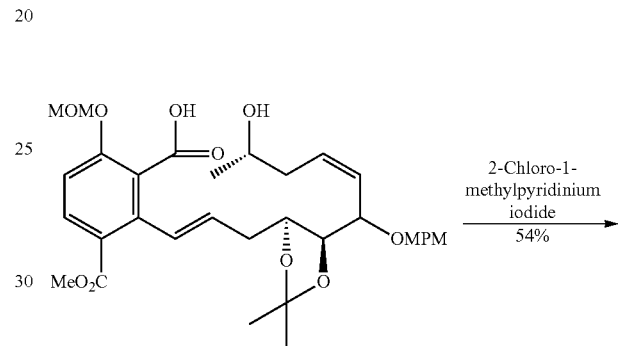
NY-56
2-Chloro-1-methylpyridinium iodide
54%
NY-57
Using same procedure for 509-HD-118, NY-56 (164 mg, 0.267 mmol) was converted to NY-57 (86 mg).
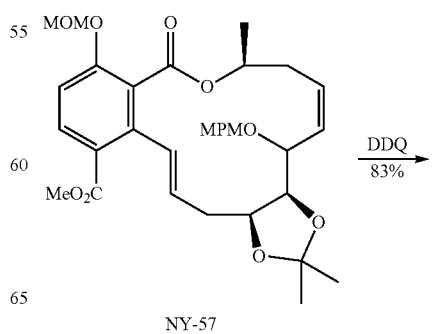
NY-57
DDQ
83%

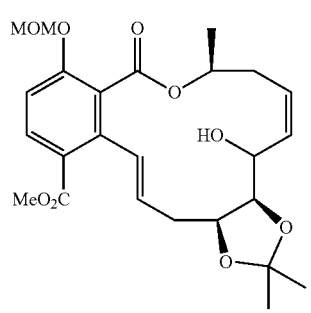

NY-58

Using same procedure for 509-HD-188, NY-57 (30 mg, 0.05 mmol) was converted to NY-58 (20 mg).

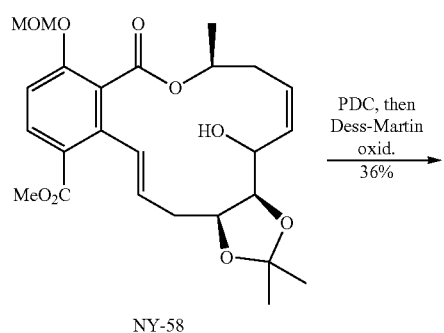

NY-58

To a solution of NY-58 (19 mg, 0.04 mmol) in CH$_2$Cl$_2$ (5 mL), MS4A (50 mg) and PDC (33 mg, 0.088 mmol) were added and the mixture was stirred at room temperature for 12 hrs. The insoluble material was filtered, washed with EtOAc and the filtrate was concentrated. The residue was dissolved in CH$_2$Cl$_2$ (5 mL), then Dess-Martin periodinate (50 mg, 0.118 mmol) was added and the mixture was stirred for 4 days. Sat. NaHCO$_3$ and 10% Na$_2$S$_2$O$_3$ were added and the mixture was extracted with EtOAc. The organic layer was washed with water, brine and dried over Na$_2$SO$_4$, filtered and concentrated. The crude product was purified on silica gel column with hexane/EtOAc, 5:1, 4:1, 3:1, 2:1 to give 6.8 mg of NY-59.

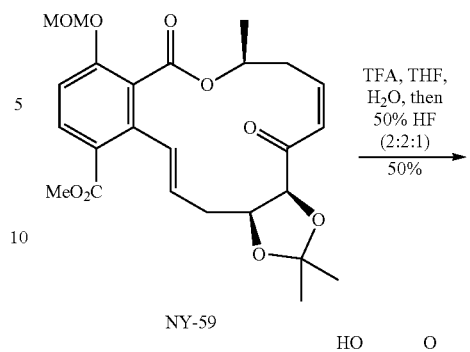

NY-59

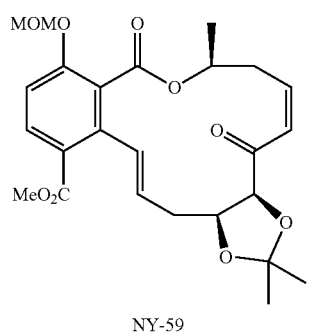

NF-1774

To a stirred solution of NY-59 (6.8 mg, 0.014 mmol) in THF (0.4 mL)-H$_2$O (0.2 mL) was added trifluoroacetic acid (0.4 mL) at 0° C. The mixture was then allowed to warm to rt. After 2 hrs, the mixture was poured into a saturated solution of NaHCO$_3$ and extracted with EtOAc. The organic layer was washed with water, brine and dried over anhydrous Na$_2$SO$_4$, filtered and concentrated. The residue was dissolved in MeCN (1.2 ml) and then 50% HF (0.2 mL) was added at 0° C. The mixture was then allowed to warm to rt. The crude product was purified on silica gel column with hexane/EtOAc, 1:1, 1:2 to give 2.8 mg of NF-1774.

Synthetic Procedure for NF-2546

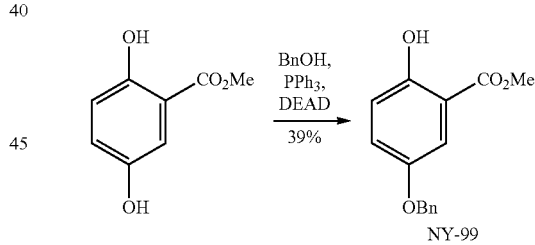

NY-99

Using same procedure for 509-HD-213, Methyl 2,5-dihydroxybenzoate (8.41 g, 50 mmol) was converted to NY-99 (5.06 g).

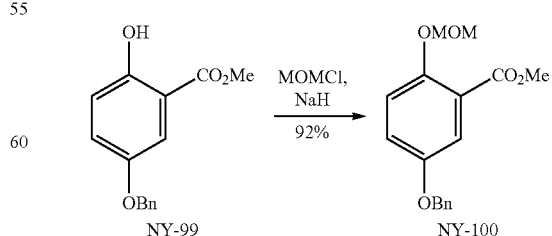

NY-99　　　　　　　　　NY-100

Using same procedure for 509-HD-209, NY-99 (5.4 g, 20.91 mmol) was converted to NY-100 (5.83 g).

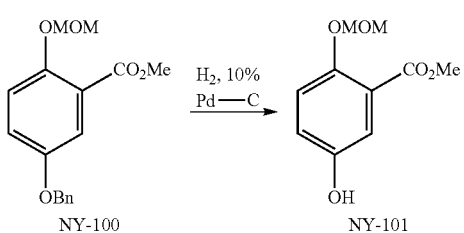

A mixture of NY-100 (5.82 g, 19.25 mmol), 10% Pd on carbon (610 mg) and MeOH (100 ml) was hydrogenated at 4 atom for 3 hrs. The catalyst was filtered and the filtrate was concentrated to give 4.16 g of NY-101. It was used without purification for the next step.

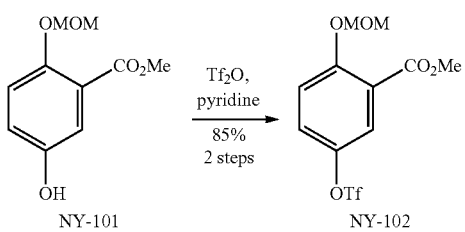

Using same procedure for 611-MS-88, NY-101 (4.15 g, 19.25 mmol) was converted to NY-102 (5.65 g).

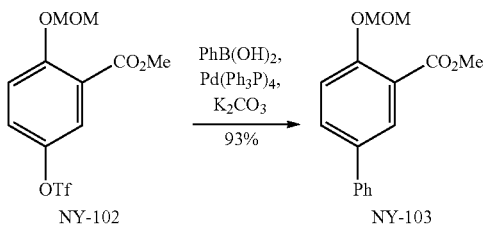

To a mixture of NY-102 (5.64 g, 16.38 mmol), PhB(OH)$_2$ (4 g, 32.81 mmol), K$_2$CO$_3$ (3.4 g, 24.6 mmol) and toluene (120 mL) under N2 bubbling, Pd(Ph3P)$_4$ (570 mg, 0.493 mmol) was added and the mixture was gradually warmed to 90° C. and stirred for 2 hrs. The reaction mixture was filtered and the filtrate was extracted with EtOAc. The organic layer was washed with sat. NaHCO$_3$, brine, dried over Na$_2$SO$_4$, filtered and concentrated. The crude product was purified on silica gel column with hexane/EtOAc, 20:1, 15:1, 12:1 to give 4.14 g of NY-103.

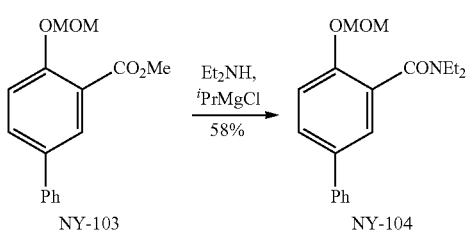

Using same procedure for NY-85, NY-103 (4.14 g, 15.2 mmol) was converted to NY-104 (2.75 g).

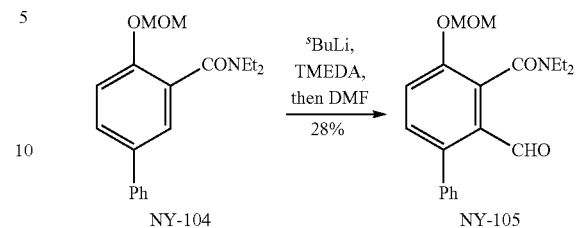

Using same procedure for NY-86, NY-104 (2.7 g, 8.61 mmol) was converted to NY-105 (822 mg).

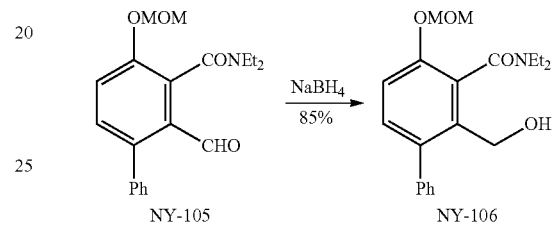

Using same procedure for NY-87, NY-105 (810 mg, 2.37 mmol) was converted to NY-106 (689 mg).

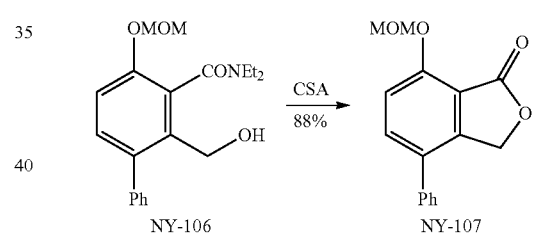

A mixture of NY-106 (682 mg, 1.986 mmol), CSA (22 mg, 0.095 mmol) and toluene (15 mL) was refluxed for 4 hrs. The reaction mixture was concentrated, then the crude product was purified on silica gel column with hexane/EtOAc, 10:1, 6:1 to give 471 mg of NY-107.

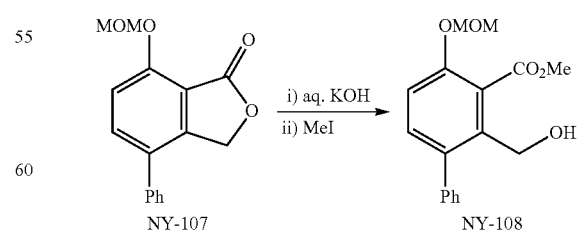

Using same procedure for NY-90, NY-107 (470 mg, 1.74 mmol) was converted to NY-108 (500 mg). NY-108 was used without purification for the next step.

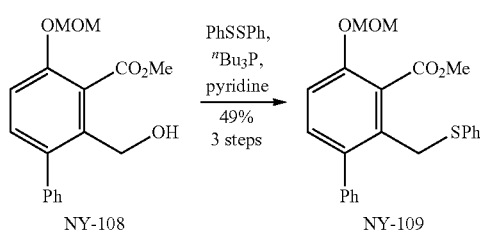

Using same procedure for NY-91, NY-108 (470 mg, 1.74 mmol) was converted to NY-109 (336 mg).

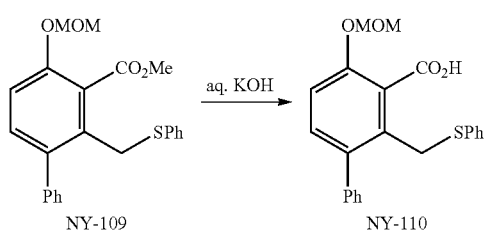

A mixture of NY-109 (330 mg, 0.837 mmol), KOH (142 mg, 2.53 mmol), water (5 mL) and DMSO (15 mL) was heated at 70° C. for 24 hrs. The reaction mixture was diluted with EtOAc and washed with 10% $KHSO_4$, water, brine, dried over $Na_2SO_4$, filtered and concentrated to give 334 mg of NY-110. NY-110 was used without purification for the next step.

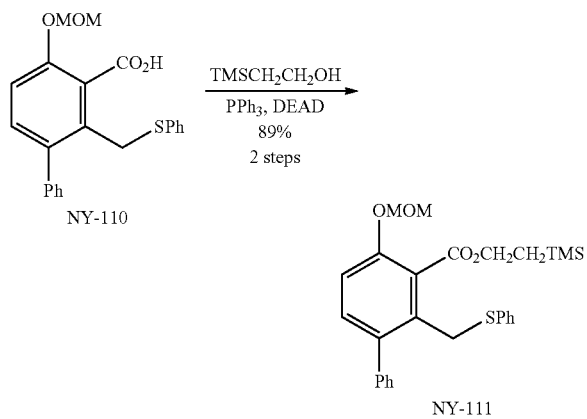

Using same procedure for 509-HD-213, NY-110 (333 mg, 0.837 mmol) was converted to NY-111 (359 mg).

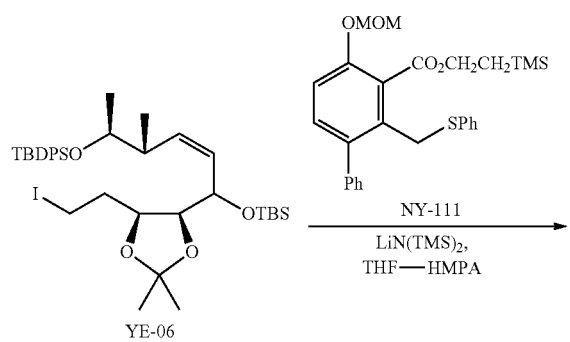

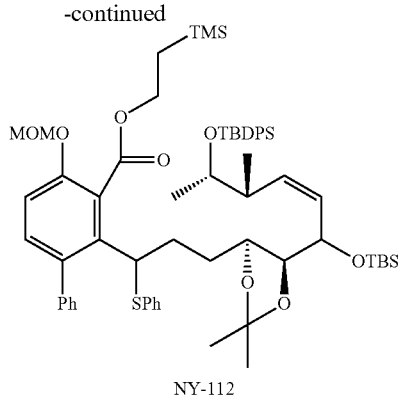

Using same procedure for 16, YE-06 (394 mg, 0.535 mmol) was converted to crude product of NY-112 (687 mg).

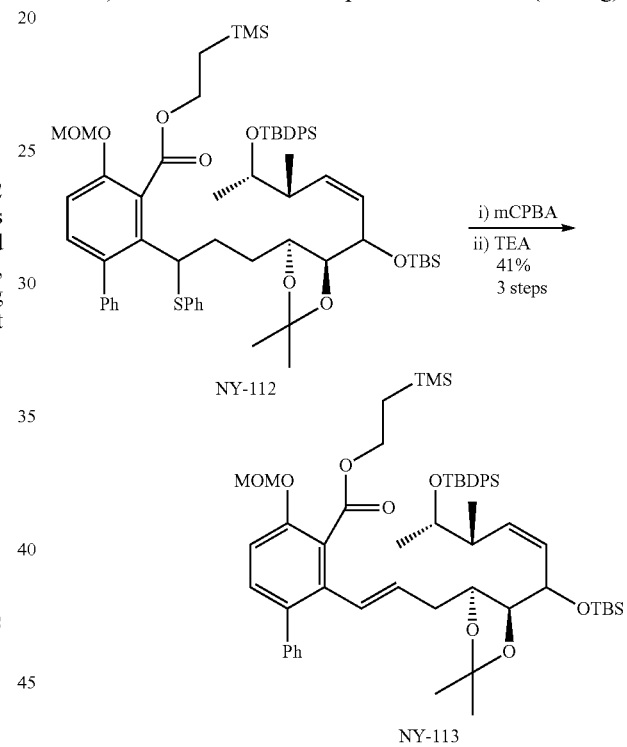

Using same procedure for 18, NY-112 (682 mg) was converted to NY-113 (215 mg).

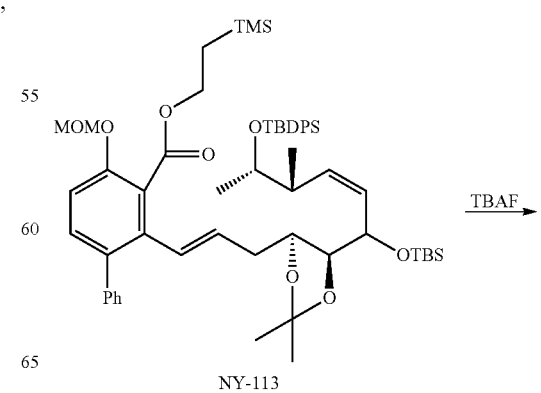

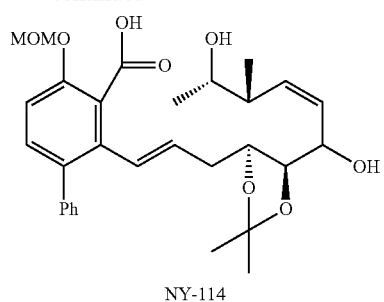
NY-114
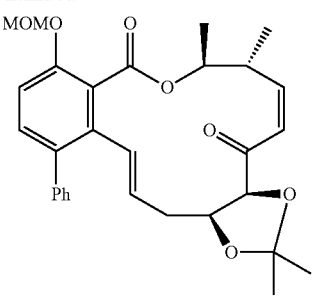
NY-116
Using same procedure for 509-HD-116, NY-113 (236 mg, 0.241 mmol) was converted to NY-114 (198 mg). NY-114 was used without purification for the next step.
Using same procedure for 509-HD-125, NY-115 (43 mg, 0.0845 mmol) was converted to NY-116 (47 mg).
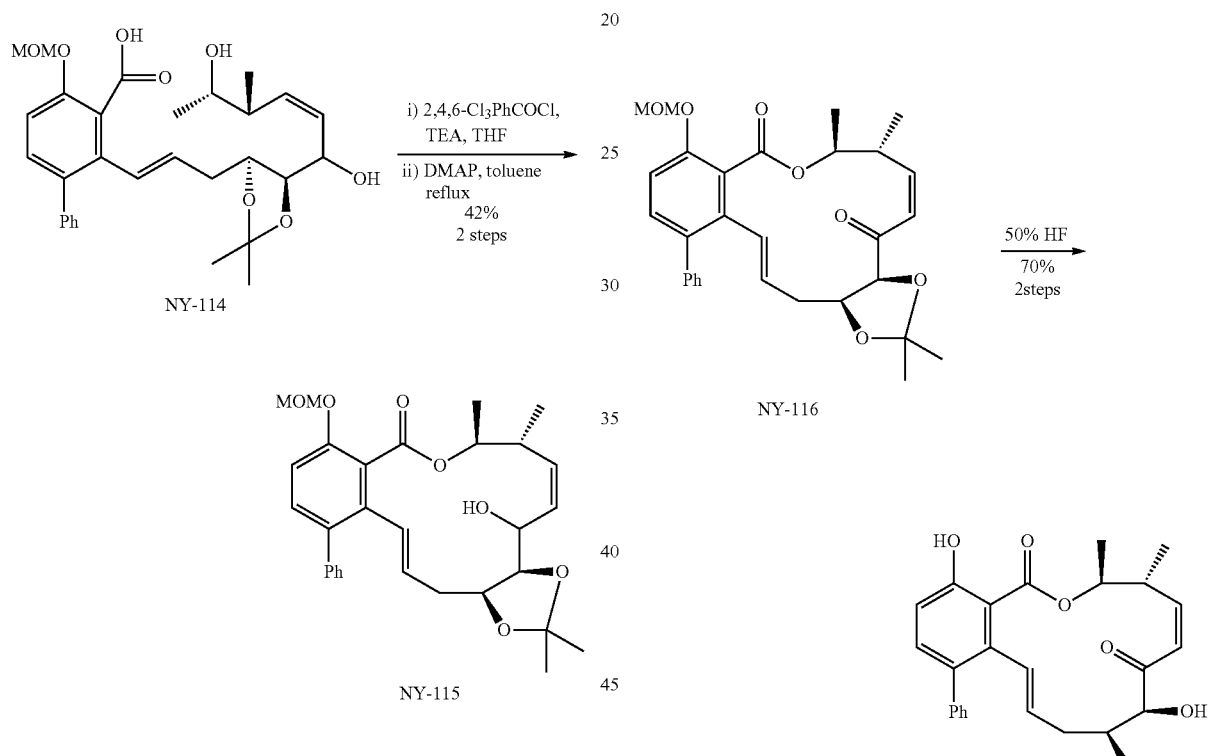
Using same procedure for TM-12, NY-114 (198 mg, 0.24 μmol) was converted to NY-115 (31 mg).
Using same procedure for B2538, NY-116 (45 mg, 0.0845 mmol) was converted to NF-2546 (29.4 mg).
Synthetic Procedure for NF2548
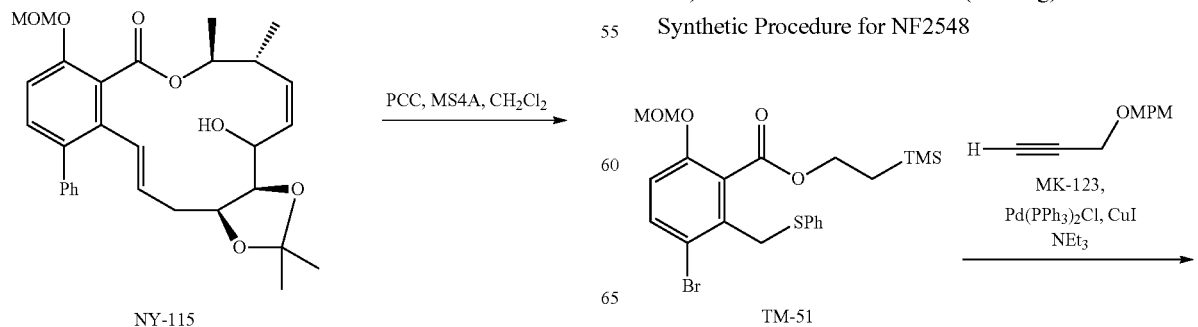

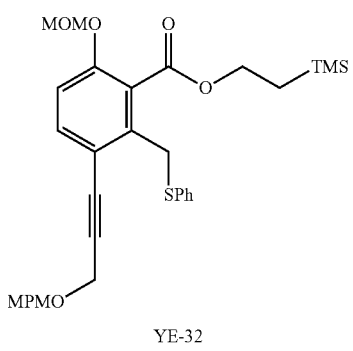

YE-32

TM-51 (1.0 g, 2.0 mmol) was dissolved in triethylamine (25 mL). MK-123 (0.55 g, 3.1 mmol), PdCl$_2$(PPh$_3$)$_2$ (220 mg, 0.31 mmol), CuI (120 mg, 0.63 mmol) were added and the mixture was stirred at 70° C., while addition of MK-123 (0.25 g, 1.4 mmol/each time) were repeated at intervals of 1 hr for five times. The mixture was cooled to rt and concentrated. The concentrate was triturated with diethyl ether and hexane, and the insoluble solid was filtered off. The filtrate was concentrated and the residue was purified by chromatography on silica gel using 5-10% EtOAc/hexane to give 0.67 g (1.2 mmol, 56%) of YE-32.

Using similar procedure for the intermediate 18 of NF2561, the iodide (430 mg, 0.58 mmol) was converted to YE-33 (430 mg, 0.40 mmol, 68% 3 steps).

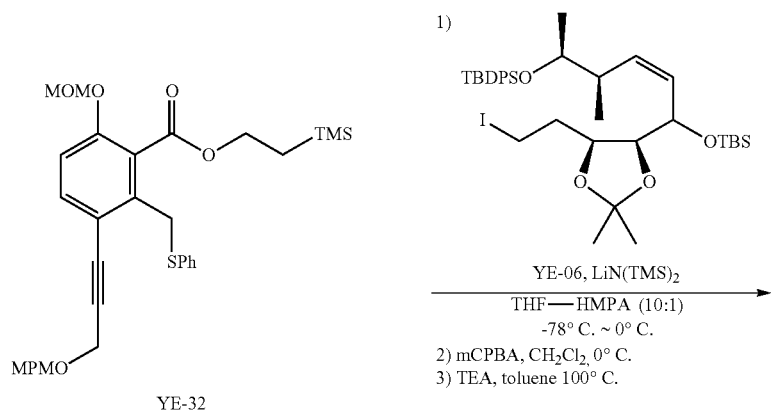

YE-32

1)

YE-06, LiN(TMS)$_2$
THF—HMPA (10:1)
-78° C. ~ 0° C.
2) mCPBA, CH$_2$Cl$_2$, 0° C.
3) TEA, toluene 100° C.

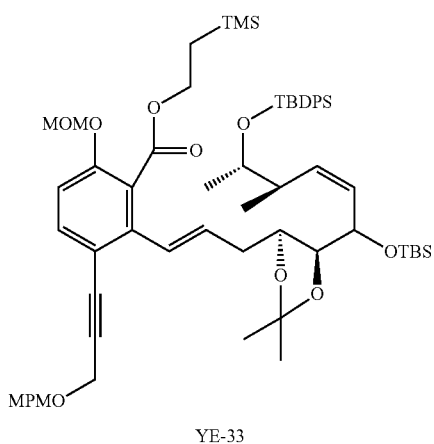

YE-33

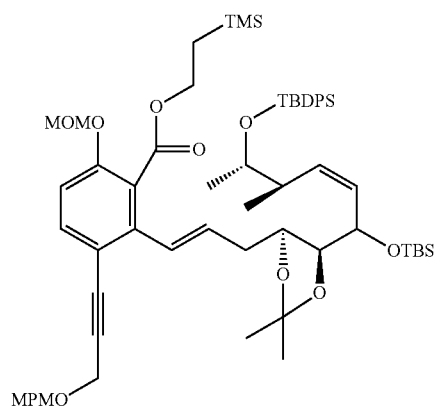

YE-33

1) TBAF, THF
2) 2,4,6-Cl₃PhCOCl, TEA, THF
3) DMAP, toluene, 100°C.
   (using high dilution conditions)

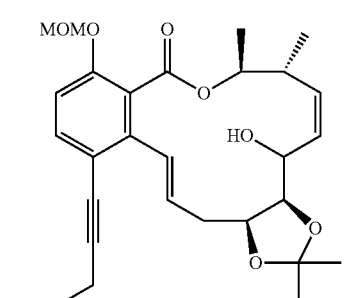

YE-34

Using similar procedure for TM-12, YE-33 (430 mg, 0.40 mmol) was converted to YE-34 (113 mg, 0.19 mmol, 47%, 3 steps).

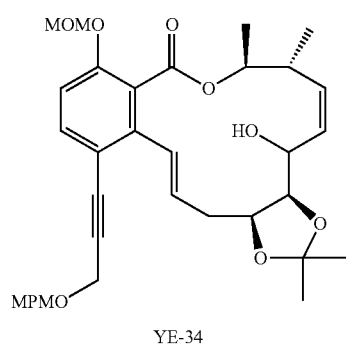

YE-34

1) PCC, MS4A
2) DDQ, CH₂Cl₂—H₂O

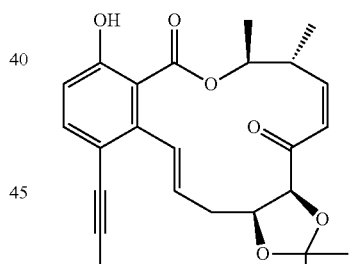

YE-35

TFA, THF, H₂O
(2:2:1), 1.5 hr

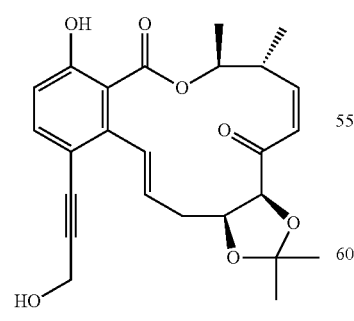

YE-35

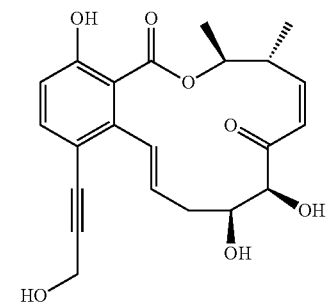

NF-2548

Using similar procedure for TM-13, YE-34 (40 mg, 0.066 mmol) was converted to enone. The following deprotection of the enone by DDQ resulted in deprotection of both MPM and MOM group and provided 16 mg of YE-35 (0.036 mmol, 55% 2 steps).

313

Using similar procedure for YE-19, YE-35 (12 mg, 0.027 mmol) was converted to NF-2548 (10.5 mg, 0.026 mmol, 96%).

Synthetic Procedure for NF2549

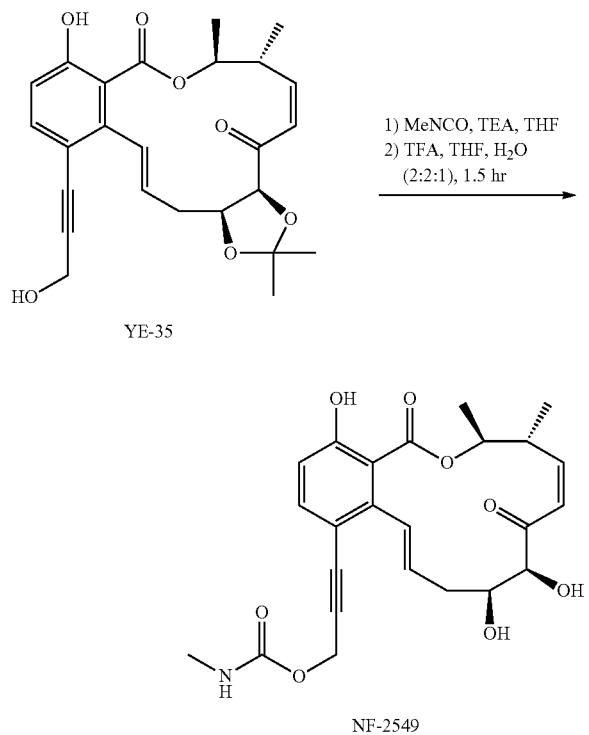

YE-35 (4 mg, 0.0091 mmol) and triethylamine (0.01 mL, 0.071 mmol) were dissolved in THF (0.6 mL). Methyl isocyanate (total 0.070 mL, 1.2 mmol) was added in four portions in 2 h intervals at rt. After 4 days, excess isocyanate was quenched with ethyleneglycol (0.15 ml). The mixture was poured into water and extracted with EtOAc. The extract was washed with 5% KHSO$_4$ aq., a saturated NaHCO$_3$ sol., brine, dried over anhydrous Na$_2$SO$_4$, filtered and concentrated. The crude product was purified by chromatography on silica gel using 15-30% EtOAc/hexane to give 4 mg (0.0080 mmol, 88%) of the N-methylcarbamate.

Using similar procedure for ER803064, the N-methylcarbamate (4 mg, 0.0080 mmol) was converted to NF2549 (3 mg, 0.0028 mmol, 35%).

Synthetic Procedure for NF2554, NF2555

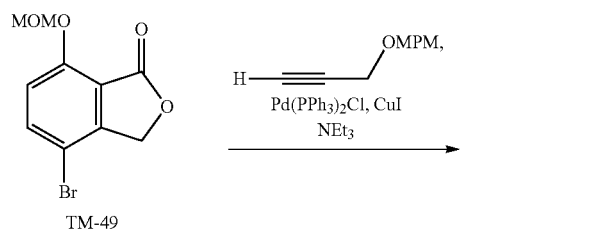

314

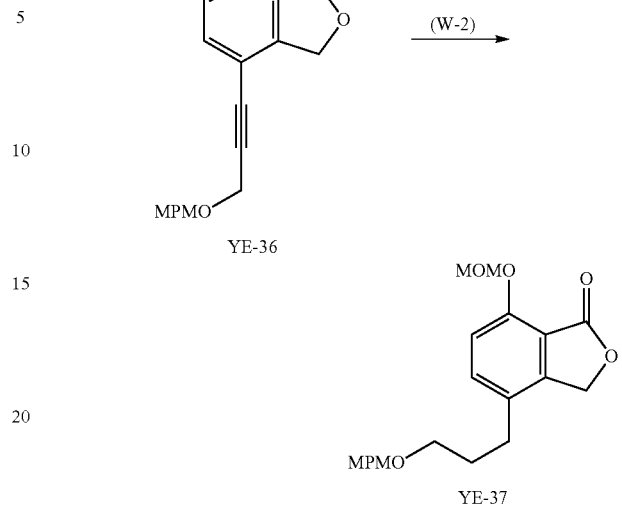

Using similar procedure for YE-32, the TM-49 (2.2 g, 8.0 mmol) was converted to YE-36 (2.1 g, 5.8 mmol, 72%).

To a stirred solution of YE-36 (2.1 g, 5.7 mmol) in EtOH (60 mL) and THF (15 mL) was added Raney Ni W-2 (water suspension, 4.5 g) under nitrogen atmosphere. The suspension was stirred under hydrogen atmosphere overnight. Then the catalyst was removed by filtration, and the filtrate was concentrated. The concentrate was purified by chromatography on silica gel using 15-33% EtOAc/hexane to give 1.6 g (4.3 mmol, 75%) of YE-37.

Using similar procedure for TM-51, YE-37 (1.18 g, 3.2 mmol) was converted to YE-38 (0.20 g, 0.40 mmol, 13%, 3 steps).

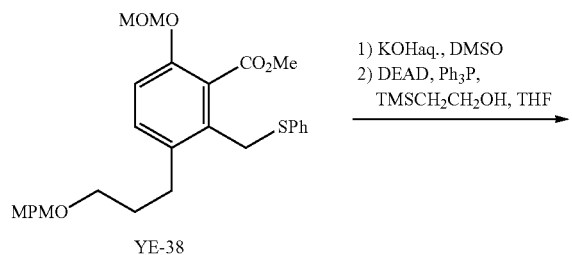
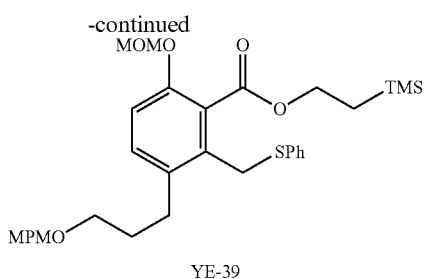
Using similar procedure for TM-39, YE-38 (340 mg, 0.68 mmol) was converted to YE-39 (350 mg, 0.64 mmol, 88% 2 steps).
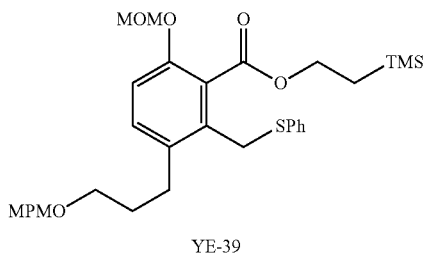
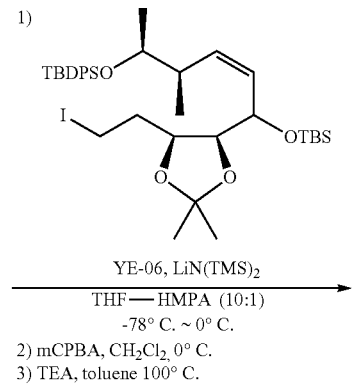
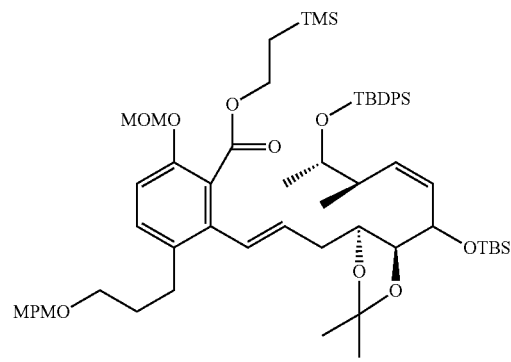

Using similar procedure for the intermediate 18 of NF2561, the iodide (230 mg, 0.30 mmol) was converted to YE-40 (115 mg, 0.11 mmol, 34% 3 steps).

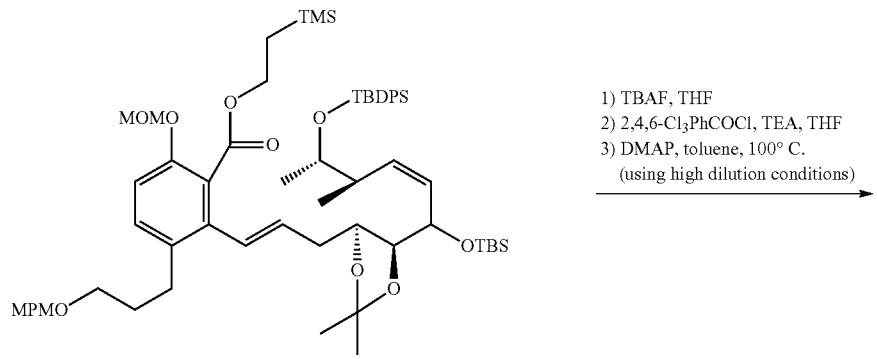

YE-40

1) TBAF, THF
2) 2,4,6-Cl₃PhCOCl, TEA, THF
3) DMAP, toluene, 100° C.
   (using high dilution conditions)

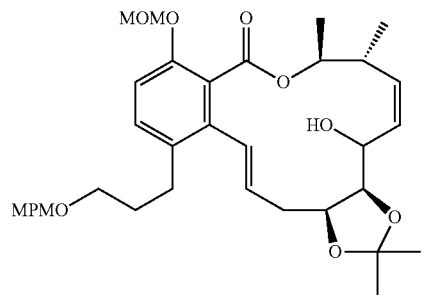

YE-41

Using similar procedure for TM-12, YE-40 (115 mg, 0.11 mmol) was converted to YE-41 (36 mg, 0.059 mmol, 55% 3 steps).

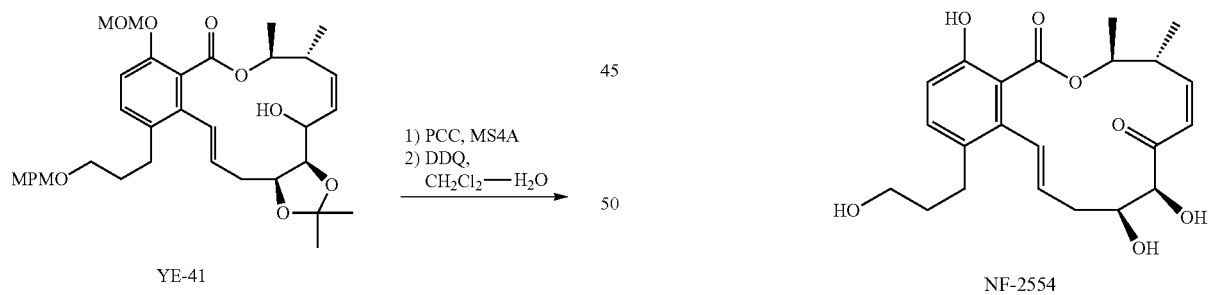

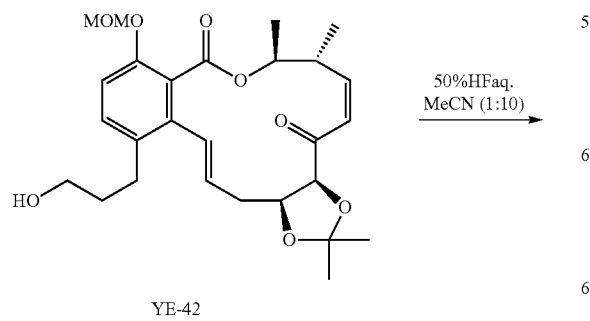

YE-42

Using similar procedure for TM-13 followed by usual deprotection of MPM group by DDQ oxidation, YE-41 (36 mg, 0.059 mmol) was converted to YE-42 (13 mg, 0.027 mmol, 45% 2 steps).

Using similar procedure for ER803064, YE-42 (5 mg, 0.010 mmol) was converted to NF2554 (4.1 mg, 0.010 mmol, 99%).

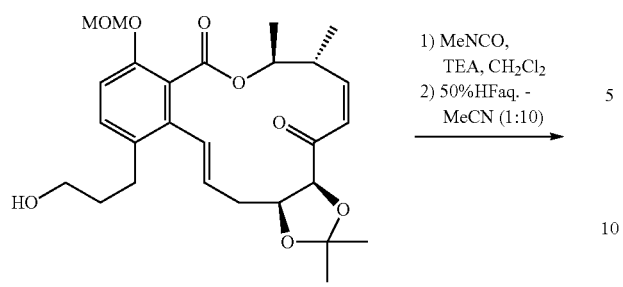

YE-42

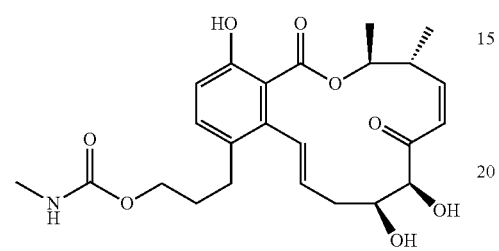

NF-2555

Using similar procedure for NF-2549, YE-42 (7 mg, 0.014 mmol) was converted to NF-2555 (1.9 mg, 0.0041 mmol, 29% 2 steps).

Synthetic Procedure for NF2550

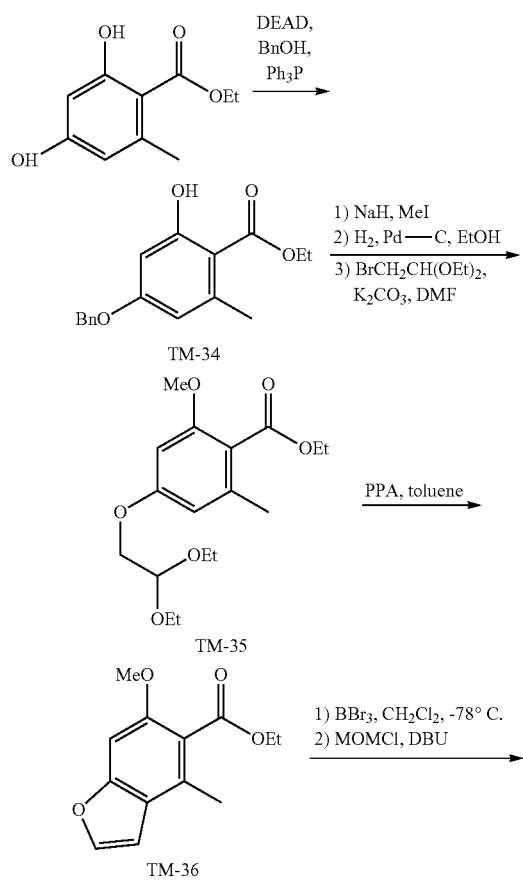

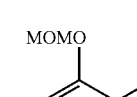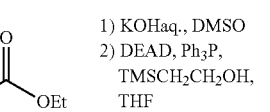

TM-37

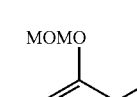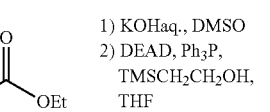

TM-38

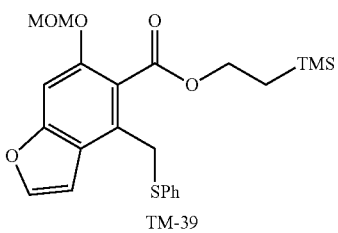

TM-39

Using similar procedure for 509-HD-207, starting material (4.91 g, 25 mmol) was converted to TM-34 (5.17 g, 18 mmol, 72%).

To a stirred suspension of NaH (60% oil dispersion, 593 mg, 14.8 mmol) in dry DMF (5 mL) was added a solution of TM-34 (3.395 g, 11.9 mmol) in dry DMF (35 mL) at 0° C. under nitrogen atmosphere. After 30 min, methyl iodide (3.7 mL, 59 mmol) was added. the mixture was allowed to warm to it and stirred for 30 min after which a saturated solution of NH₄Cl was added. The mixture was extracted with EtOAc and the organic extract was washed with water, brine, dried with anhydrous Na₂SO₄, filtered and concentrated.

The crude product (4.33 g) was dissolved in EtOH (60 mL). Then, 10% Pd on carbon (630 mg) was added. Reaction was stirred under hydrogen. After 3 hrs, reaction was stopped, catalyst was filtered through celite and mixture was concentrated under reduced pressure to give the phenol (2.94 g) as crude product.

To a solution of the phenol (2.94 g) in thy DMF (60 mL) were added anhydrous K₂CO₃ (3.28 g, 24 mmol) and 2-bromo-1,1-diethoxyethane (2.86 mL, 18 mmol) and the mixture was stirred for 5 hrs at 140° C. After cooling to rt, the mixture was poured into water and extracted with EtOAc. The organic extract was washed with a saturated solution of NH₄Cl, water, brine, dried with anhydrous Na₂SO₄, filtered and concentrated. The crude product was purified by chromatography on silica gel using 15% EtOAc/hexane to give 3.369 g (10 mmol, 87% 3 steps) of TM-35.

To a solution of TM-35 (3.02 g, 9.3 mmol) in toluene (120 mL) was added PPA (5.9 mL) and the mixture was stirred for 2 hrs at 100° C. under nitrogen atmosphere. After cooling to rt, the mixture was poured into ice/water and extracted with EtOAc. The organic extract was washed with water, a saturated solution of NaHCO$_3$, brine, dried with anhydrous Na$_2$SO$_4$, filtered and concentrated. The crude product was purified by chromatography on silica gel using 12.5% EtOAc/hexane to give 395 mg (1.7 mmol, 18%) of TM-36.

To a stirred solution of TM-36 (541 mg, 2.3 mmol) in dry CH$_2$Cl$_2$ (20 mL) was added BBr$_3$ (0.44 mL, 4.6 mmol) at −78° C. under nitrogen atmosphere. After 1 hr, the mixture was poured into water and extracted with EtOAc. The organic extract was washed with a saturated solution of NaHCO$_3$, water, brine, dried with anhydrous Na$_2$SO$_4$, filtered and concentrated. The crude product was purified by chromatography on silica gel using 5% EtOAc/hexane to give 357 mg (1.6 mmol, 70%) of the phenol.

To a stirred solution of the phenol (170 mg, 0.77 mmol) in dry THF (8 mL) were added DBU (0.23 mL, 1.5 mmol) and chloromethyl methyl ether (0.12 mL, 1.5 mmol) at rt under nitrogen atmosphere. After 3 hr, the mixture was poured into a saturated solution of NH$_4$Cl and extracted with EtOAc. The organic extract was washed with 10% KHSO$_4$ aq., water, a saturated solution of NaHCO$_3$, brine, dried with anhydrous Na$_2$SO$_4$, filtered and concentrated. The crude product was purified by chromatography on silica gel using 15% EtOAc/hexane to give 193 mg (0.73 mmol, 95%) of TM-37.

Using similar procedure for the intermediate 10 of NF2561, TM-37 (192 mg, 0.73 mmol) was converted to TM-38 (192 mg, 0.52 mmol, 71% 2 steps).

Using similar procedure for the intermediate 14 of NF2561, TM-38 (192 mg, 0.52 mmol) was converted to TM-39 (190 mg, 0.43 mmol, 83% 2 steps).

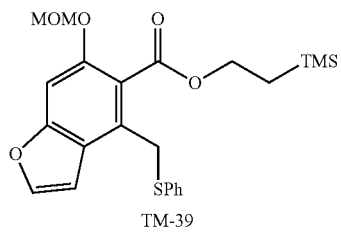

TM-39

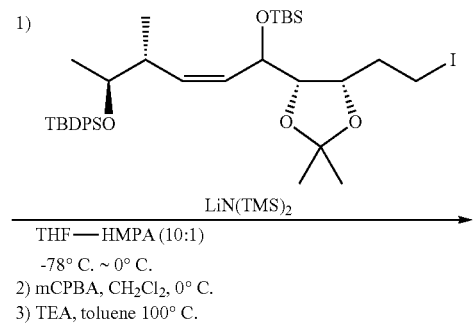

1)
LiN(TMS)$_2$
THF—HMPA (10:1)
−78° C. ~ 0° C.
2) mCPBA, CH$_2$Cl$_2$, 0° C.
3) TEA, toluene 100° C.

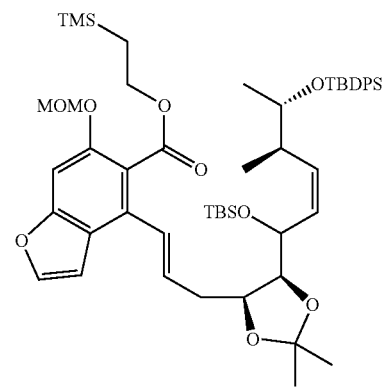

TM-40

Using similar procedure for the intermediate 18 of NF2561, the iodide (223 mg, 0.30 mmol) was converted to TM-40 (232 mg, 0.25 mmol, 81% 3 steps).

Using similar procedure for ER803064, TM-41 (41 mg, 0.087 mmol) was converted to NF2550 (20 mg, 0.052 mmol, 60% 2 steps).

Synthetic Procedure for NF2560

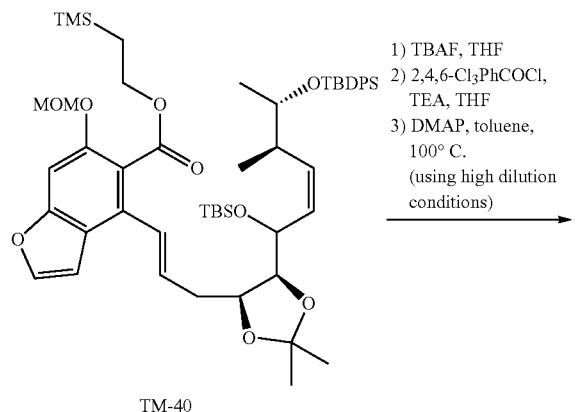

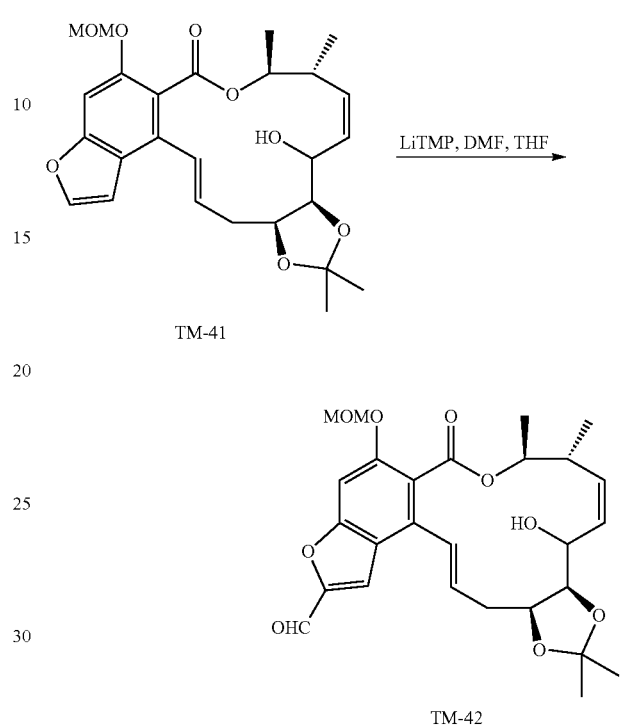

Using similar procedure for TM-12, TM-40 (232 mg, 0.25 mmol) was converted to TM-41 (81 mg, 0.17 mmol, 70% 3 steps).

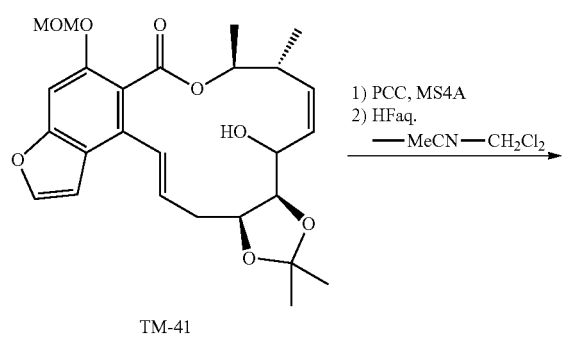

To a stirred solution of 2,2,6,6-tetramethylpiperidine (0.05 mL, 0.3 mmol) in dry THF (1.5 mL) was added 1.6M n-BuLi in hexane (0.15 mL, 0.24 mmol) at −20° C. under nitrogen atmosphere. After 30 min, the mixture was cooled to −78° C. and a solution of TM-41 (38 mg, 0.08 mmol) in dry THF (4 mL) was added. After 1 hr, dry DMF (0.06 mL) was added and the mixture was allowed to warm to rt. It was quenched with a saturated solution of NH$_4$Cl and extracted with EtOAc. The organic extract was washed with a saturated solution of NH$_4$Cl, water, brine, dried with anhydrous Na$_2$SO$_4$, filtered and concentrated. The crude product was purified by chromatography on silica gel using 40% EtOAc/hexane to give 18 mg (0.036 mmol, 45%) of TM-42.

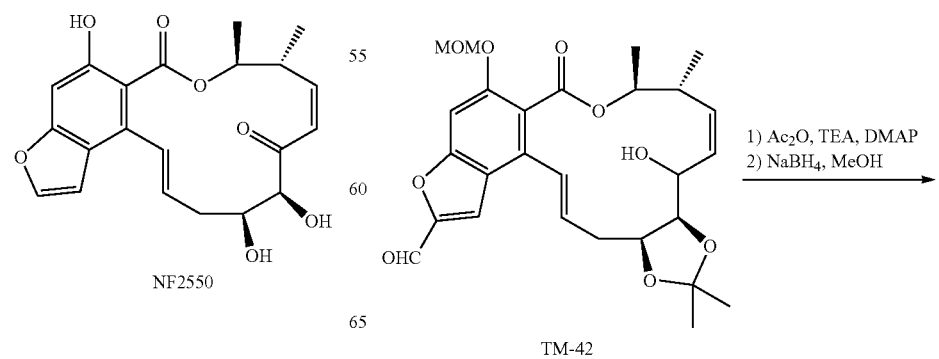

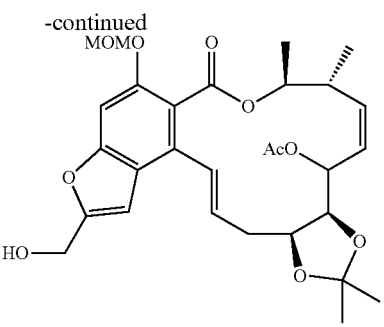

TM-43

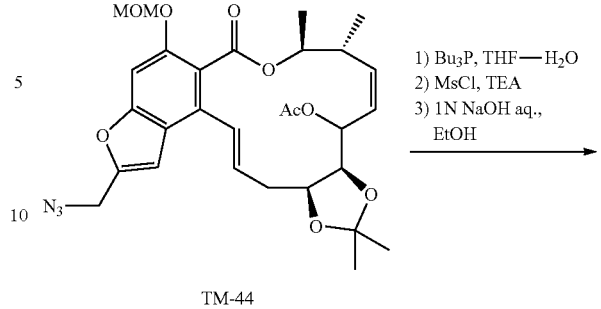

TM-44

To a stirred solution of TM-42 (54 mg, 0.11 mmol) in CH₂Cl₂ (5 mL) were added triethylamine (0.3 mL, 2.2 mmol), small amount of N,N-dimethylaminopyridine, acetic anhydride (0.1 mL, 1.1 mmol) at 0° C. The mixture was allowed to warm to rt and stirred overnight. It was quenched with a saturated solution of NH₄Cl and extracted with EtOAc. The organic extract was washed with a saturated solution of NH₄Cl, water, brine, dried with anhydrous Na₂SO₄, filtered and concentrated.

The crude acetate (61 mg) was dissolved in MeOH (5 mL) and NaBH₄ (10 mg, 0.26 mmol) was added at 0° C. After 10 min, the mixture was poured into a saturated solution of NH₄Cl and extracted with EtOAc. The organic extract was washed with a saturated solution of NH₄Cl, water, brine, dried with anhydrous Na₂SO₄, filtered and concentrated. The crude product was purified by chromatography on silica gel using 50% EtOAc/hexane to give 40 mg (0.073 mmol, 68% 2 steps) of TM-43.

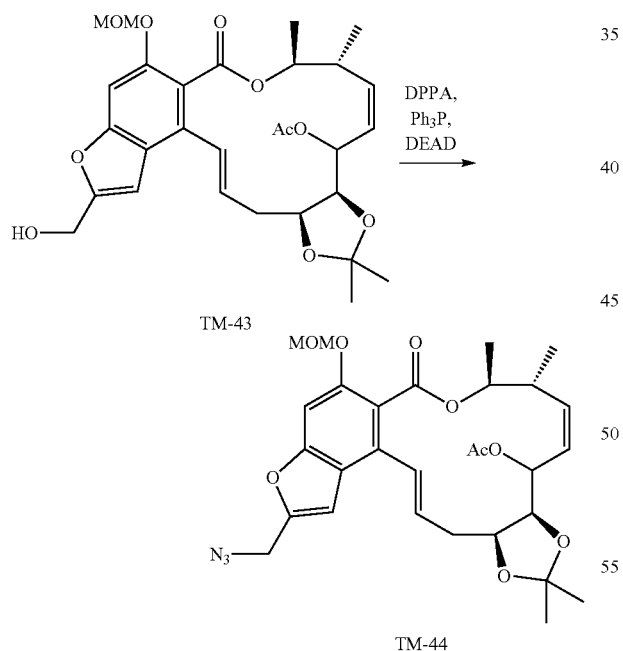

TM-43

TM-44

To a stirred solution of TM-43 (40 mg, 0.073 mmol) in dry THF (8 mL) were added triphenylphosphine (58 mg, 0.22 mmol), diphenylphosphoryl azide (0.047 mL, 0.22 mmol), 40% DEAD in toluene (0.1 mL, 0.22 mmol) at rt. After 20 hrs, the mixture was concentrated under reduced pressure and the residue was purified by chromatography on silica gel using 25% EtOAc/hexane to give 26 mg (0.046 mmol, 62%) of TM-44.

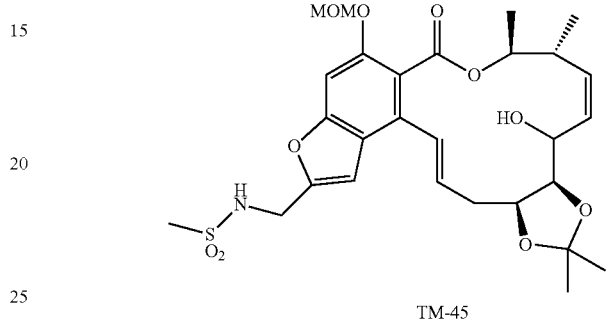

TM-45

To a stirred solution of TM-44 (26 mg, 0.046 mmol) in dry THF (2.5 mL) was added tributylphosphine (0.035 mL, 0.14 mmol) at rt under nitrogen atmosphere. After 30 min, H₂O (0.5 mL) was added. After additional 3 hrs, the mixture was diluted with EtOAc and dried with anhydrous Na₂SO₄, filtered and concentrated.

The crude amine (56 mg) was dissolved in CH₂Cl₂ (3 mL). Then triethylamine (0.036 mL, 0.26 mmol) and methanesulfonyl chloride (0.010 mL, 0.13 mmol) were added at 0° C. After 30 min, the mixture was poured into a saturated solution of NaHCO₃ and extracted with EtOAc. The organic extract was washed with a saturated solution of NaHCO₃, water, brine, dried with anhydrous Na₂SO₄, filtered and concentrated.

The crude methanesulfonamide (64 mg) was dissolved in EtOH (3 mL) and 1N NaOH aq. (0.5 mL, 0.5 mmol) was added at rt. After 24 hrs, the mixture was quenched with 1N HCl (0.5 mL) and extracted with EtOAc. The organic extract was washed with water, brine, dried with anhydrous Na₂SO₄, filtered and concentrated. The crude product was purified by chromatography on silica gel using 60% EtOAc/hexane to give 15 mg (0.026 mmol, 57% 3 steps) of TM-45.

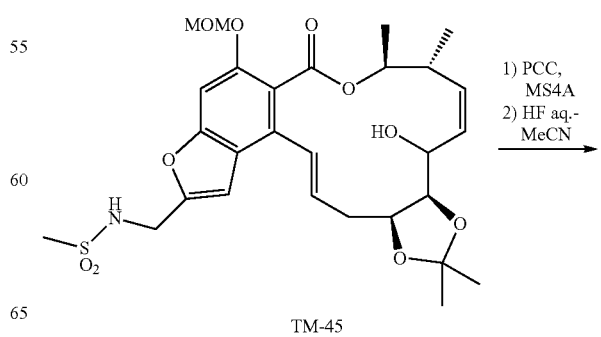

TM-45

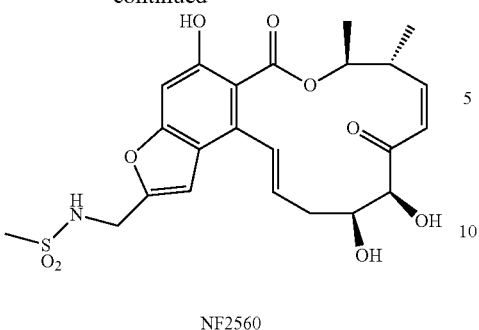

NF2560

Using similar procedure for ER803064, TM-45 (15 mg, 0.026 mmol) was converted to NF2560 (4.4 mg, 0.0089 mmol, 35% 2 steps).

Synthetic Procedure for NF2545

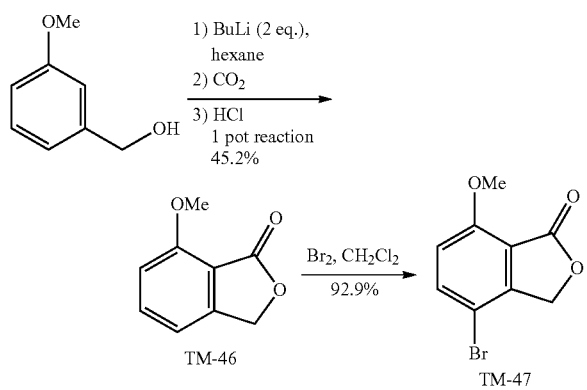

To a stirred suspension of 3-methoxybenzyl alcohol (10.78 g, 78 mmol) in hexane (100 mL) was added 1.6M n-BuLi in hexane (100 mL, 160 mmol) at −30° C. under nitrogen atmosphere. After 1.5 hrs, dry $CO_2$ was bubbled for 30 min and then the mixture was poured into water and extracted with diethyl ether. The aqueous layer was acidified by addition of 5N HCl at 0° C. and stirred overnight at rt. The precipitate was collected by filtration and washed with water, dried at 70° C. for 24 hrs to give 4.79 g (29 mmol, 37%) of TM-46.

TM-46 (4.79 g, 29 mmol) was dissolved in $CH_2Cl_2$ (150 mL). Then bromine (1.88 mL, 37 mmol) was added at 0° C. and the mixture was allowed to warm to rt. After 20 hrs, the mixture was poured into a saturated solution of $Na_2S_2O_3$ and extracted with EtOAc. The organic extract was washed with a saturated solution of $NaHCO_3$, water, brine, dried with anhydrous $Na_2SO_4$, filtered and concentrated to give 6.59 g (27 mmol, 93%) of TM-47.

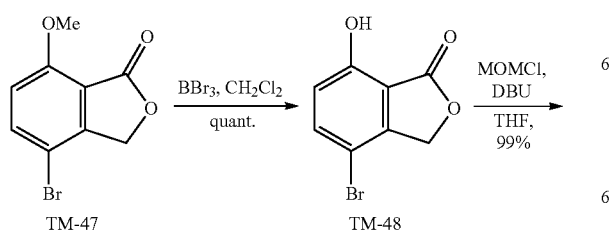

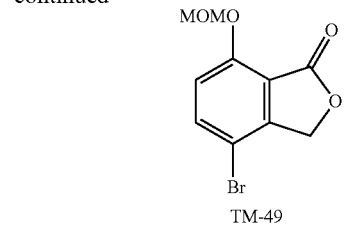

TM-49

Using similar procedure for TM-37, TM-47 (5.37 g, 22 mmol) was converted to TM-49 (5.98 g, 22 mmol, 99% 2 steps).

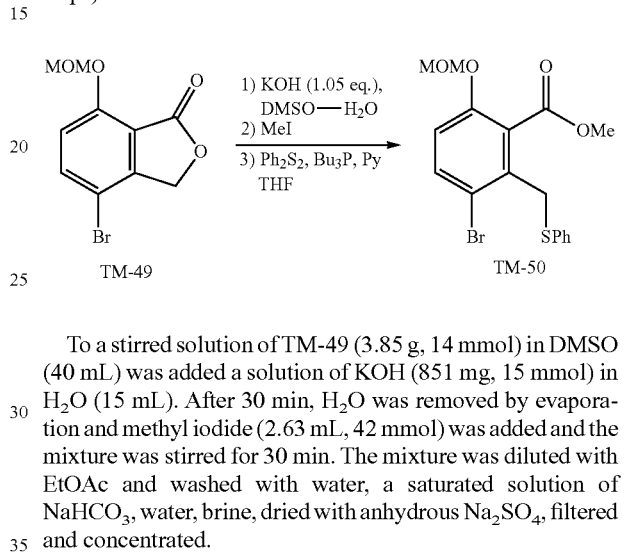

To a stirred solution of TM-49 (3.85 g, 14 mmol) in DMSO (40 mL) was added a solution of KOH (851 mg, 15 mmol) in $H_2O$ (15 mL). After 30 min, $H_2O$ was removed by evaporation and methyl iodide (2.63 mL, 42 mmol) was added and the mixture was stirred for 30 min. The mixture was diluted with EtOAc and washed with water, a saturated solution of $NaHCO_3$, water, brine, dried with anhydrous $Na_2SO_4$, filtered and concentrated.

The crude product (3.79 g) was dissolved in dry DMF (100 mL). Then diphenyl disulfide (6.16 g, 28 mmol), pyridine (4.55 mL, 56 mmol), tributylphosphine (7.03 mL, 28 mmol) were added at rt under nitrogen atmosphere and the mixture was stirred overnight. It was quenched with a saturated solution of $NaHCO_3$ and extracted with EtOAc. The organic extract was washed with 10% $KHSO_4$ aq., water, brine, dried with anhydrous $Na_2SO_4$, filtered and concentrated. The crude product was purified by chromatography on silica gel using 15% EtOAc/hexane to give 1.79 g (4.5 mmol, 32% 2 steps) of TM-50.

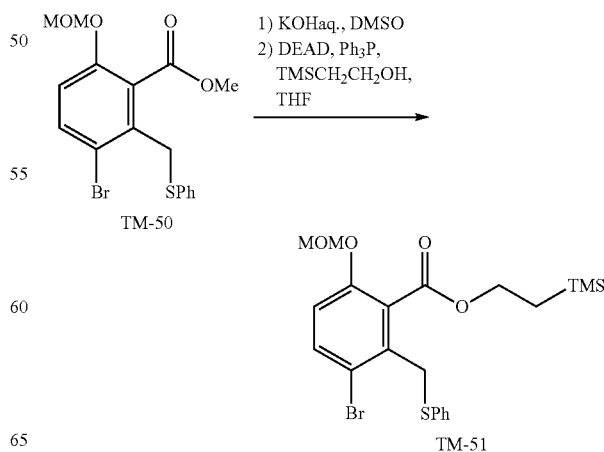

Using similar procedure for TM-39, TM-50 (1.79 g, 4.5 mmol) was converted to TM-51 (1.88 g, 3.9 mmol, 87% 2 steps).

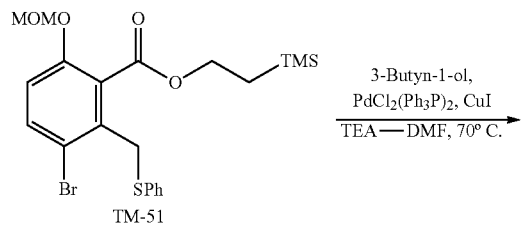

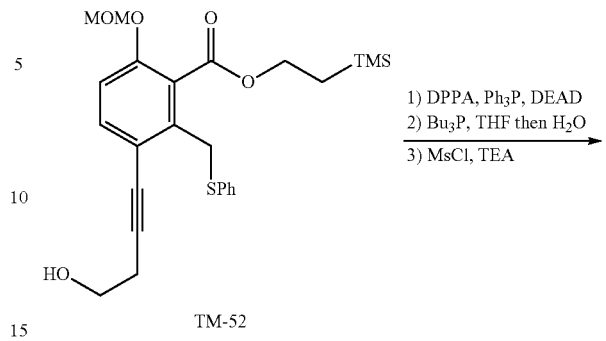

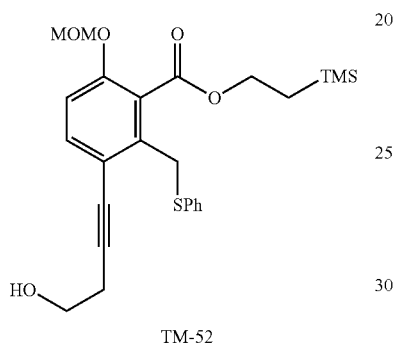

TM-51 (1.86 g, 3.8 mmol) was dissolved in DMF (30 mL). Then triethylamine (10 mL), 3-butyn-1-ol (1.16 mL, 15 mmol), $PdCl_2(PPh_3)_2$ (404 mg, 0.58 mmol), CuI (219 mg, 1.2 mmol) were added and the mixture was stirred overnight at 70° C. The mixture was diluted with 50% EtOAc/hexane and washed with water, brine, dried with anhydrous $Na_2SO_4$, filtered and concentrated. The crude product was purified by chromatography on silica gel using 30% EtOAc/hexane to give 1.76 g (3.7 mmol, 97%) of TM-52.

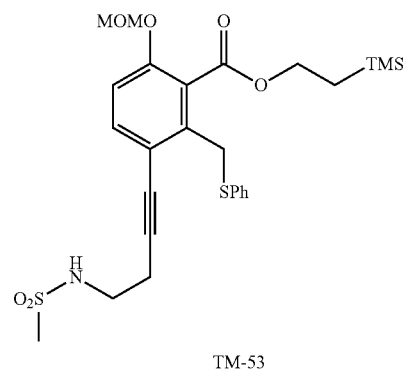

Using similar procedure for TM-45, TM-52 (754 mg, 1.6 mmol) was converted to TM-53 (586 mg, 1.1 mmol, 67% 3 steps).

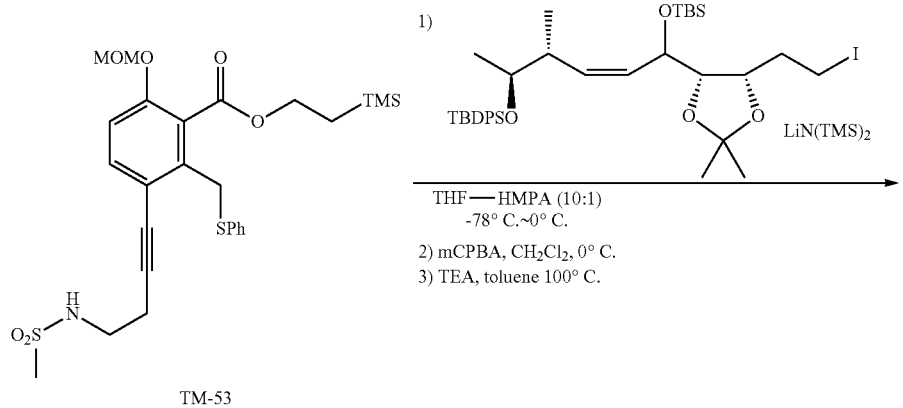

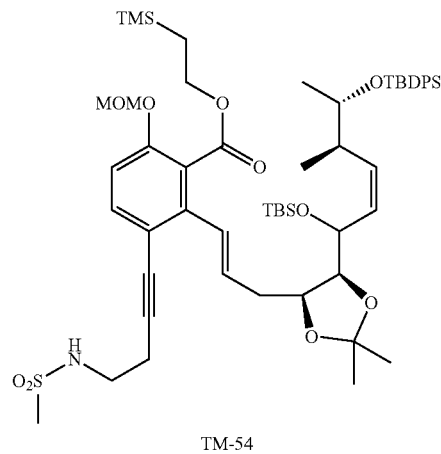
TM-54
Using similar procedure for TM-39, the iodide (350 mg, 0.48 mmol) was converted to TM-54 (224 mg, 0.25 mmol, 45% 3 steps).
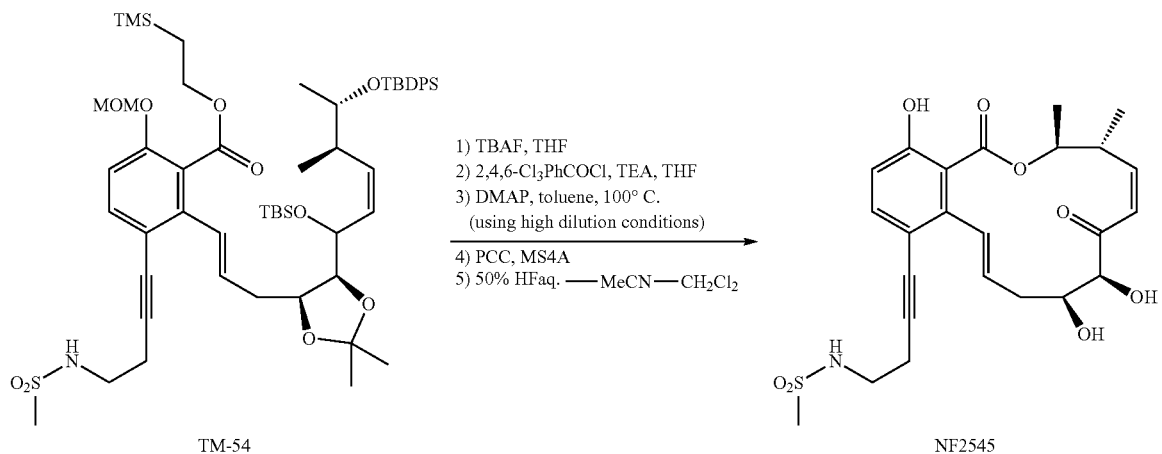
Using similar procedure for NF2550, TM-54 (224 mg, 0.21 mmol) was converted to NF2545 (2.8 mg, 0.0057 mmol, 2.7% 5 steps).
Synthetic Procedure for NF2551 and NF2552
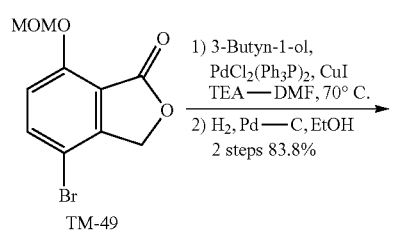
TM-49
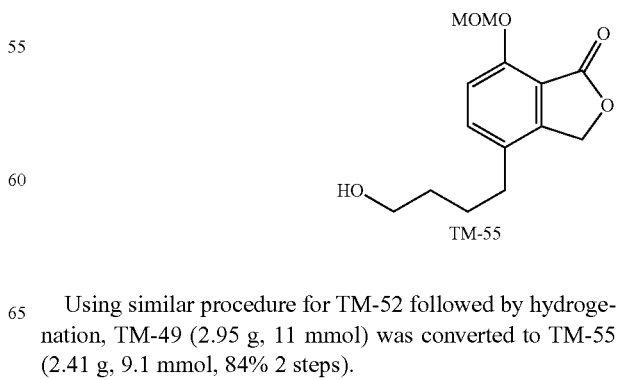
TM-55
Using similar procedure for TM-52 followed by hydrogenation, TM-49 (2.95 g, 11 mmol) was converted to TM-55 (2.41 g, 9.1 mmol, 84% 2 steps).

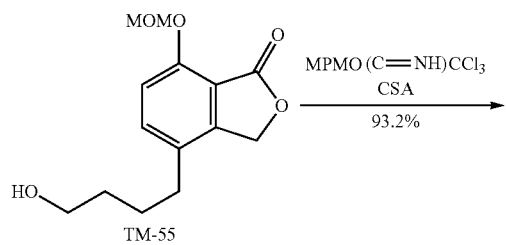

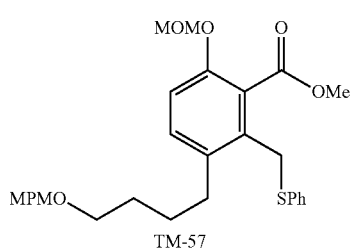

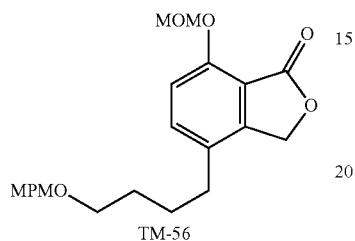

Using similar procedure for TM-50, TM-56 (3.26 g, 8.4 mmol) was converted to TM-57 (1.78 g, 3.5 mmol, 41% 3 steps).

To a stirred solution of TM-55 (2.41 g, 9.1 mmol) in cyclohexane (30 mL)-CH$_2$Cl$_2$ (15 mL) were added CSA (105 mg, 0.45 mmol) and 4-methoxybenzyl trichloroacetimidate (7.68 g, 27 mmol) at rt under nitrogen atmosphere. After 14 hrs, triethylamine (0.1 mL) was added. Then precipitate was removed by filtration and washed with hexane. The filtrate was concentrated under reduced pressure. The residue was purified by chromatography on silica gel using 30% EtOAc/hexane to give 3.26 g (8.4 mmol, 93%) of TM-56.

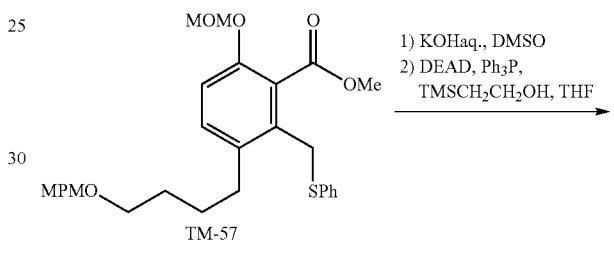

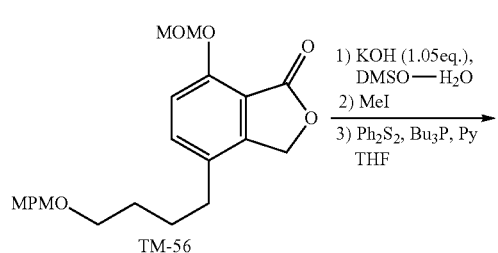

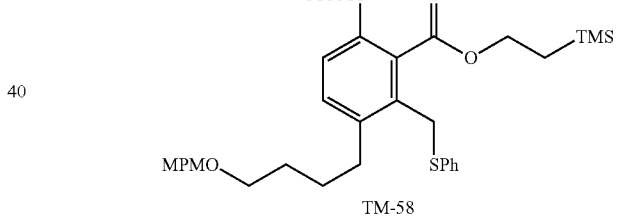

Using similar procedure for TM-39, TM-57 (366 mg, 0.72 mmol) was converted to TM-58 (381 mg, 0.64 mmol, 89% 2 steps).

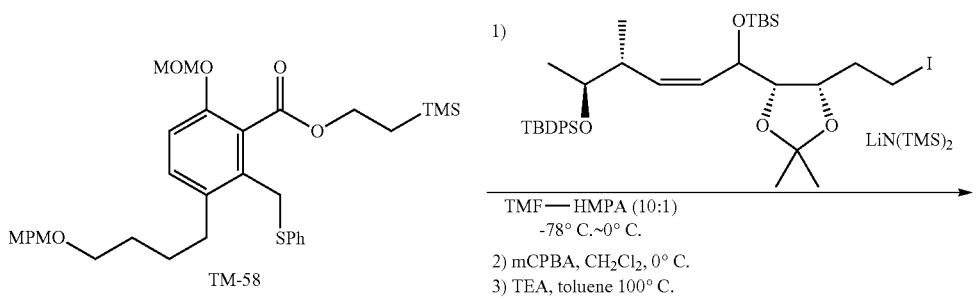

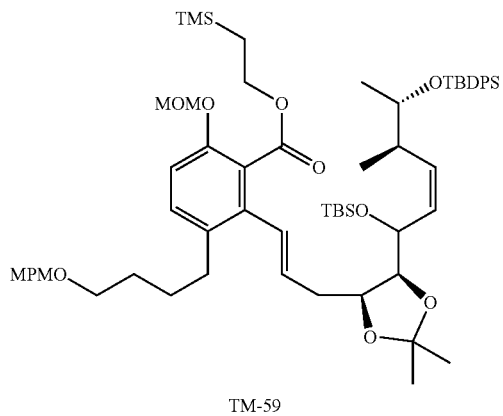
TM-59
Using similar procedure for TM-39, the iodide (223 mg, 0.30 mmol) was converted to TM-59 (132 mg, 0.12 mmol, 40% 3 steps).
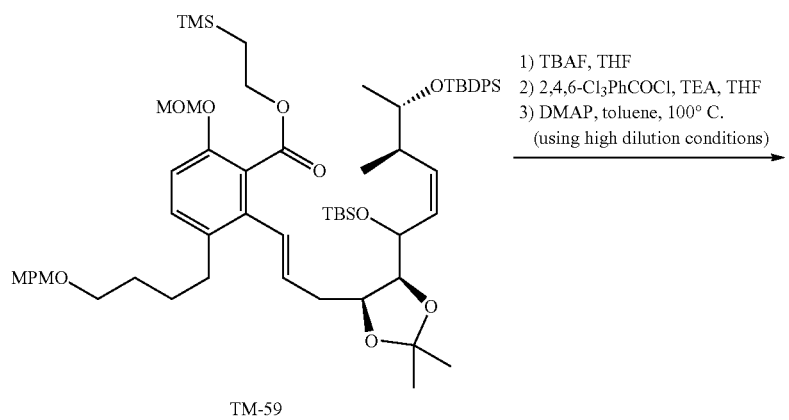
TM-59
1) TBAF, THF
2) 2,4,6-Cl₃PhCOCl, TEA, THF
3) DMAP, toluene, 100° C.
   (using high dilution conditions)
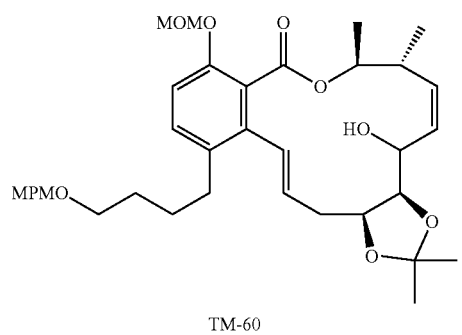
TM-60

Using similar procedure for TM-12, TM-59 (132 mg, 0.12 mmol) was converted to TM-60 (32 mg, 0.051 mmol, 43% 3 steps).

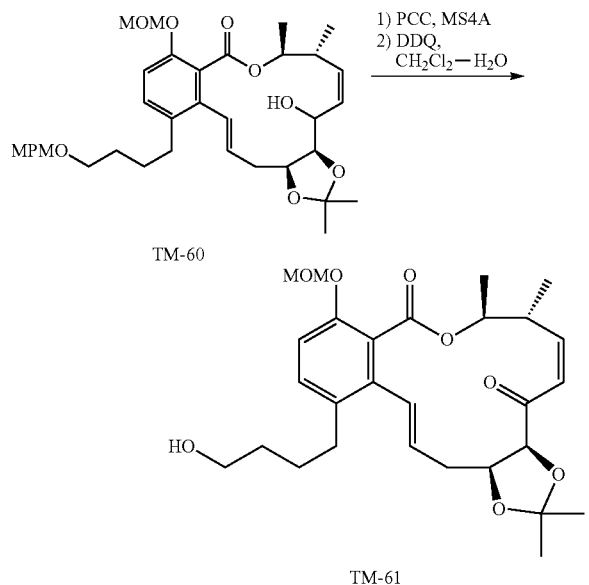

TM-60

Using similar procedure for TM-13 followed by usual deprotection of MPM group by DDQ oxidation, TM-60 (32 mg, 0.051 mmol) was converted to TM-61 (15 mg, 0.030 mmol, 58% 2 steps).

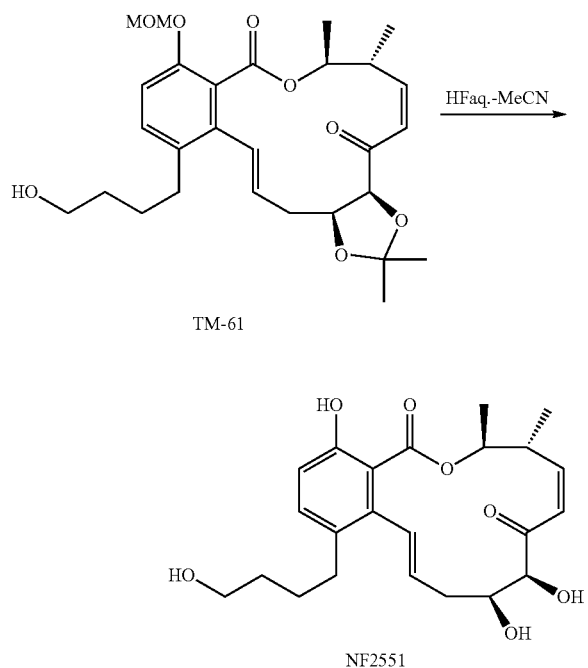

TM-61

Using similar procedure for ER803064, TM-61 (8 mg, 0.016 mmol) was converted to NF2551 (4 mg, 0.010 mmol, 60%).

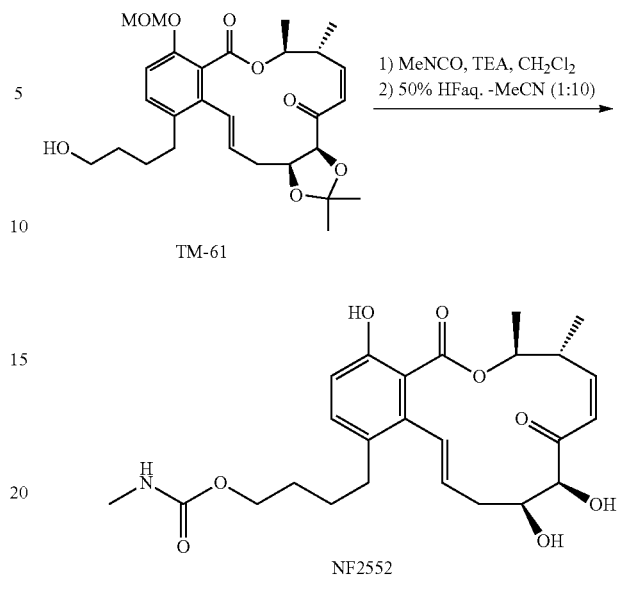

TM-61

NF2552

To a stirred solution of TM-61 (7 mg, 0.014 mmol) in CH$_2$Cl$_2$ (1 mL) were added triethylamine (0.02 mL) and methyl isocyanate (0.1 mL) at rt. After 15 hrs, the mixture was diluted with EtOAc and washed with 3% NH$_4$OH aq., 5% KHSO$_4$ aq., water, brine, dried with anhydrous Na$_2$SO$_4$, filtered and concentrated. The crude product was purified by chromatography on silica gel using 55% EtOAc/hexane to give 7 mg (0.013 mmol, 90%) of the N-methylcarbamate.

Using similar procedure for ER803064, the N-methylcarbamate (7 mg, 0.013 mmol) was converted to NF2552 (3 mg, 0.0063 mmol, 50%).

Preparation of the Intermediate for C14-O-Linked Including C$_2$-C$_4$ Analogs:

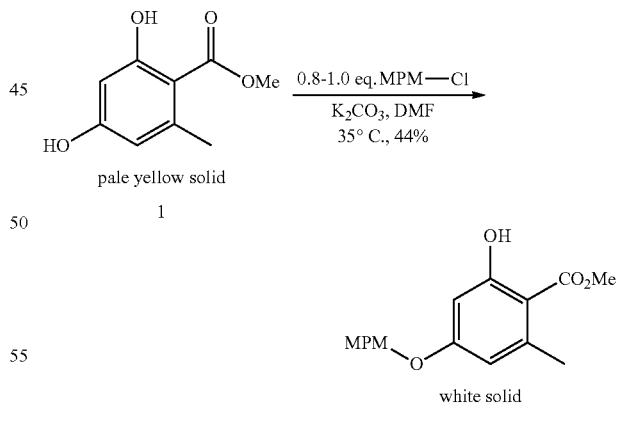

Known compound 1 (0.22 g, 1.2 mmol) and K$_2$CO$_3$ (0.25 g, 1.8 mmol) was dissolved in 12 mL of DMF. After the addition of MPM-Cl (0.17 mL, 1.2 mmol) the mixture was heated at 35° C. for 12 hours. Crude mixture was concentrated and filtered. The resulted material was purified by silica gel chromatography. CH$_2$Cl$_2$ was used to recover 445-ycs-252 (0.16 g, 0.53 mmol) from silica gel plug in 44% yield.

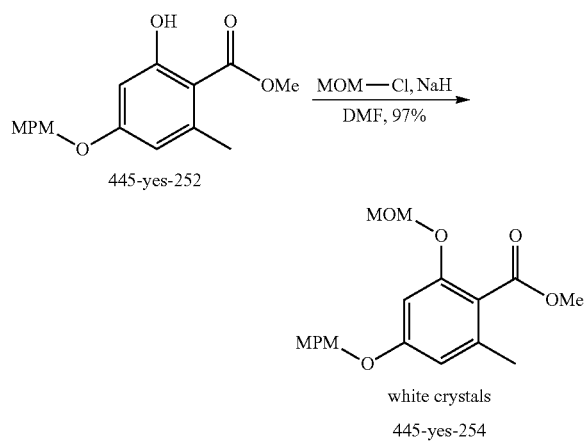

445-ycs-252

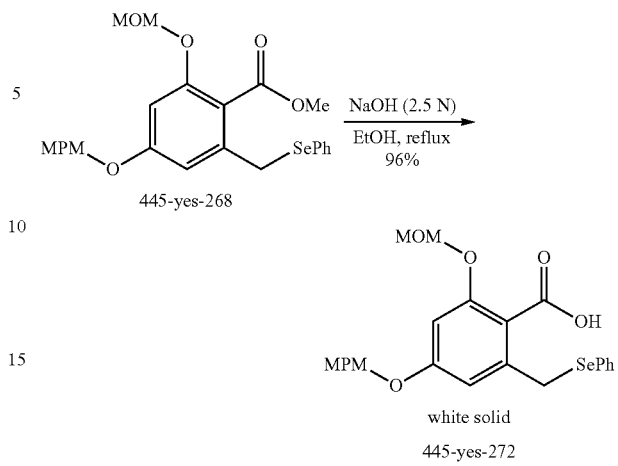

445-ycs-268

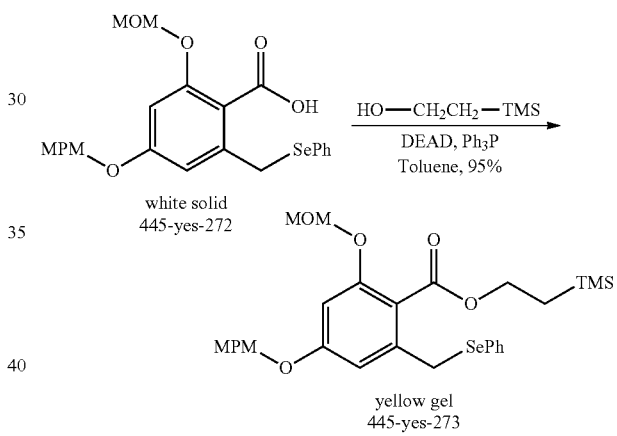

white solid
445-ycs-272 white crystals
445-ycs-254

60% of NaH in mineral oil (16 mg, 0.40 mmol) was added to 445-ycs-252 (36 mg, 0.12 mmol) in 2 mL of DMF. After the addition of MOMCl (0.17 pt, 0.22 mmol), the mixture was stirred at rt for 1 hour. DMF was evaporated under high vacuum, and the residue was dissolved in $CH_2Cl_2$, washed with $H_2O$. The crude material was purified by silica gel chromatography. 30% EtOAc in hexanes was used to elute 445-ycs-254 (40 mg, 0.12 mmol) from silica gel plug in 97% yield.

2.5 N NaOH (18 mL, 46 mmol) was added to 445-ycs-268 (7.7 g, 15 mmol) in 18 mL of EtOH. The mixture was refluxed for 12 hours before it was acidified and extracted with EtOAc. Organic phase was dried ($Na_2SO_4$) and concentrated to afford white crystalline 445-ycs-272 (7.2 g, 15 mmol) in 96% yield.

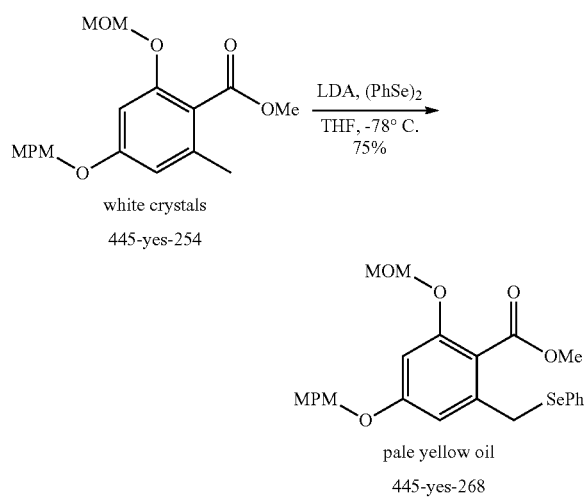

white crystals
445-ycs-254 pale yellow oil
445-ycs-268 yellow gel
445-ycs-273

2.5 M n-BuLi in hexanes (13 mL, 33 mmol) was introduced drop wise to the stirring solution of diisopropylamine (4.6 mL, 33 mmol) in 30 mL of THF at –5° C. The solution was stirred at 0° C. for 30 minutes before it was cooled to –78° C. 445-ycs-254 (6.3 g, 18 mmol) in 25 mL of THF was added to the cold LDA slowly so that the internal temperature was kept below –78° C. The mixture was stirred at –78° C. for 45 minutes, and then (PhSe)$_2$ (5.2 g, 17 mmol) in 25 mL of THF was added slowly so that the internal temperature was kept below –60° C. Reaction mixture was stirred for 40 minutes before it was quenched with aq. $NH_4Cl$ at –78° C. EtOAc was added to the mixture at rt. After separation, organic layer was dried ($Na_2SO_4$) and concentrated. 5% EtOAc in toluene was used to elute 445-ycs-268 (6.9 g, 14 mmol) from silica gel column in 75% yield.

DEAD (3.5 mL, 22 mmol) was added to a solution of 445-ycs-272 (7.2 g, 15 mmol), Ph$_3$P (5.8 g, 22 mmol) and 2-TMS-ethanol (2.6 mL, 18 mmol) in 200 mL of toluene at 0° C. The mixture was stirred at RT for 1 hour before it was quenched with aq. NaHCO$_3$. Organic phase was dried ($Na_2SO_4$), concentrated and purified by silica gel chromatography to afford 445-ycs-273 (8.2 g, 14 mmol) in 95% yield.

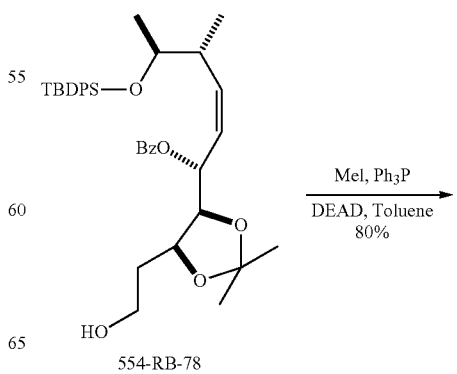

554-RB-78

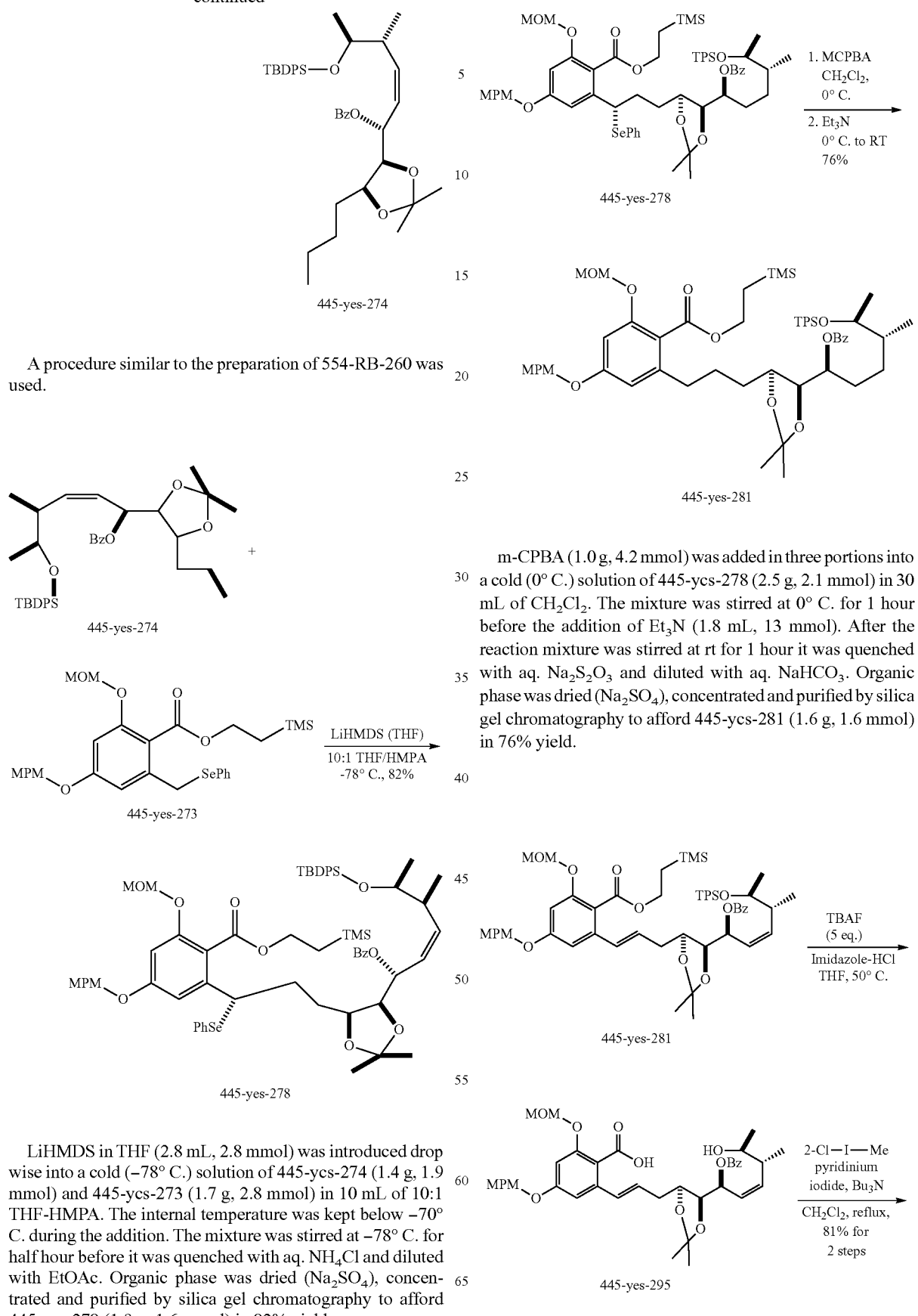

A procedure similar to the preparation of 554-RB-260 was used.

LiHMDS in THF (2.8 mL, 2.8 mmol) was introduced drop wise into a cold (−78° C.) solution of 445-ycs-274 (1.4 g, 1.9 mmol) and 445-ycs-273 (1.7 g, 2.8 mmol) in 10 mL of 10:1 THF-HMPA. The internal temperature was kept below −70° C. during the addition. The mixture was stirred at −78° C. for half hour before it was quenched with aq. NH$_4$Cl and diluted with EtOAc. Organic phase was dried (Na$_2$SO$_4$), concentrated and purified by silica gel chromatography to afford 445-ycs-278 (1.9 g, 1.6 mmol) in 82% yield.

m-CPBA (1.0 g, 4.2 mmol) was added in three portions into a cold (0° C.) solution of 445-ycs-278 (2.5 g, 2.1 mmol) in 30 mL of CH$_2$Cl$_2$. The mixture was stirred at 0° C. for 1 hour before the addition of Et$_3$N (1.8 mL, 13 mmol). After the reaction mixture was stirred at rt for 1 hour it was quenched with aq. Na$_2$S$_2$O$_3$ and diluted with aq. NaHCO$_3$. Organic phase was dried (Na$_2$SO$_4$), concentrated and purified by silica gel chromatography to afford 445-ycs-281 (1.6 g, 1.6 mmol) in 76% yield.

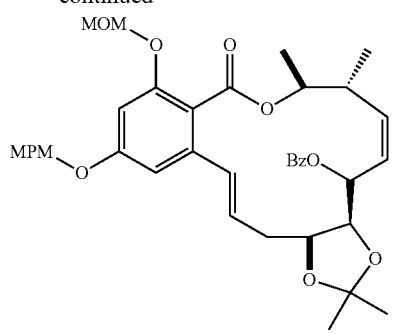

445-yes-299

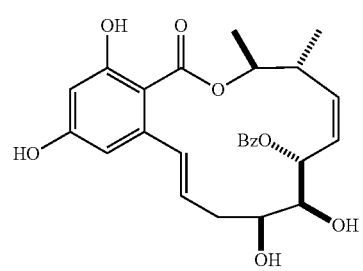

560-yes-30

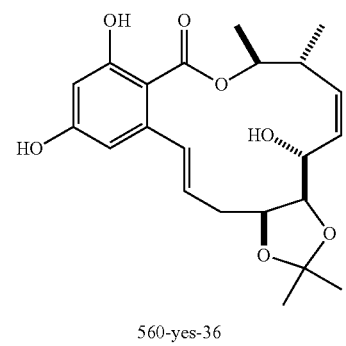

560-yes-36

In a solution of TBAF buffered with 0.33 mole equivalent of imidazole.HCl (1.3 mL, 1.3 mmol) was introduced to the solution of 445-ycs-281 (0.17 g, 0.17 mmol) in 2 mL of THF. The mixture was stirred at 50° C. for 12 hours before it was diluted with Et₂O and washed with aq. NH₄Cl. Organic phase was dried (Na₂SO₄) and concentrated to furnish crude 445-ycs-295, which dissolved in 20 mL of CH₂Cl₂ was added drop wise to the refluxing mixture of 2-chloro-1-methylpyridinium iodide (0.12 g, 0.48 mmol) and n-Bu₃N (0.11 mL, 0.48 mmol) in 12 mL of CH₂Cl₂. The mixture was refluxed for 2 hours before it was diluted with Et₂O and washed with 0.05 N HCl, H₂O and NaHCO₃. Organic phase was dried (Na₂SO₄), concentrated and purified by silica gel chromatography to afford 445-ycs-299 (90 mg, 0.13 mmol) in 81% yield for 2 steps.

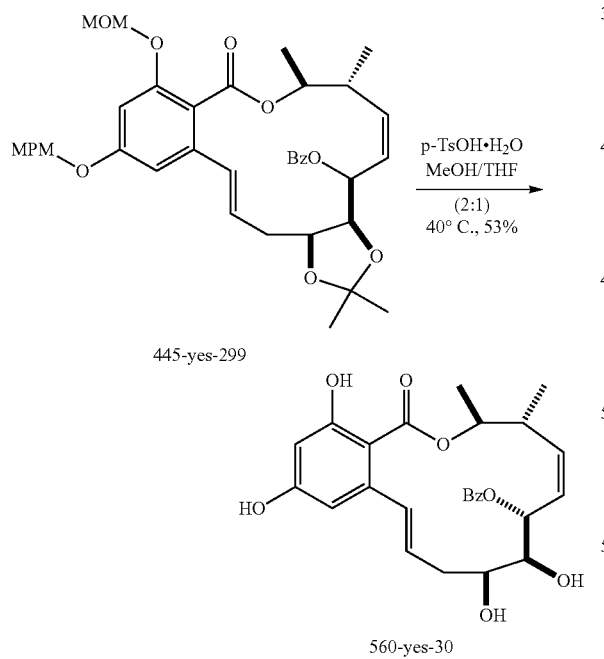

p-TsOH.H₂O (11 mg, 0.060 mmol) was added in two portions to a solution of 445-ycs-299 (40 mg, 0.060 mmol) in 4.5 mL of 2:1 MeOH-THF at rt. The solution was stirred at 40° C. for 3 days before it was concentrated and purified by silica gel chromatography to afford 560-ycs-30 (15 mg, 0.032 mmol) in 53% yield.

Catalytic amount of p-TsOH.H₂O (1 crystal) was added to the solution of 560-ycs-30 (13 mg, 0.028 mmol) and excess amount of 2-methoxypropane (2 drops) in 1 mL of CH₂Cl₂. The mixture was stirred at RT for 2 hours before the addition of NaHCO₃ and filtration. The solution was concentrated and purified by silica gel chromatography to afford 560-ycs-36 (11 mg, 0.022 mmol) in 79% yield.

Preparation of ER804104:

560-ycs-36 was used as an advanced intermediate for following analogs synthesis as examples.

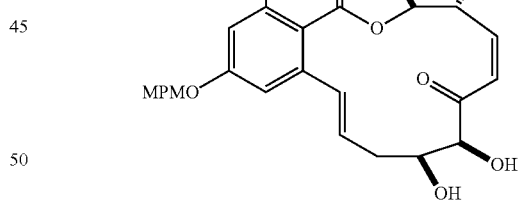

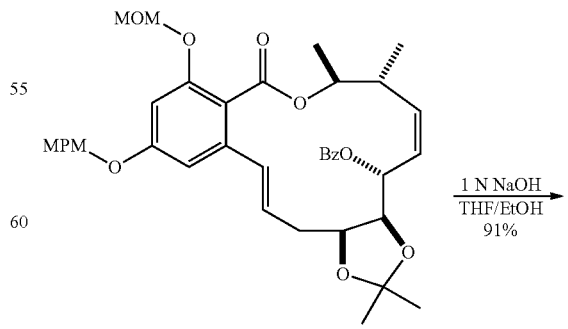

445-yes-299
white solid

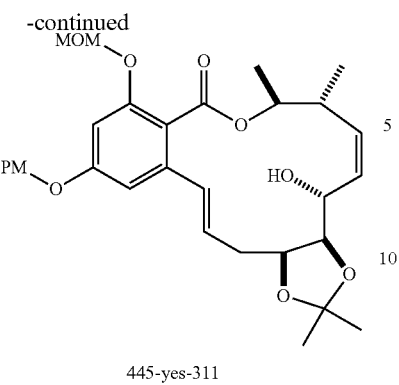

445-ycs-311

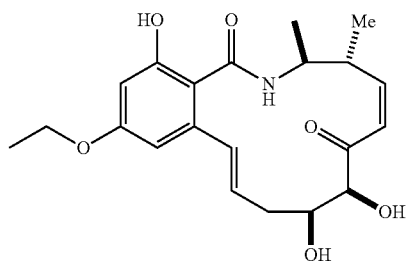

ER-804168

1 N NaOH (2.0 mL, 2.0 mmol) was introduced into a solution of 445-ycs-299 (43 mg, 0.064 mmol) in 3 mL of 2:1 EtOH-THF at rt. The solution was stirred at 40° C. for 12 hours before it was diluted with Et$_2$O and brine. Organic phase was dried (Na$_2$SO$_4$) and purified by silica gel chromatography to afford 445-ycs-311 (33 mg, 0.058 mmol) in 91% yield.

ER-804168

The synthesis of ER-804168 was the same as the synthesis of ER-803064

Synthesis of ER-805125:

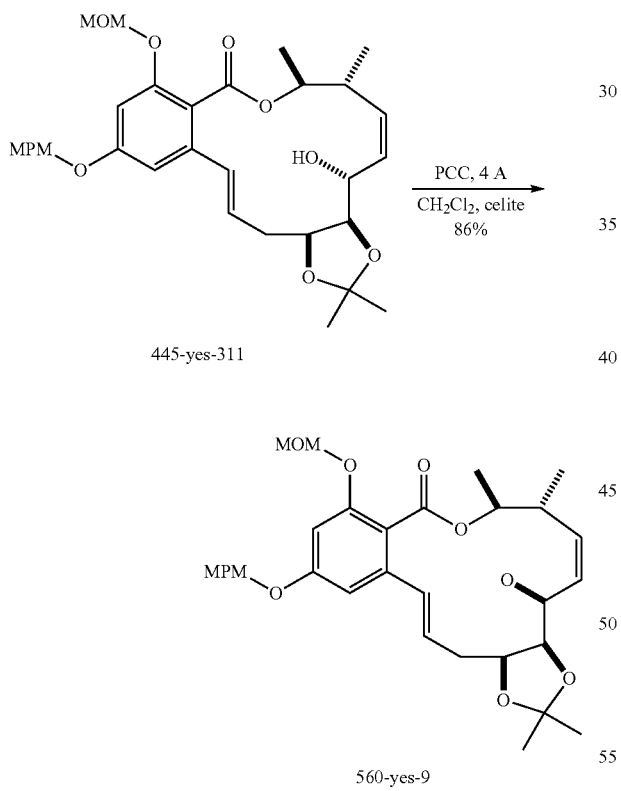

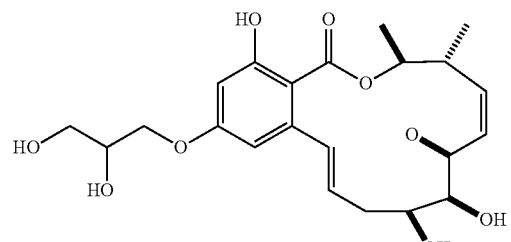

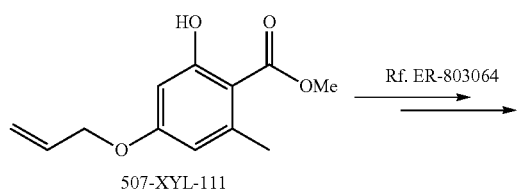

507-XYL-111

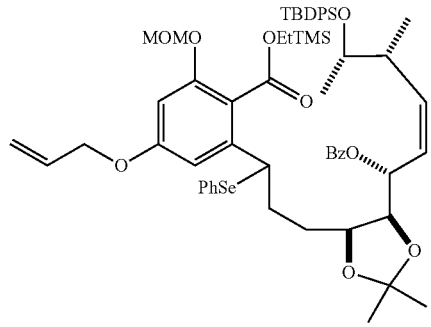

507-XYL-147

PCC (38 mg, 0.17 mmol) was added in three portions to a mixture of 445-ycs-311 (33 mg, 0.058 mmol), 4 Å molecular sieves (40 mg) and celite (40 mg) in 2 mL of CH$_2$Cl$_2$ at rt. The mixture was stirred at rt for 1 hour before it was diluted with Et$_2$O and filtered. The filtrate was concentrated and passed through a short plug of silica gel (1:1 EtOAc-Hexanes) to afford 560-ycs-9 (28 mg, 0.049 mmol) in 86% yield.

560-ycs-9 was deprotected as described for the synthesis of ER803064 to give ER804104.

The synthesis of 507-XYL-147 from 507-XYL-111 was followed the same procedures as in the synthesis of ER-803064.

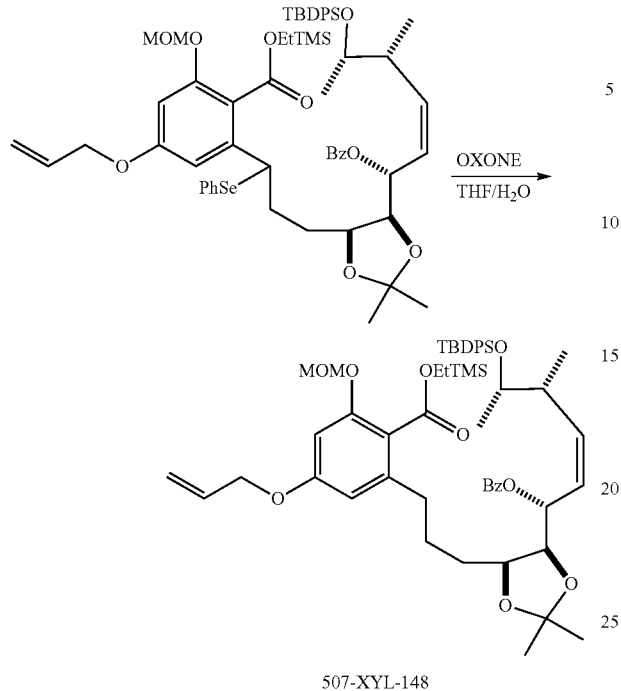

507-XYL-148

To 507-XYL-147 (1.43 g, 1.29 mmol) in a co-solvent of THF/water (5:1 v/v, 60 mL) at room temperature was added OXONE and the mixture was stirred at room temperature for six hours. The mixture was diluted with ethyl acetate and washed three times with water. The organic layer was dried (sodium sulfate), concentrated and purified by silica gel chromatography to obtain 1.05 g (86%) of the desired product, 507-XYL-148 which was confirmed by NMR and MS (M+Na=972).

The synthesis of 507-XYL-154 from 507-XYL-148 was followed the same procedures as in the synthesis of ER-803064.

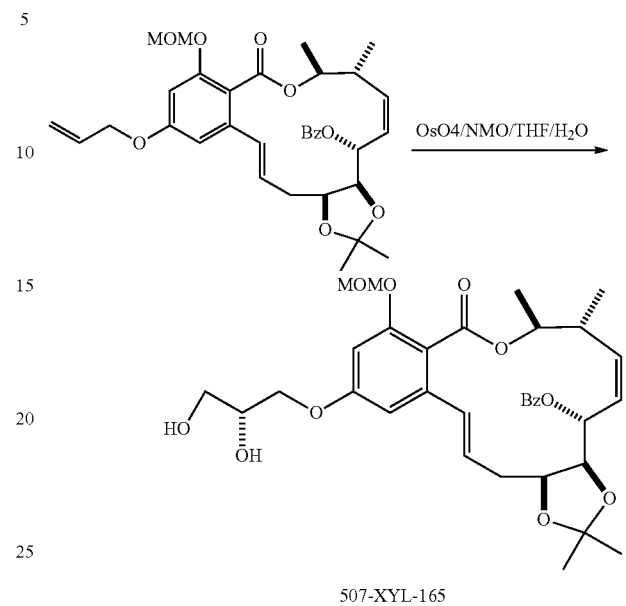

507-XYL-165

To 507-XYL-154 (340 mg, 0.57 mmol) in a co-solvent of THF/water (4:1 v/v, 12.5 mL) at 0° C. were added N-methyl morpholino-N-oxide (82.5 mg, 0.68 mmol) and then osmium tetraoxide in toluene (0.1 M, 0.6 mL, 0.06 mmol) in portions. The mixture was stirred at 0° C. for 19 hours. The reaction was quenched with saturated sodium thiosulfate solution and diluted with ethyl acetate. The mixture was washed with saturated sodium thiosulfate solution and water. The aqueous layers were back extracted twice with ethyl acetate and three times with methylene chloride. The combined organic layers were dried (sodium sulfate), concentrated and purified by preparative TLC eluting with 10% methanol in methylene chloride to yield 158 mg (44%) of desired product, 507-XYL-165 which was confirmed by NMR and MS (M+Na=649).

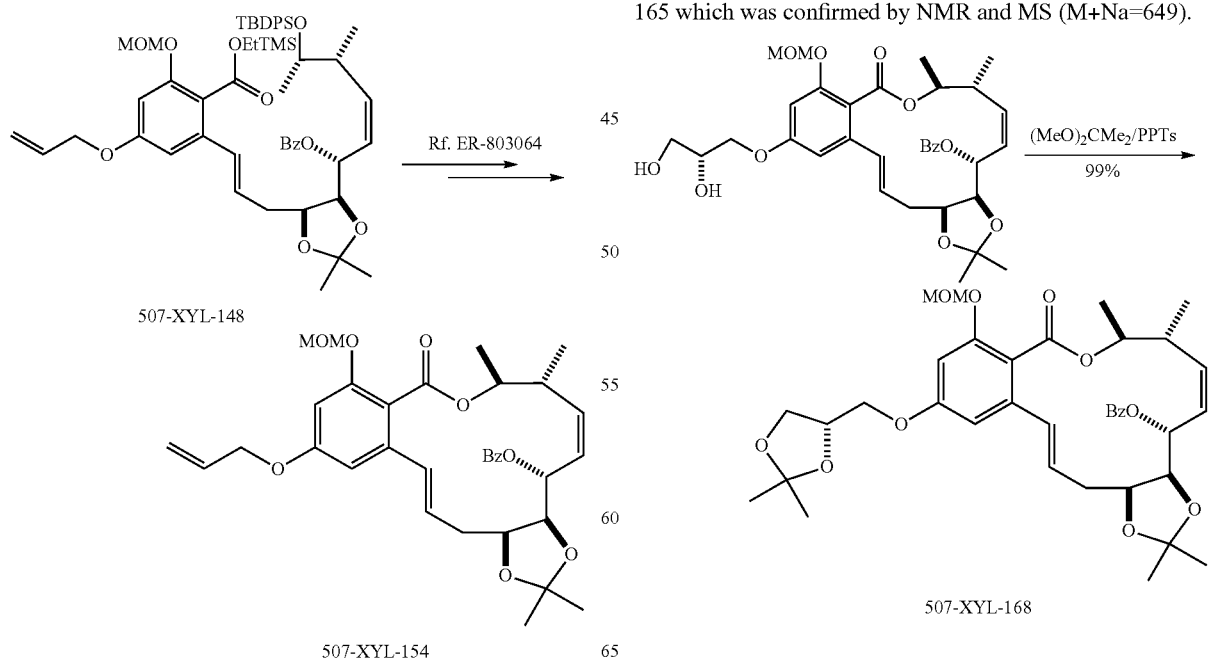

507-XYL-154

507-XYL-168

To 507-XYL-165 (120 mg, 0.197 mmol) were added methylene chloride (5 mL), 2,2-dimethoxypropane (0.2 mL, 1.63 mmol) and pyridinium tosylate (12 mg, 0.048 mmol). The mixture was stirred at room temperature for two hours. The mixture was diluted with methylene chloride and washed twice with saturated sodium bicarbonate solution. The organic layer was concentrated and purified by prep TLC to obtain 131 mg of the desired products, 507-XYL-168 which were confirmed by NMR and MS (M+Na=689).

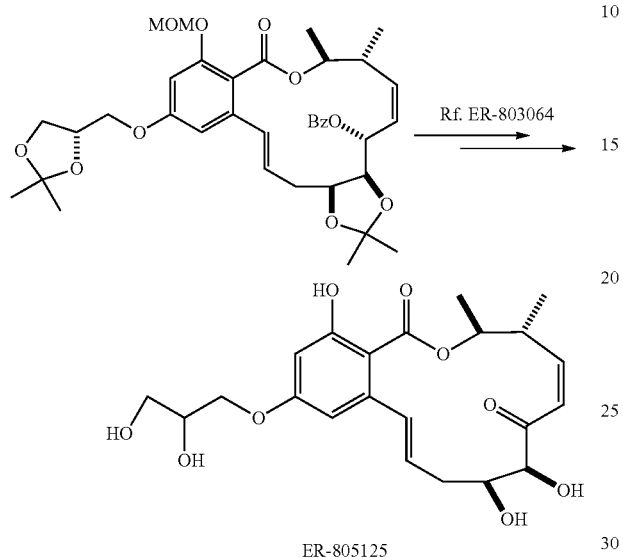

The remaining synthesis of ER-805125 from 507-XYL-168 was followed the same procedures as in the synthesis of ER-803064.

Preparation of ER-805216 and ER-805217:

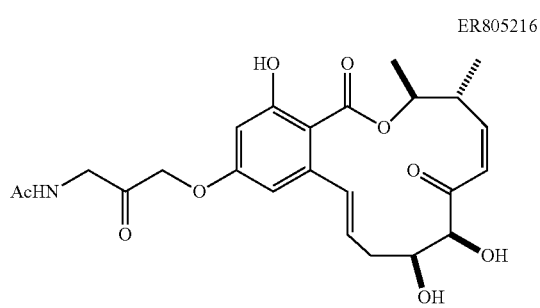

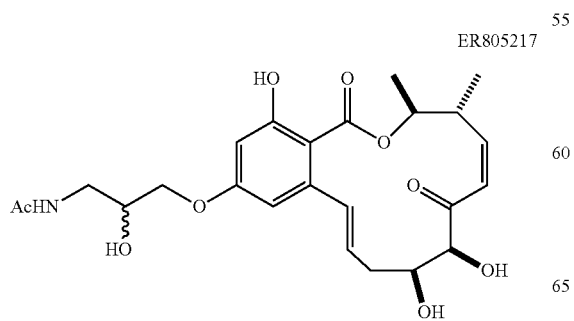

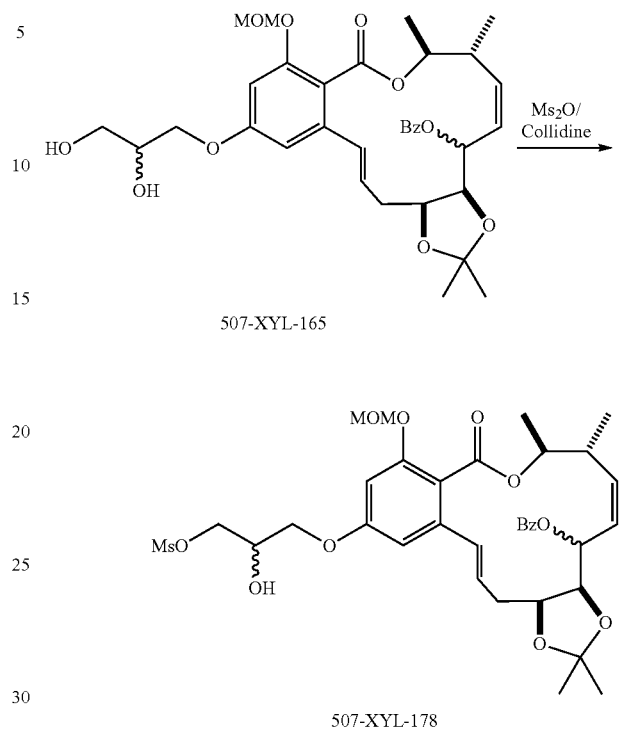

The starting material 507-XYL-165 (42 mg, 0.066 mmol) was azeotroped with toluene and dried under high vacuum for one hour. The starting material was then dissolved in dry methylene chloride (5 mL) and cooled to 0° C. To this were added collidine (20.3 uL, 0.15 mmol) and then added methanesulfonyl anhydride solution in methylene chloride (0.1 M, 0.69 mL, 0.069 mmol) drop wise over five minutes. The mixture was stirred at 0° C. for 1.5 hour and at 4° C. over night. The mixture was poured into a saturated sodium bicarbonate solution and extracted three times with methylene chloride and once with ethyl acetate. The combined organic layers were dried (sodium sulfate), concentrated and purified by preparative TLC eluting with 5% methanol in methylene chloride to provide 36 mg (77%) of the desired product, 507-XYL-178 which was confirmed by NMR and MS (M+Na=727).

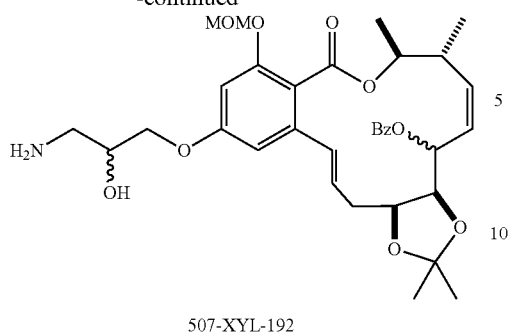

507-XYL-192

To 507-XYL-178 (36 mg, 0.05 mmol) were added 2.0M ammonia in methanol (16 mL) and concentrated aqueous ammonium hydroxide solution (3.2 mL) and the mixture was stirred at room temperature for 12 hours. The mixture was concentrated in vacuum, azeotroped with ethyl acetate, methanol and toluene, and dried under reduced pressure. The crude product, 507-XYL-192 was directly used for the next reaction.

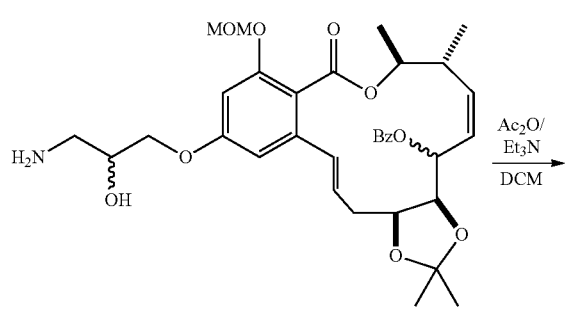

507-XYL-192

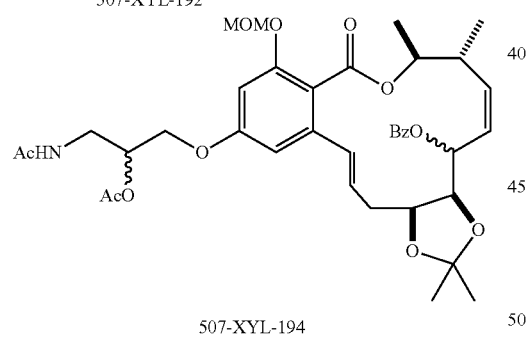

507-XYL-194

To 507-XYL-192 in methylene chloride (10 mL) at 0° C. were added triethylamine (0.2 mL, 1.51 mmol) and acetic anhydride (0.1 mL, 1.06 mmol). The mixture was stirred at room temperature over night. The reaction mixture was cooled to 0° C. and quenched with saturated sodium bicarbonate solution. The mixture was poured into excessive sodium bicarbonate solution and extracted three times with methylene chloride and three times with ethyl acetate. The combined organic layers were dried (sodium sulfate), concentrated to obtain the crude desired product, 507-XYL-194 which was confirmed by MS (M+Na=732). The crude product was directly used for the next reaction without further purification.

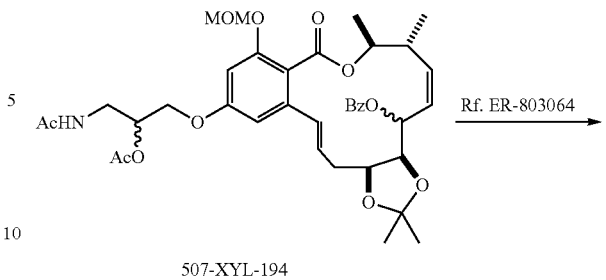

507-XYL-194

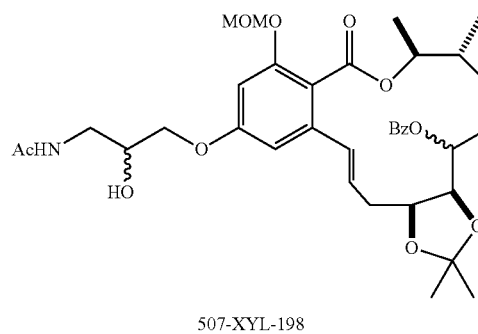

507-XYL-198

The conversion of 507-XYL-194 to 507-XYL-198 was the same as in the synthesis of ER-803064. Preparative TLC purified the crude product with 5% ethanol in ethyl acetate to give 13.6 mg (57% over three steps) of the desired product, 507-XYL-198 which was confirmed by NMR and MS (M+Na=586).

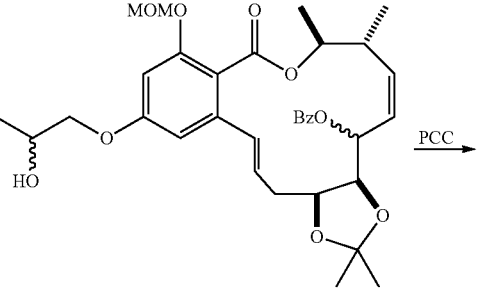

507-XYL-198

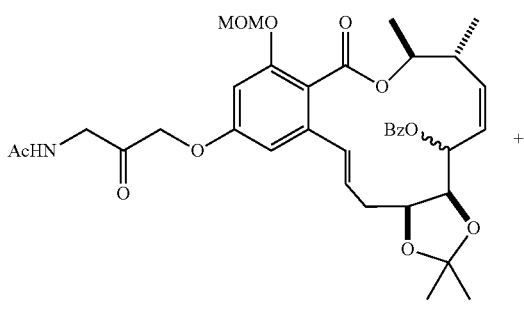

507-XYL-204a

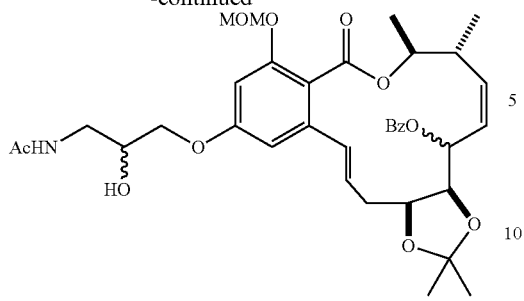

507-XYL-204b

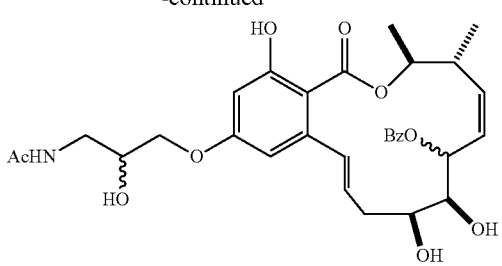

ER-805217

The oxidation of 507-XYL-198 using pyrridinium chlorochromate was followed the same procedure as in the synthesis of ER-803064. Preparative TLC purified the crude material with 8% ethanol in ethyl acetate to afford 507-XYL-204a and 507-XYL-204b, which were confirmed by NMR.

The conversion of 507-XYL-204b to ER-805217 was the same as in the synthesis of ER-803064. Purification of crude material by preparative TLC eluting with 25% ethanol in ethyl acetate afforded ER-805217, which was confirmed by NMR and MS (M+Na=500).

Preparation of ER804401:

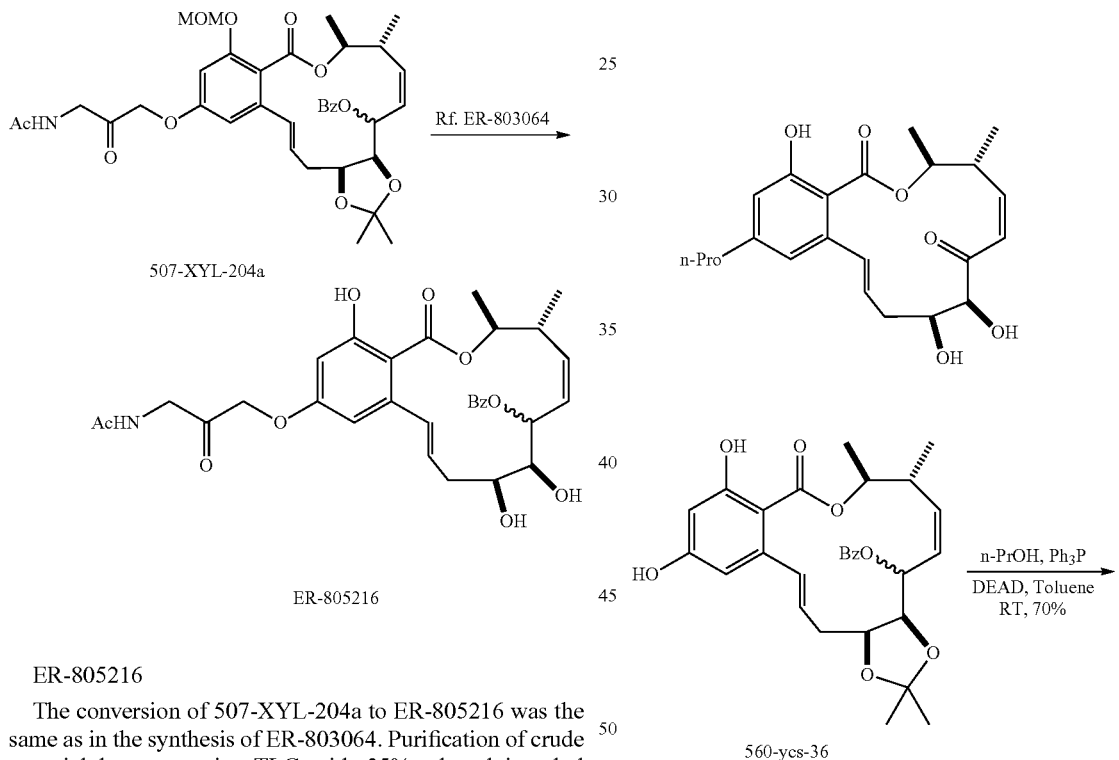

ER-805216

The conversion of 507-XYL-204a to ER-805216 was the same as in the synthesis of ER-803064. Purification of crude material by preparative TLC with 25% ethanol in ethyl acetate afforded ER-805216, which was confirmed by NMR and MS (M+Na=498).

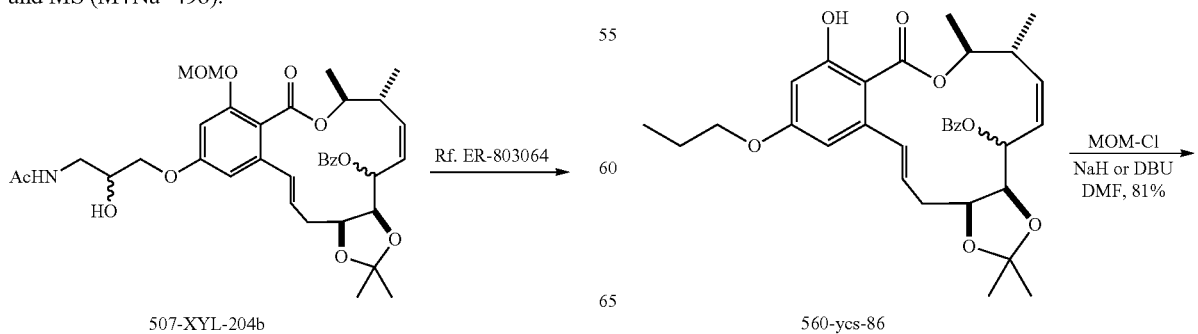

355

-continued

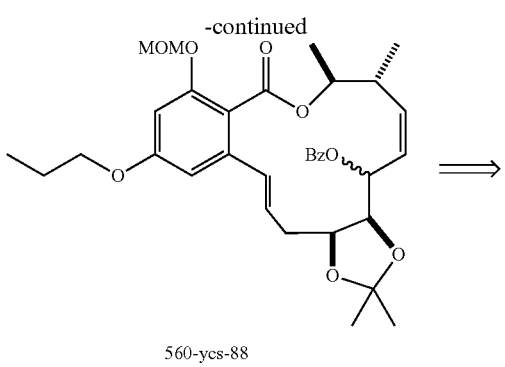

560-ycs-88

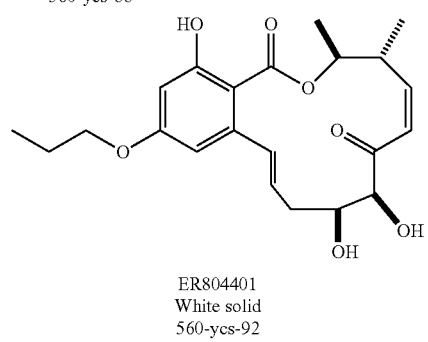

560-ycs-36

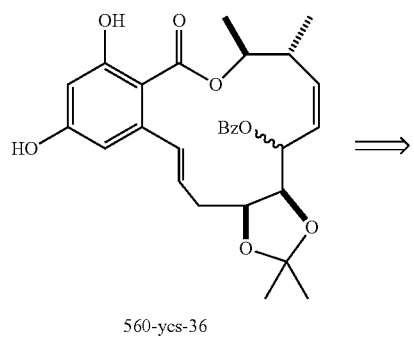

ER804504
White solid
560-ycs-103

Procedure for the preparation of 560-ycs-86 was similar to that of 445-ycs-273.

Procedure for the preparation of 560-ycs-88 was similar to that of 445-ycs-254.

Procedure for the preparation of ER804401 from 560-ycs-88 was similar to the synthesis of ER804104.

ER804504 was prepared in the similar way as ER804401 from 560-ycs-36 and n-butanol.

356

Preparation of ER804555 and ER804567:

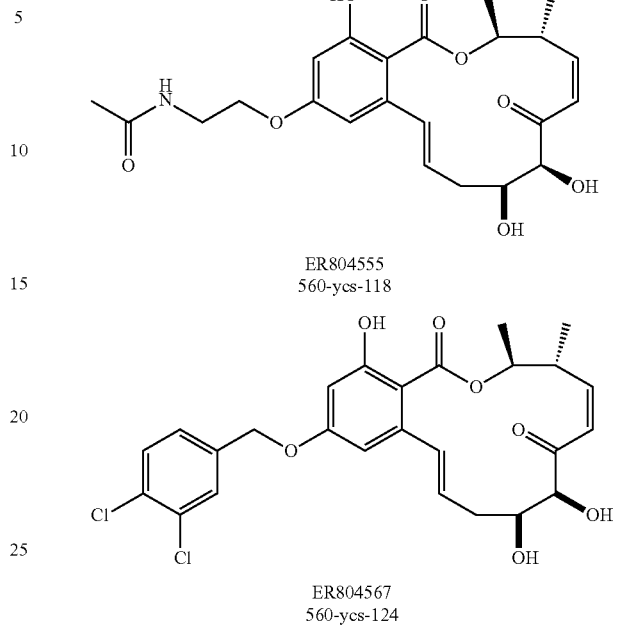

Procedure for the preparation of ER804555 from 560-ycs-36 and N-acetyl ethanolamine was similar to the synthesis of ER804401.

ER804567 was prepared in the similar way as ER804401 from 560-ycs-36 and 3,4-dichlorobenzyl alcohol.

Preparation of ER804606:

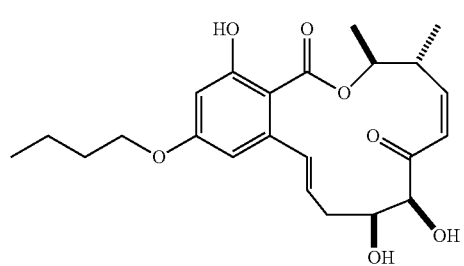

560-ycs-36

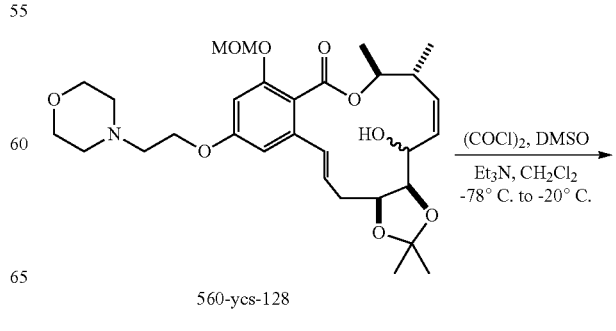

560-ycs-128

Preparation of ER804778:

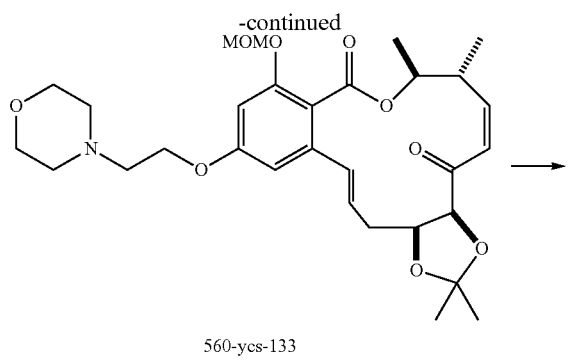

560-ycs-133

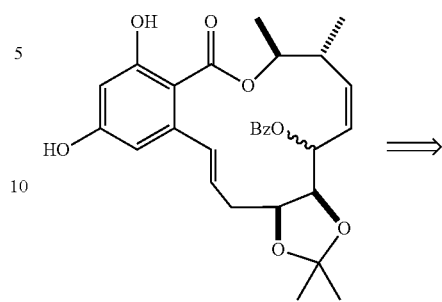

560-ycs-36

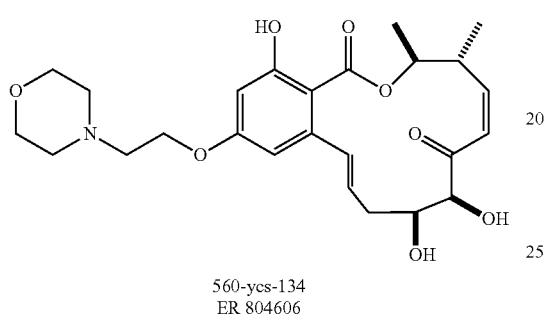

560-ycs-134
ER 804606

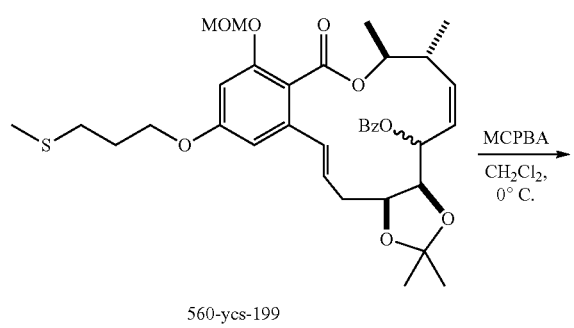

560-ycs-199

ER804606 was prepared in the similar way as ER804401 from 560-ycs-36 and 4-(2-hydroxyethyl)-morpholine except that oxidation of alcohol 560-ycs-128 into enone 560-ycs-133 was carried out under Swern conditions as below instead of using PCC.

(COCl)$_2$ (2.6 µL, 0.030 mmol) was introduced into a solution of DMSO (4.2 µL, 0.060 mmol) in 0.2 mL of CH$_2$Cl$_2$ at −78° C. The mixture was stirred at −78° C. for 15 minutes before the addition of 560-ycs-128 (6.0 mg, 0.010 mmol) in 0.8 mL of CH$_2$Cl$_2$. After the solution was stirred for 1 hour at −78° C. Et$_3$N (12 µL, 0.090 mmol) was added. The reaction mixture was allowed to warm up to −20° C. for 15 minutes and quenched with Sat. NH$_4$Cl. Organic phase was washed with NaHCO$_3$ and concentrated to furnish 560-ycs-133 (6.0 mg, 0.010 mmol) in quantitative yield.

Preparation of ER804630:

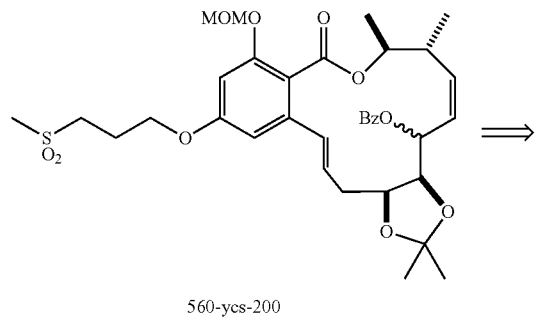

560-ycs-200

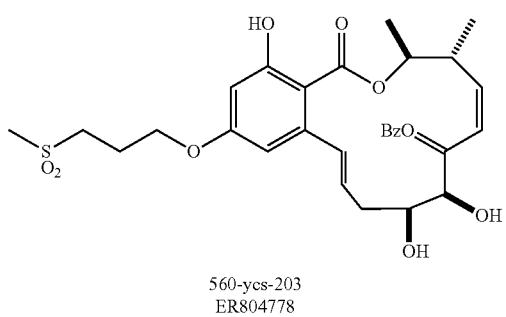

560-ycs-203
ER804778

ER804778 was prepared in the similar way as ER804401 from 560-ycs-36 and 3-methylthio-1-propanol except that 560-ycs-199 was oxidized into 560-ycs-200 by m-CPBA.

MCPBA (12 mg, 0.048 mmol) was added in three portions to the solution of 560-ycs-199 (5.2 mg, 0.0081 mmol) in 2 mL of CH$_2$Cl$_2$ at 0° C. The solution was stirred at 0° C. for 10 minutes before it was washed with Na$_2$S$_2$O$_3$ and concentrated to afford 560-ycs-200 (5.0 mg, 0.0074 mmol) in 92% yield.

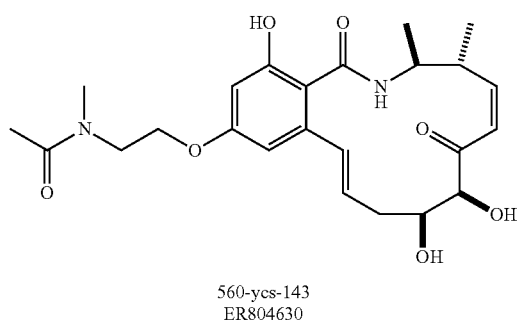

560-ycs-143
ER804630

ER804630 was prepared in the similar way as ER804401 from 560-ycs-36 and N-acetyl, N-methyl ethanolamine.

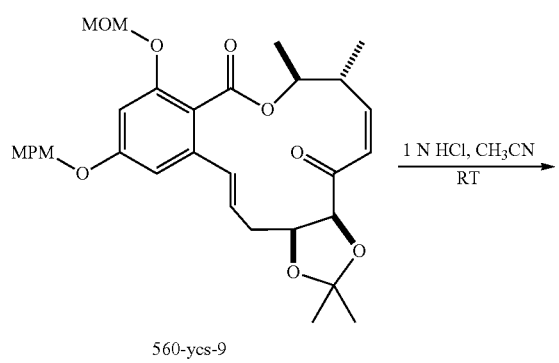

560-ycs-9

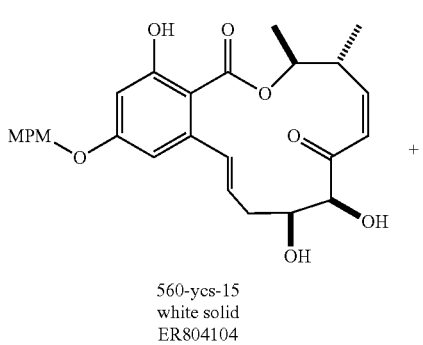

560-ycs-15
white solid
ER804104

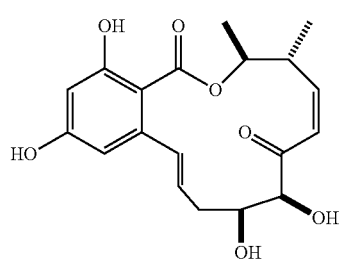

560-ycs-29
white solid
ER804131

Aq. HCl (3.0 mL, 3.0 mmol) was introduced to a solution of 560-ycs-9 (31 mg, 0.055 mmol) in 3 mL of CH₃CN at rt. The solution was stirred at rt for 12 hours before it was diluted with EtOAc and H₂O. Organic phase was washed with NaHCO₃, dried (Na₂SO₄), concentrated and purified by silica gel chromatography to afford ER804104 (12 mg, 0.025 mmol) in 45% yield and ER804131 (5.9 mg, 0.016 mmol) in 30% yield.

Alternative preparation of commonly used intermediate for C14 modification:

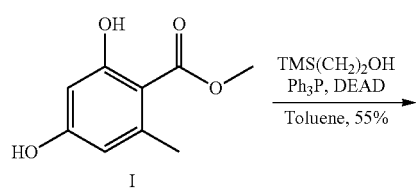

I

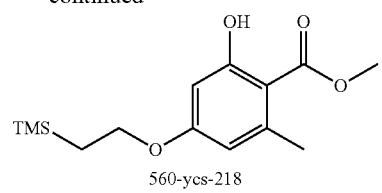

560-ycs-218

Procedure for the preparation of 560-ycs-218 was similar to that of 445-ycs-273.

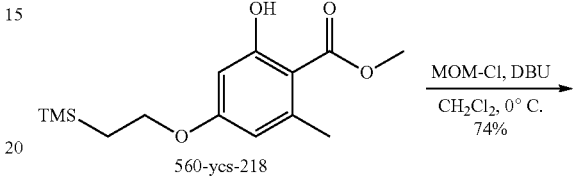

560-ycs-218

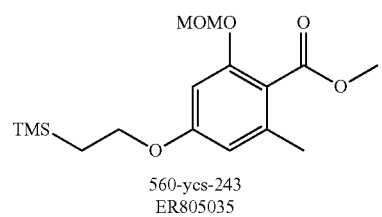

560-ycs-243
ER805035

MOM-Cl (2.8 mL, 37 mmol) was added to a solution of 560-ycs-218 (2.1 g, 7.4 mmol) and DBU (7.1 mL, 48 mmol) in 10 mL of CH₂Cl₂ at 0° C. The mixture was stirred at rt for 15 minutes before the organic phase was washed with NaHCO₃, concentrated and purified by silica gel chromatography to furnish 560-ycs-243 (1.8 g, 5.5 mmol) from silica gel plug in 74% yield.

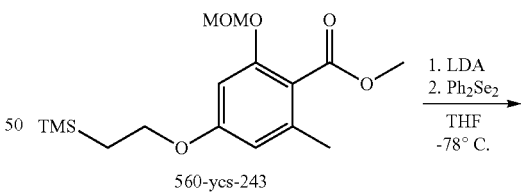

560-ycs-243

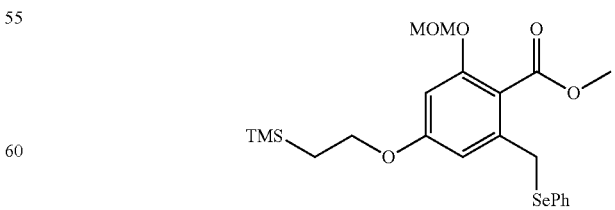

560-ycs-248

Procedure for the preparation of 560-ycs-248 was similar to that of 445-ycs-268.

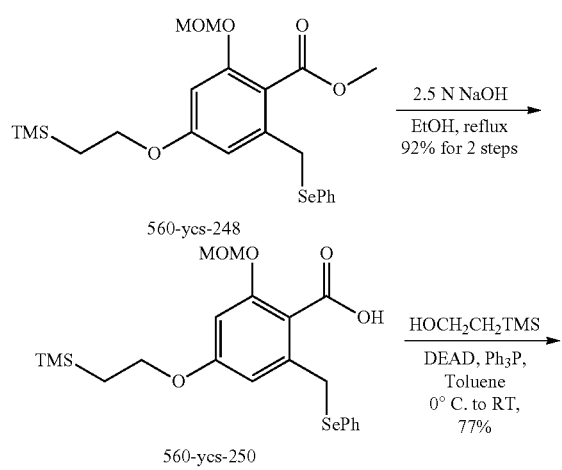
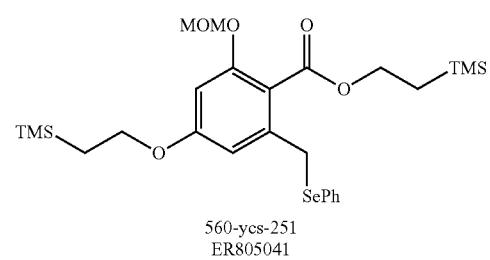
Procedure for the preparation of 560-ycs-250 was similar to that of 445-ycs-272.
Procedure for the preparation of 560-ycs-251 was similar to that of 445-ycs-273.
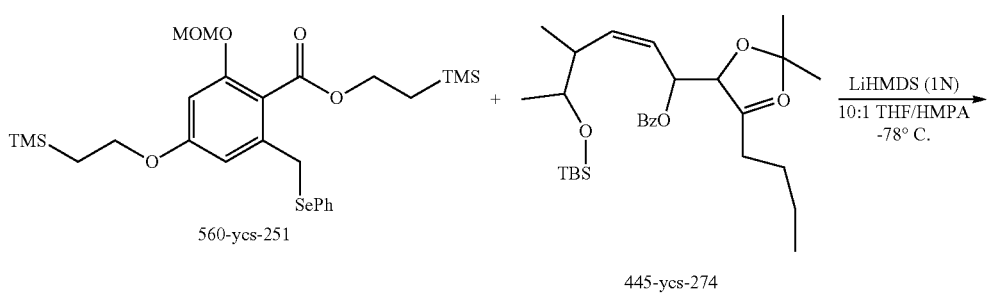
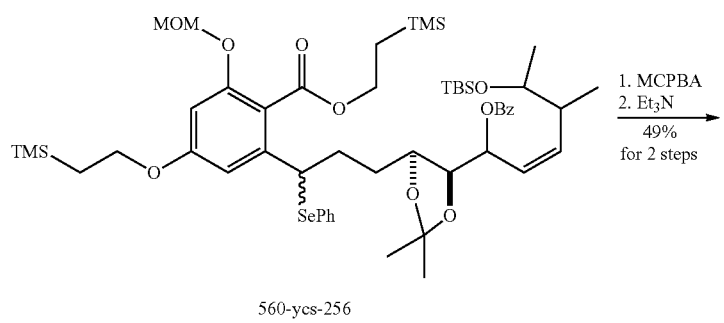
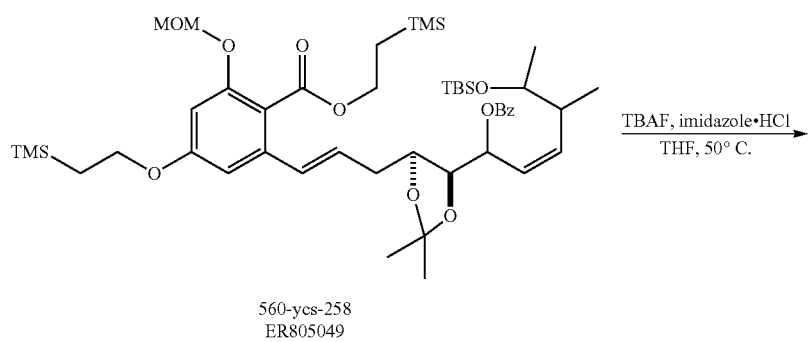

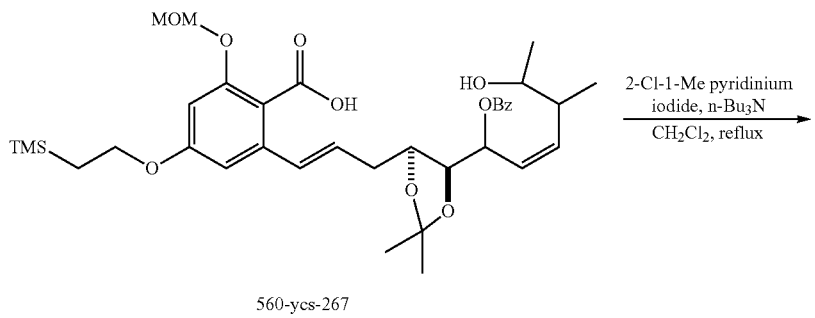

560-ycs-267

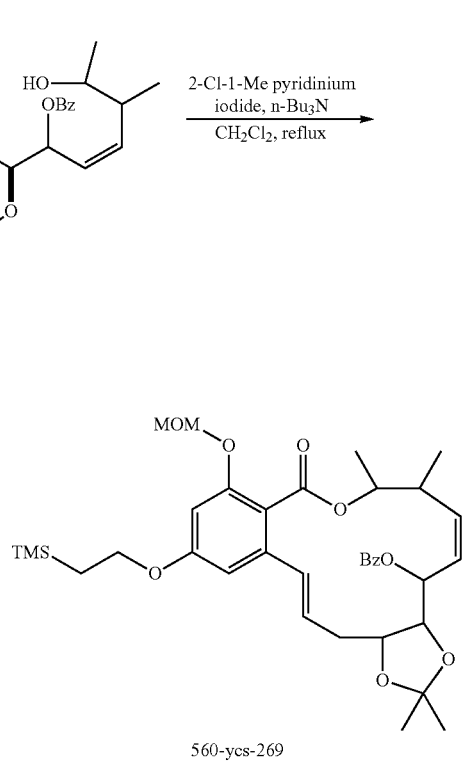

560-ycs-269

Procedure for the preparation of 560-ycs-256 was similar to that of 445-ycs-278.

Procedure for the preparation of 560-ycs-258 was similar to that of 445-ycs-281.

Procedure for the preparation of 560-ycs-267 was similar to that of 445-ycs-295.

Procedure for the preparation of 560-ycs-269 was similar to that of 445-ycs-299.

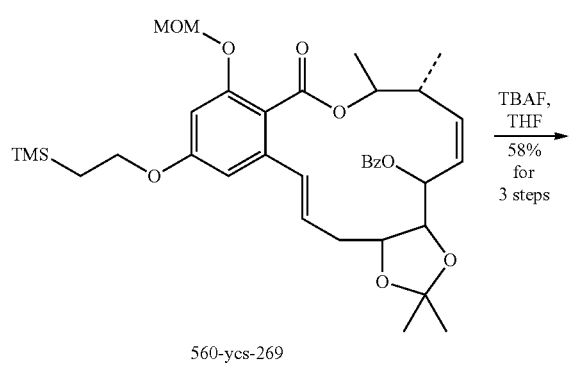

560-ycs-269

-continued

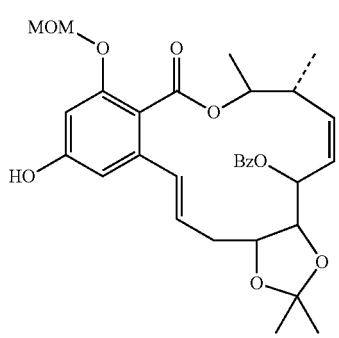

560-ycs-270
ER805102

TBAF in THF (7.0 mL, 7.0 mmol) was introduced to the solution of 560-ycs-269 (0.87 g, 1.3 mmol) in 7 mL of THF. The mixture was stirred at rt for 4 hours before it was diluted with Et$_2$O and washed with brine. Organic phase was dried (Na$_2$SO$_4$), concentrated and purified by silica gel chromatography to afford 560-ycs-270 (0.43 g, 0.78 mmol) in 58% yield over 3 steps.

Preparation of ER805190:
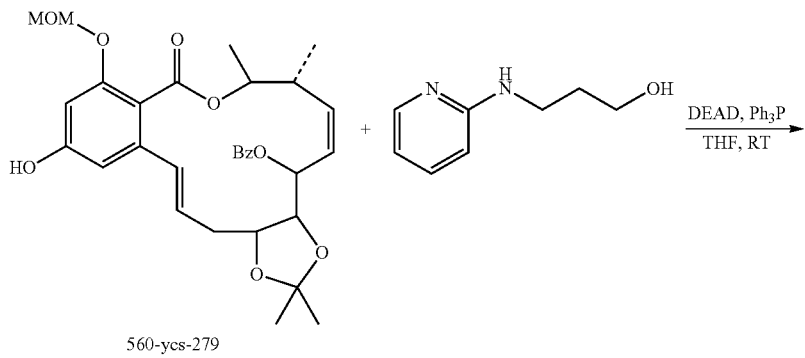
560-ycs-279
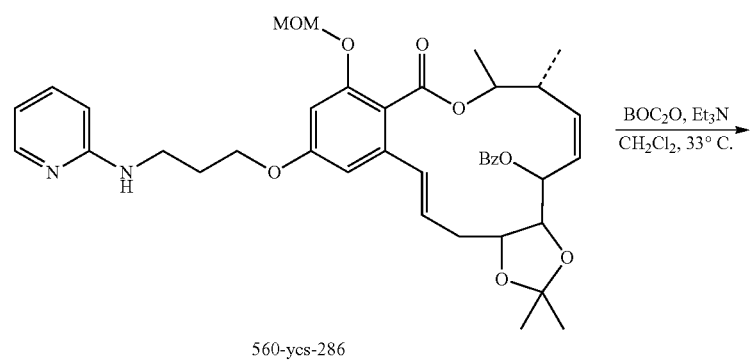
560-ycs-286
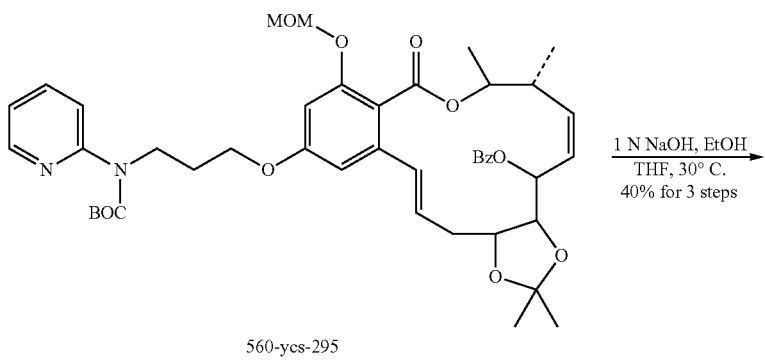
560-ycs-295
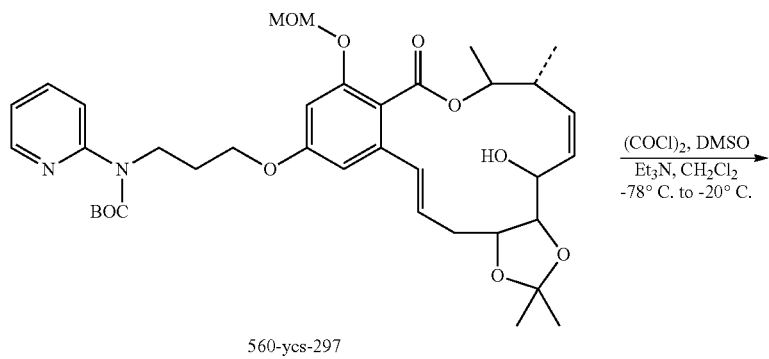
560-ycs-297

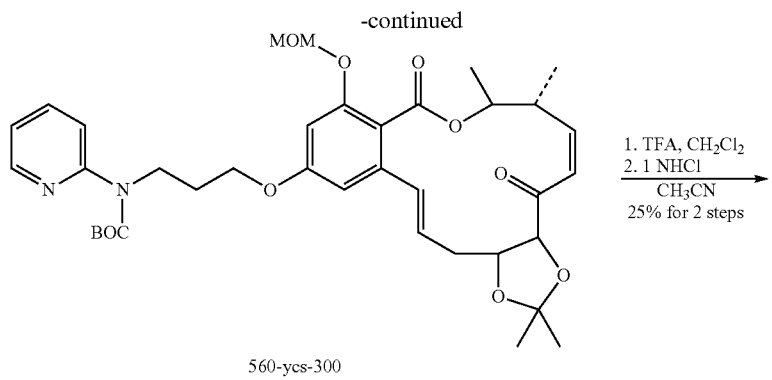

560-ycs-300

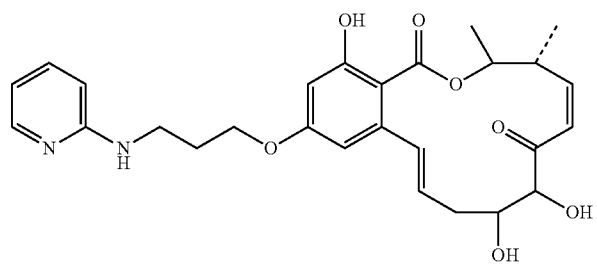

ER-805190
560-ycs-301

Transformations from 560-ycs-279 to 560-ycs-286 and from 560-yes-297 to 560-ycs-300 were similar as the procedure for the preparation of ER804606.

Transformations from 560-ycs-286 to 560-ycs-297 and from 560-ycs-300 to ER805190 were similar as the procedure for the preparation of ER805135.

Preparation of C14-C2 Linked Series:

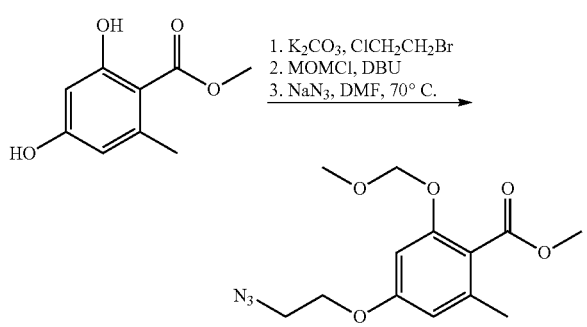

To a solution of starting diphenol (10.7 g) in acetone (100 mL), BrCH$_2$CH$_2$Cl (15 mL) and 20 g of K$_2$CO$_3$ were added. The mixture was heated at 80° C. for 1 day. It was cooled and filtered. The filtrate was diluted with EtOAc, washed with brine, dried and concentrated. The crude product was purified on silica gel column with hexanes/CH$_2$Cl$_2$, 2:1 then 1:1 to hexanes/EtOAc, 1:1 to give 12.7 g of desired product.

The MOM protection was carried out under the same conditions as previously described. After purification 12.7 g of product was obtained.

The mixture of chlorophenol (12.7 g), NaN$_3$ (6 g) in 20 mL of DMF was heated at 70° C. overnight. After cooled, it was diluted with EtOAc, washed with water, brine, dried and concentrated. The crude product was purified on silica gel column to give 10.3 g of desired azide.

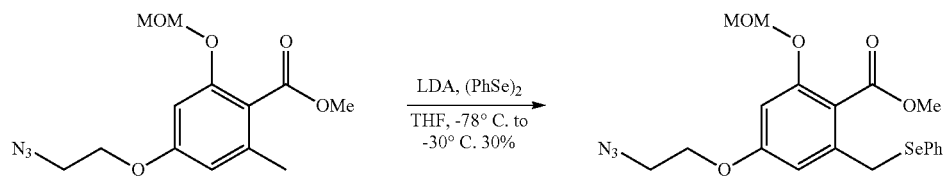

560-ys-148

-continued
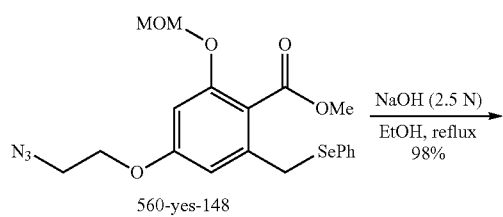
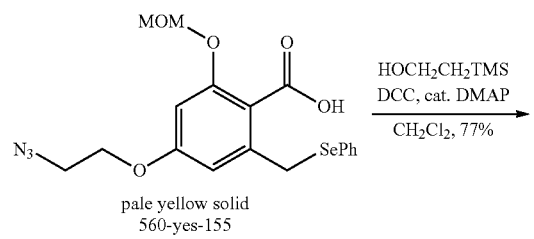
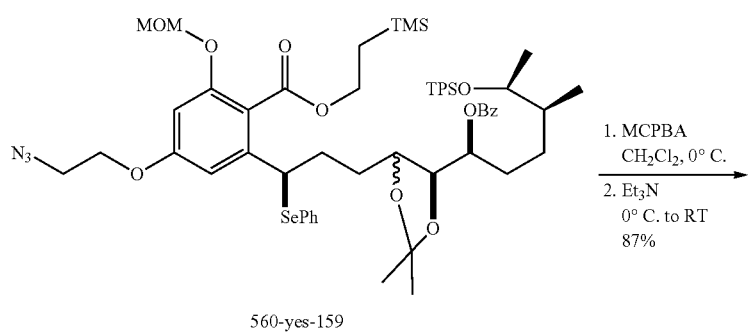
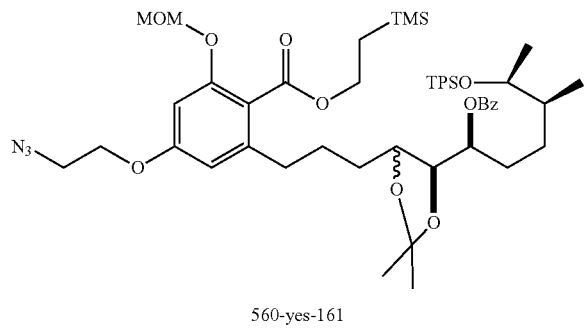
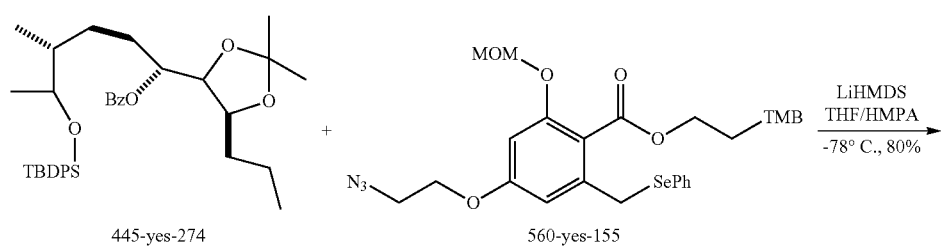
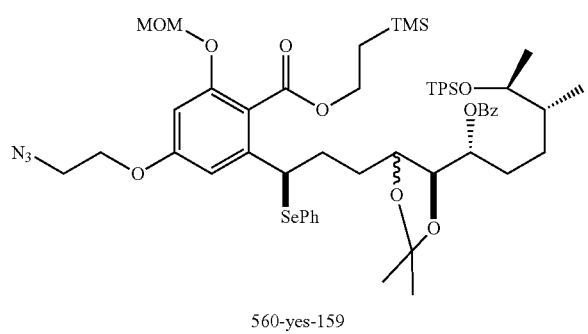

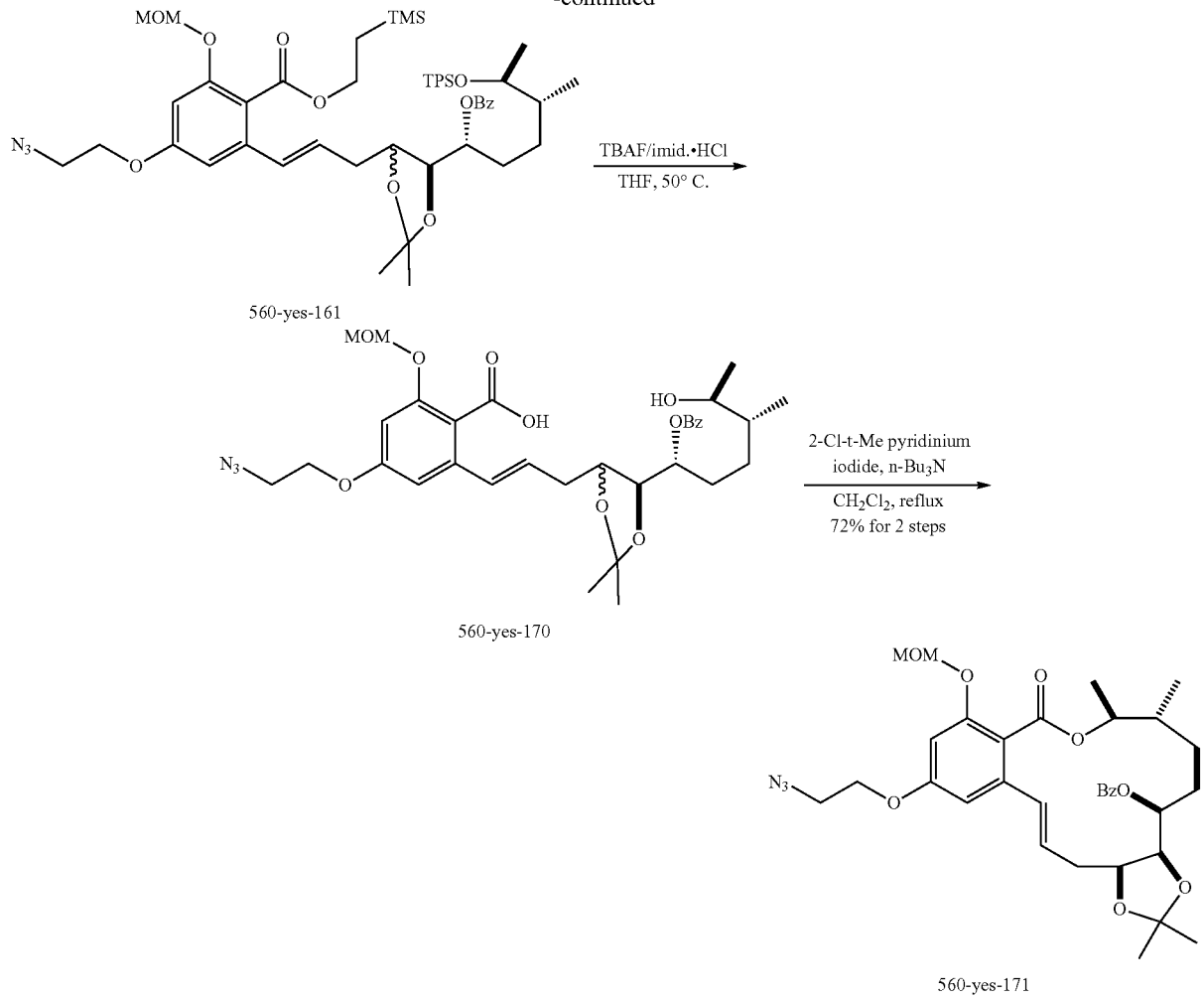
All above transformations were carried out under the conditions identical to previous series.
Preparation of ER804730:
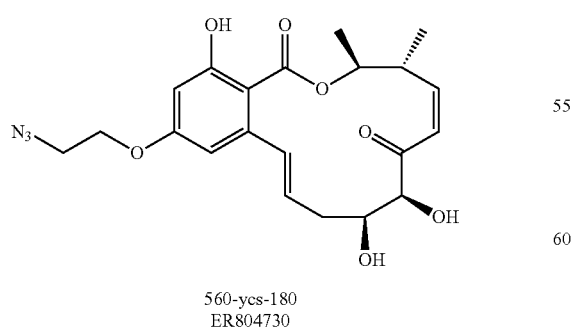
560-ycs-180
ER804730
ER804730 was prepared in the similar way as ER804104 from 560-ycs-171.

Preparation of ER805135:
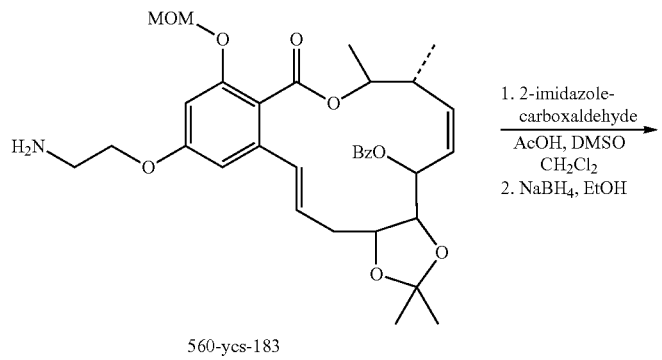
560-ycs-183
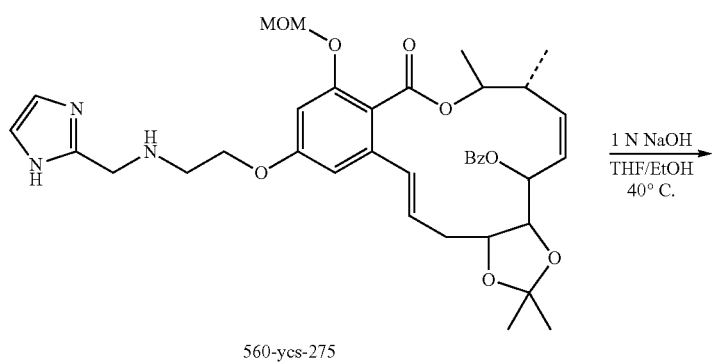
560-ycs-275
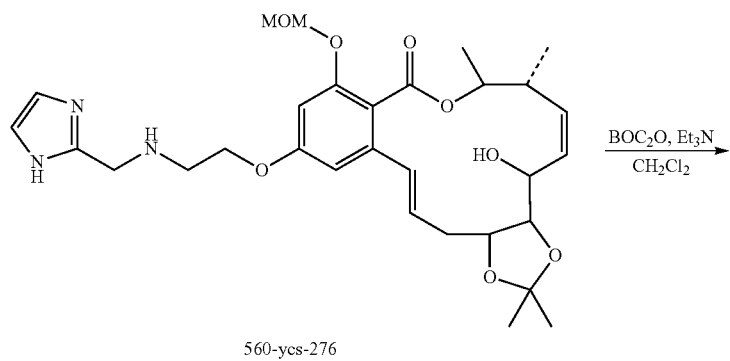
560-ycs-276
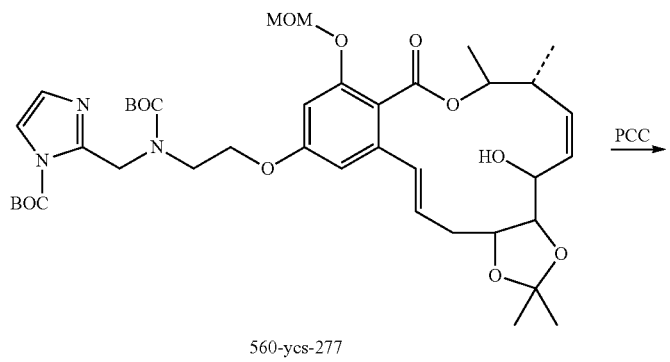
560-ycs-277

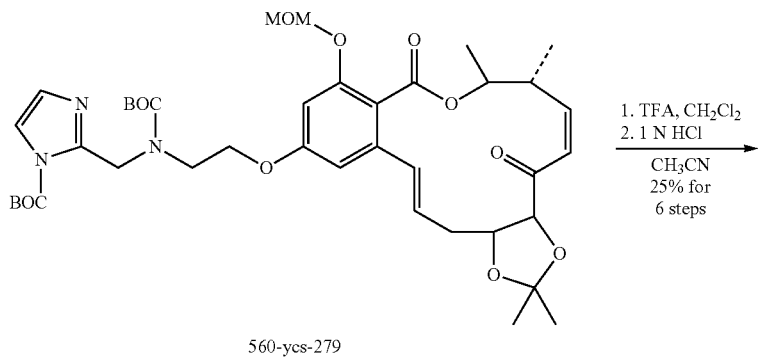

560-ycs-279

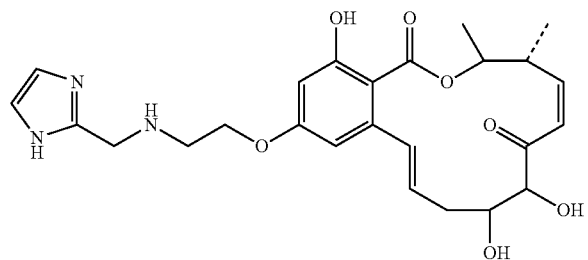

ER805135
560-ycs-281

2-Imidazole-carboxyaldehyde (96 mg, 1.0 mmol) in 0.5 mL of DMSO was introduced to a mixture of 560-ycs-183 (0.30 g, 0.50 mmol) and 4 A molecular sieves (0.30 g) in 5 mL of $CH_2Cl_2$. The mixture was stirred for 30 minutes at rt after the addition of AcOH (28 μL 0.50 mmol). $K_2CO_3$ solid (0.14 g, 1.0 mmol), celite (0.5 g) and 10 mL of $Et_2O$ were added and the mixture was filtered. The filtrate was concentrated before it was dissolved in 5 mL of EtOH and treated with $NaBH_4$ at RT for 5 minutes. The mixture was then diluted with brine and EtOAc. Organic layer was dried and concentrated to furnish 560-ycs-275 (0.27 g, 0.40 mmol) in 80% yield. MS: 676 ($M^+$+1, 100%).

Transformations from 560-ycs-275 to 560-ycs-276 and 560-ycs-277 to 560-ycs-279 were similar as the procedure for the preparation of ER804104.

$Boc_2O$ (0.27 g, 1.2 mmol) was added to a solution of 560-ycs-276 (0.29 g, 0.50 mmol) and $Et_3N$ (0.21 mL, 1.5 mmol) in 5 mL of $CH_2Cl_2$. The mixture was stirred at rt for 12 hours before it was concentrated and purified by silica gel chromatography to provide 560-ycs-277 (0.34 g, 0.44 mmol) in 88% yield. MS: 794 ($M^+$+Na, 100%).

A solution of 560-ycs-279 (0.22 g, 0.29 mmol) in 2 mL of TFA and 2 mL of $CH_2Cl_2$ was sat at rt for 30 minutes before it was concentrated and dissolved in 2 mL, of $CH_3CN$ and 2 mL of 1 N HCl. The solution was diluted with 10:1 $CHCl_3$-MeOH after it was stirred at rt for 12 hours. Organic phase was washed with $NaHCO_3$, concentrated and purified by silica gel chromatography to afford ER-805135 (60 mg, 0.12 mmol) in 25% overall yield for 6 steps.

Preparation of ER804744:

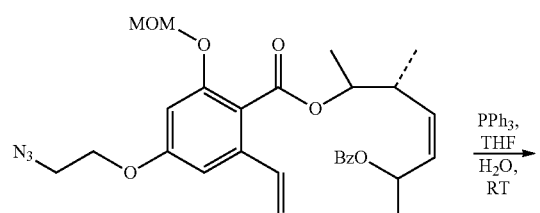

560-ycs-171

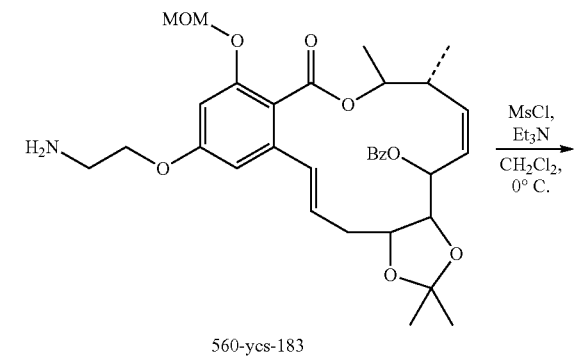

560-ycs-183

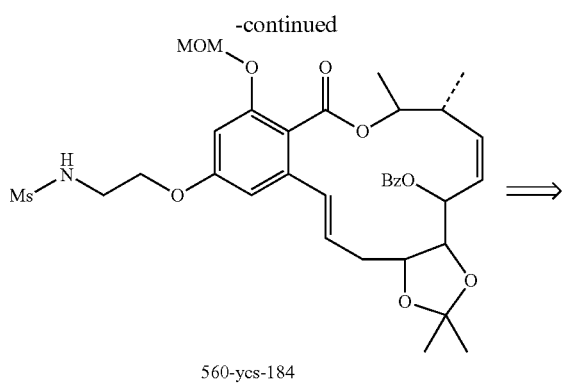

560-ycs-184

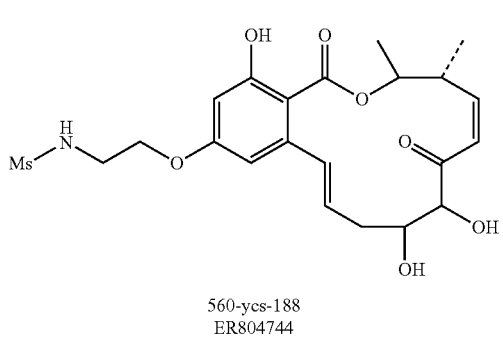

560-ycs-188
ER804744

Ph₃P (35 mg, 0.14 mmol) was added to a solution of 560-ycs-171 (28 mg, 0.045 mmol) in 3 mL of 2:1 THF-H₂O. The solution was stirred for 12 hours at it before all the volatile was evaporated and the crude residue was dissolved in 2 mL of CH₂Cl₂. Et₃N (44 μL, 0.32 mmol) and MsCl (17 μL, 0.22 mmol) was added at 0° C. The mixture was stirred at 0° C. for 10 minutes before it was washed with NaHCO₃ and concentrated to provide 560-ycs-184 (21 mg, 0.031 mmol) in 69% for 2 steps.

ER804744 was prepared in the similar way as ER804101 from 560-ycs-184.

Preparation of ER804759:

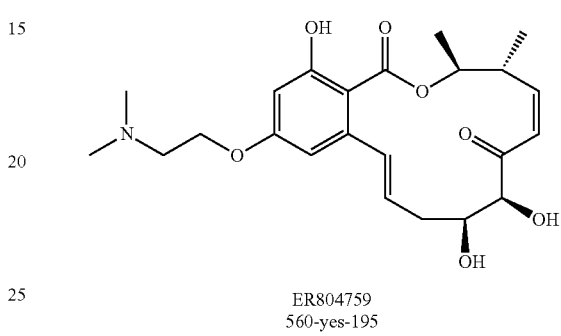

ER804759
560-yes-195

ER804759 was prepared in the similar way as ER804606 from 560-ycs-36 and 2-(N,N-dimethylamino)-1-ethanol.

Preparation of 4 Carbon Linker C (14) Common Intermediate

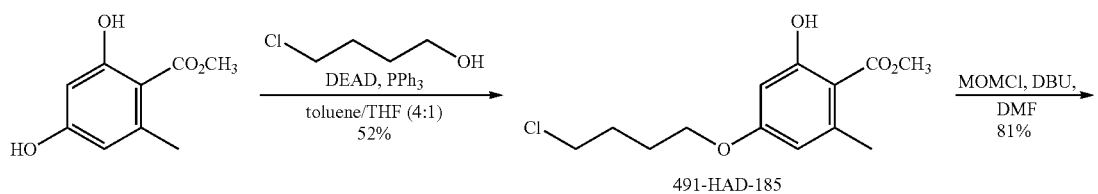

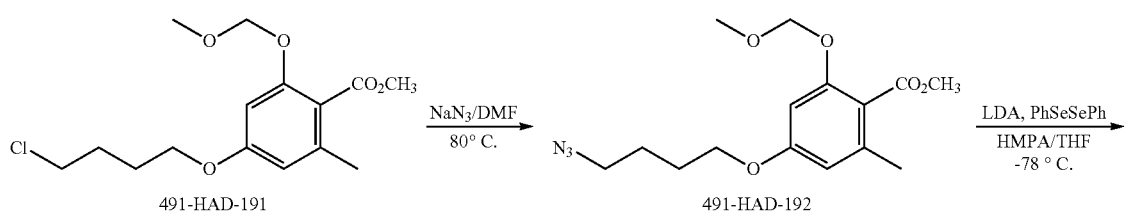

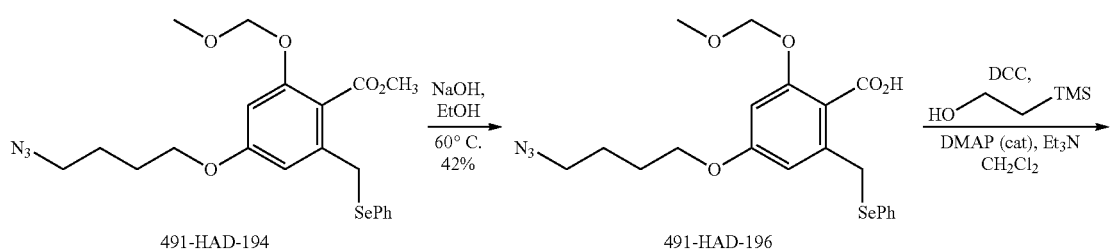

-continued
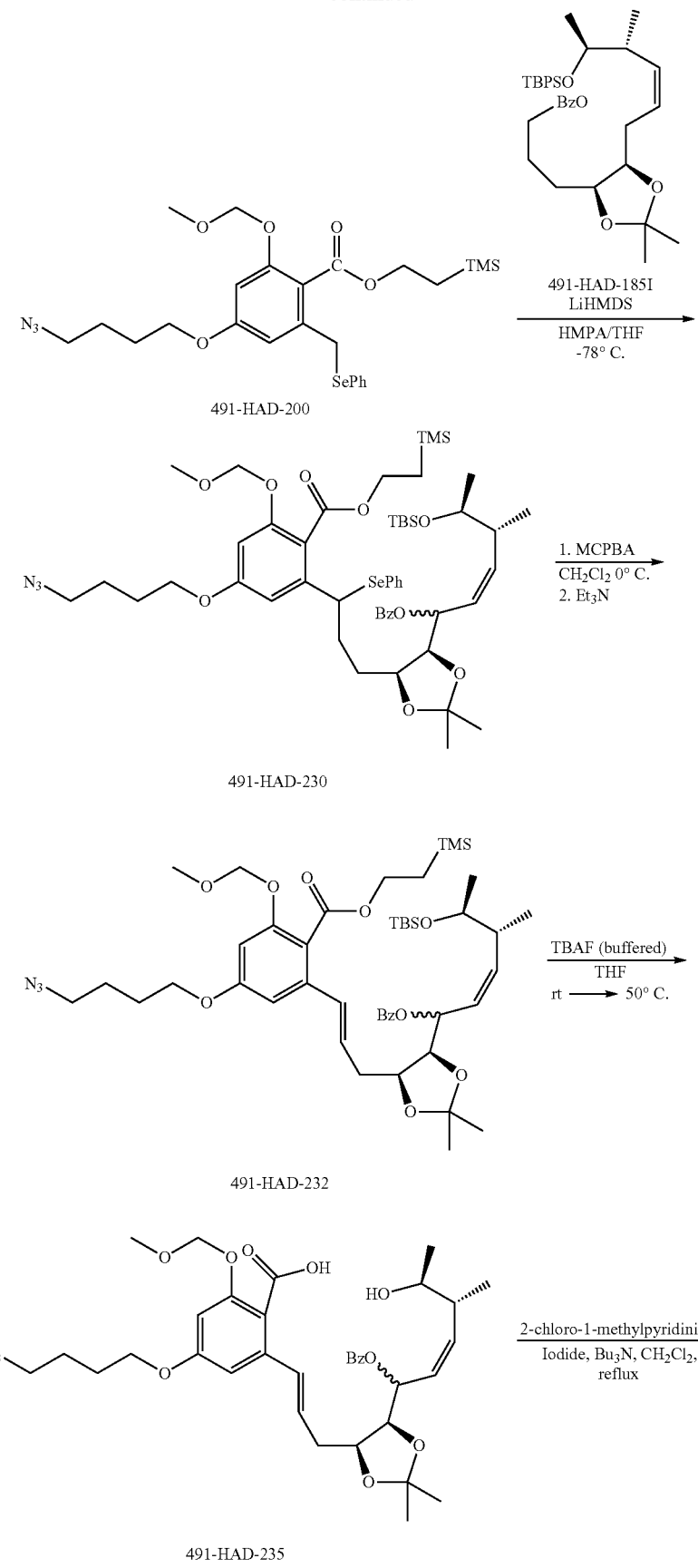

-continued

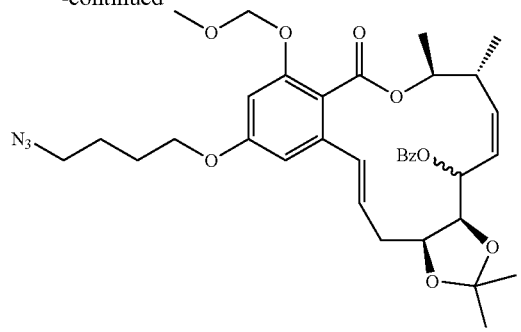

491-HAD-237

491-HAD-185I

Chlorobutan-1-ol (15.5 g, 143 mmol) and DEAD (28.8 g, 165 mmol) were added simultaneously over 45 min to a cooled (0° C. ice/water bath) solution of diphenolic toluide (20.0 g, 110 mmol) in THF (175 mL) and toluene (700 mL) under a nitrogen atmosphere. Then, the ice/water bath was removed and the reaction mixture was allowed to warm to rt. After stirred for 2.5 h, standard Mitsunobu workup conditions followed by flash chromatography (silica gel, 5-10% EtOAc/hexanes) yielded 491-HAD-185 as a colorless solid (15.66 g, 52%)

491-HAD-191

DBU (59.0 g, 388 mmol) was added drop wise to a cooled (salt/ice bath) solution of 491-HAD-185 (14.4 g, 52.9 mmol) DMF (200 mL under nitrogen atmosphere followed by chloromethyl methyl ether (26.7 g, 332 mmol). After stirred for 0.5 h, water (200 mL) was added and the aqueous phase was extracted with $CH_2Cl_2$. The combined $CH_2Cl_2$ extracts were dried with anhydrous $Na_2SO_4$ and solvent was removed by reduced pressure. Flash chromatography (silica gel, 15% EtOAc/hexanes) gave 491-HAD-191 as colorless oil (13.9 g, 81%).

491-HAD-192

Sodium azide (8.64 g, 133 mmol) was added to a solution of 491-HAD-191 in DMF (150 mL) and the suspension was heated to 80° C. After stirring 2 h water (200 mL) and $CH_2Cl_2$ (150 mL) was added. The aqueous phase was extracted several times with $CH_2Cl_2$, dried with anhydrous $Na_2SO_4$ and solvent removed under reduced pressure. Flash chromatography (silica gel, 20% EtOAc/hexanes) afforded 491-HAD-192 as pale yellow oil (12.9 g, 90%).

491-HAD-194

Lithium diisopropylamine was prepared under nitrogen atmosphere in usual manner from diisopropylamine (12.8 mL, 91.5 mmol) and n-butyllithium in 5% HMPA/THF (150 mL) in flask equipped with overhead mechanical stirring. LDA solution was cooled to −78° C. (dry ice/acetone bath). Next, a solution of 491-HAD-192 in 5% HMPA/THF (35 mL) was added. After stirring 20 min, a solution of diphenyl diselenide (12.4 g, 39.7 mmol) in 5% HMPA/THF (35 mL) was added. Small amount of intermediate was observed and additional solvent (20 mL) was added in an attempt to create a homogeneous solution. After stirred for 2.5 h, aqueous $NH_4Cl$ was added and the aqueous phase was extracted several times with EtOAc. Combined organic extracts were washed with brine, dried with anhydrous $Na_2SO_4$ and solvent was evaporated under reduced pressure. Slightly impure 491-HAD-194 was obtained as a yellow oil (3.95 g, 21%) following flash chromatography (silica gel, 20-100% hexanes/$CH_2Cl_2$, 2% EtOAc/$CH_2Cl_2$).

491-HAD-196

A solution of 491-HAD-194 (3.94 g, 8.24 mmol) in ethanol (200 proof, 24.5 mL) and 2.5 N NaOH (16.5 mL, 41.3 mmol) was heated to 60° C. After stirred for 2 days, the reaction solution was then diluted with water and hexanes and the aqueous layer was acidified with $NaHSO_3$ and extracted with EtOAc. The combined organic extracts were dried with anhydrous $Na_2SO_4$ and evaporation of the solvent under reduced pressure to afford 491-HAD-196 (3.71 g) as a pale yellow solid. 491-HAD-196 was not purified and was put directly into next step.

491-HAD-200

A flask equipped with nitrogen inlet was charged with 491-HAD-196 (3.70 g, 7.97 mmol), $CH_2Cl_2$ (56 mL), DCC (6.58 g, 31.9 mmol), DMAP (97.3 mg, 0.797 mmol) and triethylamine (4.44 mL, 31.9 mmol). After stirring several minutes 2-(trimethylsilyl)ethanol was added and the reaction mixture was heated to 35° C. for 3 days then stirred an additional 10-15 h at rt. Toluene (100 mL) was added and the reaction mixture was filtered. The filtrate was washed with saturated aqueous $NaHCO_3$ solution followed by brine, dried with anhydrous $Na_2SO_4$ and solvent was removed under reduced pressure. Flash chromatography (silica gel, 20% EtOAc/hexanes) afforded 491-HAD-200 (1.89 g, 42%) as a colorless oil.

491-HAD-230

A solution containing iodide 554-RB-260 (1.04 g, 1.72 mmol) and 491-HAD-200 (2.53 mmol) in 5% HMPA/THF (2.53 mL), under nitrogen atmosphere, was cooled to −78° C. (dry ice/acetone bath) and the reaction vessel was shielded from light. 1M LiHMDS in THF (2.53 mL, 2.53 mmol) was added over 75 min by syringe pump. After stirred for an additional 40 min at −78° C., aqueous $NH_4Cl$ was added and the aqueous phase was extracted several times with EtOAc. Combined organic extracts were washed with brine, dried with anhydrous $Na_2SO_4$ and solvent evaporated under reduced pressure. Flash chromatography (silica gel, 5-10-15% EtOAc/hexanes) gave slightly impure (small amount of 491-HAD-200) 491-HAD-230 (1.86 g) of as a colorless oil.

491-HAD-232

A solution of 491-HAD-230 (1.89 g, 1.82 mmol) in $CH_2Cl_2$ (26 mL) under a nitrogen atmosphere, was cooled to 0° C. (ice/water bath). Next m-CPBA (57% 1.65 g, 5.46 mmol) was added in one portion. After stirred for 1.5 h, triethylamine was added and ice/water bath was removed. After stirred for an addition hour at rt, the reaction mixture was cooled with ice/water bath and a solution composed of 10% v/v $Na_2S_2O_3$ (aqueous, saturated)/$NaHCO_3$ (aqueous, saturated) was added. The aqueous phase was extracted several times with $CH_2Cl_2$. Combined $CH_2Cl_2$ extracts were washed with saturated $NaHCO_3$, dried with anhydrous $Na_2SO_4$ and solvent was evaporated under reduced pressure. Hash chromatography of the residue (silica gel, 15% EtOAc/hexanes) gave 491-HAD-232 as pale yellow oil (0.96 g 63% over two steps).

491-HAD-235

To a solution of 491-HAD-232 (0.96 g, 1.1 mmol) in THF (5 mL), under nitrogen atmosphere, a TBAF (1M/THF) solution (5.45 mL, 5.45 mmol), buffered with imidazole HCl (0.14 g, 1.3 mmol) was added and the reaction solution was allowed to stir at rt. After stirred for 4 days, additional TBAF (1M in THF) (2.2 mL, 2.2 mmol) was introduced to the reaction flask and heating was increased to 50° C. After stirred for 15 h, heating was stopped and cooled to it, a saturated aqueous solution of $NH_4Cl$ was added. The aqueous phase was extracted several times with EtOAc. Combined organic phase was washed with brine, dried with anhydrous $Na_2SO_4$ and solvent was removed under reduced pressure. The crude residue was used for next step without purification.

491-HAD-237

To a solution containing 2-chloro-1-methylpyridium iodide (1.65 g, 6.47 mmol), $CH_2Cl_2$ (80 mL) and tributylamine (1.54 mL, 6.47 mmol), heated to reflux under a nitrogen atmosphere, a solution of crude 491-HAD-235 in dichloromethane (160 mL) was added over 3.5 h using syringe pump. After stirred for an additional hour, the heat was shut off and the reaction was then allowed to stir at rt overnight. The reaction solution then was concentrated under reduced pressure and the residue was diluted with EtOAc and water. The aqueous phase was extracted several times with EtOAc and the combined organic phase was washed with 0.05 M HCl (3×85 mL), saturated aqueous $NaHCO_3$, brine successively, dried with $Na_2SO_4$ and concentrated down under reduced pressure. Flash chromatography of the residue (silica gel, 30% ethyl acetate) afforded 491-had-237 as a pale yellow gel (0.46 g, 65% over two steps).

Preparation of Imidazole C.14 Analogue, ER805023:

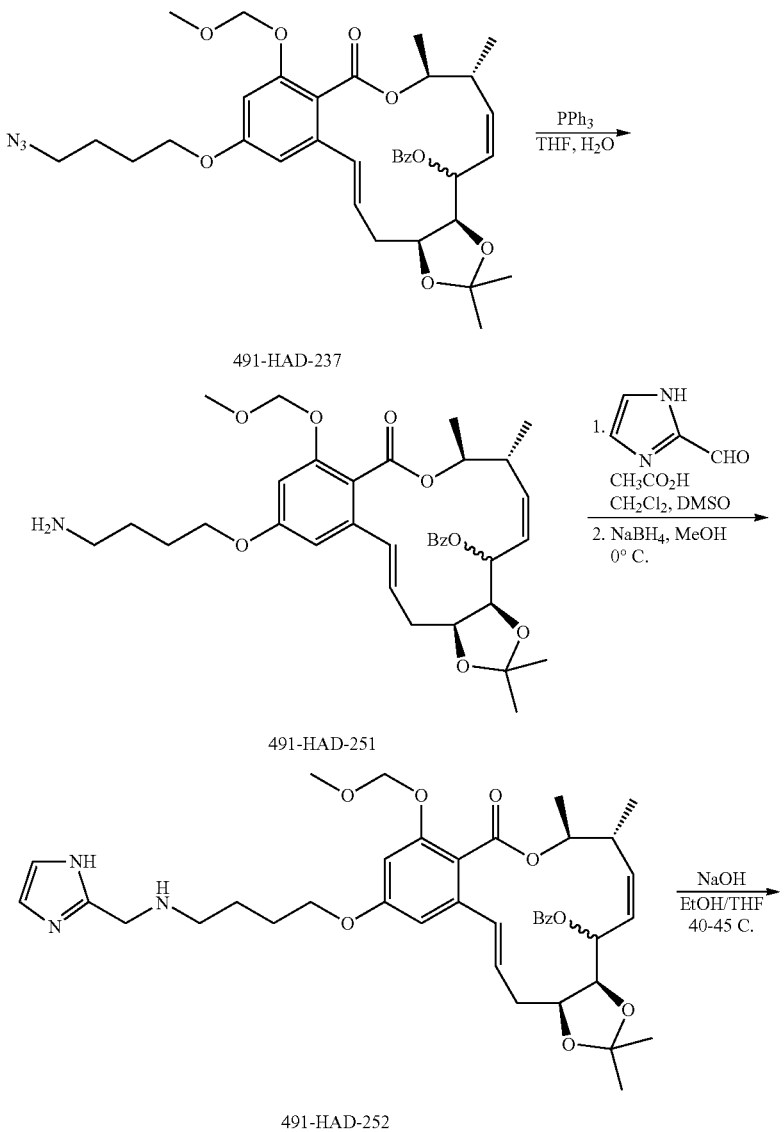

-continued

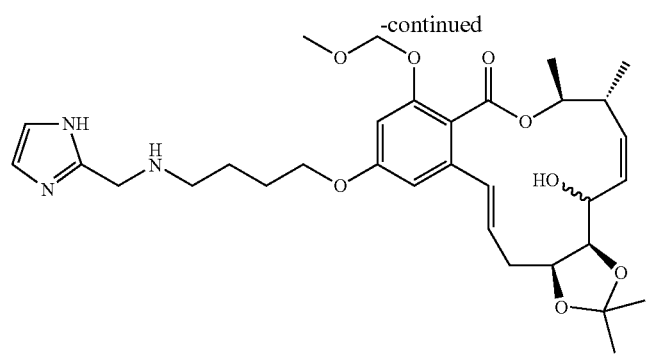

491-HAD-254

Boc₂O, Et₃N
CH₂Cl₂
(70% over 5 steps)

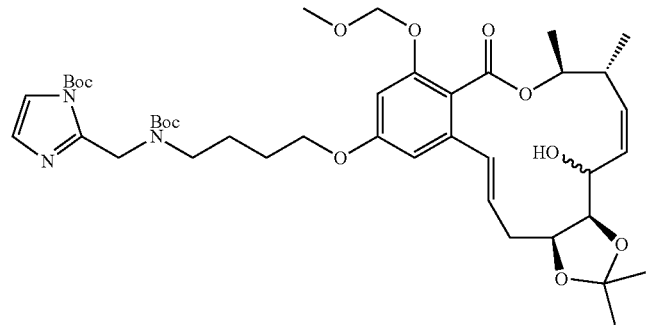

491-HAD-256

PCC, MS
Celite, CH₂Cl₂

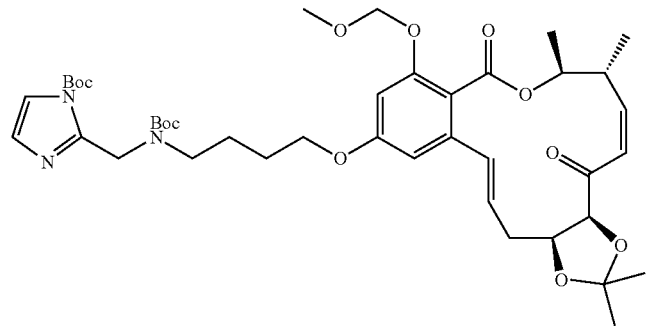

491-HAD-260

1. TFA, CH₂Cl₂
2. 1N HCl, CH₃CN
(18% over 3 steps)

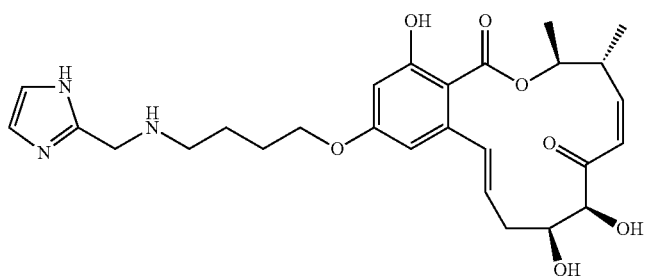

491-HAD-261

491-HAD-251

A solution of 491-HAD-237 (71.4 mg, 0.110 mmol), triphenylphosphine (86.5 mg, 0.330 mmol) in THF (2 mL) and water (1 mL) was stirred at rt. After stirred for approximately 17 h, the reaction solution was concentrated under reduced pressure. The residue was azeotroped several times with toluene and used directly in the next reaction without purification.

491-HAD-252

To a flask charged with 491-HAD-254 (0.110 mmol) and molecular sieves (4 A) in CH₂Cl₂, 2-imidazolecarboxaldehyde (21.1 mg, 0.220 mmol) in hot DMSO (0.30 mL) was added followed by acetic acid (6.3 µL). After stirred for 45 min at rt, anhydrous K₂CO₃ (0.030 g) was added. The reaction mixture was subsequently diluted with diethyl ether and filtered. Following the removal of solvent, the residue was re-dissolved in methanol and resulting solution cooled with ice/water bath and NaBH$_4$ (0.020 g, 0.53 mmol) was added. After stirred for 20 min, brine solution was added and the aqueous phase was extracted several times with EtOAc. Combined EtOAc extracts were dried with anhydrous Na$_2$SO$_4$ and concentrated. The crude residue was not purified and was used directly in next reaction.

491-HAD-254

A solution containing 491-HAD-252 (0.110 mmol), 1 N NaOH (3.30 mL, 3.30 mmol), ethanol (3.3 mL) and THF (1.6 mL) was stirred at 40-45° C. After 16 h, water was added followed by CH$_2$Cl$_2$. The aqueous phase was extracted several times with CH$_2$Cl$_2$ and the combined organic phases were dried with anhydrous Na$_2$SO$_4$ and concentrated. The crude residue was not purified and was used directly in next reaction.

491-HAD-256

A solution of 491-HAD-254 (0.110 mmol), triethylamine (46.0 μL, 0.330 mmol) and Boc anhydride (60.0 mg, 0.275 mmol) in CH$_2$Cl$_2$ was stirred under a nitrogen atmosphere at rt for 4 days. Reaction mixture was concentrated under reduced pressure. Flash chromatography (solvent gradient used: 20% EtOAc/hexanes, 30% EtOAc/hexanes, 50% EtOAc/hexanes, 75% EtOAc/hexanes) yielded 491-HAD-256 as a colorless gel (61.2 mg 70% over 4 steps).

491-HAD-260

Reaction mixture containing 491-HAD-256 (59.1 mg, 0.0739 mmol), molecular sieves (4 47.8 mg), Celite (47.8 mg) and PCC (47.8 mg, 0.222 mmol) in CH$_2$Cl$_2$ (1.70 mL) was stirred under a nitrogen atmosphere at rt for 1 hr. Triethylamine (30.8 μL, 0.222 mmol) was added and reaction mixture was stirred for an additional 15 min. Diethyl ether was added and reaction mixture was filtered through Celite. Volume of the filtrate was reduced and flash chromatography (100% EtOAc) afforded slightly impure 491-HAD-260 as a colorless oil (90.9 mg).

491-HAD-261

To a solution of 491-HAD-260 in CH$_2$Cl$_2$ (0.60 mL), under a nitrogen atmosphere, TFA was added. After stirring 30 min at rt, solvent and volatiles were removed by rotary evaporation. Acetonitrile (0.6 mL) and 1 N HCl (0.60 mL, 0.60 mmol) were added to the residue. After stirring 19 h at rt, reaction mixture was cooled with ice/water bath and a saturated aqueous solution of NaHCO$_3$ was added. Aqueous phase was extracted several times with CHCl$_3$ then once with 10% methanol/CHCl$_3$. Combined CHCl$_3$ extracts were dried with anhydrous Na$_2$SO$_4$ and concentrated by reduced pressure. Flash chromatography (MeOH: CH$_2$Cl$_2$: 2M NH$_3$/MeOH 5:95:1, 10:90:1, 15:85:1) yielded 491-HAD-261, ER805023 as an off-white solid (6.8 mg, 18% over 3 steps).

Preparation of Compound ER-804446 (C14 Difluoromethoxy)

Step 1

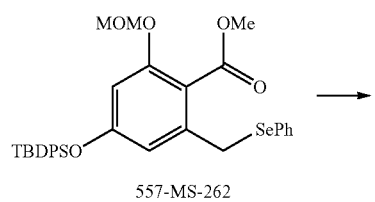

557-MS-262

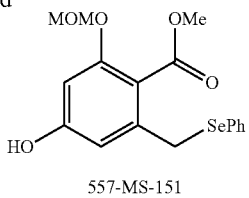

557-MS-151

To a solution of compound 557-MS-262 (4.14 g, 6.69 mmol) in THF (40 mL) was added a 1M solution of TBAF (6.69 mL; 6.69 mmol). The reaction mixture was stirred at room temperature for 30 minutes then worked up in the usual manner. Chromatographic purification gave compound 557-MS-151 (2.34 g, 92%).

Step 2

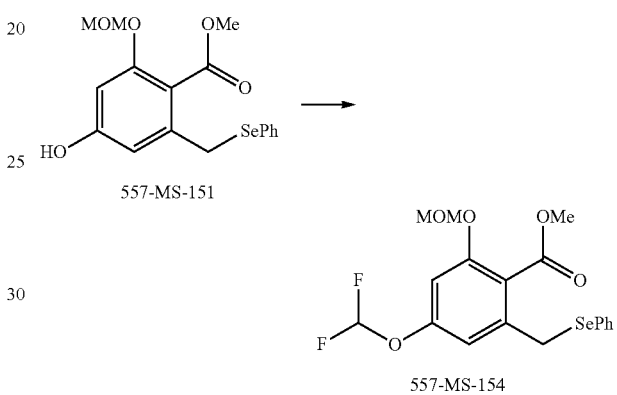

To a vigorously stirred solution of compound 557-MS-151 (520 mg, 1.36 mmol) in dioxane (2 mL) at 55-60° C., was added pre-heated (50° C.) 40% aqueous NaOH solution (2 mL). A stream of chlorodifluoromethane gas was then admitted continuously to the reaction mixture via a gas inlet tube (the tip of which was positioned just below the surface of the reaction mixture). After 25 minutes the reaction mixture was worked up in the usual manner. Chromatographic purification gave compound 557-MS-154 (329 mg, 56%).

Step 3

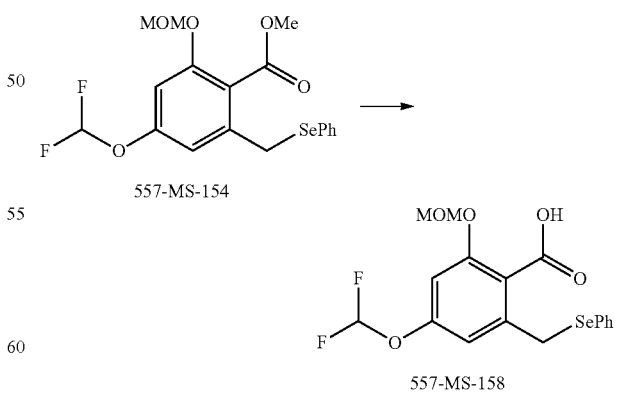

A solution of 557-MS-154 (455 mg, 1.05 mmol) in ethanol (5 mL) was treated with 40% aqueous NaOH solution (2 mL) and heated under reflux for 16 hours. The reaction mixture was cooled to room temperature, diluted with water and then washed with diethyl ether. The aqueous phase was acidified (with cooling) to pH3 by drop wise addition of concentrated aqueous hydrochloric acid. Extraction with diethyl ether (×4) followed by drying etc gave compound 557-MS-158 (384 mg, 88%).

Step 4

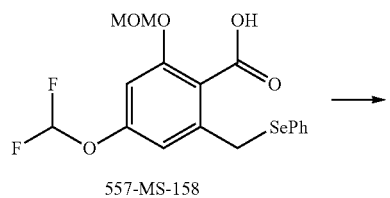

557-MS-158

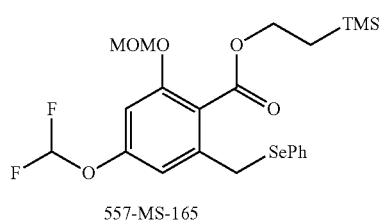

557-MS-165

A solution of compound 557-MS-158 (384 mg, 0.92 mmol) in diethyl ether (8 mL) was treated with toluene (2 mL), triphenylphosphine (290 mg, 1.10 mmol), and 2-(trimethylsilyl)ethanol (0.172 ml, 1.20 mmol), then cooled to 0° C. under an inert atmosphere. Diethyl azidodicarboxylate (0.174 ml, 1.10 mmol) was added drop wise and the reaction mixture then allowed to warm to room temperature. After 3 hours the reaction mixture was worked up in the usual manner. Chromatographic purification gave compound 557-MS-165 (410 mg, 86%).

Step 5

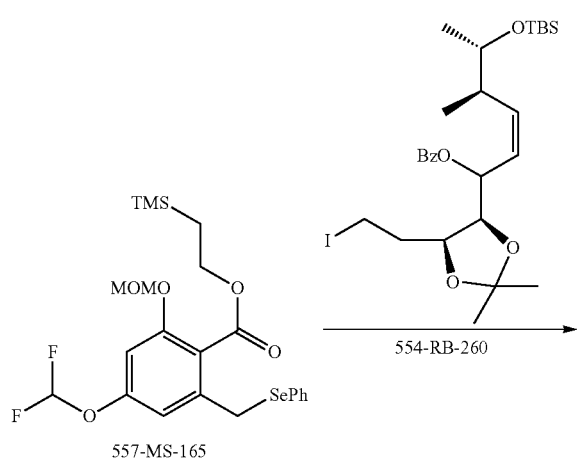

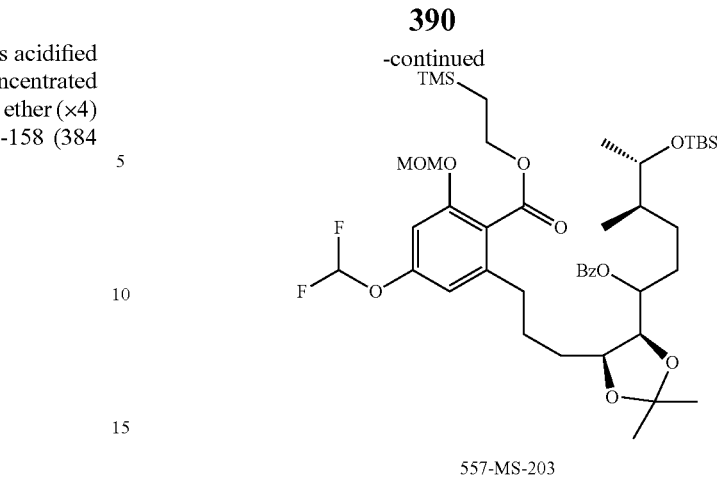

557-MS-203

A mixture of compound 557-MS-165 (410 mg, 0.79 mmol) and compound 554-RB-260 (523 mg, 0.72 mmol) was dissolved in THF (3.2 mL), treated with HMPA (0.6 mL) and then cooled to −78° C. under an inert atmosphere. A 0.5M solution of LiHMDS in THF (1.73 mL, 0.864 mmol) was then added drop wise over approximately 15 minutes. The reaction mixture was stirred at −78° C. for 40 minutes, then warmed to 0° C. The intermediate crude product was worked up in the usual manner and then dissolved in dichloromethane (12 mL) and cooled to 0° C. A solution of approximately 55% m-CPBA (452 mg) in dichloromethane (8 mL) was added portion wise. After 40 minutes triethylamine (1 mL) was added and the reaction mixture was worked up in the usual manner. Chromatographic purification gave compound 557-MS-203 (552 mg, 80%).

Step 6

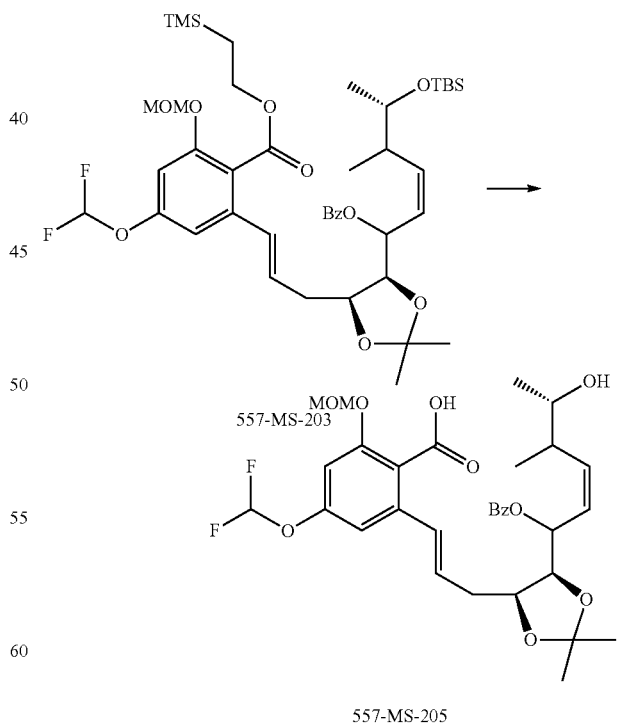

A solution of compound 557-MS-203 (552 mg, 0.575 mmol) in THF (5.75 mL) was treated with a 1M solution of TBAF in THF (11.5 mL, 11.5 mmol) then heated at 60° C. for approximately 3 hours. The usual work up gave crude compound 557-MS-205 (350 mg), which was used in the next stage without purification.

Step 7

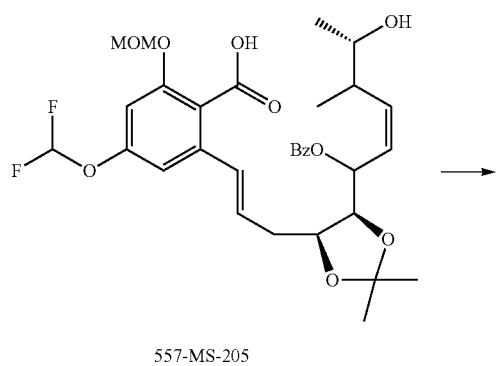

557-MS-205

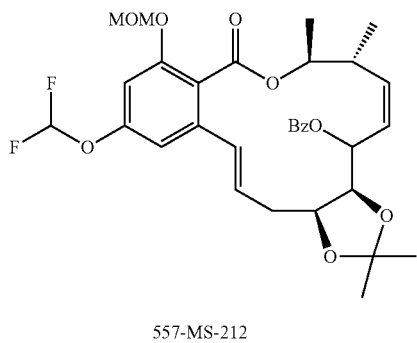

557-MS-212

A solution of crude compound 557-MS-205 (assumed to contain 0.32 mmol) in dichloroethane (66 mL) was added slowly to a heated solution (85° C.) of 2-chloro-1-methylpyridinium iodide (824 mg, 3.2 mmol) and tri-n-butylamine (0.768 mL, 3.2 mmol) in dichloroethane (100 mL). The reaction mixture was heated at 85° C. for 1 hour post complete addition then cooled to room temperature. The usual work up and chromatographic purification gave compound 557-MS-212 (93 mg, 48% from compound 557-MS-203).

Step 8

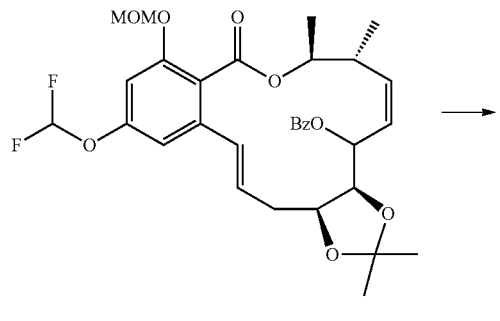

557-MS-212

-continued

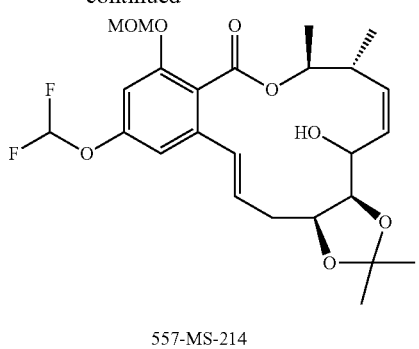

557-MS-214

A solution of compound 557-MS-212 (93 mg, 0.15 mmol) in THF (6 mL) and ethanol (12 mL) was treated with 1M aqueous NaOH solution (2.5 mL) and heated at 60° C. for 1.5 hours, then at 70° C. for 1 hour. The usual work up gave crude compound 557-MS-214 (74 mg), which was used in the next stage without purification.

Step 9

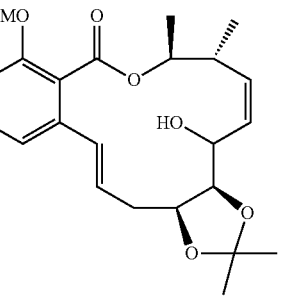

557-MS-214

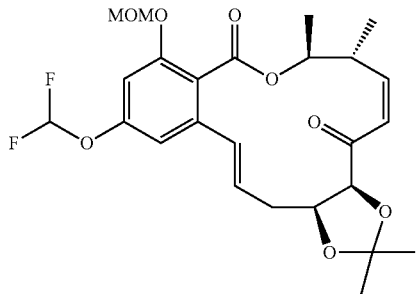

557-MS-216

A solution of crude compound 557-MS-214 (89 mg, 0.178 mmol) in dichloromethane (10 mL) was treated with PCC (462 mg, 2.14 mmol) in the presence of powdered 4 Å molecular sieves (462 mg). The reaction mixture was stirred vigorously for 120 minutes at room temperature. Basification with excess triethylamine, followed by chromatographic purification gave compound 557-MS-216 (53 mg, 60% from compound 557-MS-212).

Step 10

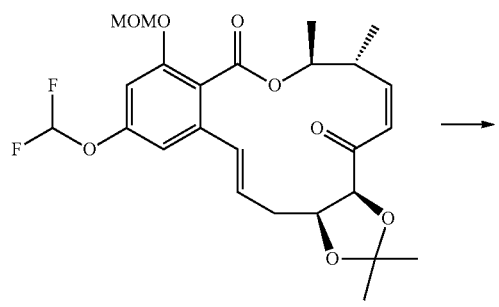
557-MS-216

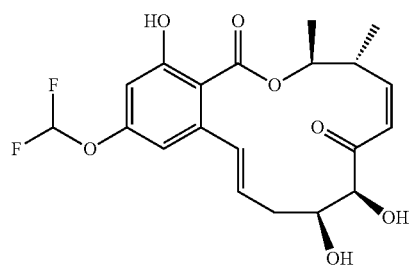
ER-804446

A solution of compound 557-MS-216 (53 mg, 0.106 mmol) in a mixture of acetonitrile (7 mL) and dichloromethane (1.7 mL) was treated with 48% aqueous hydrofluoric acid (1.7 mL). After 35 minutes at room temperature the usual work up, followed by chromatographic purification, gave compound ER-804446 (40 mg, 91%) (m/z: 411.3 [M+1; 100%]).

Preparation of Compound ER-804387 (C14 Trifluoroethoxy)

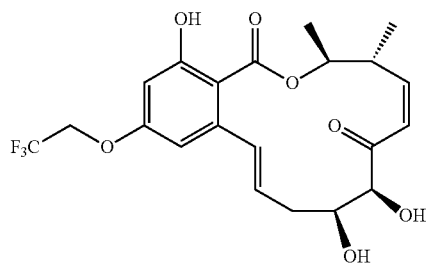

Step 1

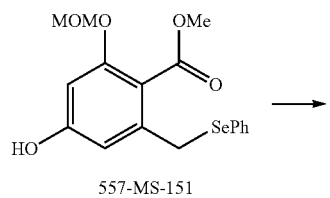
557-MS-151

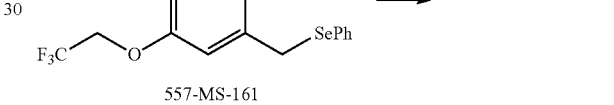
557-MS-161

To a solution of 557-MS-151 (1 g, 2.62 mmol) in acetone (20 mL) were added potassium carbonate (440 mg, 3.14 mmol) and 2,2,2-trifluoroethyl trichloromethanesulphonate (880 mg, 3.14 mmol). The reaction mixture was heated at 70° C. for 2 hours then treated with further aliquots of potassium carbonate (440 mg; 3.14 mmol) and 2,2,2-trifluoroethyl trichloromethanesulphonate (880 mg, 3.14 mmol). After a further 2 hours at 70° C. the reaction mixture was worked up in the usual manner. Chromatographic purification gave compound 557-MS-161 (760 mg, 63%).

Step 2

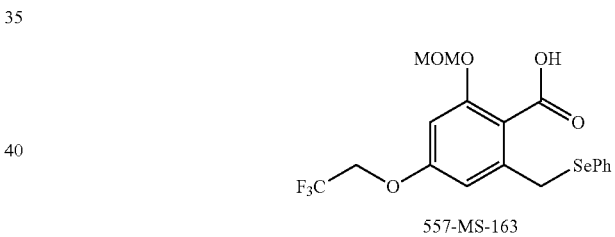
557-MS-161

557-MS-163

A solution of 557-MS-161 (760 mg, 1.64 mmol) in ethanol (5 mL) was treated with 40% aqueous NaOH solution (2 mL) and heated under reflux for 16 hours. The reaction mixture was cooled to room temperature, diluted with water and then washed with diethyl ether. The aqueous phase was acidified (with cooling) to pH3 by drop wise addition of concentrated aqueous hydrochloric acid. Extraction with diethyl ether (×4) followed by drying etc gave compound 557-MS-163 (648 mg, 88%).

Step 3

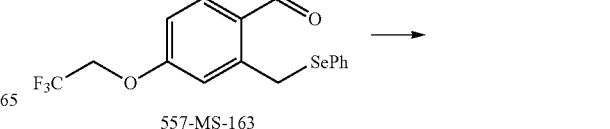
557-MS-163

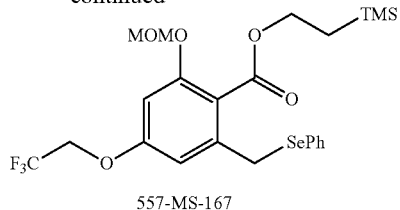

557-MS-167

A solution of compound 557-MS-163 (648 mg, 1.44 mmol) in diethyl ether (12 mL) was treated with toluene (3 mL), triphenylphosphine (454 mg, 1.73 mmol), and 2-(trimethylsilyl)ethanol (0.269 mL, 1.875 mmol), then cooled to 0° C. under an inert atmosphere. Diethyl azidodicarboxylate (0.272 mL, 1.73 mmol) was added drop wise and the reaction mixture then allowed to be warmed to room temperature. After 1.5 hours the reaction mixture was worked up in the usual manner. Chromatographic purification gave compound 557-MS-167 (730 mg, 92%).

Step 4

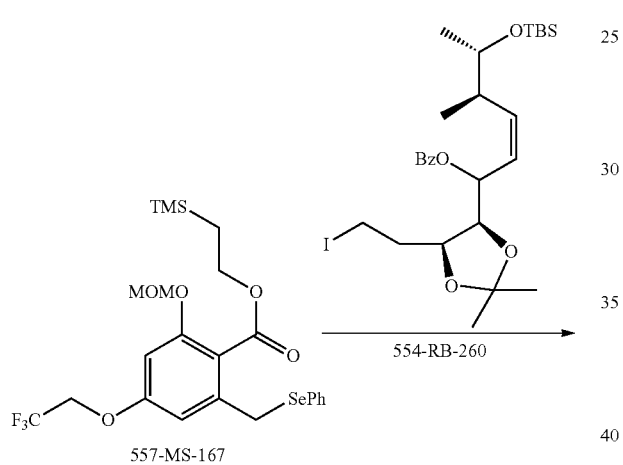

557-MS-167

A mixture of compound 557-MS-167 (730 mg, 1.33 mmol) and compound 554-RB-260 (885 mg, 1.21 mmol) was dissolved in THF (9 mL), treated with HMPA (1 mL) and then cooled to −78° C. under an inert atmosphere. A 0.5M solution of LiHMDS in THF (2.9 mL, 1.45 mmol) was then added drop wise over approximately 20 minutes. The reaction mixture was stirred at −78° C. for 35 minutes, then warmed to 0° C. The intermediate crude product was worked up in the usual manner and purified partially by chromatography. The intermediate was dissolved in dichloromethane (15 mL) and cooled to 0° C. A solution of approximately 55% meta-chloroperbenzoic acid (612 mg) in dichloromethane (10 mL) was added portion wise. After 30 minutes triethylamine (1.37 mL) was added and the usual work up, followed by chromatographic partial purification, gave impure compound 557-MS-177 (950 mg), which was used in the next stage without further purification.

Step 5

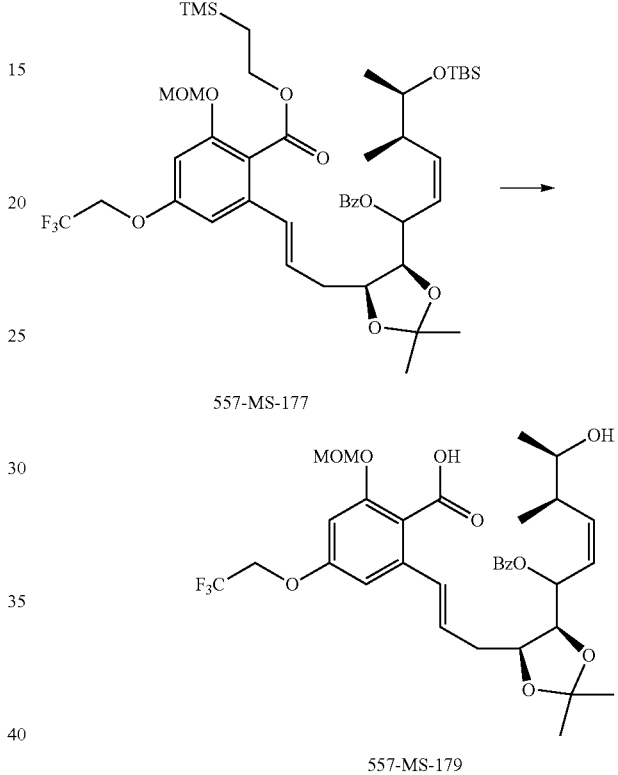

557-MS-177

557-MS-179

A solution of crude compound 557-MS-177 (475 mg, assumed to contain 0.479 mmol) in a 1M solution of TBAF in THF (9.58 mL; 9.58 mmol) was heated at 50° C. for approximately 7 hours. The usual work up gave crude compound 557-MS-179 (300 mg), which was used in the next stage without purification.

Step 6

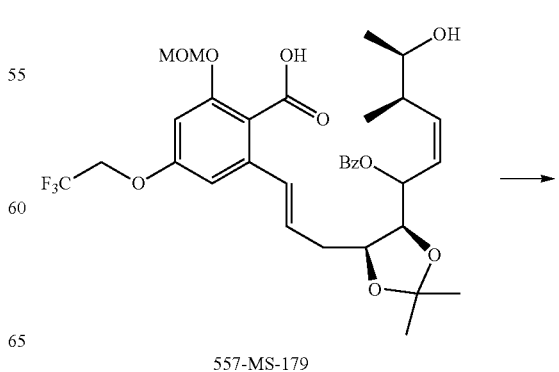

557-MS-179

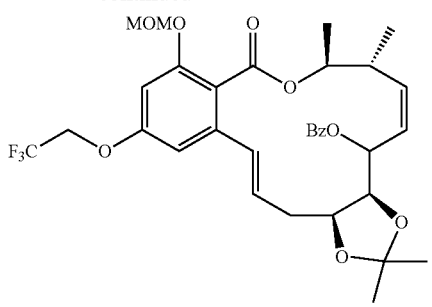

557-MS-183

A solution of crude compound 557-MS-179 (assumed to contain 0.153 mmol) in dichloroethane (30 mL) was added slowly to a heated solution (85° C.) of 2-chloro-1-methylpyridinium iodide (391 mg, 1.53 mmol) and tri-n-butylamine (0.365 mL, 1.53 mmol) in dichloroethane (100 mL). The reaction mixture was heated at 85° C. for 1 hour post complete addition then cooled to room temperature. The usual work up and chromatographic purification gave compound 557-MS-183 (40 mg, 41% from compound 557-MS-167).

Step 7

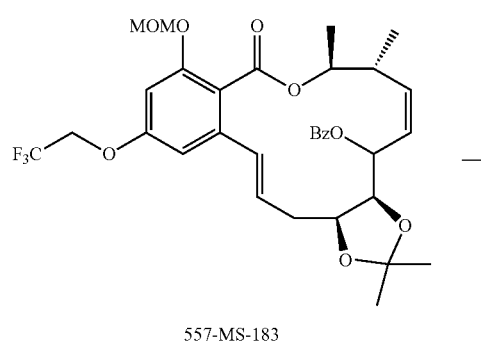

557-MS-183

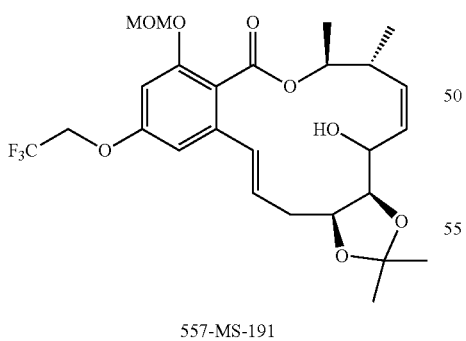

557-MS-191

A solution of compound 557-MS-183 (40 mg, 0.063 mmol) in THF (2.5 mL) and ethanol (5 mL) was treated with 1M aqueous NaOH solution (1 mL) and heated at 60° C. for 3.5 hours. The usual work up gave crude compound 557-MS-191 (32 mg), which was used in the next stage without purification.

Step 8

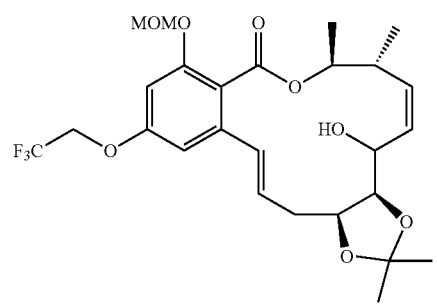

557-MS-191

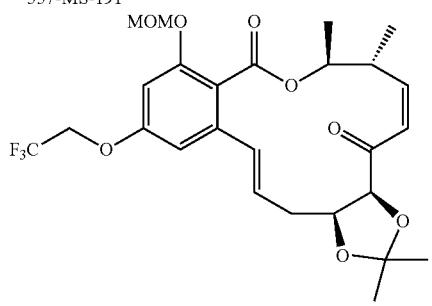

557-MS-194

A solution of crude compound 557-MS-191 (52 mg, 0.098 mmol) in dichloromethane (6 mL) was treated with PCC (253 mg, 1.18 mmol) in the presence of powdered 4 Å molecular sieves (253 mg). The reaction mixture was stirred vigorously for 3 hours at room temperature. Basification with excess triethylamine, followed by chromatographic purification gave compound 557-MS-194 (39.3 mg, 76% from compound 557-MS-183).

Step 9

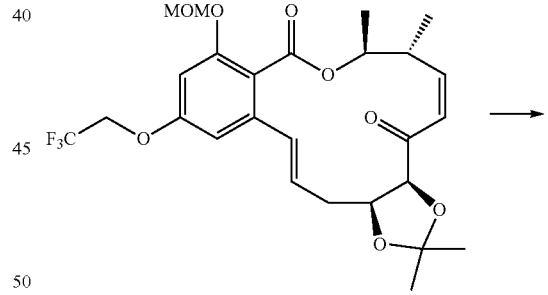

557-MS-194

557-MS-194

A solution of compound 557-MS-194 (23 mg, 0.0435 mmol) in a mixture of acetonitrile (3.2 mL) and dichloromethane (0.8 mL) was treated with 48% aqueous hydrofluoric acid (0.8 mL). After 35 minutes at room temperature the usual work up, followed by chromatographic purification, gave compound ER-804387 (15.8 mg, 82%).

Preparation of Compound B2356 (C14 Hydroxy) & Compound B2359 (C14 OMOM):

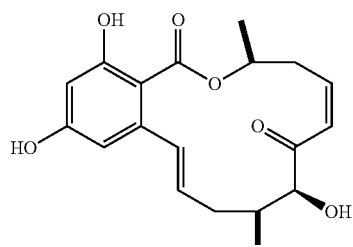
B2356

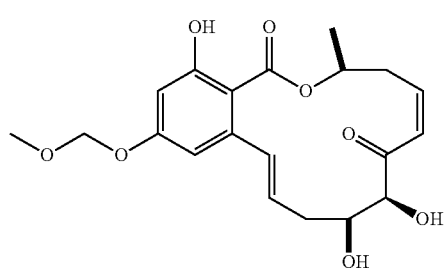
B2359

Step 1

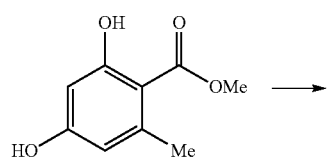

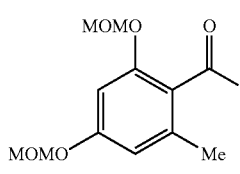
453-MS-21

A solution of methyl 2,4-dihydroxy-6-methylbenzoate (6 g, 32.95 mmol) in dry DMF (10 mL) was added to a well-stirred suspension of hexane-washed sodium hydride (3.95 g, 60% in mineral oil; approximately 98.85 mmol) in dry DMF (50 mL), at 0° C. under an inert atmosphere. The reaction mixture was stirred at 0° C. for 30 minutes then treated with methoxymethyl chloride (5.26 mL, 69.2 mmol) drop wise. The reaction mixture was stiffed for 2 hours then worked up in the usual manner to give compound 453-MS-21 (8.14 g, 91%).

Step 2

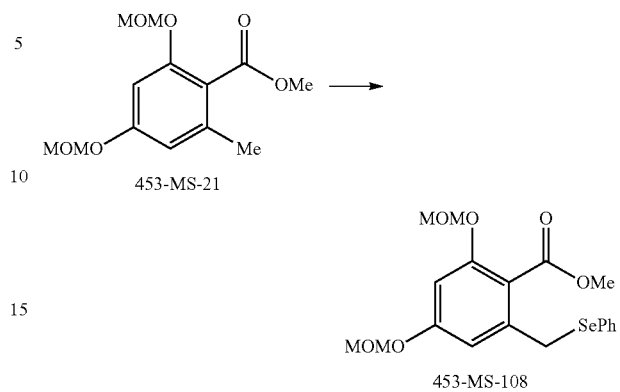

To a solution of diisopropylamine (3.14 mL, 22.4 mmol) in dry THF (45 mL), at −20° C. under an inert atmosphere, was added drop wise a 2.5M solution of n-butyllithium in hexanes (8.96 mL, 22.4 mmol). The reaction mixture was allowed to warm to 0° C., stirred for 10 minutes at 0° C., then cooled to −78° C. A solution of compound 453-MS-21 (4.03 g, 14.9 mmol) in dry THF (15 mL) was added drop wise. The reaction mixture was stirred at −78° C. for 1 hour then treated with a solution of diphenyl diselenide (5.59 g, 17.9 mmol) in dry THF (18 mL). The reaction mixture was stirred at −78° C. for 30 minutes then worked up in the usual manner. Chromatographic purification gave compound 453-MS-108 (3.47 g, 54%).

Step 3

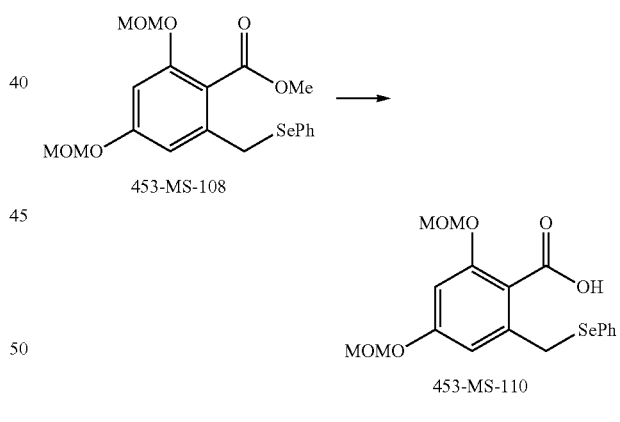

A solution of compound 453-MS-108 (2.16 g, 5.08 mmol) in ethanol (20 mL) was treated with powdered NaOH (610 mg, 15.24 mmol) and heated under reflux for 28 hours. The reaction mixture was cooled to room temperature and concentrated under reduced pressure (to a residual volume of approximately 5 mL). The residue was partitioned between water and diethyl ether. The aqueous fraction was acidified to pH3 by slow addition of 1M aqueous HCl (approximately 16 mL), with cooling. The acidic solution was extracted with diethyl ether, and the extracts then washed immediately with saturated aqueous brine solution (at least five times). Drying etc gave compound 453-MS-110 (2.016 g, 97%).

Step 4

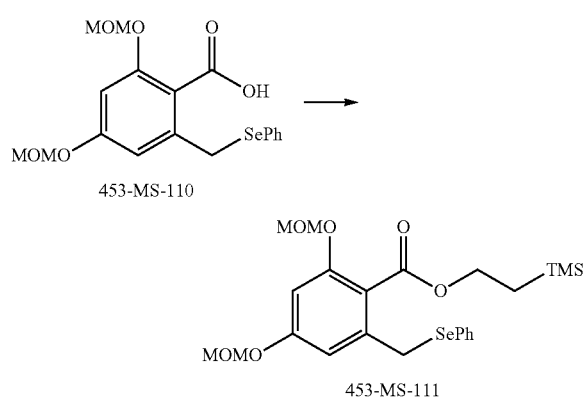

To a solution of compound 453-MS-110 (2.016 g, 4.9 mmol) in diethyl ether (40 mL), at 0° C. under an inert atmosphere, were added toluene (10 mL), triphenylphosphine (1.41 g, 5.39 mmol), and 2-(trimethylsilyl)ethanol (0.843 mL, 5.88 mmol). Diethyl azidodicarboxylate (0.849 mL, 5.39 mmol) was then added drop wise. The reaction mixture was allowed to warm to room temperature and stirred for approximately 16 hours. The usual work up followed by chromatographic purification gave compound 453-MS-111 (2.24 g, 90%).

Step 5

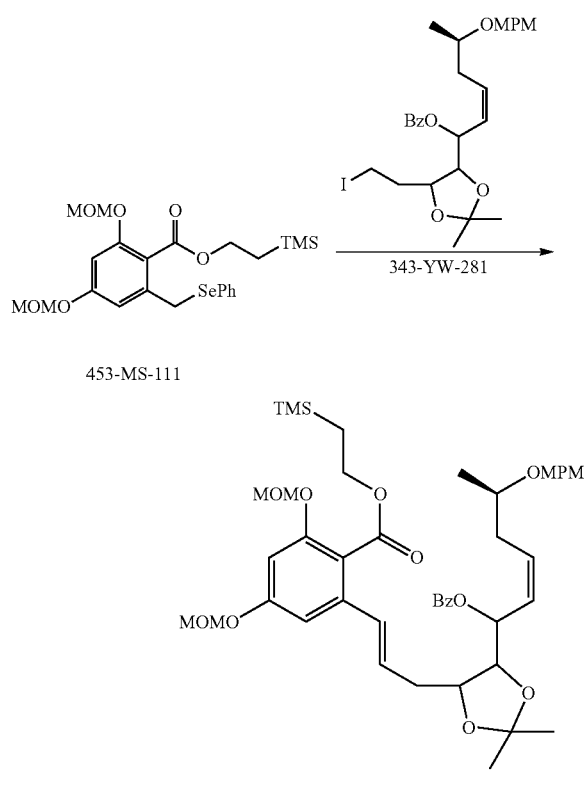

A mixture of compound 453-MS-111 (1.33 g, 2.6 mmol) and compound 343-YW-281 (866 mg, 1.46 mmol) was dissolved in a solution of 10% HMPA in THF (15 mL) and cooled to −78° C. under an inert atmosphere. A 1M solution of LiHMDS in THF (2.19 mL, 2.19 mmol) was then added drop wise over approximately 15 minutes. After another 45 minutes an extra aliquot of 1M solution of LiHMDS in THF was added (0.438 mL, 0.438 mmol). The reaction mixture was warmed to 0° C. and the intermediate crude product worked up in the usual manner, and purified partially by chromatography. The intermediate was then dissolved in dichloromethane (14 mL) and cooled to 0° C. A solution of approximately 55% meta-chloroperbenzoic acid (280 mg) in dichloromethane (6 mL) was added. After 10 minutes, extra 55% m-CPBA (28 mg) was added. The reaction mixture was stirred at 0° C. for a further 20 minutes, then treated with triethylamine (1.22 mL) and worked up in the usual manner. Chromatographic purification gave compound 453-MS-77 (625 mg, 52%).

Step 6

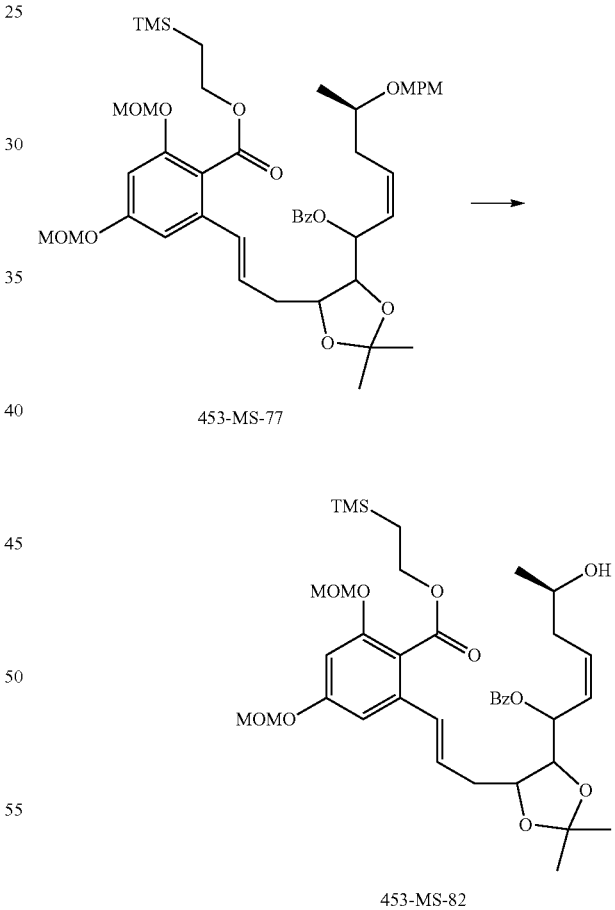

To a vigorously stirred biphasic mixture of compound 453-MS-77 (618 mg, 0.753 mmol), dichloromethane (20 mL) and water (10 mL), was added DDQ (190 mg, 0.84 mmol). After 1 hour at room temperature the reaction mixture was worked up in the usual manner. Chromatographic purification gave compound 453-MS-82 as a mixture of 4 diastereoisomers (381 mg, 72%).

Step 7

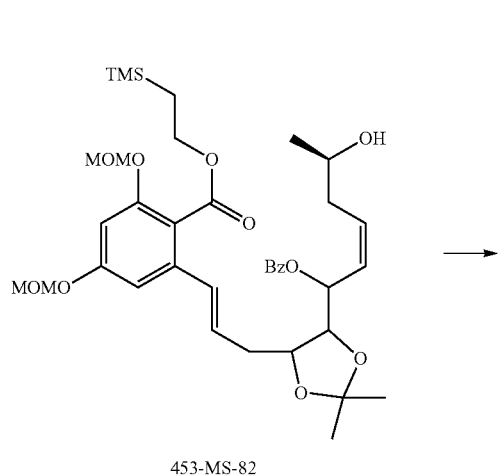

453-MS-82

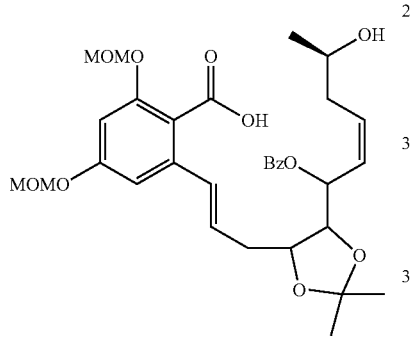

453-MS-84

A solution of compound 453-MS-82 (381 mg, 0.544 mmol) in THF (10 mL) was treated with TBAF (284 mg, 1.09 mmol) and stirred at room temperature for approximately 16 hours. The usual work up gave compound 453-MS-84 (326 mg, quantitative), as a mixture of 4 diastereoisomers.

Step 8

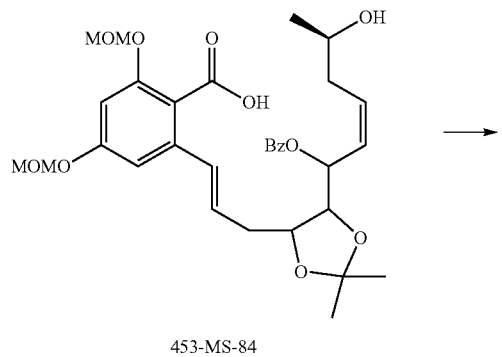

453-MS-84

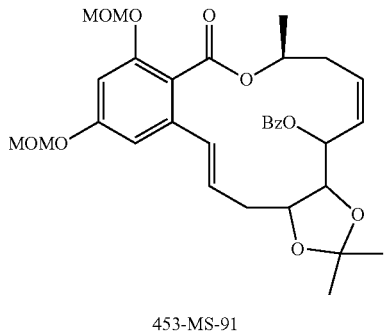

453-MS-91

To a solution of triphenylphosphine (109 mg, 0.417 mmol) in dry THF (6 mL), at room temperature under an inert atmosphere, was added diethyl azidodicarboxylate (66 µL, 0.417 mmol) drop wise over approximately 30 seconds. A solution of compound 453-MS-84 (167 mg, 0.278 mmol) in dry THF (10 mL) was added drop wise over approximately 10 minutes. The reaction mixture was stirred at room temperature for 10 minutes then treated with extra triphenylphosphine (36 mg, 0.137 mmol), followed by extra diethyl azidodicarboxylate (22 µL, 0.137 mmol). The reaction mixture was stirred for a further 10 minutes then worked up in the usual manner. Partial chromatographic purification gave compound 453-MS-91 (122 mg, 76%) as a mixture of 4 diastereoisomers.

Step 9

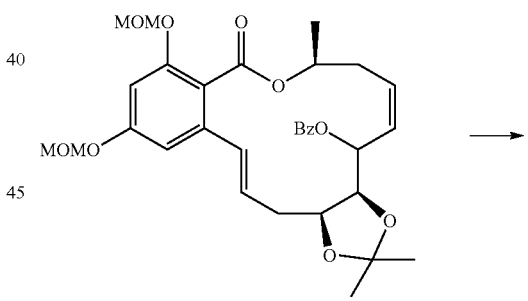

453-MS-91

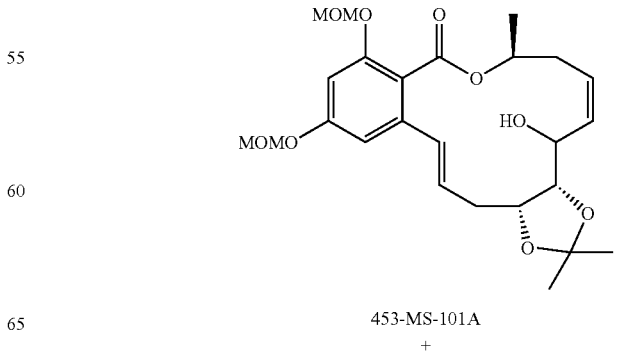

453-MS-101A
+

Step 10

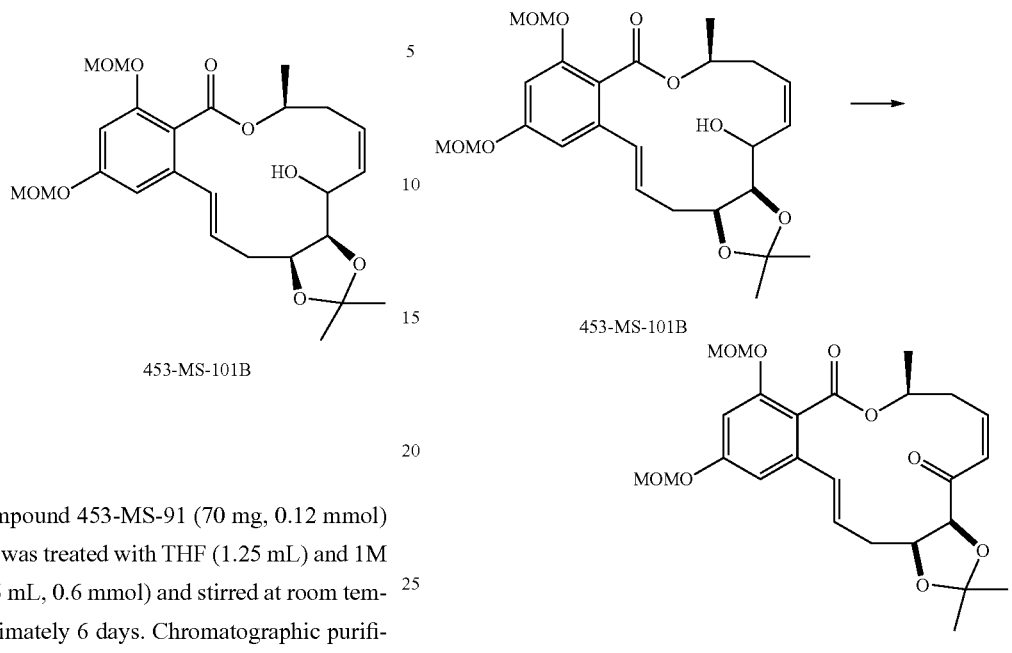

453-MS-101B

A solution of compound 453-MS-91 (70 mg, 0.12 mmol) in ethanol (2.5 mL) was treated with THF (1.25 mL) and 1M aqueous NaOH (0.6 mL, 0.6 mmol) and stirred at room temperature for approximately 6 days. Chromatographic purification gave two fractions of partially resolved diastereoisomers:

Fraction A (less polar): a mixture of 2 diastereoisomers—compound 453-MS-101A (24 mg);

Fraction B (more polar): a mixture of 2 diastereoisomers—compound 453-MS-101B (25 mg);

(total yield: 49 mg, 86%)

A solution of compound 453-MS-101B (25 mg, 52.3 µmol) in dichloromethane (1.5 mL) was treated with PCC (135 mg, 0.627 mmol) in the presence of powdered 4 Å molecular sieves (135 mg). The reaction mixture was stirred vigorously for 40 minutes at mom temperature. Basification with excess triethylamine, followed by chromatographic purification gave compound 453-MS-116 (14 mg, 63%).

Step 11

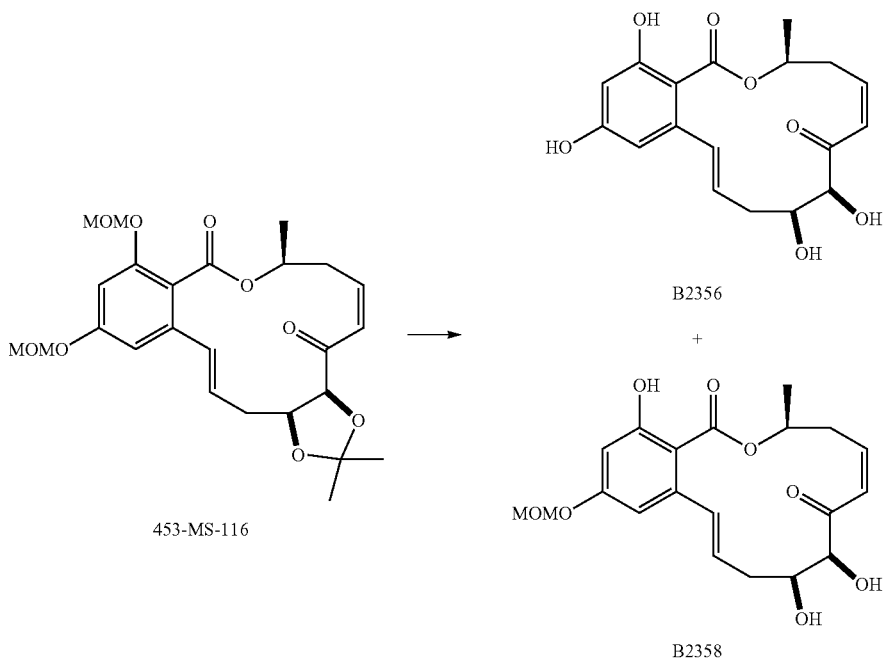

A solution of compound 453-MS-116 (13 mg, 27.3 μmol) in a mixture of dioxane (3 mL) and deuterium oxide (3 mL) was treated with Dowex® (50WX8-100, 200 mg), and stirred at room temperature for approximately 16 hours. The usual work up, followed by purification using reversed phase HPLC, gave compound B2356 (2.4 mg, 25%) [m/z: 349.3 (M+1, 60%), 161.0 (100%)], and compound B2358 (2 mg, 20%).

A solution of compound 453-MS-101A (24 mg, 50.1 μmol) in dichloromethane (2 mL) was treated with pyridinium chlorochromate (130 mg, 0.602 mmol) in the presence of powdered 4 Å molecular sieves (130 mg). The reaction mixture was stirred vigorously for 1 hour at room temperature. Basification with excess triethylamine, followed by chromatographic purification gave compound 453-MS-122 (19 mg, 80%).

Step 2

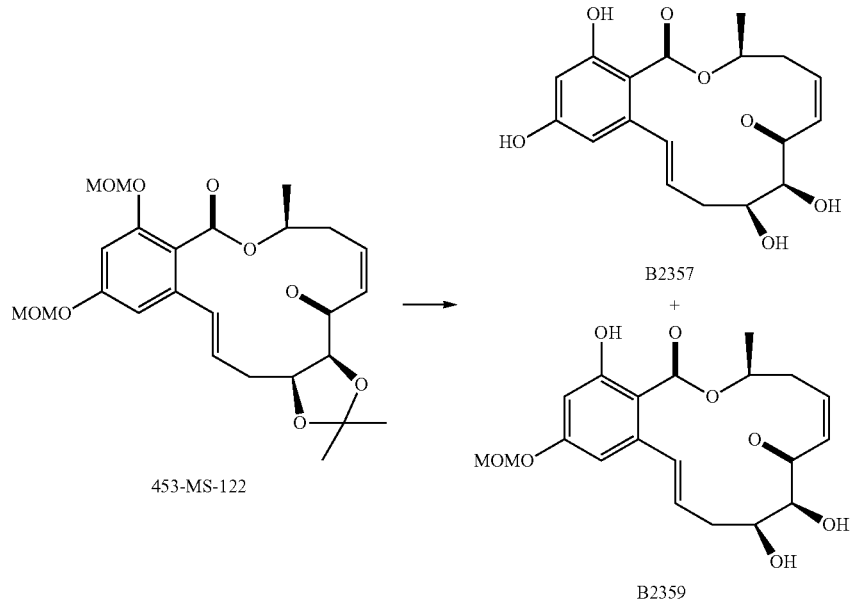

Preparation of Compound B2357 (C14 Hydroxy) & Compound B2359 (C14 OMOM):

Step 1

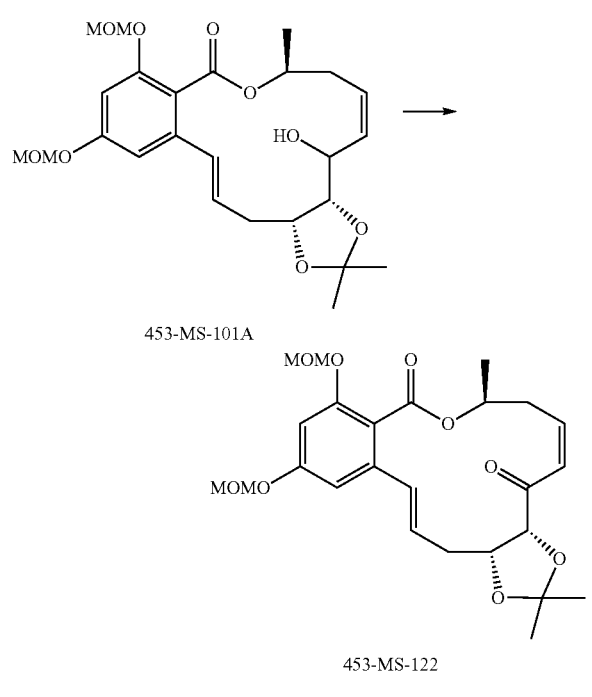

A solution of compound 453-MS-122 (21 mg, 44 μmol) in a mixture of acetonitrile (4.6 mL) and dichloromethane (1.1 mL) was treated with 48% aqueous hydrofluoric acid (1.1 mL), and stirred at room temperature for approximately 2 hours. The usual work up, followed by purification using reversed phase HPLC, gave compound B2357 (3.5 mg, 23%) [m/z: 349.2 (M+1, 50%), 161.0 (100%)], and compound B2359 (1.6 mg, 10%).

Preparation of C14-C, H, or Halogen Analogs, NF0887, NF2433, NF2435, NF2436, NF2557 and ER-805053, Synthetic Procedure for NF2433

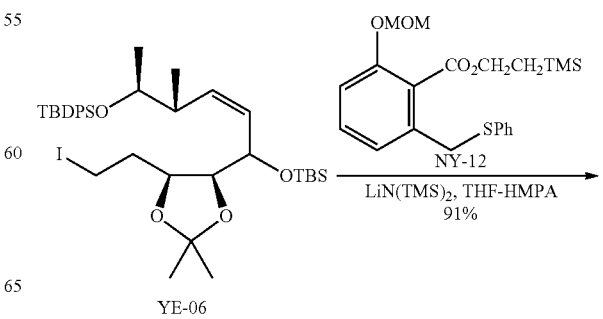

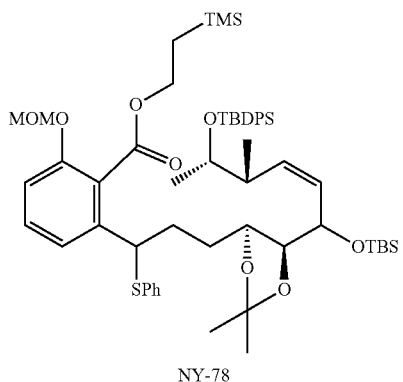
NY-78
Using same procedure for 16, YE-06 (526 mg, 0.714 mmol) was converted to NY-78 (657 mg).
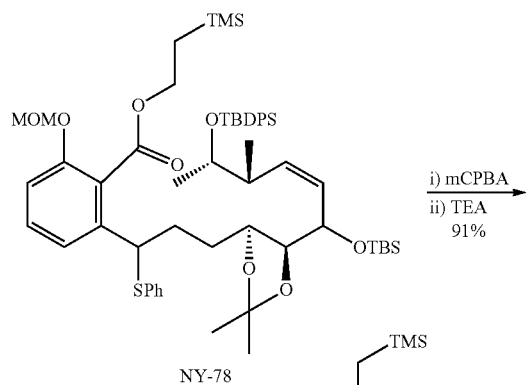
Using same procedure for 18, NY-78 (653 mg, 0.644 mmol) was converted to NY-79 (529 mg).
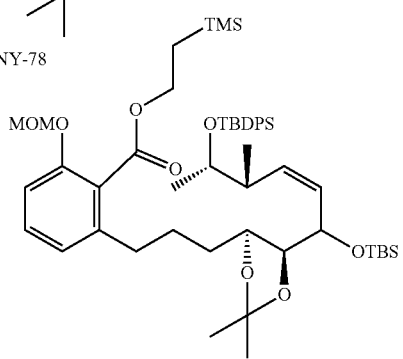
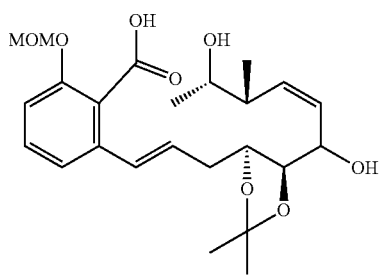
NY-80
Using same procedure for 509-HD-116, NY-79 (528 mg, 0.584 mmol) was converted to NY-80 (231 mg). NY-80 was used without purification for the next step.
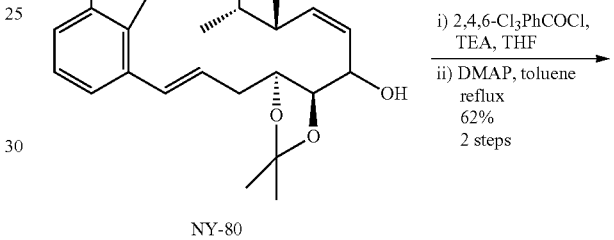
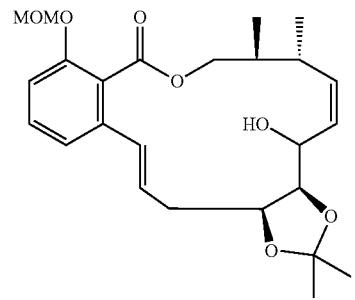
NY-81
Using same procedure for TM-12, NY-80 (230 mg, 0.511 mmol) was converted to NY-81 (157 mg).
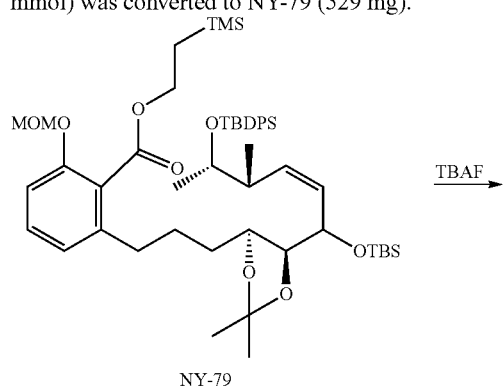
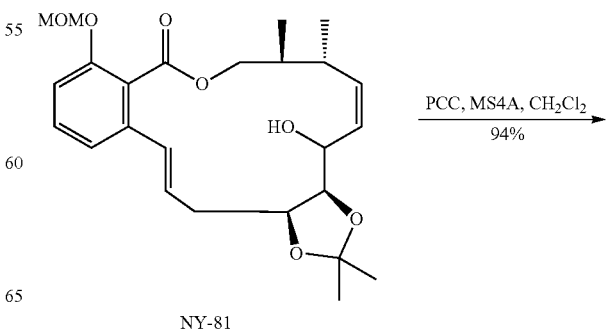

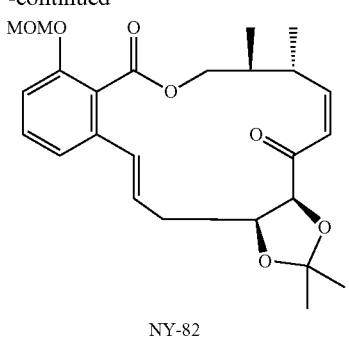

NY-82

Using same procedure for 509-HD-125, NY-81 (127 mg, 0.294 mmol) was converted to NY-82 (118 mg).

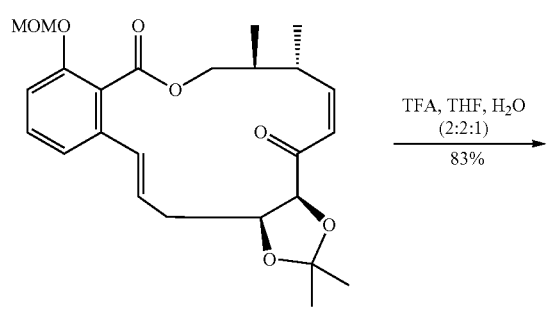

Using same procedure for NF-0675, NY-82 (118 mg, 0.274 mmol) was converted to NF-2433 (79 mg).

Synthetic Procedure for NF-2436

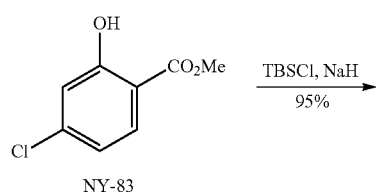

Using same procedure for 9, NY-83 (7.46 g, 40 mmol) was converted to NY-84 (11.39 g).

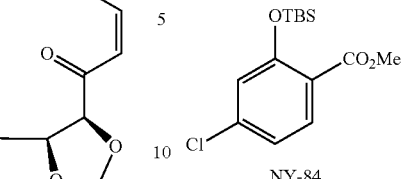

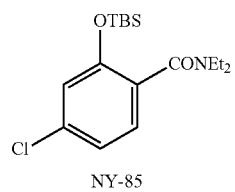

NY-85

To a mixture of NY-84 (3 g, 10 mmol), $Et_2NH$ (2.07 mL, 20 mmol) and THF (80 mL), isopropylmagenesium chloride (2M in THF, 10 mL, 20 mmol) was gradually added at −30° C. The reaction mixture was allowed to warm to 0° C. The reaction mixture was quenched with sat. $NaHCO_3$ and extracted with EtOAc. The organic layer was washed with water, brine, dried over $Na_2SO_4$, filtered and concentrated. The crude product was purified on silica gel column with hexane/EtOAc, 10:1, 8:1, 6:1 to give 3.21 g of NY-85.

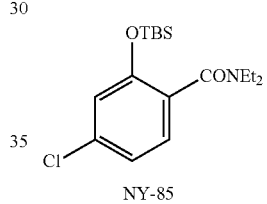

NY-85

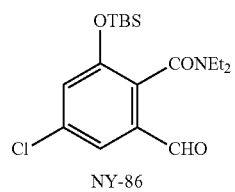

NY-86

NY-85 (3.2 g, 9.36 mmol) and TMEDA (2.2 mL, 14.58 mmol) were dissolved in THF (30 mL) and cooled to −78° C., under nitrogen. Then, sec-BuLi (1.3M/cyclohexane, 11 mL, 14.3 mmol) was slowly added and the reaction was stirred at −78° C. for 1 hr. DMF (1.4 mL, 18.08 mmol) was added to the solution, then the solution was stirred at −78° C. for 30 min. The mixture was quenched with sat. $NH_4Cl$ and extracted with EtOAc. The organic layer was washed with water, brine and dried over $Na_2SO_4$, filtered and concentrated. The crude product was purified on silica gel column with hexane/EtOAc, 6:1 to give 2.56 g of NY-86.

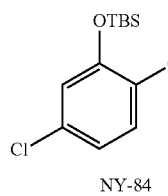

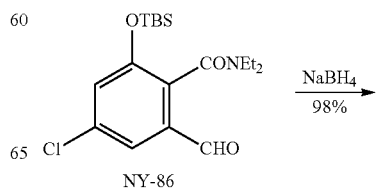

-continued

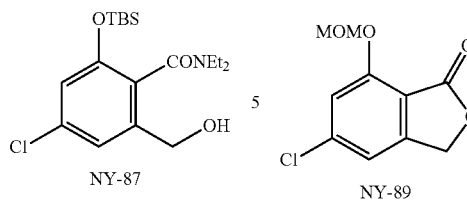

To a solution of NY-86 (2.55 g, 6.89 mmol) in MeOH (30 mL), NaBH$_4$ (260 mg, 6.87 mmol) was added at 0° C. and stirred for 30 min. The reaction mixture was quenched with sat. NH$_4$Cl and extracted with EtOAc. The organic layer was washed with water, brine, dried over Na$_2$SO$_4$, filtered and concentrated to give 2.5 g of NY-87.

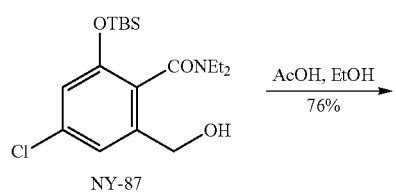

To a solution of NY-89 (1.74 g, 7.61 mmol) in DMSO (20 mL), a solution of KOH (450 mg, 8.02 mmol) in water (10 mL) was added and stirred at room temperature for 30 min. Then, the mixture was stirred at 40° C. for 30 min. MeI (9.5 mL, 153 mmol) was added to the reaction mixture, and the mixture was stirred at room temperature for 3 hrs. The reaction mixture was quenched with sat. NH$_4$Cl and extracted with EtOAc. The organic layer was washed with water, 5% citric acid, water, sat. NaHCO$_3$, brine, dried over Na$_2$SO$_4$, filtered and concentrated to give 1.93 g of NY-90.

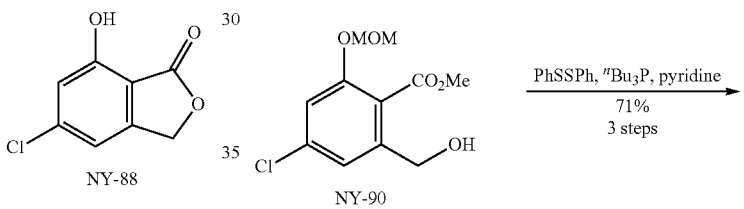

A mixture of NY-87 (2.5 g, 6.72 mmol), AcOH (1.92 mL, 33.54 mmol) and EtOH (50 mL) was refluxed for 4 hrs. The mixture was concentrated and the residue was alkalized with sat. NaHCO$_3$ and extracted with EtOAc. The aqueous layer was reextracted with EtOAc (×2) and the organic layers were washed with sat. NH$_4$Cl, water, brine, dried over Na$_2$SO$_4$, filtered and concentrated. The crude crystallized product was washed with Et$_2$O to give 718 mg of NY-88. The mother liquid was purified on silica gel column with hexane/EtOAc, 3:1, 2:1 to give additional 230 mg of NY-88.

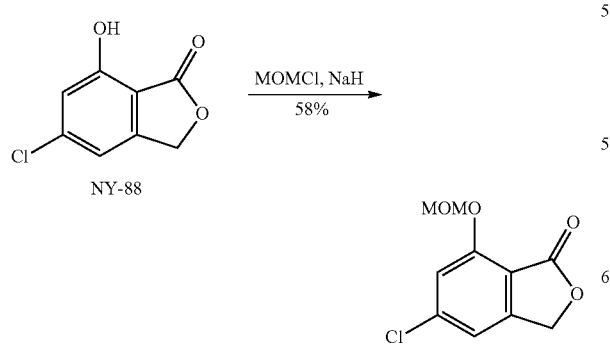

To a solution of NY-90 (1.93 g, 7.61 mmol), Ph$_2$S$_2$ (5 g, 22.9 mmol), pyridine (3.7 mL, 45.75 mmol), $^n$Bu$_3$P (5.7 mL, 22.88 mmol) were added at 0° C. The mixture was allowed to warm to room temperature and stirred for 12 hrs. The reaction mixture was diluted with EtOAc and washed with 5% citric acid (×2), water, sat. NaHCO$_3$, brine, dried over Na$_2$SO$_4$, filtered and concentrated. The crude product was purified on silica gel column with hexane/EtOAc, 15:1, 5:1 to give 1.9 g of NY-91.

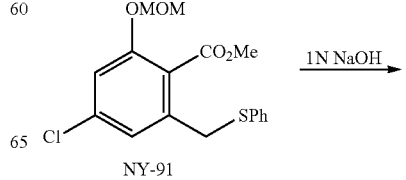

Using same procedure for 509-HD-209, NY-88 (940 mg, 5.09 mmol) was converted to NY-89 (676 mg).

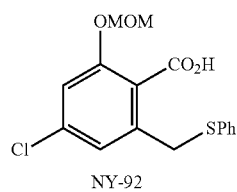

NY-92

Using same procedure for 509-HD-212, NY-91 (2.12 g, 6 mmol) was converted to NY-92 (2.07 g). NY-92 was used without purification for the next step.

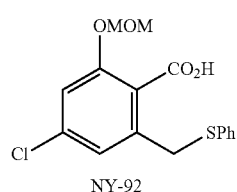

NY-92

TMSCH₂CH₂OH
PPh₃, DEAD
83%
2 steps
→

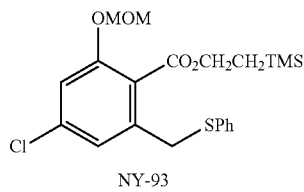

NY-93

Using same procedure for 509-HD-213, NY-92 (2.07 g, 6 mmol) was converted to NY-93 (2.19 g).

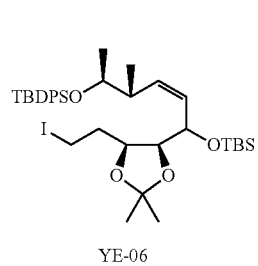

YE-06

NY-93
LiN(TMS)₂,
THF—HMPA
87%
→

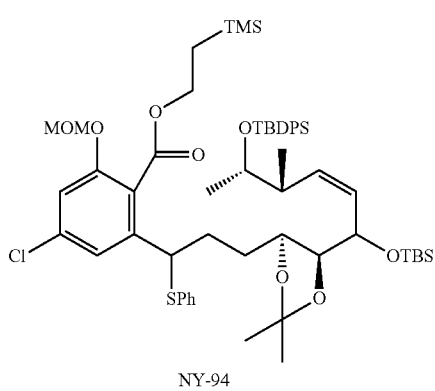

NY-94

Using same procedure for 16, YE-06 (505 mg, 0.685 mmol) was converted to NY-94 (625 mg).

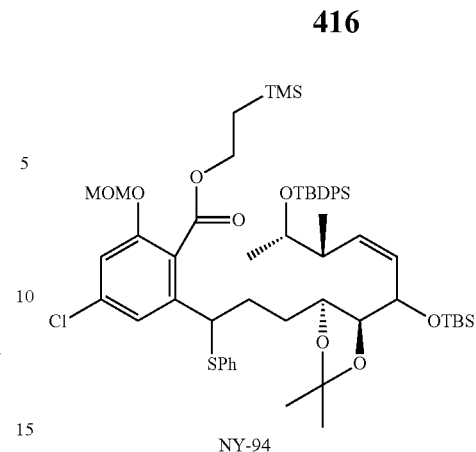

NY-94 i) mCPBA
ii) TEA
90%
→

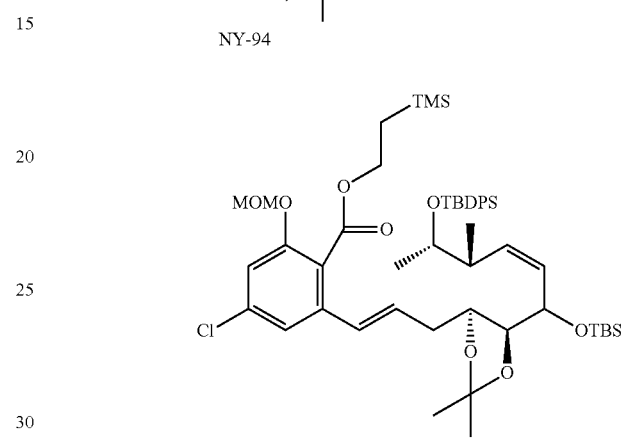

NY-95

Using same procedure for 18, NY-94 (623 mg, 0.594 mmol) was converted to NY-95 (501 mg).

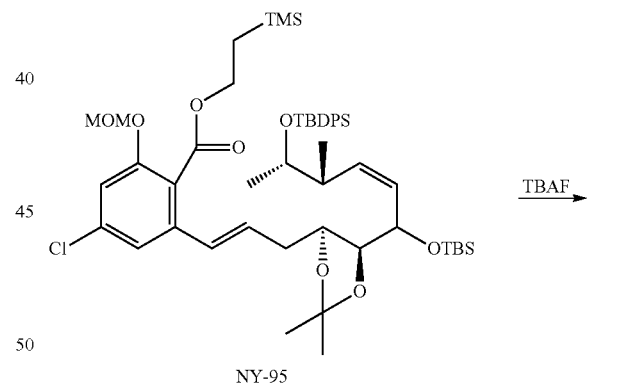

NY-95

TBAF →

NY-96

Using same procedure for 509-HD-116, NY-95 (500 mg, 0.533 mmol) was converted to NY-96 (400 mg). NY-96 was used without purification for the next step.

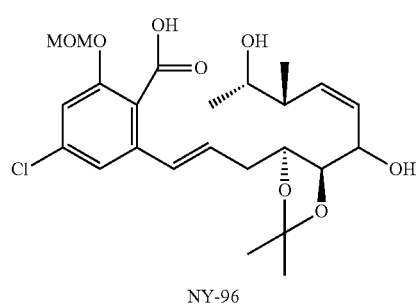

NY-96

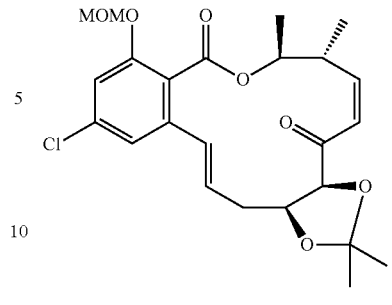

NY-98

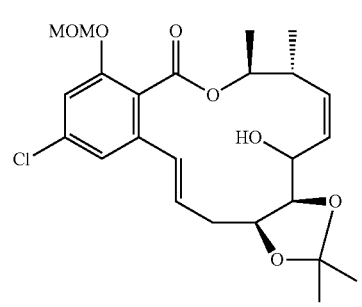

NY-97

Using same procedure for TM-12, NY-96 (400 mg, 0.533 mmol) was converted to NY-97 (142 mg).

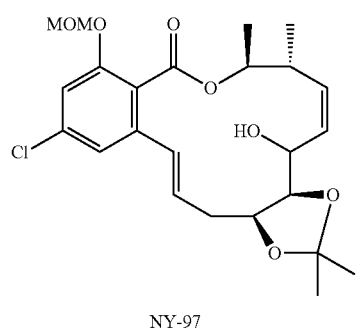

NY-97

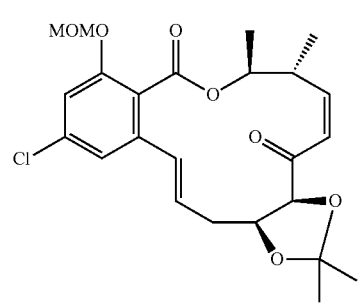

NY-98

Using same procedure for 509-HD-125, NY-97 (139 mg, 0.298 mmol) was converted to NY-98 (120 mg).

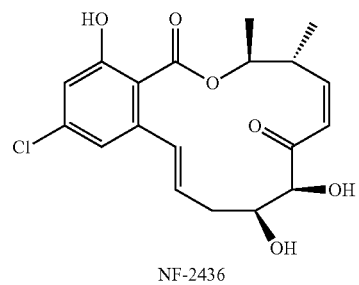

NF-2436

Using same procedure for NF-0675, NY-98 (118 mg, 0.254 mmol) was converted to NF-2436 (24 mg).

Synthetic Procedure for NF2435

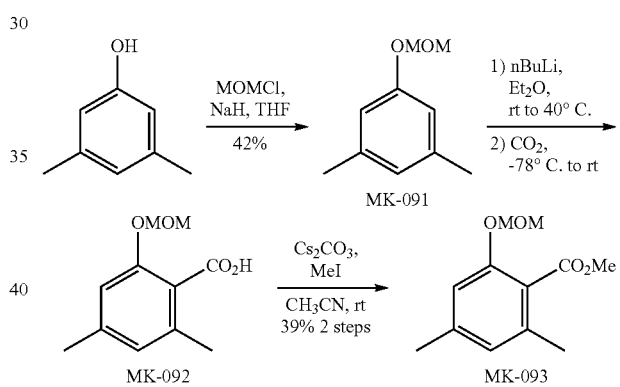

Using similar procedure for the synthesis of 509-HD-209 from 509-HD-207, 3,5-dimethylphenol (27.58 g, 225.75 mmol) was converted to colorless oil of MK-091 (15.91 g, 42%) as compound purified.

MK-091 (6.00 g, 36.10 mmol) was dissolved in 18 mL of dry $Et_2O$. To the stirred solution was added n-BuLi in hexane (1.6M, 27 mL, 43.32 mmol, 1.2 eq.) and the mixture was warmed to 40° C. After 30 min at 40° C. the color of the reaction mixture turned dark red. The mixture was cooled to −78° C. and excessive dry $CO_2$ gas (ca 30 eq.) was added by bubbling through an inlet over 30 min. Then, the resulting mixture was allowed to warm to rt. After 30 min the reaction mixture was quenched with water and washed with $Et_2O$. The basic aqueous layer was acidified with aqueous solution of $KHSO_4$ and extracted with AcOEt. The organic extract was washed with brine, dried over $Na_2SO_4$, filtered, and concentrated to yield crude colorless crystals of MK-092 (4.55 g, <60%). The crude MK-092 was used for next step without purification.

Crude MK-092 (4.55 g, assumed to contain 21.6 mmol) was dissolved in 200 mL of $CH_3CN$. To the solution were added $CsCO_3$ (5.64 g, 17.3 mmol) and MeI (2.20 mL, 34.6 mmol) and the mixture was stirred at rt overnight. After concentration of the reaction mixture, water was added and extracted with AcOEt. The organic extract was washed with saturated aqueous NaHCO$_3$ and brine, then dried over Na$_2$SO$_4$, filtered, and concentrated to give crude oil of MK-093. The crude product was purified by chromatography on silica gel (hexane/AcOEt: 10/1) to afford pale yellow oil of MK-093 (3.19 g, 39% 2 steps).

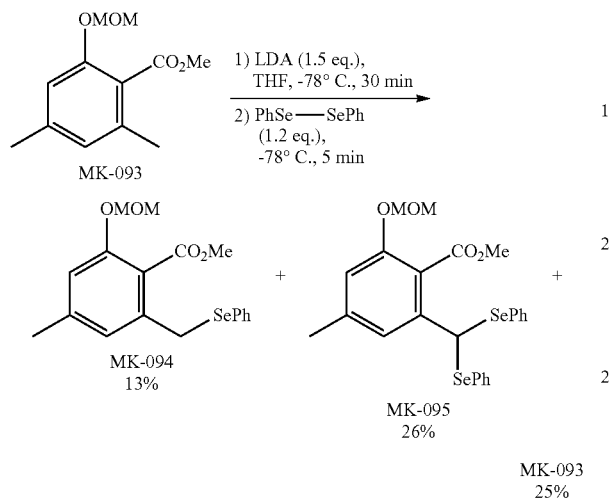

Using similar procedure for the synthesis of 509-HD-211 from 509-HD-209, MK-093 (2.86 g, 12.77 mmol) was converted to a mixture of MK-094, MK-095 and MK-093. The crude product was purified by chromatography on silica gel (hexane/AcOEt: 9/1) to afford pale yellow oil of MK-094 (652 mg, 13%), the structure of which was determined by NOESY analysis.

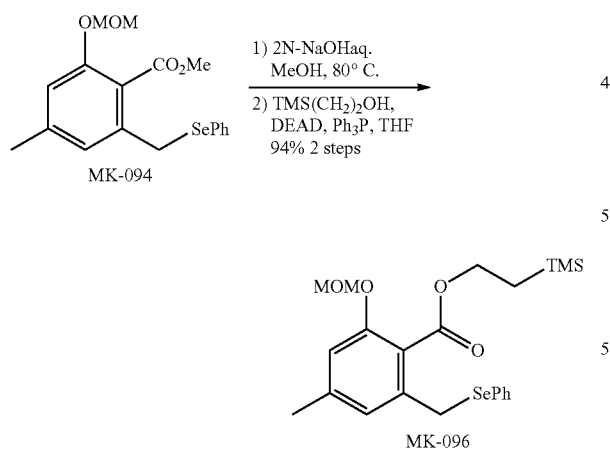

Using similar procedure for the synthesis of 509-HD-212 from 509-HD-211, MK-094 (650 mg, 1.71 mmol) was converted to crude benzoic acid.

Using similar procedure for the synthesis of MK-047 from MK-046, the crude benzoic acid was converted to pale pink oil of MK-096 (746 mg, 94% 2 steps) as compound purified.

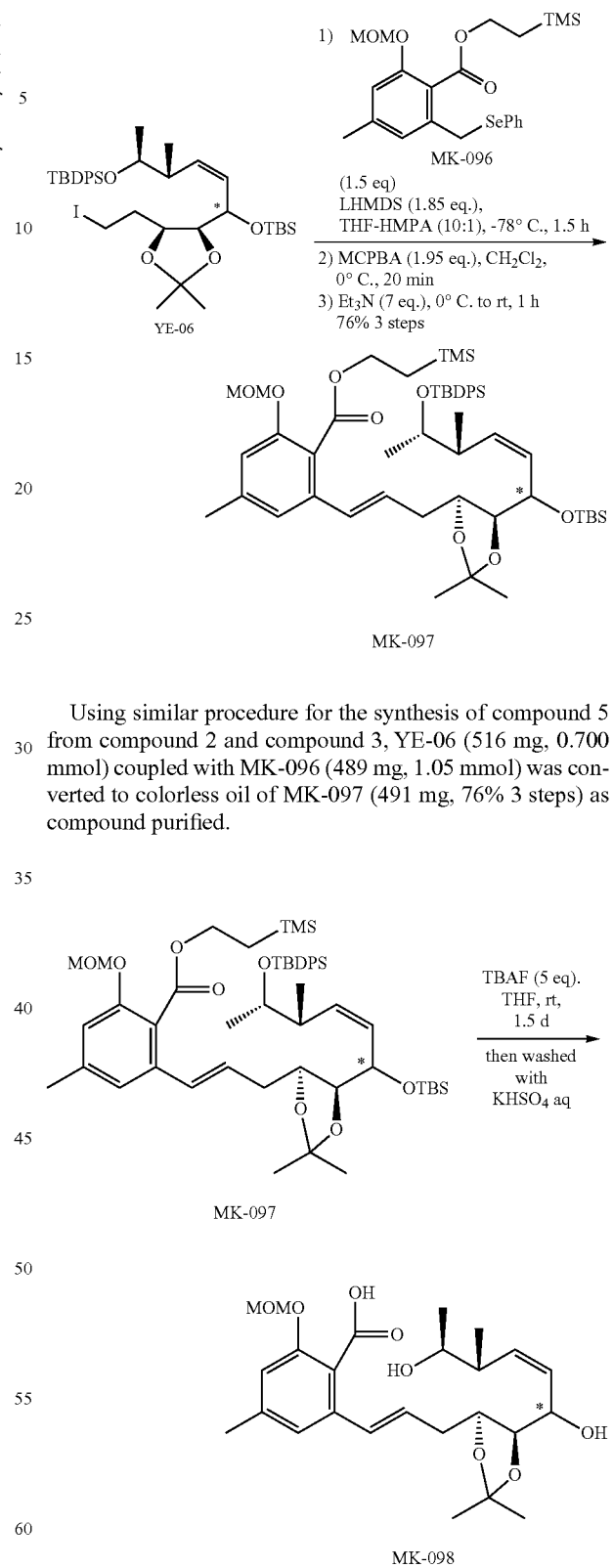

Using similar procedure for the synthesis of compound 5 from compound 2 and compound 3, YE-06 (516 mg, 0.700 mmol) coupled with MK-096 (489 mg, 1.05 mmol) was converted to colorless oil of MK-097 (491 mg, 76% 3 steps) as compound purified.

Using similar procedure for the synthesis of YE-17 from YE-16, MK-097 (491 mg, 0.535 mmol) was converted to crude oil of MK-098 (486 mg, including silyl impurity). The crude MK-098 was used for next step without purification.

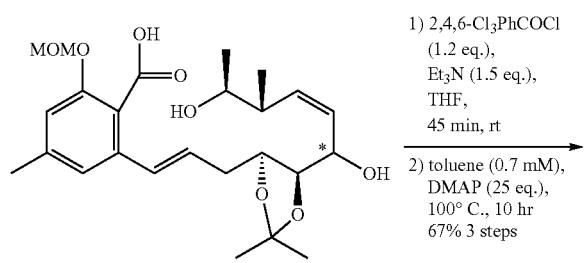

MK-098

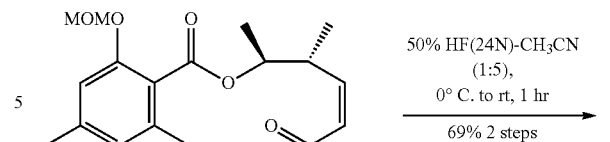

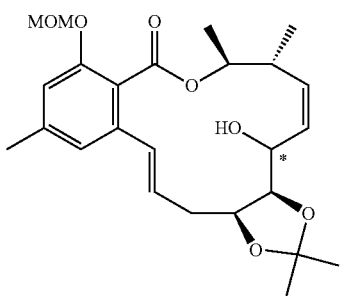

MK-099

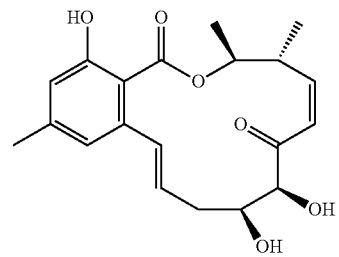

NF2435

Using similar procedure for the synthesis of YE-18 from YE-17, the crude MK-098 (486 mg, assumed to contain 0.535 mmol) was converted to colorless oil of MK-099 (159 mg, 67% 3 steps) as compound purified.

Using similar procedure for the synthesis of NF1226 from MK-035, crude MK-100 (146 mg) was converted to crude pale yellow crystals. The crude product was purified by chromatography on silica gel (hexane/AcOEt: 3/2) to afford colorless crystals of NF2435 (88 mg, 69% 2 steps).

Synthetic Procedure for NF2557, NF2558, and NF2559

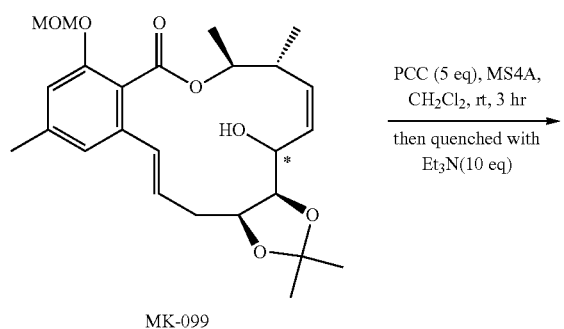

MK-099

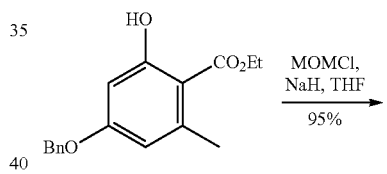

TM-34

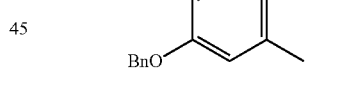

MK-120

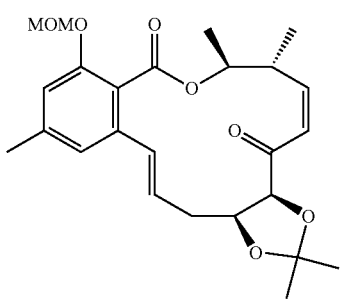

MK-100

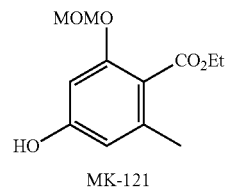

MK-121

Using similar procedure for the synthesis of 509-HD-125 from 509-HD-119B, MK-099 (158 mg, 0.354 mmol) was converted to crude pale yellow solid of MK-100 (146 mg, <93%). The crude MK-100 was used for next step without purification.

Using similar procedure for the synthesis of 509-HD-209 from 509-HD-207, TM-34 (12.23 g, 42.71 mmol) was converted to colorless oil of MK-120 (13.40 g, 95%) as compound purified.

MK-120 (13.38 g, 40.50 mmol) was dissolved in 200 mL of EtOH. 10% Pd on carbon (50% wet, 2.7 g) was added. The mixture was stirred under hydrogen at rt. After 8 hrs catalyst was filtered through Celite and the filtrate was concentrated to give crude solid. The crude product was purified by chromatography on silica gel (hexane/AcOEt: 2/1) to afford colorless crystals of MK-121 (8.67 g, 89%).

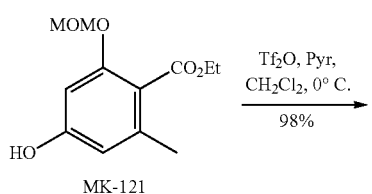

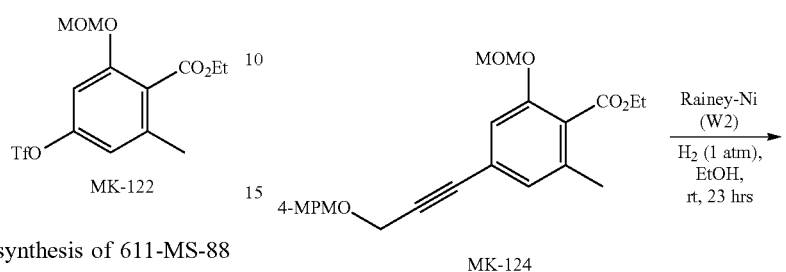

Using similar procedure for the synthesis of 611-MS-88 from 611-MS-84, MK-121 (8.66 g, 36.04 mmol) was converted to colorless crystals of MK-122 (13.20 g, 98%) as compound purified.

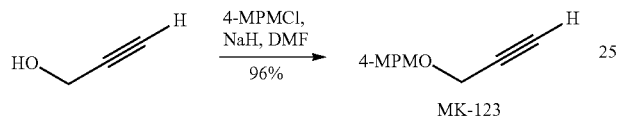

Using similar procedure for the synthesis of MK-073 from MK-072, propargyl alcohol (10.74 g, 191.6 mmol) was converted to colorless oil of MK-123 (27.03 g, 96%) as compound purified.

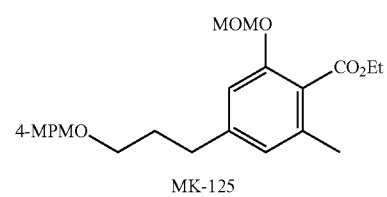

Using similar procedure for the synthesis of MK-074 from MK-073, MK-124 (14.28 g, 35.84 mmol) was converted to crude yellow oil of MK-125 (14.34 g). The crude MK-125 was used for next step without purification.

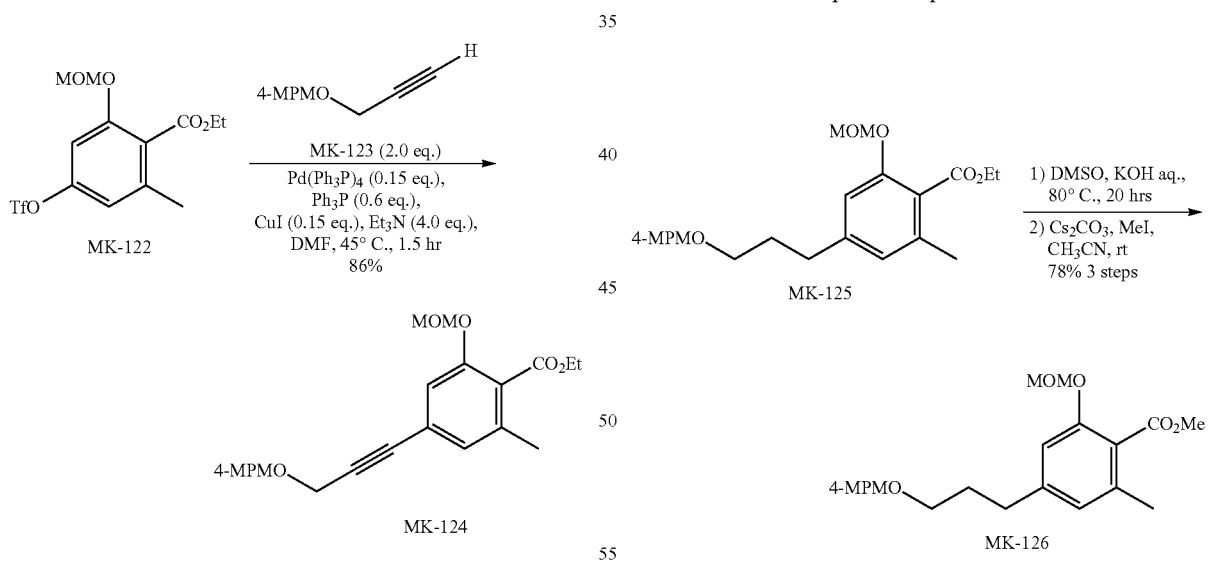

MK-122 (13.20 g, 35.46 mmol) and MK-123 (12.50 g, 70.92 mmol, 2.0 eq.) were dissolved in 440 mL of DMF. To the solution were added $Ph_3P$ (5.58 g, 21.28 mmol, 0.6 eq.), $Pd(Ph_3P)_4$ (6.15 g, 5.32 mmol, 0.15 eq.), CuI (1.01 g, 5.32 mmol, 0.15 eq.), and $Et_3N$ (19.8 mL, 141.83 mmol, 4 eq.). The mixture was heated to 45° C. and stirred for 1.5 hrs under nitrogen atmosphere. The mixture was cooled to rt and diluted with $Et_2O$-hexane, then stirred for a while. The resulting mixture was filtered through a pad of Celite to remove insoluble solid. The filtrate was washed with saturated aqueous solution of $NH_4Cl$ and brine, dried over $Na_2SO_4$, filtered, and concentrated to yield crude product. The crude product was purified by chromatography on silica gel (hexane/AcOEt: 7/1 to 5/1) to afford pale brown oil of MK-124 (12.11 g, 86%).

Using similar procedure for the synthesis of MK-114 from MK-113, crude MK-125 (14.34 g, assumed to contain 35.84 mmol) was converted to crude yellow oil of benzoic acid (14.92 g). The crude benzoic acid was used for next step without purification.

Using similar procedure for the synthesis of MK-093 from MK-092, the crude benzoic acid (14.92 g, assumed to contain 35.84 mmol) was converted to colorless oil of MK-126 (10.92 g, 78% 3 steps) as compound purified.

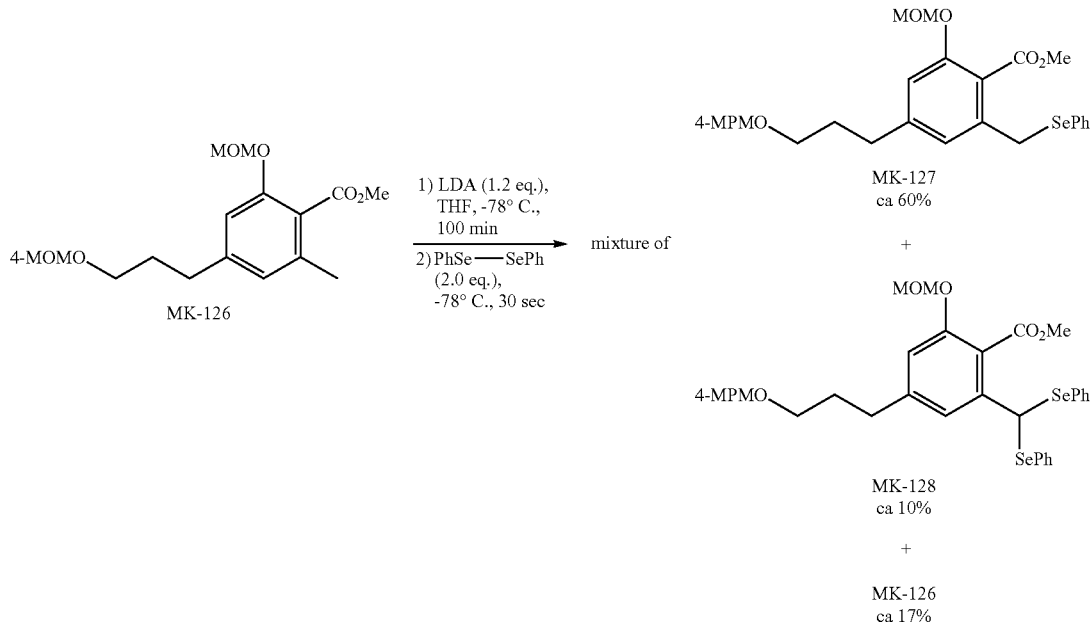

Using modified procedure for the synthesis of 509-HD-211 from 509-HD-209, MK-126 (960 mg, 2.47 mmol) was converted to crude selenide product. The crude product was purified by chromatography on silica gel (hexane/AcOEt: 6/1 to 5/1) to afford pale yellow oil (953 mg) as an inseparable mixture of desirable MK-127 (ca 710 mg, ca 60%), MK-128 (ca 10%), and MK-126 (ca 17%). The mixture was used for next step without further purification.

Using similar procedure for the synthesis of MK-114 from MK-113, the mixture (953 mg) of MK-127 (ca 710 mg, assumed to contain 1.31 mmol), MK-128, and MK-126 was converted to crude oil of benzoic acids (980 mg). The crude benzoic acids were used for next step without purification.

Using similar procedure for the synthesis of MK-047 from MK-046, the crude mixture of benzoic acids (980 mg) was converted to crude TMS-ethyl esters. The crude product was purified by chromatography on silica gel (hexane/AcOEt: 6/1) to afford colorless oil (875 mg) as an inseparable mixture

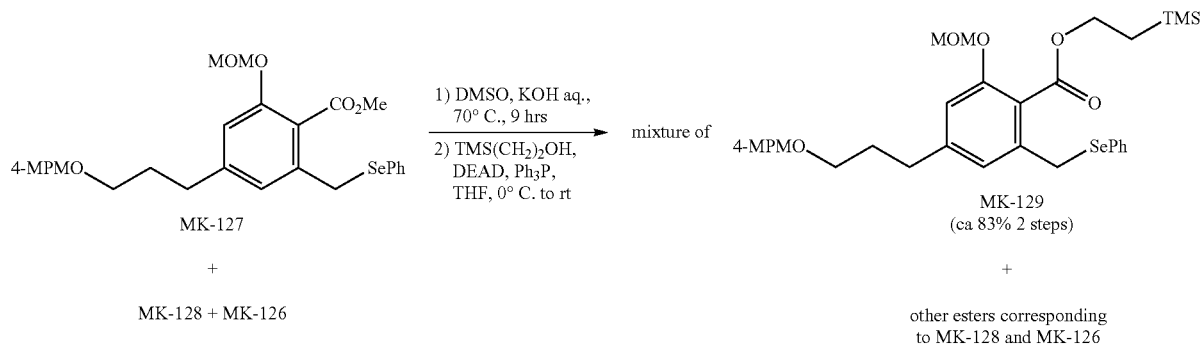

of desirable MK-129 (ca 683 mg, ca 83%) and other TMS-ethyl esters corresponding to MK-128 and MK-126. The mixture was used for next step without further purification.

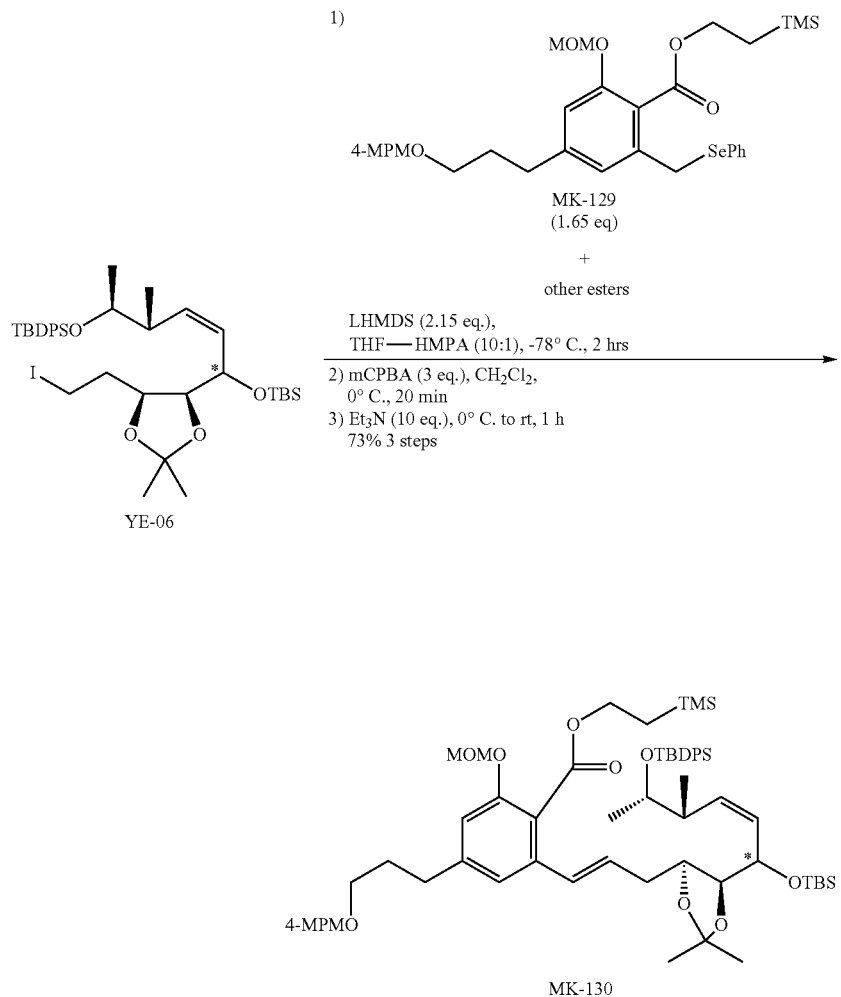

Using similar procedure for the synthesis of compound 5 from compound 2 and compound 3, YE-06 (483 mg, 0.655 mmol) coupled with the mixture (875 mg) including MK-129 (ca 683 mg, 1.08 mmol) was converted to colorless oil of MK-130 (519 mg, 73% 3 steps).

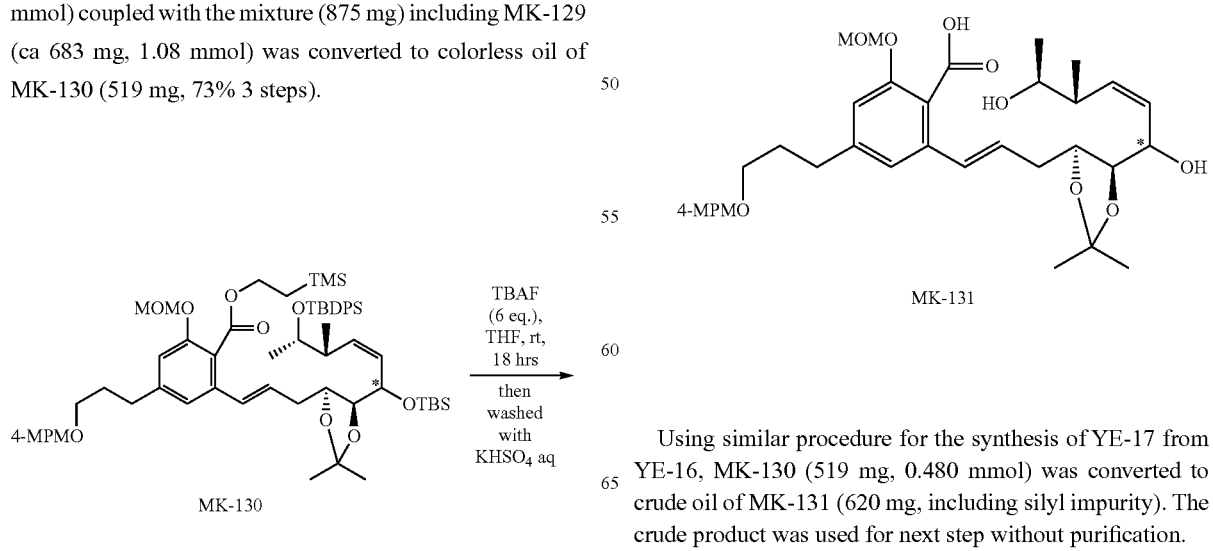

Using similar procedure for the synthesis of YE-17 from YE-16, MK-130 (519 mg, 0.480 mmol) was converted to crude oil of MK-131 (620 mg, including silyl impurity). The crude product was used for next step without purification.

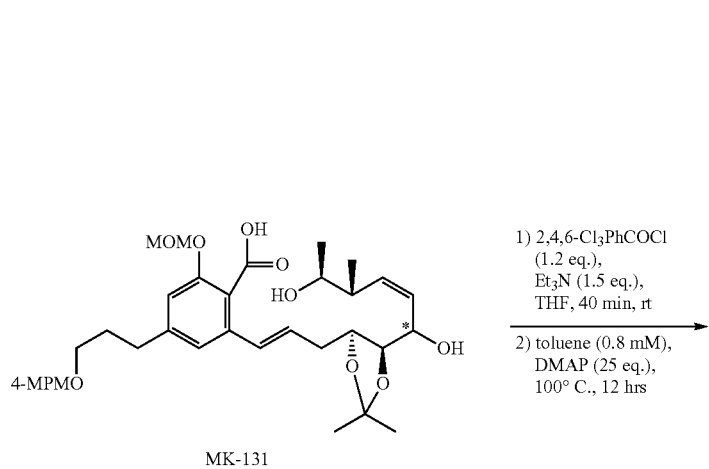

MK-131

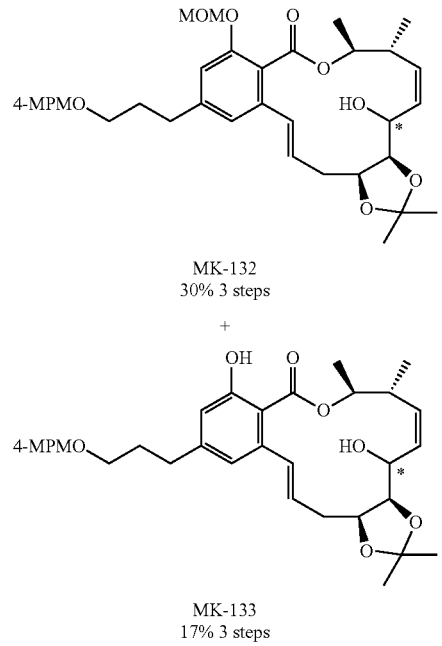

MK-132
30% 3 steps

+

MK-133
17% 3 steps

Using similar procedure for the synthesis of YE-18 from YE-17, the crude MK-131 (620 mg, assumed to contain 0.480 mmol) was converted to crude oil of lactonized product. The crude product was purified by chromatography on silica gel (hexane/AcOEt: 5/2) to afford colorless oil of MK-132 (88 mg, 30% 3 steps) and colorless oil of des-MOM form MK-133 (47 mg, 17% 3 steps) respectively.

Using similar procedure for the synthesis of 509-HD-125 from 509-HD-119B, MK-133 (46 mg, 0.0812 mmol) was converted to crude pale yellow oil of enone (35 mg, <76%). The crude enone was used for next step without purification.

Using similar procedure for the synthesis of NF0531 from NF0530, the crude enone (35 mg, assumed to contain 0.0620 mmol) was converted to colorless crystals of MK-134 (20 mg, 55% 2 steps).

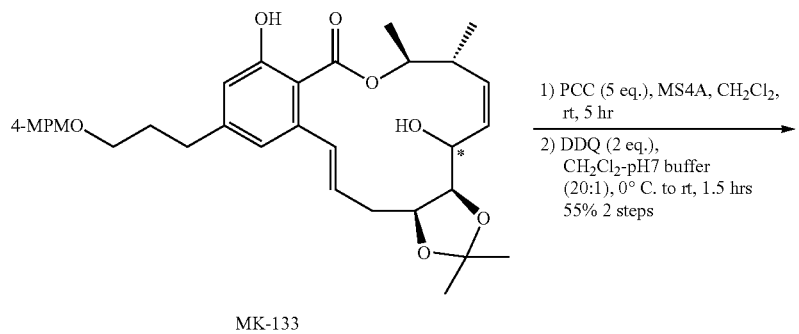

MK-133

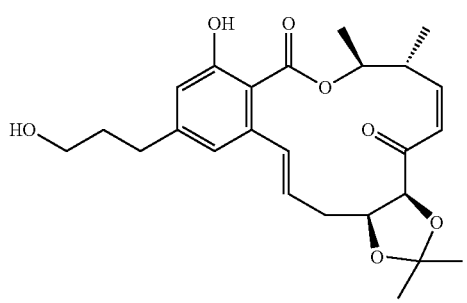

MK-134

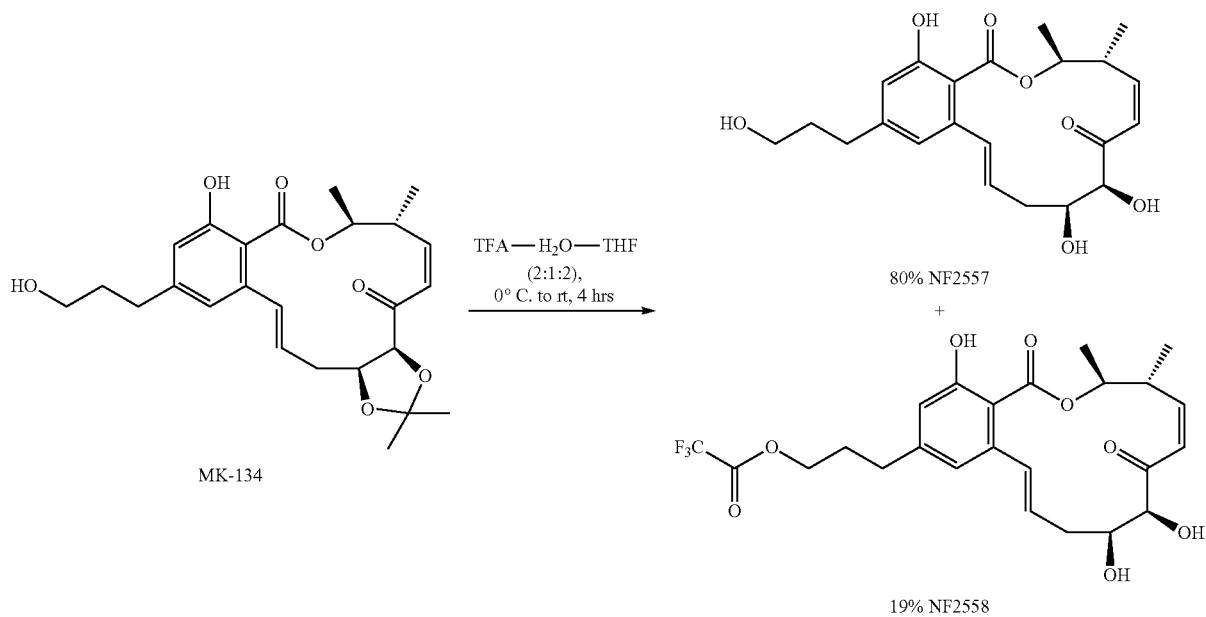

Using similar procedure for the synthesis of NF0675 from TM-13, MK-134 (7 mg, 0.0157 mmol) was converted to colorless crystals of NF2557 (5.1 mg, 80%) and colorless solid of NF2558 (1.5 mg, 19%) as compound purified, respectively.

Synthesis of ER-805053

Step 1

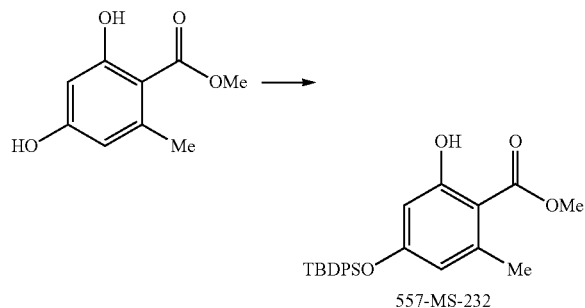

To a solution of methyl 2,4-dihydroxy-6-methylbenzoate (10.9 g, 0.0598 mol) in dry N,N-dimethylformamide (100 mL) were added imidazole (4.48 g, 0.0658 mol) and tert-butyldiphenylsilyl chloride (15.6 mL, 0.0658 mol). The reaction mixture was stirred at room temperature for 24 hours then worked up in the usual manner. The crude product was purified chromatographically to give compound 557-MS-232 (12.33 g, 49%).

Step 2

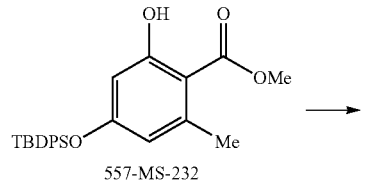

-continued

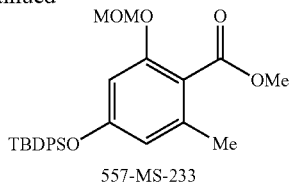

To a solution of compound 557-MS-232 (9.08 g, 0.021 mol) in dry tetrahydrofuran (100 mL), at 0° C. under an inert atmosphere, was added sodium hydride (55% dispersion in oil; 1.88 g, approximately 0.042 mol). The reaction mixture was stirred at 0° C. for 30 minutes then treated with methoxymethyl chloride (3.28 mL, 0.042 mol). The reaction mixture was allowed to warm to room temperature overnight. The usual work up gave compound 557-MS-233 (9.17 g, 91%).

Step 3

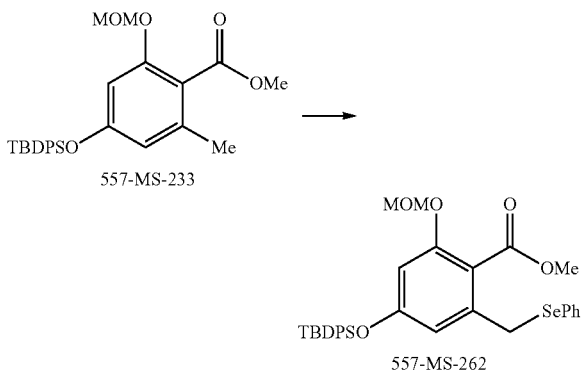

To a solution of freshly prepared lithium diisopropylamide (16.2 mmol) in dry tetrahydrofuran (15 mL), at −78° C. under an inert atmosphere, was added drop wise a solution of compound 557-MS-233 (3.93 g, 9.01 mmol) in dry tetrahydrofuran (15 mL). The reaction mixture was stirred at −78° C. for 45 minutes then a solution of diphenyl diselenide (2.53 g, 8.11 mmol) in dry tetrahydrofuran (15 mL) was added rapidly (down the inside walls of the reaction vessel so as to pre-chill the diphenyl diselenide solution). The reaction mixture was stirred at −78° C. for 45 minutes then treated drop wise with a 2M solution of acetic acid in diethyl ether (8 mL). The reaction mixture was then worked up in the usual manner. Chromatographic purification gave compound 557-MS-262 (4.57 g, 82%).

Step 4

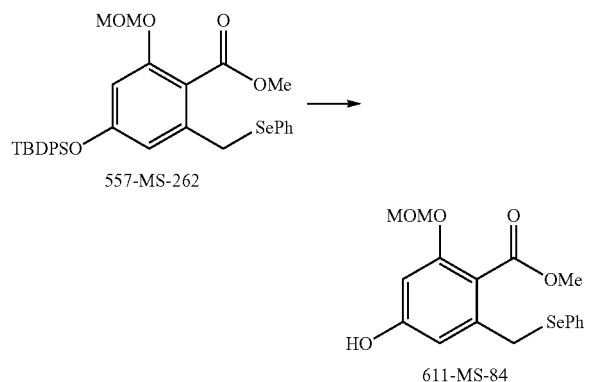

A solution of compound 557-MS-262 (6.29 g, 0.01 mol) in ethanol (100 mL) was treated with powdered sodium hydroxide (4 g, 0.1 mol) and heated under reflux for 30 minutes. The reaction mixture was cooled to 5° C. and acidified to pH6.5 with 1M HCl. The majority of the ethanol was then removed by concentration in vacuo and resultant residue partitioned between water and ethyl acetate. The organic layer was washed sequentially with saturated aqueous sodium bicarbonate solution and water. Drying etc gave a crude residue, which was purified chromatographically to give compound 611-MS-84 (3.3 g, 87%).

Step 5

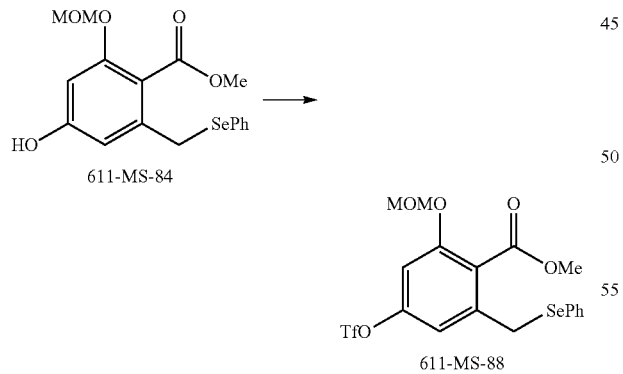

A solution of compound 611-MS-84 (1.65 g, 4.33 mmol) in dichloromethane (20 mL), at 0° C., was treated sequentially with pyridine (0.385 mL, 4.76 mmol) and trimethylsulfonic anhydride (0.764 mL, 4.54 mmol). After 25 minutes at 0° C. the reaction mixture was warmed to room temperature and worked up in the usual manner to give compound 611-MS-88 (1.5 g, 68%).

Step 6

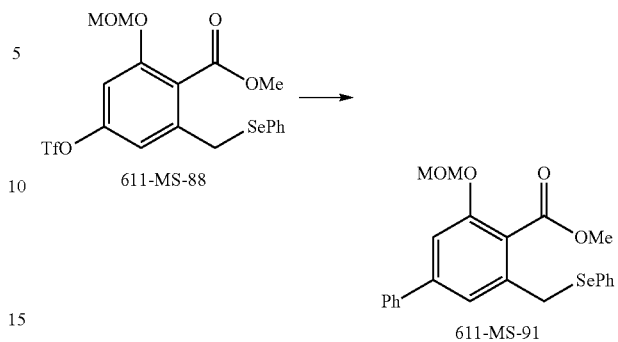

A solution of compound 611-MS-88 (1.5 g, 2.92 mmol) in 1,2-dimethoxyethane (25 mL) was heated under reflux, under an inert atmosphere, in the presence of phenyl boronic acid (713 mg, 5.84 mmol), palladium tetrakistriphenylphosphine (335 mg, 0.29 mmol), lithium chloride (247 mg, 5.84 mmol) and 2M aqueous sodium carbonate (25 mL). After 2 hours the reaction mixture was cooled to room temperature. The usual work up, followed by chromatographic purification gave compound 611-MS-91 (1.004 g, 78%).

Step 7

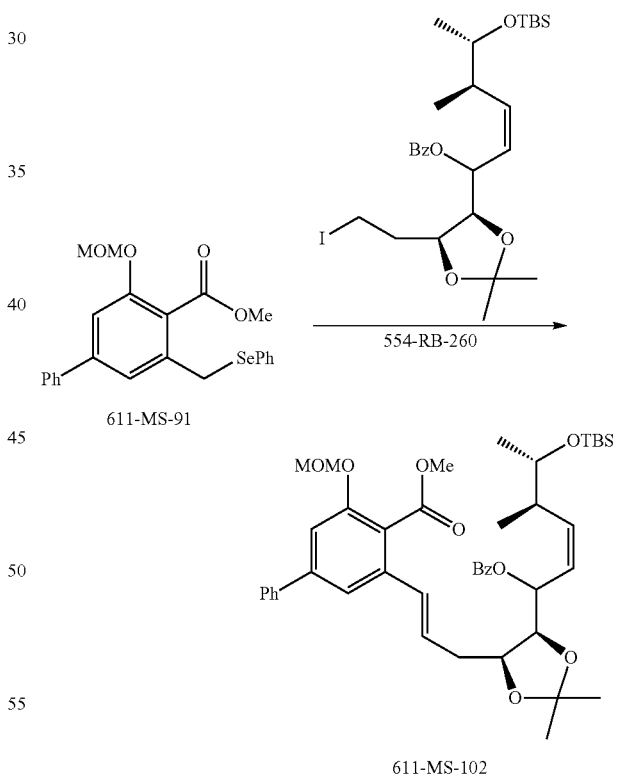

A mixture of compound 611-MS-91 (512 mg, 1.16 mmol) and compound 554-RB-260 (635 mg, 1.05 mmol) was dissolved in a solution of 10% hexamethylphosphoramide in tetrahydrofuran (8.8 mL) and cooled to −78° C. under an inert atmosphere. A 0.5M solution of lithium bis-(trimethylsilyl) amide in tetrahydrofuran (2.52 mL, 1.26 mmol) was then added drop wise over approximately 30 minutes. The reaction mixture was stirred at −78° C. for 2 hours, then warmed to 0°

C. The intermediate crude product was worked up in the usual manner and then dissolved in dichloromethane (15 mL) and cooled to 0° C. A solution of approximately 55% meta-chloroperbenzoic acid (724 mg) in dichloromethane (12 mL) was added. After 30 minutes triethylamine (1.6 mL) was added and the reaction mixture was worked up in the usual manner. Chromatographic purification gave compound 611-MS-102 (560 mg, 64%).

Step 8

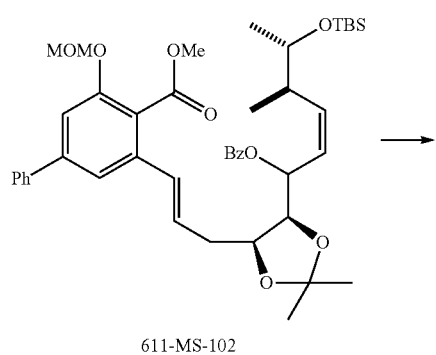

611-MS-102

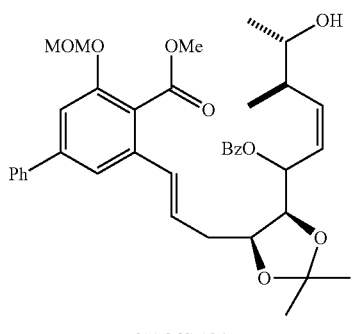

611-MS-104

A solution of compound 611-MS-102 (560 mg, 0.738 mmol) in tetrahydrofuran (5 mL) was treated with a 1M solution of tetrabutylammonium fluoride in tetrahydrofuran (0.74 mL, 0.74 mmol). The usual work up, followed by chromatographic purification gave compound 611-MS-104 (340 mg, 71%).

Step 9

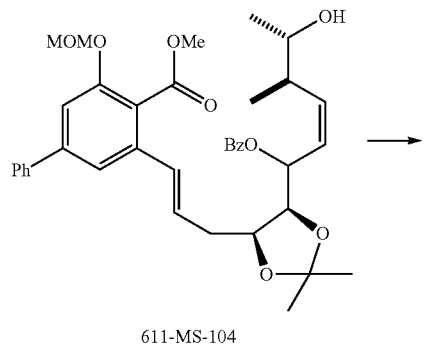

611-MS-104

-continued

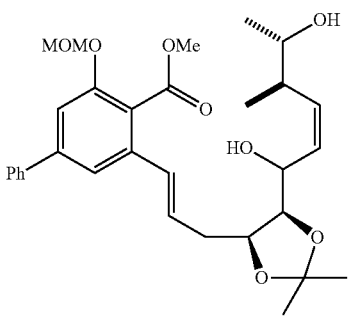

611-MS-106

A solution of compound 611-MS-104 (340 mg, 0.527 mmol) in ethanol (10 mL) was treated with powdered sodium hydroxide (211 mg, 5.27 mmol) and heated under reflux. Cooling and acidification to pH 6.5, followed the usual work up gave crude compound 611-MS-106, which was used in the next stage without purification.

Step 10

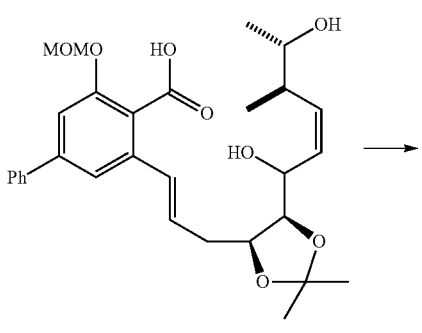

611-MS-106

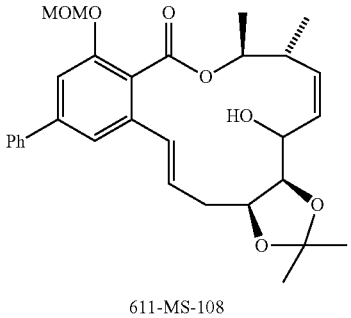

611-MS-108

A solution of crude compound 611-MS-106 (assumed to contain 0.176 mmol) in dichloromethane (20 mL) was added slowly to a heated solution (40° C.) of 2-chloro-1-methylpyridinium iodide (449 mg, 1.76 mmol) and tri-n-butylamine (0.42 mL, 1.76 mmol) in dichloromethane (60 mL). The usual work up and chromatographic purification gave compound 611-MS-108 (3 mg, 3% from compound 611-MS-104).

Step 11

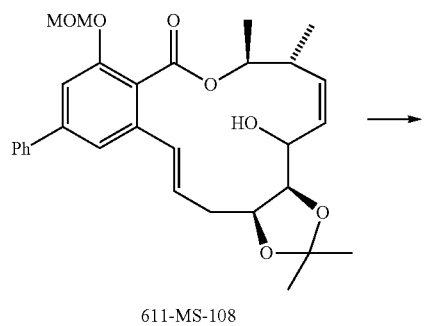

611-MS-108

A solution of compound 611-MS-108 (3 mg, 5.9 µmol) in dichloromethane (500 µL) was treated with pyridinium chlorochromate (20 mg, 88 µmol) in the presence of powdered 4 Å molecular sieves (20 mg). The reaction mixture was stirred vigorously for 4 hours at room temperature. Basification with excess triethylamine, followed by chromatographic purification gave compound 611-MS-118 (1.4 mg, 48%).

Step 12

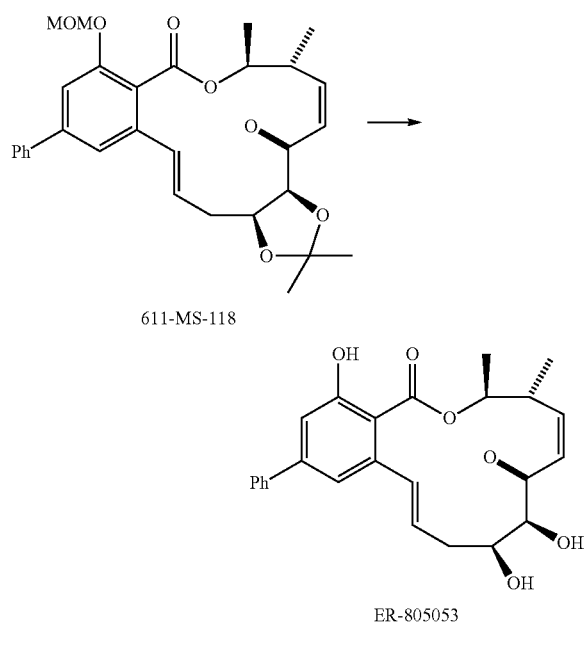

611-MS-118

ER-805053

A solution of compound 611-MS-118 (1.4 mg, 2.76 µmol) in a mixture of acetonitrile (400 µL) and dichloromethane (100 µL) was treated with 48% aqueous hydrofluoric acid (100 µL), and stirred at room temperature for 30 minutes. The usual work up followed by chromatographic purification gave compound ER-805053 (1.0 mg; 83%).

Preparation of C14-Aniline Analogs: ER805940, and ER806201:

Preparation of ER805940:

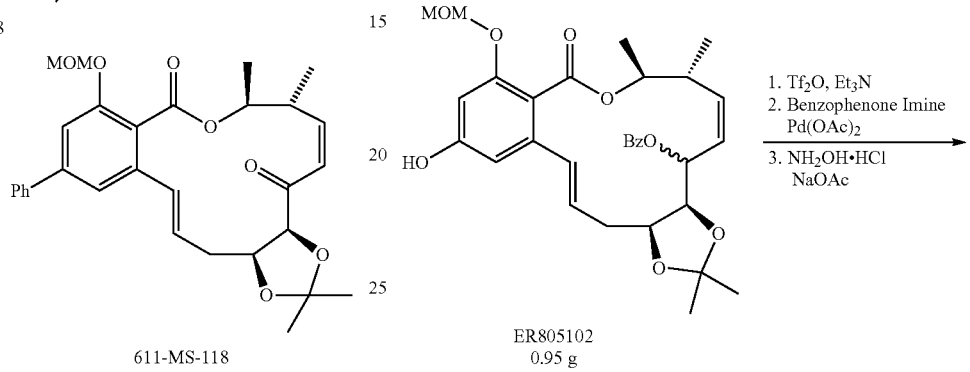

ER805102
0.95 g 629-ys-190
0.88 g

Tf$_2$O (0.42 ML, 2.5 mmole) was added to a solution of ER-805102 (0.95 g, 1.7 mmole) and Et$_3$N (0.58 ML, 4.2 mmole) in 20 ML of CH$_2$Cl$_2$ at 0° C. The mixture was stirred for 10 min before the addition of aq. NaHCO$_3$. Aq. layer was extracted twice with CH$_2$Cl$_2$. The organics were concentrated and passed through a short plug of silica gel (20% EtOAc/Hex).

The triflate thus obtained was added Pd(OAc)$_2$ (19 mg, 0.08 mmole), BINAP (64 mg, 0.10 mmole) and Cs$_2$CO$_3$ (0.66 g, 2.0 mmole) in dry box. Benzophenone imine (0.32 ML, 1.9 mmole) and 30 ML of toluene was added under nitrogen before the mixture was heated at 90° C. for 14 h. Then it was diluted with EtOAc and brine. Organic layer was dried (Na$_2$SO$_4$) and concentrated.

Crude material was dissovled in 8 ML of MeOH and 5 ML of THF before the addition of NaOAc (0.56 g, 6.8 mmole) and NH$_2$OH.HCl (0.24 g, 3.4 mmole) at RT. After 50 min, EtOAc and brine was added. Organics were dried (Na$_2$SO$_4$), concentrated and purified with silica gel (30 EtOAc/Hex) to produce crystalline 629-ys-190 (0.88 g, 1.6 mmole).

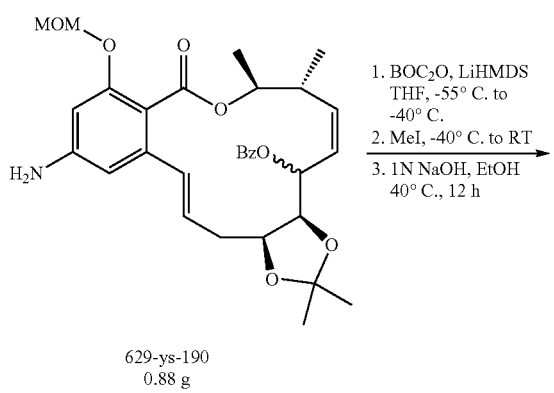

629-ys-190
0.88 g

1. BOC₂O, LiHMDS THF, −55° C. to −40° C.
2. MeI, −40° C. to RT
3. 1N NaOH, EtOH 40° C., 12 h the solution was added 72 ML of 1N NaOH and 48 ML of EtOH. After it was heated at 45° C. for 12 h, the mixture was diluted with 100 ML of water and 150 ML of CH₂Cl₂. Aq. layer was extracted twice with 50 ML of CH₂Cl₂. Organics were concentrated and purified by silica gel chromatography (30% EtOAc/Hex) to furnish colorless gel 629-ys-192 (0.58 g, 1.0 mmole).

The suspension of 629-ys-192 (0.40 g, 0.71 mmole), PCC (0.46 g, 2.1 mmole), 4 Å molecular sieves (0.50 g), and celite (0.50 g) in 8 ML of CH₂Cl₂ was stirred at RT for 2.5 h before the addition of Et₃N (0.29 ML, 2.1 mmole). After 5 min, 30 ML of Et₂O was added and the mixture was filtered. The filtrate was concentrated and passed through a short silica gel plug (75% EtOAc/Hex) to provide colorless crystalline 629-ys-198 (0.35 g, 0.63 mmole).

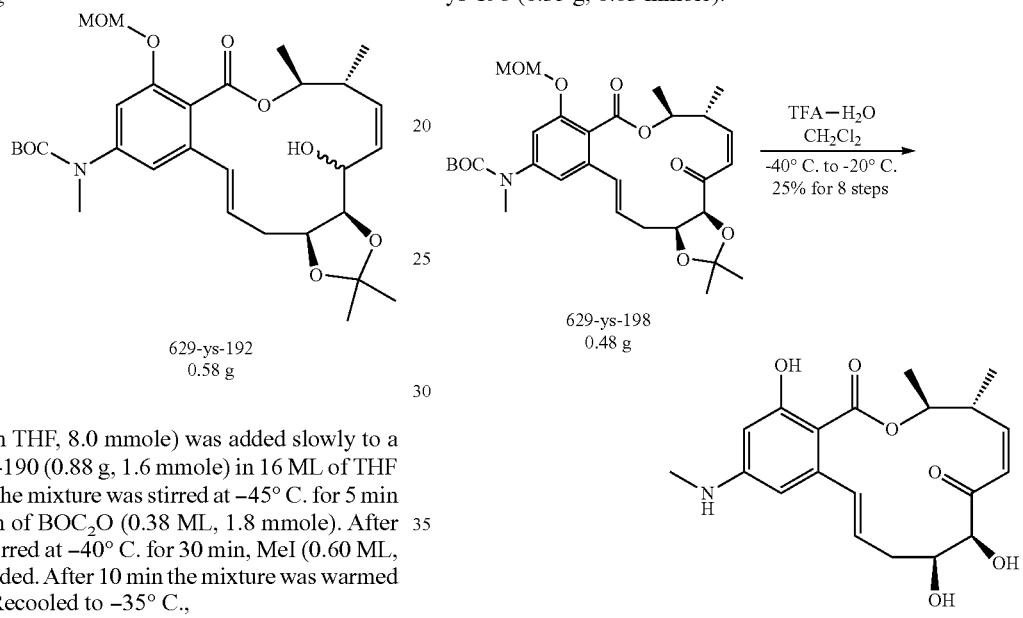

LiHMDS (1N in THF, 8.0 mmole) was added slowly to a solution of 629-ys-190 (0.88 g, 1.6 mmole) in 16 ML of THF at −55 to −50° C. The mixture was stirred at −45° C. for 5 min before the addition of BOC₂O (0.38 ML, 1.8 mmole). After the mixture was stirred at −40° C. for 30 min, MeI (0.60 ML, 9.6 mmole) was added. After 10 min the mixture was warmed up to RT for 2 h. Recooled to −35° C.,

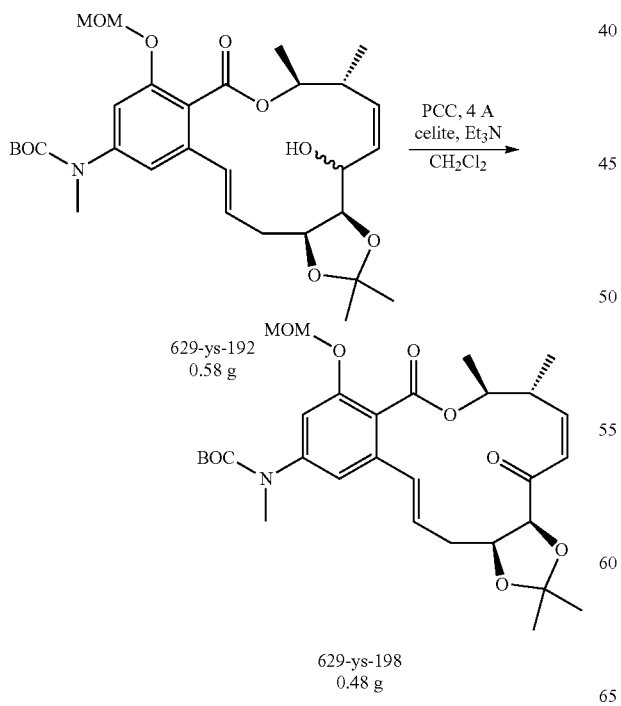

TFA (5% water, 6 ML) was added slowly to the solution of 629-ys-198 (0.35 g, 0.63 mmole) in CH₂Cl₂ at −35° C. The mixture was stirred at −20° C. for 1 h before the addition of sat. aq. NaHCO₃ (PH~8) and CH₂Cl₂. Aq. layer was extracted twice with CH₂Cl₂. The organics were dried (Na₂SO₄), concentrated and purified by silica gel chromatography (75% EtOAc/Hex) to afford ER-805940 (124 mg, 0.33 mmole) in 25% overall yield over 8 steps.

Synthesis of ER806201:
1) Synthesis of Triflate:

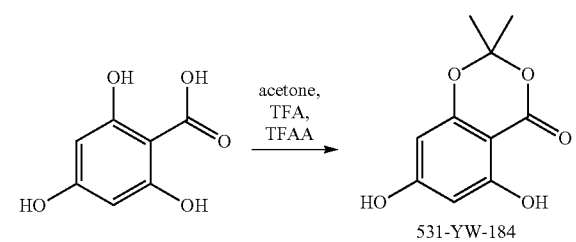

To a solution of trihydroxy-benzoic acid (120 g) in 350 mL of acetone, 500 mL of TFA (tri-fluoro acetic acid) was added at 40° C. under stirring. After 1 h at that temperature, 300 mL of TFAA (tri-fluoro acetic anhydride) was added. The mixture was heated for 3 days. The mixture was distilled under house vacuum at 50° C. to remove solvents. The crude product was then diluted with 4 L of CH₂Cl₂, washed with water, sat. NaHCO₃, dried and concentrated to give 85 g of semi pure solid. The solid was crystallized in EtOH (1 g/2 mL) to give 20 g of pure crystal. The mother liq. was then purified by silica gel with CH₂Cl₂ to 5% MeOH/CH₂Cl₂ to give 55 g of additional product, 531-YW-184.

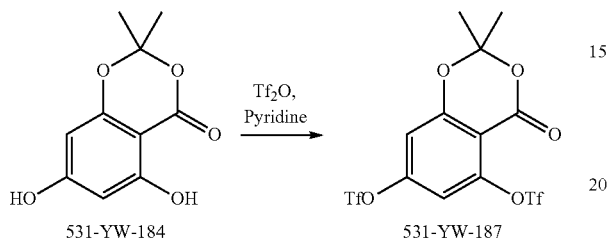

To a solution of 531-YW-184 (50 g, 238 mmol) in 156 mL of pyridine, Tf₂O (100 mL, 595 mmol, 2.5 eq.) was added at 0° C. in 3 h. Then it was warmed to rt and stirred for 2 h. The reaction mixture was diluted with water. The mixture was filtered. The solid on the filter was washed with water, dried under vac to give a solid, 531-YW-187 (100 g).

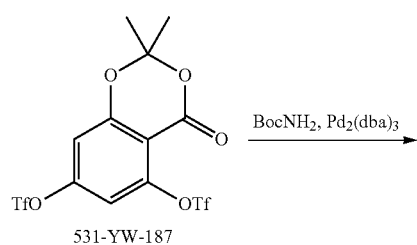

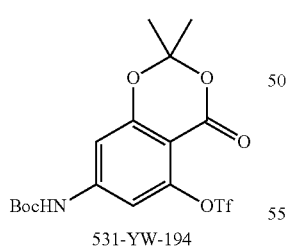

To a mixture of ditriflate, 531-YW-187 (45.35 g), BocNH₂ (17.22 g), Pd₂(dba)₃ (4.38 g) and Pt-Bu₃ (4.38 g) in 150 mL of toluene, tri-ethylamine (26.92 mL) was added. The reaction was heated under inert atmosphere at 80° C. for 4 h. The crude reaction mixture was cooled and filtered through a pad of celite. The filtrates were concentrated and purified on silica gel with Hex/EtOAc, 9:1, 4:1 to give 28.3 g of desired product, 531-YW-194.

2) Synthesis of Olefin:

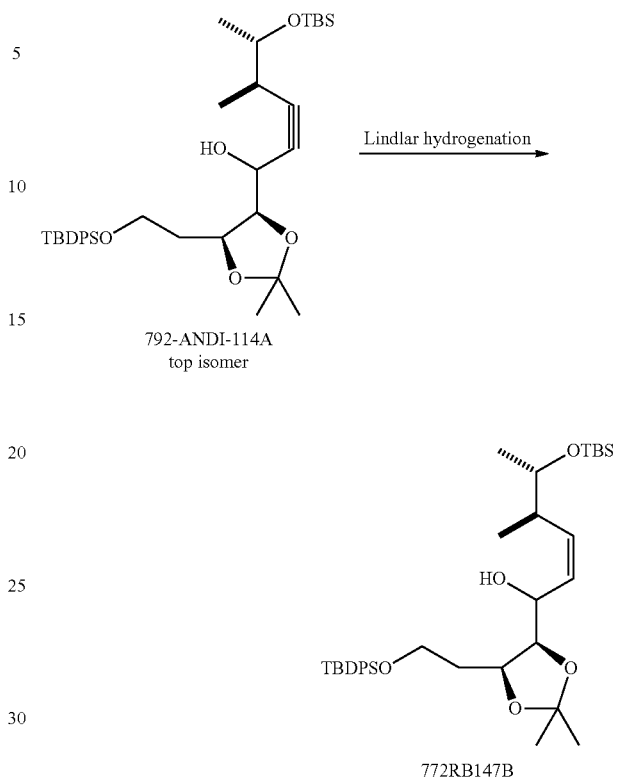

792-ANDI-114A was prepared analogously to the preparation of 554-RB-240 with appropriate protecting groups, i.e. the MPM ether was replaced with TBDPS ether.

To a solution of 792-ANDI-114A (165.9 g, 265 mmol) in 2.65 L of Hexanes, quinoline (2.65 mL) and Lindlar catalyst (28.2 g, 13.3 mmol, 0.05 eq.) were added. The mixture was degassed repeatedly under vacuum and recharged with nitrogen (3×) and hydrogen (3×). then it was set the intake of hydrogen on hydrogenator to 0.114 mol. The reaction was monitored by MS/1H NMR. After overnight, the suspension was filtered and recharged with catalyst and hydrogen. After 3 days, the reaction was filtered through celite. The filtrates were concentrated and purified on silica gel to give 104 g, 772RB147B as an oil.

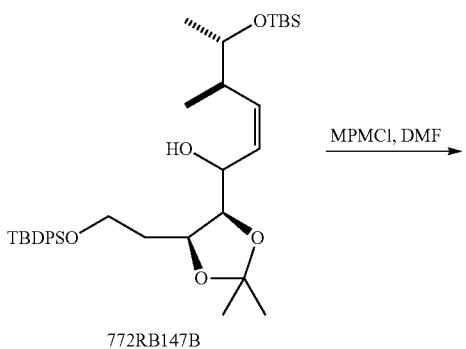

-continued

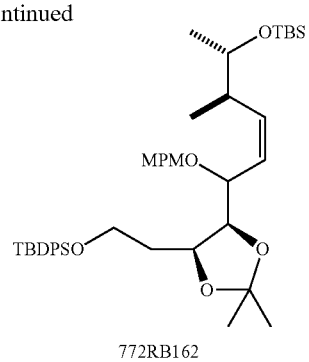
772RB162

To a solution of 772RB147B (67.4 g, 107 mmol), MPMCl (21.9 mL, 161 mmol, 1.5 eq.) and a 1M solution of NaHMDS in THF (140 mL, 140 mmol, 1.3 eq.) was added slowly with syringe pump in 2 h at 0° C. After stirred for 1.5 h at 0° C., it was quenched with sat. NH₄Cl at 0° C. and warmed to rt. The mixture was extracted with EtOAc (3×). The extracts were washed with water, brine, dried and concentrated. The crude product was purified on silica gel to give 772RB162 quantitatively.

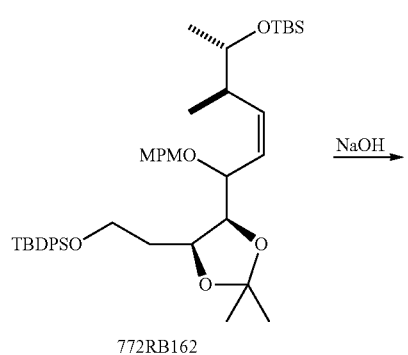
772RB162

772RB162 (119.6 g, 160 mmol) was dissolved in a mixture of 10% NaOH in methanol (3.2 L, v/v) and 3.5 mL of water. The reaction was heated at 45° C. for 48 h. After cooled, it was diluted with 9 L of CH₂Cl₂, washed with water (2×), Sat NH₄Cl, brine, dried and concentrated. The crude product was purified on silica gel with 10%-25-35% of EtOAc/Hexanes to give the 772RB164 (78 g, 96% yield).

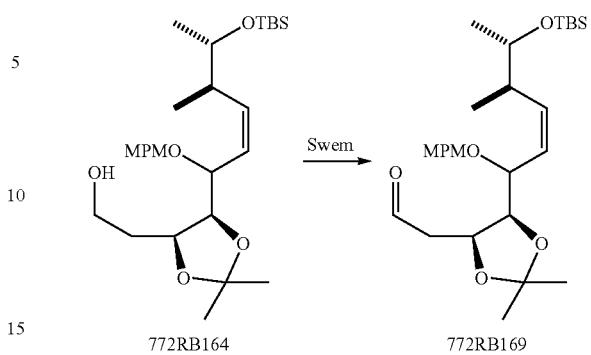
772RB164      772RB169

To a solution of (COCl)₂ (25 mL, 295 mmol, 2 eq.) in CH₂Cl₂ (870 mL), DMSO (41.85 mL, 590 mmol, 4 eq.) was slowly added at −78° C. After 30 min stirred at that temperature, a solution of 772RB164 (75 g, 147.4 mmol) in CH₂Cl₂ (160 mL) was added in 45 min. After stirred at −78° C. for 45 min, Et₃N (82.2 mL, 590 mmol, 4 eq.) was added at that temperature. After stirred for 30 min, it was warmed to 0° C. for 1.5 h. The reaction was quenched with 750 mL of saturated NH₄Cl and extracted with EtOAc (3×). The extracts were dried and concentrated. The crude product was re-suspended with 2.5 L of 1:1 solution of EtOAc/Hexanes, washed with water (3×), brine, dried and concentrated. The crude product 772RB169 was used directly for next step.

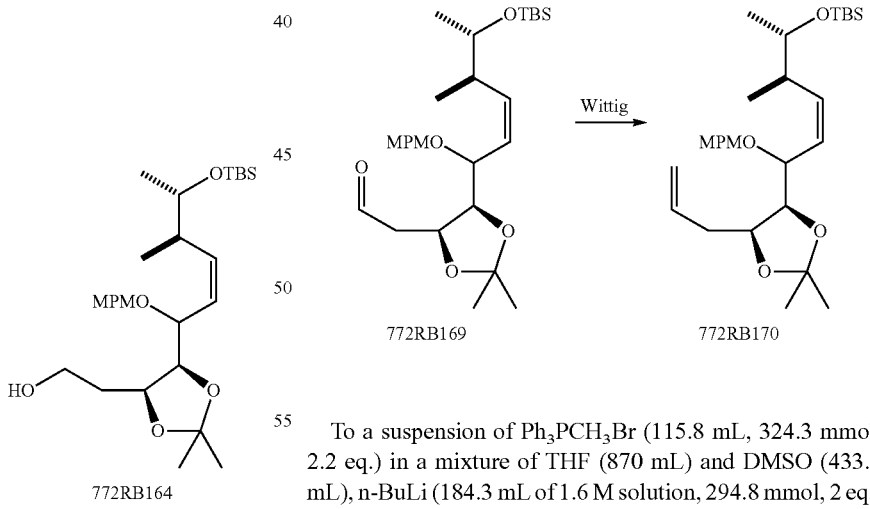
772RB169      772RB170

To a suspension of Ph₃PCH₃Br (115.8 mL, 324.3 mmol, 2.2 eq.) in a mixture of THF (870 mL) and DMSO (433.6 mL), n-BuLi (184.3 mL of 1.6 M solution, 294.8 mmol, 2 eq.) was added at 0° C. After stirred for 1 h, a solution of 772RB169 (74.7 g in 175 mL of THF, 147.4 mmol) was added at 0° C. After 30 min, it was warmed to rt. After 2 h, it was quenched with 1.1 L of Sat. NHCl₄ and extracted with EtOAc (3×). The extracts were washed with water, brine and dried and concentrated. The crude product was purified on silica gel with 5-10% EtOAc/Hexanes to give 66.5 g of 772RB170 as an oil (89% yield).

3) Coupling of Triflate and Olefin:

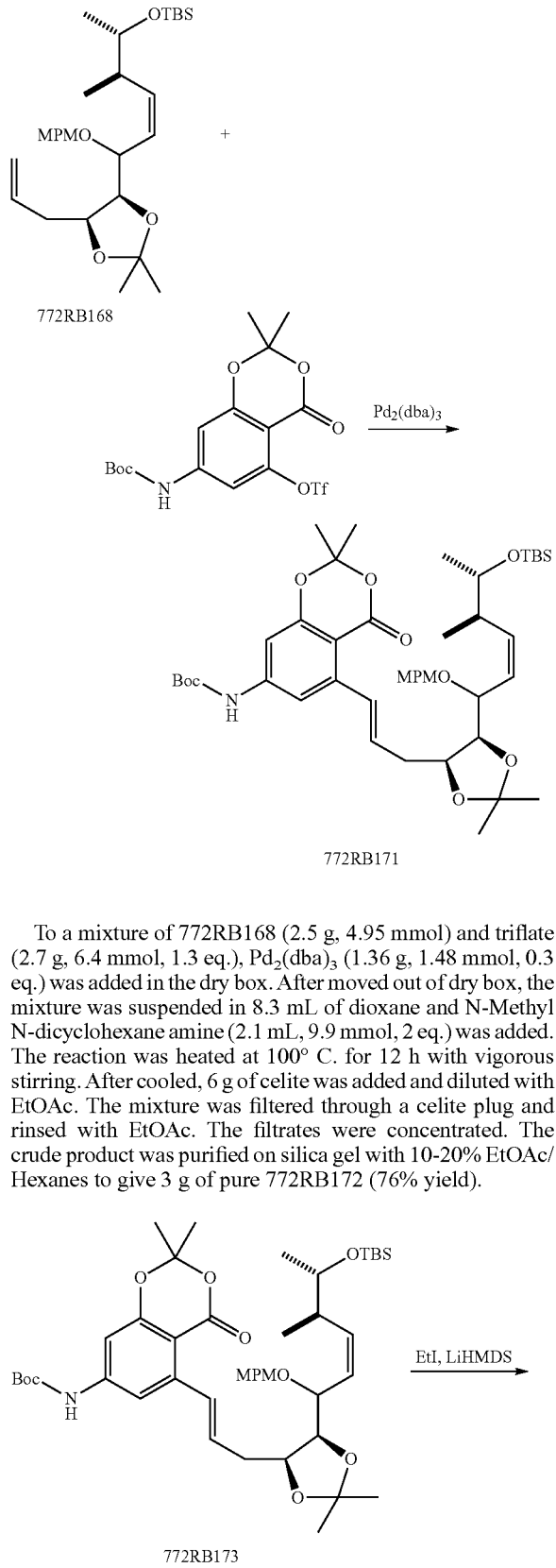

To a mixture of 772RB168 (2.5 g, 4.95 mmol) and triflate (2.7 g, 6.4 mmol, 1.3 eq.), Pd$_2$(dba)$_3$ (1.36 g, 1.48 mmol, 0.3 eq.) was added in the dry box. After moved out of dry box, the mixture was suspended in 8.3 mL of dioxane and N-Methyl N-dicyclohexane amine (2.1 mL, 9.9 mmol, 2 eq.) was added. The reaction was heated at 100° C. for 12 h with vigorous stirring. After cooled, 6 g of celite was added and diluted with EtOAc. The mixture was filtered through a celite plug and rinsed with EtOAc. The filtrates were concentrated. The crude product was purified on silica gel with 10-20% EtOAc/Hexanes to give 3 g of pure 772RB172 (76% yield).

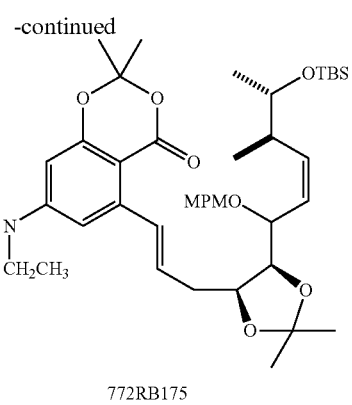

To a solution of 772RB173 (46.3 g, 58.16 mmol) in DMPU (291 mL), LiHMDS (116 mL of 1M solution in THF, 116.3 mmol, 2 eq.) was added at 0° C. After stirred for 40 min at that temperature, EtI (27.9 mL, 349 mmol, 6 eq.) was added. After 5 min, it was warmed to rt. After stirred 3 h, it was quenched with 1 L of Sat. NHCl4 at 0° C. The mixture was extracted with MTBE/Hexanes (1:1). The extracts were washed with brine, dried and concentrated. The crude product was purified on silica gel with 15-20% EtOAc/Hexanes to give 40 g of desired product, 77RB175 (84% yield).

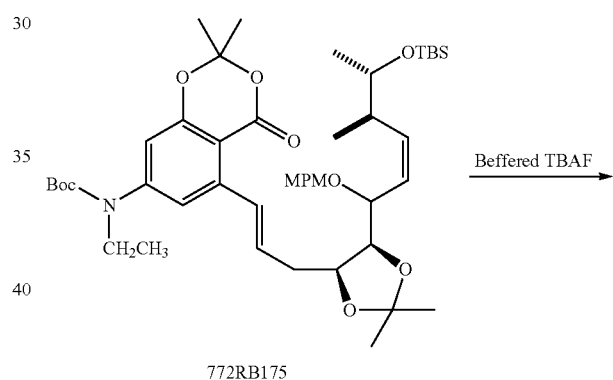

To a solution of 772RB175 (48 g, 58.2 mmol) in 230 mL, a solution of TBAF (407 mL of 1M solution, 407 mmol, 7 eq.) and imidazole.HCl (21.3 g, 203.9 mmol, 3.5 eq.) was added. The reaction was heated at 60° C. for 72 h. After cooled to rt, it was quenched with sat. NH$_4$Cl and was extracted with ether (3×). The organic layers were washed with water, brine, dried and concentrated. The crude product was purified on silica gel with 20-30% EtOAc/Hexanes to give 31.4 g (76% yield).

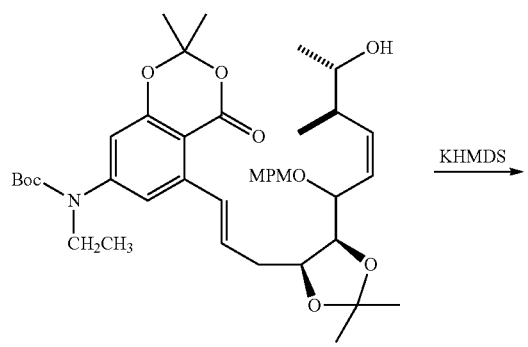

772RB177

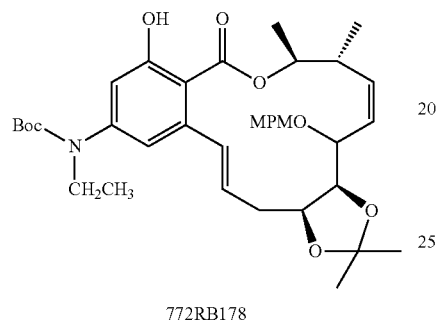

772RB178

To a solution of 772RB177 (20.3 g, 28.6 g) in 3 L of THF, 0.5M KHMDS solution (60 mL, 30 mmol, 1.05 eq.) was added slowly by syringe pump in 120 min. After stirred for 5 min, it was quenched with 1.5 L of sat. NH₄Cl. The mixture was extracted with ether (3×). The extracts were washed with brine, dried and concentrated. The crude product was purified on silica gel with 10-20%-50% EtOAc/Hexanes to give 14.2 g of desired product (76% yield).

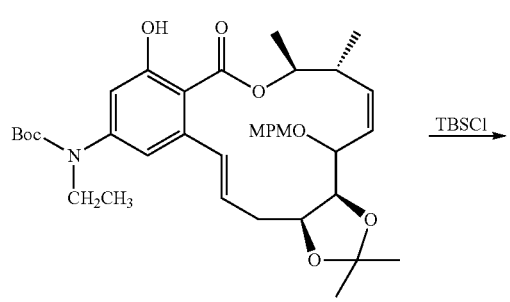

772RB178, 179

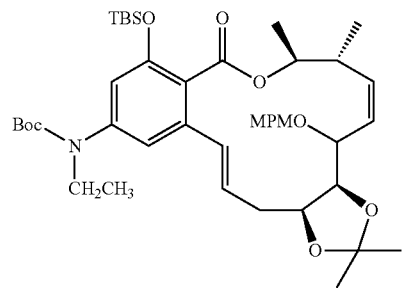

772RB181

To a solution of 772RB178, 179 (19 g, 29.15 mmol) in DMF (194 mL), imidazole (4 g, 58.3 mmol, 2 eq.) and TBSCl (5.27 g, 35 mmol, 1.2 eq.) were added. After stirred overnight, it was quenched with a saturated solution of NaHCO₃ and water. The mixture was extracted with EtOAc. The organic layer was washed with, water, brine, dried and concentrated. The crude product was purified on silica gel column to give 22 g (99% yield) of desired product.

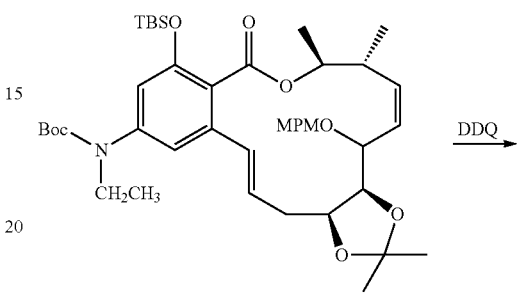

772RB181

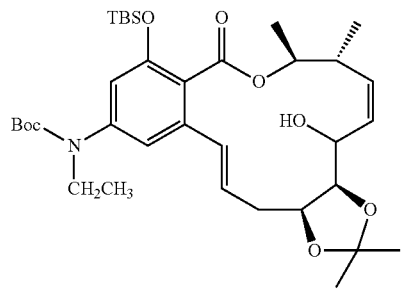

772RB182

To a solution of 772RB181 (22 g, 28.7 mmol) in a mixture of CH₂Cl₂ (230 mL) and H₂O (57.4 mL), DDQ (9.78 g, 43 mmol, 1.5 eq.) was added at 0° C. After stirred for 2 h, it was quenched with 1 L of a 1:1 mixture of aq. saturated NaHCO₃ and 10% aq. Na₂S₂O₃. The mixture was extracted with 3×1 L of ether. The extracts were washed with brine, dried and concentrated. The crude product was purified on silica gel to give 18.1 g of pure product.

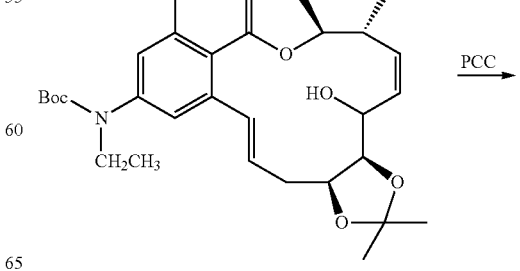

772RB182

449

-continued

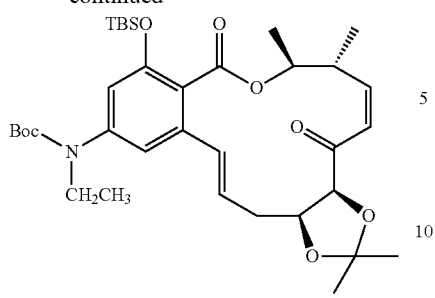

772RB183

To a solution of 772RB182 (18 g, 27.9 mmol) in 279 mL of CH$_2$Cl$_2$, dried 4 Å molecular sieves (18 g) and PCC (18 g) were added. After stirred for 90 min, it was quenched with Et$_3$N (19.45 mL). The reaction mixture was filtered through a plug of celite, the plug was rinsed with 75% EtOAc in hexanes (900 mL). The filtrates were concentrated. The crude product was purified on silica gel column with 10-15-20% EtOAc/Hexanes to give 14.6 g (81%) pure product.

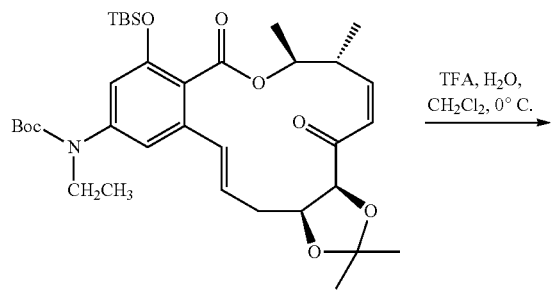

772RB183

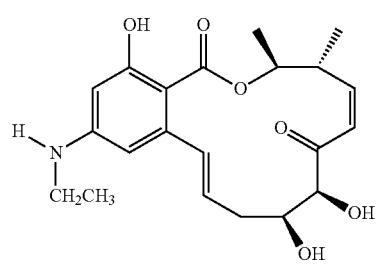

772RB186

In a 2 L flask, 772RB183 (8.5 g, 13.2 mmol) was dissolved in CH$_2$Cl$_2$ (82.5 mL) and the mixture was cooled to 0° C. Then a solution of 5% H$_2$O/TFA (4.1/78.1 mL) was added slowly (~30 min) and the mixture was stirred at 0° C. for 14.5 hrs. The reaction was monitored by TLC. Reaction mixture was diluted with CH$_2$Cl$_2$ at 0° C. Reaction was quenched with a solution of NaHCO$_3$ in water (~1.2 eq compare to TFA). Reaction was cooled to r.t. Extract 3× with CH$_2$Cl$_2$, dried with Na$_2$SO$_4$, Filtered, and concentrated. Chromatography on Si-Gel, 50-60-75% EtOAc/hexane gave ER-806201: 4.8 g, 93% yield.

450

Preparation of C5-F-Enone Series:
Preparation of ER803030:

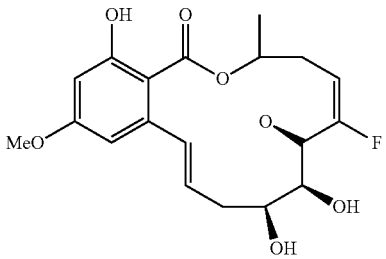

496-SG-026B

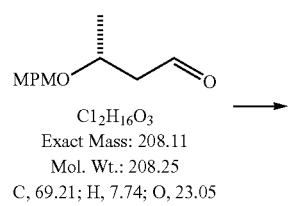

C$_{12}$H$_{16}$O$_3$
Exact Mass: 208.11
Mol. Wt.: 208.25
C, 69.21; H, 7.74; O, 23.05

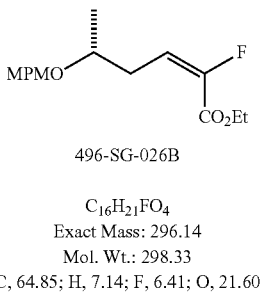

496-SG-026B

C$_{16}$H$_{21}$FO$_4$
Exact Mass: 296.14
Mol. Wt.: 298.33
C, 64.85; H, 7.14; F, 6.41; O, 21.60

To a magnetically stirred solution of 2-fluoro-2-phosphonoacetic acid triethylester (8 g, 33.3 mmol) in DMF (2.7 mL) at 0° C. was introduced sodium hydride (0.8 g, 33.3 mmol). After 1 hour of stirring at 0° C., a solution of aldehyde (3.47 g, 16.65 mmol) in THF (14 mL) was added. After 2.5 hours of stirring at 0° C., a saturated solution of ammonium chloride was added. The reaction mixture was diluted with water and extracted with ethyl acetate. The crude product was purified by flash chromatography eluting with n-hexane/ethyl acetate: (20/1) to afford 496-SG-026B (3.58 g, 72% yield).

496-SG-027B

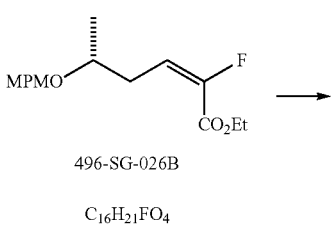

496-SG-026B

C$_{16}$H$_{21}$FO$_4$
Exact Mass: 296.14
Mol. Wt.: 296.33
C, 64.85; H, 7.14; F, 6.41; O, 21.60

496-SG-027B

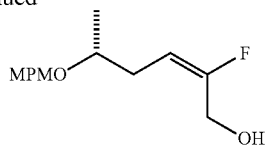

C₁₄H₁₉FO₃
Exact Mass: 254.13
Mol. Wt.: 254.30
C, 68.12; H, 7.53; F, 7.47; O, 18.87

To a magnetically stirred solution of 496-SG-026B (3.58 g, 12.1 mmol) in dichloromethane (136 mL) at 0° C. was introduced DIBAL-H (1M solution in dichloromethane, 30.2 mL, 30.2 mmol). After 0.5 hour of stirring at 0° C., the reaction mixture was warmed-up to room temperature and stirred an additional 10 minutes. The reaction was cooled back to 0° C. and a saturated solution of ammonium chloride was added (5.4 mL). After 15 minutes of stirring, the reaction mixture was diluted with ether and stirred 30 minutes at room temperature. The resulting suspension was filtered and the solid washed with ether. The solvent was removed by evaporation. The crude product was purified by flash chromatography eluting with hexanes/ethyl acetate: (3/1) to afford 496-SG-027B (2.68 g, 87% yield).

496-SG-028B

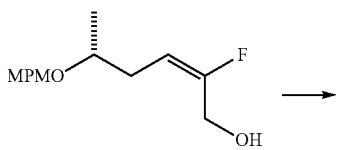

496-SG-027B

C₁₄H₁₉FO₃
Exact Mass: 254.13
Mol. Wt.: 254.30
C, 66.12; H, 7.53; F, 7.47; O, 18.87

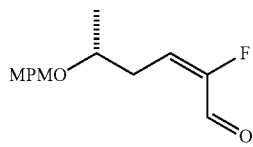

496-SG-028B

C₁₄H₁₇FO₃
Exact Mass: 252.12
Mol. Wt.: 252.28
C, 66.65; H, 6.79; F, 7.53; O, 19.03

To a magnetically stirred solution of 496-SG-027B (2.68 g, 10.55 mmol) in dichloromethane (53.2 mL) cooled to 0° C. (Ice/water, external thermometer) was introduced DMSO (2.6 mL, 36.94 mmol) followed by P₂O₅ (5.24 g, 36.94 mmol). After one hours of stirring at room temperature the reaction was cooled down to 0° C., and triethylamine (7.4 mL, 52.72 mmol) was added. After 20 minutes of stirring at room temperature the reaction mixture was diluted with water and extracted with dichloromethane. The solvent was removed by evaporation. The crude product was purified by flash chromatography eluting with hexanes/ethyl acetate: (3/1) to afford 496-SG-028B (2.66 g).

496-SG-022B

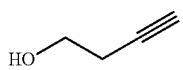 → 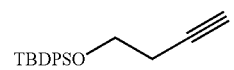

496-SG-022B

C₄H₆O
Exact Mass: 70.04
Mol. Wt.: 70.09
C, 68.54; H, 8.63; O, 22.83

C₂₀H₂₄OSi
Exact Mass: 308.16
Mol. Wt.: 308.49
C, 77.87; H, 7.84; O, 5.19; Si, 9.10

To a magnetically stirred solution of 3-butyn-1-ol (3.0 g, 42.8 mmol) and imidazole (14.6 g, 214 mmol) in dichloromethane (113 mL) at room temperature was introduced tert-butyldiphenylsilyl chloride (11.7 mL). After 18 hours of stirring at room temperature the reaction was diluted with water and extracted with ether. The solvent was removed by evaporation. The crude product was purified by flash chromatography eluting with hexanes/ethyl acetate: (2/1) to afford 496-SG-022B (13.7 g).

496-SG-029B

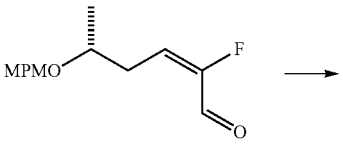

496-SG-028B

C₁₄H₁₇FO₃
Exact Mass: 252.12
Mol. Wt.: 252.28
C, 66.65; H, 6.79; F, 7.53; O, 19.03

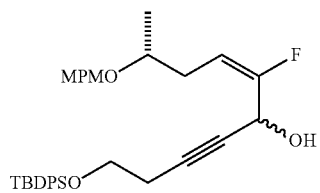

496-SG-29B

C₃₄H₄₁FO₄Si
Exact Mass: 560.28
Mol. Wt.: 560.77
C, 72.82; H, 7.37; F, 3.39; O, 11.41; Si, 5.01

To a magnetically stirred solution of 496-SG-022B (6.5 g, 21.8 mmol) in THF (208 mL) at −78° C. was introduced n-BuLi (2.5 M in hexane, 8.4 mL, 21.1 mmol). After 1 hours of stirring −78° C., a solution of 496-SG-028B (2.66 g, 10.55 mmol) in THF (128 mL) was added at −78° C. After 15 minutes of stirring at −78° C., the reaction was quenched by addition of a saturated solution of ammonium chloride. The reaction mixture was diluted with water and extracted with ethyl acetate. The solvent was removed by evaporation. The crude product was purified by flash chromatography eluting with hexanes/ethyl acetate: (5/1) to afford 496-SG-029B (4.27 g, 70%).

496-SG-30A

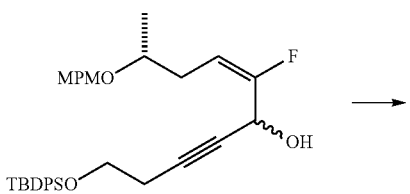

496-SG-29B
C$_{34}$H$_{41}$FO$_4$Si
Exact Mass: 560.28
Mol. Wt.: 560.77
C, 72.82; H, 7.37; F, 3.39; O, 11.41; Si, 5.01

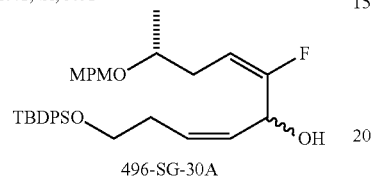

496-SG-30A
C$_{34}$H$_{43}$FO$_4$Si
Exact Mass: 562.29
Mol. Wt.: 562.79
C, 72.56; H, 7.70; F, 3.38; O, 11.37; Si, 4.99

A solution of 496-SG-29B (4.27 g, 7.61 mmol) and quinoline (0.033 mL) in hexanes with a catalytic amount of Lindlar catalyst was magnetically stirred for 1 h under hydrogen atmosphere. The reaction mixture was filtered through celite, and the solvent removed by evaporation to afford 496-SG-30A (4.28 g). The crude was used in the next step without purification.

496-SG-031B

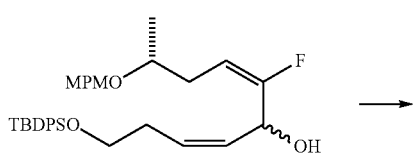

496-SG-030A
C$_{34}$H$_{43}$FO$_4$Si
Exact Mass: 562.29
Mol. Wt.: 562.79
C, 72.56; H, 7.70; F, 3.38; O, 11.37; Si, 4.99

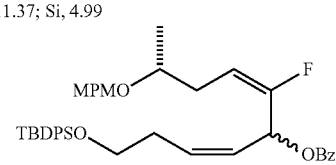

496-SG-031B
C$_{41}$H$_{47}$FO$_5$Si
Exact Mass: 666.32
Mol. Wt.: 666.89
C, 73.84; H, 7.10; F, 2.85; O, 12.00; Si, 4.21

To a magnetically stirred solution of 496-SG-030A (4.28 g 7.61 mmol), triethylamine (2.7 mL, 19.3 mmol) and a catalytic amount of DMAP in dichloromethane (267 mL) at room temperature, was introduced benzoyl chloride (1.8 mL, 15.22 mmol). After 18 hours of stirring at room temperature the reaction mixture was diluted with a 0.1 M solution of sodium hydroxide and extracted with ether. The solvent was removed by evaporation. The crude product was purified by flash chromatography eluting with hexanes/ethyl acetate: (9/1) to afford 496-SG-031B (5.0 g, 98%).

496-SG-042B

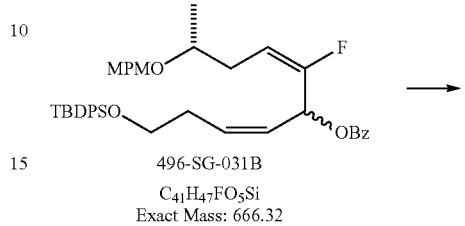

496-SG-031B
C$_{41}$H$_{47}$FO$_5$Si
Exact Mass: 666.32
Mol. Wt.: 666.89
C, 73.84; H, 7.10; F, 2.85; O, 12.00; Si, 4.21

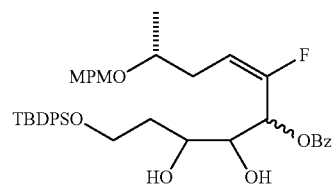

496-SG-042B
C$_{41}$H$_{49}$FO$_7$Si
Exact Mass: 700.32
Mol. Wt.: 700.91
C, 70.26; H, 7.05; F, 2.71; O, 15.98; Si, 4.01

To a magnetically stirred solution of 496-SG-031B (3.79 g, 5.68 mmol) in acetone (57 mL) at room temperature, was introduced NMO (1.33 g, 11.36 mmol) and water (2.9 mL). The reaction mixture was cooled down to 0° C., and a solution (0.1 M in toluene) osmium tetraoxide was added. After 18 hours of stirring at room temperature the reaction was quenched with sodium thiosulfate and stirred at room temperature for 20 minutes. The reaction mixture was then diluted with water and extracted with ethyl acetate. The solvent was removed by evaporation. The crude product was purified by flash chromatography eluting with hexanes/ethyl acetate: (3/1) to afford 496-SG-042B (1.5 g, 39%).

496-SG-043B

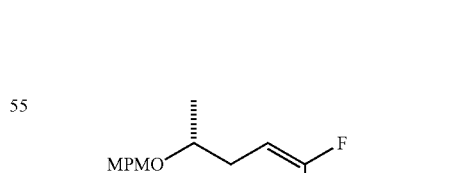

496-SG-042B
C$_{41}$H$_{49}$FO$_7$Si
Exact Mass: 700.32
Mol. Wt.: 700.91
C, 70.26; H, 7.05; F, 2.71; O, 15.98; Si, 4.01

-continued

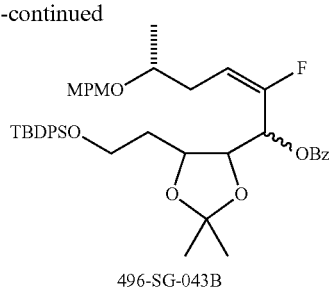

496-SG-043B
C$_{44}$H$_{53}$FO$_7$Si
Exact Mass: 740.35
Mol. Wt.: 740.97
C, 71.32; H, 7.21; F, 2.58; O, 15.11; Si, 3.79

To a magnetically stirred solution of 496-SG-042B (2.16 g, 3.08 mmol) and 2,2-dimethoxypropane (1.93 mL, 15.4 mmol) in a 2/1 mixture acetone/dichloromethane (32 mL) at room temperature, was introduced camphosufonic acid (0.8 g, 3.4 mmol). After 2 hours of stirring at room temperature the reaction was quenched with sodium bicarbonate and the reaction mixture was then diluted with water and extracted with ethyl acetate. The solvent was removed by evaporation. The crude product was purified by flash chromatography eluting with hexanes/ethyl acetate: (5/1) to afford 496-SG-043B (2.13 g, 93%).

496SG-45A

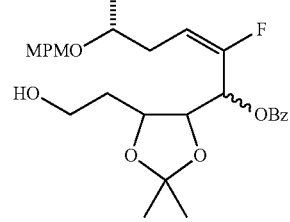

496-SG-043B
C$_{44}$H$_{53}$FO$_7$Si
Exact Mass: 740.35
Mol. Wt.: 740.97
C, 71.32; H, 7.21; F, 2.56; O, 15.11; Si, 3.79

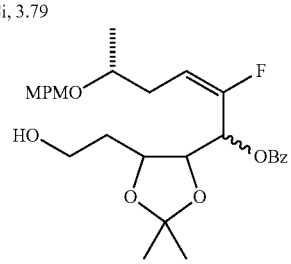

496-SG-045A
C$_{28}$H$_{35}$FO$_7$
Exact Mass: 502.24
Mol. Wt.: 502.57
C, 66.92; H, 7.02; F, 3.78; O, 22.28

To a magnetically stirred solution of 496-SG-043B (2.14 g, 2.89 mmol) in THF (52 mL) at 0° C., was introduced a 1 M solution of TBAF in THF buffered with 0.5 equivalent of imidazole hydrochloride (7.2 mL, 7.2 mmol). After 1 hour of stirring at room temperature the reaction was diluted with water and extracted with ether. The solvent was removed by evaporation to afford 496SG-45A (1.39 g). The crude product was used in the next step without purification.

496-SG-046B

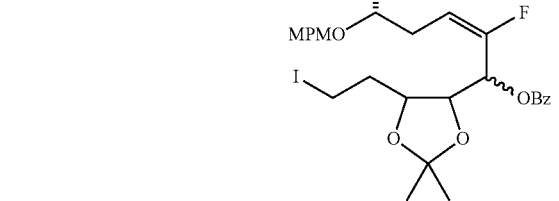

496-SG-045A
C$_{28}$H$_{35}$FO$_7$
Exact Mass: 502.24
Mol. Wt.: 502.57
C, 66.92; H, 7.02; F, 3.78; O, 22.28

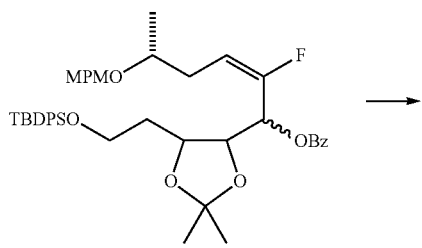

496-SG-046B
C$_{28}$H$_{34}$FIO$_6$
Exact Mass: 612.14
Mol. Wt.: 612.47
C, 54.91; H, 5.60; F, 3.10; I, 20.72; O, 15.67

Using a procedure analogous to that described for the synthesis of 343-YW-281, 496-SG-045A (1.4 g, 2.79 mmol) was reacted with triphenylphosphine (1.24 g, 4.74 mmol), DEAD (0.465 mL, 2.93 mmol) and methyl iodide (0.225 mL, 3.63 mmol) in toluene (46.5 mL). The crude product was purified by flash chromatography eluting with hexanes/ethyl acetate (5/1 and then 3/1) to afford 496-SG-046B (1.46 g, 85% yield).

496-SG-048B

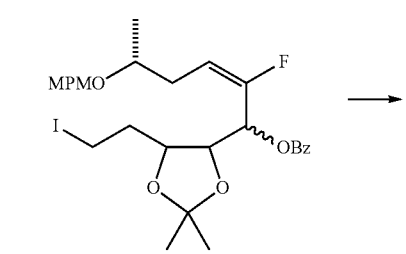

496-SG-046B
C$_{28}$H$_{34}$FIO$_6$
Exact Mass: 612.14
Mol. Wt.: 612.47
C, 54.91; H, 5.60; F, 3.10; I, 20.72; O, 15.67

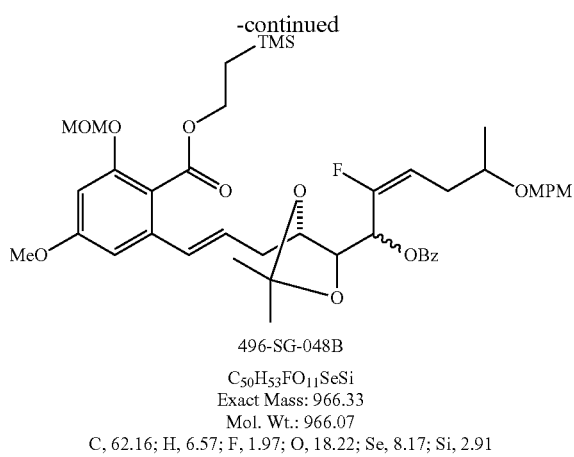

496-SG-048B

C$_{50}$H$_{53}$FO$_{11}$SeSi
Exact Mass: 966.33
Mol. Wt.: 966.07
C, 62.16; H, 6.57; F, 1.97; O, 18.22; Se, 8.17; Si, 2.91

Using a procedure analogous to that described for the synthesis of ER-803027 (stage 447-JCH-273B), 496-SG-046B (1.46 g, 2.38 mmol) was reacted with intermediate 509-HD-213 (178 g, 3.00 mmol) and LiHMDS (1M solution in THF, 3.6 mL, 3.6 mmol) in a 10/1 THF/HMPA mixture (17.3 mL) to afford after purification by flash chromatography eluting with hexanes/ethyl acetate: 496-SG-048A. Using a procedure analogous to that described for the synthesis of 447-JCH-275B, 496-SG-048A was reacted with MCPBA (0.75 g, 2.38 mmol) and triethylamine (2 mL, 14.3 mmol). The crude product was purified by flash chromatography eluting with hexanes/ethyl acetate (5/1 and then 3/1) to afford 496-SG-048B (1.38 g, 72% yield).

496-SG-052B

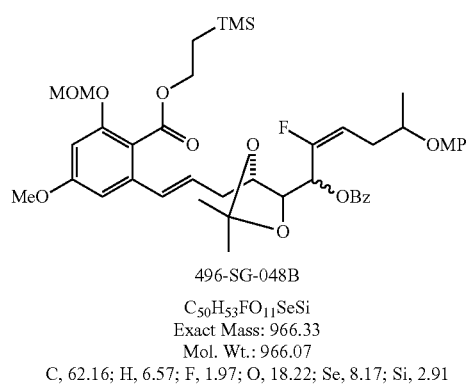

496-SG-048B

C$_{50}$H$_{53}$FO$_{11}$SeSi
Exact Mass: 966.33
Mol. Wt.: 966.07
C, 62.16; H, 6.57; F, 1.97; O, 18.22; Se, 8.17; Si, 2.91

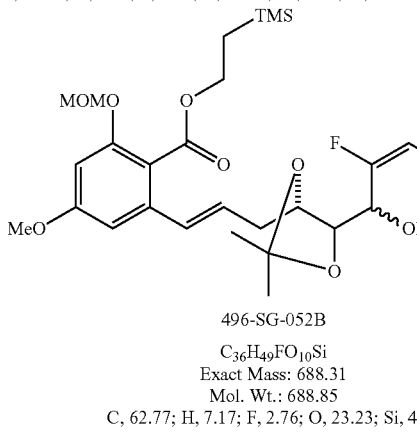

496-SG-052B

C$_{36}$H$_{49}$FO$_{10}$Si
Exact Mass: 688.31
Mol. Wt.: 688.85
C, 62.77; H, 7.17; F, 2.76; O, 23.23; Si, 4.08

496-SG-48B (1.28 g, 1.58 mmol) was reacted with DDQ (0.43 g, 1.89 mmol) in a 2/1-dichloromethane/water mixture (68 mL). The crude product was purified by flash chromatography eluting with hexanes/ethyl acetate (5/1 and then 3/1) to afford 496-SG-052B (0.88 g, 81% yield).

496-SG-053A

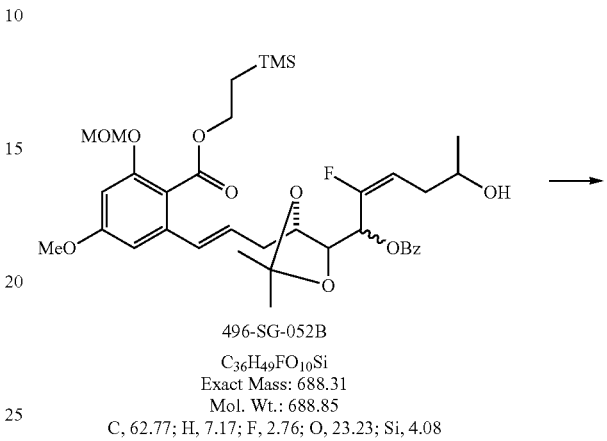

496-SG-052B

C$_{36}$H$_{49}$FO$_{10}$Si
Exact Mass: 688.31
Mol. Wt.: 688.85
C, 62.77; H, 7.17; F, 2.76; O, 23.23; Si, 4.08

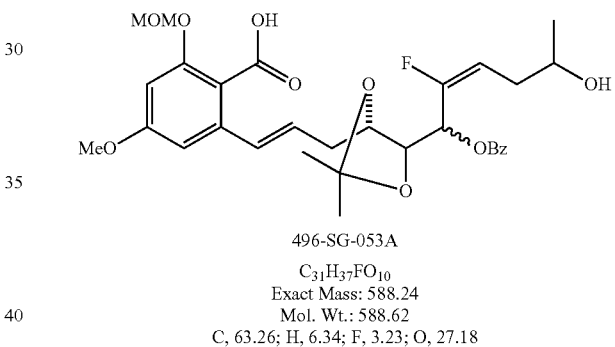

496-SG-053A

C$_{31}$H$_{37}$FO$_{10}$
Exact Mass: 588.24
Mol. Wt.: 588.62
C, 63.26; H, 6.34; F, 3.23; O, 27.18

Using a procedure analogous to that described for the synthesis of ER-803064 (stage 509-HD-116), 496-SG-052B (0.88 g, 1.28 mmol) was reacted with TBAF (1.0 g, 3.82 mmol) in THF (2.4 mL) to afford 496-SG-053A (0.74 g). The crude product was used in the next step without purification.

496-SG-058B

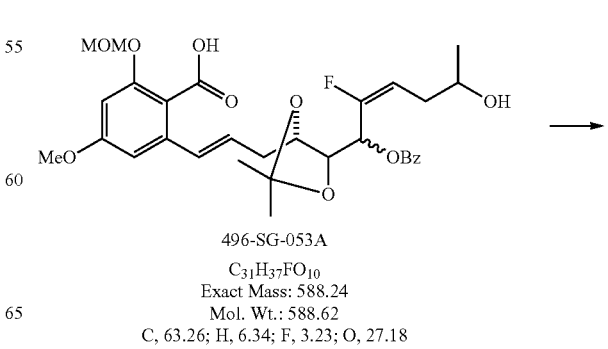

496-SG-053A

C$_{31}$H$_{37}$FO$_{10}$
Exact Mass: 588.24
Mol. Wt.: 588.62
C, 63.26; H, 6.34; F, 3.23; O, 27.18

-continued

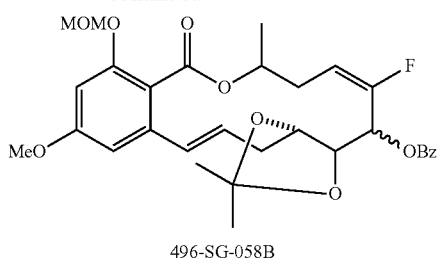

496-SG-058B

C₃₁H₃₅FO₉
Exact Mass: 570.23
Mol. Wt.: 570.60
C, 65.25; H, 6.18; F, 3.33; O, 25.24

496-SG-053A (0.20 g, 0.34 mmol) was reacted with triphenylphosphine (0.107 g, 0.408 mmol) and DEAD (0.064 mL, 0.408 mmol) in THF (90 mL). The crude product was purified on silica gel eluting with n-hexane/ethyl acetate: (2/1) to afford 496-SG-058B (0.12 g, 62% yield).

496-SG-057A, 496-SG-057B, 496-SG-057C

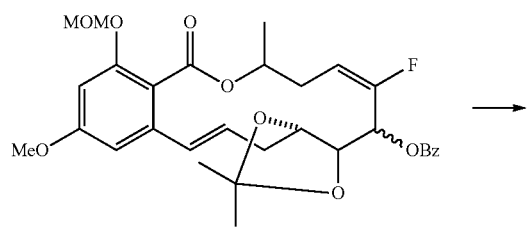

496-SG-058B

C₃₁H₃₅FO₉
Exact Mass: 570.23
Mol. Wt.: 570.60
C, 65.25; H, 6.18; F, 3.33; O, 25.24

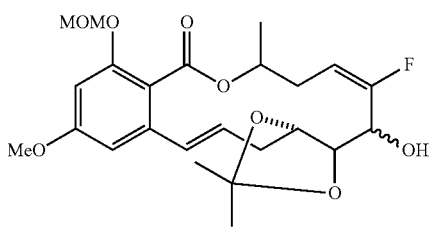

496-SG-057A, B, C

C₂₄H₃₁FO₈
Exact Mass: 466.20
Mol. Wt.: 466.50
C, 61.79; H, 6.70; F, 4.07; O, 27.44

Using a procedure analogous to that described for the synthesis of ER-803064, 496-SG-058B (0.048 g, 0.084 mmol) was reacted with sodium hydroxide (1M solution, 0.42 mL, 0.42 mmol) in a 2/1 mixture ethanol/THF (1 mL). The crude product was purified on silica gel (TLC) eluting with hexanes/ethyl acetate: (1/1) to afford 496-SG-057A (0.011 g), 496-SG-057B (0.013 g), 496-SG-057C (0.01 g).

496-SG-061A, 496-SG-061B, 496-SG-061C.

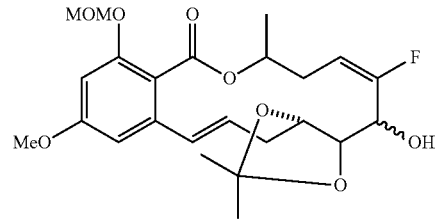

496-SG-057A, B, C

C₂₄H₃₁FO₈
Exact Mass: 466.20
Mol. Wt.: 466.50
C, 61.79; H, 6.70; F, 4.07; O, 27.44

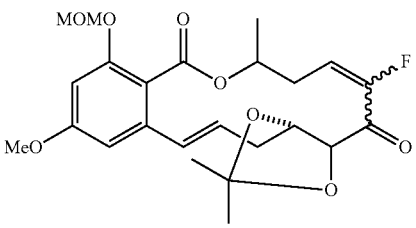

496-SG-061A, B, C

C₂₄H₂₉FO₈
Exact Mass: 464.18
Mol. Wt.: 464.48
C, 62.06; H, 6.29; F, 4.09; O, 27.56

496-SG-057A (0.01 g, 0.021 mmol), 496-SG-057B (0.012 g, 0.026 mmol), 496-SG-057C (0.0095 g, 0.02 mmol) were separately reacted with Dess-Martin reagent: (0.055 g, 0.129 mmol), (0.065 g, 0.154 mmol), (0.052 g, 0.122 mmol) and sodium carbonate (0.027 g), (0.032 g), (0.026 g) in dichloromethane (1.5 mL), (1.8 mL), (1.4 mL). After work-up, each reaction mixture was purified on silica gel (TLC) eluting with hexanes/ethyl acetate: (2/1) to afford respectively 496-SG-061A (0.009 g), 496-SG-061B (0.006 g), and 496-SG-061C (0.011 g).

496-SG-067A/ER-803029, 496-SG-067B/ER-803026, 496-SG-067C/ER-803030.

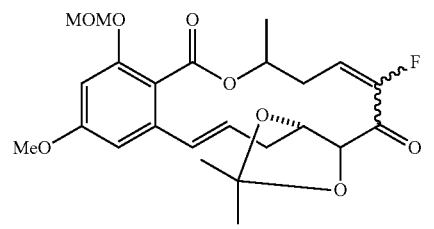

496-SG-061A, B, C

C₂₄H₂₉FO₈
Exact Mass: 464.18
Mol. Wt.: 464.48
C, 62.06; H, 6.29; F, 4.09; O, 27.56

-continued

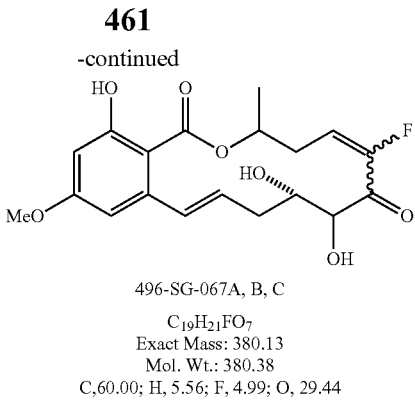

496-SG-067A, B, C

C$_{19}$H$_{21}$FO$_7$
Exact Mass: 380.13
Mol. Wt.: 380.38
C, 60.00; H, 5.56; F, 4.99; O, 29.44

Using a procedure analogous to that described for the synthesis of ER-803064 (final step), 496-SG-061A (0.007 g, 0.016 mmol), 496-SG-061B (0.004 g, 0.009 mmol), and 496-SG-061C (0.013 g, 0.027 mmol) were separately reacted with HF 48%: (0.37 mL), (0.21 mL), (0.63 mL) in acetonitrile/dichloromethane (4/1):(1.9 mL), (1.0 mL), (3 mL). After work-up, each reaction mixture was purified on silica gel (TLC) eluting with hexanes/ethyl acetate: (2/1) to afford respectively 496-SG-067A/ER-803029 (0.006 g), 496-SG-067B/ER-803026 (0.002 g), and 496-SG-067C/ER-803030 (0.006 g).

ER803916

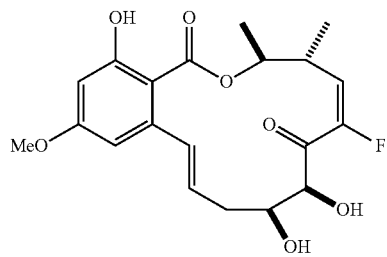

ER803916

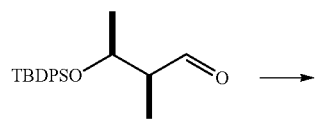

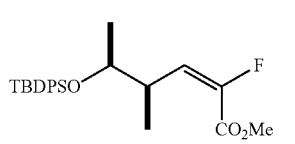

To a solution of (EtO)$_2$POCHFCO$_2$Et (5.6 mL) in a mixture of THF and DMF (100 and 25 mL), NaH (1.2 g) was added at 0° C. After stirred at 0° C. for 1 h, it was cooled to −40° C. with dry ice-acetone bath. A solution of aldehyde (3.5 g) in THF (20 mL) was added drop wise. Then, the reaction was warmed up to rt overnight. It was quenched with sat. NH$_4$Cl, and extracted with EtOAc (2×). The organic layers were washed with brine, dried and concentrated under vacuum. The crude product was purified on silica gel with 15:1, Hexanes:EtOAc to give 3.5 g of desired product, 531-yw-11, which gave satisfactory $^1$H NMR. The cis:trans ratio of the two isomers was 12:1 based on $^1$H NMR.

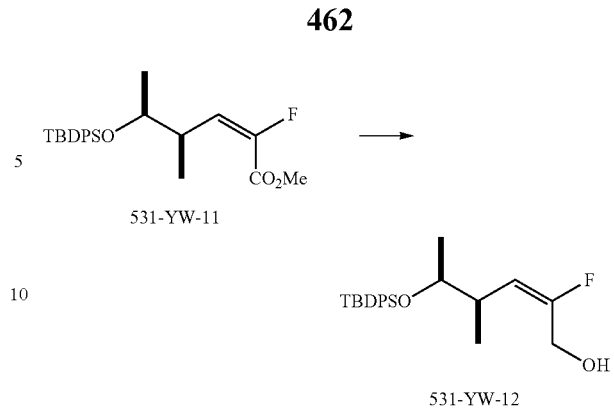

To a solution of ester, 531-W-11, (3.5 g) in ether (300 mL), a solution of DIBAL-H (15 mL) was added at 0° C. After 1 h at 0° C., it was quenched with 4 mL of MeOH, and 15 mL of aq. Sat. Na$_2$SO$_4$. After stirred for 51 hr at rt, it was filtered through a pad of celite, and the pad was washed with ether (2×). The combined filtrates were concentrated to dryness to give 3.5 g of crude product, 531-YW-12.

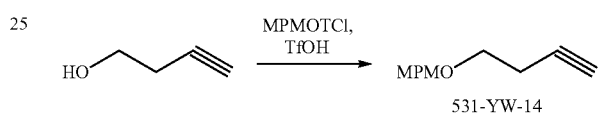

To a solution of alcohol (5.6 g) and MPMOTCl (24 g) in 120 mL of Et$_2$O, a solution of TfOH (20 mL, 0.3 mL dissolved in 25 mL of Et$_2$O) was added in 4 h. Then it was quenched with Sat. NaHCO$_3$ and extracted with Et$_2$O (2×). The organic layers were washed with brine, dried and concentrated. The crude solid was suspended with pentanes. The precipitation was filtered. The filtrates were concentrated to give 15 g of crude product. It was purified on silica gel with 8:1, Hexanes/EtOAc to give 12.7 g of the desired product, 531-YW-14

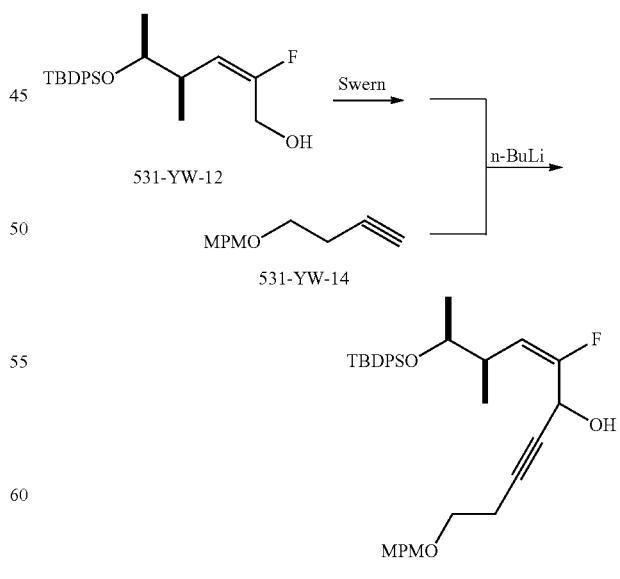

To a solution of (COCl)$_2$ (5 mL) in 250 mL of CH$_2$Cl$_2$, DMSO (10 mL) was added at −78° C. After 15 min at −78° C.

a solution of 531-YW-12 (3.8 g) in 50 mL of CH$_2$Cl$_2$ was added at that temperature. After 30 min at −78° C., Et$_3$N (15 mL) was added, the reaction was warmed to 0° C. The reaction was quenched with sat. NH$_4$Cl, extracted with EtOAc. The organic layer was washed with brine, dried and concentrated. The crude product was passed through a short silica gel pad with Hexanes/EtOAc, 8:1 to give 4.1 g of slightly impure product.

To a solution of acetylene, 531-YW-14 (3.56 g, 18.7 mmol, 1 eq.) in 200 mL of THF, a solution of n-BuLi (12.9 mL, 20.58, 1.1 eq., 1.6 mmol) was added at −78° C. The reaction was warmed to 0° C. for 5 min (by internal temperature). Then it was cooled back to −78° C. A solution of aldehyde, 531-YW-12 (9.8 mmol, 0.5 eq.) in 50 mL of THF was added. The reaction was allowed to be warmed up to 0° C. in 1 h. It was quenched with sat. NH$_4$Cl and purified as described before to give the desired acetylenic alcohol, 531-YW-15.

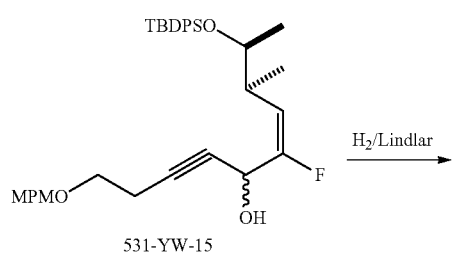

531-YW-15

The starting material (531-YW-15, 5.7 g, 10.2 mmol) was dissolved in 200 mL hexanes. Quinoline (500 μL) and Lindlar catalyst (1.0 g) were added. The reaction mixture was stirred at room temperature under H$_2$ balloon atmosphere for 1 h. Then the catalyst was filtered away. Quantitative amount of 509-HD-134 was obtained as colorless oil.

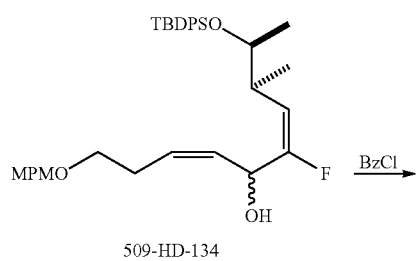

509-HD-134

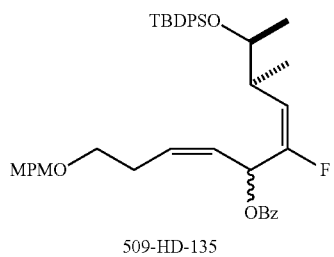

509-HD-135

509-HD-134 (5.7 g, 10.2 mmol) was dissolved in 100 mL dichloromethane at room temperature. Triethylamine (3.5 mL, 25.5 mmol), benzoyl chloride (2.4 mL, 20.4 mmol) and catalytic amount of DAMP were added, respectively. After stirring for 1 h, 0.1N sodium hydroxide solution was added and the reaction mixture was extracted with ethyl acetate. The crude product was purified on silica gel column, giving 509-HD-135 as colorless oil in 77% yield.

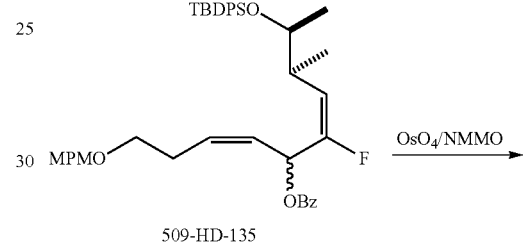

509-HD-135

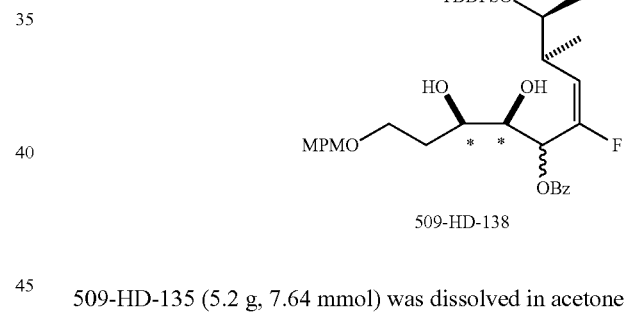

509-HD-138

509-HD-135 (5.2 g, 7.64 mmol) was dissolved in acetone and water (1:0.05) at 0° C. 4-Methylmorpholine N-oxide (1.8 g, 15.28 mmol) and solution of osmium tetraoxide (0.1M, 7.6 mL) in toluene were added. The reaction mixture was warmed up to room temperature and stirred for 20 h. It was quenched with 10% sodium thiosulfate in sat. sodium bicarbonate aqueous solution, and extracted with ethyl acetate. After purification on silica gel column, 509-HD-138 was obtained in 93% yield.

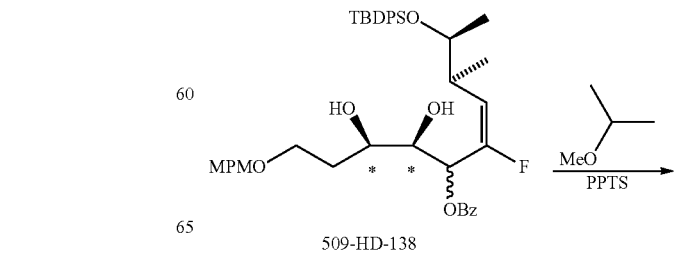

509-HD-138

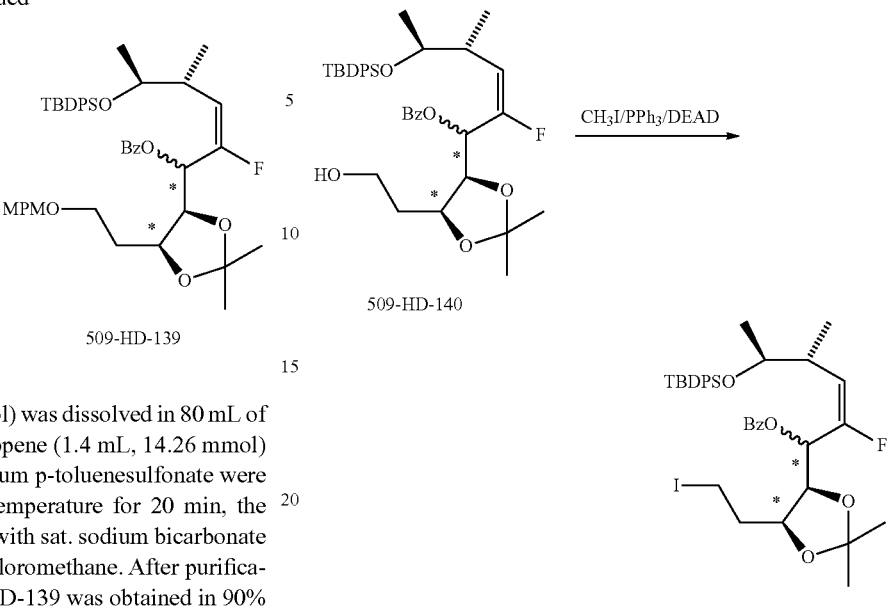

509-HD-138 (5.1 g, 7.13 mmol) was dissolved in 80 mL of dichloromethane. 2-Methoxypropene (1.4 mL, 14.26 mmol) and catalytic amount of pyridinium p-toluenesulfonate were added. After stirring at room temperature for 20 min, the reaction mixture was quenched with sat. sodium bicarbonate solution and extracted with dichloromethane. After purification on silica gel column, 509-HD-139 was obtained in 90% yield.

509-HD-140 (1.86 g, 2.93 mmol) was dissolved in 30 mL of toluene at room temperature. Triphenylphosphine (1.31 g, 4.98 mmol) was added, followed by methyl iodide (236 µL, 3.80 mmol) and diethyl azodicarboxylate (508 L, 3.22 mmol). After stirring for 10 min, the reaction mixture was triturated with toluene. After purification on silica gel column, 509-HD-141 was obtained as colorless oil in 96% yield.

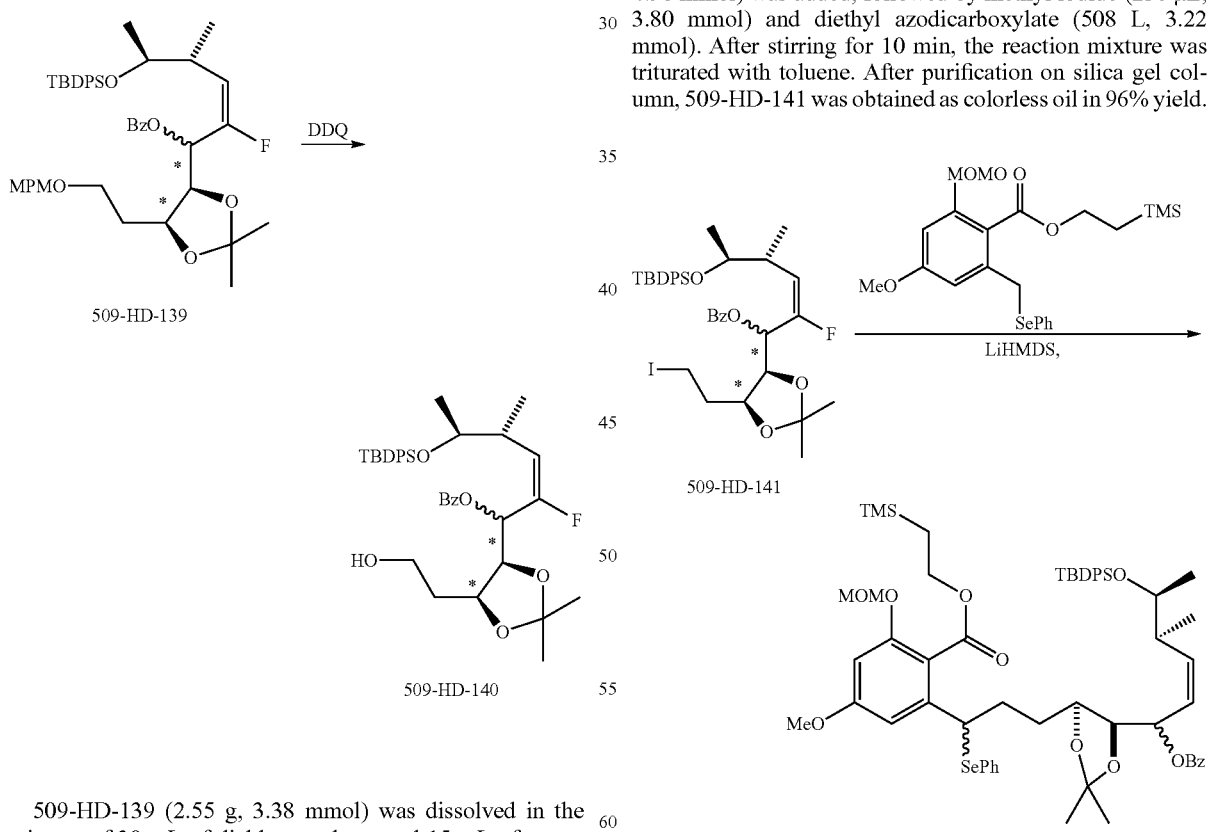

509-HD-139 (2.55 g, 3.38 mmol) was dissolved in the mixture of 30 mL of dichloromethane and 15 mL of water. 2,3-Dichloro-5,6-dicyano-1,4-benzoquinone (844 mg, 3.72 mmol) was added. After stirred at room temperature for 1 h, the reaction mixture was quenched with sat. sodium bicarbonate solution and extracted with ethyl acetate. After purification on silica gel column, 509-HD-140 was obtained as white foam in 98% yield.

509-HD-141 (2.03 g, 2.73 mmol) and 509-HD-213 (2.84 g, 5.46 mmol) were dissolved in a mixture of 35 mL of THF/HMPA (10/1) at −78° C. The solution of LiHMDS (1N, 4.6 mL) in hexanes was added. The reaction mixture was stirred for 30 min, and then it was quenched with sat. ammonium chloride and extracted with ethyl acetate. After purification on silica gel column, 509-HD-143 was obtained in 85% yield.

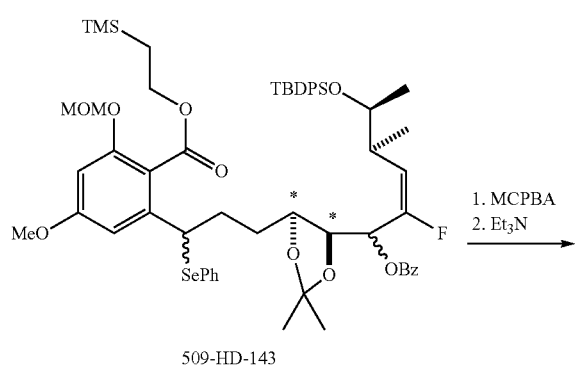

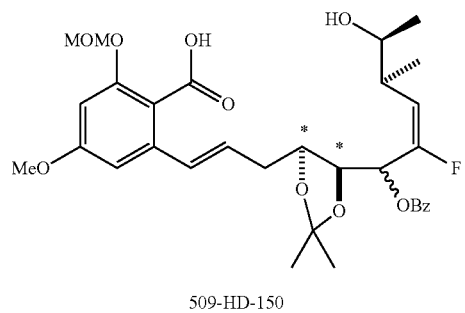

509-HD-144 (1.33 g, 1.41 mmol) was dissolved in 10 mL of THF. The THF solution of TBAF buffered with imidazole-.HCl (1N, 14.1 mL) was added. The reaction mixture was heated at 50° C. for 72 h. It was diluted with $Et_2O$ and washed with $H_2O$. After purification on silica gel column, 509-HD-150 was obtained as pale yellow foam in 95% yield.

509-HD-143 (2.85 g, 2.59 mmol) was dissolved in 50 mL of dichloromethane at 0° C. 3-Chloroperbenzoic acid (50%, 1.8 g) was added. After stirring at 0° C. for 20 min, triethylamine (2.2 mL, 15.5 mmol) was added, then the reaction mixture was warmed up to room temperature and stirred for 30 min. It was quenched with 10% sodium thiosulfate in sat. sodium bicarbonate aqueous solution, and extracted with dichloromethane. After purification on silica gel column, 509-HD-144 was obtained as white foam in 63% yield.

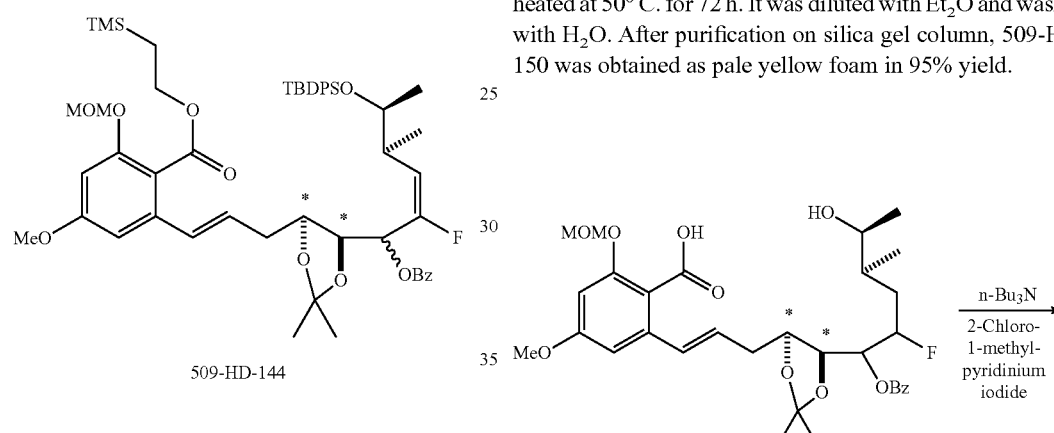

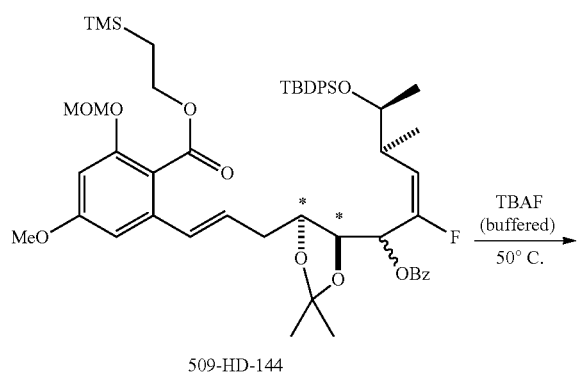

2-Chloro-1-methylpyridinium iodide (1.03 g, 4.02 mmol) and n-$Bu_3N$ (958 µl, 4.02 mmol) were dissolved in 80 mL of dichloromethane and heated to reflux. The solution of 509-HD-150 (807 mg, 1.34 mmol) in 50 mL of dichloromethane was added slowly. The reaction mixture was heated for 30 min. It was washed with 0.02N hydrochloric acid, sat. sodium bicarbonate solution and brine, respectively. After purification on silica gel column, 509-HD-152 was obtained in 50% yield.

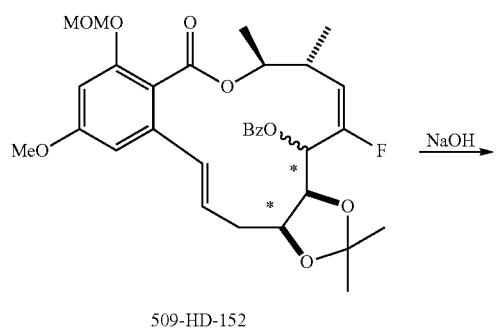

509-HD-152

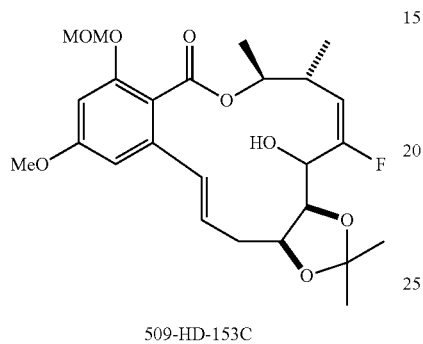

509-HD-153C

509-HD-152 (390 mg, 0.67 mmol) was dissolved in 10 ml ethyl alcohol. Sodium hydroxide (1N, 6.7 mL) solution was added. The reaction mixture was stirred for 1 h at room temperature. It was diluted with H$_2$O, extracted with EtOAc. After purification on silica gel column, 134 mg of the major desired single isomer 509-HD-153C was obtained as colorless oil.

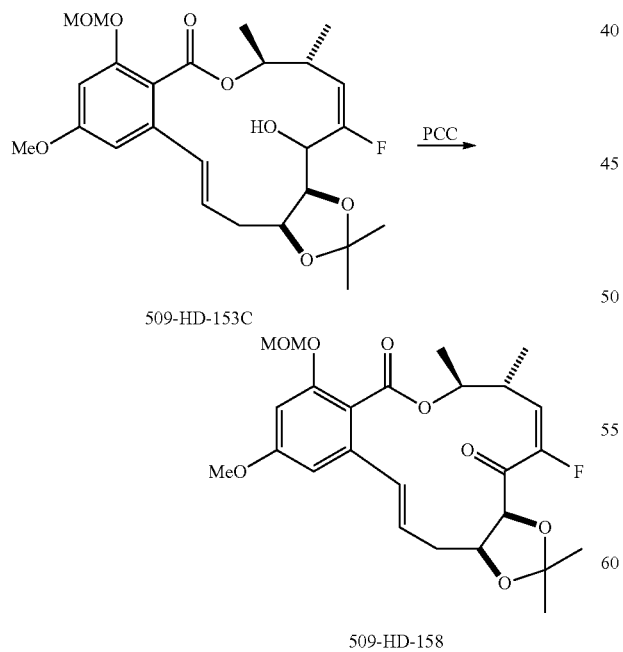

509-HD-153C

509-HD-158

509-HD-153C (94.4 mg, 0.20 mmol) was dissolved in 8 mL of dichloromethane. Molecular sieve (4 A, 423 mg) and PCC (423 mg, 2.0 mmol) were added. The reaction mixture was stirred for 12 h at room temperature. After passing through celite, 509-HD-158 was obtained as colorless oil in 52% yield.

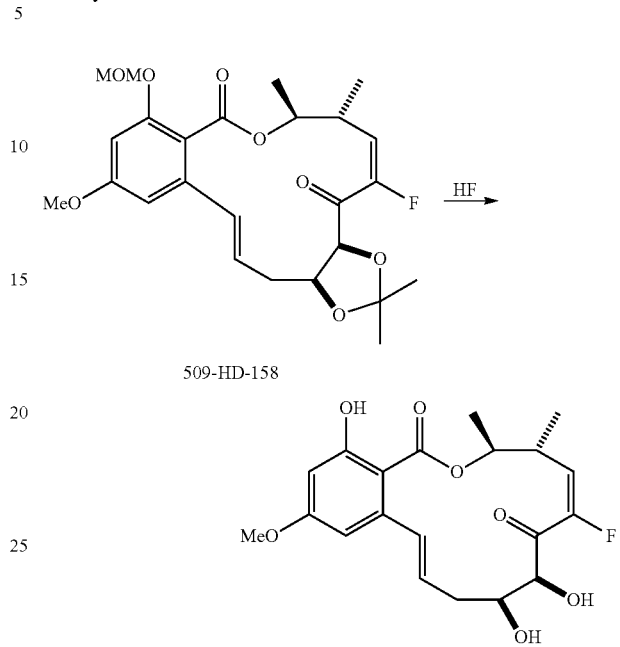

509-HD-158

ER803916

509-HD-158 (49.2 mg, 0.10 mmol) was dissolved in 1.0 mL of dichloromethane. Then hydrofluoric acid (6N, 4 mL) was added. The reaction mixture was stirred at room temperature for 30 min. It was diluted with more dichloromethane, washed with water and sat. sodium bicarbonate solution. After purification on a plug of silica gel, ER803916 was obtained as a white solid in 81% yield.

Preparation of Intermediate for the Synthesis of ER806821:

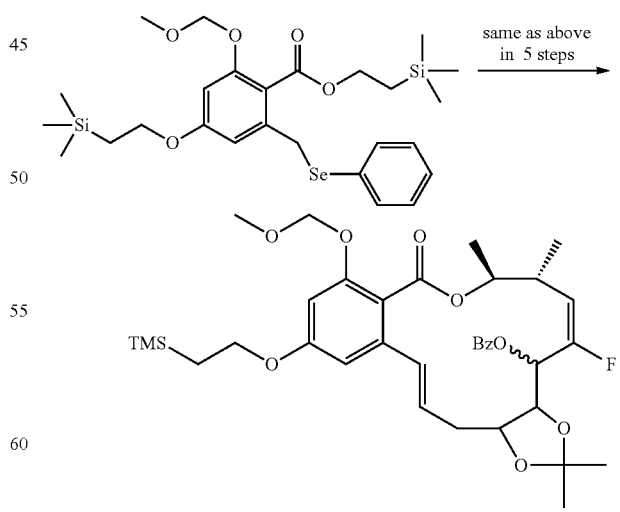

The C14-TMS-ethyl intermediate was prepared from C4-TMS ethyl selenide in analogous to the above sequences in similar yields.

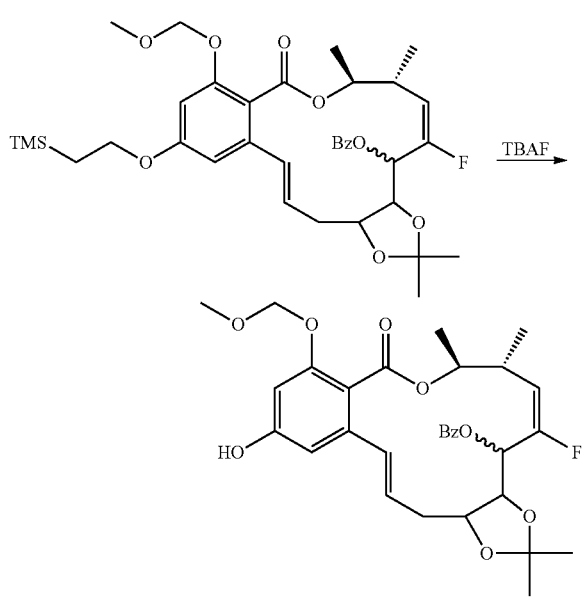

The phenol was prepared using previous describe conditions for the C14 modification series:
Preparation of ER806821:

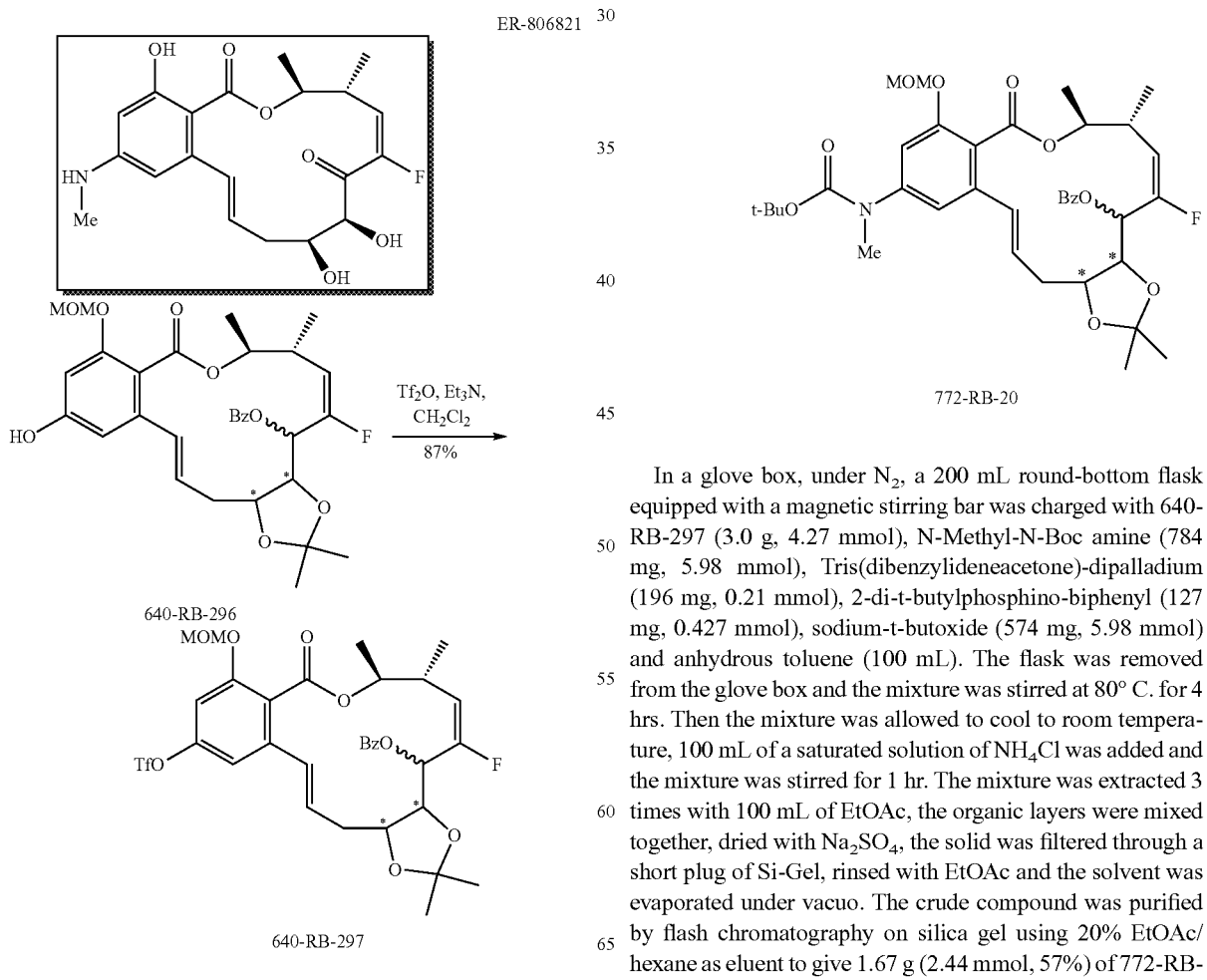

To a solution of phenol (18.8 g, 33 mmol) in $CH_2Cl_2$ (300 mL) at 0° C. was added $Et_3N$ (11.5 mL, 82.5 mmol). Then, $Tf_2O$ (8.3 mL, 49.5 mmol) in $CH_2Cl_2$ (35 mL) was added dropwise over a period of 60 min and the reaction was stirred for an additional 30 min. The reaction was quenched at 0° C. with a saturated solution of $NaHCO_3$ (200 mL), extracted 3 times with 300 mL of $CH_2Cl_2$, the combined organic layers were dried with $Na_2SO_4$, the solid was filtered and the solvent was evaporated under vacuo. The crude compound was purified by flash chromatography on silica gel using 10% EtOAc/hexane as eluent to give 20.1 g (28.6 mmol, 87%) of 640-RB-297 as white foam.

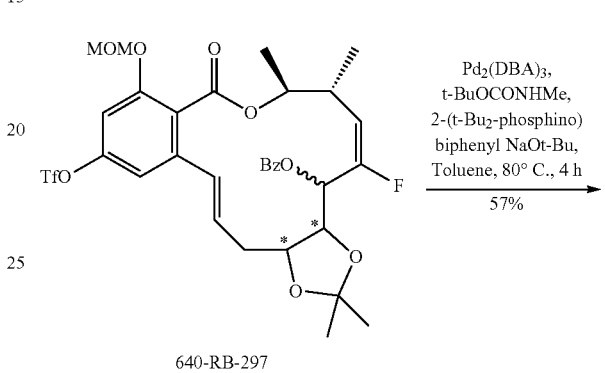

In a glove box, under $N_2$, a 200 mL round-bottom flask equipped with a magnetic stirring bar was charged with 640-RB-297 (3.0 g, 4.27 mmol), N-Methyl-N-Boc amine (784 mg, 5.98 mmol), Tris(dibenzylideneacetone)-dipalladium (196 mg, 0.21 mmol), 2-di-t-butylphosphino-biphenyl (127 mg, 0.427 mmol), sodium-t-butoxide (574 mg, 5.98 mmol) and anhydrous toluene (100 mL). The flask was removed from the glove box and the mixture was stirred at 80° C. for 4 hrs. Then the mixture was allowed to cool to room temperature, 100 mL of a saturated solution of $NH_4Cl$ was added and the mixture was stirred for 1 hr. The mixture was extracted 3 times with 100 mL of EtOAc, the organic layers were mixed together, dried with $Na_2SO_4$, the solid was filtered through a short plug of Si-Gel, rinsed with EtOAc and the solvent was evaporated under vacuo. The crude compound was purified by flash chromatography on silica gel using 20% EtOAc/hexane as eluent to give 1.67 g (2.44 mmol, 57%) of 772-RB-20 as white foam.

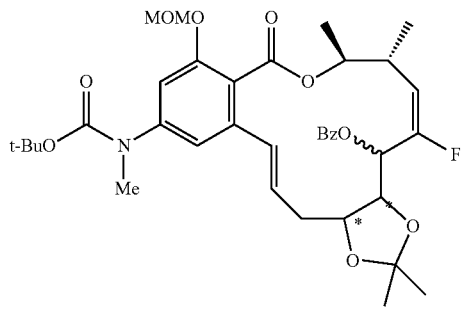

772-RB-20

70% | NaOH, EtOH, r.t. ↓

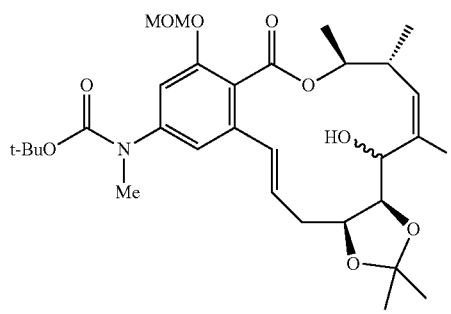

620 mg (44%)
772-RB-21A

+

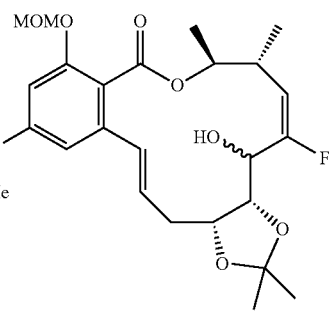

370 mg (26%)
772-RB-21B

To a solution of 772-RB-20 (1.67 g, 2.44 mmol) in EtOH (75 mL) and THF (5 mL) was added a solution of 1N NaOH (24.4 mL, 24.4 mmol) and the resulting mixture was stirred at room temperature for 4 hrs. Then, EtOH was partially evaporated, the mixture was diluted with 500 ml EtOAc, washed with water (2×250 mL) and brine (250 mL), the organic phase was dried with $Na_2SO_4$, the solid was filtered and the solvent was evaporated. The crude compound was purified by flash chromatography on silica gel using 20-30% EtOAc/hexane as eluent to give 620 mg (1.07 mmol, 44%) of 772-RB-21A and 370 mg (0.64 mmol, 26%) of 772-RB-21B (undesired stereochemistry at C8-C9) as white foams.

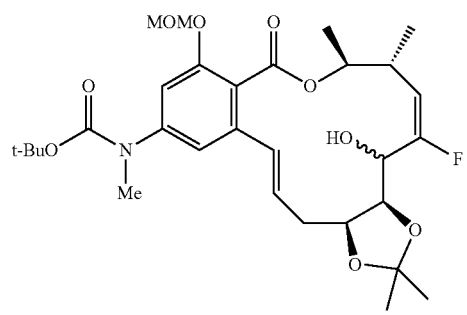

620 mg (44%)
772-RB-21A

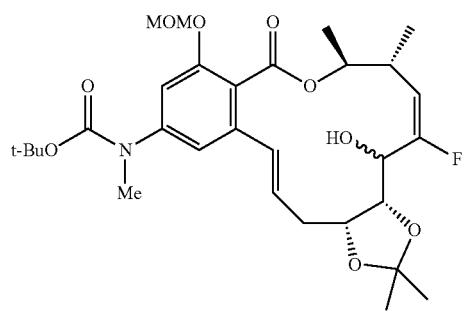

370 mg (26%)
772-RB-21B

92% | Dess-Martin periodinane, $CH_2Cl_2$, r.t. ↓

91% | Dess-Martin periodinane, $CH_2Cl_2$, r.t. ↓

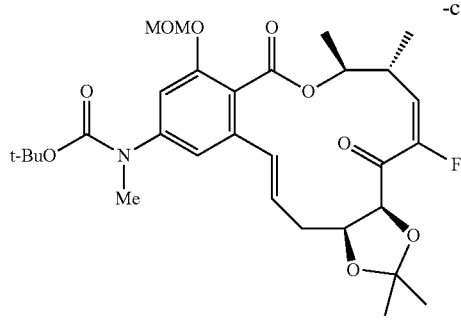

560 mg
772-RB-22

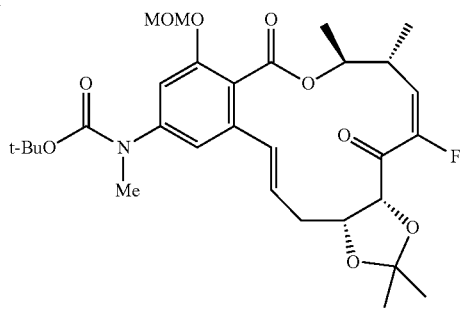

325 mg
772-RB-25

To a solution of 772-RB-21A (610 mg, 10.05 mmol) in CH$_2$Cl$_2$ (25 mL) was added pyridine (0.425 mL, 5.25 mmol) and then Dess-Martin periodinane (1.10 g, 2.6 mmol). The mixture was stirred at room temperature for 1.5 hr. It was then diluted with 100 mL of Et$_2$O, the solid was removed by filtration through celite and rinsed with 100 mL of Et$_2$O. The organic extract was dropped in a solution of 10% w/v Na$_2$S$_2$O$_4$ in saturated NaHCO$_3$ solution and stirred for 15 min. The phases were separated, the organic layer was washed with 100 mL of brine, dried with Na$_2$SO$_4$, the solid was filtered and the solvent was evaporated. The crude compound was purified by flash chromatography on silica gel using 30% EtOAc/hexane as eluent to give 560 mg (0.97 mmol, 92%) of 772-RB-22 as white foam. The other diastereomer 772-RB-21B was treated the same way to give 325 mg (0.56 mmol, 91%) of 772-RB-25 as white foam.

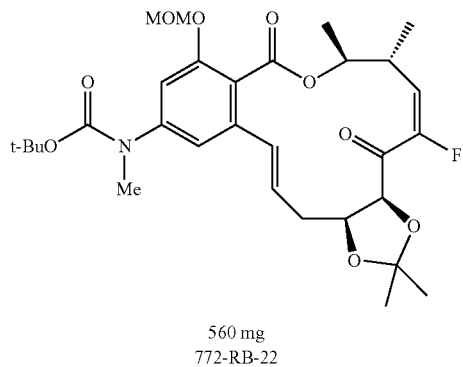

560 mg
772-RB-22

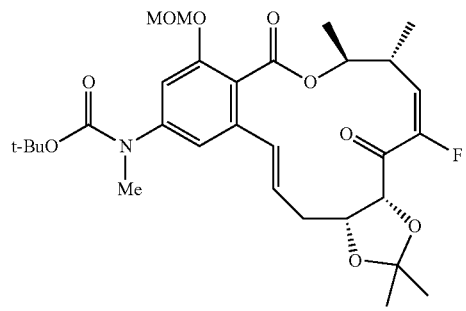

325 mg
772-RB-25

TFA, H$_2$O, CH$_2$Cl$_2$
42%
161 mg

1) TFA, H$_2$O, CH$_2$Cl$_2$
2) Si-Gel, H$_2$O, CH$_2$Cl$_2$
32%
2 steps
70 mg

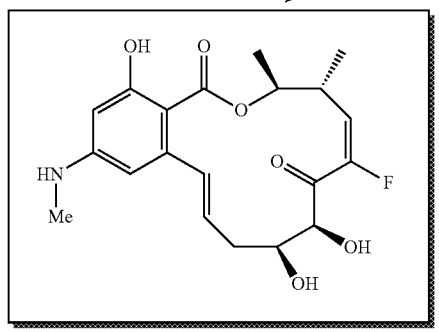

ER-806821

A solution of 772-RB-22 (140 mg, 0.242 mmol) in CH$_2$Cl$_2$ was cooled down to −35° C. in a bath of dry ice/acetone. Then a solution of 5% H$_2$O/TFA was added slowly. The mixture was warmed up slowly to −23° C. and stirred at this temperature for 50 min. Then the mixture was cooled down to −35° C., neutralized with a saturated solution of NaHCO$_3$ and allowed to warm up to room temperature The mixture was extracted 3 times with CH$_2$Cl$_2$, the combined organic layers were dried with Na$_2$SO$_4$, the solid was filtered and the solvent evaporated. This reaction was repeated 4 times. The crude compound was purified by flash chromatography on silica gel using 40% EtOAc/hexane as eluent to give 161 mg (0.42 mmol, 42%) of ER-806821. The other diastereomer 772-RB-25 was deprotected the same way and then the $C_8$-$C_9$ diol was isomerized by treatment with $H_2O$ and Silica gel in $CH_2Cl_2$ overnight to give 70 mg (0.178 mmol, 32% 2 steps) of ER-806821.

Alternative Synthesis of ER806821 and Synthesis of ER807563:

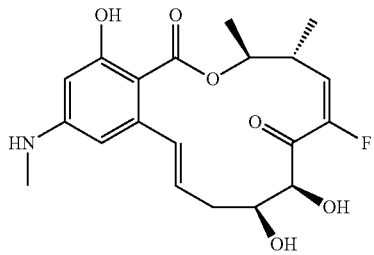
ER-806821

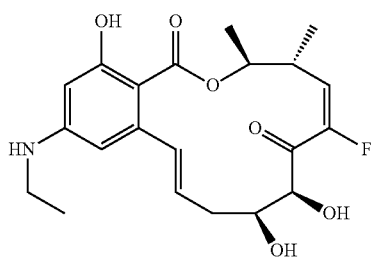
ER-807563

Synthesis of Acyclic Intermediate 20:

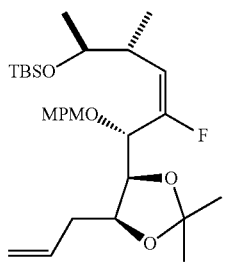

Preparation of Aldehyde 29:

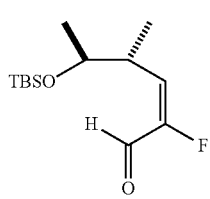
29

Aldehyde 29 was prepared according to the procedure described previously.

Preparation of Alkyne 30:

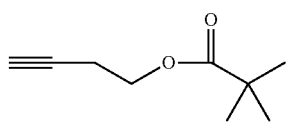
30

To a solution of 3-butyn-1-ol (8.98 g, 128 mmol, 1.0 eq.) in dichloromethane (200 mL) was added triethylamine (23.5 mL, 167 mol, 1.3 eq.) and 4-(dimethylamino)-pyridine (25 mg, 0.205 mmol, 0.0016 eq.). The resulting mixture was cooled down to 0° C., added slowly trimethyl-acetyl chloride (17.5 mL, 141 mmol, 1.1 eq.). Once exotherm was over, the reaction mixture was allowed to warm up to rt. Stirred overnight at rt. A saturated solution of $NaHCO_3$ was added, the biphasic mixture was stirred at rt during 1 h. Layers were separated. The aqueous one was extracted with dichloromethane. The organic layers were combined and dried with sodium sulfate, filtered and concentrated to dryness. The crude oil was purified by filtration on a pad of silica gel 230-400 Mesh using 20% ethyl acetate/hexane to elute. This procedure afforded alkyne 30, 17.3 g, pale yellow oil, 88% yield.

Preparation of Carbinol 31:

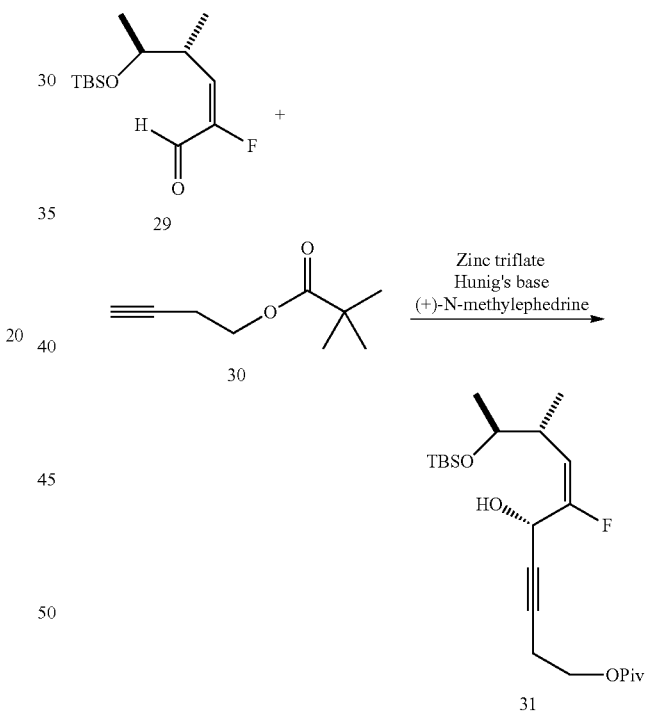

Zinc triflate (1.73 g, 7.31 mmol, 1.1 eq.) and (1S,2R)-(+)-N-methylephedrine (1.43 g, 7.90 mmol, 1.2 eq.) were added to a 100 mL round bottom flask in a dry box. The flask was transferred to a fume hood for the addition of toluene (20 mL) and N,N-diisopropylethylamine (1.39 ml, 7.94 mmol, 1.2 eq.). The resulting mixture was stirred 2 h at rt at which point alkyne 30 (1.23 g, 7.97 mmol, 1.2 eq.) was added. Stirred 60 min at rt, added aldehyde 29 (1.73 g, 6.64 mmol, 1.0 eq.) and stirred at rt 40 min. Quenched by the addition of a saturated solution of ammonium chloride. Layers were separated, the aqueous one was extracted with $Et_2O$, the organic layers were combined, washed with brine, dried with sodium sulfate, filtered and concentrated to dryness. The resulting crude oil was purified by chromatography on silica gel 230-400 Mesh using the following solvent gradient: 8%, 12% and 16% ethyl acetate/hexane to elute. This procedure afforded carbinol 31, 2.21 g, colorless oil, 80% yield, 94% de.

Preparation of Alkene 32:

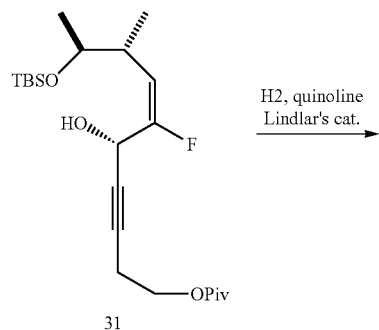

To a solution of carbinol 31 (2.60 g, 6.27 mmol, 1.0 eq.) in n-heptane (70 mL) was added quinoline (0.16 mL, 1.33 mmol, 0.21 eq.) and Lindlar catalyst (640 mg). The resulting heterogeneous mixture was stirred at rt during 1.5 h under a positive atmosphere of hydrogen. After that time, the reaction was found complete. It was then filtered on Celite and the filtrate was washed with a dilute HCl solution (prepared by mixing HCl 1 N (6.0 mL) with water (24 mL)) to remove quinoline. Layers were separated, the organic one was washed with water (3×20 mL), dried with sodium sulfate, filtered and concentrated to dryness to afford alkene 32, 2.56 g, colorless oil, 98% yield.

Preparation of Ether 33:

To a solution of alkene 32 (2.40 g, 5.76 mmol, 1.0 eq.) and the trichloroimidate of 4-methoxybenzyl alcohol (2.05 g, 7.20 mmol., 1.25 eq.) in dichloromethane (7.5 mL) was added at rt pyridinium p-toluenesulfonate (74 mg, 0.29 mmol, 0.05 eq.). The reaction mixture was stirred at rt overnight. The reaction was found incomplete and in order to push it to completion it required sequential additions of extra pyridinium p-toluenesulfonate (74 mg, 0.29 mmol, 0.05 eq.) and trichloroimidate of 4-methoxy-benzyl alcohol (2.05 g, 7.20 mmol., 1.25 eq.) and prolonged stirring at 40° C. The reaction was quenched by adding a 1:1 mixture of THF and water (10 mL) and stirring was continued for 1 h at 40° C. Dichloromethane was added, layers were separated, the organic one was washed with NaHCO₃, dried with sodium sulfate, filtered and concentrated to dryness. The crude oil was purified by chromatography on silica gel 230-400 Mesh using the following solvent gradient: 5% and 7.5% ethyl acetate/hexane to elute. This procedure afforded ether 33, 2.60 g, colorless oil, 84% yield.

Preparation of Diol 34:

To a solution of ether 33 (2.20 g, 4.10 mmol, 1.0 eq.) in THF (28 mL) was added a solution of 4-methyl morpholine N-oxide (990 mg, 8.20 mmol, 2.0 eq.) in water (28.0 mL). The mixture was added at rt a solution of osmium tetroxide (0.55 mL, 0.055 mmol, 0.013 eq., osmium tetroxide 0.1 M in water). The reaction mixture was stirred at rt during 19.5 h. Then it was quenched by the addition of 20 mL of a 1:1 solution of NaHCO₃ saturated and 10% Na₂S₂O₃ in water. Stirring was continued during 60 min at rt. Layers were separated; the aqueous one was extracted with ethyl acetate. The organic layers were combined, washed with brine, dried with sodium sulfate, filtered and concentrated to dryness. The resulting crude oil was purified by chromatography on silica gel 230-400 Mesh using the following solvent gradient: 15% and 40% ethyl acetate/hexane to elute. This procedure afforded diol 34, 2.06 g, colorless oil, 88% yield beta/alpha ratio>=10:1.

Preparation of Acetonide 35:

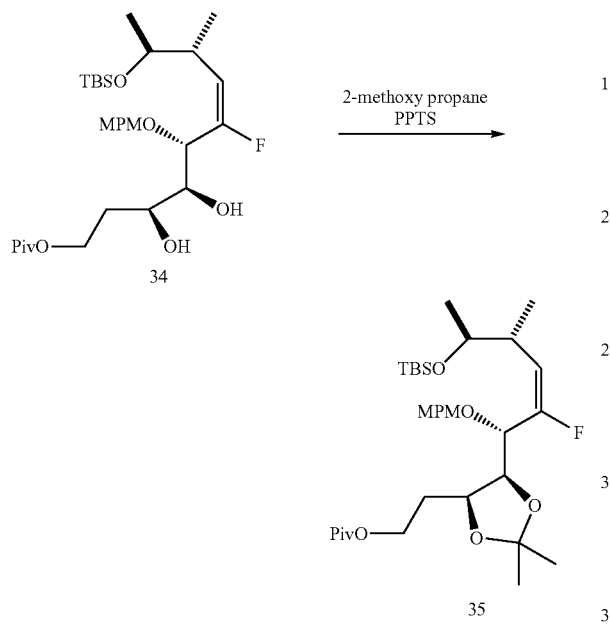

To a solution of diol 34 (2.17 g, 3.80 mmol, 1.0 eq.) and 2-methoxypropene (0.77 mL, 7.64 mmol, 2.0 eq.) in dichloromethane (40 mL) was added at rt pyridinium p-toluenesulfonate (10 mg, 0.039 mmol, 0.01 eq.). The reaction mixture was stirred at rt during 45 min and quenched by the addition of a saturated solution $NaHCO_3$. Dichloromethane was added, layers were separated, the aqueous one was extracted with dichloromethane, the organic layers were combined, washed with brine, dried with sodium sulfate, filtered and concentrated to dryness. The crude oil was purified by chromatography on silica gel 230-400 Mesh using 10% ethyl acetate/hexane to elute. This procedure afforded acetonide 35, 1.80 g, a colorless oil, 78% yield.

Preparation of Alcohol 36:

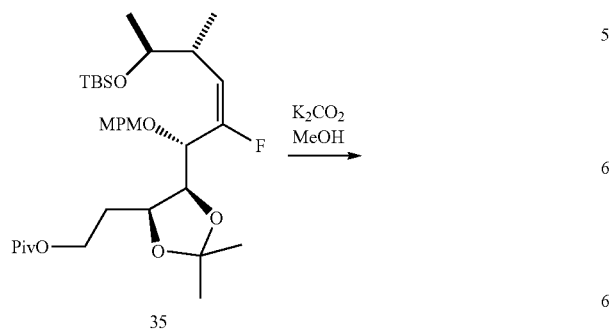

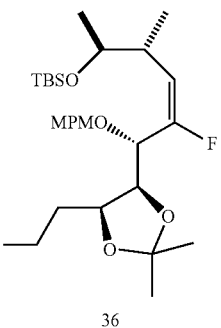

To a solution of acetonide 35 (940 mg, 1.54 mmol, 1.0 eq.) in methanol (15 mL) at rt was added potassium carbonate (261 mg, 1.85 mmol, 1.2 eq.). The resulting mixture was stirred at 50° C. during 21 h, cooled down to rt, added n-hexane (30 mL), water (15 mL) and a saturated solution of $NH_4Cl$ (30 mL). Layers were separated, the aqueous one was extracted with ethyl ether/hexane, the organic layers were combined, dried with sodium sulfate, filtered and concentrated to dryness. The resulting crude oil was purified by chromatography on silica gel 230-400 Mesh using the following solvent gradient: 20%, 60% and 80% ethyl acetate/hexane to elute. This procedure afforded alcohol 36, 787 mg, a colorless oil, 97% yield.

Preparation of Aldehyde 37:

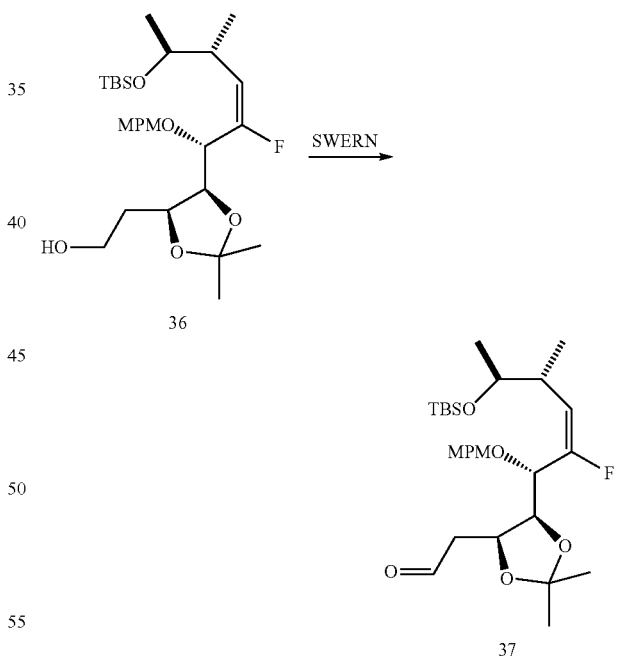

To a solution of dimethyl sulfoxide (0.44 mL, 6.19 mmol, 4.0 eq.) in dichloromethane (5.0 mL) at -78° C. was added oxalyl chloride (1.54 mL, 3.08 mmol, 2.1 eq., oxalyl chloride 2.0 M in dichloromethane). The resulting mixture was stirred 30 min at -78° C., added alcohol 36 (787 mg, 1.49 mmol, 1.0 eq.) in dichloromethane (2.0 mL to dissolve alcohol and 2×1.5 mL to rinse flask). The reaction mixture was stirred 60 min at -78° C., added triethylamine (0.87 mL, 6.22 mmol, 4.2 eq.), stirred 5 min at -78° C., then warmed up to rt and stirring was continued at that temperature during 50 min. At that point a saturated solution of NH₄Cl was added. Layers were separated and the aqueous one was extracted three times with dichloromethane. The organic layers were combined, dried with sodium sulfate, filtered and concentrated to dryness. The crude oil was dissolved in a 1:1 mixture of ethyl acetate/hexane (100 mL) and washed with water (10 mL) three times, then washed with brine, dried with sodium sulfate, filtered and concentrated to dryness. The concentrated material was azeotroped with toluene and pumped to constant weight to afford aldehyde 37, 791 mg, a colorless oil, quantitative yield.

Preparation of Alkene 20:

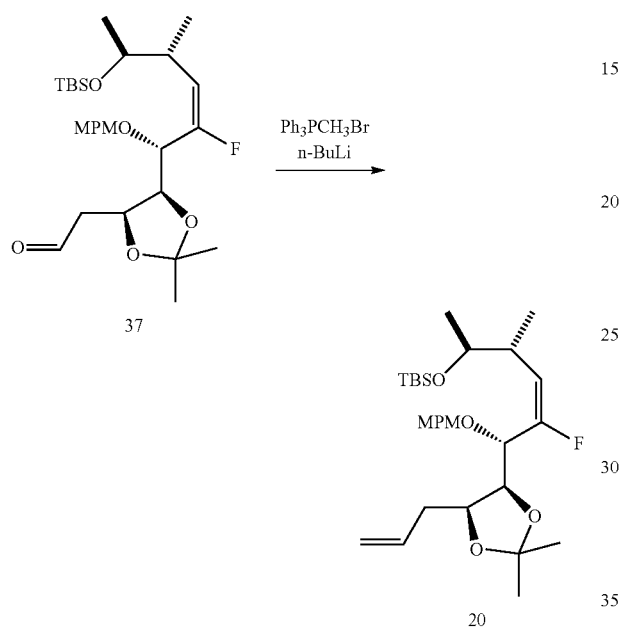

To a suspension of methyltriphenylphosphonium bromide (549 mg, 1.51 mmol, 2.2 eq.) in dimethyl sulfoxide (1.0 mL) and THF (3.6 mL) at 0° C. was added n-butyllithium (0.855 mL, 1.37 mmol, 2.0 eq., n-butyllithium 1.6 M in THF). The resulting mixture was stirred 60 min at 0° C., added aldehyde 37 (359 mg, 0.684 mmol, 1.0 eq.) in THF (2.0 mL and 3×1.0 mL for rinse). Stirred 20 min at 0° C., allowed to warm up to rt and stirred 1.5 h at that temperature. Quenched by the addition of a saturated solution of NH₄Cl, layers were separated and the aqueous one was extracted with a 1:1 mixture of ethyl ether/hexanes. The organic layers were combined, washed with brine, dried with sodium sulfate, filtered and concentrated to dryness. The resulting crude oil was purified by chromatography on silica gel 230-400 Mesh using the following solvent gradient: 5% and 6.5% ethyl acetate/hexane to elute. This procedure afforded alkene 20, 322 mg, a colorless oil, 90% yield.

B) Synthesis of ER-806821:

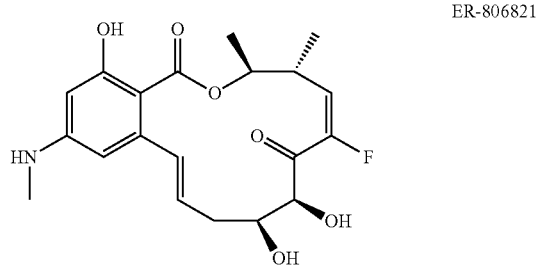

Preparation of Heck-Coupling Product 22:

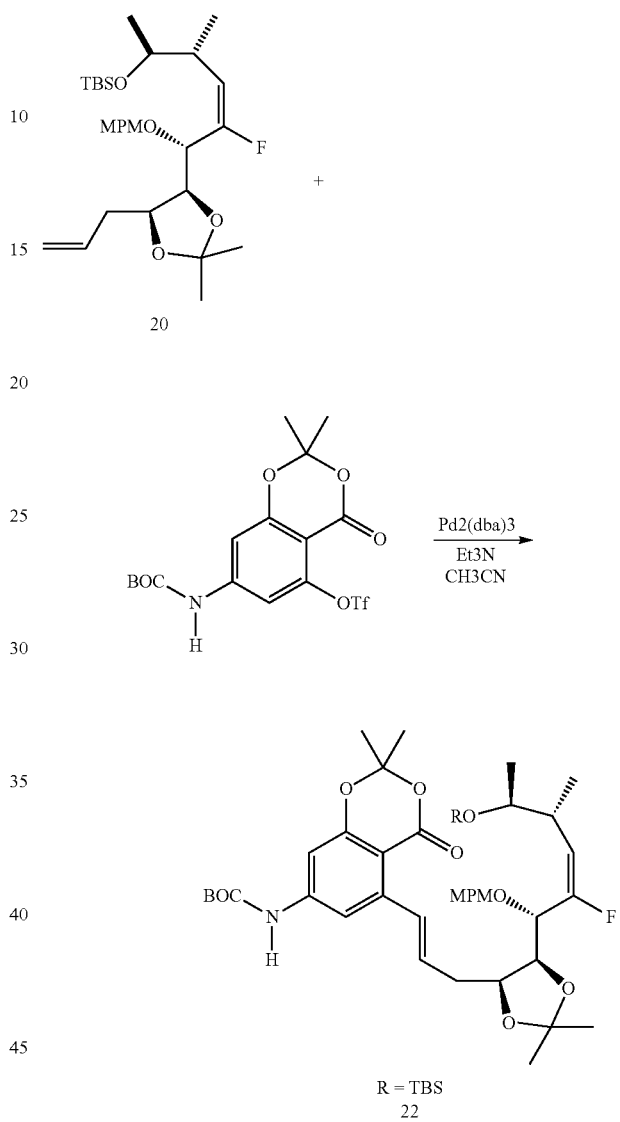

Alkene 20 (380 mg, 0.727 mmol, 1.0 eq.) and triflate 21 (321 mg, 0.727 mmol, 1.0 eq.) were combined and added tris-(dibenzylideneacetone)-dipalladium-(0) (33.2 mg, 0.036 mmol, 0.05 eq.) under inert atmosphere (dry box). Those reagents were moved out of the dry box and added at rt acetonitrile (3.0 mL) and triethylamine (0.205 mL, 1.46 mmol, 2.0 eq.). The resulting mixture was stirred at 65° C. during 19 h, cooled down to rt and filtered on Celite. The filtrate was concentrated to dryness and purified by chromatography on silica gel 230-400 Mesh using the following solvent gradient: 5%, 15%, 20% and 30% ethyl acetate/hexane to elute. This procedure afforded Heck-coupling product 22, 384 mg, white foam, 65% yield and unreacted alkene 20, 63 mg, 17%.

Preparation of N-Methylaniline 23:

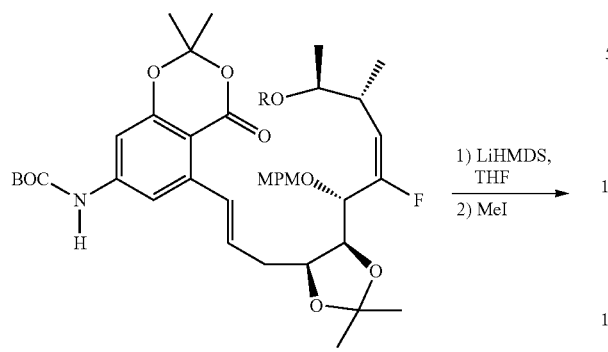

R = TBS
22

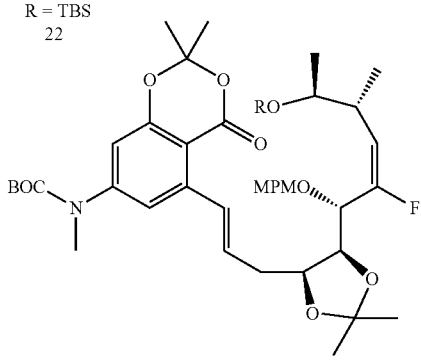

R = TBS
23

To a solution of aniline 22 (178 mg, 0.219 mmol, 1.0 eq.) in THF (0.34 mL) at 0° C. was added lithium hexamethyldisalazide (0.66 mL, 0.66 mmol, 3.0 eq., lithium hexamethyldisalazide 1.0 M in THF). The resulting mixture was stirred at 0° C. during 60 min and added methyl iodide (0.085 mL, 1.35 mmol, 6.0 eq.). The reaction mixture was stirred 10 min at 0° C., then allowed to warm up to rt and stirred at that temperature during 21 h. A saturated solution of NH$_4$Cl and methyl-t-butyl ether were added. Layers were separated and the aqueous one was extracted twice with methyl-t-butyl ether. The combined organic layers were washed with brine, dried with sodium sulfate, filtered and concentrated to dryness. The resulting foam was purified by chromatography on silica gel 230-400 Mesh using the following solvent gradient: 15% and 22% ethyl acetate/hexane to elute. This procedure afforded N-methylaniline 23, 148 mg, white foam, 82% yield.

Preparation of Macrocyclic Precursor 24:

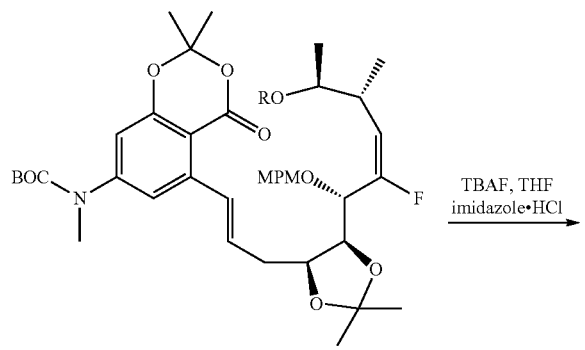

R = TBS
23

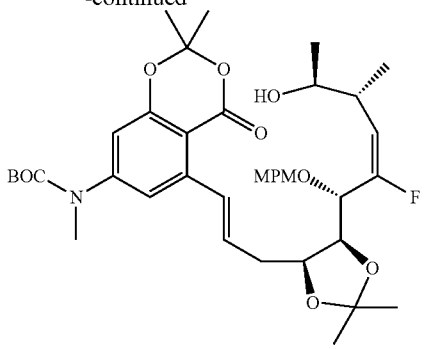

24

To N-methylaniline 23 (119 mg, 0.143 mmol, 1.0 eq.) was added a solution of TBAF (1.0 mL, 1.0 mmol, 7.0 eq.) buffered with imidazole hydrochloride. That buffered solution of TBAF was prepared by adding 5.3 g of imidazole hydrochloride to 100 mL of TBAF 1.0 M in THF and by stirring till complete dissolution. The reaction mixture was stirred at 65° C. during 16 h, cooled down to rt, added a saturated solution of NH$_4$Cl and methyl-t-butyl ether. The layers were separated and the aqueous one was extracted twice with methyl-t-butyl ether. The combined organic layers were washed with brine, dried with sodium sulfate, filtered and concentrated to dryness. The resulting foam was purified by chromatography on silica gel 230-400 Mesh using the following solvent gradient: 30% and 50% ethyl acetate/hexane to elute. This procedure afforded macrocylclic precursor 24, 94.0 mg, white foam, 92% yield.

Preparation of Macrolactone 25:

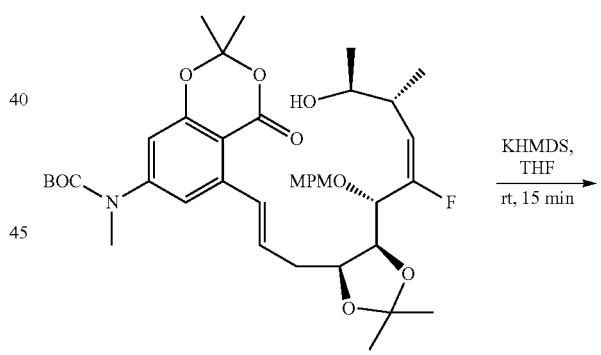

24

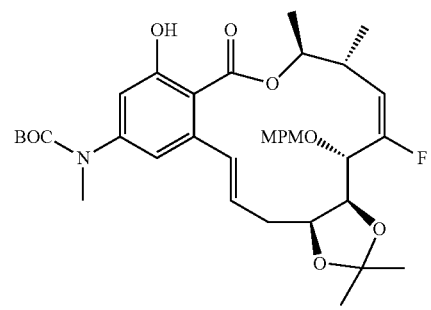

25

To a solution of macrocyclic precursor 24 (47.0 mg, 0.0658 mmol, 1.0 eq.) in THF (6.6 mL) was added potassium hexamethyldisalazide 0.5 M in toluene (0.265 mL, 0.133 mmol, 2.0 eq.). Stirred 10 min at rt, quenched with a saturated solution of NH₄Cl to bring pH to neutral. Methyl-t-butyl ether was added, layers were separated, and the aqueous one was extracted with methyl-t-butyl ether. The combined organic layers were washed with brine, dried with sodium sulfate, filtered and concentrated to dryness. The resulting foam was purified by chromatography on silica gel 230-400 Mesh using the following solvent gradient: 15% and 25% ethyl acetate/hexane to elute. This procedure afforded macrolactone 25, 23.5 mg, white foam, 55% yield.

Preparation of Ether 26:

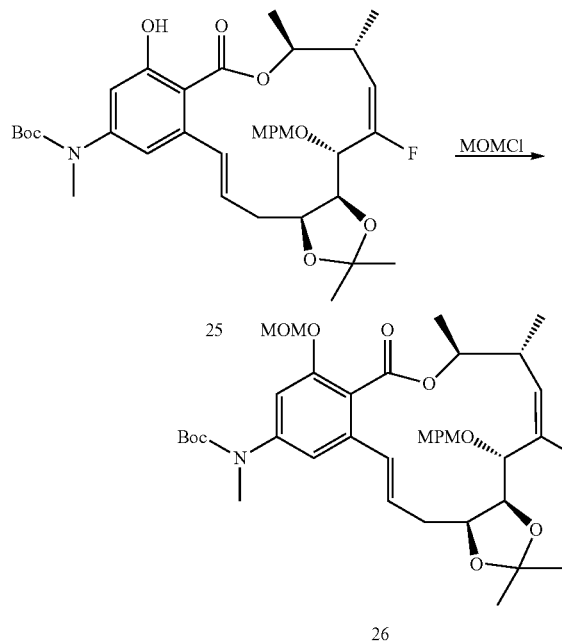

To a solution of macrolactone 25 (17.9 mg, 0.0272 mmol, 1.0 eq.) in dichloromethane (1.0 mL) at 0° C. was added N,N-diisopropylethylamine (0.125 ml, 0.712 mmol, 26.2 eq.) and MOMCl (0.042 mL, 0.550 mmol, 20.0 eq.). The reaction mixture was allowed to warm up to rt and stirred at that temperature during 3.75 h at which point it was quenched with a saturated solution of NH₄Cl. Methyl-t-butyl ether was added, layers were separated, and the aqueous one was extracted twice with methyl-t-butyl ether. The combined organic layers were washed with brine, dried with sodium sulfate, filtered and concentrated to dryness. The resulting foam was purified by chromatography on silica gel 230-400 Mesh using the following solvent gradient: 30% and 45% ethyl acetate/hexane to elute. This procedure afforded ether 26, 18.2 mg, white foam, 96% yield.

Preparation of Allylic Alcohol 27:

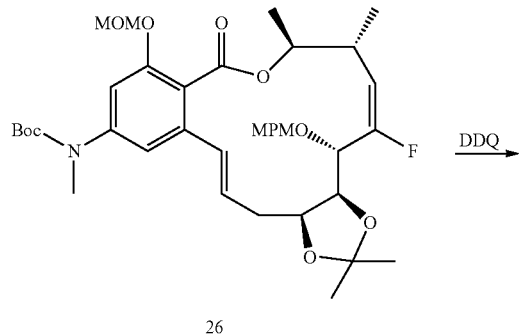

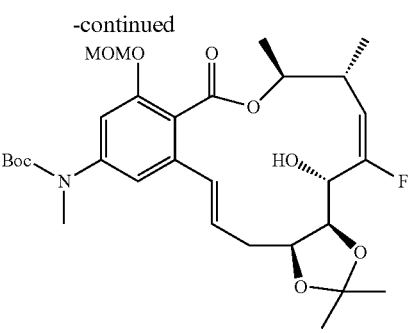

To a solution of ether 26 (18.2 mg, 0.026 mmol, 1.0 eq.) in dichloromethane (0.60 mL) at rt was added water (0.12 mL) and DDQ (12.0 mg, 0.0517 mmol, 2.0 eq.). The resulting mixture was stirred at rt during 3.5 h at which point it was cooled down to 0° C. and quenched with a 1:1 solution of NaHCO₃ saturated and 10% Na₂S₂O₃ in water. Methyl-t-butyl ether was added, layers were separated, and the aqueous one was extracted twice with methyl-t-butyl ether. The combined organic layers were washed with brine, dried with sodium sulfate, filtered and concentrated to dryness. The resulting foam was purified by HPTLC prep-plates using 35% ethyl acetate/hexane to elute. This procedure afforded alcohol 27, 12.6 mg, white foam, 84% yield.

Note: Alcohol 27 is an intermediate of the first-generation synthesis of ER-806821, its conversion into ER-806821 can be achieved using the Dess-Martin periodinane and the TFA procedures.

C) Synthesis of ER-807563

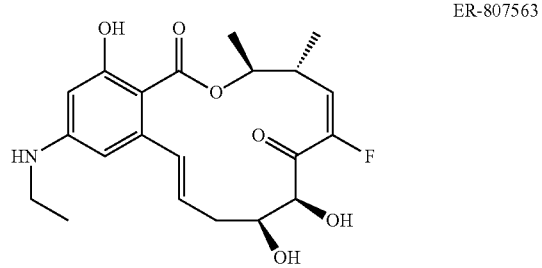

Preparation of N-Ethylaniline 39:

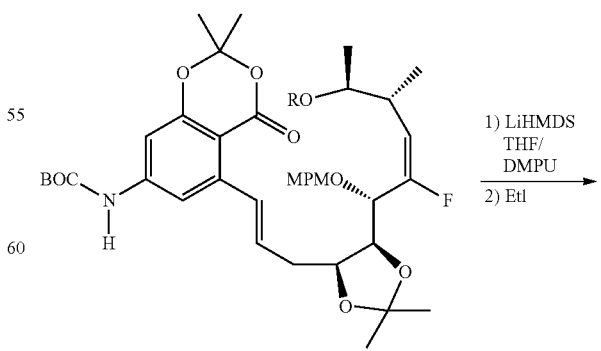

-continued

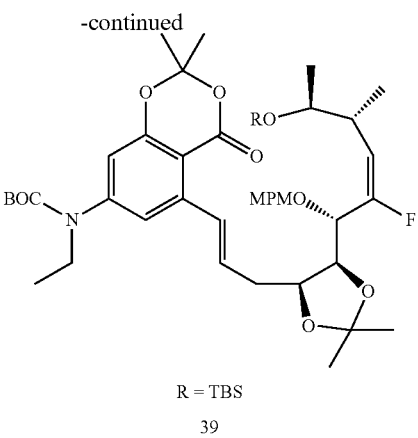

R = TBS
39

To a solution of aniline 22 (386 mg, 0.474 mmol, 1.0 eq.) in DMPU (1.6 mL) at 0° C. was added lithium hexamethyldisalazide (0.950 mL, 0.950 mmol, 2.0 eq., lithium hexamethyldisalazide 1.0 M in THF). The resulting mixture was stirred at 0° C. during 30 min and added ethyl iodide (0.230 mL, 2.88 mmol, 6.1 eq.). The reaction mixture was stirred 10 min at 0° C., then allowed to warm up to rt and stirred at that temperature during 1 h. A saturated solution of NH$_4$Cl, methyl-t-butyl ether and n-hexanes were added. Layers were separated and the aqueous one was extracted twice with methyl-t-butyl ether/hexane (1:1 mixture). The combined organic layers were washed with brine/water (1:1 mixture), then with brine, dried with sodium sulfate, filtered and concentrated to dryness. The resulting foam was purified by chromatography on silica gel 230-400 Mesh using the following solvent gradient: 15% and 20% ethyl acetate/hexane to elute. This procedure afforded N-ethyl-aniline 39, 349 mg, white foam, 87% yield.

Preparation of Macrocyclic Precursor 40:

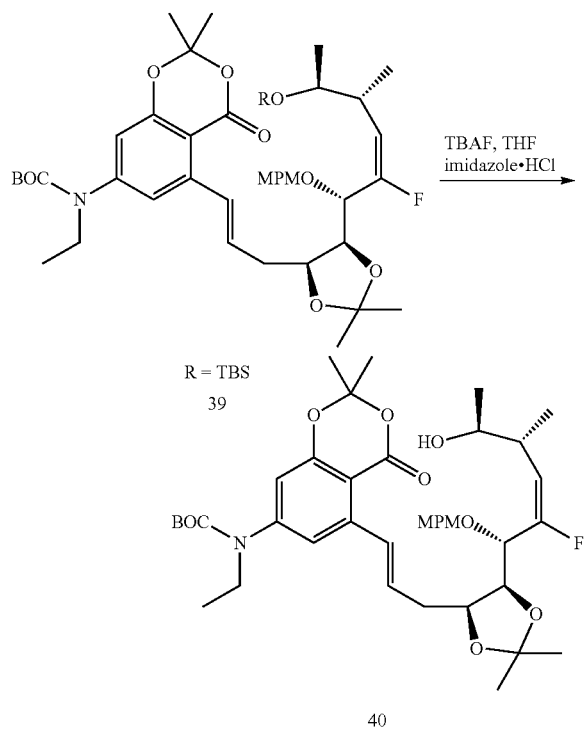

N-ethylaniline 39 (817 mg, 0.970 mmol, 1.0 eq.) was added a solution of TBAF (6.8 mL, 6.8 mmol, 7.0 eq.) previously buffered with imidazole hydrochloride. That buffered solution of TBAF was prepared by adding 5.3 g of imidazole hydrochloride to 100 mL of TBAF 1.0 M in THF and by stirring till complete dissolution. The reaction mixture was stirred at 65° C. during 16 h, cooled down to rt, added a saturated solution of NH$_4$Cl, water and methyl-t-butyl ether. The layers were separated and the aqueous one was extracted twice with methyl-t-butyl ether. The combined organic layers were washed with brine/water (1:1 mixture), then washed with brine, dried with sodium sulfate, filtered and concentrated to dryness. The resulting foam was purified by chromatography on silica gel 230-400 Mesh using the following solvent gradient: 20%, 30% and 45% ethyl acetate/hexane to elute. This procedure afforded macrocylclic precursor 40, 635 mg, white foam, 90% yield.

Preparation of Macrolactone 41:

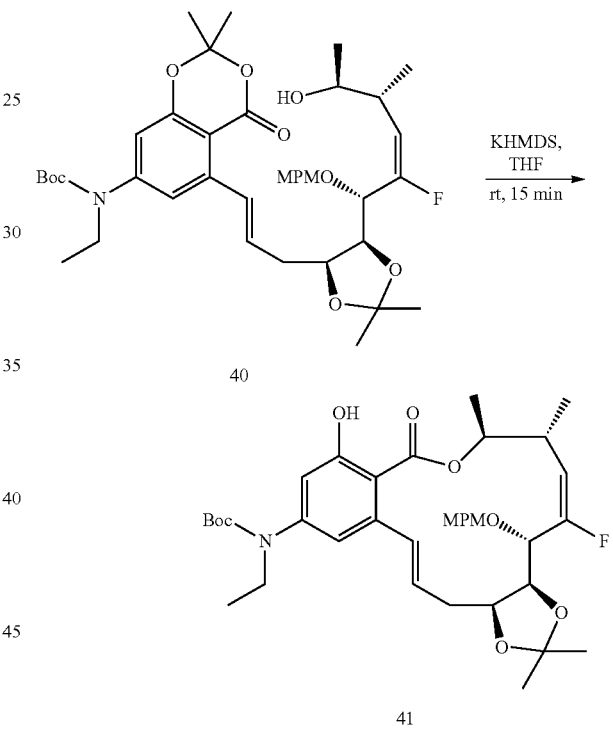

To a solution of macrocyclic precursor 40 (303 mg, 0.416 mmol, 1.0 eq.) in THF (40 mL) was added potassium hexamethyldisalazide (1.70 mL, 0.85 mmol, 2.0 eq., potassium hexamethyldisalazide 0.5 M in toluene) over 3 min. The reaction mixture was stirred 10 min at rt and quenched with a saturated solution of NH$_4$Cl. Methyl-t-butyl ether and water were added, layers were separated, and the aqueous one was extracted with methyl-t-butyl ether. The combined organic layers were washed with a saturated solution of NH$_4$Cl, then washed with brine, dried with sodium sulfate, filtered and concentrated to dryness. The resulting foam was purified by chromatography on silica gel 230-400 Mesh using the following solvent gradient: 15% and 18% ethyl acetate/hexane to elute. This procedure afforded macrolactone 41, 134 mg, white foam, 48% yield.

Preparation of Allylic Alcohol 42:

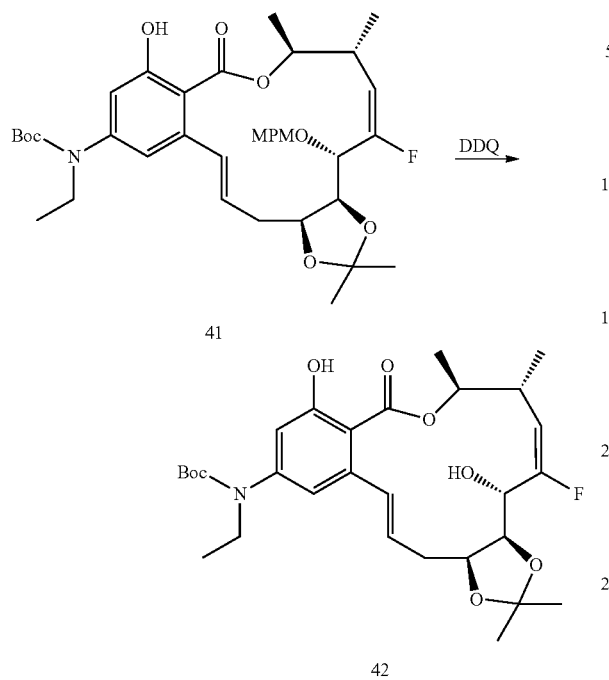

To a solution of macrolactone 41 (146.5 mg, 0.219 mmol, 1.0 eq.) in dichloromethane (0.50 mL) was added water (0.50 mL). The resulting mixture was cooled down to 0° C. and was added a saturated solution of DDQ in dichloromethane (3.0 mL, 0.265 mmol, 1.2 eq., this saturated solution of DDQ in dichloromethane contained at rt 20.5 mg of DDQ 98% pure/mL of dichloromethane). The biphasic reaction mixture was stirred 5 min at 0° C., then 6 h at rt. At that point, it was cooled down to 0° C., added dichloromethane and quenched with a 1:1 solution of NaHCO₃ saturated and 10% Na₂S₂O₃ in water. Stirring was continued for 15 min. Layers were separated and the aqueous one was extracted with dichloromethane. The combined organic layers were washed with a 1:1 solution of NaHCO₃ saturated and 10% Na₂S₂O₃ in water, then washed with brine, dried with sodium sulfate, filtered and concentrated to dryness. The resulting foam was purified by chromatography on silica gel 230-400 Mesh using the following solvent gradient: dichloromethane, 3%, 5% and 7.5% methyl-t-butyl ether/dichloromethane to elute. This procedure afforded allylic alcohol 42, 102 mg, white foam, 85% yield.

Preparation of Enone 43:

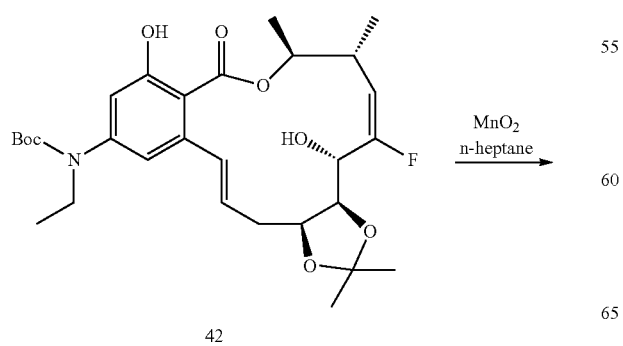

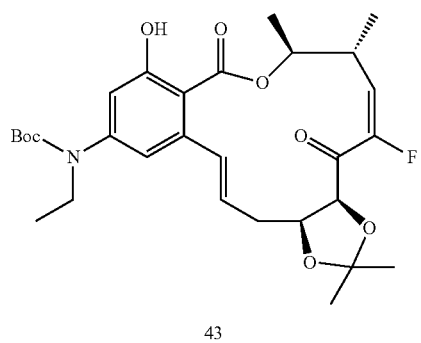

To a solution of allylic alcohol 42 (20.5 mg, 0.0372 mmol, 1.0 eq.) in n-heptane (1.0 mL) at rt was added MnO₂ (16 mg, 0.184 mmol, 5 eq.). The resulting heterogeneous mixture was stirred at 65° C. during 12 h. This process gave only a small amount of desired material and in order to push the reaction to completion, fresh MnO₂ (16 mg) was added on a daily basis until the reaction went to completion after one week of stirring at 65° C. Upon completion, ethyl acetate was added and the solids were filtered off on a short silica gel column (230-400 Mesh) using ethyl acetate as solvent. The filtrate was concentrated down to dryness and purified by chromatography on silica gel 230-400 Mesh using 10% acetone/toluene as solvent. This procedure afforded enone 43, 7.0 mg, white foam, 35% yield (not optimized).

Preparation of ER-807563:

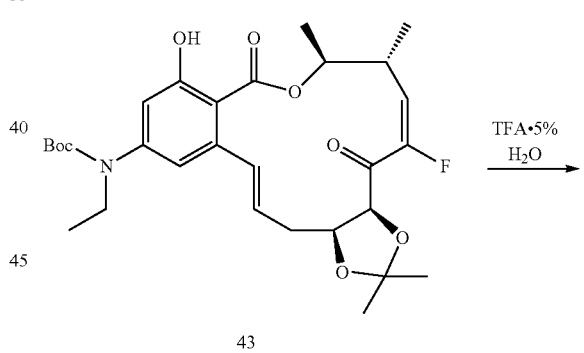

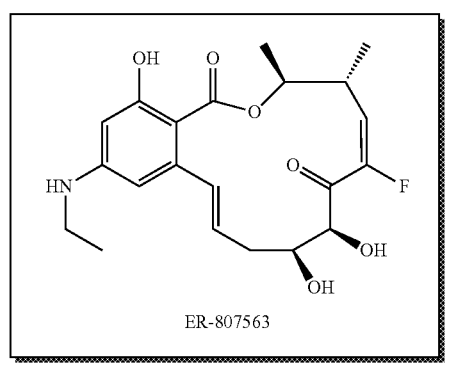

Enone 43 is treated according to the same TEA protocol as for the preparation of ER-805940.

Preparation of NF2561

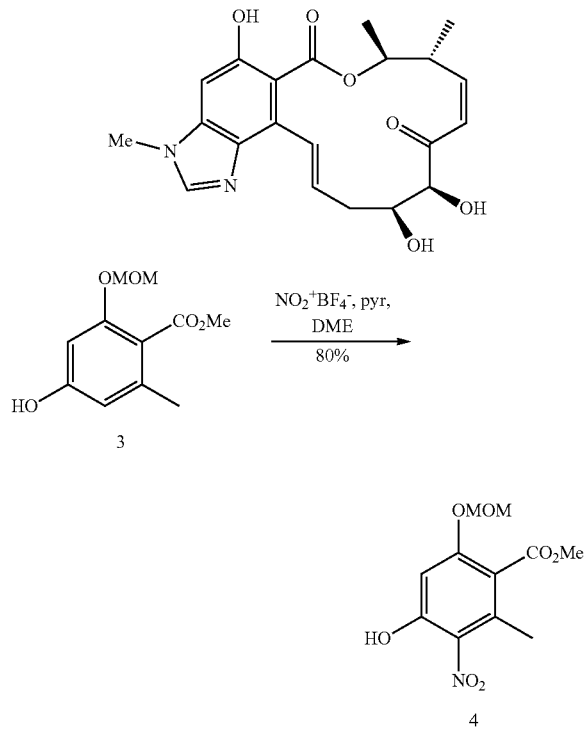

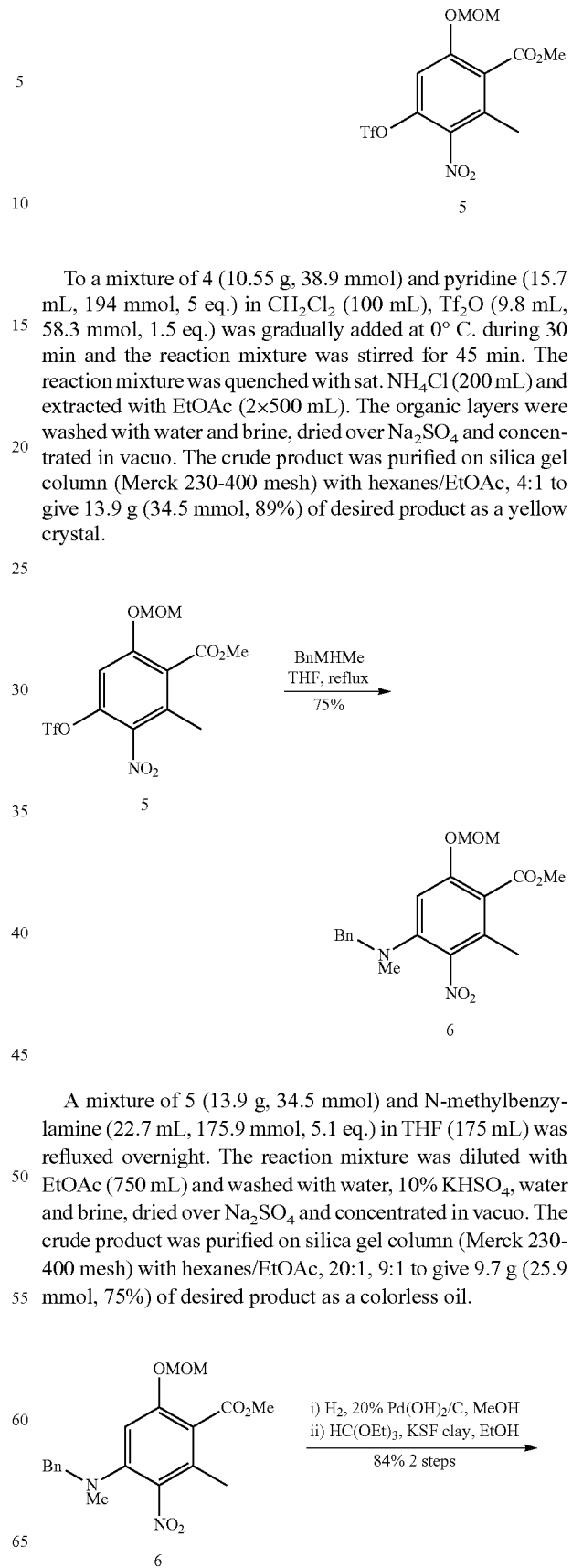

To a solution of 3 (10.0 g, 44.2 mmol) in DME (500 mL), pyridine (5.36 mL, 66.3 mmol, 1.5 eq.) followed by nitronium tetrafluoroborate (8.8 g, 66.3 mmol, 1.5 eq.) were added at −60° C. in dry ice-acetone bath and stirred for 1 h at −50° C. Then, pyridine (5.36 mL, 66.3 mmol, 1.5 eq.) followed by nitronium tetrafluoroborate (8.8 g, 66.3 mmol, 1.5 eq.) were added again at −60° C. in dry ice-acetone bath and stirred for 1 h at −50° C. One more time, pyridine (5.36 mL, 66.3 mmol, 1.5 eq.) followed by nitronium tetrafluoroborate (8.8 g, 66.3 mmol, 1.5 eq.) were added at −60 C in dry ice-acetone bath and stirred for 1 h at −50° C. The reaction mixture was quenched at −58° C. with sat. NH$_4$Cl (1 L) and extracted with EtOAc (2×1 L). The organic layers were washed with water and brine, dried over Na$_2$SO$_4$ and concentrated in vacuo. The crude product was purified on silica gel column (Merck 230-400 mesh) with hexanes/EtOAc, 3:1 to give 9.59 g (35.4 mmol, 80%) of desired product as a yellow crystal.

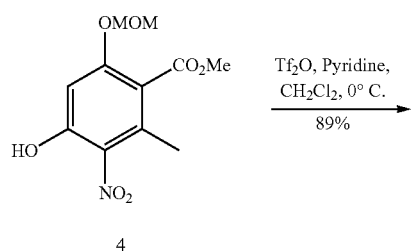

To a mixture of 4 (10.55 g, 38.9 mmol) and pyridine (15.7 mL, 194 mmol, 5 eq.) in CH$_2$Cl$_2$ (100 mL), Tf$_2$O (9.8 mL, 58.3 mmol, 1.5 eq.) was gradually added at 0° C. during 30 min and the reaction mixture was stirred for 45 min. The reaction mixture was quenched with sat. NH$_4$Cl (200 mL) and extracted with EtOAc (2×500 mL). The organic layers were washed with water and brine, dried over Na$_2$SO$_4$ and concentrated in vacuo. The crude product was purified on silica gel column (Merck 230-400 mesh) with hexanes/EtOAc, 4:1 to give 13.9 g (34.5 mmol, 89%) of desired product as a yellow crystal.

A mixture of 5 (13.9 g, 34.5 mmol) and N-methylbenzylamine (22.7 mL, 175.9 mmol, 5.1 eq.) in THF (175 mL) was refluxed overnight. The reaction mixture was diluted with EtOAc (750 mL) and washed with water, 10% KHSO$_4$, water and brine, dried over Na$_2$SO$_4$ and concentrated in vacuo. The crude product was purified on silica gel column (Merck 230-400 mesh) with hexanes/EtOAc, 20:1, 9:1 to give 9.7 g (25.9 mmol, 75%) of desired product as a colorless oil.

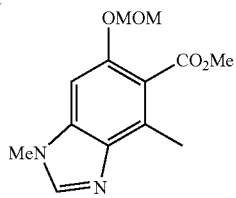

A mixture of 6 (9.2 g, 24.6 mmol) and 20% Pd(OH)₂/C (1.75 g) in EtOH (200 mL) was hydrogenated under 1 atm of hydrogen for 4 hrs. The catalyst was filtered off and the filtrate was concentrated in vacuo. The crude diamine was obtained as yellow oil. It was used without purification.

A mixture of the crude diamine, triethyl orthoformate (13.1 mL, 78.7 mmol, 3.2 eq.) and montmorillonite KSF (2.7 g) in EtOH (200 mL) was refluxed for 100 min.
The insoluble material was filtered off and the filtrate was concentrated in vacuo. The crude product was purified on silica gel column (Merck 230-400 mesh, 350 g) with hexanes/EtOAc, 1:1, 1:2 and EtOAc to give 84% (2 steps) of desired product as a yellow oil.

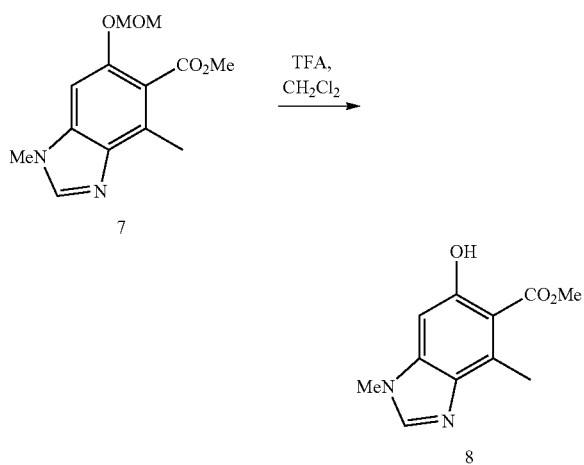

To a solution of 7 (5.75 g, 21.8 mmol) in CH₂Cl₂ (125 mL), TFA (16.8 mL, 218 mmol, 10 eq.) was added at 0° C. Then, the reaction mixture was warmed to room temperature and stirred for 1.5 hrs. The reaction mixture was poured into ice water and neutralized with NaHCO₃ and extracted with EtOAc (800 mL+2×125 mL). The organic layers were washed with water and brine, dried over Na₂SO₄. Na₂SO₄ was filtered and washed with CH₂Cl₂ and the filtrate was concentrated in vacuo. The crude product was obtained as white crystal and use without purification for the next step.

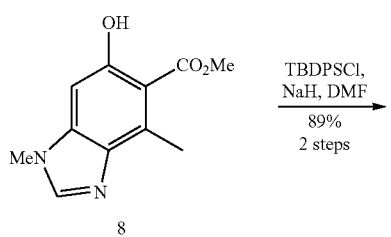

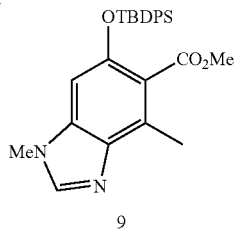

To a mixture of 60% NaH in mineral oil (2.3 g, 56.6 mmol, 2.6 eq.) and DMF (40 mL), a solution of the crude phenol 8 in DMF (60 mL) was gradually added at 0° C. and stirred for 1 hr. Then, TBDPSCl (9.6 mL, 37.0 mmol, 1.7 eq.) was added and the reaction mixture was warmed to room temperature and stirred for 1.5 hr. The reaction mixture was poured slowly in sat. NH₄Cl at 0° C. and extracted with EtOAc (3×150 mL). The organic layers were washed with water (×2) and brine, dried over Na₂SO₄ and concentrated in vacuo. The crude product was purified on silica gel column (Merck 230-400 mesh) with hexane/EtOAc, 3:1, 1:1, 2:3 to give 8.89 g (19.4 mmol, 89% 2 steps) of desired product as a colorless oil.

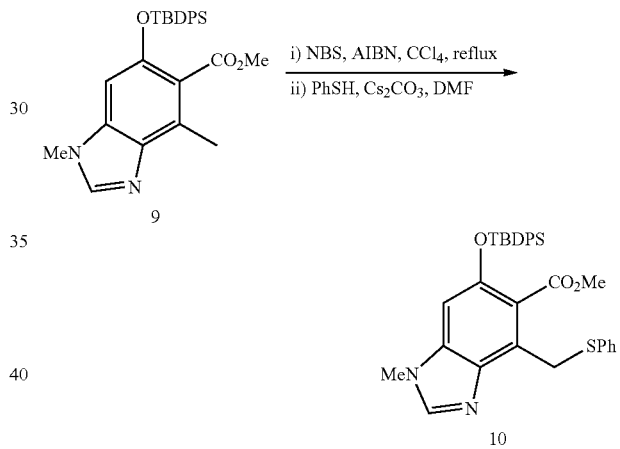

A mixture of 9 (8.39 g, 18.3 mmol), NBS (3.6 g, 20.1 mmol, 1.1 eq.) and AIBN (1.2 g, 7.3 mmol, 0.4 eq.) in CCl₄ (250 mL) was heated slowly to 50° C. and stirred for 4 hrs. The reaction mixture was cooled to room temperature and insoluble material was filtered off with celite, rinsed with CCl₄ and the filtrate was concentrated in vacuo. The crude bromide was used without purification. To a mixture of Cs₂CO₃ (9.2 g, 28.4 mmol, 1.55 eq.) and DMF (90 mL), PhSH (2.9 mL, 28.4 mmol, 1.55 eq.) was added at room temperature and the reaction mixture was stirred for 50 min. Then, a solution of the crude bromide in DMF (210 mL) was added and the reaction mixture was stirred for 1 hr. The reaction mixture was quenched with sat. NH₄Cl (300 mL) and extracted with EtOAc (3×300 mL). The organic layers were washed with water (×2) and brine, dried over Na₂SO₄ and concentrated in vacuo. The crude product was purified on silica gel column (Merck 230-400 mesh, 550 g) with hexanes/EtOAc, 2:1, 1:1, 1:3 to give 8.52 g (15.0 mmol, 82% 2 steps) of desired product.

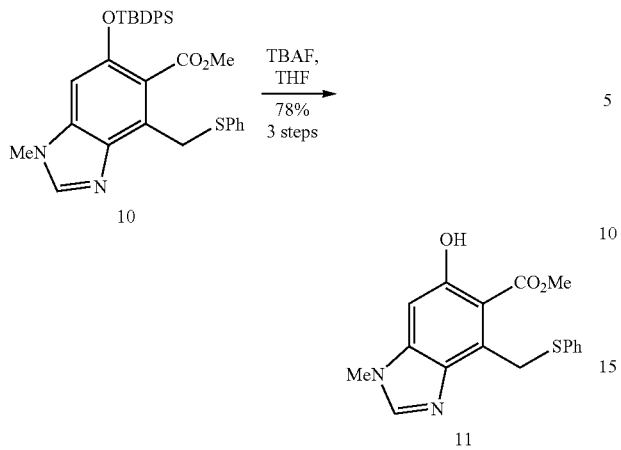

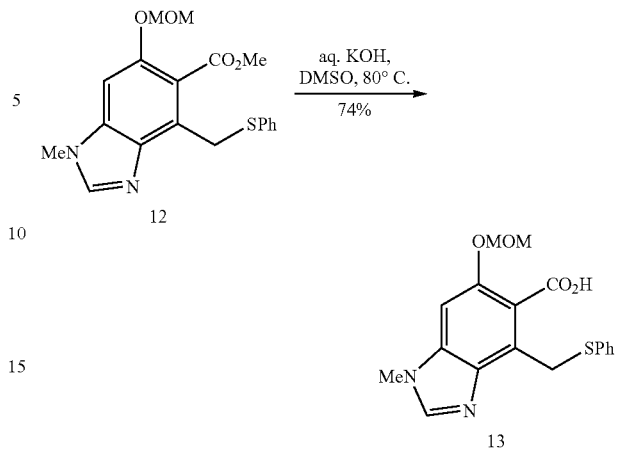

To a solution of 10 (8.47 g, 14.9 mmol) in THF (200 mL), TBAF (1.0M solution in THF, 22.4 mL, 1.5 eq.) was added at 0° C. and the reaction mixture was warmed to room temperature and stirred for 75 min. The reaction mixture was quenched with sat. $NH_4Cl$ (150 mL) and extracted with EtOAc (3×200 mL). The organic layer was washed with water and brine, dried over $Na_2SO_4$ and concentrated in vacuo. The crude product was purified on silica gel column (Merck 230-400 mesh, 550 g) with hexanes/EtOAc, 2:1, 1:1, 1:2 to give 4.7 g (14.3 mmol, 96%) of desired product.

A mixture of 12 (4.5 g, 12.1 mmol), KOH 2M aq sol. (30 mL, 60.4 mmol, 5 eq.) and DMSO (100 mL) was stirred at 80° C. for 1.5 hrs. The reaction mixture was cooled and adjusted to pH5 with 1N HCl (Be careful, MOM group can be easily hydrolyzed if pH too acidic). The resulted crystal (desired product) was filtered and washed water. Total 3.22 g of crude product was obtained.

11) Esterification

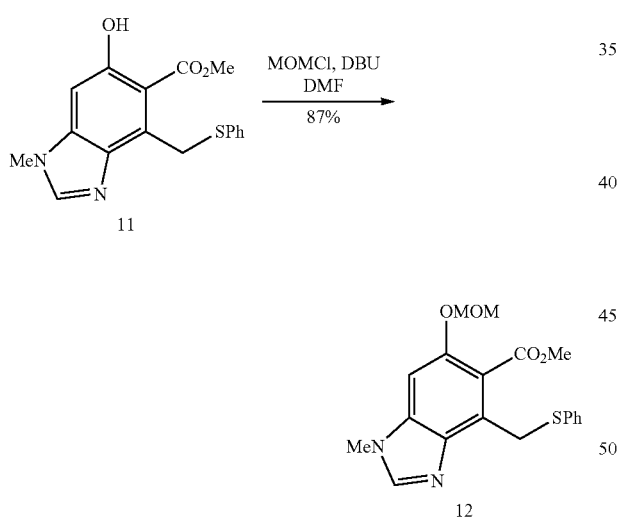

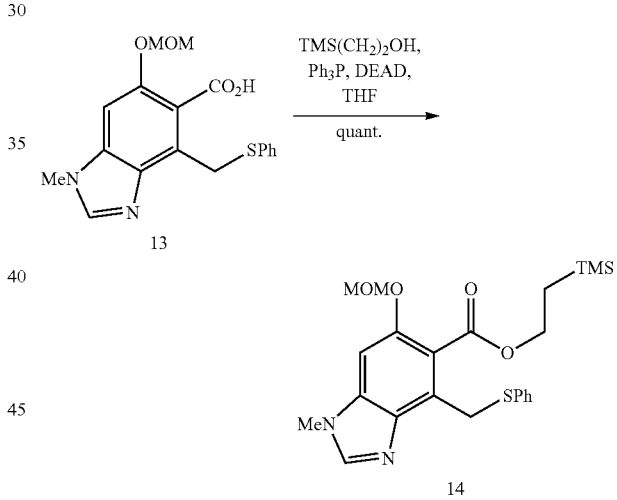

To a solution of phenol 11 (4.41 g, 13.4 mmol) in DMF (100 mL) were added DBU (3.0 mL, 20.1 mmol, 1.5 eq.) and MOMCl (1.5 mL, 20.1 mmol, 1.5 eq.) at rt. and the reaction mixture was stirred for 1.5 hr. Then, DBU (1.5 mL, 10.1 mmol, 0.75 eq.) and MOMCl (0.75 ml, 10.1 mmol, 0.75 eq.) were added and the reaction mixture was stirred for 1 hr.

The reaction mixture was quenched with sat. $NH_4Cl$ (100 mL) and extracted with EtOAc (3×150 mL). The organic layers were washed with water and brine, dried over $Na_2SO_4$ and concentrated in vacuo. The crude product was purified on silica gel column (Merck 230-400 mesh) with hexanes/EtOAc, 1:1, and 1:3 to give 87% of desired product To a solution of $PPh_3$ (2.3 eq) in THF (30 mL), DEAD (2.6 eq.) was added at 0° C. and the reaction mixture was stirred for 30 min. Then, a mixture of 13 (1 eq) and TMS ethanol (1.5 eq.) in THF (50 mL) was added and the reaction mixture was warmed to room temperature and stirred for overnight. Furthermore, $PPh_3$ (2.3 eq.) and DEAD (2.6 eq.) was added and stirred for 10 min. Then, TMS ethanol (1.5 eq.) was added and stirred for 20 min. The reaction mixture was concentrated in vacuo. $Et_2O$ was added to the residue and stirred. The resulted solid ($Ph_3P(O)$) was filtered off and the filtrate was concentrated in vacuo. The crude product was purified on silica gel column (Merck 230-400 mesh) with $CH_2Cl_2$/MeOH, 200:1, 100:1 to give a mixture of desired product and 1,2-dicarbethoxyhydrazine (not separated). This mixture was purified on silica gel column (Merck 230-400 mesh) with hexanes/EtOAc, 2:1, 1:1, and 2:3 to give the desired product as white crystal.

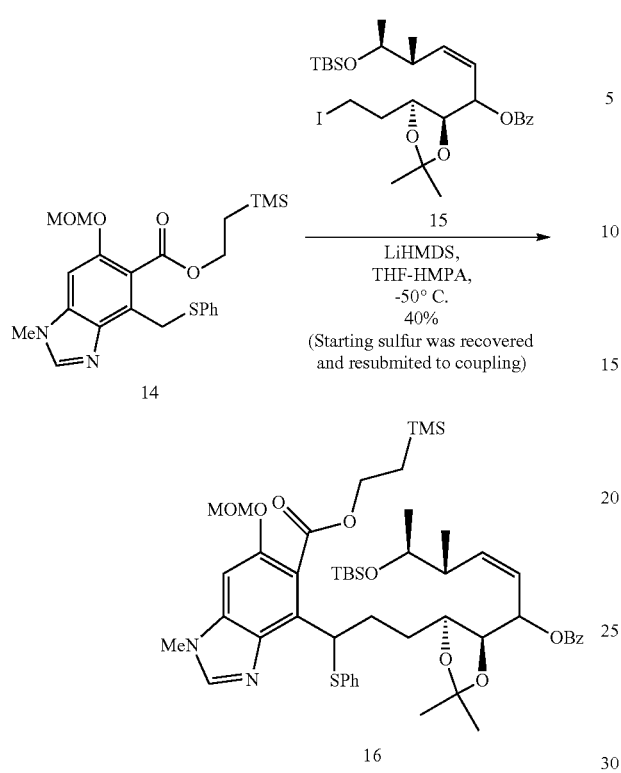

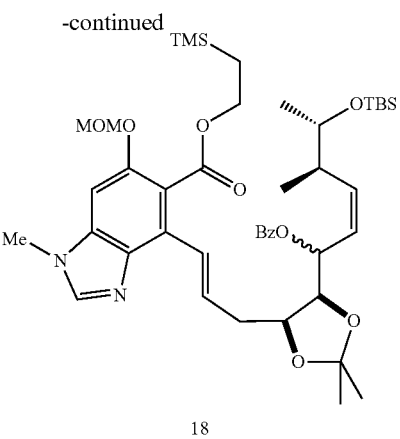

To a solution of 14 (730 mg, 1.59 mmol, 1.5 eq.) and iodide 15 (639 mg, 1.06 mmol, 1 eq.) in dry THF (25 mL)-HMPA (2.5 mL), LiHMDS (1.0M solution in THF, 2.65 mL, 2.5 eq.) was added over a period of 25 min at −50° C. and the reaction mixture was for 30 min. Then, LiHMDS (1.0M solution in THF, 1.3 mL, 1.25 eq.) was added at −50° C. and the reaction was stirred for 1 hr. The reaction mixture was quenched with sat. NH$_4$Cl (50 mL) and extracted with EtOAc (3×50 mL). The organic layer was washed with water and brine, dried over Na$_2$SO$_4$ and concentrated in vacuo. The crude product was purified on silica gel column (Merck 230-400 mesh) with hexanes/EtOAc, 4:1, 1:1, 1:3 to give 440 mg (0.471 mmol, 44%) of desired product as a colorless amorphous.

To a solution of 16 (980 mg, 1.22 mmol) in CH$_2$Cl$_2$ (45 mL), mCPBA (0.5 eq calculated if mCPBA was 100%, 91 mg) was added at 0° C. and stirred for 25 min, then mCPBA (91 mg) was added and stirred for 25 min, mCPBA (45 mg) was added and stirred for 25 min, mCPBA (35 mg) was added and stirred for 20 min. The reaction mixture was quenched with sat. Na$_2$S$_2$O$_3$ (80 mL) and extracted with EtOAc (400 ml+2×80 mL). The organic layer was washed with sat. NaHCO$_3$ (×2) and brine, dried over Na$_2$SO$_4$ and concentrated in vacuo to give 1.02 g of crude sulfoxide as colorless amorphous.

A solution of crude sulfoxide and Et$_3$N (10 drops) in toluene (50 mL) was refluxed for 1 hr. The reaction mixture was concentrated in vacuo and the crude product was purified on silica gel column (Merck 230-400 mesh) with hexanes/EtOAc, 3:1, 1:1, 1:3 to give 980 mg (1.19 mmol, 98% 2 steps) of desired product as colorless amorphous.

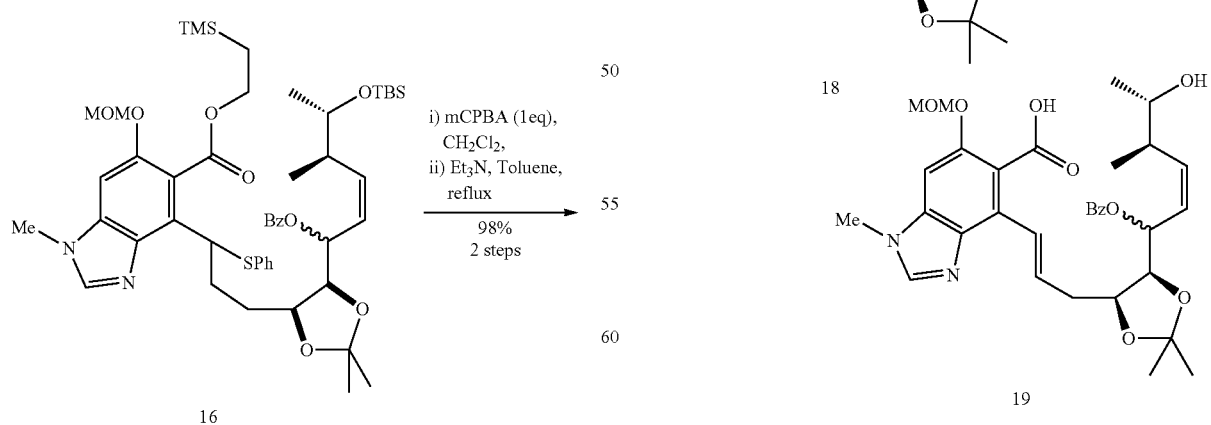

To a solution of 18 (924 mg, 1.12 mmol) in THF (25 mL), Imidazole HCl (293 mg, 2.8 mmol, 2.5 eq) and TBAF (1.0M solution in THF, 5.6 ml, 5 eq) were added and the mixture was heated to 50° C. After 1 hr and 3 hrs, Imidazole HCl (293 mg, 2.8 mmol, 2.5 eq.) and TBAF (1.0M solution in THF, 5.6 mL, 5 eq.) were added. After 24 hrs, TBAF (1.0M solution in THF, 11.2 mL, 10 eq) was added and the reaction mixture was stirred for 84 hrs at 50° C. The reaction mixture was quenched with sat. NH$_4$Cl (40 mL) and saturated with NaCl (10 mL) and extracted with EtOAc (5×100 mL). The organic layers were dried over Na$_2$SO$_4$ and concentrated in vacuo. The crude product was purified on silica gel column (Merck 230-400 mesh) with EtOAc, EtOAc/MeOH, 99:1, 95:5 to give 740 mg of desired product (not pure) as a colorless amorphous.

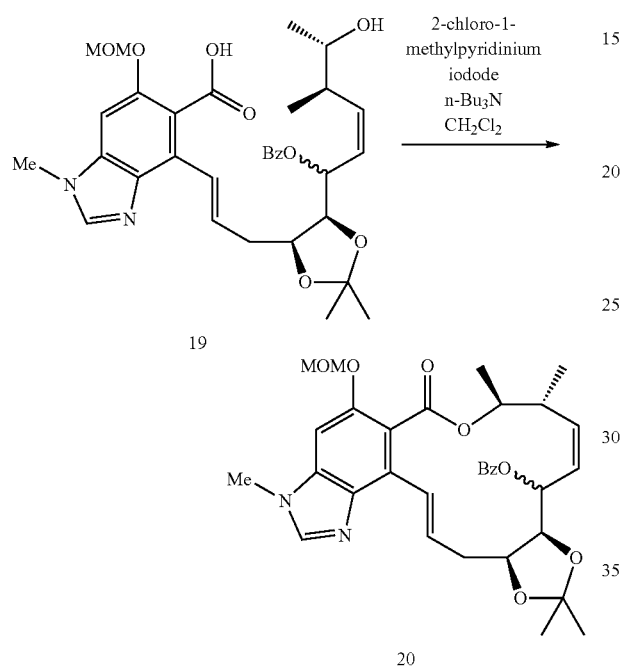

To a refluxed mixture of 2-chloro-1-methylpyridinium iodide (4.21 mmol, 4.0 eq.) and n-Bu$_3$N (1.0 mL, 4.21 mmol, 4 eq.) in CH$_2$Cl$_2$ (50 mL), a solution of 19 (640 mg, 1.05 mmol) in CH$_2$Cl$_2$ (25 mL) was added drop-wise with syringe pump during 1 hr and then the reaction mixture was stirred for 30 min. The reaction mixture was concentrated in vacuo and the residue was diluted with EtOAc (750 mL), washed with water, sat. NH$_4$Cl, water and brine, dried over Na$_2$SO$_4$, filtered and concentrated in vacuo. The crude product was purified on silica gel column (Merck 230-400 mesh) with hexanes/EtOAc, 1:1, 1:5 CH$_2$Cl$_2$/MeOH, 95:5 to give 560 mg of desired product (not pure) as colorless amorphous.

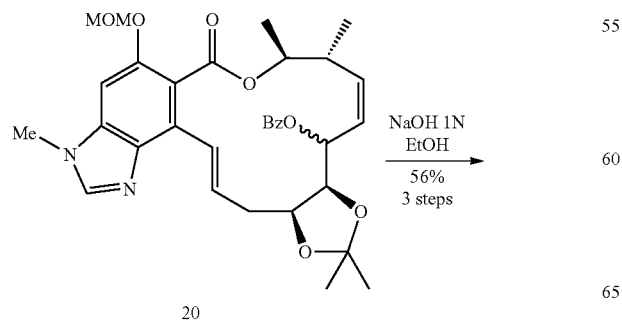

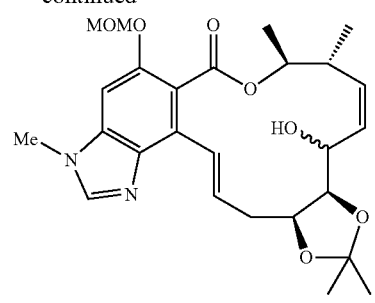

The hydrolysis was carried out as it described before in the synthesis of ER803064.

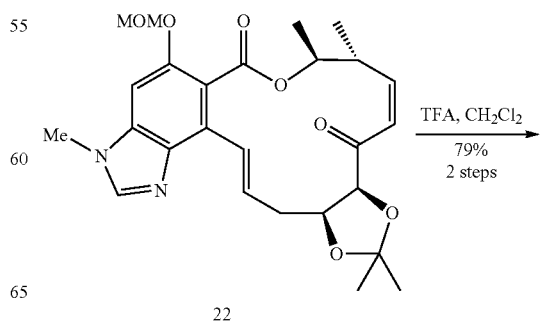

To a solution of 21 (260 mg, 0.596 mmol) in CH$_2$Cl$_2$ (45 mL), powdered Molecular Sieves 4 A (640 mg) and PCC (642 mg, 2.98 mmol, 5 eq.) were added at room temperature and the reaction mixture was stirred for 1 hrs. The reaction mixture was filtered through Celite and the filtrate was concentrated in vacuo. The crude product was purified on silica gel column (Merck 230-400 mesh) with CH$_2$Cl$_2$/MeOH, 99:1, 95:5 to give 185 mg of desired product (including pyridinium impurity).

503

-continued

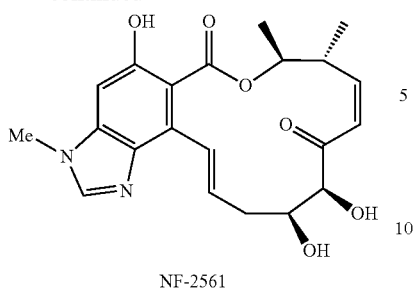

NF-2561

To a solution of 22 (185 mg, 0.382 mmol) in CH₂Cl₂ (10 mL), TFA (0.88 mL, 11.5 mmol, 30 eq.) was added at 0° C. and the reaction mixture was warmed to room temperature and stirred for 1.5 hrs. The reaction mixture was concentrated in vacuo. The crude product was purified on silica gel column (Merck 230-400 mesh) with CH₂Cl₂/MeOH, 98:2, 95:5, 92:8 to give 120 mg (0.300 mmol, 79%, 50% 2 steps) of desired product, NF2561. The pure product was lyophilized with Water/MeCN, 1:1 to give a white foam.

ER805911 and ER805977:

ER805911

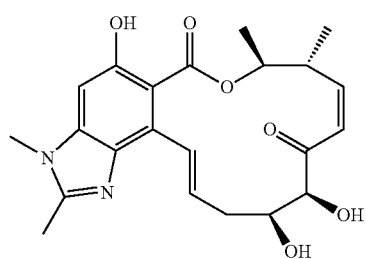

ER805977

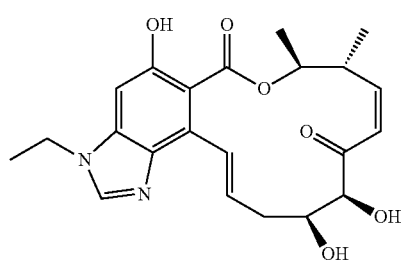

These analogs were prepared using appropriate alternative reagents using the above synthesis. The modified steps are described below:

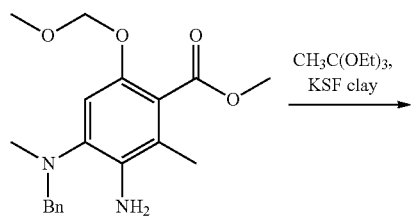

CH₃C(OEt)₃, KSF clay →

504

-continued

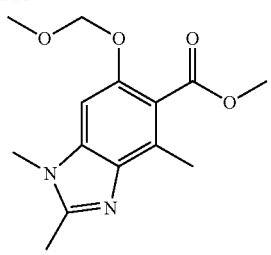

A mixture of the crude diamine (24.5 mmol), triethyl acetylformate (13.5 mL, 3 eq.) and montmorillonite KSF (2.5 g) in EtOH (150 mL) was refluxed for 2 h. The insoluble material was filtered off and the filtrate was concentrated in vacuo. The crude product was purified on silica gel column (Merck 230-400 mesh, 350 g) with hexane/EtOAc, 1:1, 1:2 and EtOAc to give 81% (2 steps) of desired product as yellow oil. The product was carried forward in an analogous manner as described for NF2561 to give ER805911.

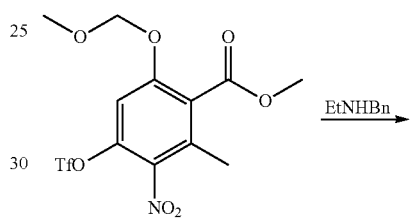

A mixture of triflate (9.3 g, 23 mmol) and N-ethylbenzylamine (15.2 mL, 117.8 mmol, 5.1 eq.) in THF (175 mL) was refluxed 26 h. The reaction mixture was diluted with EtOAc (750 mL) and washed with water, 10% KHSO₄, water and brine, dried over Na₂SO₄ and concentrated in vacuo. The crude product was purified on silica gel column (Merck 230-400 mesh) with hexane/EtOAc, 20:1, 9:1 to give 6.25 g (16.1 mmol, 70%) of desired product as a colorless oil. It was carried forward similarly as described for NF2561 to give ER805977.

Preparation of C10 Analogs, ER804747:

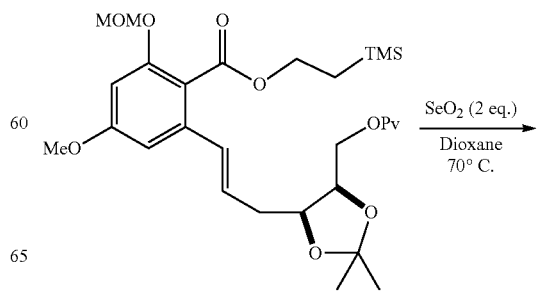

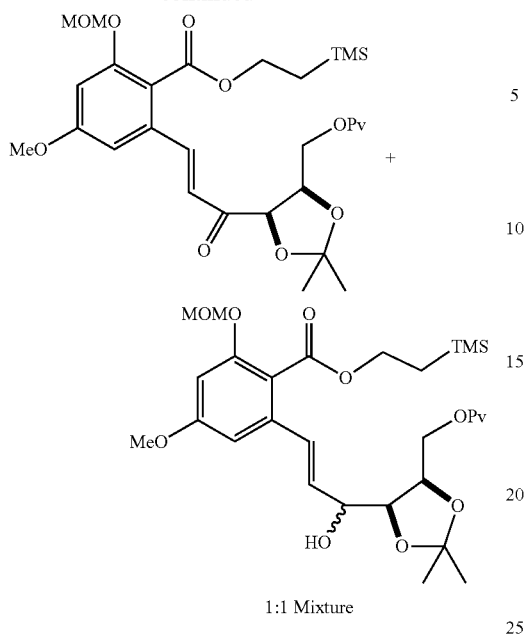

1:1 Mixture

The suspension of selenium dioxide (677 mg) and 531-YW-4 (1.96 g) in dioxane (30 mL) was kept at 70° C. for 10 hours. The mixture was concentrated and purified with flush chromatograph (hexanes/acetate 5/1 to 2/1) to give 593-YJ-22-1 (396 mg) and 593-YJ-22-2 (683 mg).

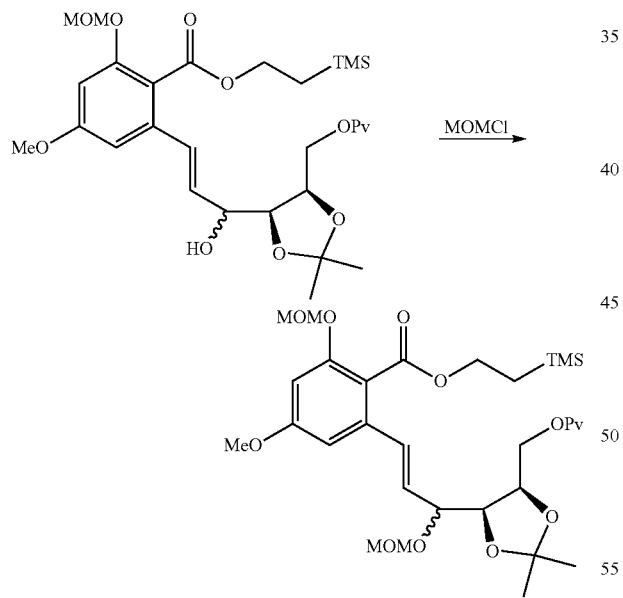

Sodium hydride (60%, 59 mg) was added to the solution of 593-YJ-22-2 (788 mg) in DMF (15 mL), followed by the addition of methoxymethyl chloride (160 mg) at room temperature. The mixture was kept stirring at room temperature overnight and quenched with aqueous ammonium chloride. The aqueous phase was extracted with ether and the combined organic phase was concentrated. The residue was purified by flush chromatograph (hexane/acetate 4/1) to yield 593-YJ-25 (431 mg).

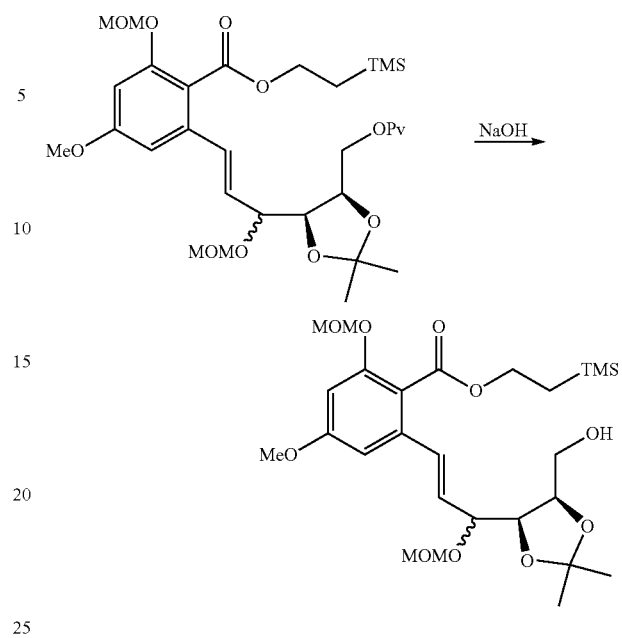

The solution of 593-YJ-25 (431 mg) and sodium hydroxide (1.0 N, 1.0 mL) in ethanol (5 mL) was kept stirring overnight at room temperature. The mixture was concentrated and diluted with aqueous ammonium chloride. The aqueous phase was extracted with ether and the combined organic phase was concentrated. The residue was purified by TLC (hexanes/acetate 2/1) to yield 593-YJ-29 (184 mg).

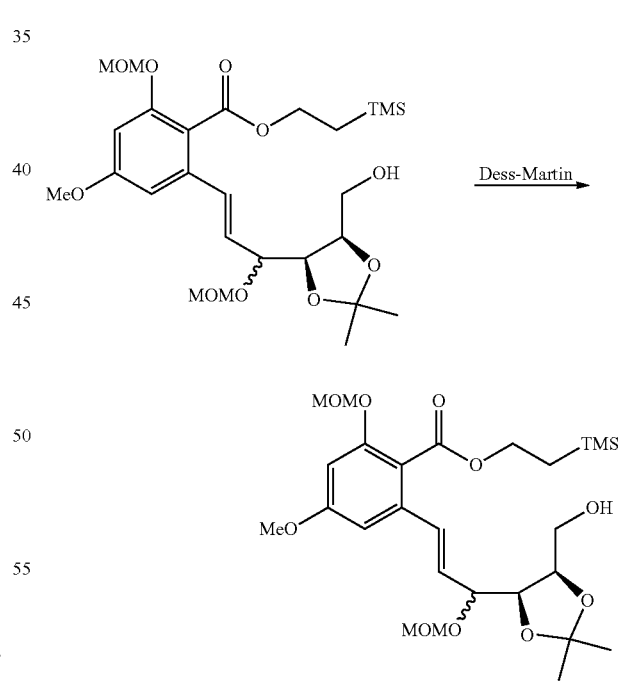

Dess-Martin periodinane was added to 593-YJ-29 (184 mg) in methylene chloride (10 mL) at room temperature. The mixture was diluted with ether in 2 hours and filtrated through Celite. The filtrate was concentrated and the residue was purified by TLC (hexanes/acetate 2/1) to give 593-YJ-31 (138 mg).

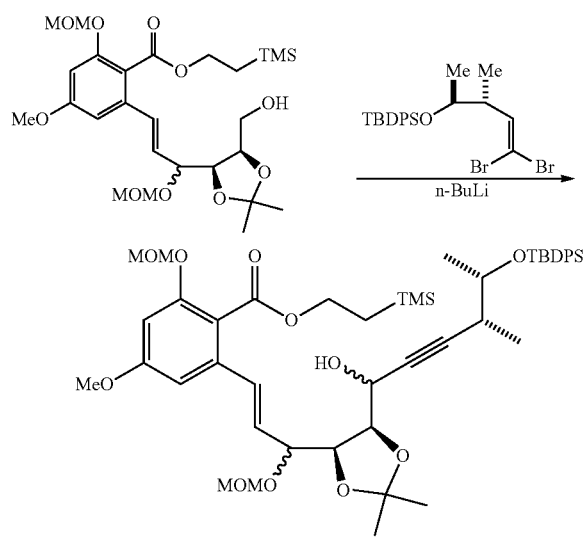

n-Butyllithium (2.5 M, 0.56 mL) was added to 554-RB-228 (450 mg) in THF (5 mL) at −78° C. After one hour 593-YJ-31 (138 mg) was added. The reaction was kept at 0° C. for one hour and warmed to room temperature before it was quenched with aqueous ammonium chloride. The aqueous phase was extracted with ether and the combined organic phase was dried over sodium sulfate. The solvent was stripped off and the residue was purified with TLC (hexane/acetate 3/1) to 593-YJ-32 (168 mg, 75%).

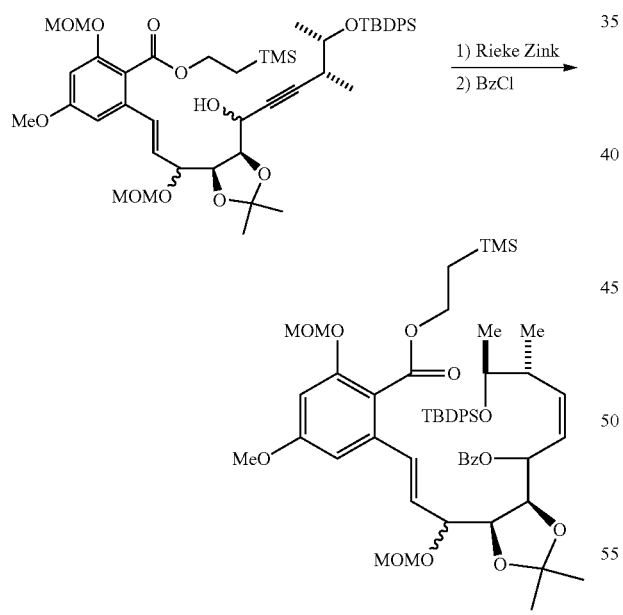

The suspension of Rieke zink and 593-YJ-32 (168 mg) in methanol (10 mL) and water (1.0 mL) was kept at 70° C. for 4 hours. The mixture was filtrated through Celite and dried over sodium sulfate. The organics was concentrated and further dried azeotropically to give 593-YJ-33 (200 mg). The crude 593-YJ-33 was subjected to triethylamine (2.7 mL) and benzoyl chloride (1.1 mL) and purified with TLC (hexanes/acetate 4/1) to give 593-YJ-35 (358 mg).

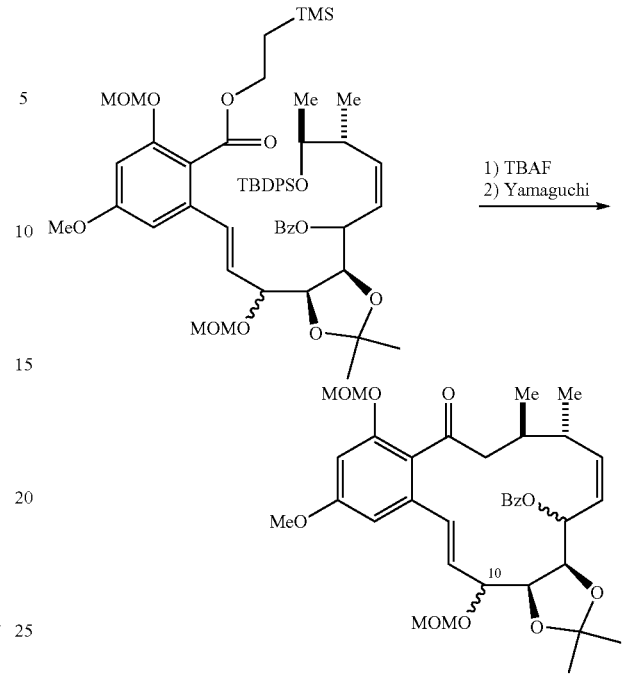

The solution of 593-YJ-35 (358 mg) and imidazole hydrochlorite buffered TBAF (1.0 M, 0.96 mL) in THF (10 mL) was kept stirring overnight at 50° C., and then diluted with water. The aqueous phase was extracted with ether and concentrated. The residue was purified with TLC (methylene chloride/methanol, 10/1) to give 593-YJ-36 (41 mg).

593-YJ-36 (41 mg) was added to the reflux of 2-chloro-1-methylpyridium iodide (52 mg) and tributylamine (43 mg) in methylene chloride (20 ml). After 2 hours reflux the mixture was stirred overnight. The mixture was diluted with ether and washed with HCl (1.0 N) and water. The residue was purified with TLC (hexane/acetate 1/1) to give 593-YJ-39-1 (4.3 mg).

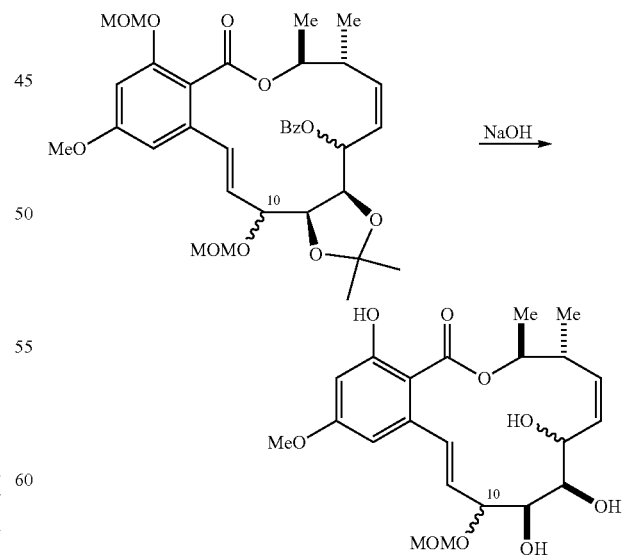

The solution of 593-YJ-39 (4.3 mg) and sodium hydroxide (1.0 N, 1.0 mL) in ethanol (5 mL) was kept stirring overnight at room temperature. The mixture was concentrated and diluted with aqueous ammonium chloride. The aqueous phase was extracted with ether and the combined organic phase was concentrated. The residue was purified by TLC (hexanes/acetate 2/1) to yield 593-YJ-57 (4.0 mg).

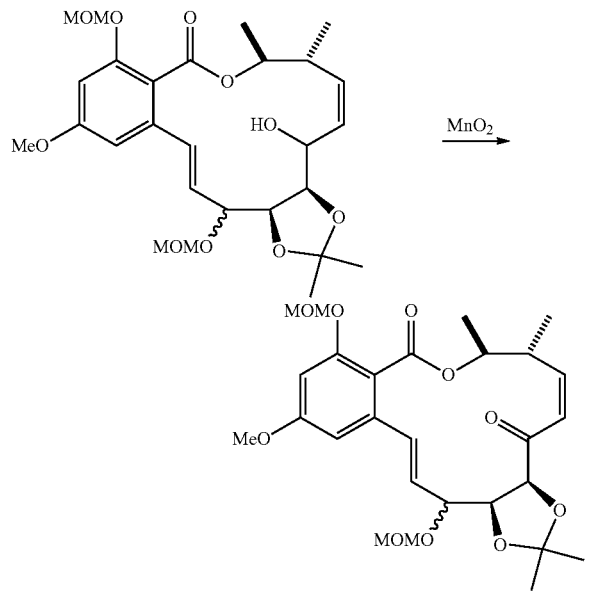

The suspension of MnO, (90%, 15 mg) and 593-YJ-57 (4.0 mg) in methylene chloride (2 mL) was kept stirring overnight. The mixture was filtrated through Celite and concentrated. The residue was purified with TLC (hexanes/acetate 2/3) to give 593-YJ-58 (2.0 mg).

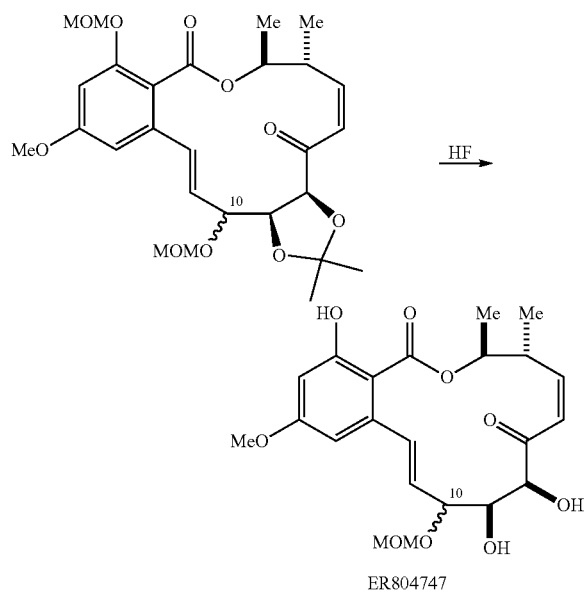

Hydrofluoric acid (49%, 0.6 mL) was added to 593-YJ-58 (2.0 mg) in acetonitrile (1.5 mL) and stirred for 20 minutes. The mixture was diluted with water and extracted with methylene chloride. The organic phase was concentrated and purified with a short silica gel pad to produce 593-YJ-59 (0.5 mg, ER-804747).

Preparation of C15-Methoxy-Analog, NF1872

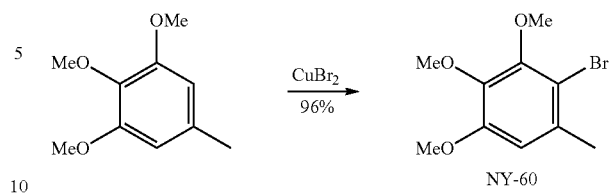

To a solution of 3,4,5-trimethoxytoluene (5.47 g, 30 mmol) in DME (80 mL), $CuBr_2$ (6.8 g, 30.45 mmol) was gradually added and the mixture was stirred at room temperature for 30 min. Then, CuBr2 (8.4 g, 37.61 mmol) was added in several times. The mixture was stirred for 12 hrs. The insoluble material was filtered and the filtrate was concentrated. The crude product was purified on silica gel column with hexane/EtOAc, 4:1 to give 7.5 g of NY-60.

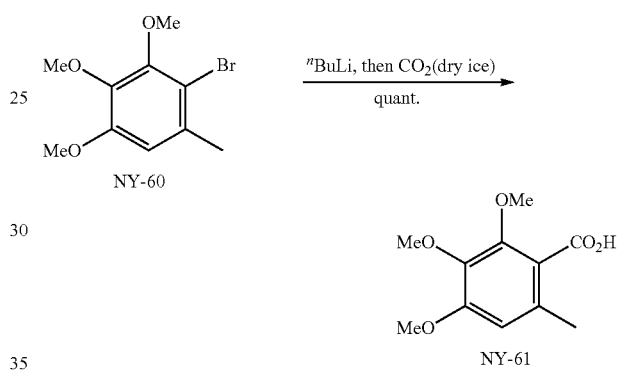

NY-60 (7.39 g, 28.3 mmol) was dissolved in $Et_2O$ (300 mL) and cooled to −78° C., under nitrogen. Then, n-BuLi (1.6M/hexane, 21 mL, 33.6 mmol) was slowly added and the reaction was stirred at −78° C. for 40 min. Dry ice was added to the solution, then the solution was allowed to warm to rt and was stirred for 15 min. The mixture was quenched with water, acidified with 2N HCl, extracted with EtOAc (×2). The organic layers were washed with water, brine and dried over $MgSO_4$, filtered and concentrated to give 6.38 g of NY-61.

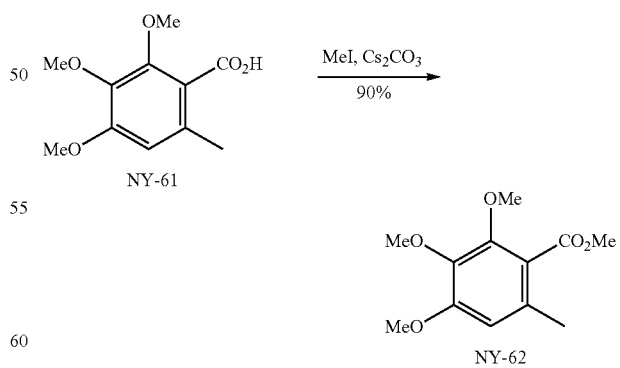

To a solution of NY-61 (6.37 g, 28.16 mmol) in DMF (200 mL), $Cs_2CO_3$ (9.17 g, 28.14 mmol) was added and stirred at room temperature for 10 min. Then, MeI (10 mL, 160.6 mmol) was added and the reaction mixture was stirred for 12 hrs. The reaction mixture was poured into ice-cooled sat.

NH₄Cl and extracted with EtOAc (×3). The organic layers were washed with water (×3), brine, dried over Na₂SO₄, filtered and concentrated. The crude product was purified on silica gel column with hexane/EtOAc, 4:1 to give 6.07 g of NY-62.

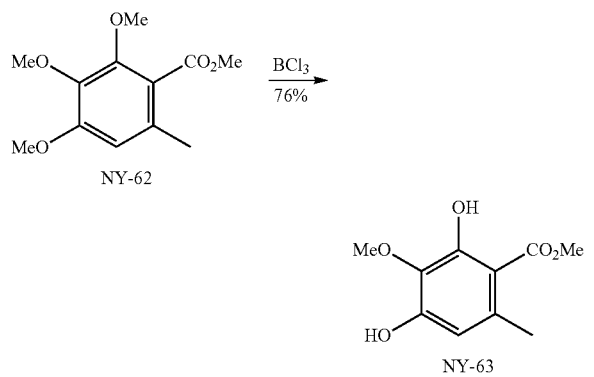

NY-62 (6.07 g, 25.26 mmol) was dissolved in CH₂Cl₂ (80 mL) and cooled to −78° C., under nitrogen. Then, BCl₃ (1M/ CH₂Cl₂, 26 mL, 26 mmol) was slowly added and the reaction was stirred at −78° C. for 1 hr. The solution was stirred at 0° C. for 15 min, at room temperature for 1 hr. To the mixture which was recooled to −78° C., additional BCl₃ (1M/CH₂Cl₂, 52 mL, 52 mmol) was slowly added and the solution was allowed to warm to room temperature and was stirred for 15 hrs. The reaction mixture was poured into ice-water and extracted with EtOAc (×2). The organic layers were washed with water (×2), brine, dried over MgSO₄, filtered and concentrated. The crude product was purified by recrystallization from hexane/EtOAc to give 4.1 g of NY-63.

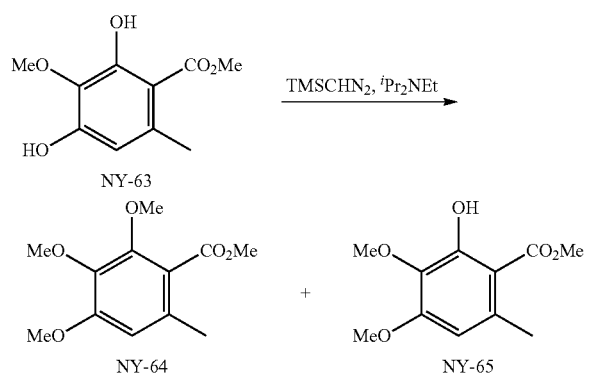

To a mixture of NY-63 (4.09 g, 19.27 mmol), MeOH (1.77 m L), ⁱPr₂NEt (3.7 mL, 21.24 mmol) and MeCN (80 mL), trimethylsilyldiazomethane (2M/hexane, 10.6 mL, 21.2 mmol) gradually added at 30° C. The reaction mixture was allowed to warm to room temperature and stirred for 24 hrs. The reaction mixture was quenched with water and diluted with EtOAc. The organic layer was washed with 10% citric acid and the aqueous layer was reextracted with EtOAc. The organic layers were washed with water, brine, dried over Na₂SO₄, filtered and concentrated. The crude product was purified on silica gel column with hexane/EtOAc, 20:1, 15:1, 10:1 to give 2.29 g of mixture of NY-64 and NY-65.

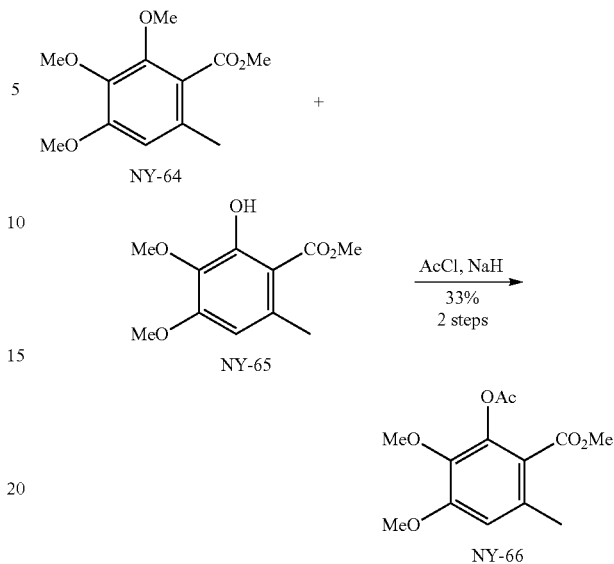

Using same procedure for NY-07, NY-65 was converted to NY-66 (1.73 g). (NY-64 was separated by column chromatography)

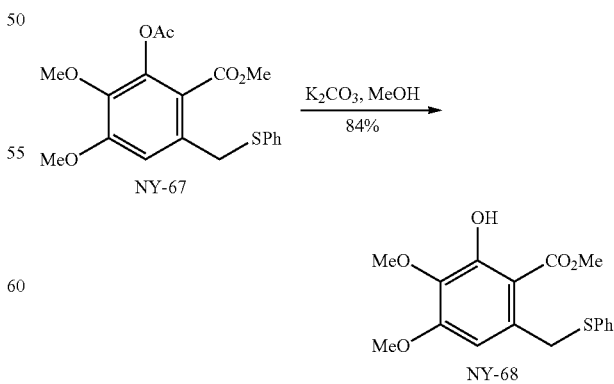

Using same procedure for 10, NY-66 (1.72 g, 6.41 mmol) was converted to NY-67 (2.07 g).

Using same procedure for NY-09, NY-67 (2.06 g, 5.47 mmol) was converted to NY-68 (1.54 g).
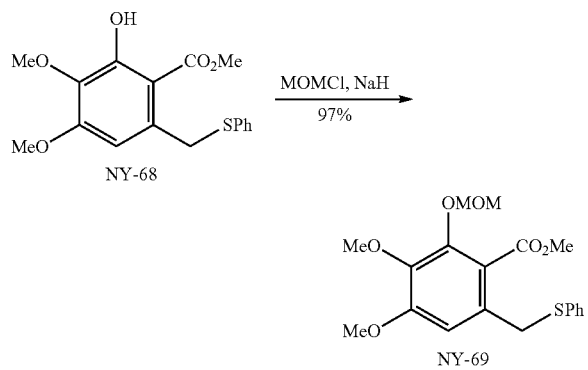
Using same procedure for 509-HD-209, NY-68 (1.48 g, 4.43 mmol) was converted to NY-69 (1.62 g).
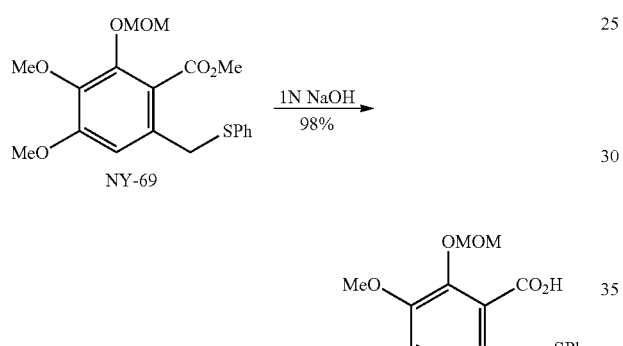
Using same procedure for 509-HD-212, NY-69 (1.62 g, 4.28 mmol) was converted to NY-70 (1.53 g).
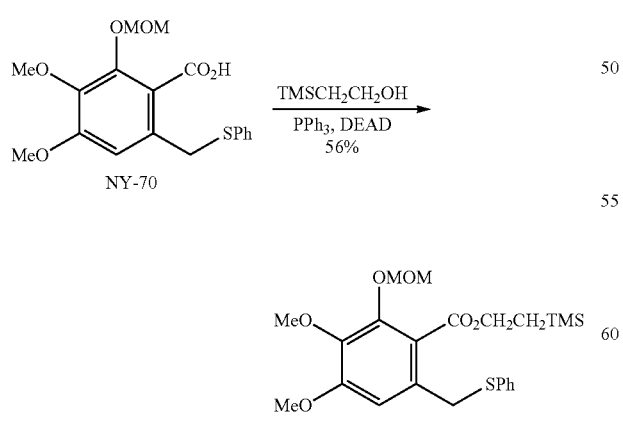
Using same procedure for 509-HD-213, NY-70 (1.51 g, 4.14 mmol) was converted to NY-71 (1.08 g).
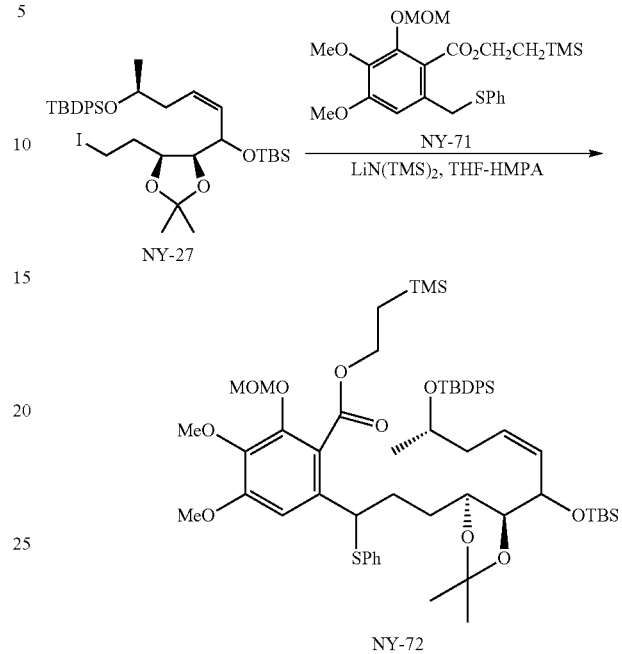
Using same procedure for 16, NY-27 (511 mg, 0.707 mmol) was converted to NY-72 (971 mg).
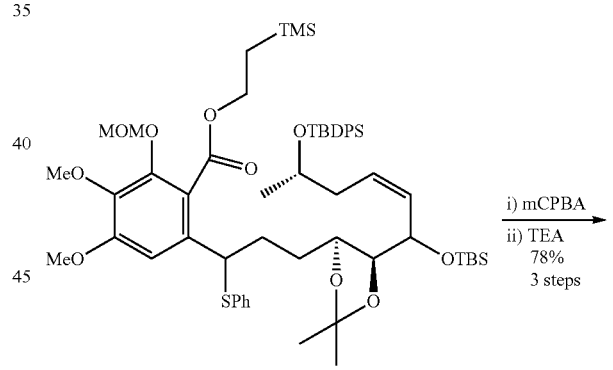
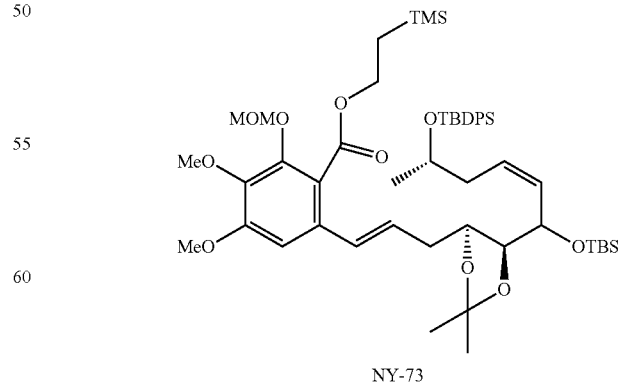

Using same procedure for 18, NY-72 (971 mg, 0.707 mmol) was converted to NY-33 (521 mg).
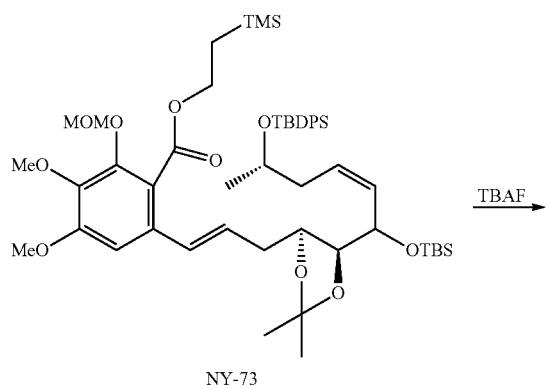
NY-73
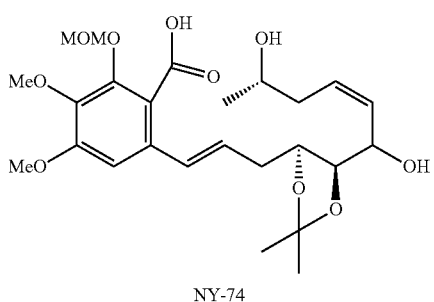
NY-74
Using same procedure for 509-HD-116, NY-73 (521 mg, 0.549 mmol) was converted to NY-74 (444 mg). NY-74 was used without purification for the next step.
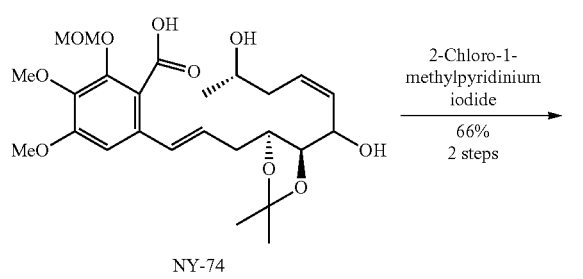
NY-74
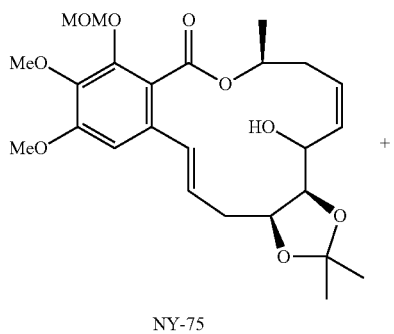
NY-75
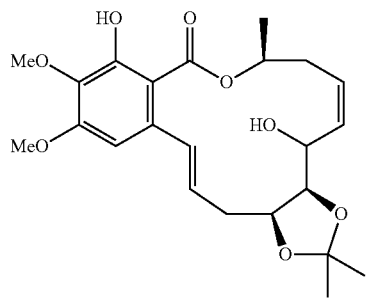
NY-76
Using same procedure for 509-HD-118, NY-74 (444 mg, 0.549 mmol)
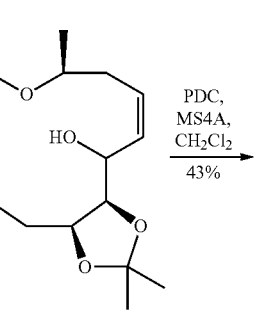
NY-75
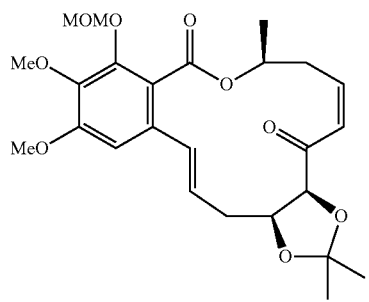
NY-77
was converted to NY-75 (86 mg) and NY-76 (114 mg).
Using same procedure for TM-13, NY-75 (45 mg, 0.094 mmol) was converted to NY-77 (19.2 mg).
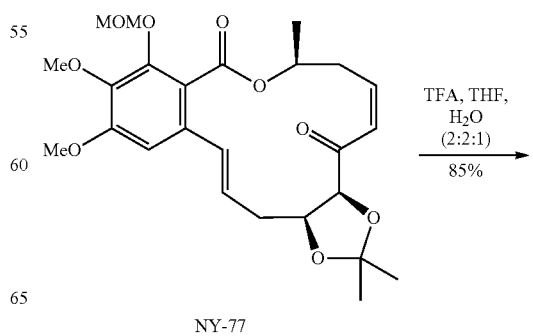
NY-77

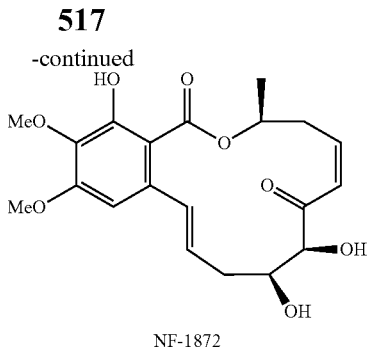

NF-1872

Using same procedure for NF-0675, NY-77 (18 mg, 0.038 mmol) was converted to NF-1872 (12.6 mg).

Preparation of C16 Analogs: NF0934, NF1418 and NF1419

Synthetic Procedure for NF-0934

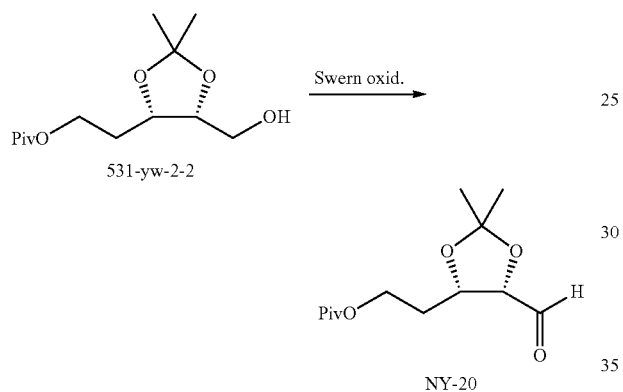

Using same procedure for 554-RB-238, 531-yw-2-2 (5 g, 19.21 mmol) was converted to NY-20 (5.08 g). NY-20 was used without purification for the next step.

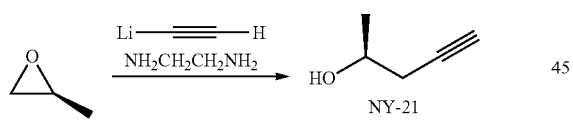

To a suspension of lithium acetylide-ethylenediamine complex (24.92 g, 0.271 mol) in DMSO (250 mL), (S)-propylene oxide (14.3 g, 0.246 mol) was slowly added at 0° C. Then, the mixture was warmed to room temperature and stirred for 24 hrs. The mixture was poured into ice-water and extracted with Et₂O (×4). The organic layers were washed with sat. NH₄Cl, brine and dried over MgSO₄, filtered and concentrated. The crude product was used without purification for the next step.

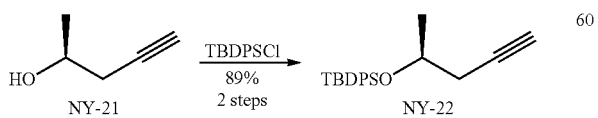

Using same procedure for 554-RB-225, NY-21 (8 g, 95.1 mmol) was converted to NY-22 (27.33 g).

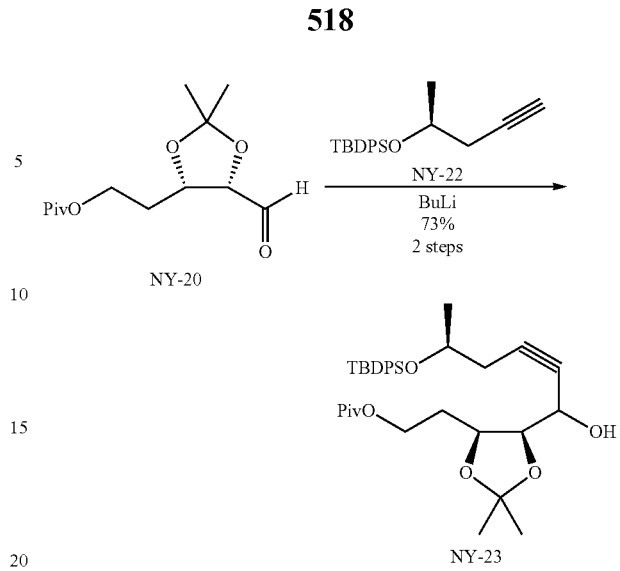

Using same procedure for NY-01, NY-20 (5.08 g, 19.21 mmol) was converted to NY-23 (4.22 g) as one of diastereomers.

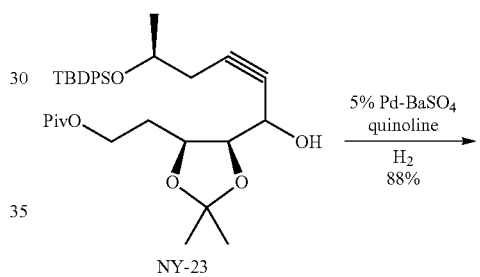

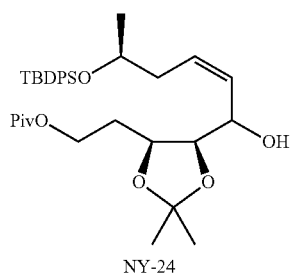

Using same procedure for 343-yw-279, NY-23 (4.2 g, 7.23 mmol) was converted to NY-24 (3.7 g).

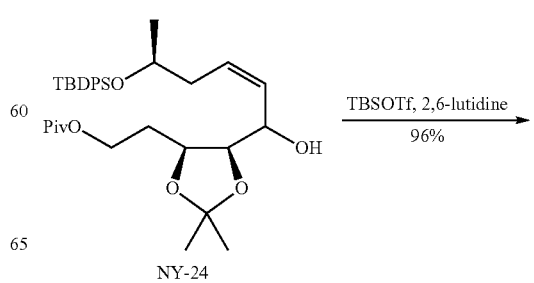

-continued

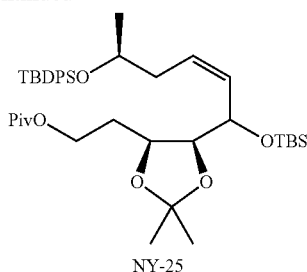

NY-25

To a solution of NY-24 (3.69 g, 6.33 mmol) in CH$_2$Cl$_2$ (70 mL), 2,6-lutidine (3.7 mL, 31.8 mmol) and TBSOTf (3.63 mL, 15.8 mmol) were added at 0° C. Then, the mixture was warmed to room temperature and stirred for 30 min. The mixture was quenched with MeOH and poured into cold sat. NaHCO$_3$ and extracted with EtOAc. The organic layer was washed with water, 5% citric acid, water, sat. NaHCO$_3$, brine and dried over Na$_2$SO$_4$, filtered and concentrated. The crude product was purified on silica gel column with hexane/EtOAc, 100:1, 50:1, 30:1 to give 4.23 g of NY-25.

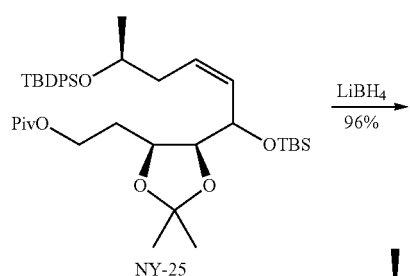

NY-25 (4.2 g, 6.03 mmol) was dissolved in dry Et$_2$O (50 mL) and the solution was cooled to 0° C. in ice/water bath. Then LiBH$_4$ (135 mg, 6.2 mmol) was added portionwise, the mixture was allowed to warm slowly to rt and stirred for 2 days after which a saturated solution of NH$_4$Cl was added slowly. The mixture was extracted with EtOAc and the organic extract was washed with a saturated solution of NH$_4$Cl, water, brine, dried with anhydrous Na$_2$SO$_4$, filtered and concentrated. The crude product was purified on silica gel column with hexane/EtOAc, 8:1 to give 3.55 g of NY-26.

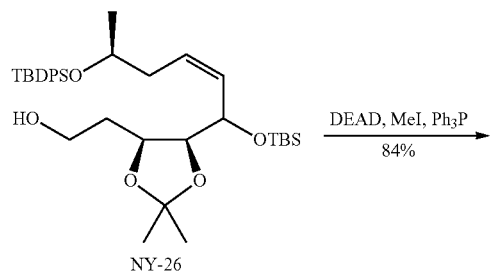

-continued

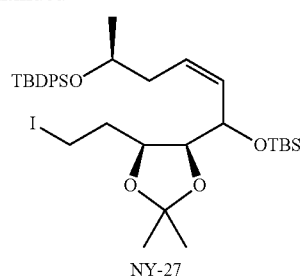

NY-27

Using same procedure for 554-RB-260, NY-26 (568 mg, 0.927 mmol) was converted to NY-27 (565 mg).

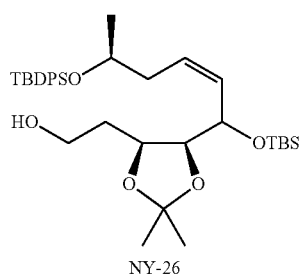

Using same procedure for 10, NY-28 (2.7 g, 15 mmol) was converted to NY-29 (2.45 g).

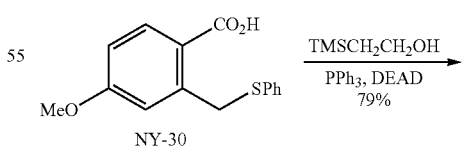

Using same procedure for 509-HD-212, NY-29 (2.45 g, 8.5 mmol) was converted to NY-11 (2.19 g).

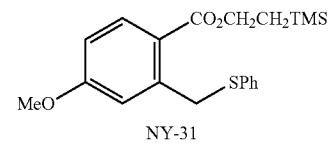

Using same procedure for 509-HD-213, NY-30 (2.18 g, 3.06 mmol) was converted to NY-31 (2.35 g).

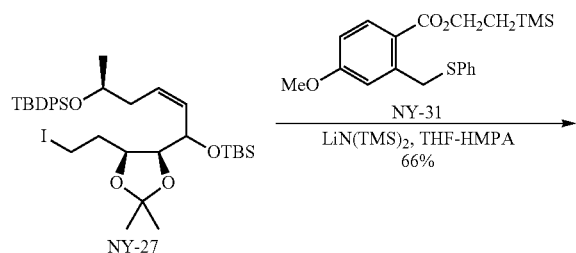
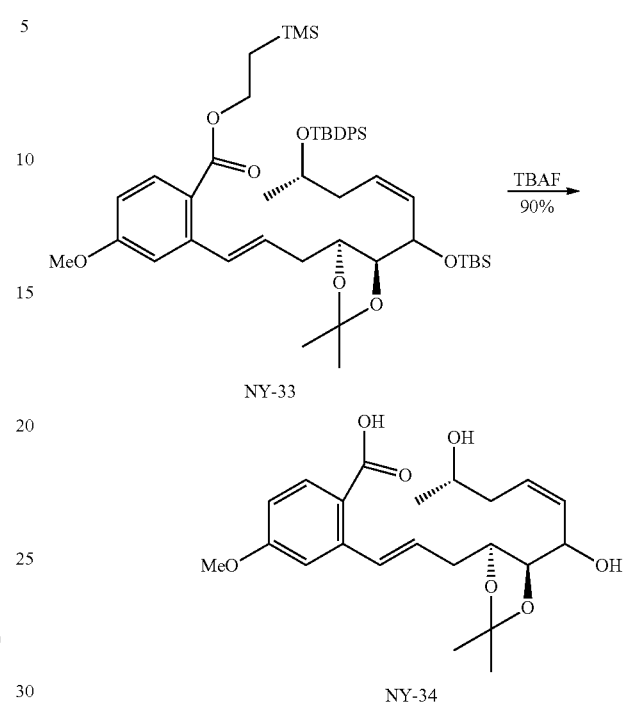
Using same procedure for 18, NY-32 (229 mg, 0.236 mmol) was converted to NY-33 (136 mg).
Using same procedure for 16, NY-27 (260 mg, 0.36 mmol) was converted to NY-32 (229 mg).
Using same procedure for 509-HD-116, NY-33 (136 mg, 0.585 mmol) was converted to NY-34 (119 mg).
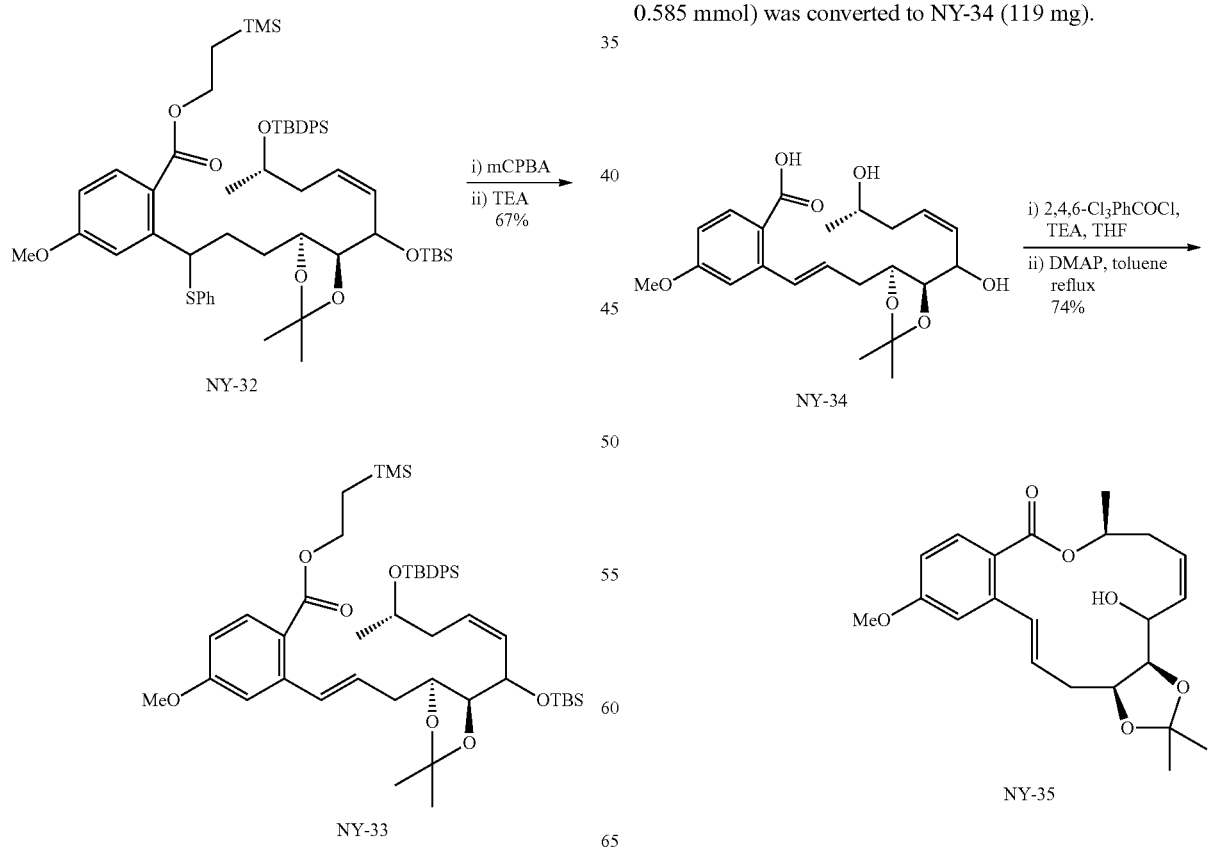
Using same procedure for TM-12, NY-34 (116 mg, 0.285 mmol) was converted to NY-35 (146 mg).

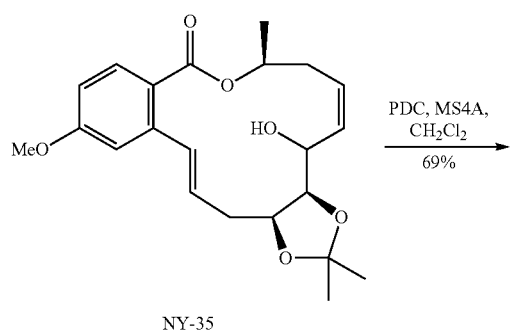

NY-35

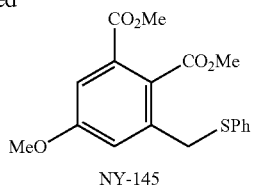

NY-145

Using same procedure for 10, NY-144 (7.11 g, 29.84 mmol) was converted to NY-145 (7.32 g).

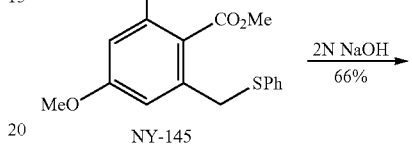

NY-36

Using same procedure for TM-13, NY-35 (80 mg, 0.206 mmol) was converted to NY-36 (55 mg).

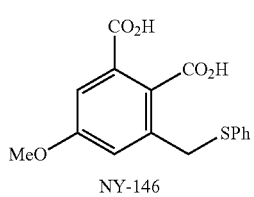

NY-146

Using same procedure for NY-45, NY-145 (7.32 g, 21.13 mmol) was converted to NY-146 (4.46 g).

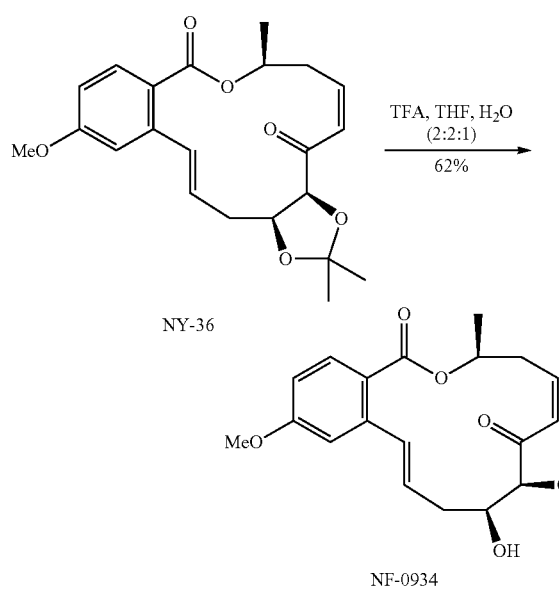

NY-36

NF-0934

Using same procedure for NF-0675, NY-36 (52 mg, 0.135 mmol) was converted to NF-0934 (29 mg).

Synthetic Procedure for NF-1418

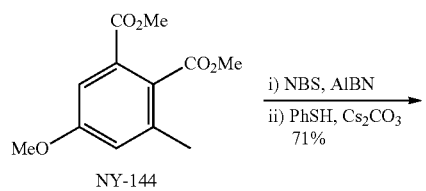

NY-144

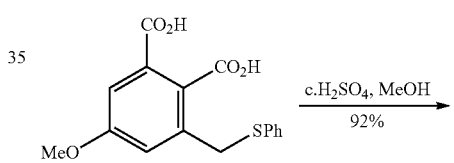

NY-146

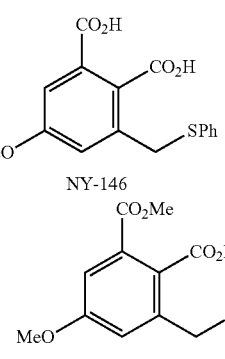

NY-147        NY-148

Using same procedure for NY-48, NY-146 (318 mg, 1 mmol) was converted to mixture of NY-147 and NY-148 (305 mg).

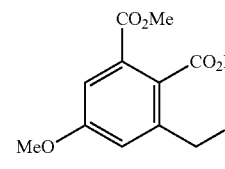

NY-147

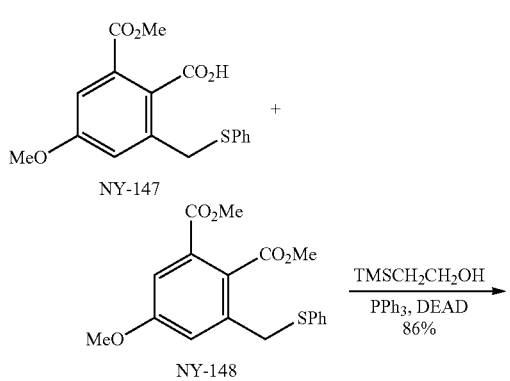

NY-148

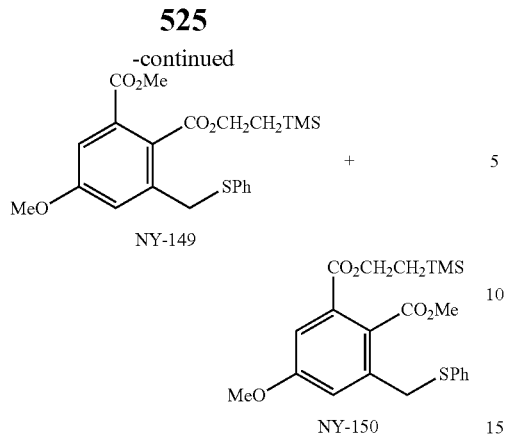
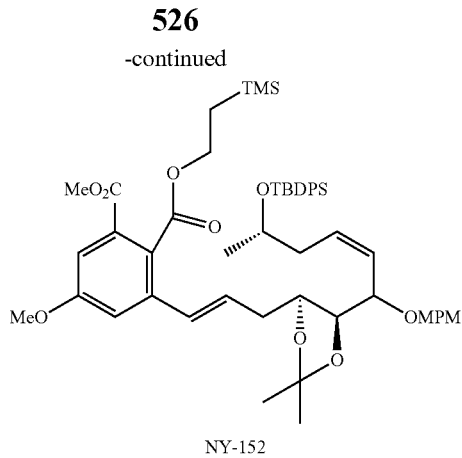
Using same procedure for 509-HD-213, NY-147 and NY-148 (303 mg, 0.912 mmol) was converted to NY-149 (297 mg) and NY-150 (42 mg).
Using same procedure for 18, NY-151 (306 mg) was converted to NY-152 (250 mg).
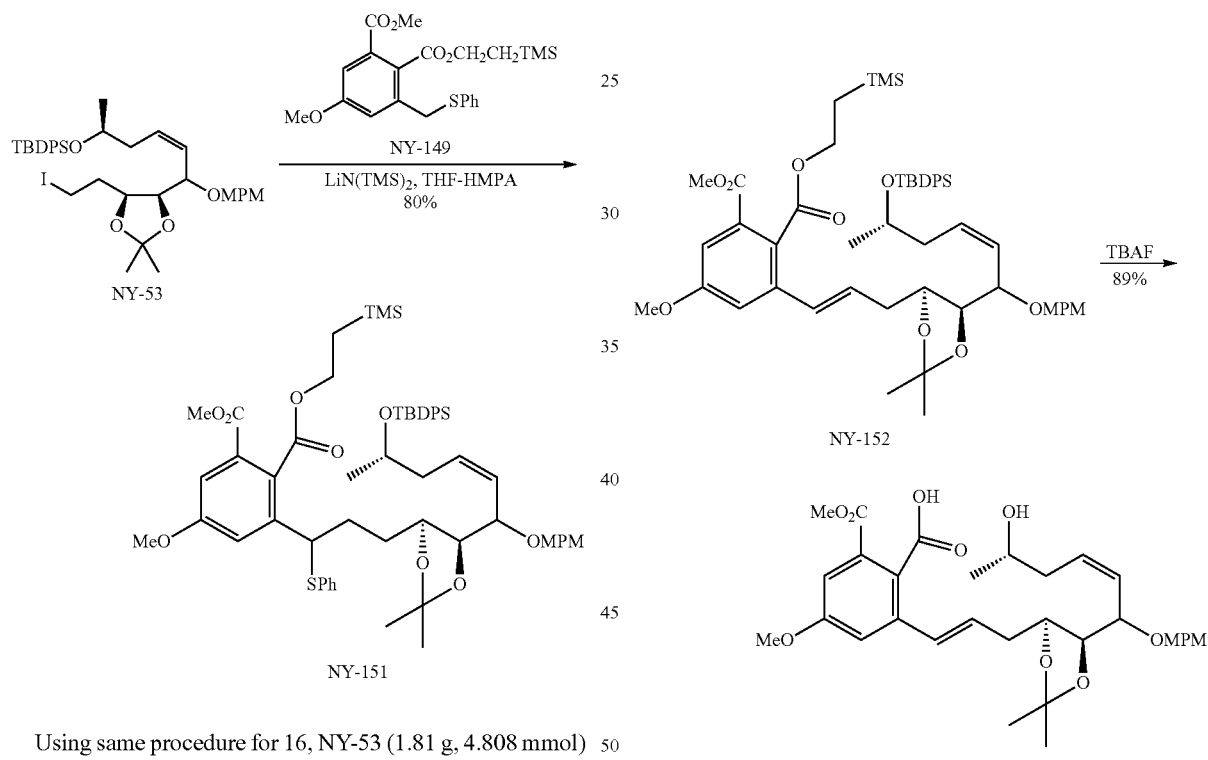
Using same procedure for 16, NY-53 (1.81 g, 4.808 mmol) was converted to NY-151 (2.06 g).
Using same procedure for 509-HD-116, NY-152 (230 mg, 0.233 mmol) was converted to NY-153 (197 mg).
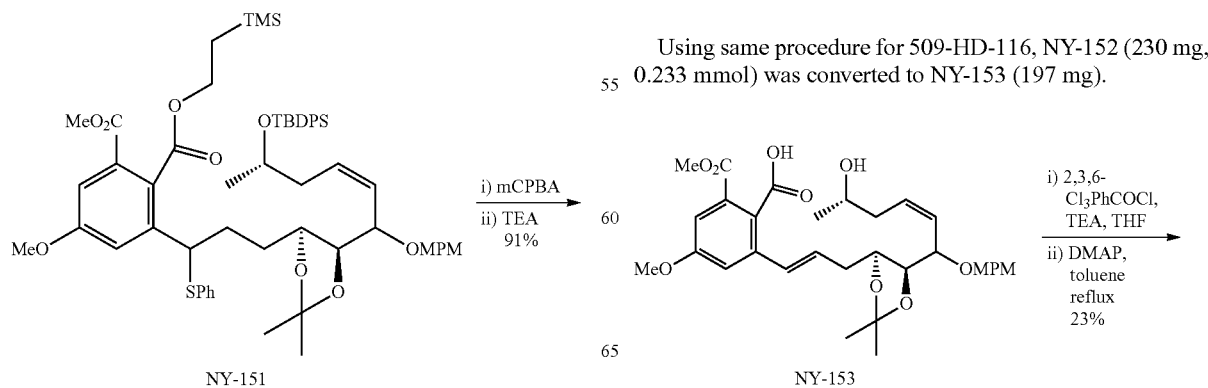

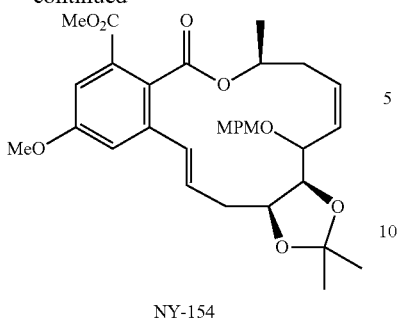

NY-154

Using same procedure for TM-12, NY-153 (136 mg, 0.233 mmol) was converted to NY-154 (30 mg).

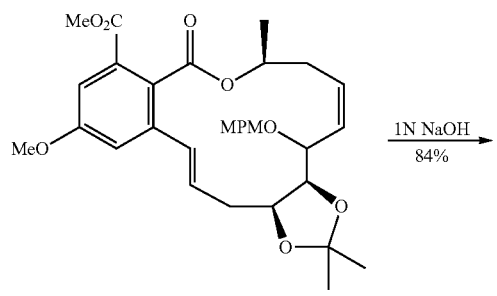

A mixture of NY-154 (28 mg, 0.0494 mmol), 1N NaOH (125 μL, 0.125 mmol) and DME (0.5 mL) was stirred at room temperature for 18 hrs. The reaction mixture was washed with Et₂O. The aqueous layer was neutralized with sat. NH₄Cl and extracted with EtOAc. The organic layers were washed with brine, dried over Na₂SO₄, filtered and concentrated to give 23 mg of NY-155. NY-155 was used without purification for the next step.

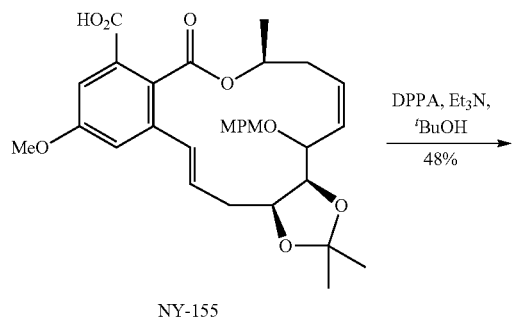

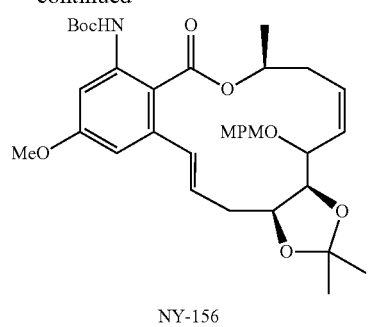

NY-156

A mixture of NY-155 (22 mg, 0.0398 mmol), diphenylphosphoryl azide (8.6 μL, 0.0399 mmol), Et₃N (4 mg, 0.0395 mmol), ᵗBuOH (0.3 mL) and toluene (1.5 mL) was refluxed for 3 hrs. The reaction mixture was diluted with EtOAc and washed with 5% citric acid, water, sat. NaHCO₃, brine, dried over Na₂SO₄, filtered and concentrated. The crude product was purified on silica gel column with hexane/EtOAc, 5:1, 3:1 to give 12 mg of NY-156.

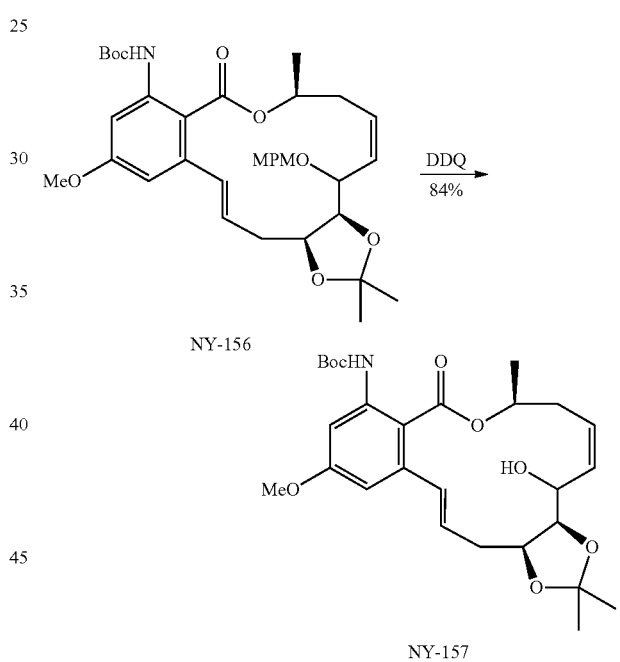

Using same procedure for 509-HD-188, NY-156 (11 mg, 0.0176 mmol) was converted to NY-157 (7.5 mg).

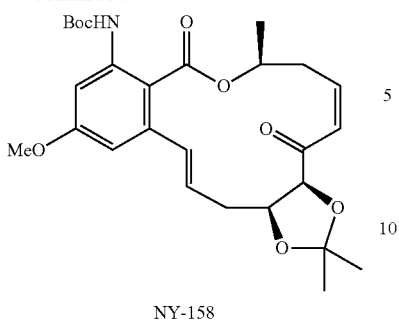

NY-158

Using same procedure for TM-13, NY-157 (7.5 mg, 0.0149 mmol) was converted to NY-158 (5.3 mg).

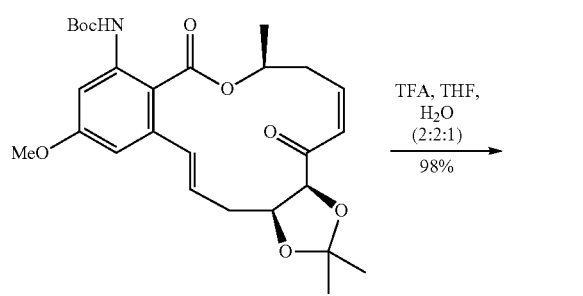

NY-158

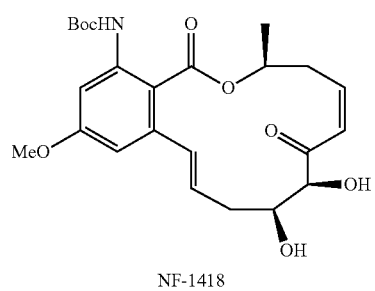

NF-1418

Using same procedure for NF-0675, NY-158 (5.2 mg, 0.0104 mmol) was converted to NF-1418 (4.7 mg).

Synthetic Procedure for NF-1419

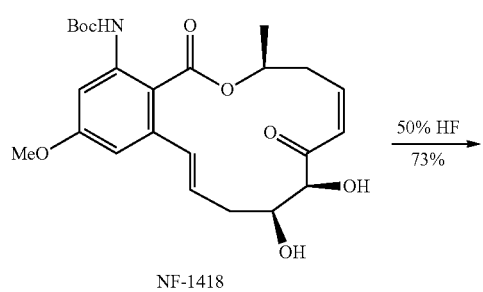

NF-1418

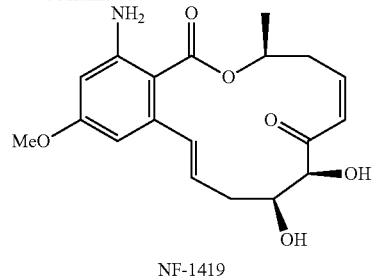

NF-1419

Using same procedure for B2538, NF-1418 (4 mg, 0.00937 mmol) was converted to NF-1419 (2.3 mg).

Measurement of Effect of Compounds on TNF-α and β-Actin PLAP (Placental Alkaline Phosphatase) Transcription.

NF-κB is a critical nuclear factor to regulate various genes involved in immune and inflammatory responses. (see, Ghosh et al, *Annu Rev Immunol.* 1998, 16, 225). It is well characterized that TNFα gene transcription is regulated by NF-th activation (see, Drouet et al. *J. Immunol.* 1991, 147, 1694), therefore, the assay with TNFα-PLAP transcription was employed to evaluate the inhibitory effect of test compounds on NF-κB activation.

A TNFα-PLAP plasmid (TNFα-promoter+5'-UTR (1.4 kb)+PLAP+SV40 polyA+PGK-neo, Goto et al. *Mol. Pharmacol.* 1996, 49, 860) was constructed with slight modification in which TNFα-3'-UTR (772 b.p.) was inserted between PLAP and SV40 polyA (TNFα-promoter+5'-UTR (1.4 kb)+PLAP+TNFα-3'-UTR+SV40 polyA+PGKneo). Then the THP-1-33 cells were established by stably transfecting the modified TNFα-PLAP plasmid into THP-1 cells (human acute monocytic leukemia). In order to simultaneously evaluate non-specific effects of test compounds on transcription, B164 cells were also established by stably transfecting β-actin-PLAP plasmid β-actin-promoter (4.3 kb)+PLAP+SV40 polyA+PGKneo) into THP-1 cells. THP-1-33 cells (TNFα-PLAP) produce PLAP activity by the stimulation with LPS; on the other hand, B164 cells β-actin-PLAP) constantly produce PLAP activity without stimuli.

THP-1-33 cells and B164 cells were maintained in RPMI1640 containing 10% heat-inactivated endotoxin-free fetal bovine serum (FBS) and G418 (1 mg/ml). These cells were seeded at a density of $1.0 \times 10^4$ cells/well onto 96-well plate, and then were cultured in the presence or absence of test compounds for 30 min, followed by stimulation with 100 ng/mL of lipopolysaccharide (*E. coli* 0127:B08 or 011:B4). After the cultivation for 40-48 hrs, culture supernatant was harvested and alkaline phosphatase activity in the supernatant was measured.

Alkaline phosphatase activity was quantified with the use of a chemiluminescent substrate, 4-methoxy-4-(3-phosphatephenyl)spiro[1,2-dioxetane-3,2'-adamantane]. To inactivate tissue-nonspecific alkaline phosphatase mainly derived from FBS, samples were heated at 65° C. for 30 min before the chemiluminescent assay. Aliquots of 10 μL of culture supernatant were mixed with 50 μL of assay buffer (0.28 M $Na_2CO_3$—$NaHCO_3$, pH 10.0, containing 8 mM $MgSO_4$) in a 96-well Microlite™ plate (opaque), and then 50 μL of chemiluminescent substrate was added and mixed. After 60 min incubation at room temperature, steady state chemiluminesce was measured with a microplate luminometer.

The PLAP activity of each sample was calculated as follows:

TNFα-PLAP % of control=$(A-B)\times 100/(C-B)$

β-actin-PLAP % of control=$(A)\times 100/(C)$

A: sample/chemiluminescence of the sample cultured with the test drug & stimulated with LPS B: blank/chemiluminescence of unstimulated sample C: control/chemiluminescence of the sample cultured with LPS The IC50 value of each test compound was calculated from dose-inhibitory response curve.

| Drug | Drug Trade Name | Approved Use | Manufacturer/Distributor | Approval Date |
|---|---|---|---|---|
| alitretinoin | Panretin | Topical treatment of cutaneous lesions in patients with AIDS-related Kaposi's sarcoma. | Ligand Pharmaceuticals | Feb. 02, 1999 |
| allopurinol | Zyloprim | Patients with leukemia, lymphoma and solid tumor malignancies who are receiving cancer therapy which causes elevations of serum and urinary uric acid levels and who cannot tolerate oral therapy. | Glaxo Smith Kline | May 17, 1996 |
| altretamine | Hexalen | Single agent palliative treatment of patients with persistent or recurrent ovarian cancer following first-line therapy with a cisplatin and/or alkylating agent based combination. | US Bioscience | Dec. 26, 1990 |
| amifostine | Ethyol | To reduce the cumulative renal toxicity associated with repeated administration of cisplatin in patients with advanced ovarian cancer | US Bioscience | Dec. 08, 1995 |
| amifostine | Ethyol | Reduction of platinum toxicity in non-small cell lung cancer | US Bioscience | Mar. 15, 1996 |
| amifostine | Ethyol | To reduce post-radiation xerostomia for head and neck cancer where the radiation port includes a substantial portion of the parotid glands. | US Bioscience | Jun. 24, 1999 |
| anastrozole | Arimidex | for the adjuvant treatment of postmenopausal women with hormone receptor positive early breast cancer | AstraZeneca | Sep. 05, 2002 |
| anastrozole | Arimidex | Treatment of advanced breast cancer in postmenopausal women with disease progression following tamoxifen therapy. | AstraZeneca Pharmaceuticals | Dec. 27, 1995 |
| anastrozole | Arimidex | For first-line treatment of postmenopausal women with hormone receptor positive or hormone receptor unknown locally advanced or metastatic breast cancer. | AstraZeneca Pharmaceuticals | Sep. 01, 2000 |
| arsenic trioxide | Trisenox | Second line treatment of relapsed or refractory APL following ATRA plus an anthracycline. | Cell Therapeutic | Sep. 25, 2000 |
| bexarotene | Targretin | For the treatment by oral capsule of cutaneous manifestations of cutaneous T-cell lymphoma in patients who are refractory to at least one prior systemic therapy. | Ligand Pharmaceuticals | Dec. 29, 1999 |
| bexarotene | Targretin | For the topical treatment of cutaneous manifestations of cutaneous T-cell lymphoma in patients who are refractory to at least one prior systemic therapy. | Ligand Pharmaceuticals | Jun. 28, 2000 |
| bleomycin | Blenoxane | Sclerosing agent for the treatment of malignant pleural effusion (MPE) and prevention of recurrent pleural effusions. | Bristol-Myers Squibb | Feb. 20, 1996 |
| busulfan intravenous | Busulfex | Use in combination with cyclophoshamide as conditioning regimen prior to allogeneic hematopoietic progenitor cell transplantation for chronic myelogenous leukemia. | Orphan Medical, Inc | Feb. 04, 1999 |
| busulfan oral | Myleran | Chronic Myelogenous Leukemia-palliative therapy | Glaxo Smith Kline | Jun. 26, 1954 |
| capecitabine | Xeloda | Initial therapy of patients with metastatic colorectal carcinoma when treatment with fluoropyrimidine therapy alone is preferred. Combination chemotherapy has shown a survival benefit compared to 5-FU/LV alone. A survival benefit over 5_FU/LV has not been demonstrated with Xeloda monotherapy. | Roche | Apr. 30, 2001 |
| capecitabine | Xeloda | Treatment in combination with docetaxel of patients with metastatic breast cancer after failure of prior anthracycline containing chemotherapy | Roche | Sep. 07, 2001 |
| capecitabine | Xeloda | Treatment of metastatic breast cancer resistant to both paclitaxel and an anthracycline containing chemotherapy regimen or resistant to paclitaxel and for whom further anthracycline therapy may be contraindicated, e.g., patients who have received cumulative | Roche | Apr. 30, 1998 |

| Drug | Drug Trade Name | Approved Use | Manufacturer/Distributor | Approval Date |
|---|---|---|---|---|
| | | doses of 400 mg/m2 of doxorubicin or doxorubicin equivalents | | |
| carboplatin | Paraplatin | Palliative treatment of patients with ovarian carcinoma recurrent after prior chemotherapy, including patients who have been previously treated with cisplatin. | Bristol-Myers Squibb | Mar. 03, 1989 |
| carboplatin | Paraplatin | Initial chemotherapy of advanced ovarian carcinoma in combination with other approved chemotherapeutic agents. | Bristol-Myers Squibb | Jul. 05, 1991 |
| carmustine with Polifeprosan 20 Implant | Gliadel Wafer | For use in addition to surgery to prolong survival in patients with recurrent glioblastoma multiforme who qualify for surgery. | Guilford Pharmaceuticals Inc. | Sep. 23, 1996 |
| celecoxib | Celebrex | Reduction of polyp number in patients with the rare genetic disorder of familial adenomatous polyposis. | Searle | Dec. 23, 1999 |
| chlorambucil | Leukeran | Chronic Lymphocytic Leukemia-palliative therapy | Glaxo Smith Kline | |
| cisplatin | Platinol | as a single agent for patients with transitional cell bladder cancer which is no longer amenable to local treatments such as surgery and/or radiotherapy. | Bristol-Myers Squibb | Apr. 22, 1993 |
| cisplatin | Platinol | Metastatic testicular-in established combination therapy with other approved chemotherapeutic agents in patients with metastatic testicular tumors whoc have already received appropriate surgical and/or radiotherapeutic procedures. An established combination therapy consists of Platinol, Blenoxane and Velbam. | Bristol-Myers Squibb | Dec. 19, 1978 |
| cisplatin | Platinol | Metastatic ovarian tumors - in established combination therapy with other approved chemotherapeutic agents: Ovarian-in established combination therapy with other approved chemotherapeutic agents in patients with metastatic ovarian tumors who have already received appropriate surgical and/or radiotherapeutic procedures. An established combination consists of Platinol and Adriamycin. Platinol, as a single agent, is indicated as secondary therapy in patients with metastatic ovarian tumors refractory to standard chemotherapy who have not previously received Platinol therapy. | Bristol-Myers Squibb | Dec. 19, 1978 |
| cisplatin-epinephrine gel | IntraDose (R), FocaCis (R) | not approved | Matrix Pharmaceutical | |
| cladribine | Leustatin, 2-CdA | Treatment of active hairy cell leukemia. | R. W. Johnson Pharmaceutical Research Institute | Feb. 26, 1993 |
| cytarabine liposomal | DepoCyt | Intrathecal therapy of lymphomatous meningitis | Skye Pharmaceuticals | Apr. 01, 1999 |
| daunorubicin liposomal | DanuoXome | First line cytotoxic therapy for advanced, HIV related Kaposi's sarcoma. | Nexstar, Inc. | Apr. 08, 1996 |
| daunorubicin, daunomycin | Daunorubicin | Leukemia/myelogenous/monocytic/erythroid of adults/remission induction in acute lymphocytic leukemia of children and adults. | Bedford Labs | Jan. 30, 1998 |
| daunorubicin, daunomycin | Cerubidine | In combination with approved anticancer drugs for induction of remission in adult ALL. | Wyeth Ayerst Res | Mar. 11, 1987 |
| dexrazoxane | Zinecard | reducing the incidence and severity of cardiomyopathy associated with doxorubicin administration in women with metastatic breast cancer who have received a cumulative doxorubicin dose of 300 mg/m2 and who will continue to receive doxorubicin therapy to maintain tumor control. It is not recommended for use with the initiation of doxorubicin therapy. | Pharmacia | Oct. 31, 2002 |
| dexrazoxane | Zinecard | Prevention of cardiomyopathy associated with doxorubicin administration | Pharmacia & Upjohn Company | May 26, 1995 |
| docetaxel | Taxotere | Treatment of patients with locally advanced or metastatic breast cancer who have progressed during anthracycline-based therapy or have relapsed during anthracycline-based adjuvant therapy. | Aventis Pharmaceutical | May 14, 1996 |

| Drug | Drug Trade Name | Approved Use | Manufacturer/Distributor | Approval Date |
|---|---|---|---|---|
| docetaxel | Taxotere | For locally advanced or metastatic non-small cell lung cancer after failure of prior platinum-based chemotherapy. | Aventis Pharmaceutical | Dec. 23, 1999 |
| docetaxel | Taxotere | For the treatment of locally advanced or metastatic breast cancer which has progressed during anthracycline-based treatment or relapsed during anthracycline-based adjuvant therapy. | Aventis Pharmaceutical | Jun. 22, 1998 |
| doxorubicin | Adriamycin PFS Injection | Antibiotic, antitumor agent. | Pharmacia & Upjohn Company | Dec. 23, 1987 |
| doxorubicin liposomal | Doxil | Treatment of AIDS-related Kaposi's sarcoma in patients with disease that has progressed on prior combination chemotherapy or in patients who are intolerant to such therapy. | Sequus Pharmaceuticals, Inc. | Nov. 17, 1995 |
| doxorubicin liposomal | Doxil | Treatment of metastatic carcinoma of the ovary in patient with disease that is refractory to both paclitaxel and platinum based regimens | Sequus Pharmaceuticals, Inc. | Jun. 28, 1999 |
| Elliott's B Solution | Elliott's B Solution | Diluent for the intrathecal administration of methotrexate sodium and cytarabine for the prevention or treatment of meningeal leukemia or lymphocytic lymphoma. | Orphan Medical, Inc | Sep. 27, 1996 |
| epirubicin | Ellence | A component of adjuvant therapy in patients with evidence of axillary node tumor involvement following resection of primary breast cancer. | Pharmacia & Upjohn Company | Sep. 15, 1999 |
| estramustine | Emcyt | palliation of prostate cancer | Pharmacia & Upjohn Company | Dec. 24, 1981 |
| etoposide phosphate | Etopophos | Management of refractory testicular tumors, in combination with other approved chemotherapeutic agents. | Bristol-Myers Squibb | May 17, 1996 |
| etoposide phosphate | Etopophos | Management of refractory testicular tumors and small cell lung cancer. | Bristol-Myers Squibb | Feb. 27, 1998 |
| etoposide phosphate | Etopophos | Management of small cell lung cancer, first-line, in combination with other approved chemotherapeutic agents. | Bristol-Myers Squibb | May 17, 1996 |
| etoposide, VP-16 | VePesid | In combination with other approved chemotherapeutic agents as first line treatment in patients with small cell lung cancer. | Bristol-Myers Squibb | Dec. 30, 1986 |
| etoposide, VP-16 | Vepesid | Refractory testicular tumors-in combination therapy with other approved chemotherapeutic agents in patients with refractory testicular tumors who have already received appropriate surgical, chemotherapeutic and radiotherapeutic therapy. | Bristol-Myers Squibb | Nov. 10, 1983 |
| etoposide, VP-16 | Vepesid | In combination with other approved chemotherapeutic agents as first line treatment in patients with small cell lung cancer. | Bristol-Myers Squibb | Dec. 30, 1986 |
| exemestane | Aromasin | Treatment of advance breast cancer in postmenopausal women whose disease has progressed following tamoxifen therapy. | Pharmacia & Upjohn Company | Oct. 21, 1999 |
| fludarabine | Fludara | Palliative treatment of patients with B-cell lymphocytic leukemia (CLL) who have not responded or have progressed during treatment with at least one standard alkylating agent containing regimen. | Berlex Laboratories Inc. | Apr. 18, 1991 |
| fluorouracil, 5-FU | Adrucil | prolong survival in combination with leucovorin | ICN Puerto Rico | Apr. 25, 1962 |
| fulvestrant | Faslodex | the treatment of hormone receptor-positive metastatic breast cancer in postmenopausal women with disease progression following antiestrogen therapy | IPR | Apr. 25, 2002 |
| gemcitabine | Gemzar | For use in combination with cisplatin for the first-line treatment of patients with inoperable, locally advanced (Stage IIIA or IIIB) or metastatic (Stage IV) non-small cell lung cancer. | Eli Lilly And Company | Aug. 25, 1998 |
| gemcitabine | Gemzar | Treatment of patients with locally advanced (nonresectable stage II or III) or metastatic (stage IV) adenocarcinoma of the pancreas. Indicated for first-line treatment and for patients previously treated with a 5-fluorouracil-containing regimen. | Eli Lilly And Company | May 15, 1996 |

| Drug | Drug Trade Name | Approved Use | Manufacturer/Distributor | Approval Date |
|---|---|---|---|---|
| gemtuzumab-ozogamicin | Mylotarg | Treatment of CD33 positive acute myeloid leukemia in patients in first relapse who are 60 years of age or older and who are not considered candidates for cytotoxic chemotherapy. | Wyeth Ayerst Res | May 17, 2000 |
| goserelin acetate | Zoladex Implant | Palliative treatment of advanced breast cancer in pre- and perimenopausal women. | AstraZeneca Pharmaceuticals | Dec. 18, 1995 |
| hydroxyurea | Hydrea Capsules | Decrease need for transfusions in sickle cell anemia | Bristol-Myers Squibb | Feb. 25, 1998 |
| idarubicin | Idamycin | For use in combination with other approved antileukemic drugs for the treatment of acute myeloid leukemia (AML) in adults. | Adria Laboratories | Sep. 27, 1990 |
| idarubicin | Idamycin | In combination with other approved antileukemic drugs for the treatment of acute non-lymphocytic leukemia in adults. | Pharmacia & Upjohn Company | Feb. 17, 1997 |
| ifosfamide | IFEX | Third line chemotherapy of germ cell testicular cancer when used in combination with certain other approved antineoplastic agents. | Bristol-Myers Squibb | Dec. 30, 1988 |
| imatinib mesylate | Gleevec | metastatic or unresectable malignant gastrointestinal stromal tumors | Novartis | Feb. 01, 2002 |
| imatinib mesylate | Gleevec | Initial therapy of chronic myelogenous leukemia | Novartis | May 10, 2001 |
| irinotecan | Camptosar | Treatment of patients with metastatic carcinoma of the colon or rectum whose disease has recurred or progressed following 5-FU-based therapy. | Pharmacia & Upjohn Company | Jun. 14, 1996 |
| irinotecan | Camptosar | For first line treatment n combination with 5-FU/leucovorin of metastatic carcinoma of the colon or rectum. | Pharmacia & Upjohn Company | Apr. 20, 2000 |
| irinotecan | Camptosar | Follow up of treatment of metastatic carcinoma of the colon or rectum whose disease has recurred or progressed following 5-FU-based therapy. | Pharmacia & Upjohn Company | Oct. 22, 1998 |
| letrozole | Femara | Treatment of advanced breast cancer in postmenopausal women. | Novartis | Jul. 25, 1997 |
| letrozole | Femara | First-line treatment of postmenopausal women with hormone receptor positive or hormone receptor unknown locally advanced or metastatic breast cancer. | Novartis | Jan. 10, 2001 |
| leucovorin | Wellcovorin, Leucovorin | Leucovorin calcium is indicated fro use in combination with 5-fluorouracil to prolong survival in the palliative treatment of patients with advanced colorectal cancer. | Immunex Corporation | Jun. 20, 1952 |
| leucovorin | Leucovorin | In combination with fluorouracil to prolong survival in the palliative treatment of patients with advanced colorectal cancer. | Lederle Laboratories | Dec. 12, 1991 |
| levamisole | Ergamisol | Adjuvant treatment in combination with 5-fluorouracil after surgical resection in patients with Dukes' Stage C colon cancer. | Janssen Research Foundation | Jun. 18, 1990 |
| liposomal daunorubicin | DaunoXome | "DaunoXome is indicated as a first line cytotoxic therapy for advanced HIV-associated Kaposi's Sarcoma. DaunoXome is not recommended in patients with less than advnanced HIV-related Kaposi's Sarcoma." | Vestar, Inc | Jan. 28, 1994 |
| melphalan, L-PAM | Alkeran | Systemic administration for palliative treatment of patients with multiple myeloma for whom oral therapy is not appropriate. | Glaxo Smith Kline | Nov. 18, 1992 |
| mesna | Mesnex | Prevention of ifosfamide-induced hemorrhagic cystitis | Asta Medica | Dec. 30, 1988 |
| methotrexate | Methotrexate | osteosarcoma | Lederle Laboratories | Apr. 07, 1988 |
| methoxsalen | Uvadex | For the use of UVADEX with the UVAR Photopheresis System in the palliative treatment of the skin manifestations of cutaneous T-cell lymphoma (CTCL) that is unresponsive to other forms of treatment. | Therakos | Feb. 25, 1999 |
| mitomycin C | Mitozytrex | therapy of disseminated adenocarcinoma of the stomach or pancreas in proven combinations with other approved chemotherapeutic agents and as palliative treatment when other modalities have failed. | Supergen | Nov. 14, 2002 |
| mitoxantrone | Novantrone | For use in combination with corticosteroids as initial chemotherapy for the treatment of patients with pain related to advanced hormone-refractory prostate cancer. | Immunex Corporation | Nov. 13, 1996 |

| Drug | Drug Trade Name | Approved Use | Manufacturer/Distributor | Approval Date |
|---|---|---|---|---|
| mitoxantrone | Novantrone | For use with other approved drugs in the initial therapy for acute nonlymphocytic leukemia (ANLL) in adults. | Lederle Laboratories | Dec. 23, 1987 |
| paclitaxel | Paxene | treatment of advanced AIDS-related Kaposi's sarcoma after failure of first line or subsequent systemic chemotherapy | Baker Norton Pharmaceuticals, Inc | Dec. 24, 1997 |
| paclitaxel | Taxol | For first-line therapy for the treatment of advanced carcinoma of the ovary in combination with cisplatin. | Bristol-Myers Squibb | Apr. 09, 1998 |
| paclitaxel | Taxol | Treatment of breast cancer after failure of combination chemotherapy for metastatic disease or relapse within 6 months of adjuvant chemotherapy. Prior therapy should have included an anthracycline unless clinically contraindicated. | Bristol-Myers Squibb | Apr. 13, 1994 |
| paclitaxel | Taxol | for use in combination with cisplatin, for the first-line treatment of non-small cell lung cancer in patients who are not candidates for potentially curative surgery and/or radiation therapy. | Bristol-Myers Squibb | Jun. 30, 1998 |
| paclitaxel | Taxol | For the adjuvant treatment of node-positive breast cancer administered sequentially to standard doxorubicin-containing combination therapy. | Bristol-Myers Squibb | Oct. 25, 1999 |
| paclitaxel | Taxol | First line ovarian cancer with 3 hour infusion. | Bristol-Myers Squibb | Jun. 20, 2000 |
| paclitaxel | Taxol | New dosing regimen for patients who have failed initial or subsequent chemotherapy for metastatic carcinoma of the ovary | Bristol-Myers Squibb | Jun. 22, 1994 |
| paclitaxel | Taxol | Treatment of patients with metastatic carcinoma of the ovary after failure of first-line or subsequent chemotherapy. | Bristol-Myers Squibb | Dec. 29, 1992 |
| paclitaxel | Taxol | second line therapy for AIDS related Kaposi's sarcoma. | Bristol-Myers Squibb | Aug. 04, 1997 |
| pamidronate | Aredia | Treatment of osteolytic bone metastases of breast cancer in conjunction with standard antineoplastic therapy. | Novartis | Sep. 22, 1998 |
| Pegademase | Adagen (Pegademase Bovine) | Enzyme replacement therapy for patients with severe combined immunodeficiency asa result of adenosine deaminase deficiency. | Enzon | Mar. 21, 1990 |
| pentostatin | Nipent | Single agent treatment for adult patients with alpha interferon refractory hairy cell leukemia. | Parke-Davis Pharmaceutical Co. | Oct. 11, 1991 |
| pentostatin | Nipent | Single-agent treatment for untreated hairy cell leukemia patients with active disease as defined by clinically significant anemia, neutropenia, thrombocytopenia, or disease-related symptoms. (Supplement for front-line therapy.) | Parke-Davis Pharmaceutical Co. | Sep. 29, 1993 |
| porfimer sodium | Photofrin | For use in photodynamic therapy (PDT) for palliation of patients with completely obstructing esophageal cancer, or patients with partially obstructing esophageal cancer who cannot be satisfactorily treated with ND-YAG laser therapy. | QLT Photherapeutics Inc. | Dec. 27, 1995 |
| porfimer sodium | Photofrin | For use in photodynamic therapy (PDT) for reduction of obstruction and palliation of symptoms in patients with completely or partially obstructing endobroncial nonsmall cell lung cancer (NSCLC). | QLT Photherapeutics Inc. | Dec. 22, 1998 |
| porfimer sodium | Photofrin | For use in photodynamic therapy for treatment of microinvasive endobronchial nonsmall cell lung cancer in patients for whom surgery and radiotherapy are not indicated. | QLT Photherapeutics Inc. | Jan. 09, 1998 |
| streptozocin | Zanosar | Antineoplastic agent. | Pharmacia & Upjohn Company | May 07, 1982 |
| talc | Sclerosol | For the prevention of the recurrence of malignant pleural effusion in symptomatic patients. | Bryan | Dec. 24, 1997 |
| tamoxifen | Nolvadex | For use in women with axillary node-negative breast cancer adjuvant therapy. | AstraZeneca Pharmaceuticals | Jun. 21, 1990 |
| tamoxifen | Nolvadex | As a single agent to delay breast cancer recurrence following total mastectomy and axillary dissection in postmenopausal women with breast cancer (T1-3, N1, M0) | AstraZeneca Pharmaceuticals | Dec. 03, 1986 |
| tamoxifen | Nolvadex | to reduce the incidence of breast cancer in women at high risk for breast cancer | AstraZeneca Pharmaceuticals | Oct. 29, 1998 |

| Drug | Drug Trade Name | Approved Use | Manufacturer/Distributor | Approval Date |
|---|---|---|---|---|
| tamoxifen | Nolvadex | Metastatic breast cancer in men. | AstraZeneca Pharmaceuticals | Apr. 01, 1993 |
| tamoxifen | Nolvadex | to reduce the incidence of breast cancer in women at high risk for breast cancer | AstraZeneca Pharmaceuticals | Oct. 29, 1998 |
| tamoxifen | Nolvadex | In women with DCIS, following breast surgery and radiation, Nolvadex is indicated to reduce the risk of invasive breast cancer. | AstraZeneca Pharmaceuticals | Jun. 29, 2000 |
| tamoxifen | Nolvadex | Equal bioavailability of a 20 mg Nolvadex tablet taken once a day to a 10 mg Nolvadex tablet taken twice a day. | AstraZeneca Pharmaceuticals | Mar. 21, 1994 |
| tamoxifen | Nolvadex | For use in premenopausal women with metastatic breast cancer as an alternative to oophorectomy or ovarian irradiation | AstraZeneca Pharmaceuticals | Mar. 16, 1989 |
| temozolamide | Temodar | Treatment of adult patients with refractory anaplastic astrocytoma, i.e., patients at first relapse with disease progression on a nitrosourea and procarbazine containing regimen | Schering | Aug. 11, 1999 |
| teniposide, VM-26 | Vumon | In combination with other approved anticancer agents for induction therapy in patients with refractory childhood acute lymphoblastic leukemia (all). | Bristol-Myers Squibb | Jul. 14, 1992 |
| topotecan | Hycamtin | Treatment of patients with metastatic carcinoma of the ovary after failure of initial or subsequent chemotherapy. | Glaxo Smith Kline | May 28, 1996 |
| topotecan | Hycamtin | Treatment of small cell lung cancer sensitive disease after failure of first-line chemotherapy. In clinical studies submitted to support approval, sensitive disease was defined as disease responding to chemotherapy but subsequently progressing at least 60 days (in the phase 3 study) or at least 90 days (in the phase 2 studies) after chemotherapy | Glaxo Smith Kline | Nov. 30, 1998 |
| toremifene | Fareston | Treatment of advanced breast cancer in postmenopausal women. | Orion Corp. | May 29, 1997 |
| tretinoin, ATRA | Vesanoid | Induction of remission in patients with acute promyelocytic leukemia (APL) who are refractory to or unable to tolerate anthracycline based cytotoxic chemotherapeutic regimens. | Roche | Nov. 22, 1995 |
| valrubicin | Valstar | For intravesical therapy of BCG-refractory carcinoma in situ (CIS) of the urinary bladder in patients for whom immediate cystectomy would be associated with unacceptable morbidity or mortality. | Anthra --> Medeva | Sep. 25, 1998 |
| vinorelbine | Navelbine | Single agent or in combination with cisplatin for the first-line treatment of ambulatory patients with unresectable, advanced non-small cell lung cancer (NSCLC). | Glaxo Smith Kline | Dec. 23, 1994 |
| vinorelbine | Navelbine | Navelbine is indicated as a single agent or in combination with cisplatin for the first-line treatment of ambulatory patients with unreseactable, advanced non-small cell lung cancer (NSCLC). In patients with Stage IV NSCLC, Navelbine is indicated as a single agent or in combination with cisplatin. In Stage III NSCLC, Navelbine is indicated in combination with cisplatin. | GlaxoSmithKline | Nov. 05, 2002 |
| zoledronate | Zometa | the treatment of patients with multiple myeloma and patients with documented bone metastases from solid tumors, in conjunction with standard antineoplastic therapy. Prostate cancer should have progressed after treatment with at least one hormonal therapy | Novartis | Feb. 22, 2002 |

We claim:

1. A method for treating rheumatoid arthritis, psoriasis, asthma, sepsis, inflammatory bowel disease, atopic dermatitis and Crohn's disease comprising:
administering to a subject in need thereof a therapeutically effective amount of a compound

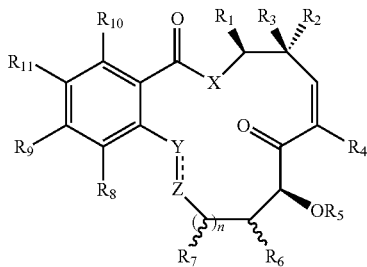

or pharmaceutically acceptable salt, ester, or salt of ester thereof;
wherein $R_1$ is hydrogen, aliphatic, heteroaliphatic, alicyclic, or aryl;
$R_2$ is methyl and $R_3$ is hydrogen or halogen;
$R_4$ is hydrogen or halogen;
$R_5$ is hydrogen or an oxygen protecting group;
$R_6$ is hydrogen, hydroxyl, or protected hydroxyl;
n is 1;
$R_7$ is hydrogen;
$R_8$ is hydrogen, halogen, hydroxyl, protected hydroxyl or alkyloxy;
$R_9$ is $NR_{12}R_{13}$;
wherein $R_{12}$ and $R_{13}$ are, independently for each occurrence, hydrogen, aliphatic, heteroaliphatic, alicyclic, or aryl; or a protecting group, and each of $R_{12}$ and $R_{13}$ are optionally further substituted with one or more occurrences of hydroxyl, protected hydroxyl, alkyloxy, amino, protected amino, alkylamino, aminoalkyl, or halogen,
$R_{10}$ is hydroxyl, protected hydroxyl, or amino;
$R_{11}$ is hydrogen;
X is O, NH, or N-alkyl;
Y is $CHR_{17}$, O, $CR_{17}$ or $NR_{17}$; and Z is $CHR_{18}$, C=O, or $CR_{18}$, wherein each occurrence of $R_{17}$ and $R_{18}$ is hydrogen, or $R_{17}$ and $R_{18}$ taken together is —O—, or —$CH_2$—, and Y and Z are connected by a single or double bond; and optionally
a pharmaceutically acceptable carrier or diluent.

2. The method of claim 1, wherein the method is for treating rheumatoid arthritis.

3. The method of claim 1, wherein the method is for treating psoriasis.

4. The method of claim 1, wherein the method is for treating asthma.

5. The method of claim 1, wherein:
wherein $R_1$ is hydrogen, straight or branched $C_{1-6}$alkyl, straight or branched $C_{1-6}$heteroalkyl, or aryl,
wherein the alkyl, heteroalkyl, and aryl groups may optionally be substituted with one or more occurrences of halogen, hydroxyl or protected hydroxyl;
$R_2$ is methyl and $R_3$ is hydrogen or halogen;
$R_4$ is hydrogen or halogen;
$R_5$ is hydrogen or an oxygen protecting group;
$R_6$ is hydrogen, hydroxyl, or protected hydroxyl;
$R_7$ is hydrogen;
$R_8$ is hydrogen;
$R_9$ is $NR_{12}R_{13}$;
wherein $R_{12}$ and $R_{13}$ are, independently for each occurrence, hydrogen, aliphatic, heteroaliphatic, alicyclic, or aryl, or a protecting group, and each of $R_{12}$ and $R_{13}$ are optionally further substituted with one or more occurrences of hydroxyl, protected hydroxyl, alkyloxy, amino, protected amino, alkylamino, aminoalkyl, or halogen;
$R_{10}$ is hydroxyl, protected hydroxyl, or amino;
$R_{11}$ is hydrogen;
X is O, NH, or N-alkyl;
Y is $CHR_{17}$, O, $CR_{17}$ or $NR_{17}$; and Z is $CHR_{18}$, C=O, or $CR_{18}$, wherein each occurrence of $R_{17}$ and $R_{18}$ is hydrogen, or $R_{17}$ and $R_{18}$ taken together is —O—, or —$CH_2$—, and Y and Z are connected by a single or double bond.

6. The method of claim 5, wherein in the compound X is oxygen.

7. The method of claim 5, wherein in the compound $R_4$ is halogen.

8. The method of claim 5, wherein in the compound $R_4$ is hydrogen.

9. The method of claim 5, wherein in the compound Y and Z together represent —CH=CH—.

10. The method of claim 5, wherein in the compound Y and Z together represent trans —CH=CH—.

11. The method of claim 5, comprising administering a compound wherein $R_1$ and $R_2$ are each methyl and $R_3$ is hydrogen and the compound is of the structure:

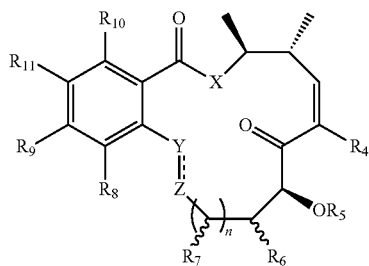

wherein $R_4$-$R_{11}$, X, Y and Z are as defined in claim 5.

12. The method of claim 11, wherein in the compound X is oxygen.

13. The method of claim 11, wherein in the compound $R_4$ is halogen.

14. The method of claim 11, wherein in the compound $R_4$ is hydrogen.

15. The method of claim 11, wherein in the compound Y and Z together represent —CH=CH—.

16. The method of claim 11, wherein in the compound $R_4$ is hydrogen, and Y and Z together represent —CH=CH—.

17. The method of claim 15 or 16, wherein in the compound —CH=CH— is trans.

18. The method of claim 5, wherein X is oxygen, $R_1$ and $R_2$ are each methyl, $R_3$ is hydrogen, $R_4$ is hydrogen and Y and Z together represent —CH=CH—.

19. A method of claim 1, comprising administering a compound of the structure:

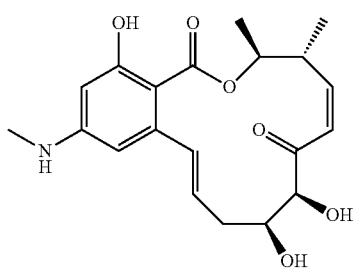

or pharmaceutically acceptable salt, ester, or salt of ester thereof.

20. A method of claim 1, comprising administering a compound of the structure:

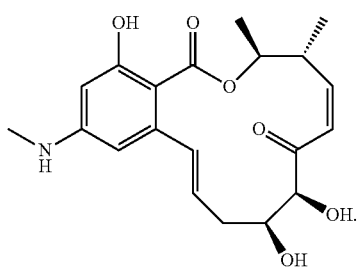

21. A method of claim 1, comprising administering a compound of the structure:

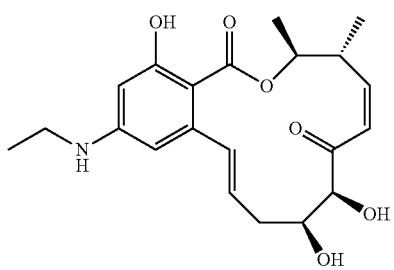

or pharmaceutically acceptable salt, ester, or salt of ester thereof.

22. A method of claim 1, comprising administering a compound of the structure:

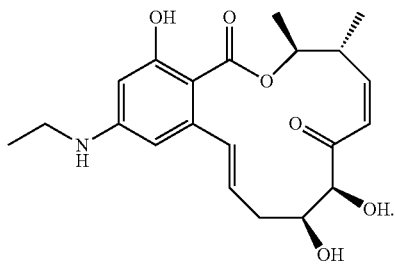

23. A method of claim 1, comprising administering a compound of the structure:

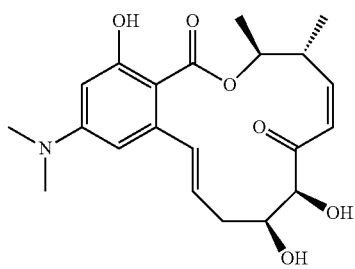

or pharmaceutically acceptable salt, ester, or salt of ester thereof.

24. A method of claim 1, comprising administering a compound of the structure:

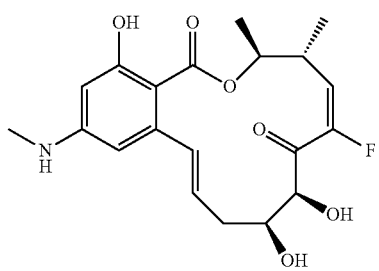

or pharmaceutically acceptable salt, ester, or salt of ester thereof.

25. A method of claim 1, comprising administering a compound of the structure:

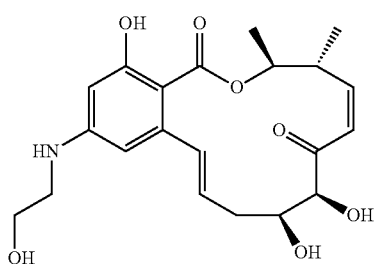

or pharmaceutically acceptable salt, ester, or salt of ester thereof.

26. A method of claim 1, comprising administering a compound of the

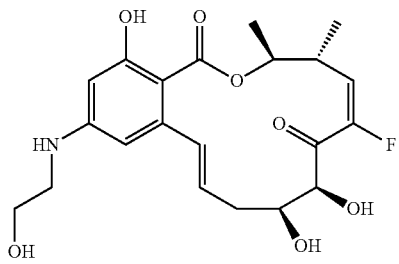

or pharmaceutically acceptable salt, ester, or salt of ester thereof.

27. A method for the treatment of psoriasis, comprising administering a compound according to any one of claims 5, 11, 19, 20, 21, and 22.

28. The method of claim 27, wherein in the step of administering, the composition is administered topically.

29. A method for the treatment of psoriasis, comprising administering a compound of the structure:

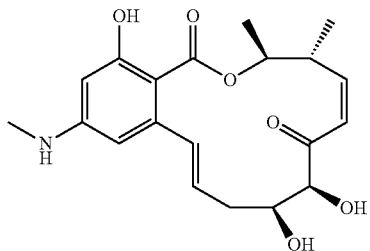

or pharmaceutically acceptable salt, ester, or salt of ester thereof.

30. A method for the treatment of psoriasis, comprising administering a compound of the structure:

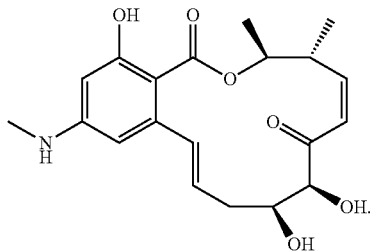

31. A method for the treatment of psoriasis, comprising administering a compound of the structure:

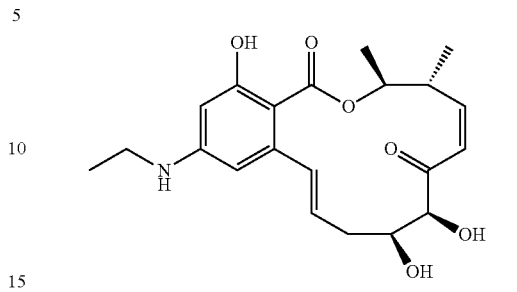

or pharmaceutically acceptable salt, ester, or salt of ester thereof.

32. A method for the treatment of psoriasis, comprising administering a compound of the structure:

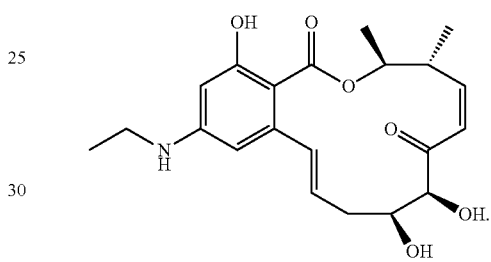

* * * * *